United States Patent
Hou et al.

(10) Patent No.: US 9,781,933 B2
(45) Date of Patent: Oct. 10, 2017

(54) TETRAZOLINONE COMPOUND AND USE THEREOF

(71) Applicant: Sumitomo Chemical Company, Limited, Tokyo (JP)

(72) Inventors: Zengye Hou, Takarazuka (JP); Teruki Takahashi, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 31 days.

(21) Appl. No.: 14/907,415

(22) PCT Filed: Jul. 25, 2014

(86) PCT No.: PCT/JP2014/070293
§ 371 (c)(1),
(2) Date: Jan. 25, 2016

(87) PCT Pub. No.: WO2015/016335
PCT Pub. Date: Feb. 5, 2015

(65) Prior Publication Data
US 2016/0174558 A1 Jun. 23, 2016

(30) Foreign Application Priority Data

Jul. 31, 2013 (JP) .................... 2013-158731

(51) Int. Cl.
| | | |
|---|---|---|
| *C07D 401/04* | (2006.01) | |
| *C07D 401/14* | (2006.01) | |
| *C07D 403/12* | (2006.01) | |
| *C07D 405/14* | (2006.01) | |
| *C07D 409/14* | (2006.01) | |
| *C07D 413/14* | (2006.01) | |
| *C07D 417/14* | (2006.01) | |
| *A01N 43/713* | (2006.01) | |
| *A01N 43/76* | (2006.01) | |
| *A01N 43/78* | (2006.01) | |

(52) U.S. Cl.
CPC .......... *A01N 43/713* (2013.01); *A01N 43/76* (2013.01); *A01N 43/78* (2013.01); *C07D 401/04* (2013.01); *C07D 401/14* (2013.01); *C07D 403/12* (2013.01); *C07D 405/14* (2013.01); *C07D 409/14* (2013.01); *C07D 413/14* (2013.01); *C07D 417/14* (2013.01)

(58) Field of Classification Search
None
See application file for complete search history.

(56) References Cited

U.S. PATENT DOCUMENTS

| | | |
|---|---|---|
| 7,056,941 B1 | 6/2006 | Muller et al. |
| 2008/0108668 A1 | 5/2008 | Liu et al. |
| 2008/0275070 A1 | 11/2008 | Liu et al. |

FOREIGN PATENT DOCUMENTS

| | | |
|---|---|---|
| WO | 9400436 A1 | 1/1994 |
| WO | 9905139 A1 | 2/1999 |
| WO | 2013092224 A1 | 6/2013 |
| WO | 2013162072 A1 | 10/2013 |
| WO | 2013162077 A1 | 10/2013 |

OTHER PUBLICATIONS

Office Action dated Nov. 28, 2016 in CN Application No. 201480042477.4.
International Search Report and Written Opinion (English language) dated Oct. 21, 2014 in International Application No. PCT/JP2014/070293.
Extended Search Report dated Feb. 2, 2017 in EP Application No. 14831507.0.

*Primary Examiner* — Alicia L Otton
(74) *Attorney, Agent, or Firm* — Panitch Schwarze Belisario & Nadel LLP

(57) ABSTRACT

A tetrazolinone compound represented by formula (1):

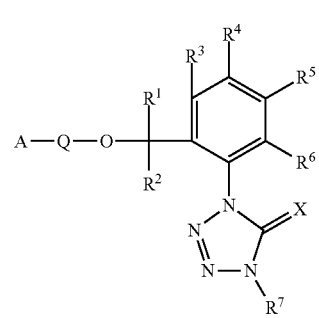

wherein Q represents a divalent 5-membered aromatic heterocyclic group optionally having one or more atoms or groups selected from Group $P^2$; A represents a 5- to 10-membered monocyclic or fused ring heterocyclic group optionally having one or more atoms or groups selected from Group $P^1$; $R^1$ and $R^2$ each represents a hydrogen atom, etc.; $R^3$ represents a C1-C6 alkyl group optionally having one or more halogen atoms, etc.; $R^4$, $R^5$, and $R^6$ each represents a hydrogen atom, etc.; and X represents an oxygen atom or a sulfur atom, has excellent control activity against pests.

9 Claims, No Drawings

TETRAZOLINONE COMPOUND AND USE THEREOF

CROSS-REFERENCE TO RELATED APPLICATION

This application is a Section 371 of International Application No. PCT/JP2014/070293, filed Jul. 25, 2014, which was published in the Japanese language on Feb. 5, 2015, under International Publication No. WO 2015/016335 A1, and the disclosure of which is incorporated herein by reference.

TECHNICAL FIELD

The present invention relates to a tetrazolinone compound and use thereof.

BACKGROUND ART

Heretofore, various chemicals have been developed so as to control pests and provided in practice use, but in some cases, these chemicals may not exert enough activity.

Meanwhile, there have been known, as compounds having a tetrazolinone ring, compounds represented by formula (A):

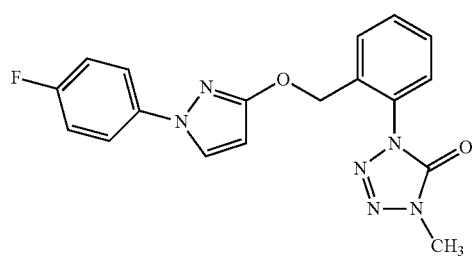

(A)

(see WO 99/05139 A).

The present invention provides compounds having excellent control activity against pests.

DISCLOSURE OF THE INVENTION

The present inventors have intensively studied so as to find compounds having excellent control activity against pests, and found that a tetrazolinone compound represented by the following formula (1) has excellent control activity against pests, thus completing the present invention.

The present invention includes the followings [1] to [10].

[1] A tetrazolinone compound represented by formula (1):

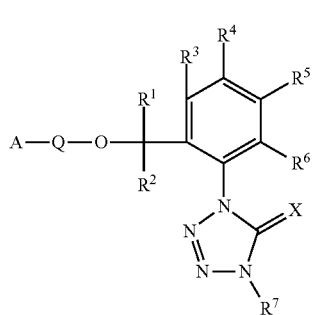

(1)

wherein
$R^1$ and $R^2$ each independently represents a hydrogen atom, a halogen atom, or a C1-C3 alkyl group;
$R^3$ represents a C1-C6 alkyl group, a C3-C6 cycloalkyl group, a halogen atom, a C1-C6 haloalkyl group, a C2-C6 alkenyl group, a C1-C6 alkoxy group, a C1-C6 alkylthio group, a C2-C6 alkynyl group, a nitro group, a cyano group, an aminocarbonyl group optionally having a C1-C6 alkyl group, a C2-C6 haloalkenyl group, a C2-C6 haloalkynyl group, a C3-C6 halocycloalkyl group, a C1-C6 haloalkoxy group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a C2-C6 alkoxycarbonyl group, a hydroxy group, a sulfanyl group, an amino group optionally having a C1-C6 alkyl group, a pentafluorosulfanyl group, a C3-C9 trialkylsilyl group, a C5-C14 trialkylsilylethynyl group, a C1-C6 alkylsulfonyl group, a C1-C6 haloalkylsulfonyl group, a C1-C6 alkylsulfinyl group, a C1-C6 haloalkylsulfinyl group, a C2-C5 alkoxyalkyl group, or a C2-C5 alkylthioalkyl group;
$R^4$, $R^5$, and $R^6$ each independently represents a hydrogen atom, a halogen atom, a C1-C3 alkyl group, a C1-C3 haloalkyl group, a C2-C3 alkenyl group, a C2-C3 haloalkenyl group, or a C1-C3 alkoxy group;
$R^7$ represents a C1-C3 alkyl group optionally having one or more halogen atoms;
Q represents a divalent 5-membered aromatic heterocyclic group optionally having one or more atoms or groups selected from Group $P^2$, provided that the heterocyclic group has one or more heteroatoms selected from a nitrogen atom, an oxygen atom, and a sulfur atom, the number of nitrogen atom is 0, 1, 2, 3, or 4, and the number of oxygen atom and sulfur atom is 0 or 1;
X represents an oxygen atom or a sulfur atom;
A represents a 5- to 10-membered monocyclic or fused ring heterocyclic group optionally having one or more atoms or groups selected from Group $P^1$, provided that the heterocyclic group has one or more heteroatoms selected from the group consisting of a nitrogen atom, an oxygen atom, and a sulfur atom, the number of nitrogen atom is 0, 1, 2, 3, or 4, and the number of oxygen atom and sulfur atom is 0, 1, 2, or 3:
Group $P^1$: Group consisting of a halogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a hydroxycarbonyl group, a formyl group, a C2-C6 alkoxycarbonyl group, a nitro group, a cyano group, a hydroxy group, a C1-C6 alkylsulfonyl group, a C1-C6 haloalkylsulfonyl group, a C6-C16 arylsulfonyl group, a C6-C16 haloarylsulfonyl group, a C1-C6 alkylsulfinyl group, a C1-C6 haloalkylsulfinyl group, an amino group optionally having a C1-C6 alkyl group, an aminosulfonyl group optionally having a C1-C6 alkyl group, and an aminocarbonyl group optionally having a C1-C6 alkyl group; and Group P²: Group consisting of a halogen atom, a C1-C4 alkyl group, a C1-C4 haloalkyl group, a cyano group, a C3-C6 cycloalkyl group, a C3-C6 halocycloalkyl group, a C1-C4 alkoxy group, a C1-C4 haloalkoxy group, a C1-C4 alkylthio group, and a C1-C4 haloalkylthio group, and a salt thereof.

[2] The tetrazolinone compound according to [1], wherein Q is a pyrazolyl group optionally having one or more atoms or groups selected from Group P²;

A is a pyridyl group optionally having one or more atoms or groups selected from Group P¹;

$R^1$, $R^2$, $R^4$, $R^5$, and $R^6$ are hydrogen atoms;

$R^3$ is a C1-C3 alkyl group optionally having one or more halogen atoms, a C3-C4 cycloalkyl group optionally having one or more halogen atoms, a halogen atom, a C1-C3 alkoxy group optionally having one or more halogen atoms, or a C1-C3 alkylthio group optionally having one or more halogen atoms;

$R^7$ is a methyl group; and

X is an oxygen atom.

[3] The tetrazolinone compound according to [1], wherein Q is a thiazolyl group optionally having one or more atoms or groups selected from Group P²;

A is a pyridyl group optionally having one or more atoms or groups selected from Group P¹;

$R^1$, $R^2$, $R^4$, $R^5$, and $R^6$ are hydrogen atoms;

$R^3$ is a C1-C3 alkyl group optionally having one or more halogen atoms, a C3-C4 cycloalkyl group optionally having one or more halogen atoms, a halogen atom, a C1-C3 alkoxy group optionally having one or more halogen atoms, or a C1-C3 alkylthio group optionally having one or more halogen atoms;

$R^7$ is a methyl group; and

X is an oxygen atom.

[4] The tetrazolinone compound according to [1], wherein Q is Q0;

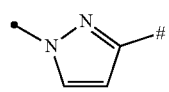

in which the symbol ● represents a binding site for A, and the symbol # represents a binding site for an oxygen atom;

A is a 2-pyridyl group, a 3-pyridyl group, a 2-quinolyl group, a 3-quinolyl group, a 3,4-methylenedioxyphenyl group, a 2-indolyl group, a 2-benzoimidazolyl group, a 3-thienyl group, a 2,3-dihydrobenzofuran-7-yl group, a 2-pyrimidinyl group, a 2-thiazolyl group, a pyrazinyl group, a 3-pyridazinyl group, a 2-benzoxazolyl group, a 2-benzothiazolyl group, a 2-quinazolyl group, or a 2-quinoxalinyl group;

$R^1$, $R^2$, $R^4$, $R^5$, and $R^6$ are hydrogen atoms;

$R^3$ is a C1-C3 alkyl group optionally having one or more halogen atoms, a C3-C4 cycloalkyl group optionally having one or more halogen atoms, a halogen atom, a C1-C3 alkoxy group optionally having one or more C1-C3 alkylthio group optionally having one or more halogen atoms;

$R^7$ is a methyl group; and

X is an oxygen atom.

[5] The tetrazolinone compound according to [1], [2], or [4], wherein Q is Q0; and A is a 3-pyridyl group optionally having a C1-C3 alkyl group optionally having one or more halogen atoms, a halogen atom, a C1-C3 alkoxy group optionally having one or more halogen atoms, or a cyano group.

[6] A pest control agent comprising the tetrazolinone compound according to any one of [1] to [5].

[7] A method for controlling pests, which comprises treating plants or soil with an effective amount of the tetrazolinone compound according to any one of [1] to [5].

[8] Use of the tetrazolinone compound according to any one of [1] to [5] for controlling pests.

[9] A pyrazole compound represented by formula (II):

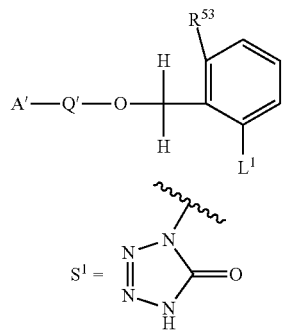

wherein Q' is a pyrazolyl group optionally having one or more atoms or groups selected from Group P²;

A' is a pyridyl group optionally having one or more atoms or groups selected from Group P¹;

$R^{53}$ is a C1-C3 alkyl group optionally having one or more halogen atoms, a C3-C4 cycloalkyl group optionally having one or more halogen atoms, a halogen atom, a C1-C3 alkoxy group optionally having one or more halogen atoms, or a C1-C3 alkylthio group optionally having one or more halogen atoms; and $L^1$ is a nitro group, an amino group, an isocyanate group, a carboxyl group, a C2-C6 alkoxycarbonyl group, a halogen atom, a halogenated acyl group, $NSO$, $CON_3$, $CONH_2$, $CONHCl$, $CONHBr$, $CONHOH$, or $S^1$.

[10] The pyrazole compound according to [9], wherein Q' is Q0;

A' is a a 3-pyridyl group optionally having C1-C3 alkyl group optionally having one or more halogen atoms, a halogen atom, a C1-C3 alkoxy group optionally having one or more halogen atoms, or a cyano group; and $L^1$ is a nitro group, an amino group, an isocyanate group, or $S^1$.

According to the present invention, pests can be controlled.

MODE FOR CARRYING OUT THE INVENTION

A compound of the present invention is a tetrazolinone compound represented by formula (1) (hereinafter sometimes referred to as the present compound (1)).

Formula (1)

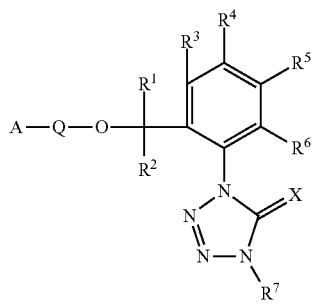
(1)

wherein $R^1$, $R^2$, $R^3$, $R^4$, $R^5$, $R^6$, $R^7$, Q, A, and X are the same as defined above.

The present invention provides the present compound (1) having control activity against pests, and a salt thereof.

The present invention also provides, as a compound to be used in the production of the present compound (1), a pyrazole compound represented by formula (II) (hereinafter sometimes referred to as the present pyrazole compound):

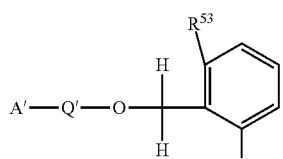
(II)

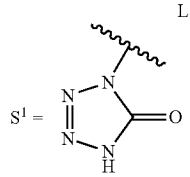

wherein
Q' is a pyrazolyl group optionally having one or more atoms or groups selected from Group $P^2$;
A' is a pyridyl group optionally having one or more atoms or groups selected from Group $P^1$;
$R^{53}$ is a C1-C3 alkyl group optionally having one or more halogen atoms, a C3-C4 cycloalkyl group optionally having one or more halogen atoms, a halogen atom, a C1-C3 alkoxy group optionally having one or more halogen atoms, or a C1-C3 alkylthio group optionally having one or more halogen atoms; and
$L^1$ represents a nitro group, an amino group, an isocyanate group, a carboxyl group, a C2-C6 alkoxycarbonyl group, a halogen atom, a halogenated acyl group, NSO, $CON_3$, $CONH_2$, CONHCl, CONHBr, CONHOH, or $S^1$.

Substituents as used herein will be mentioned in detail below.

The "divalent 5-membered aromatic heterocyclic group optionally having one or more atoms or groups selected from Group $P^2$ (provided that the heterocyclic group has one or more heteroatoms selected from a nitrogen atom, an oxygen atom, and a sulfur atom, the number of nitrogen atoms is 0, 1, 2, 3, or 4, and the number of oxygen atoms and sulfur atoms is 0 or 1)" includes, for example, a thiophene-di-yl group, a furan-di-yl group, a pyrrole-di-yl group, a pyrazole-di-yl group, an imidazole-di-yl group, a thiazole-di-yl group, an isothiazole-di-yl group, an oxazole-di-yl group, an isoxazole-di-yl group, a triazole-di-yl group, a tetrazole-di-yl group, an oxadiazole-di-yl group, and a thiadiazole-di-yl group, and preferably includes a pyrazole-di-yl group.

More specifically, the divalent 5-membered aromatic heterocyclic group represents, for example, any one of the following Groups Q1 to Q41 (in which the symbol ● represents a binding site for A, and the symbol # represents a binding site for an oxygen atom);

Q:

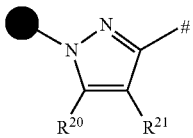
Q1

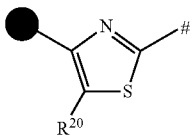
Q2

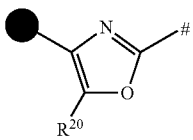
Q3

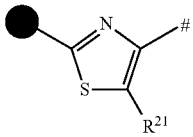
Q4

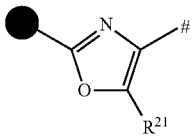
Q5

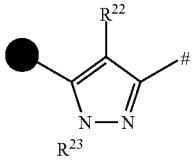
Q6

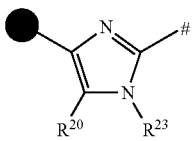
Q7

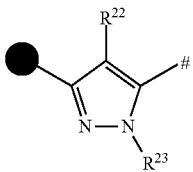
Q8

-continued
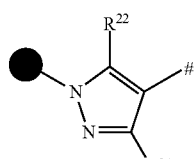 Q9
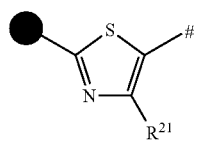 Q10
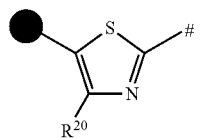 Q11
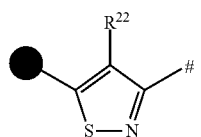 Q12
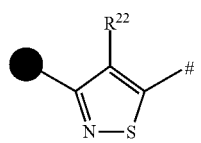 Q13
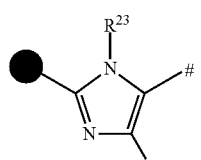 Q14
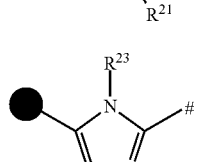 Q15
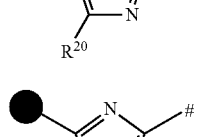 Q16
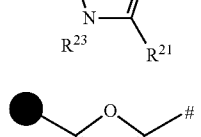 Q17
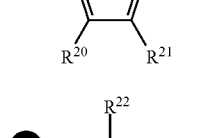 Q18
-continued
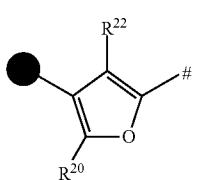 Q19
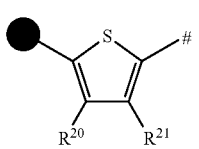 Q20
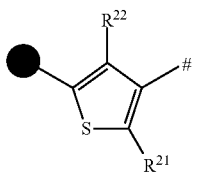 Q21
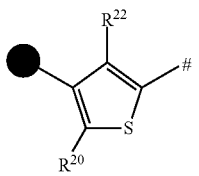 Q22
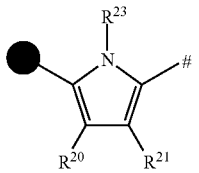 Q23
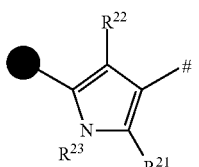 Q24
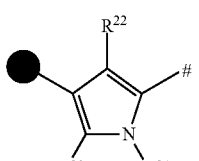 Q26
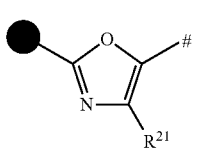 Q27
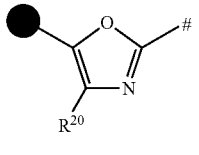 Q28

-continued

Q29 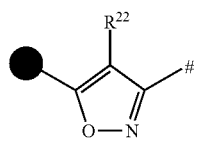

Q30 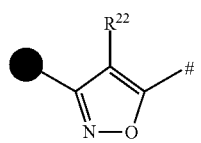

Q31 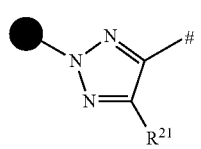

Q32 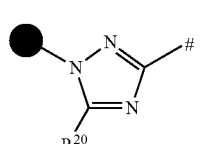

Q33 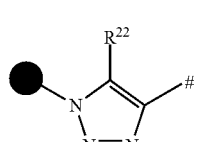

Q34 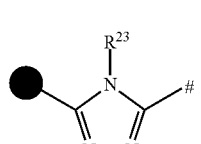

Q35 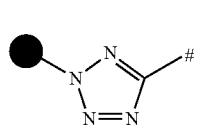

Q36 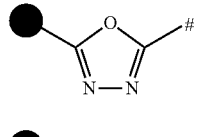

Q37 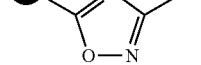

Q38 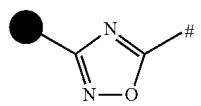

Q39 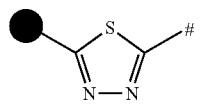

Q40 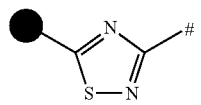

Q41 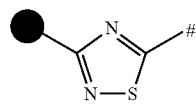

wherein $R^{20}$, $R^{21}$, and $R^{22}$ represent a hydrogen atom, a halogen atom, a C1-C4 alkyl group, a C1-C4 haloalkyl group, a cyano group, a C3-C6 cycloalkyl group, a C3-C6 halocycloalkyl group, a C1-C4 alkoxy group, a C1-C4 haloalkoxy group, a C1-C4 alkylthio group, or a C1-C4 haloalkylthio group, and $R^{23}$ represents a hydrogen atom, a C1-C4 alkyl group, a C1-C4 haloalkyl group, a C3-C6 cycloalkyl group, or a C3-C6 halocycloalkyl group.

The "5- to 10-membered monocyclic or fused ring heterocyclic group optionally having one or more atoms or groups selected from Group $P^1$ (provided that the heterocyclic group has one or more heteroatoms selected from a nitrogen atom, an oxygen atom, and a sulfur atom, the number of nitrogen atoms is 0, 1, 2, 3, or 4, and the number of oxygen atoms and sulfur atoms is 0, 1, 2, or 3)" may be either saturated or unsaturated and includes, for example, a pyridyl group, a pyrimidinyl group, a pyrazinyl group, a pyridazinyl group, a thienyl group, a furyl group, a pyrrolyl group, a pyrazolyl group, an imidazolyl group, a thiazolyl group, an isothiazolyl group, an oxazolyl group, an isoxazolyl group, a triazolyl group, a tetrazolyl group, a thiadiazolyl group, a benzofuryl group, a benzothienyl group, an indolyl group, a benzoimidazolyl group, an indazolyl group, a benzothiazolyl group, a benzoxazolyl group, a benzoisothiazolyl group, a benzoisoxazolyl group, a pyrazolopyrrolyl group, a pyrazolopyrazolyl group, a pyrazoloimidazolyl group, an imidazopyrimidinyl group, an imidazopyrazinyl group, a triazolopyridyl group, a triazolopyrimidyl group, a triazoloquinolyl group, a 2,3-dihydrobenzofuryl group, a 2,3-dihydrobenzothienyl group, a 1,3-benzodioxolyl group, a quinolyl group, an isoquinolyl group, a cinnolinyl group, a pthalazinyl group, a quinazolinyl group, a quinoxalinyl group, a naphthyridinyl group, a chromanyl group, an isochromanyl group, a thienopyridyl group, a thienopyrazolyl group, and a thienoquinolyl group, and preferably includes a pyridyl group.

More specifically, the 5- to 10-membered monocyclic or fused ring heterocyclic group represents, for example, any one of the following groups A1 to A97 (in which the symbol # represents a binding site for Q):

A:

A1
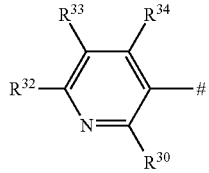

A2
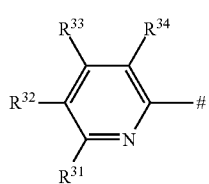

-continued
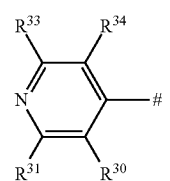 A3
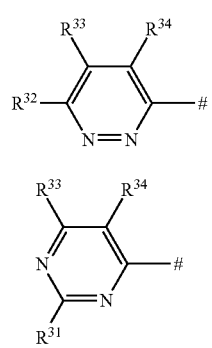 A4
A5
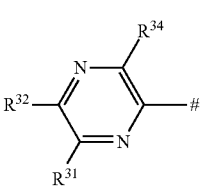 A6
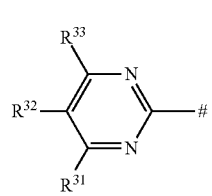 A7
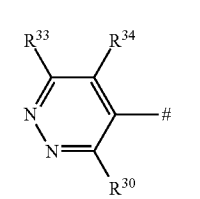 A8
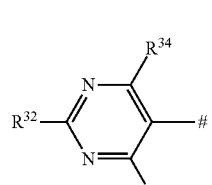 A9
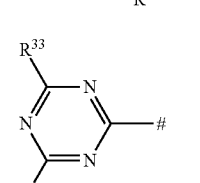 A10
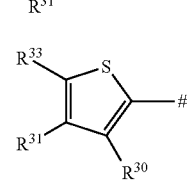 A11
-continued
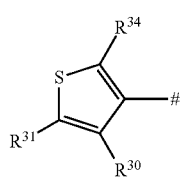 A12
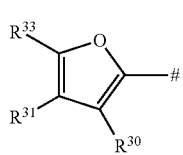 A13
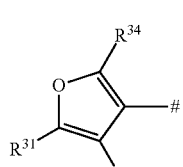 A14
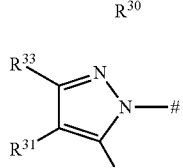 A15
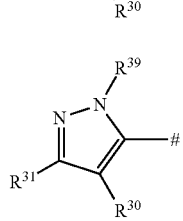 A16
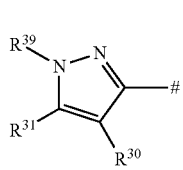 A17
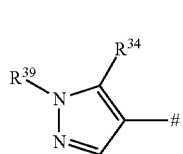 A18
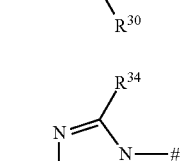 A19
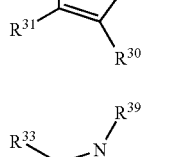 A20
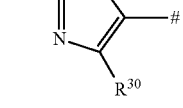

-continued
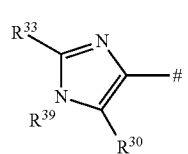 A21
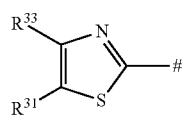 A22
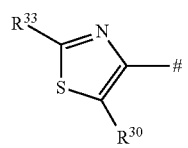 A23
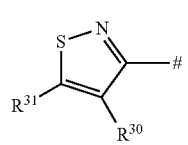 A24
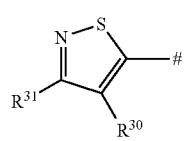 A25
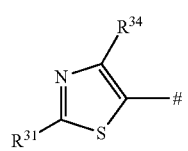 A26
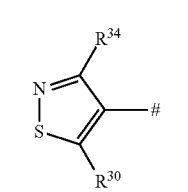 A27
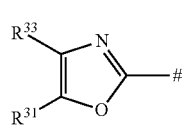 A28
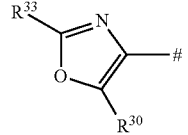 A29
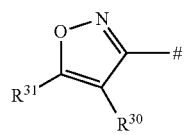 A30
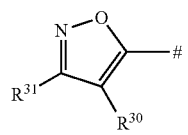 A31
-continued
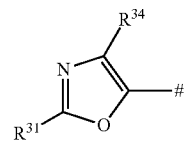 A32
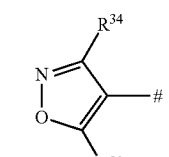 A33
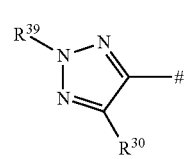 A34
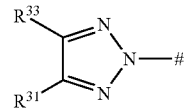 A35
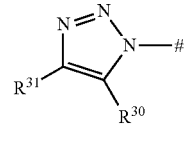 A36
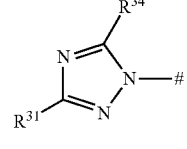 A37
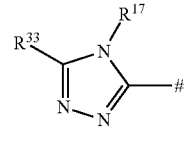 A38
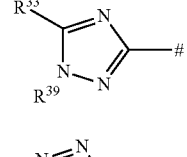 A39
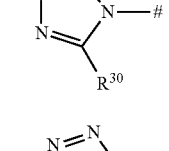 A40
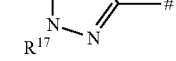 A41
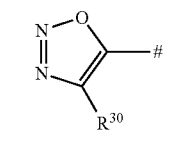 A42

-continued
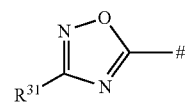 A43
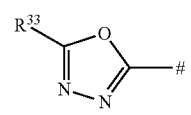 A44
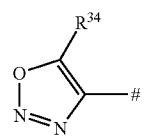 A45
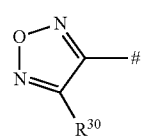 A46
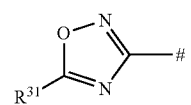 A47
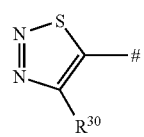 A48
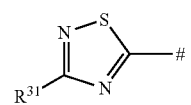 A49
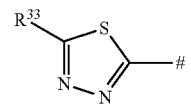 A50
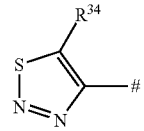 A51
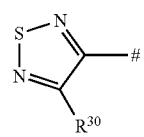 A52
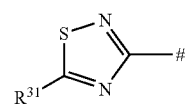 A53
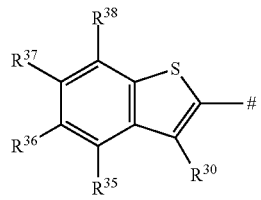 A54
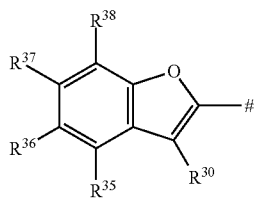 A55
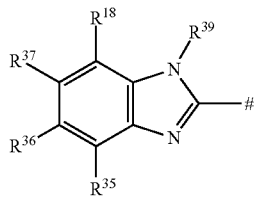 A56
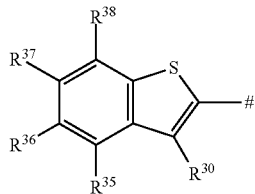 A57
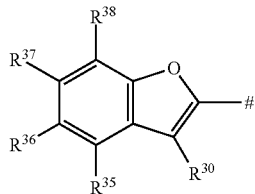 A58
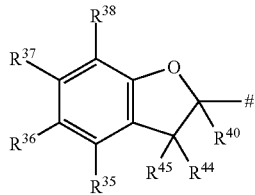 A59
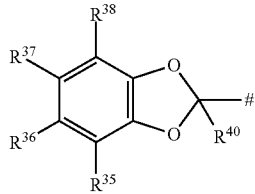 A60
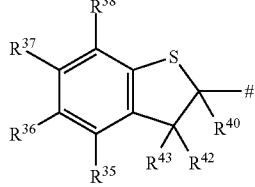 A61

-continued

A62 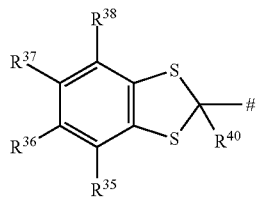

A63 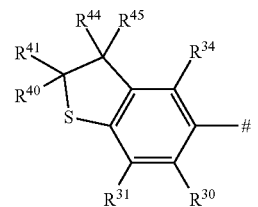

A64 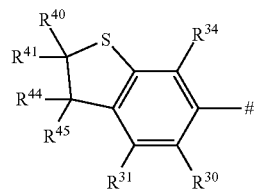

A65 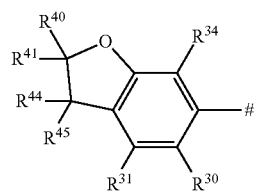

A66 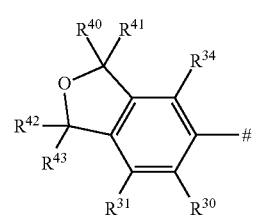

A67 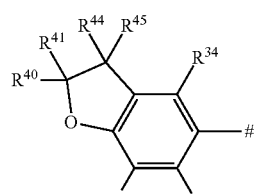

A68 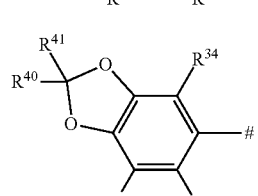

A69 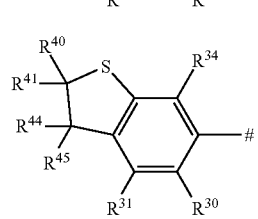

-continued

A70 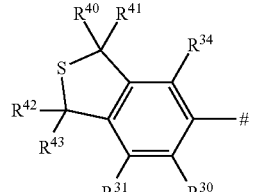

A71 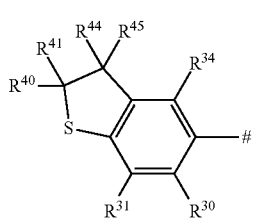

A72 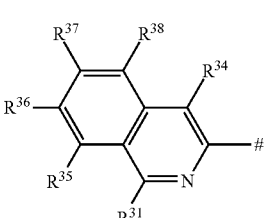

A73 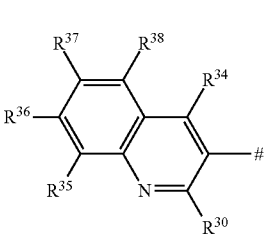

A74 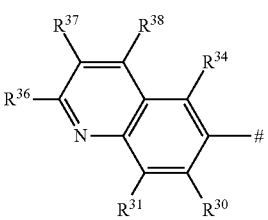

A75 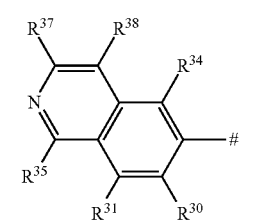

$R^{30}$, $R^{31}$, $R^{32}$, $R^{33}$, $R^{34}$, $R^{35}$, $R^{36}$, $R^{37}$, $R^{38}$, $R^{44}$, $R^{45}$, $R^{46}$, and $R^{47}$ represent a hydrogen atom, a halogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a formyl group, a nitro group, or a cyano group, and $R^{39}$, $R^{40}$, $R^{41}$, $R^{42}$, and $R^{43}$ represent a hydrogen atom, a halogen atom, a C1-C4 alkyl group, a C1-C4 haloalkyl group, a C1-C4 alkoxy group, a C1-C4 haloalkoxy group, a nitro group, or a cyano group.

Examples of the halogen atom include a fluorine atom, a chlorine atom, a bromine atom, or an iodine atom.

Examples of the C1-C3 alkyl group include a methyl group, an ethyl group, a propyl group, or an isopropyl group.

The C1-C6 alkyl group represents a straight or branched alkyl group having 1-6 carbon atoms, and examples thereof include a methyl group, an ethyl group, a propyl group, an isopropyl group, a butyl group, an isobutyl group, a sec-butyl group, a tert-butyl group, a pentyl group, and a hexyl group.

The C1-C6 haloalkyl group represents a group in which at least one hydrogen atom of a straight or branched alkyl group having 1-6 carbon atoms is substituted with a halogen atom, and examples thereof include a fluoromethyl group, a chloromethyl group, a dichloromethyl group, a difluoromethyl group, a trifluoromethyl group, a trichloromethyl group, a tribromomethyl group, a 2,2,2-trifluoroethyl group, a 2,2,2-trichloroethyl group, a pentafluoroethyl group, a chlorofluoromethyl group, a dichlorofluoromethyl group, a chlorodifluoromethyl group, a 2,2-difluoroethyl group, a 2-chloro-2-fluoroethyl group, a 2-chloro-2,2-difluoroethyl group, a 2,2-dichloro-2-fluoroethyl group, a 2-fluoropropyl group, a 3-fluoropropyl group, a 2,2-difluoropropyl group, a 3,3,3-trifluoropropyl group, a 3-(fluoromethyl)-2-fluoroethyl group, a 4-fluorobutyl group, and a 2,2-difluorohexyl group.

Examples of the C3-C6 cycloalkyl group include a cyclopropyl group, a cyclobutyl group, a cyclopentyl group, and a cyclohexyl group.

The C2-C6 alkenyl group represents a straight or branched alkenyl group having 2-6 carbon atoms, and examples thereof include a vinyl group, a 1-propenyl group, an isopropenyl group, a 2-propenyl group, a 1-butenyl group, a 1-methyl-1-propenyl group, a 2-butenyl group, a 1-methyl-2-propenyl group, a 3-butenyl group, a 2-methyl-1-propenyl group, a 2-methyl-2-propenyl group, a 1,3-butadienyl group, a 1-pentenyl group, a 1-ethyl-2-propenyl group, a 2-pentenyl group, a 1-methyl-1-butenyl group, a 3-pentenyl group, a 1-methyl-2-butenyl group, a 4-pentenyl group, a 1-methyl-3-butenyl group, a 3-methyl-1-butenyl group, a 1,2-dimethyl-2-propenyl group, a 1,1-dimethyl-2-propenyl group, a 2-methyl-2-butenyl group, a 3-methyl-2-butenyl group, a 1,2-dimethyl-1-propenyl group, a 2-methyl-3-butenyl group, a 3-methyl-3-butenyl group, a 1,3-pentadienyl group, a 1-vinyl-2-propenyl group, a 1-hexenyl group, and a 5-hexenyl group.

The C1-C6 alkoxy group represents a straight or branched alkoxy group having 1-6 carbon atoms, and examples thereof include a methoxy group, an ethoxy group, a propyloxy group, an isopropyloxy group, a butyloxy group, an isobutyloxy group, a sec-butyloxy group, a tert-butyloxy group, a pentyloxy group, an isoamyloxy group, a neopentyloxy group, a 2-pentyloxy group, a 3-pentyloxy group, a 2-methylbutyloxy group, a hexyloxy group, an isohexyloxy group, a 3-methylpentyloxy group, and a 4-methylpentyloxy group.

The C1-C6 alkylthio group represents a straight or branched alkylthio group having 1-6 carbon atoms, and examples thereof include a methylthio group, an ethylthio group, an n-propylthio group, an isopropylthio group, an n-butylthio group, a sec-butylthio group, a tert-butylthio group, an n-pentylthio group, an isopentylthio group, a neopentylthio group, an n-hexylthio group, an isohexylthio group, and a sec-hexylthio group.

The C2-C6 alkynyl group represents a straight or branched alkynyl group having 2-6 carbon atoms, and examples thereof include an ethynyl group, a propargyl group, a 1-butyn-3-yl group, a 3-methyl-1-butyn-3-yl group, a 2-butynyl group, a 3-butynyl group, a 2-pentynyl group, a 3-pentynyl group, a 4-pentynyl group, a 1-hexynyl group, and a 5-hexynyl group.

The aminocarbonyl group optionally having a C1-C6 alkyl group represents an aminocarbonyl group in which one or two hydrogen atoms on nitrogen are optionally substituted with the same or different C1-C6 alkyl groups, and the total number of carbon atoms of an alkyl group on a nitrogen atom is within a range of 1 to 6. Examples of the aminocarbonyl group optionally having a C1-C6 alkyl group include an aminocarbonyl group, a methylaminocarbonyl group, an ethylaminocarbonyl group, a propylaminocarbonyl group, an isopropylaminocarbonyl group, a butylaminocarbonyl group, a dimethylaminocarbonyl group, a diethylaminocarbonyl group, a dipropylaminocarbonyl group, a diisopropylaminocarbonyl group, a pentylaminocarbonyl group, and a hexylaminocarbonyl group.

The C2-C6 haloalkenyl group represents a group in which at least one hydrogen atom of a straight or branched alkenyl group having 2-6 carbon atoms is substituted with a halogen atom, and examples thereof include a 2-fluorovinyl group, a 2-chlorovinyl group, a 2-bromovinyl group, a 2-iodovinyl group, a 2,2-difluorovinyl group, a 2,2-dichlorovinyl group, a 2,2-dibromovinyl group, a 3,3-difluoro-2-propenyl group, a 3,3-dichloro-2-propenyl group, a 3,3-dibromo-2-propenyl group, a 3-chloro-2-propenyl group, a 3-bromo-2-propenyl group, a 1-chloro-1-propenyl group, a 2-bromo-1-methylvinyl group, a 1-trifluoromethylvinyl group, a 3,3,3-trichloro-1-propenyl group, a 3-bromo-3,3-difluoro-1-propenyl group, a 2,3,3,3-tetrachloro-1-propenyl group, a 1-trifluoromethyl-2,2-difluorovinyl group, a 2-chloro-2-propenyl group, a 3,3-difluoro-2-propenyl group, a 2,3,3-trichloro-2-propenyl group, a 3-chloro-2-butenyl group, a 4,4,4-trifluoro-2-butenyl group, a 3,4,4-trifluoro-3-butenyl group, a 3,4,4-tribromo-3-butenyl group, a 3-bromo-2-methyl-2-propenyl group, a 3,3-difluoro-2-methyl-2-propenyl group, a 3,3,3-trifluoro-2-methyl-1-propenyl group, a 3-chloro-4,4,4-trifluoro-2-butenyl group, a 3,3,3-trifluoro-1-methyl-1-propenyl group, a 3,4,4-trifluoro-1,3-butadienyl group, a 3,4-dibromo-1-pentenyl group, a 4,4-difluoro-3-methyl-3-butenyl group, a 3,3,4,4,5,5,5-heptafluoro-1-pentenyl group, a 5,5-difluoro-4-pentenyl group, a 4,5,5-trifluoro-4-pentenyl group, a 3,4,4,4-tetrafluoro-3-trifluoromethyl-1-butenyl group, a 4,4,4-trifluoro-3-methyl-2-butenyl group, a 3,5,5-trifluoro-2,4-pentadienyl group, a 4,4,5,5,6,6,6-heptafluoro-2-hexenyl group, a 3,4,4,5,5,5-hexafluoro-3-trifluoromethyl-1-pentenyl group, a 4,5,5,5-tetrafluoro-4-trifluoromethyl-2-pentenyl group, and a 5-bromo-4,5,5-trifluoro-4-trifluoromethyl-2-pentenyl group.

The C2-C6 haloalkynyl group represents a group in which at least one hydrogen atom of a straight or branched alkynyl group having 2-6 carbon atoms is substituted with a halogen atom, and examples thereof include a fluoroethynyl group, a 3-chloro-2-propynyl group, a 3-bromo-2-propynyl group, a 3-iodo-2-propynyl group, a 3-chloro-1-propynyl group, a 5-chloro-4-pentynyl group, a 3,3,3-trifluoro-1-propynyl group, a 3-fluoro-2-propynyl group, a perfluoro-2-butynyl group, a perfluoro-2-pentynyl group, a perfluoro-3-pentynyl group, and a perfluoro-1-hexynyl group.

The C3-C6 halocycloalkyl group represents a group in which at least one hydrogen atom of a cycloalkyl group having 3-6 carbon atoms is substituted with a halogen atom, and examples thereof include a 2-fluorocyclopropyl group, a 2,2-difluorocyclopropyl group, a 2-chloro-2-fluorocyclopropyl group, a 2,2-dichlorocyclopropyl group, a 2,2-dibromocyclopropyl group, a 2,2,3,3-tetrafluorocyclobutyl group, a 2-chlorocyclohexyl group, a 4,4-difluorocyclohexyl group, and a 4-chlorocyclohexyl group.

The C1-C6 haloalkoxy group represents a group in which at least one hydrogen atom of a straight or branched alkoxy group having 1-6 carbon atoms is substituted with a halogen atom, and examples thereof include a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2-chloro-2-fluoroethoxy group, a 2-chloro-2,2-difluoroethoxy group, a heptafluoropropoxy group, a heptachloropropoxy group, a heptabromopropoxy group, a heptaiodopropoxy group, a 3,3,3-trifluoropropoxy group, a 3,3,3-trichloropropoxy group, a 3,3,3-tribromopropoxy group, a 3,3,3-triiodopropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, a 3-bromopropoxy group, a 3,3,3-trifluoropropoxy group, a nonafluorobutoxy group, a nonachlorobutoxy group, a nonabromobutoxy group, a nonaiodobutoxy group, a perfluoropentyloxy group, a perchloropentyloxy group, a perbromopentyloxy group, a perfluorohexyloxy group, a perchlorohexyloxy group, a perbromohexyloxy group, and a periodohexyloxy group.

The C1-C6 haloalkylthio group represents a group in which at least one hydrogen atom of a straight or branched alkylthio group having 1-6 carbon atoms is substituted with a halogen atom, and examples thereof include a fluoromethylthio group, a difluoromethylthio group, a trifluoromethylthio group, a trichloromethylthio group, a tribromomethylthio group, a triiodomethylthio group, a chlorofluoromethylthio group, a pentafluoroethylthio group, a pentachloroethylthio group, a pentabromoethylthio group, a pentaiodoethylthio group, a 2,2,2-trichloroethylthio group, a 2,2,2-trifluoroethylthio group, a 2,2,2-tribromoethylthio group, a 2,2,2-triiodoethylthio group, a 2,2-difluoroethylthio group, a heptafluoropropylthio group, a heptachloropropylthio group, a heptabromopropylthio group, a heptaiodopropylthio group, a 3,3,3-trifluoropropylthio group, a 3,3,3-trichloropropylthio group, a 3,3,3-tribromopropylthio group, a 3,3,3-triiodopropylthio group, a 2,2-difluoropropylthio group, a 2,3,3-trifluoropropylthio group, a nonafluorobutylthio group, a nonachlorobutylthio group, a nonabromobutylthio group, a nonaiodobutylthio group, a perfluoropentylthio group, a perchloropentylthio group, a perbromopentylthio group, a perfluorohexylthio group, a perchlorohexylthio group, a perbromohexylthio group, and a periodohexylthio group.

Examples of the C3-C6 cycloalkyloxy group include a cyclopropyloxy group, a cyclobutyloxy group, a cyclopentyloxy group, and a cyclohexyloxy group.

The C3-C6 halocycloalkyloxy group represents a group in which at least one hydrogen atom of a cycloalkyloxy group having 3-6 carbon atoms is substituted with a halogen atom, and examples thereof include a 2-fluorocyclopropyloxy group, a 2,2-difluorocyclopropyloxy group, a 2-chloro-2-fluorocyclopropyloxy group, a 2,2-dichlorocyclopropyloxy group, a 2,2-dibromocyclopropyloxy group, a 2,2,3,3-tetrafluorocyclobutyloxy group, a 2-chlorocyclohexyloxy group, a 4,4-difluorocyclohexyloxy group, and a 4-chlorocyclohexyloxy group.

Examples of the C3-C6 cycloalkylthio group include a cyclopropylthio group, a cyclobutylthio group, a cyclopentylthio group, and a cyclohexylthio group.

The C3-C6 alkenyloxy group represents a straight or branched alkenyloxy group having 3-6 carbon atoms, and examples thereof include a 2-propenyloxy group, a 2-butenyloxy group, a 1-methyl-2-propenyloxy group, a 3-butenyloxy group, a 2-methyl-2-propenyloxy group, a 2-pentenyloxy group, a 3-pentenyloxy group, a 4-pentenyloxy group, a 1-methyl-3-butenyloxy group, a 1,2-dimethyl-2-propenyloxy group, a 1,1-dimethyl-2-propenyloxy group, a 2-methyl-2-butenyloxy group, a 3-methyl-2-butenyloxy group, a 2-methyl-3-butenyloxy group, a 3-methyl-3-butenyloxy group, a 1-vinyl-2-propenyloxy group, and a 5-hexenyloxy group.

The C3-C6 alkynyloxy group represents a straight or branched alkynyloxy group having 3-6 carbon atoms, and examples thereof include a propargyloxy group, a 1-butyn-3-yloxy group, a 3-methyl-1-butyn-3-yloxy group, a 2-butynyloxy group, a 3-butynyloxy group, a 2-pentynyloxy group, a 3-pentynyloxy group, a 4-pentynyloxy group, and a 5-hexynyloxy group.

The C3-C6 haloalkenyloxy group represents a group in which at least one hydrogen atom of a straight or branched alkenyloxy group having 3-6 carbon atoms is substituted with a halogen atom, and examples thereof include a 3-chloro-2-propenyloxy group, a 3-bromo-2-propenyloxy group, a 3-bromo-3,3-difluoro-1-propenyloxy group, a 2,3,3,3-tetrachloro-1-propenyloxy group, a 2-chloro-2-propenyloxy group, a 3,3-difluoro-2-propenyloxy group, a 2,3,3-trichloro-2-propenyloxy group, a 3,3-dichloro-2-propenyloxy group, a 3,3-dibromo-2-propenyloxy group, a 3-fluoro-3-chloro-2-propenyloxy group, a 4-bromo-3-chloro-3,4,4-trifluoro-1-butenyloxy group, a 1-bromomethyl-2-propenyloxy group, a 3-chloro-2-butenyloxy group, a 4,4,4-trifluoro-2-butenyloxy group, a 4-bromo-4,4-difluoro-2-butenyloxy group, a 3-bromo-3-butenyloxy group, a 3,4,4-trifluoro-3-butenyloxy group, a 3,4,4-tribromo-3-butenyloxy group, a 3-bromo-2-methyl-2-propenyloxy group, a 3,3-difluoro-2-methyl-2-propenyloxy group, a 3-chloro-4,4,4-trifluoro-2-butenyloxy group, a 4,4-difluoro-3-methyl-3-butenyloxy group, a 5,5-difluoro-4-pentenyloxy group, a 4,5,5-trifluoro-4-pentenyloxy group, a 4,4,4-trifluoro-3-methyl-2-butenyloxy group, a 3,5,5-trifluoro-2,4-pentadienyloxy group, a 4,4,5,5,6,6-heptafluoro-2-hexenyloxy group, a 4,5,5,5-tetrafluoro-4-trifluoromethyl-2-pentenyloxy group, and a 5-bromo-4,5,5-trifluoro-4-trifluoromethyl-2-pentenyloxy group.

The C3-C6 haloalkynyloxy group represents a group in which at least one hydrogen atom of a straight or branched alkynyloxy group having 3-6 carbon atoms is substituted with a halogen atom, and examples thereof include a 3-chloro-2-propynyloxy group, a 3-bromo-2-propynyloxy group, a 3-iodo-2-propynyloxy group, a 5-chloro-4-pentynyloxy group, a 3-fluoro-2-propynyloxy group, a perfluoro-2-butynyloxy group, a perfluoro-3-butynyloxy group, a perfluoro-2-pentynyloxy group, a perfluoro-3-pentynyloxy group, a perfluoro-4-pentynyloxy group, and a perfluoro-5-hexynyloxy group.

The C3-C6 alkenylthio group represents a straight or branched alkenylthio group having 3-6 carbon atoms, and examples thereof include a 2-propenylthio group, a 2-butenylthio group, a 1-methyl-2-propenylthio group, a 3-butenylthio group, a 2-methyl-2-propenylthio group, a 2-pentenylthio group, a 3-pentenylthio group, a 4-pentenylthio group, a 1-methyl-3-butenylthio group, a 1,2-dimethyl-2-propenylthio group, a 1,1-dimethyl-2-propenylthio group, a 2-methyl-2-butenylthio group, a 3-methyl-2-butenylthio group, a 2-methyl-3-butenylthio group, a 3-methyl-3-butenylthio group, a 1-vinyl-2-propenylthio group, and a 5-hexenylthio group.

The C3-C6 alkynylthio group represents a straight or branched alkynylthio group having 3-6 carbon atoms, and examples thereof include a propargylthio group, a 1-butyn-3-ylthio group, a 3-methyl-1-butyn-3-ylthio group, a 2-butynylthio group, a 3-butynylthio group, a 2-pentynylthio group, a 3-pentynylthio group, a 4-pentynylthio group, and a 5-hexynylthio group.

The C3-C6 haloalkenylthio group represents a group in which at least one hydrogen atom of a straight or branched alkenylthio group having 3-6 carbon atoms is substituted with a halogen atom, and examples thereof include a 3-chloro-2-propenylthio group, a 3-bromo-2-propenylthio group, a 3-bromo-3,3-difluoro-1-propenylthio group, a 2,3,3,3-tetrachloro-1-propenylthio group, a 2-chloro-2-propenylthio group, a 3,3-difluoro-2-propenylthio group, a 2,3,3-trichloro-2-propenylthio group, a 3,3-dichloro-2-propenylthio group, a 3,3-dibromo-2-propenylthio group, a 3-fluoro-3-chloro-2-propenylthio group, a 4-bromo-3-chloro-3,4,4-trifluoro-1-butenylthio group, a 1-bromomethyl-2-propenylthio group, a 3-chloro-2-butenylthio group, a 4,4,4-trifluoro-2-butenylthio group, a 4-bromo-4,4-difluoro-2-butenylthio group, a 3-bromo-3-butenylthio group, a 3,4,4-trifluoro-3-butenylthio group, a 3,4,4-tribromo-3-butenylthio group, a 3-bromo-2-methyl-2-propenylthio group, a 3,3-difluoro-2-methyl-2-propenylthio group, a 3-chloro-4,4,4-trifluoro-2-butenylthio group, a 4,4-difluoro-3-methyl-3-butenylthio group, a 5,5-difluoro-4-pentenylthio group, a 4,5,5-trifluoro-4-pentenylthio group, a 4,4,4-trifluoro-3-methyl-2-butenylthio group, a 3,5,5-trifluoro-2,4-pentadienylthio group, a 4,4,5,5,6,6,6-heptafluoro-2-hexenylthio group, a 4,5,5,5-tetrafluoro-4-trifluoromethyl-2-pentenylthio group, and a 5-bromo-4,5,5-trifluoro-4-trifluoromethyl-2-pentenylthio group.

The C3-C6 haloalkynylthio group represents a group in which at least one hydrogen atom of a straight or branched alkynylthio group having 3-6 carbon atoms is substituted with a halogen atom, and examples thereof include a 3-chloro-2-propynylthio group, a 3-bromo-2-propynylthio group, a 3-iodo-2-propynylthio group, a 5-chloro-4-pentynylthio group, a 3-fluoro-2-propynylthio group, a perfluoro-2-butynylthio group, a perfluoro-3-butynylthio group, a perfluoro-2-pentynylthio group, a perfluoro-3-pentynylthio group, a perfluoro-4-pentynylthio group, and a perfluoro-5-hexynylthio group.

The C2-C6 alkylcarbonyl group represents a group in which the total number of carbon atoms of the alkyl moiety and the carbonyl moiety is within a range of 2 to 6, and the C2-C6 alkylcarbonyl group may be either straight or branched, and examples thereof include an acetyl group, a propionyl group, a butanoyl group, a pentanoyl group, and a hexanoyl group.

The C2-C6 haloalkylcarbonyl group represents a group in which at least one hydrogen atom of a straight or branched alkylcarbonyl group having 2-6 carbon atoms is substituted with a halogen atom, and examples thereof include a trichloroacetyl group, a fluoroacetyl group, a difluoroacetyl group, a trifluoroacetyl group, a pentafluoropropionyl group, a pentachloropropionyl group, a pentabromopropionyl group, a pentaiodopropionyl group, a 3,3,3-trichloropropionyl group, a 3,3,3-trifluoropropionyl group, a 3,3,3-tribromopropionyl group, a 3,3,3-triiodopropionyl group, a heptafluorobutanoyl group, a heptachlorobutanoyl group, a heptabromobutanoyl group, a heptaiodobutanoyl group, a 4,4,4-trifluorobutanoyl group, a 4,4,4-trichlorobutanoyl group, a 4,4,4-tribromobutanoyl group, a 4,4,4-triiodobutanoyl group, a nonafluoropentanoyl group, a nonachloropentanoyl group, a nonabromopentanoyl group, a nonaiodopentanoyl group, and a perfluorohexanoyl group.

The C2-C6 alkylcarbonyloxy group represents a group in which the total number of carbon atoms of the alkyl moiety and the carbonyloxy moiety is within a range of 2 to 6, and the C2-C6 alkylcarbonyloxy group may be either straight or branched, and examples thereof include an acetoxy group, a propionyloxy group, a butanoyloxy group, a pentanoyloxy group, and a hexanoyloxy group.

The C2-C6 alkylcarbonylthio group represents a group in which the total number of carbon atoms of the alkyl moiety and the carbonylthio moiety is within a range of 2 to 6, and the C2-C6 alkylcarbonylthio group may be either straight or branched, and examples thereof include an acetylthio group, propionylthio group, a butanoylthio group, a pentanoylthio group, and a hexanoylthio group.

The C2-C6 alkoxycarbonyl group represents a group in which the total number of carbon atoms of the alkoxy moiety and the carbonyl moiety is within a range of 2 to 6, and the C2-C6 alkoxycarbonyl group may be either straight or branched, and examples thereof include a methoxycarbonyl group, an ethoxycarbonyl group, a propyloxycarbonyl group, an isopropyloxycarbonyl group, a butyloxycarbonyl group, an isobutyloxycarbonyl group, a sec-butyloxycarbonyl group, a tert-butyloxycarbonyl group, a pentyloxycarbonyl group, an isoamyloxycarbonyl group, a neopentyloxycarbonyl group, a 2-pentyloxycarbonyl group, a 3-pentyloxycarbonyl group, and a 2-methylbutyloxycarbonyl group.

The amino group optionally having a C1-C6 alkyl group represents a group in which one or two hydrogen atoms on nitrogen are substituted with the same or different C1-C6 alkyl group, and examples thereof include an amino group, an N-methylamino group, an N-ethylamino group, an N-propylamino group, an N-isopropylamino group, an N-butylamino group, an N,N-dimethylamino group, an N,N-diethylamino group, an N,N-dipropylamino group, an N-ethyl-N-methylamino group, and an N-propyl-N-methylamino group.

Examples of the C3-C9 trialkylsilyl group include a trimethylsilyl group, a tert-butyldimethylsilyl group, a triethylsilyl group, an isopropyldimethylsilyl group, and a triisopropylsilyl group.

The C5-C14 trialkylsilylethynyl group represents an ethynyl group bound to a trialkylsilyl group in which three hydrogen atoms on a silyl group are substituted with the same or different alkyl groups, and the number of carbon atoms as a trialkylsilylethynyl group is within a range of 5 to 14. The C5-C14 trialkylsilylethynyl group is straight or branched, and examples thereof include a trimethylsilylethynyl group, a tert-butyldimethylsilylethynyl group, a triethylsilylethynyl group, an isopropyldimethylsilylethynyl group, a triisopropylsilylethynyl group, a tri(tert-butyl)silylethynyl group, and a tri(n-butyl)silylethynyl group.

The C1-C6 alkylsulfonyl group may be either straight or branched, and examples thereof include a methylsulfonyl group, an ethylsulfonyl group, a propylsulfonyl group, an isopropylsulfonyl group, a butylsulfonyl group, an isobutylsulfonyl group, a sec-butylsulfonyl group, a pentylsulfonyl group, an isoamylsulfonyl group, a neopentylsulfonyl group, a 2-pentylsulfonyl group, a 3-pentylsulfonyl group, a 2-methylbutylsulfonyl group, a hexylsulfonyl group, an isohexylsulfonyl group, a 3-methylpentylsulfonyl group, and a 4-methylpentylsulfonyl group.

The C1-C6 haloalkylsulfonyl group represents a group in which at least one hydrogen atom of a straight or branched alkylsulfonyl group having 1-6 carbon atoms is substituted with a halogen atom, and examples thereof include a trifluoromethylsulfonyl group, a trichloromethylsulfonyl group, a tribromomethylsulfonyl group, a triiodomethylsulfonyl group, a pentafluoroethylsulfonyl group, a pentachloroethylsulfonyl group, a pentabromoethylsulfonyl group, a pentaiodoethylsulfonyl group, a 2,2,2-trichloroethylsulfonyl group, a 2,2,2-trifluoroethylsulfonyl group, a 2,2,2-tribromoethylsulfonyl group, a 2,2,2-triiodoethylsulfonyl group, a heptafluoropropylsulfonyl group, a heptachloropropylsulfonyl group, a heptabromopropylsulfonyl group, a heptaiodopropylsulfonyl group, a 3,3,3-trifluoropropylsulfonyl group, a 3,3,3-trichloropropylsulfonyl group, a 3,3,3-tribromopropylsulfonyl group, a 3,3,3-triiodopropylsulfonyl group, a nonafluorobutylsulfonyl group, a nonachlorobutylsulfonyl group, a nonabromobutylsulfonyl group, a nonaiodobutylsulfonyl group, a perfluoropentylsulfonyl group, a perchloropentylsulfonyl group, a perbromopentylsulfonyl group, a perfluorohexylsulfonyl group, a perchlorohexylsulfonyl group, a perbromohexylsulfonyl group, and a periodohexylsulfonyl group.

The C1-C6 alkylsulfinyl group may be either straight or branched, and examples thereof include a methylsulfinyl group, an ethylsulfinyl group, a propylsulfinyl group, an isopropylsulfinyl group, a butylsulfinyl group, an isobutylsulfinyl group, a sec-butylsulfinyl group, a pentylsulfinyl group, an isoamylsulfinyl group, a neopentylsulfinyl group, a 2-pentylsulfinyl group, a 3-pentylsulfinyl group, a 2-methylbutylsulfinyl group, a hexylsulfinyl group, an isohexylsulfinyl group, a 3-methylpentylsulfinyl group, and a 4-methylpentylsulfinyl group.

The C1-C6 haloalkylsulfinyl group represents a group in which at least one hydrogen atom of a straight or branched alkylsulfinyl group having 1-6 carbon atoms is substituted with a halogen atom, and examples thereof include a trifluoromethylsulfinyl group, a trichloromethylsulfinyl group, a tribromomethylsulfinyl group, a triiodomethylsulfinyl group, a pentafluoroethylsulfinyl group, a pentachloroethylsulfinyl group, a pentabromoethylsulfinyl group, a pentaiodoethylsulfinyl group, a 2,2,2-trichloroethylsulfinyl group, a 2,2,2-trifluoroethylsulfinyl group, a 2,2,2-tribromoethylsulfinyl group, a 2,2,2-triiodoethylsulfinyl group, a heptafluoropropylsulfinyl group, a heptachloropropylsulfinyl group, a heptabromopropylsulfinyl group, a heptaiodopropylsulfinyl group, a 3,3,3-trifluoropropylsulfinyl group, a 3,3,3-trichloropropylsulfinyl group, a 3,3,3-tribromopropylsulfinyl group, a 3,3,3-triiodopropylsulfinyl group, a nonafluorobutylsulfinyl group, a nonachlorobutylsulfinyl group, a nonabromobutylsulfinyl group, a nonaiodobutylsulfinyl group, a perfluoropentylsulfinyl group, a perchloropentylsulfinyl group, a perbromopentylsulfinyl group, a perfluorohexylsulfinyl group, a perchlorohexylsulfinyl group, a perbromohexylsulfinyl group, and a periodohexylsulfinyl group.

The C2-C5 alkoxyalkyl group represents a group in which the total number of carbon atoms of the alkoxy moiety and the alkyl moiety is within a range of 2 to 5, and may be either straight or branched, and examples thereof include a methoxymethyl group, an ethoxymethyl group, a propyloxymethyl group, an isopropyloxymethyl group, a butyloxymethyl group, an isobutyloxymethyl group, a sec-butyloxymethyl group, a 1-methoxyethyl group, a 2-methoxyethyl group, a 2-propyloxyethyl group, a 2-isopropyloxyethyl group, a 3-methoxypropyl group, a 3-ethoxypropyl group, a 3-methoxybutyl group, and a 4-methoxybutyl group.

The C2-C5 alkylthioalkyl group may be either straight or branched, and examples thereof include a methylthiomethyl group, an ethylthiomethyl group, a propylthiomethyl group, an isopropylthiomethyl group, a butylthiomethyl group, an isobutylthiomethyl group, a sec-butylthiomethyl group, a 1-methylthioethyl group, a 2-methylthioethyl group, a 2-propylthioethyl group, a 2-isopropylthioethyl group, a 3-methylthiopropyl group, a 3-ethylthiopropyl group, a 3-methylthiobutyl group, and a 4-methylthiobutyl group.

Examples of the C1-C3 haloalkyl group include a chloromethyl group, a dichloromethyl group, a fluoromethyl group, a difluoromethyl group, a chlorofluoromethyl group, a dichlorofluoromethyl group, a chlorodifluoromethyl group, a trifluoromethyl group, a trichloromethyl group, a tribromomethyl group, a 2-fluoroethyl group, a 2,2-difluoroethyl group, a 2,2,2-trifluoroethyl group, a 2-chloroethyl group, a 2,2-dichloroethyl group, a 2,2,2-trichloroethyl group, a pentafluoroethyl group, a pentachloroethyl group, a 2-chloro-2-fluoroethyl group, a 2-chloro-2,2-difluoroethyl group, a 2-fluoropropyl group, a 3-fluoropropyl group, a 2,2-difluoropropyl group, a 2,3-difluoropropyl group, a 3,3,3-trifluoropropyl group, a heptafluoropropyl group, and a 1-(fluoromethyl)-2-fluoroethyl group.

Examples of the C2-C3 alkenyl group include a vinyl group, a 1-propenyl group, and a 2-propenyl group.

The C2-C3 haloalkenyl group represents a group in which at least one hydrogen atom of a straight or branched alkenyl group having 2-3 carbon atoms is substituted with a halogen atom, and examples thereof include a 2-fluorovinyl group, a 2-chlorovinyl group, a 2-bromovinyl group, a 2-iodovinyl group, a 2,2-difluorovinyl group, a 2,2-dichlorovinyl group, a 2,2-dibromovinyl group, a 3,3-difluoro-2-propenyl group, a 3,3-dichloro-2-propenyl group, a 3,3-dibromo-2-propenyl group, a 3-chloro-2-propenyl group, a 3-bromo-2-propenyl group, a 1-chloro-1-propenyl, a 2-bromo-1-methylvinyl group, a 1-trifluoromethylvinyl group, a 3,3,3-trichloro-1-propenyl group, a 3-bromo-3,3-difluoro-1-propenyl group, a 2,3,3,3-tetrachloro-1-propenyl group, a 1-trifluoromethyl-2,2-difluorovinyl group, a 2-chloro-2-propenyl group, a 3,3-difluoro-2-propenyl group, and a 2,3,3-trichloro-2-propenyl group.

Examples of the C1-C3 alkoxy group include a methoxy group, an ethoxy group, a propyloxy group, and an isopropyloxy group.

Examples of the C6-C16 arylsulfonyl group include a phenylsulfonyl group, a 1-naphthylsulfonyl group, a 2-naphthylsulfonyl group, a 1-acenaphthylsulfonyl group, a 1-phenanthrylsulfonyl group, a 9-anthrylsulfonyl group, and a 1-pyrenylsulfonyl group.

The C6-C16 haloarylsulfonyl group represents a group in which at least one hydrogen atom of an arylsulfonyl group having 6-16 carbon atoms is substituted with a halogen atom, and examples thereof include a 2-fluorophenylsulfonyl group, a 3-fluorophenylsulfonyl group, a 4-fluorophenylsulfonyl group, a 2-chlorophenylsulfonyl group, a 3-chlorophenylsulfonyl group, a 4-chlorophenylsulfonyl group, a 2-bromophenylsulfonyl group, a 3-bromophenylsulfonyl group, a 4-bromophenylsulfonyl group, a 4-iodophenylsulfonyl group, a 2,4-difluorophenylsulfonyl group, a 2,4-dichlorophenylsulfonyl group, a 2,6-dichlorophenylsulfonyl group, a 2,4,6-trifluorophenylsulfonyl group, a 3,4,5-trifluorophenylsulfonyl group, a 2,4,6-trichlorophenylsulfonyl group, a 3,4,5-trichlorophenylsulfonyl group, a pentafluorophenylsulfonyl group, a 3-bromo-4-fluorophenylsulfonyl group, a 4-bromo-3-fluorophenylsulfonyl group, a 4-bromo-2-fluorophenylsulfonyl group, a 2-bromo-6-fluorophenylsulfonyl group, a 2-chloro-4-fluorophenylsulfonyl group, a 2-chloro-6-fluorophenylsulfonyl group, a 2-fluoro-1-naphthylsulfonyl group, a 3-chloro-1-naphthylsulfonyl group, a 4-bromo-1-naphthylsulfonyl group, a 5-fluoro-2-naphthylsulfonyl group, a 1-chloro-2-naphthylsulfonyl group, a 3-bromo-2-naphthylsulfonyl group, a 3-fluoro-1-acenaphthylsulfonyl group, a 9-fluoro-1-phenanthrylsulfonyl group, a 10-fluoro-9-anthrylsulfonyl group, and a 6-fluoro-1-pyrenylsulfonyl group.

The aminosulfonyl group optionally having a C1-C6 alkyl group represents an aminosulfonyl group in which one or two hydrogen atoms on nitrogen are optionally substituted with the same or different C1-C6 alkyl groups, and the total number of carbon atoms on a nitrogen atom is within a range of 1 to 6. Examples of the aminosulfonyl group optionally having a C1-C6 alkyl group include an aminosulfonyl group, an N-methylaminosulfonyl group, an N-ethylaminosulfonyl group, an N-propylaminosulfonyl group, an N-isopropylaminosulfonyl group, an N-butylaminosulfonyl group, an N-pentylaminosulfonyl group, an N-hexylaminosulfonyl group, an N,N-dimethylaminosulfonyl group, an N,N-diethylaminosulfonyl group, an N,N-dipropylaminosulfonyl group, an N,N-diisopropylaminosulfonyl group, an N-ethyl-N-methylaminosulfonyl group, an N-propyl-N-methylaminosulfonyl group, an N-butyl-N-methylaminosulfonyl group, and an N-pentyl-N-methylaminosulfonyl group.

The C1-C4 alkyl group may be either straight or branched, and examples thereof include a methyl group, an ethyl group, a propyl group, an isopropyl group, a butyl group, an isobutyl group, a sec-butyl group, or a tert-butyl group.

The C1-C4 haloalkyl group represents a group in which at least one hydrogen atom of a straight or branched alkyl group having 1-4 carbon atoms is substituted with a halogen atom, and examples thereof include a fluoromethyl group, a chloromethyl group, a dichloromethyl group, a difluoromethyl group, a trifluoromethyl group, a trichloromethyl group, a tribromomethyl group, a 2,2,2-trifluoroethyl group, a 2,2,2-trichloroethyl group, a pentafluoroethyl group, a chlorofluoromethyl group, a dichlorofluoromethyl group, a chlorodifluoromethyl group, a 2,2-difluoroethyl group, a 2-chloro-2-fluoroethyl group, a 2-chloro-2,2-difluoroethyl group, a 2,2-dichloro-2-fluoroethyl group, a 2-fluoropropyl group, a 3-fluoropropyl group, a 2,2-difluoropropyl group, a 3,3,3-trifluoropropyl group, and a 4-fluorobutyl group.

The C1-C4 alkoxy group may be either straight or branched, and examples thereof include a methoxy group, an ethoxy group, a propyloxy group, an isopropyloxy group, a butyloxy group, an isobutyloxy group, a sec-butyloxy group, and a tert-butyloxy group.

The C1-C4 haloalkoxy group represents a group in which at least one hydrogen atom of a straight or branched alkoxy group having 1-4 carbon atoms is substituted with a halogen atom, and examples thereof include a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2,2,2-trifluoroethoxy group, a 2-chloro-2-fluoroethoxy group, a 2-chloro-2,2-difluoroethoxy group, a heptafluoropropoxy group, a heptachloropropoxy group, a heptabromopropoxy group, a heptaiodopropoxy group, a 3,3,3-trifluoropropoxy group, a 3,3,3-trichloropropoxy group, a 3,3,3-tribromopropoxy group, a 3,3,3-triiodopropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, a 3-bromopropoxy group, a 2,3,3-trifluoropropoxy group, a nonafluorobutoxy group, a nonachlorobutoxy group, a nonabromobutoxy group, and a nonaiodobutoxy group.

Examples of the C1-C4 alkylthio group include a methylthio group, an ethylthio group, an n-propylthio group, an isopropylthio group, an n-butylthio group, an isobutylthio group, and a tert-butylthio group.

The C1-C4 haloalkylthio group represents a group in which at least one hydrogen atom of a straight or branched alkylthio group having 1-4 carbon atoms is substituted with a halogen atom, and examples thereof include a fluoromethylthio group, a difluoromethylthio group, a trifluoromethylthio group, a trichloromethylthio group, a tribromomethylthio group, a triiodomethylthio group, a chlorofluoromethylthio group, a pentafluoroethylthio group, a pentachloroethylthio group, a pentabromoethylthio group, a pentaiodoethylthio group, a 2,2,2-trichloroethylthio group, a 2,2,2-trifluoroethylthio group, a 2,2,2-tribromoethylthio group, a 2,2,2-triiodoethylthio group, and a 2,2-difluoroethylthio group.

The C1-C3 alkyl group optionally having one or more halogen atoms represents a straight or branched alkyl group having 1-3 carbon atoms, which optionally has one or more halogen atoms, and examples thereof include a methyl group, an ethyl group, a propyl group, an isopropyl group, a fluoromethyl group, a chloromethyl group, a dichloromethyl group, a difluoromethyl group, a trifluoromethyl group, a trichloromethyl group, a tribromomethyl group, a 2,2,2-trifluoroethyl group, a 2,2,2-trichloroethyl group, a pentafluoroethyl group, a chlorofluoromethyl group, a dichlorofluoromethyl group, a chlorodifluoromethyl group, a 2,2-difluoroethyl group, a 2-chloro-2-fluoroethyl group, a 2-chloro-2,2-difluoroethyl group, a 2,2-dichloro-2-fluoroethyl group, a 2-fluoropropyl group, a 3-fluoropropyl group, a 2,2-difluoropropyl group, a 3,3,3-trifluoropropyl group, and a 3-(fluoromethyl)-2-fluoroethyl group.

The C3-C4 cycloalkyl group also includes a cycloalkyl group having an alkyl group, and examples thereof include a cyclopropyl group, a cyclobutyl group, and a 2-methylcyclopropyl group.

The C3-C4 cycloalkyl group optionally having one or more halogen atoms also includes a cycloalkyl group having an alkyl group, which optionally has one or more halogen atoms, and examples thereof include a cyclopropyl group, a cyclobutyl group, a 2-methylcyclopropyl group, a 2-fluorocyclopropyl group, a 2,2-difluorocyclopropyl group, a 2-chlorocyclopropyl group, a 2,2-dichlorocyclopropyl group, and a 2,2-dibromocyclopropyl group.

The C1-C3 alkoxy group optionally having one or more halogen atoms represents a straight or branched alkoxy group having 1-3 carbon atoms, which optionally has one or more halogen atoms, and examples thereof include a methoxy group, an ethoxy group, a propyloxy group, an isopropyloxy group, a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2,2,2-trifluoroethoxy group, a 2-chloro-2-fluoroethoxy group, a 2-chloro-2,2-difluoroethoxy group, a heptafluoropropoxy group, a heptachloropropoxy group, a heptabromopropoxy group, a heptaiodopropoxy group, a 3,3,3-trifluoropropoxy group, a 3,3,3-trichloropropoxy group, a 3,3,3-tribromopropoxy group, a 3,3,3-triiodopropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, and a 3-bromopropoxy group.

Examples of the C1-C3 alkylthio group include a methylthio group, an ethylthio group, an n-propylthio group, and an isopropylthio group.

The C1-C3 alkylthio group optionally having one or more halogen atoms represents a straight or branched alkylthio group having 1-3 carbon atoms, which optionally has one or more halogen atoms, and examples thereof include a methylthio group, an ethylthio group, a propylthio group, an isopropylthio group, a trifluoromethylthio group, a trichloromethylthio group, a chloromethylthio group, a dichloromethylthio group, a fluoromethylthio group, a difluoromethylthio group, a chlorofluoromethylthio group, a dichlorofluoromethylthio group, a chlorodifluoromethylthio group, a pentafluoroethylthio group, a pentachloroethylthio group, a 2,2,2-trichloroethylthio group, a 2,2,2-trifluoroethylthio group, a 2,2,2-tribromoethylthio group, a 2,2,2-triiodoethylthio group, a 2-fluoroethylthio group, a 2-chloroethylthio group, a 2,2-difluoroethylthio group, a 2,2,2-trifluoroethylthio group, a 2-chloro-2-fluoroethylthio group, a 2-chloro-2,2-difluoroethylthio group, a heptafluoropropylthio group, a heptachloropropylthio group, a heptabromopropylthio group, a heptaiodopropylthio group, a 3,3,3-trifluoropropylthio group, a 3,3,3-trichloropropylthio group, a 3,3,3-tribromopropylthio group, a 3,3,3-triiodopropylthio group, a 2-fluoropropylthio group, a 3-fluoropropylthio group, a 2,2-difluoropropylthio group, a 2,3-difluoropropylthio group, a 2-chloropropylthio group, a 3-chloropropylthio group, a 2,3-dichloropropylthio group, a 2-bromopropylthio group, and a 3-bromopropylthio group.

The pyrazolyl group optionally having one or more atoms or groups selected from Group $P^1$ represents a group in which hydrogen atoms of a pyrazolyl group are optionally substituted with one or more atoms or groups selected from Group $P^1$ and, when the number of atoms or groups selected from Group $P^1$ is 2 or more, those atoms or groups may be the same or different to each other. Examples of the pyrazolyl group optionally having one or more atoms or groups selected from Group $P^1$ include a 1-(pyridin-2-yl)-1H-pyrazol-3-yl, a 1-(pyridin-3-yl)-1H-pyrazol-3-yl, a 1-(pyridin-4-yl)-1H-pyrazol-3-yl, a 1-(6-chloro-2-methoxypyridin-3-yl)-1H-pyrazol-3-yl, a 1-(2,6-dimethoxypyridin-3-yl)-1H-pyrazol-3-yl, a 1-(5-chloro-2-methoxypyridin-3-yl)-1H-pyrazol-3-yl, a 1-(2-methoxyquinolin-3-yl)-1H-pyrazol-3-yl, a 1-(6-methyl-2-methoxypyridin-3-yl)-1H-pyrazol-3-yl, a 1-(3,4-methylenedioxyphenyl)-1H-pyrazol-3-yl, a 1-(2-methoxypyridin-3-yl)-1H-pyrazol-3-yl, a 1-(6-chloropyridin-3-yl)-1H-pyrazol-3-yl, a 1-(6-bromo-2-methoxypyridin-3-yl)-1H-pyrazol-3-yl, a 1-(6-cyano-2-methoxypyridin-3-yl)-1H-pyrazol-3-yl, and a 1-(5-trifluoromethyl-pyridin-2-yl)-1H-pyrazol-3-yl.

The pyridyl group optionally having one or more atoms or groups selected from Group $P^2$ represents a group in which hydrogen atoms of a pyridyl group are optionally substituted with one or more atoms or groups selected from Group $P^2$ and, when the number of atoms or groups selected from Group $P^2$ is 2 or more, those atoms or groups may be the same or different to each other. Examples of the pyridyl group optionally having one or more atoms or groups selected from Group $P^2$ include a pyridin-2-yl, a pyridin-3-yl, a pyridin-4-yl, a 6-chloro-2-methoxypyridin-3-yl, a 2,6-dimethoxypyridin-3-yl, a 5-chloro-2-methoxypyridin-3-yl, a 6-methyl-2-methoxypyridin-3-yl, a 2-methoxypyridin-3-yl, a 6-chloropyridin-3-yl, a 6-bromo-2-methoxypyridin-3-yl, a 6-cyano-2-methoxypyridin-3-yl, a 5-trifluoromethyl-pyridin-2-yl, a 5-methylpyridin-2-yl, and a 6-methylpyridin-2-yl.

The thiazolyl group optionally having one or more atoms or groups selected from Group $P^1$ represents a group in which hydrogen atoms of a thiazolyl group are optionally substituted with one or more atoms or groups selected from Group $P^1$ and, when the number of atoms or groups selected from Group $P^1$ is 2 or more, those atoms or groups may be the same or different to each other. Examples of the thiazolyl group optionally having one or more atoms or groups selected from Group $P^1$ include a 4-(pyridin-2-yl)thiazol-2-yl, a 4-(pyridin-3-yl)thiazol-2-yl, a 4-(pyridin-4-yl)thiazol-2-yl, a 4-(5-methylpyridin-2-yl)thiazol-2-yl, and a 4-(6-methylpyridin-2-yl)thiazol-2-yl.

Examples of the aspect of the present compound are compounds in which the substituent in formula (1) is shown below.

A tetrazolinone compound in which A is A1; Q is Q1; $R^1$, $R^2$, $R^4$, $R^5$, $R^6$, $R^8$, and $R^9$ are hydrogen atoms; $R^3$ is a C1-C3 alkyl group optionally having one or more halogen atoms, a C3-C4 cycloalkyl group, a halogen atom, a C1-C3 alkoxy group optionally having one or more halogen atoms, or a C1-C3 alkylthio group; $R^7$ is a methyl group; and X is an oxygen atom. A tetrazolinone compound in which A is A1; Q is Q1; $R^1$, $R^2$, $R^4$, $R^5$, $R^6$, $R^8$, and $R^9$ are hydrogen atoms; $R^3$ is a C1-C3 alkyl group optionally having one or more halogen atoms; and X is an oxygen atom.

A tetrazolinone compound in which A is A1; Q is Q1; $R^1$, $R^2$, $R^4$, $R^5$, $R^6$, $R^8$, and $R^9$ are hydrogen atoms; $R^3$ is a C3-C4 cycloalkyl group; $R^7$ is a methyl group; and X is an oxygen atom.

A tetrazolinone compound in which A is A1; Q is Q1; $R^1$, $R^2$, $R^4$, $R^5$, $R^6$, $R^8$, and $R^9$ are hydrogen atoms; $R^3$ is a halogen atom; $R^7$ is a methyl group; and X is an oxygen atom.

A tetrazolinone compound in which A is A1; Q is Q1; $R^1$, $R^2$, $R^4$, $R^5$, $R^6$, $R^8$, and $R^3$ are hydrogen atoms; $R^3$ is a C1-C3 alkoxy group optionally having one or more halogen atoms; $R^7$ is a methyl group; and X is an oxygen atom.

A tetrazolinone compound in which A is A1; Q is Q1; $R^1$, $R^2$, $R^4$, $R^5$, $R^6$, $R^8$, and $R^9$ are hydrogen atoms; $R^3$ is a C1-C3 alkylthio group; $R^7$ is a methyl group; and X is an oxygen atom.

A tetrazolinone compound in which A is A1; Q is Q1; $R^1$, $R^2$, $R^4$, $R^5$, $R^6$, $R^8$, and $R^9$ are hydrogen atoms; $R^{30}$, $R^{32}$, $R^{33}$, and $R^{34}$ represent a hydrogen atom, a halogen atom, a C1-C4 alkyl group, a C1-C4 haloalkyl group, a C1-C4 alkoxy group, a C1-C4 haloalkoxy group, a nitro group, or a cyano group; $R^3$ is a C1-C3 alkyl group optionally having one or more halogen atoms, a C3-C4 cycloalkyl group, a halogen atom, a C1-C3 alkoxy group optionally having one or more halogen atoms, or a C1-C3 alkylthio group; $R^7$ is a methyl group; and X is an oxygen atom.

A tetrazolinone compound in which A is A1; Q is Q1; $R^1$, $R^2$, $R^4$, $R^5$, $R^6$, $R^8$, and $R^9$ are hydrogen atoms; $R^{30}$, $R^{32}$, $R^{33}$, and $R^{34}$ represent a hydrogen atom, a halogen atom, a C1-C4 alkyl group, a C1-C4 haloalkyl group, a C1-C4 alkoxy group, a C1-C4 haloalkoxy group, a nitro group, or a cyano group; $R^3$ is a C1-C3 alkyl group optionally having one or more halogen atoms; and X is an oxygen atom.

A tetrazolinone compound in which A is A1; Q is Q1; $R^1$, $R^2$, $R^4$, $R^5$, $R^6$, $R^8$, and $R^9$ are hydrogen atoms; $R^{30}$, $R^{32}$, $R^{33}$, and $R^{34}$ represent a hydrogen atom, a halogen atom, a C1-C4 alkyl group, a C1-C4 haloalkyl group, a C1-C4 alkoxy group, a C1-C4 haloalkoxy group, a nitro group, or a cyano group; $R^3$ is a C3-C4 cycloalkyl group; $R^7$ is a methyl group; and X is an oxygen atom.

A tetrazolinone compound in which A is A1; Q is Q1; $R^1$, $R^2$, $R^4$, $R^5$, $R^6$, $R^8$, and $R^9$ are hydrogen atoms; $R^{30}$, $R^{32}$, $R^{33}$, and $R^{34}$ represent a hydrogen atom, a halogen atom, a C1-C4 alkyl group, a C1-C4 haloalkyl group, a C1-C4 alkoxy group, a C1-C4 haloalkoxy group, a nitro group, or a cyano group; $R^3$ is a halogen atom; $R^7$ is a methyl group; and X is an oxygen atom.

A tetrazolinone compound in which A is A1; Q is Q1; $R^1$, $R^2$, $R^4$, $R^5$, $R^6$, $R^8$, and $R^9$ are hydrogen atoms; $R^{30}$, $R^{32}$, $R^{33}$, and $R^{34}$ represent a hydrogen atom, a halogen atom, a C1-C4 alkyl group, a C1-C4 haloalkyl group, a C1-C4 alkoxy group, a C1-C4 haloalkoxy group, a nitro group, or a cyano group; $R^3$ is a C1-C3 alkoxy group optionally having one or more halogen atoms; $R^7$ is a methyl group; and X is an oxygen atom.

A tetrazolinone compound in which A is A1; Q is Q1; $R^1$, $R^2$, $R^4$, $R^5$, $R^6$, $R^8$, and $R^9$ are hydrogen atoms; $R^{30}$, $R^{32}$, $R^{33}$, and $R^{34}$ represent a hydrogen atom, a halogen atom, a C1-C4 alkyl group, a C1-C4 haloalkyl group, a C1-C4 alkoxy group, a C1-C4 haloalkoxy group, a nitro group, or a cyano group; $R^3$ is a C1-C3 alkylthio group; $R^7$ is a methyl group; and X is an oxygen atom.

A tetrazolinone compound in which A is A1; Q is Q1; $R^1$, $R^2$, $R^4$, $R^5$, $R^6$, $R^8$, and $R^9$ are hydrogen atoms; $R^{30}$, $R^{32}$, $R^{33}$, and $R^{34}$ represent a hydrogen atom, a halogen atom, a C1-C4 alkyl group, a C1-C4 alkoxy group, or a cyano group; $R^3$ is a C1-C3 alkyl group optionally having one or more halogen atoms, a C3-C4 cycloalkyl group, a halogen atom, a C1-C3 alkoxy group optionally having one or more halogen atoms, or a C1-C3 alkylthio group; $R^7$ is a methyl group; and X is an oxygen atom.

A tetrazolinone compound in which A is A2; Q is Q1; $R^1$, $R^2$, $R^4$, $R^5$, $R^6$, $R^8$, and $R^9$ are hydrogen atoms; $R^3$ is a C1-C3 alkyl group optionally having one or more halogen atoms, a C3-C4 cycloalkyl group, a halogen atom, a C1-C3 alkoxy group optionally having one or more halogen atoms, or a C1-C3 alkylthio group; $R^7$ is a methyl group; and X is an oxygen atom.

A tetrazolinone compound in which A is A2; Q is Q1; $R^1$, $R^2$, $R^4$, $R^5$, $R^6$, $R^8$, and $R^9$ are hydrogen atoms; $R^3$ is a C1-C3 alkyl group optionally having one or more halogen atoms; and X is an oxygen atom.

A tetrazolinone compound in which A is A2; Q is Q1; $R^1$, $R^2$, $R^4$, $R^5$, $R^6$, $R^8$, and $R^9$ are hydrogen atoms; $R^3$ is a C3-C4 cycloalkyl group; $R^7$ is a methyl group; and X is an oxygen atom.

A tetrazolinone compound in which A is A2; Q is Q1; $R^1$, $R^2$, $R^4$, $R^5$, $R^6$, $R^8$, and $R^9$ are hydrogen atoms; $R^3$ is a halogen atom; $R^7$ is a methyl group; and X is an oxygen atom.

A tetrazolinone compound in which A is A2; Q is Q1; $R^1$, $R^2$, $R^4$, $R^5$, $R^6$, $R^8$, and $R^9$ are hydrogen atoms; $R^{31}$, $R^{32}$, $R^{33}$, and $R^{34}$ represent a hydrogen atom, a halogen atom, a C1-C4 alkyl group, a C1-C4 haloalkyl group, a C1-C4 alkoxy group, a C1-C4 haloalkoxy group, a nitro group, or a cyano group; $R^3$ is a C1-C3 alkyl group optionally having one or more halogen atoms, a C3-C4 cycloalkyl group, a halogen atom, a C1-C3 alkoxy group optionally having one or more halogen atoms, or a C1-C3 alkylthio group; $R^7$ is a methyl group; and X is an oxygen atom.

A tetrazolinone compound in which A is A2; Q is Q1; $R^1$, $R^2$, $R^4$, $R^5$, $R^6$, $R^8$, and $R^9$ are hydrogen atoms; $R^{31}$, $R^{32}$, $R^{33}$, and $R^{34}$ represent a hydrogen atom, a halogen atom, a C1-C4 alkyl group, a C1-C4 haloalkyl group, a C1-C4 alkoxy group, a C1-C4 haloalkoxy group, a nitro group, or a cyano group; $R^3$ is a C1-C3 alkyl group optionally having one or more halogen atoms; and X is an oxygen atom.

A tetrazolinone compound in which A is A2; Q is Q1; $R^1$, $R^2$, $R^4$, $R^5$, $R^6$, $R^8$, and $R^9$ are hydrogen atoms; $R^{31}$, $R^{32}$, $R^{33}$, and $R^{34}$ represent a hydrogen atom, a halogen atom, a C1-C4 alkyl group, a C1-C4 haloalkyl group, a C1-C4 alkoxy group, a C1-C4 haloalkoxy group, a nitro group, or a cyano group; $R^3$ is a C3-C4 cycloalkyl group; $R^7$ is a methyl group; and X is an oxygen atom.

A tetrazolinone compound in which A is A2; Q is Q1; $R^1$, $R^2$, $R^4$, $R^5$, $R^6$, $R^8$, and $R^9$ are hydrogen atoms; $R^{31}$, $R^{32}$, $R^{33}$, and $R^{34}$ present a hydrogen atom, a halogen atom, a C1-C4 alkyl group, a C1-C4 haloalkyl group, a C1-C4 alkoxy group, a C1-C4 haloalkoxy group, a nitro group, or a cyano group; $R^3$ is a halogen atom; $R^7$ is a methyl group; and X is an oxygen atom.

A tetrazolinone compound in which A is a thiazolyl group optionally having one or more atoms or groups selected from the group consisting of a C1-C4 alkyl group, a halogen atom, and a C1-C4 haloalkyl group; Q is a pyridyl group optionally having one or more atoms or groups selected from the group consisting of a halogen atom, a C1-C4 alkyl group, a C1-C4 haloalkyl group, a C1-C4 alkoxy group, a C1-C4 haloalkoxy group, a nitro group, and a cyano group; $R^1$, $R^2$, $R^4$, $R^5$, and $R^6$ are hydrogen atoms; $R^3$ is a C1-C3 alkyl group optionally having one or more halogen atoms, a C3-C4 cycloalkyl group optionally having one or more halogen atoms, a halogen atom, a C1-C3 alkoxy group optionally having one or more halogen atoms, or a C1-C3 alkylthio group optionally having one or more halogen atoms; $R^7$ is a methyl group; and X is an oxygen atom.

A tetrazolinone compound in which A is A1; Q is Q2; $R^1$, $R^2$, $R^4$, $R^5$, $R^6$, and $R^{20}$ are hydrogen atoms; $R^3$ is a C1-C3 alkyl group optionally having one or more halogen atoms, a C3-C4 cycloalkyl group, a halogen atom, a C1-C3 alkoxy group optionally having one or more halogen atoms, or a C1-C3 alkylthio group; $R^7$ is a methyl group; and X is an oxygen atom.

A tetrazolinone compound in which A is A1; Q is Q2; $R^1$, $R^2$, $R^4$, $R^5$, $R^6$, and $R^{20}$ are hydrogen atoms; $R^3$ is a C1-C3 alkyl group optionally having one or more halogen atoms; and X is an oxygen atom.

A tetrazolinone compound in which A is A1; Q is Q2; $R^1$, $R^2$, $R^4$, $R^5$, $R^6$, and $R^{20}$ are hydrogen atoms; $R^3$ is a C3-C4 cycloalkyl group; $R^7$ is a methyl group; and X is an oxygen atom.

A tetrazolinone compound in which A is A1; Q is Q2; $R^1$, $R^2$, $R^4$, $R^5$, $R^6$, and $R^{20}$ are hydrogen atoms; $R^3$ is a halogen atom; $R^7$ is a methyl group; and X is an oxygen atom.

A tetrazolinone compound in which A is A1; Q is Q2; $R^1$, $R^2$, $R^4$, $R^5$, $R^6$, and $R^{20}$ are hydrogen atoms; $R^3$ is a C1-C3 alkoxy group optionally having one or more halogen atoms; $R^7$ is a methyl group; and X is an oxygen atom.

A tetrazolinone compound in which A is A1; Q is Q2; $R^1$, $R^2$, $R^4$, $R^5$, $R^6$, and $R^{20}$ are hydrogen atoms; $R^3$ is a C1-C3 alkylthio group; $R^7$ is a methyl group; and X is an oxygen atom.

A tetrazolinone compound in which A is A1; Q is Q2; $R^1$, $R^2$, $R^4$, $R^5$, $R^6$, and $R^{20}$ are hydrogen atoms; $R^{30}$, $R^{32}$, $R^{33}$, and $R^{34}$ represent a hydrogen atom, a halogen atom, a C1-C4 alkyl group, a C1-C4 haloalkyl group, a C1-C4 alkoxy group, a C1-C4 haloalkoxy group, a nitro group, or a cyano group; $R^3$ is a C1-C3 alkyl group optionally having one or more halogen atoms, a C3-C4 cycloalkyl group, a halogen atom, a C1-C3 alkoxy group optionally having one or more halogen atoms, or a C1-C3 alkylthio group; $R^7$ is a methyl group; and X is an oxygen atom.

A tetrazolinone compound in which A is A1; Q is Q2; $R^1$, $R^2$, $R^4$, $R^5$, $R^6$, and $R^{20}$ are hydrogen atoms; $R^{30}$, $R^{32}$, $R^{33}$, and $R^{34}$ represent a hydrogen atom, a halogen atom, a C1-C4 alkyl group, a C1-C4 haloalkyl group, a C1-C4 alkoxy group, a C1-C4 haloalkoxy group, a nitro group, or a cyano group; $R^3$ is a C1-C3 alkyl group optionally having one or more halogen atoms; and X is an oxygen atom.

A tetrazolinone compound in which A is A1; Q is Q2; $R^1$, $R^2$, $R^4$, $R^5$, $R^6$, and $R^{20}$ are hydrogen atoms; $R^{30}$, $R^{32}$, $R^{33}$, and $R^{34}$ represent a hydrogen atom, a halogen atom, a C1-C4 alkyl group, a C1-C4 haloalkyl group, a C1-C4 alkoxy group, a C1-C4 haloalkoxy group, a nitro group, or a cyano group; $R^3$ is a C3-C4 cycloalkyl group; $R^7$ is a methyl group; and X is an oxygen atom.

A tetrazolinone compound in which A is A1; Q is Q2; $R^1$, $R^2$, $R^4$, $R^1$, $R^6$, and $R^{20}$ are hydrogen atoms; $R^{30}$, $R^{32}$, $R^{33}$, and $R^{34}$ represent a hydrogen atom, a halogen atom, a C1-C4 alkyl group, a C1-C4 haloalkyl group, a C1-C4 alkoxy group, a C1-C4 haloalkoxy group, a nitro group, or a cyano group; $R^3$ is a halogen atom; $R^7$ is a methyl group; and X is an oxygen atom.

A tetrazolinone compound in which A is A1; Q is Q2; $R^1$, $R^2$, $R^4$, $R^5$, $R^6$, and $R^{20}$ are hydrogen atoms; $R^{30}$, $R^{32}$, $R^{33}$, and $R^{34}$ represent a hydrogen atoms, a halogen atom, a C1-C4 alkyl group, a C1-C4 haloalkyl group, a C1-C4 alkoxy group, a C1-C4 haloalkoxy group, a nitro group, or a cyano group; $R^3$ is a C1-C3 alkoxy group optionally having one or more halogen atoms; $R^7$ is a methyl group; and X is an oxygen atom.

A tetrazolinone compound in which A is A1; Q is Q2; $R^1$, $R^2$, $R^4$, $R^5$, $R^6$, and $R^{20}$ are hydrogen atoms; $R^{30}$, $R^{32}$, $R^{33}$, and $R^{34}$ represent a hydrogen atoms, a halogen atom, a C1-C4 alkyl group, a C1-C4 haloalkyl group, a C1-C4 alkoxy group, a C1-C4 haloalkoxy group, a nitro group, or a cyano group; $R^3$ is a C1-C3 alkylthio group; $R^7$ is a methyl group; and X is an oxygen atom.

A tetrazolinone compound in which A is A1; Q is Q2; $R^1$, $R^2$, $R^4$, $R^5$, $R^6$, and $R^{20}$ are hydrogen atoms; $R^{30}$, $R^{32}$, $R^{33}$, and $R^{34}$ represent a hydrogen atom, a halogen atom, a C1-C4 alkyl group, a C1-C4 alkoxy group, or a cyano group; $R^3$ is a C1-C3 alkyl group optionally having one or more halogen atoms, a C3-C4 cycloalkyl group, a halogen atom, a C1-C3 alkoxy group optionally having or one or more halogen atoms, or a C1-C3 alkylthio group; $R^7$ is a methyl group; and X is an oxygen atom.

A tetrazolinone compound in which A is A2; Q is Q2; $R^1$, $R^2$, $R^4$, $R^5$, $R^6$, and $R^{20}$ are hydrogen atoms; $R^3$ is a C1-C3 alkyl group optionally having one or more halogen atoms, a C3-C4 cycloalkyl group, a halogen atom, a C1-C3 alkoxy group optionally having one or more halogen atoms, or a C1-C3 alkylthio group; $R^7$ is a methyl group; and X is an oxygen atom.

A tetrazolinone compound in which A is A2; Q is Q2; $R^1$, $R^2$, $R^4$, $R^5$, $R^6$, and $R^{20}$ are hydrogen atoms; $R^3$ is a C1-C3 alkyl group optionally having one or more halogen atoms; and X is an oxygen atom.

A tetrazolinone compound in which A is A2; Q is Q2; $R^1$, $R^2$, $R^4$, $R^5$, $R^6$, and $R^{20}$ are hydrogen atoms; $R^3$ is a C3-C4 cycloalkyl group; $R^7$ is a methyl group; and X is an oxygen atom.

A tetrazolinone compound in which A is A2; Q is Q2; $R^1$, $R^2$, $R^4$, $R^5$, $R^6$, and $R^{20}$ are hydrogen atoms; $R^3$ is a halogen atom; $R^7$ is a methyl group; and X is an oxygen atom.

A tetrazolinone compound in which A is A2; Q is Q2; $R^1$, $R^2$, $R^4$, $R^5$, $R^6$, and $R^{20}$ are hydrogen atoms; $R^{30}$, $R^{32}$, $R^{33}$, and $R^{34}$ represent a hydrogen atom, a halogen atom, a C1-C4 alkyl group, a C1-C4 haloalkyl group, a C1-C4 alkoxy group, a C1-C4 haloalkoxy group, a nitro group, or a cyano group; $R^3$ is a C1-C3 alkyl group optionally having one or more halogen atoms, a C3-C4 cycloalkyl group, a halogen atom, a C1-C3 alkoxy group optionally having one or more halogen atoms, or a C1-C3 alkylthio group; $R^7$ is a methyl group; and X is an oxygen atom.

A tetrazolinone compound in which A is A2; Q is Q2; $R^1$, $R^2$, $R^4$, $R^5$, $R^6$, and $R^{20}$ are hydrogen atoms; $R^{31}$, $R^{32}$, $R^{33}$, and $R^{34}$ represent a hydrogen atom, a halogen atom, a C1-C4 alkyl group, a C1-C4 haloalkyl group, a C1-C4 alkoxy group, a C1-C4 haloalkoxy group, a nitro group, or a cyano group; $R^3$ is a C1-C3 alkyl group optionally having one or more halogen atoms; and X is an oxygen atom.

A tetrazolinone compound in which A is A2; Q is Q2; $R^1$, $R^2$, $R^4$, $R^5$, $R^6$, and $R^{20}$ are hydrogen atoms; $R^{31}$, $R^{32}$, $R^{33}$, and $R^{34}$ represent a hydrogen atom, a halogen atom, a C1-C4 alkyl group, a C1-C4 haloalkyl group, a C1-C4 alkoxy group, a C1-C4 haloalkoxy group, a nitro group, or a cyano group; $R^3$ is a C3-C4 cycloalkyl group; $R^7$ is a methyl group; and X is an oxygen atom.

A tetrazolinone compound in which A is A2; Q is Q2; $R^1$, $R^2$, $R^4$, $R^5$, $R^6$, and $R^{20}$ are hydrogen atoms; $R^{31}$, $R^{32}$, $R^{33}$, and $R^{34}$ represent a hydrogen atom, a halogen atom, a C1-C4 alkyl group, a C1-C4 haloalkyl group, a C1-C4 alkoxy group, a C1-C4 haloalkoxy group, a nitro group, or a cyano group; $R^3$ is a halogen atom; $R^7$ is a methyl group; and X is an oxygen atom.

A tetrazolinone compound in which A is a pyrazolyl group optionally having one or more atoms or groups selected from the group consisting of a C1-C4 alkyl group, a halogen atom, and a C1-C4 haloalkyl group; Q is a pyridyl group optionally having one or more atoms or groups selected from the group consisting of a halogen atom, a C1-C4 alkyl group, a C1-C4 haloalkyl group, a C1-C4 alkoxy group, a C1-C4 haloalkoxy group, a nitro group, and a cyano group; and $R^1$, $R^2$, $R^4$, $R^5$, and $R^6$ are hydrogen atoms;

A tetrazolinone compound in which $R^3$ is a C1-C3 alkyl group optionally having one or more halogen atoms, a C3-C4 cycloalkyl group optionally having one or more halogen atoms, a halogen atom, a C1-C3 alkoxy group optionally having one or more halogen atoms, or a C1-C3 alkylthio group optionally having one or more halogen atoms; $R^7$ is a methyl group; and X is an oxygen atom.

A tetrazolinone compound in which A is A1; Q is Q1; $R^1$, $R^2$, $R^4$, $R^3$, and $R^6$ are hydrogen atoms; $R^3$ is a C1-C3 alkyl group optionally having one or more halogen atoms, a C3-C4 cycloalkyl group optionally having one or more halogen atoms, a halogen atom, a C1-C3 alkoxy group optionally having one or more halogen atoms, or a C1-C3 alkylthio group optionally having one or more halogen atoms; $R^7$ is a methyl group; $R^{20}$ and $R^{21}$ each independently represents a hydrogen atom, a C1-C4 alkyl group, a halogen atom, or a C1-C4 haloalkyl group; $R^{30}$, $R^{32}$, $R^{33}$, and $R^{34}$ each independently represents a hydrogen atom, a halogen atom, a C1-C4 alkyl group, a C1-C4 haloalkyl group, a C1-C4 alkoxy group, a C1-C4 haloalkoxy group, a nitro group, or a cyano group; and X is an oxygen atom.

A tetrazolinone compound in which A is A1; Q is Q1; $R^1$, $R^2$, $R^4$, $R^5$, $R^6$, $R^{20}$, and $R^{21}$ are hydrogen atoms; $R^3$ is a methyl group, an ethyl group, a cyclopropyl group, a chlorine atom, a bromine atom, a methoxy group, an ethoxy group, or a methylthio group; $R^7$ is a methyl group; $R^{30}$ is a methoxy group, an ethoxy group, a trifluoromethyl group, a trifluoromethoxy group, a methyl group, an ethyl group, or a fluorine atom; $R^{31}$ is a methyl group, an ethyl group, a methoxy group, an ethoxy group, a fluorine atom, a chlorine atom, a bromine atom, a cyano group, a trifluoromethyl group, or a nitro group; $R^{32}$ and $R^{33}$ each independently represents a hydrogen atom, a fluorine atom, or a chlorine atom; and X is an oxygen atom.

A tetrazolinone compound in which A is A1; Q is Q2; $R^1$, $R^2$, $R^4$, $R^5$, and $R^6$ are hydrogen atoms; $R^3$ is a C1-C3 alkyl group optionally having one or more halogen atoms, a C3-C4 cycloalkyl group optionally having one or more halogen atoms, a halogen atom, a C1-C3 alkoxy group optionally having one or more halogen atoms, or a C1-C3 alkylthio group optionally having one or more halogen atoms; $R^7$ is a methyl group; $R^{20}$ and $R^{21}$ each independently represents a hydrogen atom, a C1-C4 alkyl group, a halogen atom, or a C1-C4 haloalkyl group; $R^{30}$, $R^{32}$, $R^{33}$, and $R^{34}$ each independently represents a hydrogen atom, a halogen atom, a C1-C4 alkyl group, a C1-C4 haloalkyl group, a C1-C4 alkoxy group, a C1-C4 haloalkoxy group, a nitro group, or a cyano group; and X is an oxygen atom.

A tetrazolinone compound in which A is A1; Q is Q2; $R^1$, $R^2$, $R^4$, $R^5$, $R^6$, and $R^{20}$ are hydrogen atoms; $R^3$ is a methyl group, an ethyl group, a cyclopropyl group, a chlorine atom, a bromine atom, a methoxy group, an ethoxy group, or a methylthio group; $R^7$ is a methyl group; $R^{30}$ is a methoxy group, an ethoxy group, a trifluoromethyl group, a trifluoromethoxy group, a methyl group, an ethyl group, or a fluorine atom; $R^{31}$ is a methyl group, an ethyl group, a methoxy group, an ethoxy group, a fluorine atom, a chlorine atom, a bromine atom, a cyano group, a trifluoromethyl group, or a nitro group; $R^{32}$ and $R^{33}$ each independently represents a hydrogen atom, a fluorine atom, or a chlorine atom; and X is an oxygen atom.

A tetrazolinone compound in which A is A2; Q is Q1; $R^1$, $R^2$, $R^4$, $R^5$, and $R^6$ are hydrogen atoms; $R^3$ is a C1-C3 alkyl group optionally having one or more halogen atoms, a C3-C4 cycloalkyl group optionally having one or more halogen atoms, a halogen atom, a C1-C3 alkoxy group optionally having one or more halogen atoms, or a C1-C3 alkylthio group optionally having one or more halogen atoms; $R^7$ is a methyl group; $R^{20}$ and $R^{21}$ each independently represents a hydrogen atom, a C1-C4 alkyl group, a halogen atom, or a C1-C4 haloalkyl group; $R^{31}$, $R^{32}$, $R^{33}$, and $R^{34}$ each independently represents a hydrogen atom, a halogen atom, a C1-C4 alkyl group, a C1-C4 haloalkyl group, a C1-C4 alkoxy group, a C1-C4 haloalkoxy group, a nitro group, or a cyano group; and X is an oxygen atom.

A tetrazolinone compound in which A is A2; Q is Q1; $R^1$, $R^2$, $R^4$, $R^5$, $R^6$, $R^{20}$, and $R^{21}$ are hydrogen atoms; $R^3$ is a methyl group, an ethyl group, a cyclopropyl group, a chlorine atom, a bromine atom, a methoxy group, an ethoxy group, or a methylthio group; $R^7$ is a methyl group; $R^{31}$ is a methoxy group, an ethoxy group, a trifluoromethyl group, a trifluoromethoxy group, a methyl group, an ethyl group, or a fluorine atom; $R^{32}$ is a methyl group, an ethyl group, a methoxy group, an ethoxy group, a fluorine atom, a chlorine atom, a bromine atom, a cyano group, a trifluoromethyl group, or a nitro group; $R^{33}$ and $R^{34}$ each independently represents a hydrogen atom, a fluorine atom, or a chlorine atom; and X is an oxygen atom.

A tetrazolinone compound in which A is A2; Q is Q2; $R^1$, $R^2$, $R^4$, $R^3$, and $R^6$ are hydrogen atoms; $R^3$ is a C1-C3 alkyl group optionally having one or more halogen atoms, a C3-C4 cycloalkyl group optionally having one or more halogen atoms, a halogen atom, a C1-C3 alkoxy group optionally having one or more halogen atoms, or a C1-C3 alkylthio group optionally having one or more halogen atoms; $R^7$ is a methyl group; $R^{20}$ and $R^{21}$ each independently represents a hydrogen atom, a C1-C4 alkyl group, a halogen atom, or a C1-C4 haloalkyl group; $R^{31}$, $R^{32}$, $R^{33}$, and $R^{34}$ each independently represents a hydrogen atom, a halogen atom, a C1-C4 alkyl group, a C1-C4 haloalkyl group, a C1-C4 alkoxy group, a C1-C4 haloalkoxy group, a nitro group, or a cyano group; and X is an oxygen atom.

A tetrazolinone compound in which A is A2; Q is Q2; $R^1$, $R^2$, $R^4$, $R^5$, $R^6$, and $R^{20}$ are hydrogen atoms; $R^3$ is a methyl group, an ethyl group, a cyclopropyl group, a chlorine atom, a bromine atom, a methoxy group, an ethoxy group, or a methylthio group; $R^7$ is a methyl group; $R^{31}$ is a methoxy group, an ethoxy group, a trifluoromethyl group, a trifluoromethoxy group, a methyl group, an ethyl group, or a fluorine atom; $R^{32}$ is a methyl group, an ethyl group, a methoxy group, an ethoxy group, a fluorine atom, a chlorine atom, a bromine atom, a cyano group, a trifluoromethyl group, or a nitro group; $R^{34}$ and $R^{34}$ each independently represents a hydrogen atom, a fluorine atom, or a chlorine atom; and X is an oxygen atom.

A tetrazolinone compound in which A is A68; Q is Q1; $R^1$, $R^2$, $R^4$, $R^5$, and $R^6$ are hydrogen atoms; $R^3$ is a C1-C3 alkyl group optionally having one or more halogen atoms, a C3-C4 cycloalkyl group optionally having one or more halogen atoms, a halogen atom, a C1-C3 alkoxy group optionally having one or more halogen atoms, or a C1-C3 alkylthio group optionally having one or more halogen atoms; $R^7$ is a methyl group; $R^{20}$ and $R^{21}$ each independently represents a hydrogen atom, a C1-C4 alkyl group, a halogen atom, or a C1-C4 haloalkyl group; $R^{30}$, $R^{31}$, $R^{34}$, $R^{40}$, and $R^{41}$ each independently represents a hydrogen atom, a halogen atom, a C1-C4 alkyl group, a C1-C4 haloalkyl group, a C1-C4 alkoxy group, a C1-C4 haloalkoxy group, a nitro group, or a cyano group; and X is an oxygen atom.

A tetrazolinone compound in which A is A68; Q is Q1; $R^1$, $R^2$, $R^4$, $R^5$, $R^6$, $R^{20}$, and $R^{21}$ are hydrogen atoms; $R^3$ is a methyl group, an ethyl group, a cyclopropyl group, a chlorine atom, a bromine atom, a methoxy group, an ethoxy group, or a methylthio group; $R^7$ is a methyl group; $R^{30}$, $R^{31}$, $R^{34}$, $R^{40}$, and $R^{41}$ each independently represents a hydrogen atom, a fluorine atom, or a chlorine atom; and X is an oxygen atom.

A tetrazolinone compound in which A is A68; Q is Q2; $R^1$, $R^2$, $R^4$, $R^5$, and $R^6$ are hydrogen atoms; $R^3$ is a C1-C3 alkyl group optionally having one or more halogen atoms, a C3-C4 cycloalkyl group optionally having one or more halogen atoms, a halogen atom, a C1-C3 alkoxy group optionally having one or more halogen atoms, or a C1-C3 alkylthio group optionally having one or more halogen atoms; $R^7$ is a methyl group; $R^{20}$ and $R^{21}$ each independently represents a hydrogen atom, a C1-C4 alkyl group, a halogen atom, or a C1-C4 haloalkyl group; $R^{30}$, $R^{31}$, $R^{34}$, $R^{40}$, and $R^{41}$ each independently represents a hydrogen atom, a halogen atom, a C1-C4 alkyl group, a C1-C4 haloalkyl group, a C1-C4 alkoxy group, a C1-C4 haloalkoxy group, a nitro group, or a cyano group; and X is an oxygen atom.

A tetrazolinone compound in which A is A68; Q is Q2; $R^1$, $R^2$, $R^4$, $R^5$, $R^6$, and $R^{20}$ are hydrogen atoms; $R^3$ is a methyl group, an ethyl group, a cyclopropyl group, a chlorine atom, a bromine atom, a methoxy group, an ethoxy group, or a methylthio group; $R^7$ is a methyl group; $R^{30}$, $R^{31}$, $R^{34}$, $R^{40}$, and $R^{41}$ each independently represents a hydrogen atom, a fluorine atom, or a chlorine atom; and X is an oxygen atom.

A tetrazolinone compound in which A is A73; Q is Q1; $R^1$, $R^2$, $R^4$, $R^5$, and $R^6$ are hydrogen atoms; $R^3$ is a C1-C3 alkyl group optionally having one or more halogen atoms, a C3-C4 cycloalkyl group optionally having one or more halogen atoms, a halogen atom, a C1-C3 alkoxy group optionally having one or more halogen atoms, or a C1-C3 alkylthio group optionally having one or more halogen atoms; $R^7$ is a methyl group; $R^{20}$ and $R^{21}$ each independently represents a hydrogen atom, a C1-C4 alkyl group, a halogen atom, or a C1-C4 haloalkyl group; $R^{30}$, $R^{35}$, $R^{36}$, $R^{37}$, $R^{38}$, and $R^{34}$ each independently represents a hydrogen atom, a halogen atom, a C1-C4 alkyl group, a C1-C4 haloalkyl group, a C1-C4 alkoxy group, a C1-C4 haloalkoxy group, a nitro group, or a cyano group; and X is an oxygen atom.

A tetrazolinone compound in which A is A73; Q is Q1; $R^1$, $R^2$, $R^4$, $R^5$, $R^6$, $R^{20}$, and $R^{21}$ are hydrogen atoms; $R^3$ is a methyl group, an ethyl group, a cyclopropyl group, a chlorine atom, a bromine atom, a methoxy group, an ethoxy group, or a methylthio group; $R^7$ is a methyl group; $R^{30}$ is a methoxy group, an ethoxy group, a trifluoromethyl group, a trifluoromethoxy group, a methyl group, an ethyl group, or a fluorine atom; $R^{35}$, $R^{36}$, $R^{37}$, $R^{38}$, and $R^{34}$ each independently represents a methyl group, an ethyl group, a methoxy group, an ethoxy group, a fluorine atom, a chlorine atom, a bromine atom, a cyano group, a trifluoromethyl group, or a nitro group; and X is an oxygen atom.

A tetrazolinone compound in which A is A73; Q is Q2; $R^1$, $R^2$, $R^4$, $R^5$, and $R^6$ are hydrogen atoms; $R^3$ is a C1-C3 alkyl group optionally having one or more halogen atoms, a C3-C4 cycloalkyl group optionally having one or more halogen atoms, a halogen atom, a C1-C3 alkoxy group optionally having one or more halogen atoms, or a C1-C3 alkylthio group optionally having one or more halogen atoms; $R^7$ is a methyl group; $R^{20}$ and $R^{21}$ each independently represents a hydrogen atom, a C1-C4 alkyl group, a halogen atom, or a C1-C4 haloalkyl group; $R^{30}$, $R^{35}$, $R^{36}$, $R^{37}$, $R^{38}$, and $R^{34}$ each independently represents a hydrogen atom, a halogen atom, a C1-C4 alkyl group, a C1-C4 haloalkyl group, a C1-C4 alkoxy group, a C1-C4 haloalkoxy group, a nitro group, or a cyano group; and X is an oxygen atom.

A tetrazolinone compound in which A is A73; Q is Q2; $R^1$, $R^2$, $R^4$, $R^5$, $R^6$ and $R^{20}$ are hydrogen atoms; $R^3$ is a methyl group, an ethyl group, a cyclopropyl group, a chlorine atom, a bromine atom, a methoxy group, an ethoxy group, or a methylthio group; $R^7$ is a methyl group; $R^{30}$ is a methoxy group, an ethoxy group, a trifluoromethyl group, a trifluoromethoxy group, a methyl group, an ethyl group, or a fluorine atom; and $R^{35}$, $R^{36}$, $R^{37}$, $R^{38}$, and $R^{34}$ each independently represents a methyl group, an ethyl group, a methoxy group, an ethoxy group, a fluorine atom, a chlorine atom, a bromine atom, a cyano group, a trifluoromethyl group, or a nitro group.

Next, a process for producing the present compound will be described.

The present compound can be produced, for example, by the following Production Processes.

(Production Process A)

The present compound represented by formula (1) can be produced by reacting a compound represented by formula (A1) (hereinafter referred to as the compound (A1)) with a compound represented by formula (A2) (hereinafter referred to as the compound (A2)) in the presence of a base:

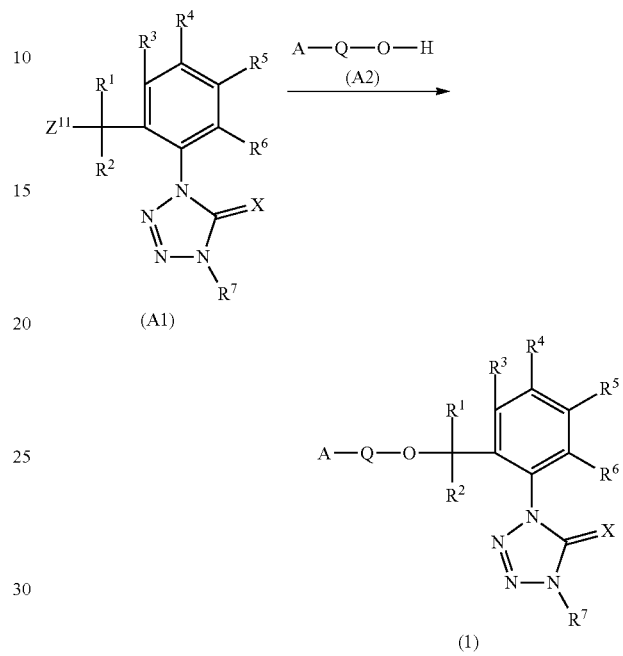

wherein $R^1$, $R^2$, $R^3$, $R^4$, $R^5$, $R^6$, $R^7$, A, Q, and X are the same as defined above, $Z^{11}$ represents a leaving group such as a chlorine atom, a bromine atom, an iodine atom, a methanesulfonyloxy group, a trifluoromethanesulfonyloxy group, or a p-toluenesulfonyloxy group.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (A2) is usually used in the proportion within a range of 1 to 10 mols, and the base is usually used in the proportion within a range of 0.5 to 5 mols, based on 1 mol of the compound (A1).

The reaction temperature of the reaction is usually within a range of −20 to 150° C. The reaction time is usually within a range of 0.1 to 24 hours.

If necessary, sodium iodide, tetrabutylammonium iodide, and the like may be added in the reaction, and these compounds are usually used in the proportion of 0.001 to 1.2 mols based on 1 mol of the compound (A1).

After completion of the reaction, the present compound represented by formula (1) can be isolated by performing post-treatment operations such as extraction of the reaction mixture with an organic solvent, and drying and concentration of the organic layer. The isolated present compound can be further purified by chromatography, recrystallization, and the like.

(Production Process B)

The present compound represented by formula (1) can be produced by subjecting a compound represented by formula (B1) (hereinafter referred to as the compound (B1)) and a compound represented by formula (B2) (hereinafter referred to as the compound (B2)) to a coupling reaction in the presence of a base and a catalyst:

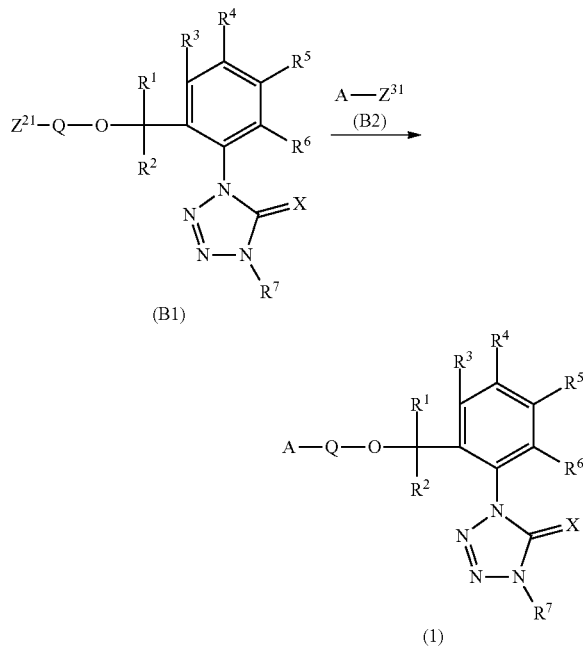

wherein $R^1$, $R^2$, $R^3$, $R^4$, $R^5$, $R^6$, $R^7$, A, Q, and X are the same as defined above, $Z^{21}$ represents a chlorine atom, a bromine atom, or an iodine atom, and $Z^{31}$ represents $B(OH)_2$, a dialkoxyboryl group, or a trifluoroborate ($BF_3^-K^+$).

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; alcohols such as methanol, ethanol, propanol, and butanol; water; and mixtures thereof.

It is possible to usually use, as the compound (B2) to be used in the reaction, commercially available compounds, or compounds produced by a known method mentioned in N. Miyaura and A. Suzuki, Chem. Rev., 1995, 95, 2457. Regarding the compound (B2) to be used in the reaction, it is possible to produce a boric acid ester derivative by reacting an iodine compound of A (A-I), a bromo compound of A (A-Br), or a chloro compound of A (A-Cl) with an alkyllithium such as butyllithium, followed by a reaction with a boric acid ester. It is possible to produce a boric acid derivative by optionally hydrolyzing the boric acid ester derivative obtained by the above-mentioned reaction. It is also possible to produce a trifluoroborate ($BF_3^-K^+$) by fluorinating the boric acid ester with potassium hydrogen fluoride in accordance with a known method mentioned in Molander et al. Acc. Chem. Res., 2007, 40, 275.

Examples of the catalyst to be used in the reaction include palladium(II) acetate, dichlorobis(triphenylphosphine)palladium, tetrakistriphenylphosphinepalladium(0), palladium(II) acetate/triscyclohexylphosphine, bis(diphenylphoshineferrocenyl)palladium(II) dichloride, 1,3-bis(2,6-diisopropylphenyl)imidazol-2-ylidene(1,4-naphthoquinone) palladium dimer, allyl(chloro) (1,3-dimesityl-1,3-dihydro-2H-imidazol-2-ylidene)palladium or palladium (II) acetate/dicyclohexyl(2',4',6'-triisopropylbiphenyl-2-yl)phosphine, tris(dibenzylideneacetone)dipalladium, and the like.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (B2) is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (B1).

The reaction temperature of the reaction is usually within a range of 0 to 150° C. The reaction time of the reaction is usually within a range of 0.1 to 24 hours.

After completion of the reaction, the present compound represented by formula (1) can be isolated by performing post-treatment operations such as extraction of the reaction mixture with an organic solvent, and drying and concentration of the organic layer. The isolated present compound can be further purified by chromatography, recrystallization, and the like.

(Production Process C)

The present compound represented by formula (1) can be produced by subjecting a compound represented by formula (C1) (hereinafter referred to as the compound (C1)) and a compound represented by formula (C2) (hereinafter referred to as the compound (C2)) to a coupling reaction in the presence of a base and a catalyst:

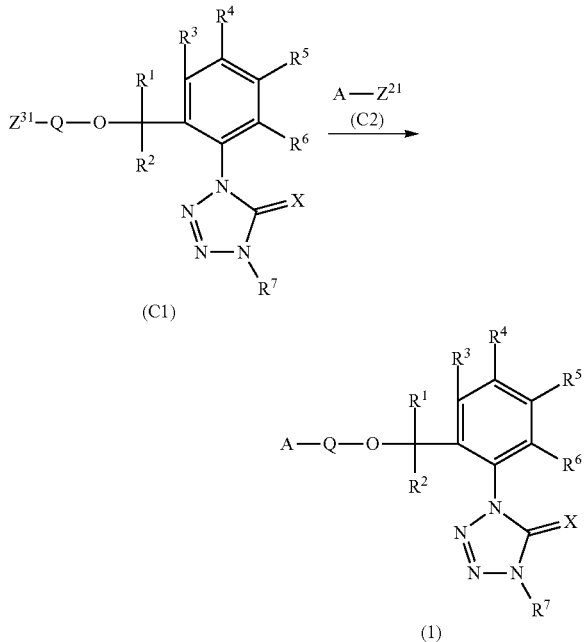

wherein $R^1$, $R^2$, $R^3$, $R^4$, $R^5$, $R^6$, $R^7$, A, Q, $Z^{21}$, $Z^{31}$, and X are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

It is possible to usually use, as the compound (C2) to be used in the reaction, commercially available products.

Examples of the catalyst to be used in the reaction include palladium(II) acetate, dichlorobis(triphenylphosphine)palladium, tetrakistriphenylphosphinepalladium(0), palladium (II) acetate/tricyclohexylphosphine, bis(diphenylphoshine-ferrocenyl)palladium(II) dichloride, 1,3-bis(2,6-diisopropylphenyl)imidazol-2-ylidene(1,4-naphthoquinone) palladium dimer, allyl(chloro) (1,3-dimesityl-1,3-dihydro-2H-imidazol-2-ylidene)palladium or palladium (II) acetate/dicyclohexyl(2',4',6'-triisopropylbiphenyl-2-yl)phosphine, tris(dibenzylideneacetone)dipalladium, and the like.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (C2) is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (C1).

The reaction temperature of the reaction is usually within a range of 0 to 150° C. The reaction time of the reaction is usually within a range of 0.1 to 24 hours.

After completion of the reaction, the present compound represented by formula (1) can be isolated by performing post-treatment operations such as extraction of the reaction mixture with an organic solvent, and drying and concentration of the organic layer. The isolated present compound can be further purified by chromatography, recrystallization, and the like.

(Production Process D)

The present compound represented by formula (1) can be produced by reacting a compound represented by formula (1-3) (hereinafter referred to as the compound (1-3)) with a compound represented by formula (E1) (hereinafter referred to as the compound (E1)) in the presence of a base:

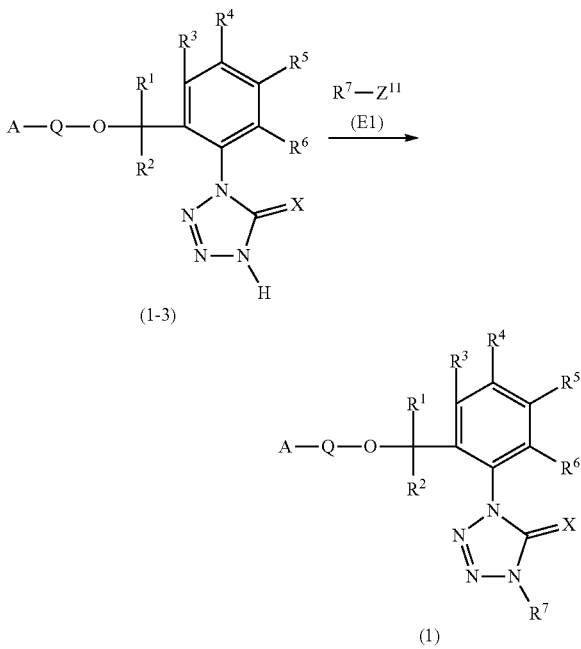

wherein $R^1$, $R^2$, $R^3$, $R^4$, $R^5$, $R^6$, $R^7$, A, Q, $Z^{11}$, and X are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

It is possible to usually use, as the compound (E1) to be used in the reaction, commercially available compounds. Specific examples thereof include halogenated alkyls such as chlorodifluoromethane, methyl bromide, ethyl bromide, n-propyl bromide, methyl iodide, ethyl iodide, and 1,1-difluoro-2-iodoethane; sulfuric acid esters such as dimethyl sulfate; and sulfonic acid esters such as methyl p-toluenesulfonate, ethyl p-toluenesulfonate, n-propyl p-toluenesulfonate, methyl methanesulfonate, ethyl methanesulfonate, and n-propyl methanesulfonate.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (E1) is usually used in the proportion within a range of 1 to 10 mols, and the base is usually used in the proportion within a range of 1 to 10 mols, based on 1 mol of the compound (1-3).

The reaction temperature of the reaction is usually within a range of −20 to 150° C. The reaction time is usually within a range of 0.1 to 24 hours.

After completion of the reaction, the present compound represented by formula (1) can be isolated by performing post-treatment operations such as extraction of the reaction mixture with an organic solvent, and drying and concentration of the organic layer. The isolated present compound can be further purified by chromatography, recrystallization, and the like.

(Production Process E)

Among the present compounds represented by formula (1), a compound in which X is a sulfur atom (hereinafter referred to as the compound (1-S)) can be produced by reacting a compound in which X is an oxygen atom (hereinafter referred to as the compound (1-O)), among the present compounds represented by formula (1), with a sulfurizing agent:

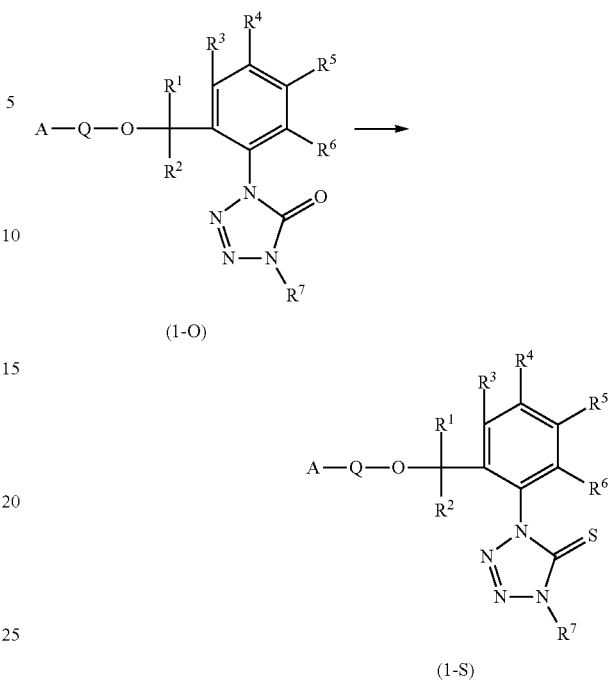

wherein $R^1$, $R^2$, $R^3$, $R^4$, $R^5$, $R^6$, $R^7$, A, and Q are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; nitriles such as acetonitrile and propionitrile; and mixtures thereof.

Examples of the sulfurizing agent to be used in the reaction include phosphorous pentasulfide and Lawesson's reagent (2,4-Bis(4-methoxyphenyl)-1,3,2,4-dithiadiphosphetane 2,4-disulfide).

In the reaction, the sulfurizing agent is preferably used in the proportion of 0.5 to 1.5 mols based on 1 mol of the compound (1-O).

The reaction temperature of the reaction is usually within a range of −20 to 150° C. The reaction time is usually within a range of 0.1 to 24 hours.

In the reaction, if necessary, organic bases such as pyridine and triethylamine, and inorganic bases such as alkali metal hydroxide and alkali metal carbonate may be added, and the amount of the based to be added is within a range of 0.5 to 1.5 mols based on the compound (1-O).

After completion of the reaction, the compound (1-S) can be isolated by performing post-treatment operations such as extraction of the reaction mixture with an organic solvent, and drying and concentration of the organic layer. The isolated present compound can be further purified by chromatography, recrystallization, and the like.

(Production Process F)

Among the present compounds represented by formula (1), a compound represented by formula (1-4) in which $R^3$ is $R^{71}$ (hereinafter referred to as the compound (1-4)) can be produced by subjecting a compound represented by formula (G1) (hereinafter referred to as the compound (G1)) and a compound represented by formula (G21) (hereinafter referred to as the compound (G21)) to a coupling reaction in the presence of a base and a catalyst:

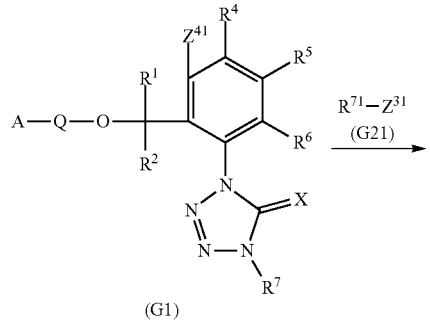

(G1)

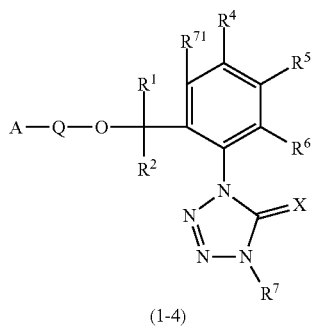

(1-4)

wherein $R^1$, $R^2$, $R^4$, $R^5$, $R^6$, $R^7$, A, Q, and $Z^{31}$ are the same as defined above, $Z^{4'}$ represents a chlorine atom, a bromine atom, an iodine atom, or a trifluoromethanesulfonyloxy group, and $R^{7'}$ represents a C1-C6 alkyl group optionally having one or more halogens, a C2-C6 alkenyl group optionally having one or more halogens, a C2-C6 alkynyl group optionally having one or more halogens, or a C3-C6 cycloalkyl group optionally having one or more halogens.

The reaction can be carried out in accordance with Production Process B.

Among the present compounds represented by formula (1), a compound represented by formula (1-5) in which $R^4$ is $R^{72}$ (hereinafter referred to as the compound (1-5)) can be produced by subjecting a compound represented by formula (G2) (hereinafter referred to as the compound (G2)) and a compound represented by formula (G22) (hereinafter referred to as the compound (G22)) to a coupling reaction in the presence of a base and a catalyst:

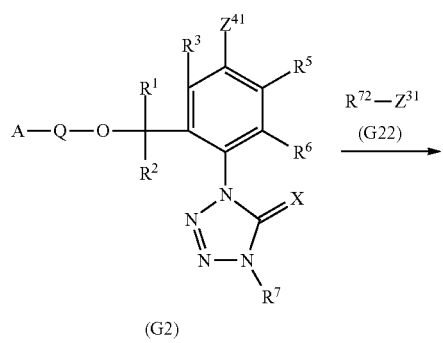

(G2)

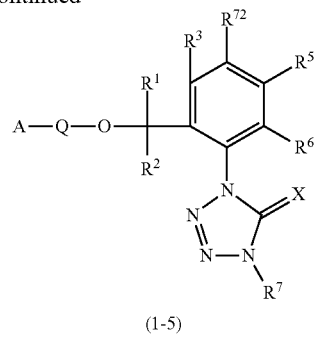

(1-5)

wherein $R^1$, $R^2$, $R^3$, $R^5$, $R^6$, $R^7$, A, Q, $Z^{31}$, and $Z^{41}$ are the same as defined above, and $R^{72}$ represents a C1-C3 alkyl group.

The reaction can be carried out in accordance with Production Process B.

Among the present compounds represented by formula (1), a compound represented by formula (1-6) in which $R^5$ is $R^{72}$ (hereinafter referred to as the compound (1-6)) can be produced by subjecting a compound represented by formula (G3) (hereinafter referred to as the compound (G3)) and the compound (G22) to a coupling reaction in the presence of a base and a catalyst:

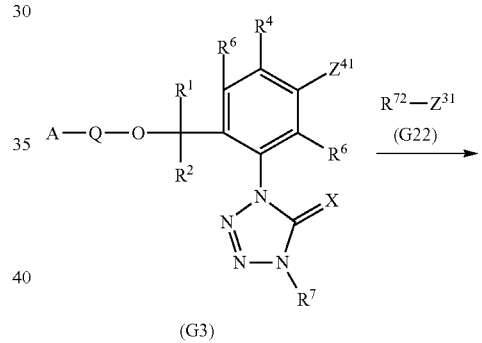

(G3)

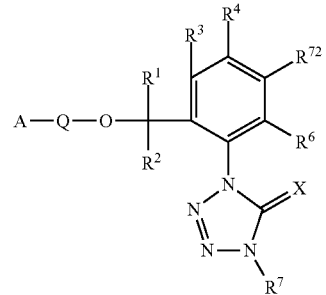

(1-6)

wherein $R^1$, $R^2$, $R^3$, $R^4$, $R^6$, $R^7$, A, Q, $R^{72}$, $Z^{31}$, and $Z^{41}$ are the same as defined above.

The reaction can be carried out in accordance with Production Process B.

Among the present compounds represented by formula (1), a compound represented by formula (1-7) in which $R^9$ is $R^{72}$ (hereinafter referred to as the compound (1-7)) can be produced by subjecting a compound represented by formula (G4) (hereinafter referred to as the compound (G4)) and the compound (G22) to a coupling reaction in the presence of a base and a catalyst:

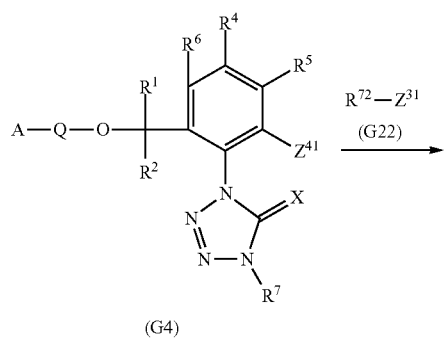

(G4)

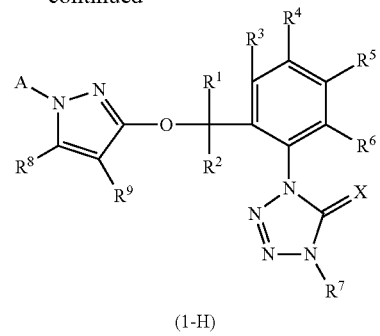

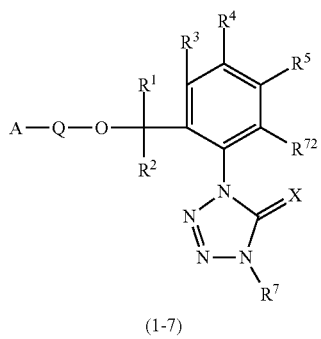

(1-7)

wherein $R^1$, $R^2$, $R^3$, $R^4$, $R^5$, $R^7$, Q, A, X, $R^{72}$, $Z^{31}$, and $Z^{41}$ are the same as defined above.

The reaction can be carried out in accordance with Production Process B.

In accordance with Production Process B, it is possible to produce a compound in which two or more substituents selected from $R^3$, $R^4$, $R^5$, and $R^6$ are $R^{71}$ and/or $R^{72}$, among the present compounds represented by formula (1).

It is also possible to produce the compound (1) by using the other known coupling reaction in place of the coupling reaction of the Production Process B.

(Production Process G)

Among the present compounds represented by formula (1), a compound represented by formula (1-H) in which Q is Q1 (hereinafter referred to as the compound (1-H)) can be produced by subjecting a compound represented by formula (H1) (hereinafter referred to as the compound (H1)) and a compound represented by formula (H2) (hereinafter referred to as the compound (H2)) to a coupling reaction in the presence of a base and a catalyst:

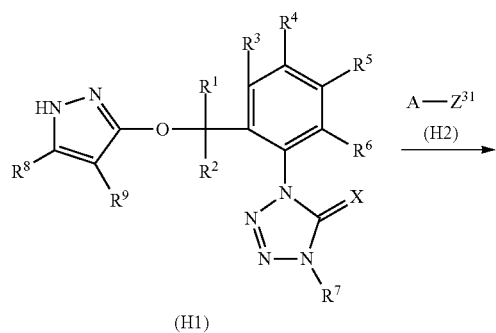

(H1)

(1-H)

wherein $R^1$, $R^2$, $R^3$, $R^4$, $R^5$, $R^6$, $R^7$, A, X, and $Z^{31}$ are the same as defined above, and $R^3$ and $R^9$ each independently represents a hydrogen atom, a halogen atom, a C1-C4 alkyl group, or a C1-C4 haloalkyl group.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

It is possible to usually use, as the compound (H2) to be used in the reaction, commercially available compounds.

Examples of the catalyst to be used in the reaction include copper(II) acetate, copper(I) iodide, copper(II) bromide, copper(II) chloride, palladium(II) acetate, dichlorobis(triphenylphosphine)palladium, tetrakistriphenylphosphinepalladium(0), palladium(II) acetate/tricyclohexylphosphine, bis(diphenylphoshineferrocenyl)palladium(II) dichloride, 1,3-bis(2,6-diisopropylphenyl)imidazol-2-ylidene(1,4-naphthoquinone)palladium dimer, allyl(chloro) (1,3-dimesityl-1,3-dihydro-2H-imidazol-2-ylidene)palladium or palladium (II) acetate/dicyclohexyl(2',4',6'-triisopropylbiphenyl-2-yl)phosphine, tris(dibenzylideneacetone)dipalladium, and the like.

Examples of the base to be used in the reaction include organic bases such as pyridine, triethylamine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (H2) is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (H1).

The reaction temperature of the reaction is usually within a range of 0 to 150° C. The reaction time of the reaction is usually within a range of 0.1 to 24 hours.

After completion of the reaction, the compound (1-H) can be isolated by performing post-treatment operations such as extraction of the reaction mixture with an organic solvent, and drying and concentration of the organic layer. The isolated present compound can be further purified by chromatography, recrystallization, and the like.

The process for the production of the present pyrazole compounds ZS3, ZS4, ZS5, ZS7, and ZS8 will be described in detail below.

(Synthesis Process A)

A compound represented by the following formula (ZS3) formula (hereinafter referred to as the compound (ZS3)) can be produced by reacting a compound represented by the following formula (ZS1) formula with a compound represented by the following formula (ZS2) in the presence of a base:

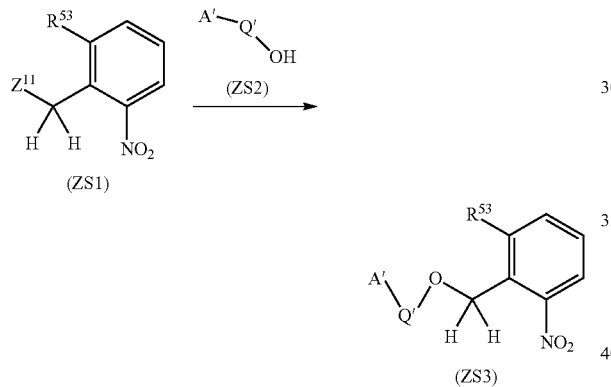

wherein $Z^{11}$, A', Q', and $R^{53}$ are the same as defined above.

The reaction can be carried out in accordance with Production Process A.

(Synthesis Process B)

A compound represented by the following formula (ZS4) (hereinafter referred to as the compound (ZS4)) can be produced by reacting the compound (ZS3) with hydrogen in the presence of a catalyst:

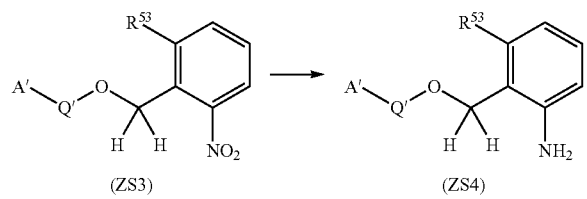

wherein A', Q', and $R^{53}$ are the same as defined above.

The reaction is usually performed in a solvent.

Examples of the solvent to be used in the reaction include alcohols such as methanol, ethanol, propanol, and butanol; esters such as ethyl acetate and butyl acetate; halogenated hydrocarbons such as carbon tetrachloride, chloroform, dichloromethane, 1,2-dichloroethane, tetrachloroethane, and chlorobenzene; ethers such as diethyl ether, tetrahydrofuran, 1,4-dioxane, ethylene glycol dimethyl ether, anisole, methyl tert-butyl ether, and diisopropyl ether; hydrocarbons such as n-heptane, n-hexane, cyclohexane, n-pentane, toluene, and xylene; water; and mixtures thereof.

Examples of the catalyst to be used in the reaction include palladium, platinum, osmium, ruthenium, rhodium, Raney nickel, and the like.

In the reaction, the catalyst is usually used in the proportion within a range of 0.0001 to 1 mol based on 1 mol of the compound (XE1).

The reaction temperature of the reaction is usually within a range of –20 to 150° C. The reaction time is usually within a range of 0.1 to 24 hours.

After completion of the reaction, the compound (XF2) can be isolated by performing post-treatment operations such as extraction of the reaction mixture with an organic solvent, and drying and concentration of the organic layer. The isolated compound may be further purified by operations such as distillation, chromatography, and recrystallization.

(Synthesis Process C)

A compound represented by the following formula (ZS5) (hereinafter referred to as the compound (ZS5)) can be produced by reacting the compound (ZS4) with an isocyanating agent.

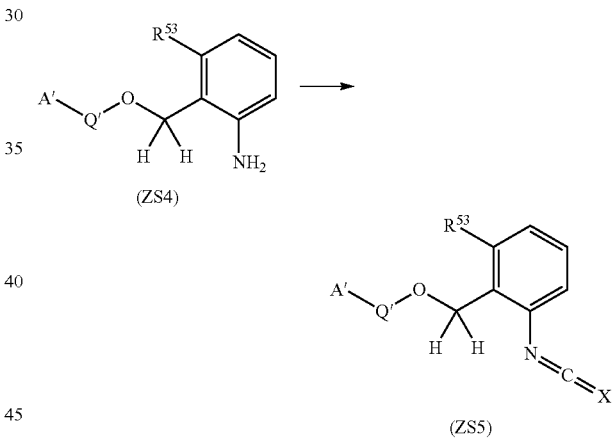

wherein A', Q', $R^{53}$, and X are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; esters such as ethyl acetate and methyl acetate; ketones such as acetone, methyl ethyl ketone, and methyl isobutyl ketone; nitriles such as acetonitrile and propionitrile; and mixtures thereof.

Examples of the isocyanating agent to be used in the reaction include phosgene, diphosgene, triphosgene, thiophosgene, N,N-carbodiimidazole, and N,N-thiocarbodiimidazole.

In the reaction, based on 1 mol of the compound (XB1), isocyanating agent is usually used in the proportion within a range of 0.34 to 10 mols.

The reaction temperature of the reaction is usually within a range of −20 to 150° C. The reaction time is usually within a range of 0.1 to 24 hours.

In the reaction, if necessary, organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; and alkali metal hydrogen carbonates such as lithium hydrogen carbonate, sodium hydrogen carbonate, potassium hydrogen carbonate, and cesium hydrogen carbonate may be added, and these compounds are usually used in the proportion within a range of 0.05 to 5 mols based on 1 mol of the compound (XB1).

After completion of the reaction, the compound (XA1) can be isolated by performing post-treatment operations such as extraction of the reaction mixture with an organic solvent, and drying and concentration of the organic layer. The isolated compound may be further purified by operations such as distillation, chromatography, and recrystallization.

(Synthesis Process D)

A compound represented by the following formula (ZS7) (hereinafter referred to as the compound (ZS7)) can be produced by reacting the compound (ZS6) with a halogenating agent:

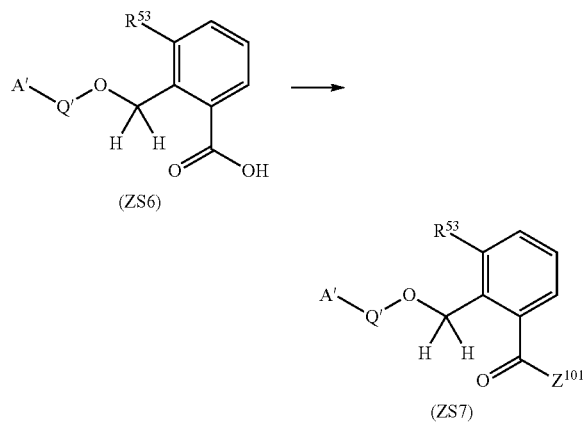

(ZS6)

(ZS7)

wherein A', Q', and $R^{53}$ are the same as defined above, and $Z^{101}$ represents a chlorine atom or a bromine atom.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; esters such as ethyl acetate and methyl acetate; ketones such as acetone, methyl ethyl ketone, and methyl isobutyl ketone; nitriles such as acetonitrile and propionitrile; and mixtures thereof.

Examples of the halogenating agent to be used in the reaction include phosphorus oxychloride, phosphorus trichloride, phosphorus pentachloride, thionyl chloride, phosphorus oxybromide, phosphorus tribromide, phosphorus pentabromide, phosphorus triiodide, oxalyl dichloride, oxalyl dibromide, triphosgene, diphosgene, phosgene, and sulfuryl chloride.

In the reaction, the halogenating agent is usually used in the proportion within a range of 0.33 to 10 mols based on 1 mol of the compound (XC1).

The reaction temperature of the reaction is usually within a range of −20 to 150° C. The reaction time is usually within a range of 0.1 to 24 hours.

In the reaction, the catalyst may be added and N,N-dimethylformamide, or the like is used. The amount of the catalyst to be used in usually in the proportion within a range of 0.001 to 1 mol based on 1 mol of the compound (XC1).

In the reaction, if necessary, organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; and alkali metal hydrogen carbonates such as lithium hydrogen carbonate, sodium hydrogen carbonate, potassium hydrogen carbonate, and cesium hydrogen carbonate may be added, and these compounds are usually used in the proportion within a range of 0.05 to 5 mols based on 1 mol of the compound (XC1).

After completion of the reaction, the compound (XA2) can be isolated by performing post-treatment operations such as extraction of the reaction mixture with an organic solvent, and drying and concentration of the organic layer. The isolated compound can be further purified by operations such as distillation, chromatography, and recrystallization (Synthesis Process E)

A compound represented by the following formula (ZS8) formula can be produced by reacting the compound (ZS5) or the compound (ZS7) with an azidation agent:

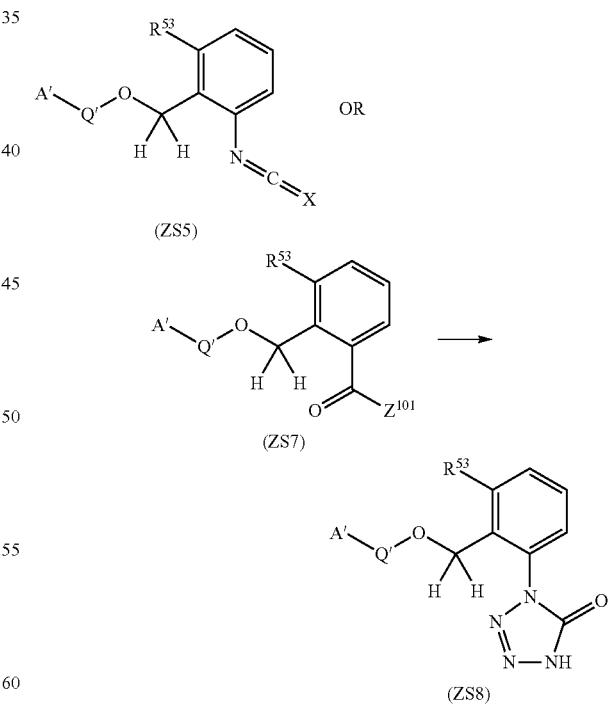

(ZS5)

(ZS7)

(ZS8)

wherein A', Q', $R^{53}$, $Z^{101}$ and X are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; and mixtures thereof.

Examples of the azidation agent to be used in the reaction include inorganic azides such as sodium azide, barium azide, and lithium azide; and organic azides such as trimethylsilyl azide and diphenylphosphoryl azide.

In the reaction, the azidation agent is usually used in the proportion within a range of 1 to 10 mols based on 1 mol of the compound (XA1) or the compound (XA2).

The reaction temperature of the reaction is usually within a range of −20 to 150° C. The reaction time is usually within a range of 0.1 to 24 hours.

In the reaction, if necessary, Lewis acid such as aluminum chloride or zinc chloride may be added, and these compounds are usually used in the proportion within a range of 0.05 to 5 mols based on 1 mol of the compound (XA1) or the compound (XA2).

After completion of the reaction, the compound (XA3) can be isolated by performing post-treatment operations such as extraction of the reaction mixture with an organic solvent, and drying and concentration of the organic layer. The isolated compound (XA3) can be further purified by chromatography, recrystallization, and the like.

The process for synthesis of an intermediate compound will be described in detail below.

(Reference Production Process A)

A compound represented by the following formula (XA3) (hereinafter referred to as the compound (XA3)) can be produced by reacting a compound represented by the following formula (XA1) (hereinafter referred to as the compound (XA1)) or a compound represented by formula (XA2) (hereinafter referred to as the compound (XA2)) with an azidation agent:

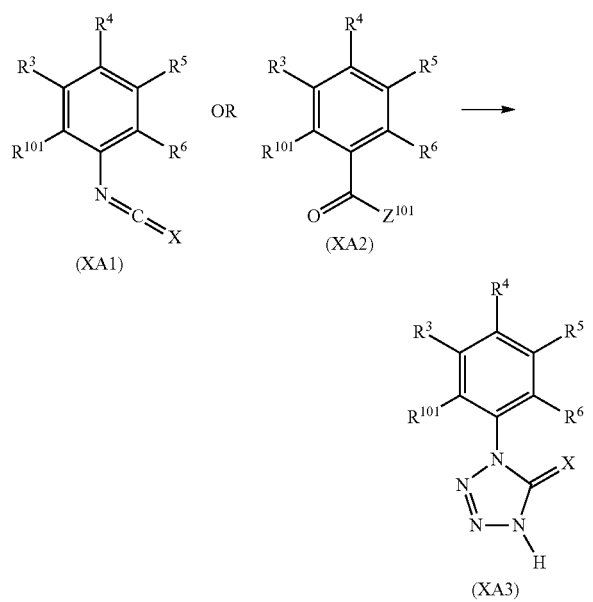

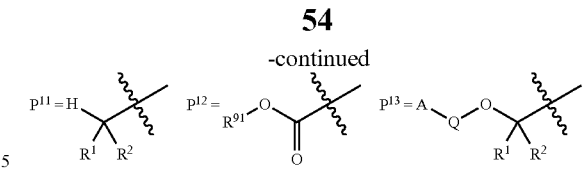

wherein $R^1$, $R^2$, $R^3$, $R^4$, $R^5$, $R^6$, A, Q, X, and $Z^{101}$ are the same as defined above, $R^{101}$ represents $P^{11}$, $P^{12}$, or $P^{13}$, $R^{91}$ represents a C1-C12 alkyl group, and the wavy line represents a binding site.

The reaction can be carried out in accordance with the above Synthesis Process E.

(Reference Production Process B)

The compound (XA1) can be produced by reacting a compound represented by the following formula (XB1) (hereinafter referred to as the compound (XB1)) with an isocyanating agent:

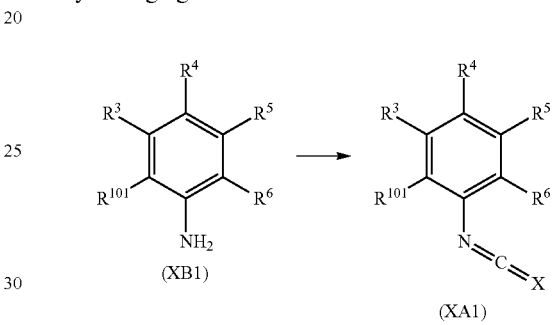

wherein $R^3$, $R^4$, $R^5$, $R^6$, $R^{101}$, and X are the same as defined above.

The reaction can be carried out in accordance with the above Synthesis Process C.

(Reference Production Process C)

The compound (XA2) can be produced by reacting a compound represented by the following formula (XC1) (hereinafter referred to as the compound (XC1)) with a halogenating agent:

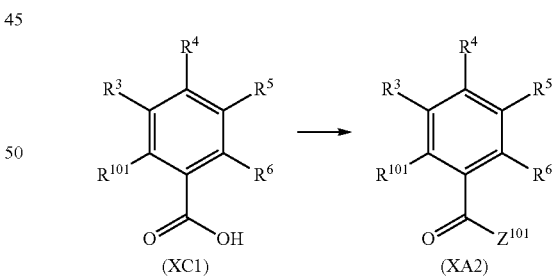

wherein $R^3$, $R^4$, $R^5$, $R^6$, $R^{101}$, and $Z^{101}$ are the same as defined above.

The reaction can be carried out in accordance with the above Synthesis Process D.

(Reference Production Process D)

The compound (XA1) can be produced by reacting the compound (XB1) with a carbamating agent to obtain a compound represented by the following formula (XD1) (hereinafter referred to as the compound (XD1)), followed by a reaction with an isocyanating agent:

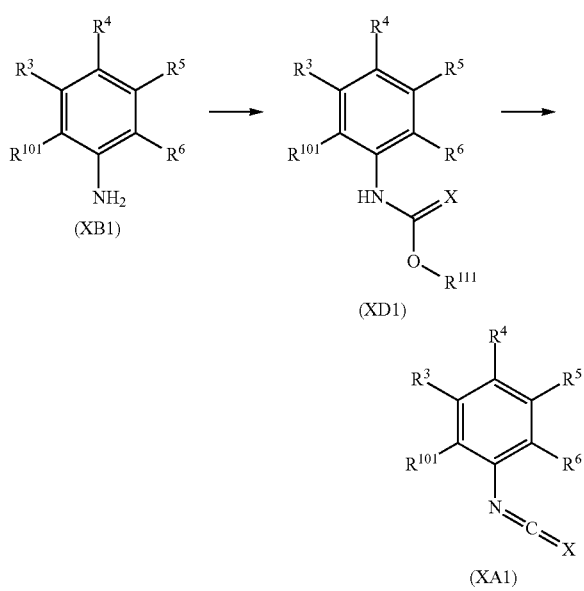

wherein $R^3$, $R^4$, $R^5$, $R^6$, $R^{101}$, and X are the same as defined above, and $R^{111}$ represents a C1-C12 alkyl group or a phenyl group.

The process for producing the compound (XD1) from the compound (XB1) will be described below.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

Examples of the carbamating agent to be used in the reaction include phenyl chlorocarbonate, methyl chlorocarbonate, ethyl chlorocarbonate, n-propyl chlorocarbonate, isopropyl chlorocarbonate, n-butyl chlorocarbonate, tert-butyl chlorocarbonate, di-tert-butyl dicarbonate, dimethyl dicarbonate, diethyl dicarbonate, O-phenyl chlorothioformate, O-methyl chlorothioformate, O-ethyl chlorothioformate, and the like.

In the reaction, the carbamating agent is usually used in the proportion within a range of 1 to 10 mols based on 1 mol of the compound (XB1).

The reaction temperature of the reaction is usually within a range of −20 to 150° C. The reaction time is usually within a range of 0.1 to 24 hours.

In the reaction, if necessary, organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; and alkali metal hydrogen carbonates such as lithium hydrogen carbonate, sodium hydrogen carbonate, potassium hydrogen carbonate, and cesium hydrogen carbonate may be added, and these compounds are usually used in the proportion within a range of 0.05 to 5 mols based on 1 mol of the compound (XB1).

After completion of the reaction, the compound (XD1) can be isolated by performing post-treatment operations such as extraction of the reaction mixture with an organic solvent, and drying and concentration of the organic layer. The isolated compound may be further purified by operations such as distillation, chromatography, and recrystallization.

The process for producing the compound (XA1) from the compound (XD1) will be described below.

The reaction is usually performed in a solvent.

Examples of the solvent to be used in the reaction include ethers such as tetrahydrofuran, dioxane, ethylene glycol dimethyl ether, and methyl tert-butyl ether; aromatic hydrocarbons such as toluene and xylene; halogenated hydrocarbons such as carbon tetrachloride, chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; and mixtures thereof.

Examples of the isocyanating agent to be used in the reaction include phosphorus pentachloride, phosphorus oxychloride, diphosphorus pentaoxide, trichlorosilane, dichlorosilane, monochlorosilane, boron trichloride, 2-chloro-1,3,2-benzodioxaborole, diiodosilane, methyltrichlorosilane, dimethyldichlorosilane, chlorotrimethylsilane, and the like.

In the reaction, the isocyanating agent is usually used in the proportion within a range of 1 to 10 mols based on 1 mol of the compound (XD1).

The reaction temperature of the reaction is usually within a range of −20 to 250° C. The reaction time of the reaction is usually within a range of 0.1 to 24 hours.

In the reaction, if necessary, organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; and alkali metal hydrogen carbonates such as lithium hydrogen carbonate, sodium hydrogen carbonate, potassium hydrogen carbonate, and cesium hydrogen carbonate may be added, and these compounds are usually used in the proportion within a range of 0.05 to 5 mols based on 1 mol of the compound (XD1).

After completion of the reaction, the compound (XA1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process E)

A compound represented by the following formula (XE2) (hereinafter referred to as the compound (XE2)) can be produced by reacting a compound represented by the following formula (XE1) (hereinafter referred to as the compound (XE1)) with hydrogen in the presence of a catalyst:

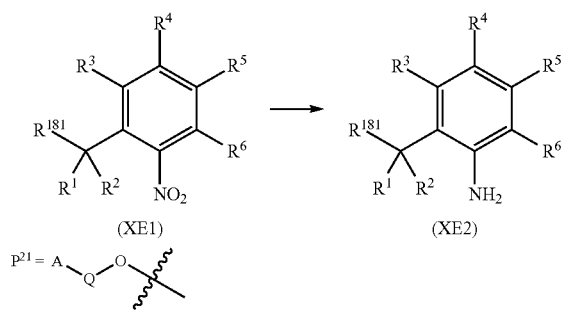

(XE1)   (XE2)

$P^{21} = A\diagdown Q\diagdown O\diagdown$ wherein $R^1$, $R^2$, $R^3$, $R^4$, $R^5$, $R^6$, A, and Q are the same as defined above, $R^{181}$ represents a hydrogen atom or $P^{21}$, and the wavy line represents a binding site.

The reaction can be carried out in accordance with Synthesis Process B.

(Reference Production Process F)

The compound (XE2) can be produced by reacting the compound (XE1) with a reducing agent in the presence of an acid:

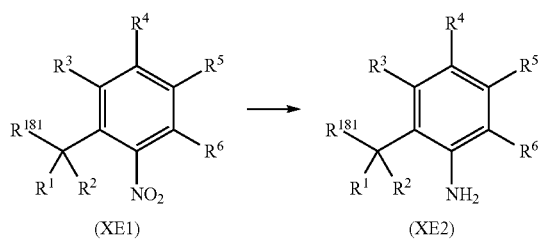

(XE1)   (XE2)

wherein $R^1$, $R^2$, $R^3$, $R^4$, $R^5$, $R^6$, and $R^{181}$ are the same as defined above.

The reaction is usually performed in a solvent.

Examples of the solvent to be used in the reaction include aliphatic carboxylic acids such as acetic acid; alcohols such as methanol and ethanol; water; and mixtures thereof.

Examples of the reducing agent to be used in the reaction include iron, tin, and zinc.

Examples of the acid to be used in the reaction include hydrochloric acid, sulfuric acid, acetic acid, an aqueous ammonium chloride solution, and the like.

In the reaction, the reducing agent is usually used in the proportion within a range of 1 to 30 mols based on 1 mol of the compound (XE1).

The reaction temperature of the reaction is usually within a range of −20 to 150° C. The reaction time is usually within a range of 0.1 to 24 hours.

After completion of the reaction, the compound (XE2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process G)

A compound represented by the following formula (XG2) (hereinafter referred to as the compound (XG2)) can be produced by reacting a compound represented by the following formula (XG1) (hereinafter referred to as the compound (XG1)) with the compound (E1) in the presence of a base:

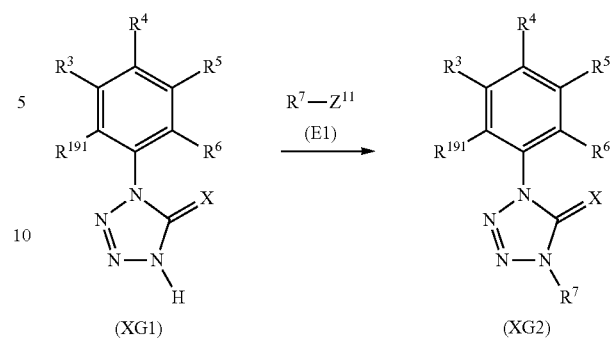

(XG1)   (XG2)

wherein $R^3$, $R^4$, $R^5$, $R^6$, $R^7$, X, and $Z^{11}$ are the same as defined above, and $R^{191}$ represents $P^{11}$ or $P^{12}$.

The reaction can be carried out in accordance with Production Process E.

(Reference Production Process H)

A compound represented by the following formula (XH2) (hereinafter referred to as the compound (XH2)) can be produced by reacting a compound represented by the following formula (XH1) (hereinafter referred to as the compound (XH1)) with a halogenating agent:

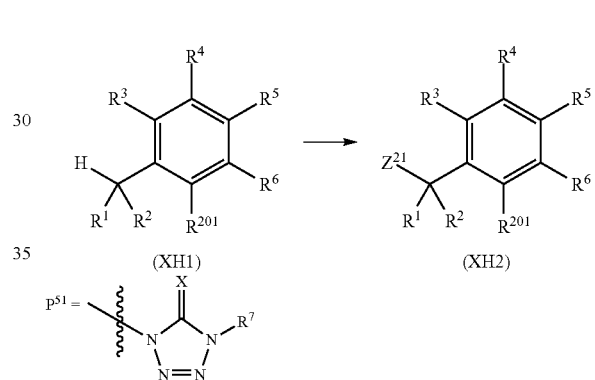

(XH1)   (XH2)

$P^{51} = $ wherein $R^1$, $R^2$, $R^3$, $R^4$, $R^5$, $R^6$, $R^7$, $Z^{21}$, and X are the same as defined above, and $R^{201}$ represents $P^{51}$ or a nitro group.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, fluorobenzene, difluorobenzene, trifluorobenzene, chlorobenzene, dichlorobenzene, trichlorobenzene, α,α,α-trifluorotoluene, and α,α,α-trichlorotoluene; esters such as ethyl acetate and methyl acetate; ketones such as acetone, methyl ethyl ketone, and methyl isobutyl ketone; nitriles such as acetonitrile and propionitrile; and mixtures thereof.

Examples of the halogenating agent usable in the reaction include a chlorinating agent, a brominating agent, or an iodinating agent, for example, chlorine, bromine, iodine, sulfuryl chloride, N-chlorosuccinimide, N-bromosuccinimide, 1,3-dibromo-5,5-dimethylhydantoin, iodosuccinimide, tert-butyl hypochlorite, N-chloroglutarimide, N-bromoglutarimide, N-chloro-N-cyclohexyl-benzenesulfonimide, N-bromophthalimide, and the like.

In the reaction, a radical initiator can also be used.

Examples of the radical initiator to be used in the reaction include benzoyl peroxide, azobisisobutyronitrile (AIBN), diacyl peroxide, dialkylperoxydicarbonate, tert-alkylperoxyester, monoperoxycarbonate, di(tert-alkylperoxy)ketal, and ketone peroxide.

In the reaction, the halogenating agent is usually used in the proportion within a range of 1 to 10 mols, and the radical initiator is usually used in the proportion within a range of 0.01 to 5 mols, based on 1 mol of the compound (XH1).

The reaction temperature of the reaction is usually within a range of −20 to 150° C. The reaction time is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process I)

A compound represented by the following formula (XJ2) (hereinafter referred to as the compound (XJ2)) can be produced by reacting the compound (XH2) with a compound represented by the following formula (XJ1) (hereinafter referred to as the compound (XJ1)):

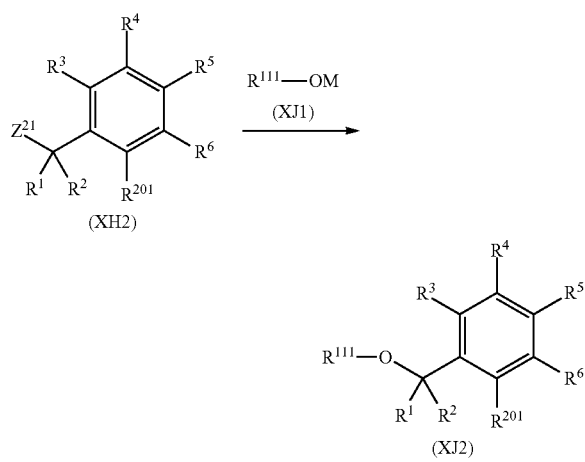

wherein $R^1$, $R^2$, $R^3$, $R^4$, $R^5$, $R^6$, $R^{111}$, $R^{201}$, and $Z^{21}$ are the same as defined above, and M represents sodium, potassium, or lithium.

The reaction is usually performed in a solvent.

Examples of the solvent to be used in the reaction include ethers such as diethyl ether, tetrahydrofuran, 1,4-dioxane, ethylene glycol dimethyl ether, anisole, methyl tert-butyl ether, and diisopropyl ether; hydrocarbons such as n-heptane, n-hexane, cyclohexane, n-pentane, toluene, and xylene; halogenated hydrocarbons such as carbon tetrachloride, chloroform, dichloromethane, 1,2-dichloroethane, tetrachloroethane, and chlorobenzene; nitriles such as acetonitrile and propionitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the compound (XJ1) usable in the reaction, sodium methoxide, sodium ethoxide, sodium n-propoxide, sodium n-butoxide, sodium isopropoxide, sodium sec-butoxide, sodium tert-butoxide, potassium methoxide, potassium ethoxide, potassium n-propoxide, potassium n-butoxide, potassium isopropoxide, potassium sec-butoxide, potassium tert-butoxide, sodium phenoxide, and the like.

In the reaction, the compound (XJ1) is usually used in the proportion within a range of 1 to 10 mols based on 1 mol of the compound (XH2).

The reaction temperature of the reaction is usually within a range of −20 to 150° C. The reaction time is usually within a range of 0.1 to 24 hours.

After completion of the reaction, the compound (XJ2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process J)

A compound represented by the following formula (XK1) (hereinafter referred to as the compound (XK1)) can be produced by reacting the compound (XH2) with water in the presence of a base:

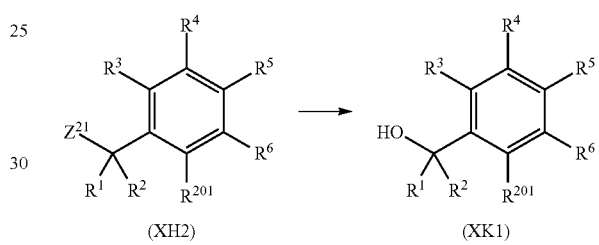

wherein $R^1$, $R^2$, $R^3$, $R^4$, $R^5$, $R^6$, $R^{201}$, and $Z^{21}$ are the same as defined above.

The reaction is usually performed in water, or a solvent containing water.

Examples of the solvent to be used in the reaction include ethers such as diethyl ether, tetrahydrofuran, 1,4-dioxane, ethylene glycol dimethyl ether, anisole, methyl tert-butyl ether, and diisopropyl ether; hydrocarbons such as n-heptane, n-hexane, cyclohexane, n-pentane, toluene, and xylene; halogenated hydrocarbons such as carbon tetrachloride, chloroform, dichloromethane, 1,2-dichloroethane, tetrachloroethane, and chlorobenzene; nitriles such as acetonitrile and propionitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; metal organic acid salts such as lithium formate, lithium acetate, sodium formate, sodium acetate, potassium formate, and potassium acetate; metal nitrates such as silver nitrate and sodium nitrate; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; and alkali metal alkoxides such as sodium methoxide, sodium ethoxide, sodium tert-butoxide, and potassium tert-butoxide.

In the reaction, the base is usually used in the proportion within a range of 1 to 100 mols based on 1 mol of the compound (XH2).

In the reaction, water is usually used in the proportion within a range of 1 mol to large excess based on 1 mol of the compound (XH2).

The reaction temperature of the reaction is usually within a range of −20 to 150° C. The reaction time is usually within a range of 0.1 to 24 hours.

After completion of the reaction, the compound (XK1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process K)

The compound (XH2) can be produced by reacting the compound (XJ2) with a halogenating agent:

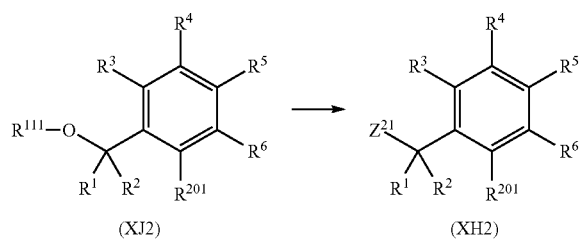

wherein $R^1$, $R^2$, $R^3$, $R^4$, $R^5$, $R^6$, $R^{111}$, $R^{201}$, and $Z^{21}$ are the same as defined above.

The reaction is usually performed in a solvent.

Examples of the solvent to be used in the reaction include hydrocarbons such as n-heptane, n-hexane, cyclohexane, n-pentane, toluene, and xylene; halogenated hydrocarbons such as carbon tetrachloride, chloroform, dichloromethane, 1,2-dichloroethane, tetrachloroethane, and chlorobenzene; ketones such as acetone, methyl ethyl ketone, and methyl isobutyl ketone; nitriles such as acetonitrile and propionitrile; organic acids such as formic acid, acetic acid, and trifluoroacetic acid; water; and mixtures thereof.

Examples of the halogenating agent to be used in the reaction include hydrochloric acid, hydrobromic acid, and hydroiodic acid.

In the reaction, the halogenating agent is usually used in the proportion of 1 mol or more based on 1 mol of the compound (XJ2).

The reaction temperature of the reaction is usually within a range of −20 to 150° C. The reaction time is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process L)

The compound (XH2) can be produced by reacting the compound (XK1) with a halogenating agent:

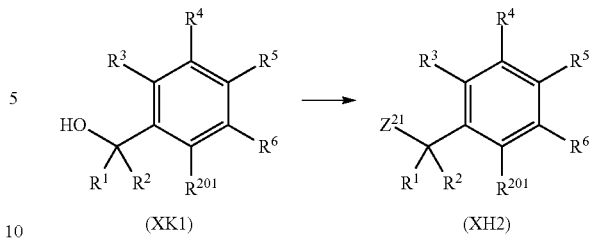

wherein $R^1$, $R^2$, $R^3$, $R^4$, $R^5$, $R^6$, $R^{201}$, and $Z^{21}$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; esters such as ethyl acetate and methyl acetate; ketones such as acetone, methyl ethyl ketone, and methyl isobutyl ketone; nitriles such as acetonitrile and propionitrile; organic acids such as formic acid, acetic acid, and trifluoroacetic acid; water; and mixtures thereof.

Examples of the halogenating agent to be used in the reaction include bromine, chlorine, sulfuryl chloride, hydrochloric acid, hydrobromic acid, hydroiodic acid, boron tribromide, phosphorus tribromide, trimethylsilyl chloride, trimethylsilyl bromide, trimethylsilyl iodide, thionyl chloride, thionyl bromide, phosphorus oxychloride, phosphorus trichloride, phosphorus pentachloride, thionyl chloride, phosphorus oxybromide, phosphorus pentabromide, phosphorus triiodide, oxalyl dichloride, oxalyl dibromide, acetyl chloride, carbon tetrabromide, N-bromosuccinimide, lithium chloride, sodium iodide, acetyl bromide, and the like.

In the reaction, the halogenating agent is usually used in the proportion within a range of 1 to 10 mols based on 1 mol of the compound (XK1).

In order to accelerate the reaction, additives may be added according to the halogenating agent to be used, and specific examples thereof include zinc chloride for acetyl chloride, triphenylphosphine for carbon tetrabromide, dimethyl sulfide for N-bromosuccinimide, boron trifluoride diethyl ether complex for sodium iodide, boron trifluoride diethyl ether complex for acetyl bromide, triethylamine and methanesulfonyl chloride for lithium chloride, aluminum chloride for sodium iodide, trimethylsilyl chloride for sodium iodide, and the like. Any additives are usually used in the proportion within a range of 0.01 to 5 mols based on 1 mol of the compound (XK1).

The reaction temperature of the reaction is usually within a range of −20 to 150° C. The reaction time is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process M)

A compound represented by the following formula (XM3) (hereinafter referred to as the compound (XM3)) can be produced by reacting the compound (XK1) with a generally available compound represented by the following formula (XM2) (hereinafter referred to as the compound (XM2)) in the presence of a base:

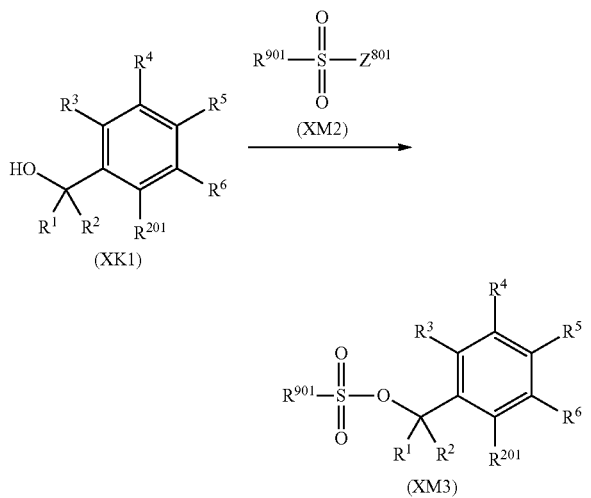

wherein $R^1$, $R^2$, $R^3$, $R^4$, $R^5$, $R^6$, and $R^{201}$ are the same as defined above, $R^{901}$ represents a C1-C6 alkyl group, a C1-C6 haloalkyl group, a C6-C16 aryl group, or a C6-C16 haloaryl group, and $Z^{801}$ represents a fluorine atom, a chlorine atom, bromine atom, or an iodine atom.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; nitriles such as acetonitrile and propionitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; and mixtures thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium methoxide, sodium ethoxide, sodium tert-butoxide, and potassium tert-butoxide.

In the reaction, the compound (XM2) is usually used in the proportion within a range of 1 to 10 mols, and the base is usually used in the proportion within a range of 1 to 5 mols, based on 1 mol of the compound (XK1).

The reaction temperature of the reaction is usually within a range of −20 to 150° C. The reaction time is usually within a range of 0.1 to 24 hours.

If necessary, sodium iodide, tetrabutylammonium iodide, and the like may be added in the reaction, and these compounds are usually used within a range of 0.001 to 1.2 mols based on 1 mol of the compound (XK1).

After completion of the reaction, the compound (XM3) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process N)

A compound represented by the following formula (XN12) (hereinafter referred to as the compound (XN12)) can be produced by subjecting a compound represented by the following formula (XN11) (hereinafter referred to as the compound (XN11)) and the compound (G21) to a coupling reaction in the presence of a base and a catalyst:

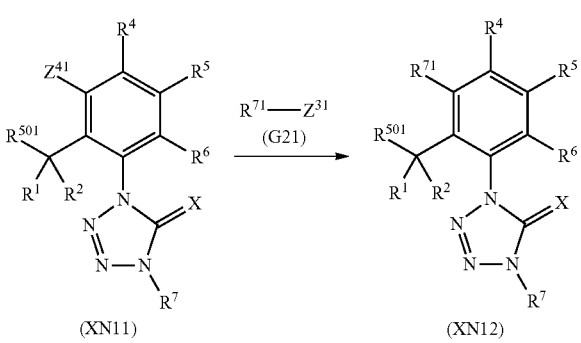

wherein $R^{501}$ represents a hydrogen atom or $OR^{111}$, and $R^{111}$, $R^1$, $R^2$, $R^4$, $R^5$, $R^6$, $R^7$, $R^{71}$, X, $Z^{31}$, and $Z^{41}$ are the same as defined above.

The reaction can be carried out in accordance with Production Process B.

A compound represented by the following formula (XN22) (hereinafter referred to as the compound (XN22)) can be produced by subjecting a compound represented by the following formula (XN21) (hereinafter referred to as the compound (XN21)) and the compound (G22) to a coupling reaction in the presence of a base and a catalyst:

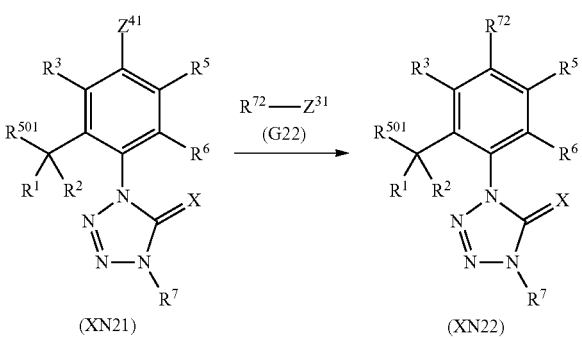

wherein $R^1$, $R^2$, $R^6$, $R^3$, $R^5$, $R^6$, $R^7$, $R^{72}$, $R^{501}$, X, $Z^{31}$, and $Z^{41}$ are the same as defined above.

The reaction can be carried out in accordance with Production Process B.

A compound represented by the following formula (XN32) (hereinafter referred to as the compound (XN32)) can be produced by subjecting a compound represented by the following formula (XN31) (hereinafter referred to as the compound (XN31)) and the compound (G22) to a coupling reaction in the presence of a base and a catalyst:

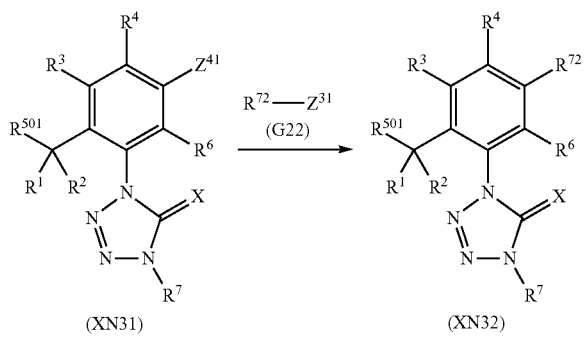

wherein $R^1$, $R^2$, $R^3$, $R^4$, $R^6$, $R^7$, $R^{72}$, $R^{501}$, X, $Z^{31}$, and $Z^{41}$ are the same as defined above.

The reaction can be carried out in accordance with Production Process B.

A compound represented by the following formula (XN42) (hereinafter referred to as the compound (XN42)) can be produced by subjecting a compound represented by the following formula (XN41) (hereinafter referred to as the compound (XN41)) and the compound (G22) to a coupling reaction in the presence of a base and a catalyst:

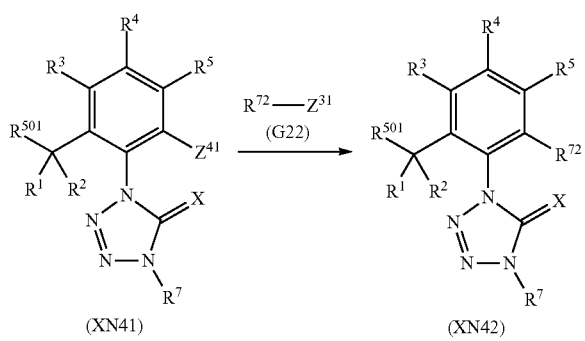

wherein $R^1$, $R^2$, $R^3$, $R^4$, $R^5$, $R^7$, $R^{72}$, $R^{501}$, X, $Z^{31}$, and $Z^{41}$ are the same as defined above.

The reaction can be carried out in accordance with Production Process B.

In accordance with Production Process B, it is possible to produce a compound in which two or more substituents selected from $R^3$, $R^4$, $R^5$, and $R^6$ are $R^{71}$ and/or $R^{72}$, among compounds represented by the following formula (XN50):

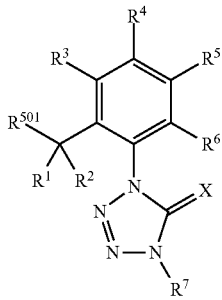

wherein $R^1$, $R^2$, $R^3$, $R^4$, $R^5$, $R^6$, $R^7$, $R^{501}$ and X are the same as defined above.

Furthermore, it is possible to produce the compound (XN50) by using the other known coupling reaction in place of the coupling reaction mentioned in Production Process B. (Reference Production Process O)

A compound represented by the following formula (XW2) (hereinafter referred to as the compound (XW2)) can be produced by reacting a compound represented by the following formula (XW1) formula (hereinafter referred to as the compound (XW1)) with a compound represented by the following formula (XW3) (hereinafter referred to as the compound (XW3)) in the presence of a reaction accelerator:

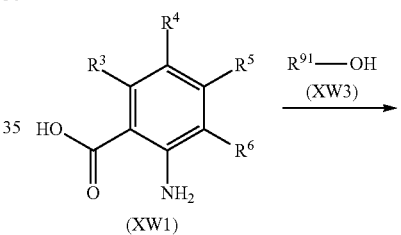

wherein $R^3$, $R^4$, $R^5$, $R^6$, and $R^{91}$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; and mixtures thereof, and the compound (XW3) may be used as the solvent.

Examples of the compound (XW3) usable in the reaction include methyl alcohol, ethyl alcohol, propyl alcohol, isopropyl alcohol, n-butyl alcohol, sec-butyl alcohol, t-butanol, n-pentanol, and the like.

Examples of the reaction accelerator to be used in the reaction include mineral acids such as hydrochloric acid and sulfuric acid; carbodiimides such as dicyclohexylcarbodiimide, diisopropylcarbodiimide, and N'-(3-dimethylaminopropyl)-N-ethylcarbodiimide; organic acids such as methanesulfonic acid and toluenesulfonic acid; Mitsunobu reaction reagents such as triphenylphosphine/diethyl azodicarboxylate; thionyl chloride, boron trifluoride-ethyl ether complex, and the like.

In the reaction, the reaction accelerator is usually used in the proportion within a range of 0.01 to 10 mols based on 1 mol of the compound (XW1).

In the reaction, if necessary, organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; and alkali metal hydrogen carbonates such as lithium hydrogen carbonate, sodium hydrogen carbonate, potassium hydrogen carbonate, and cesium hydrogen carbonate may be added, and these compounds are usually used in the proportion within a range of 0.001 to 5 mols based on 1 mol of the compound (XW1).

In the reaction, an excess amount of compound (XW3) is used based on the compound (XW1).

The reaction temperature of the reaction is usually within a range of −78 to 100° C. The reaction time of the reaction is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process P)

The compound (XW2) can be produced by reacting the compound (XW1) with a halogenating agent to obtain a compound represented by the following formula (XV1) (hereinafter referred to as the compound (XV1)), and then reacting the compound (XV1) with the compound (XW3):

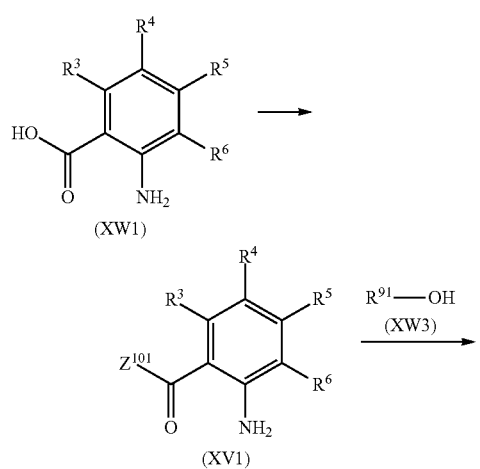

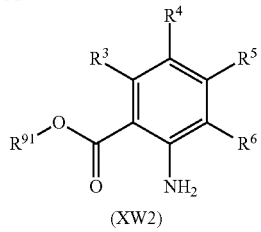

wherein $R^3$, $R^4$, $R^5$, $R^6$, $R^{91}$, and $Z^{101}$ are the same as defined above.

The process for producing the compound (XV1) by reacting the compound (XW1) with a halogenating agent can be carried out in accordance with Reference Production Process C.

The process for producing the compound (XW2) from the compound (XV1) will be described below.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; and mixtures thereof, and the compound (XW3) may be used as the solvent.

In the reaction, an excess amount of compound (XW3) is used based on the compound (XV1).

The reaction temperature of the reaction is usually within a range of −78 to 100° C. The reaction time of the reaction is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process Q)

The compound (XW2) can be produced by reacting the compound (XW1) with an alkylating agent:

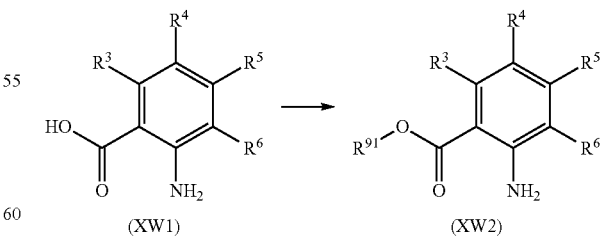

wherein $R^3$, $R^4$, $R^5$, $R^6$, and $R^{91}$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

Examples of the alkylating agent usable in the reaction include diazomethane, trimethylsilyldiazomethane, chlorodifluoromethane; halogenated alkyls such as methyl bromide, ethyl bromide, n-propyl bromide, methyl iodide, ethyl iodide, and n-propyl bromide; sulfuric acid esters such as dimethyl sulfate, diethyl sulfate, and di-n-propyl sulfate; and sulfonic acid esters such as methyl p-toluenesulfonate, ethyl p-toluenesulfonate, n-propyl p-toluenesulfonate, methyl methanesulfonate, ethyl methanesulfonate, and n-propyl methanesulfonate.

In the reaction, the alkylating agent is usually used in the proportion within a range of 1 to 10 mols based on 1 mol of the compound (XW1).

In the reaction, if necessary, organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; quaternary ammonium salts such as tetra(n-butyl) ammonium hydroxide may be added, and these compounds are usually used in the proportion within a range of 0.001 to 5 mols based on 1 mol of the compound (XW1).

The reaction temperature of the reaction is usually within a range of −78 to 100° C. The reaction time of the reaction is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process T)

A compound represented by the following formula (XS2) (hereinafter referred to as the compound (XS2)) can be produced by reacting a compound represented by the following formula (XS1) (hereinafter referred to as the compound (XS1)) with the compound (A2) in the presence of a base:

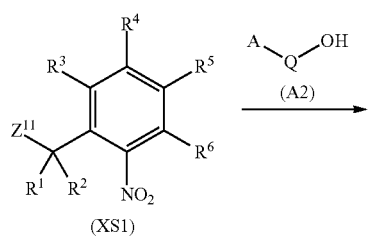

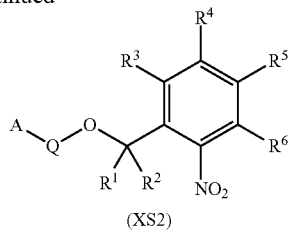

wherein $R^1$, $R^2$, $R^3$, $R^4$, $R^5$, $R^6$, A, Q, and $Z^{11}$ are the same as defined above.

The reaction can be carried out in accordance with Production Process A.

(Reference Production Process AA)

A compound represented by the following formula (XAA2) formula can be produced by reacting a compound represented by formula (XAA1) with a reducing agent:

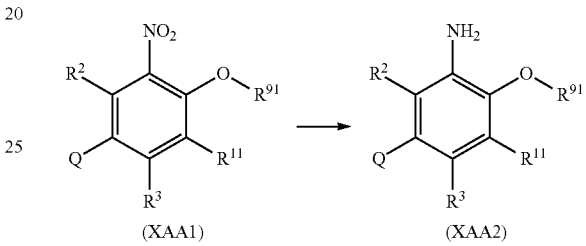

wherein $R^2$, $R^3$, $R^{11}$, $R^{91}$, and Q are the same as defined above.

The reaction can be carried out in accordance with Reference Production Process F.

Although a form used for the present compound may be the present compound as itself, the present compound is usually used after mixing with solid carriers, liquid carriers, surfactants, and the like, and optionally adding auxiliary agents for formulation, such as stickers, dispersers, and stabilizers to thereby formulate into wettable powders, water dispersible granules, flowables, granules, dry flowables, emulsifiable concentrates, aqueous solutions, oil solutions, smoking agents, aerosols, microcapsules, and the like. In these formulations, the present compound is usually contained within a range of 0.1 to 99', and preferably 0.2 to 90% by weight.

Examples of the solid carriers include clays (for example, kaolin, diatomaceous earth, synthetic hydrated silicon dioxide, Fubasami clay, bentonite, and acid clay), talcs or other inorganic minerals (for example, sericite, quartz powder, sulfur powder, activated charcoal, calcium carbonate, and hydrated silica) in the form of fine powders or particulates, and examples of the liquid carries include water, alcohols (for example, methanol and ethanol), ketones (for example, acetone and methyl ethyl ketone), aromatic hydrocarbons (for example, benzene, toluene, xylene, ethylbenzene, and methyl naphthalene), aliphatic hydrocarbons (for example, n-hexane, cyclohexane, and kerosene), esters (for example, ethyl acetate and butyl acetate), nitriles (for example, acetonitrile and isobutyronitrile), ethers (for example, dioxane and diisopropylether), acid amides (for example, DMF and dimethylacetamide), and halogenated hydrocarbons (for example, dichloroethane, trichloroethylene, and carbon tetrachloride).

Examples of the surfactants include alkyl sulfates, alkyl sulfonates, alkyl aryl sulfonates, alkyl aryl ethers, and polyoxyethylenated compounds thereof, polyethylene glycol ethers, polyhydric alcohol esters, and sugar alcohol derivatives.

Examples of other auxiliary agents for formulation include stickers and dispersers, specifically casein, gelatin, polysaccharides (for example, starch, gum arabic, cellulose derivatives, and alginic acid), lignin derivatives, bentonite, sugars, water-soluble synthetic polymers (for example, polyvinyl alcohol, polyvinylpyrrolidone, and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or esters thereof, and the like.

The method for applying the present control agent is not particularly limited, as long as the applying form is a form by which the present control agent may be applied substantially, and includes, for example, an application to plants such as a foliage application; an application to area for cultivating plants such as a submerged treatment; and an application to soil such as seed disinfection.

The present control agent may be used as a mixture with various oils such as mineral oils or vegetable oils, or surfactants. Specific examples of oils or surfactants, which can be used as a mixture with various oils or surfactants, include Nimbus (registered trademark), Assist (registered trademark), Aureo (registered trademark), Iharol (registered trademark), Silwet L-77 (registered trademark), BreakThru (registered trademark), Sundancell (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7 (registered trademark), Emulad (registered trademark), TRITON X 45 (registered trademark), AGRAL 90 (registered trademark), AGROTIN (registered trademark), ARPON (registered trademark), EnSpray N (registered trademark), BANOLE (registered trademark), and the like.

The present control agent can also be used as a mixture with or together with other fungicides, insecticides, acaricides, nematicides, and plant growth regulators.

Examples of these other fungicides include the followings.

(1) Azole Fungicides
such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, flutriafol, simeconazole, ipconazole, azaconazole, diniconazole-M, etaconazole, imibenconazole, oxpoconazole, triadimefon, and uniconazole;

(2) Amine Fungicides
such as fenpropimorph, tridemorph, fenpropidin, spiroxamine; aldimorph, dodemorph, and piperalin;

(3) Benzimidazole Fungicides
such as carbendazim, benomyl, thiabendazole, thiophanate-methyl, fuberidazole, and thiophanate;

(4) Dicarboximide Fungicides
such as procymidone, iprodione, and vinclozolin;

(5) Anilinopyridine Fungicides
such as cyprodinil, pyrimethanil, and mepanipyrim;

(6) Phenylpyrrole Fungicides
such as fenpiclonil and fludioxonil;

(7) Strobilurin Fungicides
such as kresoxim-methyl, azoxystrobin, trifloxystrobin, fluoxastrobin, picoxystrobin, pyraclostrobin, dimoxystrobin, pyribencarb, metominostrobin, orysastrobin, enestrobin, pyraoxystrobin, pyrametostrobin, fenaminstrobin, enoxastrobin, coumoxystrobin, triclopyricarb, and mandestrobin;

(8) Phenylamide Fungicides
such as metalaxyl, metalaxyl-M or mefenoxam, benalaxyl, benalaxyl-M or kiralaxyl, furalaxyl, ofurace, and oxadixyl;

(9) Carboxylic Acid Amide Fungicides
such as dimethomorph, iprovalicarb, benthivalicarb-isopropyl, mandipropamid, valiphenal or valifenalate, and flumorph;

(10) Carboxamide Fungicides
such as carboxin, mepronil, flutolanil, thifluzamide, furametpyr, boscalid, penthiopyrad, fluopyram, bixafen, penflufen, sedaxane, fluxapyroxad, isopyrazam, benzovindiflupyr, isofetamid, N-[2-(3,4-difluorophenyl)phenyl]-3-trifluoromethylpyrazine-2-carboxylic acid amide, N-(1,1,3-trimethylindan-4-yl)-1-methyl-3-difluoromethylpyrazole-4-carboxylic acid amide (including racemate or enantiomer, a mixture of enantiomer of R form and enantiomer of S form at an optional ratio, benodamil, fenfuram, and oxycarboxin;

(11) Other Fungicides
such as diethofencarb, thiuram, fluazinam, mancozeb, chlorothalonil, captan, dichlofluanid, folpet, quinoxyfen, fenhexanid, fanoxadon, fenamidon, zoxamide, ethaboxam, amisulbrom, cyazofamid, metrafenone, pyriofenone, cyflufenamid, proquinazid, flusulfamide, fluopicolide, fosetyl-aluminum, propamocarb, propamocarb hydrochloride, cymoxanil, pencycuron, tolclofos-methyl, carpropamid, diclocymet, fenoxanil, tricyclazole, pyroquilon, probenazole, isotianil, tiadinil, tebufloquin, diclomezine, kasugamycin, ferimzone, fthalide, validamycin, hydroxyisoxazole, iminoctadine acetate, isoprothiolane, oxolinic acid, oxytetracycline, streptomycin, copper oxychloride, copper hydroxide, copper hydroxide sulfate, organocopper, Bordeaux mixture, sulfur, ametoctradin, fenpyrazamine, oxathiapiprolin, picarbutrazox, 3-chloro-4-(2,6-difluorophenyl)-6-methyl-5-phenylpyridazine, 3-cyano-4-(2,6-difluorophenyl)-6-methyl-5-phenylpyridazine, acibenzolar-S-methyl, anilazine, bethoxadin, binapacryl, biphenyl, blastcidin-S, bupirimate, captafol, chloroneb, dicloran, diflumetrim, dimethirimol, dinocap, dithianon, dodine, edifenphos, ethirimol, etridiazole, fenarimol, fentin-acetate, fentin-hydroxide, ferbam, flumetver, fluoroimide, flutianil, furmecyclox, iodocarb, iprobenfos, laminarin, maneb, meptyldinocap, methasulfocarb, metiram, naftifin, nuarimol, octhilinone, and pefurazoate, phosphorous acid, potassium salt of phosphorous acid, sodium salt of phosphorous acid, ammonium salt of phosphorous acid, polyoxin, propineb, prothiocarb, pyrazophos, pyributicarb, pyrifenox, pyrrolnitrin, chinomethionate, PCNB, TCNB, silthiofam, tecloftalam, terbinafin, tolprocarb, tolylfluanid, triarimol, triazoxide, triforine, trimorphamide, zineb, ziram, (3S,6S,7R,8R)-3-{[(3-hydroxy-4-methoxy-2-pyridinyl)car-
bonyl]amino}-6-methyl-4,9-dioxo-8-(phenylmethyl)-1,5-
dioxonan-7-yl 2-methylpropanoate or

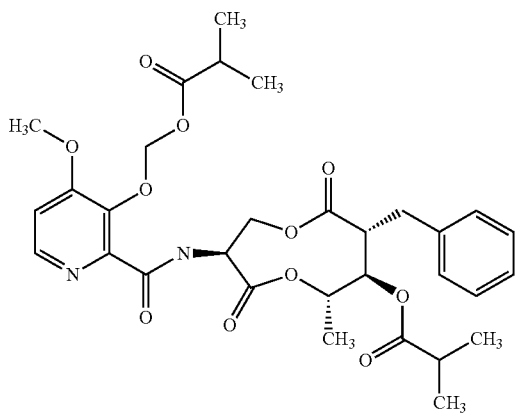 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

or
{[4-methoxy-2-({[(3S,7R,8R,9S)-9-methyl-8-(2-methyl-1-
oxopropoxy)-2,6-dioxo-7-(phenylmethyl)-1,5-dioxonan-
3-yl]amino}carbonyl)-3-pyridinyl]oxy}methyl 2-methyl-
propanoate
or

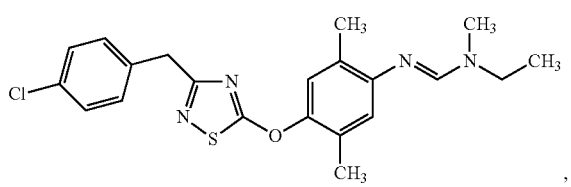 [SMILES: CCN(C)/C=N/c1cc(C)c(Oc2nc(Cc3ccc(Cl)cc3)ns2)cc1C]

or
N'-[4-({3-[(4-chlorophenyl)methyl]-1,2,4-thiadiazol-5-
yl}oxy)-2,5-dimethylphenyl]-N-ethyl-N-methylmetha-
neimidamide or

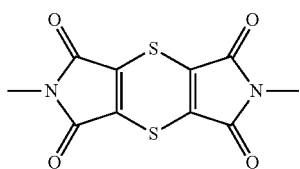

or
2,6-dimethyl-1H,5H-[1,4]dithiino[2,3-c:5,6-c']dipyrrole-1,
3,5,7(2H, 6H)-tetrone or

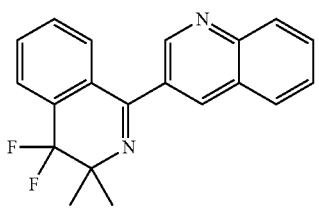 [SMILES: CC1(C)N=C(c2cnc3ccccc3c2)c2ccccc2C1(F)F]

3-(4,4-difluoro-3,3-dimethyl-3,4-dihydroisoquinolin-1-yl)
quinoline or

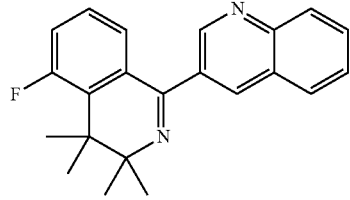 [SMILES: CC1(C)N=C(c2cnc3ccccc3c2)c2cccc(F)c2C1(C)C]

or
3-(5-fluoro-3,3,4,4-tetramethyl-3,4-dihydroisoquinolin-1-
yl)quinoline, or

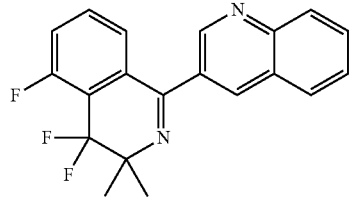 [SMILES: CC1(C)N=C(c2cnc3ccccc3c2)c2cccc(F)c2C1(F)F]

or
3-(4,4, 5-trifluoro-3,3-dimethyl-3,4-dihydroisoquinolin-1-
yl) quinoline or

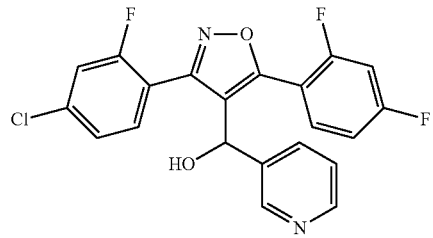 [SMILES: OC(c1cccnc1)c1c(-c2ccc(Cl)cc2F)noc1-c1ccc(F)cc1F]

or
[3-(4-chloro-2-fluorophenyl)-5-(2, 4-difluorophenyl)-1,2-
oxazol-4-yl](pyridin-3-yl)methanol
or
(S)-[3-(4-chloro-2-fluorophenyl)-5-(2, 4-difluorophenyl)-1,
2-oxazol-4-yl](pyridin-3-yl)methanol
or
(R)-[3-(4-chloro-2-fluorophenyl)-5-(2, 4-difluorophenyl)-1,
2-oxazol-4-yl](pyridin-3-yl)methanol or

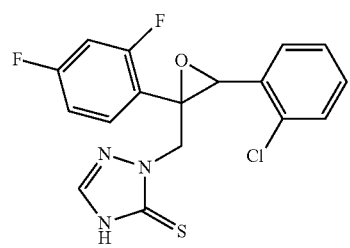 [SMILES: Fc1ccc(C2(Cn3nc[nH]c3=S)OC2c2ccccc2Cl)c(F)c1]

2-{[3-(2-chlorophenyl)-2-(2,4-difluorophenyl)oxiran-2-yl]
methyl}-2,4-dihydro-3H-1,2,4-triazole-3-thione or
2-{[rel-(2R,3S)-3-(2-chlorophenyl)-2-(2,4-difluorophenyl)
oxiran-2-yl]methyl}-2, 4-dihydro-3H-1, 2,4-triazole-3-
thione or 2-{[rel-(2R,3R)-3-(2-chlorophenyl)-2-(2, 4-difluorophenyl) oxiran-2-yl]methyl}-2, 4-dihydro-3H-1,2,4-triazole-3-thione or
2-{[(2R,3S)-3-(2-chlorophenyl)-2-(2,4-difluorophenyl)oxiran-2-yl]methyl}-2,4-dihydro-3H-1,2,4-triazole-3-thione, or
2-{[(2S,3R)-3-(2-chlorophenyl)-2-(2,4-difluorophenyl)oxiran-2-yl]methyl}-2,4-dihydro-3H-1,2,4-triazole-3-thione or
2-{[(2R,3R)-3-(2-chlorophenyl)-2-(2, 4-difluorophenyl) oxiran-2-yl]methyl}-2,4-dihydro-3H-1,2,4-triazole-3-thione, or
2-{[(2S,3S)-3-(2-chlorophenyl)-2-(2,4-difluorophenyl)oxiran-2-yl]methyl}-2,4-dihydro-3H-1,2,4-triazole-3-thione, or

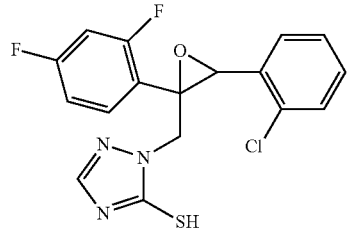 [SMILES: Fc1ccc(C2(Cn3ncnc3S)OC2c2ccccc2Cl)c(F)c1]

or
1-{[3-(2-chlorophenyl)-2-(2,4-difluorophenyl)oxiran-2-yl]methyl}-1H-1,2,4-triazole-5-thiol, or
1-{[rel-(2R,3S)-3-(2-chlorophenyl)-2-(2,4-difluorophenyl) oxiran-2-yl]methyl}-1H-1,2,4-triazole-5-thiol or
1-{[rel-(2R,3R)-3-(2-chlorophenyl)-2-(2, 4-difluorophenyl) oxiran-2-yl]methyl}-1H-1,2,4-triazole-5-thiol, or
1-{[(2R,3S)-3-(2-chlorophenyl)-2-(2,4-difluorophenyl)oxiran-2-yl]methyl}-1H-1,2, 4-triazole-5-thiol or
1-{[(2S,3R)-3-(2-chlorophenyl)-2-(2,4-difluorophenyl)oxiran-2-yl]methyl}-1H-1,2,4-triazole-5-thiol or
1-{[(2R,3R)-3-(2-chlorophenyl)-2-(2,4-difluorophenyl)oxiran-2-yl]methyl}-1H-1,2, 4-triazole-5-thiol or
1-{[(2S,3S)-3-(2-chlorophenyl)-2-(2,4-difluorophenyl)oxiran-2-yl]methyl}-1H-1,2,4-triazole-5-thiol or

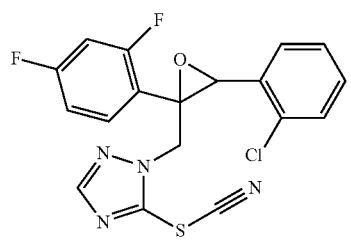 [SMILES: N#CSc1ncnn1CC1(c2ccc(F)cc2F)OC1c1ccccc1Cl]

or
1-{[3-(2-chlorophenyl)-2-(2,4-difluorophenyl)oxiran-2-yl]methyl}-1H-1,2,4-triazol-5-yl thiocyanate or
1-{[rel-(2R,3S)-3-(2-chlorophenyl)-2-(2,4-difluorophenyl) oxiran-2-yl]methyl}-1H-1,2,4-triazol-5-yl thiocyanate or
1-{[rel-(2R,3R)-3-(2-chlorophenyl)-2-(2, 4-difluorophenyl) oxiran-2-yl]methyl}-1H-1,2,4-triazol-5-yl thiocyanate or
1-{[(2R,3S)-3-(2-chlorophenyl)-2-(2,4-difluorophenyl)oxiran-2-yl]methyl}-1H-1,2,4-triazol-5-yl thiocyanate or
1-{[(2S,3R)-3-(2-chlorophenyl)-2-(2,4-difluorophenyl)oxiran-2-yl]methyl}-1H-1,2,4-triazol-5-yl thiocyanate or
1-{[(2R,3R)-3-(2-chlorophenyl)-2-(2, 4-difluorophenyl) oxiran-2-yl]methyl}-1H-1,2,4-triazol-5-yl thiocyanate or
1-{[(2S,3S)-3-(2-chiorophenyl)-2-(2, 4-difluorophenyl) oxiran-2-yl]methyl}-1H-1,2,4-triazol-5-yl thiocyanate or

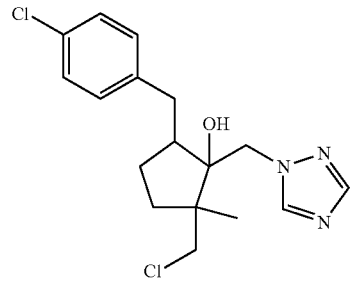 [SMILES: CC1(CCl)CCC(Cc2ccc(Cl)cc2)C1(O)Cn1cncn1]

or
5-(4-chlorobenzyl)-2-chloromethyl-2-methyl-1-(1H-1, 2,4-triazol-1-ylmethyl)cyclopentanol, or
(1RS, 2SR, 5SR)-5-(4-chlorobenzyl)-2-chloromethyl-2-methyl-1-(1H-1,2,4-triazol-1-ylmethyl)cyclopentanol or
(1RS, 2RS, 5RS)-2-chloromethyl-5-(4-fluorobenzyl)-2-methyl-1-(1H-1,2,4-triazol-1-ylmethyl)cyclopentanol or
(1RS, 2RS, 5SR)-2-chloromethyl-5-(4-fluorobenzyl)-2-methyl-1-(1H-1,2,4-triazol-1-ylmethyl)cyclopentanol or
(1RS,2SR,5RS)-2-chloromethyl-5-(4-fluorobenzyl)-2-methyl-1-(1H-1,2,4-triazol-1-ylmethyl)cyclopentanol or
(1R,2S,5S)-2-chloromethyl-5-(4-fluorobenzyl)-2-methyl-1-(H-1,2,4-triazol-1-ylmethyl)cyclopentanol or
(1S,2R,5R)-2-chloromethyl-5-(4-fluorobenzyl)-2-methyl-1-(H-1,2,4-triazol-1-ylmethyl)cyclopentanol or
(1R,2R,5R)-2-chloromethyl-5-(4-fluorobenzyl)-2-methyl-1-(1H-1,2,4-triazol-1-ylmethyl)cyclopentanol or
(1S,2S,5S)-2-chloromethyl-5-(4-fluorobenzyl)-2-methyl-1-(H-1,2,4-triazol-1-ylmethyl)cyclopentanol or
(1R,2R,5S)-2-chloromethyl-5-(4-fluorobenzyl)-2-methyl-1-(1H-1,2,4-triazol-1-ylmethyl)cyclopentanol or
(1S,2S,5R)-2-chloromethyl-5-(4-fluorobenzyl)-2-methyl-1-(1H-1,2,4-triazol-1-ylmethyl)cyclopentanol or
(1R,2S,5R)-2-chloromethyl-5-(4-fluorobenzyl)-2-methyl-1-(H-1,2,4-triazol-1-ylmethyl)cyclopentanol or
(1S,2R,5S)-2-chloromethyl-5-(4-fluorobenzyl)-2-methyl-1-(H-1,2,4-triazol-1-ylmethyl)cyclopentanol or

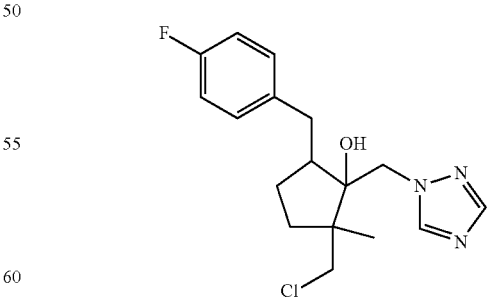

or
2-chloromethyl-5-(4-fluorobenzyl)-2-methyl-1-(1H-1,2,4-triazol-1-ylmethyl)cyclopentanol or
(1RS,2SR,5SR)-2-chloromethyl-5-(4-fluorobenzyl)-2-methyl-1-(1H-1,2,4-triazol-1-ylmethyl)cyclopentanol or (1RS,2RS,5RS)-2-chloromethyl-5-(4-fluorobenzyl)-2-methyl-1-(1H-1,2,4-triazol-1-ylmethyl)cyclopentanol or
(1RS,2RS,5SR)-2-chloromethyl-5-(4-fluorobenzyl)-2-methyl-1-(1H-1,2,4-triazol-1-ylmethyl)cyclopentanol or
(1RS,2SR,5RS)-2-chloromethyl-5-(4-fluorobenzyl)-2-methyl-1-(1H-1,2,4-triazol-1-ylmethyl)cyclopentanol or
(1R,2S,5S)-2-chloromethyl-5-(4-fluorobenzyl)-2-methyl-1-(1H-1,2,4-triazol-1-ylmethyl)cyclopentanol or
(1S,2R,5R)-2-chloromethyl-5-(4-fluorobenzyl)-2-methyl-1-(H-1,2,4-triazol-1-ylmethyl)cyclopentanol or
(1R,2R,5R)-2-chloromethyl-5-(4-fluorobenzyl)-2-methyl-1-(H-1, 2,4-triazol-1-ylmethyl)cyclopentanol or
(1S,2S,5S)-2-chloromethyl-5-(4-fluorobenzyl)-2-methyl-1-(1H-1,2,4-triazol-1-ylmethyl)cyclopentanol or
(1R,2R,5S)-2-chloromethyl-5-(4-fluorobenzyl)-2-methyl-1-(H-1,2,4-triazol-1-ylmethyl)cyclopentanol or
(1S,2S,5R)-2-chloromethyl-5-(4-fluorobenzyl)-2-methyl-1-(1H-1,2,4-triazol-1-ylmethyl)cyclopentanol or
(1R,2S,5R)-2-chloromethyl-5-(4-fluorobenzyl)-2-methyl-1-(H-1,2,4-triazol-1-ylmethyl)cyclopentanol or
(1S,2R,5S)-2-chloromethyl-5-(4-fluorobenzyl)-2-methyl-1-(H-1,2,4-triazol-1-ylmethyl)cyclopentanol or

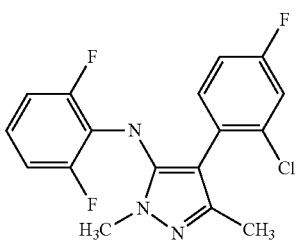 [SMILES: Cc1nn(C)c(Nc2c(F)cccc2F)c1-c1ccc(F)cc1Cl]

or
5-amino-4-(2-chloro-4-fluorophenyl)-N-(2,6-difluorophenyl)-1,3-dimethyl-1H-pyrazole or

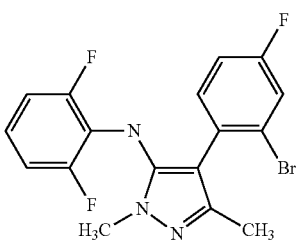 [SMILES: Cc1nn(C)c(Nc2c(F)cccc2F)c1-c1ccc(F)cc1Br]

5-amino-4-(2-bromo-4-fluorophenyl)-N-(2, 6-difluorophenyl)-1,3-dimethyl-1H-pyrazole or

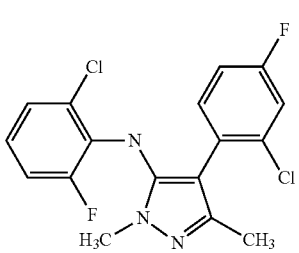 [SMILES: Cc1nn(C)c(Nc2c(F)cccc2Cl)c1-c1ccc(F)cc1Cl]

5-amino-4-(2-chloro-4-fluorophenyl)-N-(2-chloro-6-fluorophenyl)-1, 3-dimethyl-1H-pyrazole or

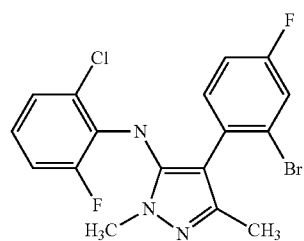 [SMILES: Cc1nn(C)c(Nc2c(F)cccc2Cl)c1-c1ccc(F)cc1Br]

or
5-amino-4-(2-bromo-4-fluorophenyl)-N-(2-chloro-6-fluorophenyl)-1, 3-dimethyl-1H-pyrazole or

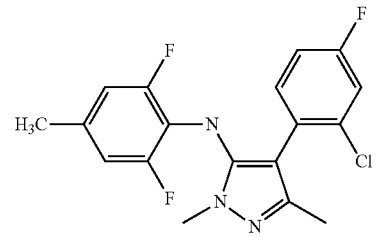 [SMILES: Cc1cc(F)c(Nc2c(-c3ccc(F)cc3Cl)c(C)nn2C)c(F)c1]

5-amino-4-(2-chloro-4-fluorophenyl)-N-(2, 6-difluoro-4-methylphenyl)-1, 3-dimethyl-1H-pyrazole or

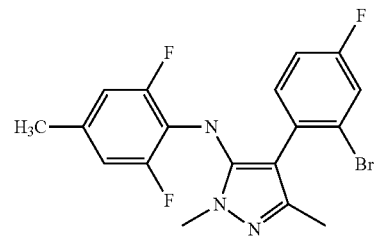

5-amino-4-(2-bromo-4-fluorophenyl)-N-(2,6-difluoro-4-methylphenyl)-1,3-dimethyl-1H-pyrazole or

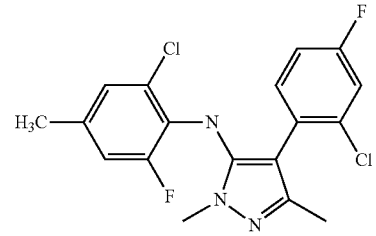 [SMILES: Cc1cc(F)c(Nc2c(-c3ccc(F)cc3Cl)c(C)nn2C)c(Cl)c1]

or
5-amino-N-(2-chloro-6-fluoro-4-methylphenyl)-4-(2-chloro-4-fluorophenyl)-1,3-dimethyl-1H-pyrazole or

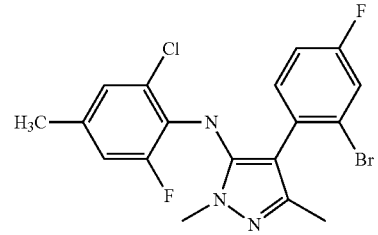

or 5-amino-4-(2-bromo-4-fluorophenyl)-N-(2-chloro-6-fluoro-4-methylphenyl)-1,3-dimethyl-1H-pyrazole or

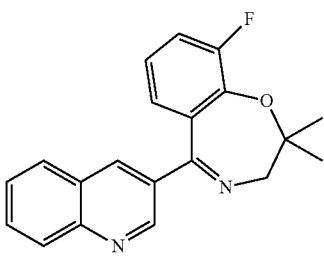 [SMILES: CC1(C)CN=C(c2cnc3ccccc3c2)c2cccc(F)c2O1]

or
9-fluoro-2,3-dihydro-2,2-dimethyl-5-(quinolin-3-yl)-1,4-benzooxazepine, or

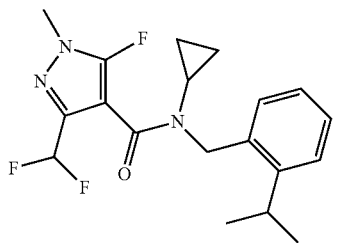 [SMILES: CC(C)c1ccccc1CN(C(=O)c1c(C(F)F)nn(C)c1F)C1CC1]

or
N-cyclopropyl-3-(difluoromethyl)-5-fluoro-N-(2-isopropylbenzyl)-1-methyl-1H-pyrazole-4-carboxamide or
N-cyclopropyl-3-(difluoromethyl)-5-fluoro-N-(2-isopropylbenzyl)-1-methyl-1H-pyrazole-4-carboxamide;

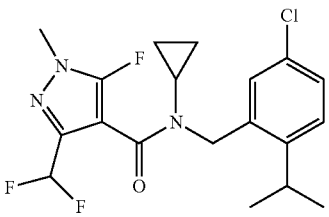 [SMILES: CC(C)c1ccc(Cl)cc1CN(C(=O)c1c(C(F)F)nn(C)c1F)C1CC1]

N-cyclopropyl-3-(difluoromethyl)-5-fluoro-N-(5-chloro-2-isopropylbenzyl)-1-methyl-1H-pyrazole-4-carboxamide or
N-cyclopropyl-3-(difluoromethyl)-5-fluoro-N-(5-chloro-2-isopropylbenzyl)-1-methyl-1H-pyrazole-4-carboxamide;

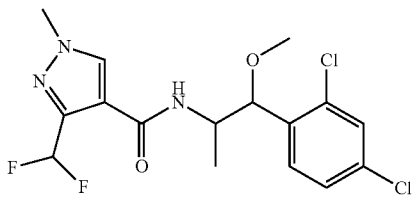 [SMILES: COC(c1ccc(Cl)cc1Cl)C(C)NC(=O)c1cn(C)nc1C(F)F]

N-[1-(2,4-dichlorophenyl)-1-methoxypropan-2-yl]-3-difluoromethyl-1-methyl-1H-pyrazole-4-carboxamide or N-[(1R,2R) 1-(2,4-dichlorophenyl)-1-methoxypropan-2-yl]-3-difluoromethyl-1-methyl-1H-pyrazole-4-carboxamide or
N-[(1R,2S)1-(2,4-dichlorophenyl)-1-methoxypropan-2-yl]-3-difluoromethyl-1-methyl-1H-pyrazole-4-carboxamide or
N-[(1S,2R)1-(2,4-dichlorophenyl)-1-methoxypropan-2-yl]-3-difluoromethyl-1-methyl-1H-pyrazole-4-carboxamide or
N-[(1S,2S)1-(2,4-dichlorophenyl)-1-methoxypropan-2-yl]-3-difluoromethyl-1-methyl-1H-pyrazole-4-carboxamide, or
rel-N-[(1R,2R)1-(2,4-dichlorophenyl)-1-methoxypropan-2-yl]-3-difluoromethyl-1-methyl-1H-pyrazole-4-carboxamide, or
rel-N-[(1R,2S)1-(2,4-dichlorophenyl)-1-methoxypropan-2-yl]-3-difluoromethyl-1-methyl-1H-pyrazole-4-carboxamide or
N-[(1R,2RS) 1-(2,4-dichlorophenyl)-1-methoxypropan-2-yl]-3-difluoromethyl-1-methyl-1H-pyrazole-4-carboxamide or
N-[(1S,2RS)1-(2,4-dichlorophenyl)-1-methoxypropan-2-yl]-3-difluoromethyl-1-methyl-1H-pyrazole-4-carboxamide or
N-[(1RS,2R)1-(2,4-dichlorophenyl)-1-methoxypropan-2-yl]-3-difluoromethyl-1-methyl-1H-pyrazole-4-carboxamide or
N-[(1RS,2S)1-(2,4-dichlorophenyl)-1-methoxypropan-2-yl]-3-difluoromethyl-1-methyl-1H-pyrazole-4-carboxamide or

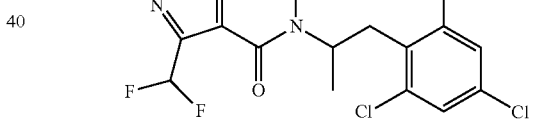

or
3-difluoromethyl-N-methoxy-1-methyl-N-[1-methyl-2-(2,4,6-trichlorophenyl)ethyl]pyrazole-4-carboxamide, or
3-difluoromethyl-N-methoxy-1-methyl-N-[(1R)-1-methyl-2-(2,4,6-trichlorophenyl)ethyl]pyrazole-4-carboxamide or
3-difluoromethyl-N-methoxy-1-methyl-N-[(1S)-1-methyl-2-(2,4,6-trichlorophenyl)ethyl]pyrazole-4-carboxamide or

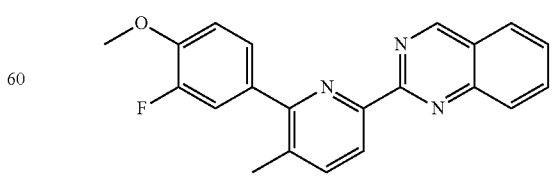

2-[6-(3-fluoro-4-methoxyphenyl)-5-methylpyridin-2-yl]quinazoline or

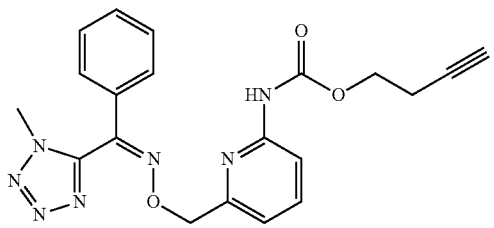 [SMILES: C#CCCOC(=O)Nc1cccc(CO/N=C(/c2ccccc2)c2nnnn2C)n1]

or 3-butyn-1-yl N-{6-[{(Z)-[(1-methyl-1H-tetrazol-5-yl)phe-nylmethylene]amino}oxy)methyl]-2-pyridinyl}carbamate or

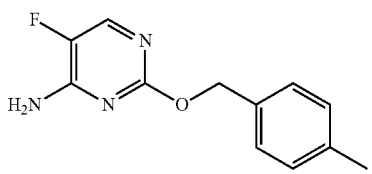 [SMILES: Cc1ccc(COc2ncc(F)c(N)n2)cc1]

or 5-fluoro-2-[(4-methylphenyl)methoxy]-4-pyrimidineamine or

Examples of these other insecticides, acaricides, and nematicides include:

(1) Organophosphorus Compounds
such as acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos:CYAP, demeton-S-methyl, diazinon, dichlorvos: DDVP, dicrotophos, dimethoate, dimethylvinphos, disulfoton, EPN, ethion, ethoprophos, famphur, fenamiphos, fenitrothion:MEP, fenthion:MPP, heptenophos, isofenphos, isopropyl-O-(methoxyaminothiophosphoryl)salicylate or isocarbophos, isoxathion, malathion, mecarbam, methamidophos, methidathion:DMTP, mevinphos, monocrotophos, naled:BRP, omethoate, oxydemeton-methyl, parathion, parathion-methyl or methyl parathion, phenthoate:PAP, phorate, phosalone, phosmet:PMP, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon:DEP, and vamidothion;

(2) Carbamate Compounds
such as alanycarb, aldicarb, bendiocarb, benfuracarb, butocarboxim, butoxycarboxim, carbaryl:NAC, carbofuran, carbosulfan, ethiofencarb, fenobucarb:BPMC, formetanate, furathiocarb, isoprocarb:MIPC, methiocarb, methomyl, metolcarb, oxamyl, pirimicarb, propoxur:PHC, thiodicarb, thiofanox, triazamate, trimethacarb, XMC, and xylylcarb;

(3) Synthetic Pyrethroid Compounds
such as acrinathrin, allethrin, bifenthrin, bioallethrin, bioresmethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, fluvalinate, tau-fluvalinate, halfenprox, heptafluthrin, imiprothrin, kadethrin, meperfluthrin, momfluorothrin, permethrin, phenothrin, prallethrin, pyrethrins, resmethrin, silafluofen, tefluthrin, tetramethrin, tetramethylfluthrin, tralomethrin, and transfluthrin;

(4) Nereistoxin Compounds
such as bensultap, cartap, cartap hydrochloride, thiocyclam, thiosultap-disodium or bisultap, and thiosultap-monosodium or monosultap;

(5) Neonicotinoid Compounds
such as acetamiprid, clothianidin, dinotefuran, flupyradifurone, imidacloprid, nitenpyram, sulfoxaflor, thiacloprid, and thiamethoxam;

(6) Benzoylurea Compounds
such as bistrifluron, chlorfluazuron, diflubenzuron, flucycloxuron, flufenoxuron, hexaflumuron, lufenuron, novaluron, noviflumuron, teflubenzuron, and triflumuron;

(7) Phenylpyrazole Compounds
such as ethiprole, fipronil, and flufiprole;

(8) Hydrazine Compounds
such as chromafenozide, halofenozide, methoxyfenozide, and tebufenozide;

(9) Organochlorine Compounds
such as chlordane, endosulfan, and alpha-endosulfan;

(10) Diamide Compounds
such as chlorantraniliprole, cyantraniliprole, cycloniliprole, flubendiamide, and tetraniliprole;

(11) Natural Insecticides
such as machine oil, nicotine-sulfate, and rotenone;

(12) Agricultural Inoculants
such as live spores derived from and crystal toxins produced from *Bacillus thuringiensis*, var. *aizawai*, var. *kurstaki*, var. *israelensis*, and var. *tenebriosis*, and mixtures thereof, *Bacillus firmus*, CNCM 1-1582 film strain, etc., *Bacillus sphaericus*, *Beauveria bassiana*, GHA strain, etc., *Beauveria brongniartii*, *Paecilomyces fumosoroseus*, *Paecilomyces lilacinus*, *Paecilomyces tenuipes*, *Trichoderma harzianum*, *Verticillium lecani*, and *Pasteuria penetrans*;

(13) Nematicidally Active Compounds
such as dazomet, fluensulfone, fosthiazate, imicyafos, metam, potassium antimonyl tartrate trihydrate, tioxazafen, *Arthrobotrys dactyloides*, *Bacilus firmus* CNCM 1-1582 strain, etc., *Bacillus megaterium*, *Hirsutella rhossiliensis*, *Hirsutella minnesotensis*, *Monacrosporium phymatopagus*, *Pasteuria nishizawae*, *Pasteuria penetrans*, *Pasteuria usgae*, *Verticillium chlamydosporium*, Harpin protein,

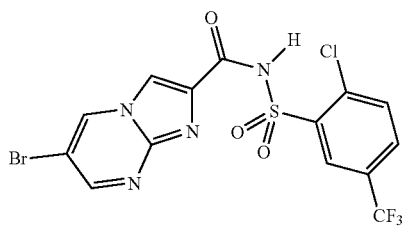 [SMILES: O=C(NS(=O)(=O)c1cc(C(F)(F)F)ccc1Cl)c1cn2cc(Br)cnc2n1]

or 6-bromo-N-{[2-chloro-5-(trifluoromethyl)phenyl]sulfonyl}-imidazo[1,2-a]pyrimidine-2-carboxamide or

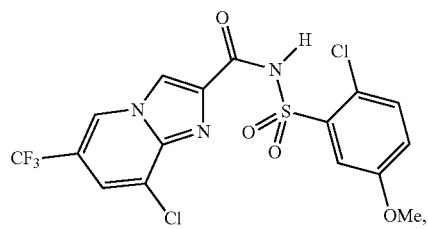 [SMILES: COc1ccc(Cl)c(S(=O)(=O)NC(=O)c2cn3cc(C(F)(F)F)cc(Cl)c3n2)c1]

or 8-chloro-N-[(2-chloro-5-methoxyphenyl)sulfonyl]-6-(trifluoromethyl)-imidazo[1,2-a]pyridine-2-carboxamide or;

(14) Other Nematicidally Active Compounds
such as acequinocyl, amitraz, benzoximate, bifenazate, bromopropylate, chinomethionat, clofentezine, cyenopyrafen, cyflumetofen, cyhexatin or tricyclohexyltin hydroxide, dicofol, etoxazole, fenazaquin, fenbutatin oxide, fenpyroximate, fluacrypyrim, fluazuron, flufenoxystrobin, hexythiazox, propargite:BPPS, pyflubumide, pyridaben, pyrimidifen, pyriminostrobin, spirodiclofen, spiromesifen, tebufenpyrad, and tetradifon; and

(15) Other Insecticides
such as abamectin, emamectin-benzoate, lepimectin, milbemectin, spinetoram, spinosad, afidopyropen, aluminium phosphide, calcium phosphide, phosphine, zinc phosphide, azadirachtin, buprofezin, chlorfenapyr, chloropicrin, cyromazine, diafenthiuron, DNOC, fenoxycarb, flometoquin, flonicamid, hydramethylnon, hydroprene, indoxacarb, kinoprene, metaflumizone, methoprene, methoxychlor, methyl bromide, metoxadiazone, pymetrozine, pyrazophos, pyridalyl, pyrifluquinazone, pyriproxyfen, sodium aluminium fluoride or chiolite, spirotetramat, sulfluramid, sulfuryl fluoride, tolfenpyrad, and triflumezopyrim.

Examples of these other herbicides or plant growth regulators include:
2,4-D, 2,4-DB, acetochlor, acifluorfen, alachlor, ametryn, amicarbazone, aminopyralid, atrazine, benefin, bentazon, bromoxynil, carfentrazone, carfentrazone-ethyl, chloransulam, chlorimuron, chlorimuron-ethyl, chloridazon, clethodim, clodinafop, clomazone, copyralid, cloransulammethyl, desmedipham, dicamba, diclofop, diclosulam, diflufenzopyr, dimethanamid, diquat, diuron, EPTC, ethalfluralin, ethofumesate, fenoxaprop, fenoxaprop-P-ethyl, florasulam, fluazifop-P-butyl, flufenacet, flumetsulam, flumiclorac, flumioxazin, fluthiacet, fomesafen, foramsulfuron, glufosinate, glufosinate-ammonium, glyphosate, glyphosate glyphosate-trimesium, glyphosate-isopropylamine, glyphosate-potassium, halosulfuron, halosulfuron-methyl, haloxyfop-R-methyl, hexazinone, imazamox, imazapic, imazaquin, imazethapyr, iodosulfuron, isoxaflutole, lactofen, lenacil, linuron, mesosulfuron, mesotrione, metam, metamitron, metolachlor, metribuzin, metsulfuron, MPCA, MSMA, nicosulfuron, oryzalin, oxyfluorfen, paraquat, pendimethalin, phenmedipham, picloram, pyrimisulfuron, pinoxaden, promethryn, pyrafulfen-ethyl, pyrithiobac, pyroxsulam, pyroxasulfone, quizalofop-p-ethyl, salflufenacil, sethoxydim, simazine, sulfentrazone, tebuthiuron, tembotrione, tepraloxydim, thifensulfuron, tribenuron-methyl, triclopyr, trifloxysulfuron, trifluaralin, triflusulfuron-methyl, ethephon, chlormequat-chloride, mepiquat-chloride, Gibberellin A3 (Gibberellin A typified by Gibberellin A3), abscisic acid, Kinetin, benzyladenine, 1,3-diphenylurea, forchlorfenuron, thidiazuron, 4-oxo-4-(2-phenylethyl)aminobutyric acid, methyl 5-(trifluoromethyl)benzo[b]thiophene-2-carboxylate, 5-(trifluoromethyl)benzo[b]thiophene-2-carboxylic acid, and the like.

The method for applying the present control agent is not particularly limited, as long as the applying form is a form by which the present control agent may be applied substantially, and includes, for example, an application to plants such as a foliage application; an application to area for cultivating plants such as a submerged treatment; and an application to soil such as seed disinfection.

The application dose of the present control agent varies depending on weather conditions, dosage forms, timing of application, methods of application, areas to be applied, target diseases, target crops, and the like, and is usually within a range of 1 to 500 g, and preferably 2 to 200 g, per 1,000 m² of the area to be applied. The emulsifiable concentrate, the wettable powder, or the suspension concentrate is usually applied by diluting with water. In this case, the concentration of the present compound after dilution is usually within a range of 0.0005 to 2% by weight, and preferably 0.005 to 1% by weight. The dust formulation or the granular formulation is usually applied, as itself without dilution. In the application to seeds, the amount of the present compound is usually within a range of 0.001 to 100 g, and preferably 0.01 to 50 g, per 1 kg of the seeds.

In the present invention, examples of the place where the pests live include paddy fields, fields, tea gardens, orchards, non-agricultural lands, houses, nursery trays, nursery boxes, nursery soils, and nursery bed.

Also, in another embodiment, for example, the present control agent can be administered to the inside (inside of the body) or the outside (body surface) of the below-mentioned vertebrate to thereby exterminate systemically or unsystemically the living things or parasites which are parasitic on the vertebrate. Examples of a method of the internal administration include oral administration, anal administration, transplantation, administration via injection subcutaneously, intramuscularly or intravenously. Examples of a method of the external administration include transdermal administration. Also, the present compound can be ingested to a livestock animal so as to exterminate sanitary insects which occur in the excrement of the animal.

When the present control agent is applied to the animals such as the livestock animal and pets on which pests are parasitic, the dose varies depending on the administration method etc., and it is desirable in general to administer the present compound so that a dose of the active ingredient (the present compound or salts thereof) is generally within a range of 0.1 mg to 2,000 mg, and preferably 0.5 mg to 1,000 mg, per 1 kg of body weight of the animal.

The present control agent can be used as an agent for controlling plant diseases in agricultural lands such as fields, paddy fields, lawns, and orchards. The present control agent can control diseases occurred in the agricultural lands for cultivating the following "plants".

Crops: corn, rice, wheat, barley, rye, oat, sorghum, cotton, soybean, peanut, buckwheat, beet, rapeseed, sunflower, sugar cane, tobacco, and the like; Vegetables: olanaceous vegetables (for example, eggplant, tomato, pimento, pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), ammiaceous vegetables (for example, carrot, parsley, celery, and parsnip), chenopodiaceous vegetables (for example, spinach and Swiss chard), lamiaceous vegetables (for example, *Perilla frutescens*, mint, and basil), strawberry, sweet potato, *Dioscorea japonica, colocasia,* and the like; Flowers; Ornamental foliage plants:

Fruits: pomaceous fruits (for example, apple, pear, Japanese pear, Chinese quince, and quince), stone fruits (for example, peach, plum, nectarine, *Prunus* mume, cherry fruit, apricot, and prune), citrus fruits (for example, Citrus unshiu, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, kaki persimmon, olive, Japanese plum, banana, coffee, date palm, coconuts, and the like.

Trees other than fruit trees: tea, mulberry, flowering plant, roadside trees (for example, ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir wood, hemlock, juniper, *Pinus, Picea*, and *Taxus* cuspidate); and the like.

The above-mentioned "plants" include genetically modified crops.

The pests which can be controlled by the present control agent include plant pathogens such as filamentous fungus, as well as harmful arthropods such as harmful insects and harmful mites, and nemathelminth such as nematodes, and specifically include the following examples, but are not limited thereto.

The method for applying the present compound is not particularly limited, as long as the applying form is a form by which the present compound may be applied substantially, and includes, for example, an application to plants such as a foliage application; an application to area for cultivating plants such as a submerged treatment; and an application to soil such as seed disinfection.

The application dose of the present compound varies depending on weather conditions, dosage forms, timing of application, methods of application, areas to be applied, target diseases, target crops, and the like, and is usually within a range of 1 to 500 g, and preferably 2 to 200 g, per 1,000 m$^2$ of the area to be applied. The emulsifiable concentrate, the wettable powder, or the suspension concentrate is usually applied by diluting with water. In this case, the concentration of the present compound after dilution is usually within a range of 0.0005 to 2% by weight, and preferably 0.005 to 1% by weight. The dust formulation or the granular formulation is usually applied, as itself without dilution. In the application to seeds, the amount of the present compound is usually within a range of 0.001 to 100 g, and preferably 0.01 to 50 g, per 1 kg of the seeds.

In the present invention, examples of the place where the pests live include paddy fields, fields, tea gardens, orchards, non-agricultural lands, houses, nursery trays, nursery boxes, nursery soils, and nursery bed.

Also, in another embodiment, for example, the present compound can be administered to the inside (inside of the body) or the outside (body surface) of the below-mentioned vertebrate to thereby exterminate systemically or unsystemically the living things or parasites which are parasitic on the vertebrate. Examples of a method of the internal administration include oral administration, anal administration, transplantation, administration via injection subcutaneously, intramuscularly or intravenously. Examples of a method of the external administration include transdermal administration. Also, the present compound can be ingested to a livestock animal so as to exterminate sanitary insects which occur in the excrement of the animal.

When the present compound is applied to the animals such as the livestock animal and pets on which pests are parasitic, the dose varies depending on the administration method etc., and it is desirable in general to administer the present compound so that a dose of the active ingredient (the present compound or salts thereof) is generally within a range of 0.1 mg to 2,000 mg, and preferably 0.5 mg to 1,000 mg, per 1 kg of body weight of the animal.

The present compound can be used as an agent for controlling plant diseases in agricultural lands such as fields, paddy fields, lawns, and orchards. The present compound can control diseases occurred in the agricultural lands for cultivating the following "plants".

Crops: corn, rice, wheat, barley, rye, oat, sorghum, cotton, soybean, peanut, buckwheat, beet, rapeseed, sunflower, sugar cane, tobacco, and the like; Vegetables: olanaceous vegetables (for example, eggplant, tomato, pimento, pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), ammiaceous vegetables (for example, carrot, parsley, celery, and parsnip), chenopodiaceous vegetables (for example, spinach and Swiss chard), lamiaceous vegetables (for example, *Perilla frutescens*, mint, and basil), strawberry, sweet potato, *Dioscorea japonica, colocasia*, and the like; Flowers; Ornamental foliage plants:

Fruits: pomaceous fruits (for example, apple, pear, Japanese pear, Chinese quince, and quince), stone fruits (for example, peach, plum, nectarine, *Prunus mume*, cherry fruit, apricot, and prune), citrus fruits (for example, Citrus unshiu, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, kaki persimmon, olive, Japanese plum, banana, coffee, date palm, coconuts, and the like;

Trees other than fruit trees: tea, mulberry, flowering plant, roadside trees (for example, ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir wood, hemlock, juniper, *Pinus, Picea*, and *Taxus* cuspidate); and the like.

The above-mentioned "plants" include genetically modified crops.

The pests which can be controlled by the present compound include plant pathogens such as filamentous fungus, as well as harmful arthropods such as harmful insects and harmful mites, and nemathelminth such as nematodes, and specifically include the following examples, but are not limited thereto.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*); Wheat diseases: powdery mildew (*Erysiphe graminis*), fusarium blight (*Fusarium gaminearum, F. avenaceum, F. culmorum, Microdochium nivale*), rust (*Puccinia striiformis, P. graminis, P. recondita*), snow mould (*Micronectriella nivale*), typhulasnow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), tan spot (*Pyrenophora triticrepentis*), damping-off by Rhizoctonia (*Rhizoctonia solani*), and take all disease (*Gaeumannomyces graminis*); Barly diseases: powdery mildew (*Erysiphe graminis*), fusarium blight (*Fusarium gaminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia leaf spot (*Ramularia collo-cygni*), and damping-off by Rhizoctonia (*Rhizoctonia solani*); Corn diseases: rust (*Puccinia sorghi*), southern rust (*Puccinia polysora*), northern leaf blight (*Setosphaeria turcica*), southern leaf blight (*Cochliobolus heterostrophus*), anthracnose (*Colletotrichum gfaminicola*), gray leaf spot (*Cercospora zeae-maydis*), eyespot (*Kabatiella zeae*), and phaeosphaeria leaf spot (*Phaeosphaeria maydis*);

Cotton diseases: anthracnose (*Colletotrichum gossypii*), grey mildew (*Ramuraria areola*), and *alternaria* leaf spot (*Alternaria macrospora, A. gossypii*); Coffee diseases: rust (*Hemileia vastatrix*); Rapeseed diseases: *sclerotinia* rot (*Sclerotinia sclerotiorum*), black spot (*Alternaria brassicae*), and black leg (*Phoma lingam*); Citrus diseases: melanose (*Diaporthe citri*), scab (*Elsinoe fawcetti*), and fruit rot (*Penicillium digitatum, P. italicum*); Apple diseases: blossom blight (*Monilinia mali*), canker (*Valsa ceratosperma*), powdery mildew (*Podosphaera leucotricha*), *alternaria* leaf spot (*Alternaria alternata* apple pathotype), scab (*Venturia inaequalis*), and bitter rot (*Glomerella cingulata*); Pear diseases: scab (*Venturia nashicola, V. pirina*), black spot (*Alternaria alternata* Japanese pear pathotype), and rust (*Gymnosporangium haraeanum*); Peach diseases: brown rot (*Monilinia fructicola*), scab (*Cladosporium carpophilum*), and *Phomopsis* rot (*Phomopsis* sp.); Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*); Japanese persimmon diseases: anthracnose (*Gloeosporium kaki*) and leaf spot (*Cercospora kaki, Mycosphaerella nawae*); Diseases of gourd family: anthracnose (*Colletotrichum lagenarium*), powdery mildew (*Sphaerotheca fuliginea*), gummy stem blight (*Didymella bryoniae*), target spot (*Corynespora cassiicola*), *fusarium* wilt (*Fusarium oxysporum*), downy mildew (*Pseudoperonospora cubensis*), phytophthora rot (*Phytophthora* sp.), and damping-off (*Pythium* sp.);

Tomato diseases: early blight (*Alternaria solani*), leaf mold (*Cladosporium fulvum*), leaf mold (*Pseudocercospora fuligena*), and late blight (*Phytophthora infestans*); Eggplant diseases: brown spot (*Phomopsis vexans*) and powdery mildew (*Erysiphe cichoracearum*); Cruciferous vegetables diseases: *alternaria* leaf spot (*Alternaria japonica*), white spot (*Cercosporella brassicae*), clubroot (*Plasmodiophora parasitica*), and downy mildew (*Peronospora parasitica*); Welsh onion diseases: rust (*Puccinia allii*); Soybean diseases: purple stain (*Cercospora kikuchii*), sphaceloma scad (*Elsinoe glycines*), pod and stem blight (*Diaporthe phaseolorum* var. *sojae*), rust (*phakopsora pachyrhizi*), target spot (*Corynespora cassiicola*), anthracnose (*Colletotrithum glycines, C. truncatum*), Rhizoctonia aerial blight (*Rhizoctonia solani*), *septoria* brown spot (*Septoria glycines*), and frog eye leaf spot (*Cercospora sojina*); Kindney bean diseases: anthracnose (*Colletotrichum lindemthianum*);

Peanut diseases: early leaf spot (*Cercospora personata*), late leaf spot (*Cercospora arachidicola*), and southern blight (*Sclerotium rolfsii*); Garden pea diseases: powdery mildew (*Erysiphe pisi*); Potato diseases: early blight (*Alternaria solani*), late blight (*Phytophthora infestans*), and *verticillium* wilt (*verticillium albo-atrum, V. dahliae, V. nigrescens*); Strawberry diseases: powdery mildew (*Sphaerotheca humuli*); Tea diseases: net blister blight (*Exobasidium reticulatum*), white scab (*Elsinoe leucospila*), gray blight (*Pestalotiopsis* sp.), and anthracnose (*Colletotrichum theae-sinensis*); Tabacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*);

Sugar beet diseases: *cercospora* leaf spot (*Cercospora beticola*), leaf blight (*Thanatephorus cucumeris*), root rot (*Thanatephorus cucumeris*), and *aphanomyces* root rot (*Aphanomyces sochlioides*); Rose diseases: black spot (*Diplocarpon rosae*) and powdery mildew (*Sphaerotheca pannosa*); Chrysanthemum diseases: leaf blight (*Septoria chrysanthemi-indici*) and white rust (*Puccinia horiana*); Onion diseases: *botrytis* leaf blight (*Botrytis cinerea, B. byssoidea, B. squamosa*), gray-mold neck rot (*Botrytis slli*), and small sclerotial rot (*Botrytis squamosa*); various crops diseases: gray mold (*Botrytis cinerea*) and *sclerotinia* rot (*Sclerotinia sclerotiorum*); Japanese radish diseases: *alternaria* leaf spot (*Alternaria brassicicola*); Turfgrass diseases: dollar spot (*Sclerotinia homeocarpa*) and brown patch and large patch (*Rhizoctonia solani*); and Banana diseases: Sigatoka disease (*Mycosphaerella fijiensis, Mycosphaerella musicola*).

Hemiptera: planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*) and green rice leafhopper (*Nephotettix virescens*); aphids (Aphididae) such as cotton aphid (*Aphis gossypii*), green peach aphid (*Myzus persicae*), cabbage aphid (*Brevicoryne brassicae*), potato aphid (*Macrosiphum euphorbiae*), foxglove aphid (*Aulacorthum solani*), oat bird-cherry aphid (*Rhopalosiphum padi*), and tropical citrus aphid (*Toxoptera citricidus*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), stink bug (*Halyomorpha mista*), and tarnished plant bug (*Lygus lineolaris*); whiteflies (Aleyrodidae) such as greenhouse whitefly (*Trialeurodes vaporariorum*) and silverleaf whitefly (*Bemisia argentifolii*); scales (Coccidae) such as Calformia red scale (*Aonidiella aurantii*), San Jose scale (*Comstockaspis perniciosa*), citrus north scale (*Unaspis citri*), red wax scale (*Ceroplastes rubens*), and cottonycushion scale (*Icerya purchasi*); lace bugs (Tingidae); and jumping plant lices (Homoptera, Psylloidea).

Lepidoptera: pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), Thoricoplusia spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit *tortrix* (*Adoxophyes orana fasciata*), smaller tea *tortrix* (*Adoxophyes* sp.), oriental tea *tortrix* (*Homona magnanima*), apple *tortrix* (*Archips fuscocupreanus*), and codling moth (*Cydia pomonella*); leafblotch miners (Gracillariidae) such as tea leafroller (*Caloptilia theivora*), and apple leafminer (*Phyllonorycter ringoneella*); leaf miners (Gracillariidae) such as tea leafroller (*Caloptilia theivora*) and apple leafminer (*Phyllonorycter ringoneella*); codling moths (Carposimidae) such as peach fruit moth (*Carposina niponensis*); lyonetiid moths (Lyonetiidae) such as *Lyonetia* spp.; tussock moths (Lymantriidae) such as *Lymantria* spp. and *Euproctis* spp.; yponomeutid moths (Yponomeutidae) such as diamondback (*Plutella xylostella*); gelechild moths (Gelechiidae) such as pink bollworm (*Pectinophora gossypiella*) and potato tubeworm (*Phthorimaea operculella*); tiger moths and allies (Arctiidae) such as fall webworm (*Hyphantria cunea*); and tineid moths (Tineidae) such as casemaking clothes moth (*Tinea translucens*), and webbing clothes moth (*Tineola bisselliella*).

Thysanoptera: thrips such as yellow citrus thrip (*Frankliniella occidentalis*), melon thrip (*Thrips palmi*), yellow tea thrip (*Scirtothrips dorsalis*), onion thrips (*Thrips tabaci*), flower thrip (*Frankliniella intonsa*), and tobacco thrip (*Frankliniella fusca*).

Diptera: houseflies (*Musca domestica*), common mosquito (*Culex pipiens pallens*), horsefly (*Tabanus trigonus*), onion maggot (*Hylemya anitgua*), seedcorn maggot (*Hylemya platura*), *Anopheles sinensis*, rice leafminer (*Agromyza oryzae*), rice leafminer (*Hydrellia griseola*), rice stem maggot (*Chlorops oryzae*), melon fly (*Dacus cucurbitae*), Meditterranean fruit fly (*Ceratitis capitata*), and legume leafminer (*Liriomyza trifolii*).

Coleoptera: twenty-eight-spotted ladybirds (*Epilachna vigintioctopunctata*), cucurbit leaf beetle (*Aulacophora femoralis*), yellow striped flea beetle (*Phyllotreta striolata*), rice leaf beetle (*Oulema oryzae*), rice curculio (*Echinocnemus squameus*), rice water weevil (*Lissorhoptrus oryzophilus*), boll weevil (*Anthonomus grandis*), azuki bean weevil (*Callosobruchus chinensis*), hunting billbug (*Sphenophorus venatus*), Japanese beetle (*Popillia japonica*), cupreous chafer (*Anomala cuprea*), corn root worms (*Diabrotica* spp.), Colorado beetle (*Leptinotarsa decemlineata*), click beetles (*Agriotes* spp.), cigarette beetle (*Lasioderma serricorne*), varied carper beetle (*Anthrenus verbasci*), red flour beetle (*Tribolium castaneum*), powder post beetle (*Lyctus brunneus*), white-spotted longicorn beetle (*Anoplophora malasiaca*), and pine shoot beetle (*Tomicus piniperda*).

Orthoptera: asiatic locusts (*Locusta migratoria*), African mole cricket (*Gryllotalpa africana*), rice grasshopper (*Oxya yezoensis*), and rice grasshopper (*Oxya japonica*).

Hymenoptera: cabbage sawflies (*Athalia rosae*), leafcutting ant (*Acromyrmex* spp.), and fire ant (*Solenopsis* spp.).

Nematodes: white-tip nematode (*Aphelenchoides besseyi*), strawberry bud nematode (*Nothotylenchus acris*), soybean cyst nematode (*Heterodera glycines*), southern root-knot nematode (*Meloidogyne incognita*), cobb's root-lesion nematode (*Pratylenchus penetrans*), and false root-knot nematode (Nacobbus *aberrans*).

Blattariae: German cockroach (*Blattella germanica*), smoky-brown cockroach (*Periplaneta fuliginosa*), American cockroach (*Periplaneta* America), brown cockroach (*Periplaneta brunnea*), and oriental cockroach (*Blatta orientalis*).

Acarina: Tetranychidae (for example, two-spotted spider mite (*Tetranychus urticae*), citrus red mite (*Panonychus citri*), and *Oligonychus* spp.); Eriophyidae (for example, pink citrus rust mite (*Aculops pelekassi*)); Tarsonemidae (for example, broad mite (*Polyphagotarsonemus latus*)); Tenuipalpidae; Tuckerellidae; Tuckerellidae Acaridae (for example, common grain mite (*Tyrophagus putrescentiae*)); Pyroglyphidae (for example, Americal house dust mite (*Dermatophagoides farinae*) and house dust mite (*Dermatophagoides ptrenyssnus*)); Cheyletidae (for example, cheyletid mite (*Cheyletus eruditus*), *Cheyletus malaccensis*, and *Cheyletus moorei*; and Dermanyssidae.

The formulation comprising the present compound or salts thereof can be used in the field relating to a treatment of livestock diseases or livestock industry, and can exterminate the living things or parasites which are parasitic on the inside and/or the outside of vertebrates such as human being, cow, sheep, pig, poultry, dog, cat, and fish, so as to maintain public health. Examples of the pests include ticks (*Ixodes* spp.) (for example, *Ixodes scapularis*), *Boophilus* spp. (for example, cattle tick (*Boophilus microplus*)), *Amblyomma* spp., *Hyalomma* spp., *Rhipicephalus* spp. (for example, kennel tick (*Rhipicephalus sanguineus*)), *Haemaphysalis* spp. (for example, *Haemaphysalis longicornis*), *dermacentor* spp., *Ornithodoros* spp. (for example, *Ornithodoros moubata*), red mite (*Dermahyssus gallinae*), ghost ant (*Ornithonyssus sylviarum*), *Sarcoptes* spp. (for example, *Sarcoptes scabiei*), *Psoroptes* spp., *Chorioptes* spp., *Demodex* spp., *Eutrombicula* spp., *Ades* spp. (for example, Asian tiger mosquito (*Aedes albopictus*)), *Anopheles* spp., *Culex* spp., *Culicodes* spp., *Musca* spp., *Hypoderma* spp., *Gasterophilus* spp., *Haematobia* spp., *Tabanus* spp., *Simulium* spp., *Triatoma* spp., lice (*Phthiraptera*) (for example, *Damalinia* spp.), *Linognathus* spp., *Haematopinus* spp., *Ctenocephalides* spp. (for example, cat flea (*Ctenocephalides felis*)) *Xenosylla* spp., Pharaoh's ant (*monomorium pharaonis*) and nematodes (for example, hairworm (for example, *Nippostrongylus brasiliensis*, *Trichostrongylus axei*, *Trichostrongylus colubriformis*), *Trichinella* spp. (for example, *Trichinella spiriralis*), barber pole worm (*Haemonchus contortus*), *Nematodirus* spp. (for example, *Nematodirus battus*), *Ostertagia circumcincta*, *Cooperia* spp., *Hymenolepis nana*, and the like.

EXAMPLES

The present invention will be described in more detail below by way of Production Examples, Formulation Examples, and Test Examples, but the present invention is not limited to these Examples.

First, Production Examples will be shown.

Production Example 1

A mixture of 0.5 g of 1-(2-[{(1H-pyrazol-3-yl)}oxymethyl]-3-methylphenyl)-4-methyl-1,4-dihydrotetrazol-5-one mentioned in Reference Production Example 26, 0.4 g of 6-chloro-2-methoxypyridine-3-boronic acid, 0.48 g of copper(II) acetate, 0.75 g of Molecular Sieves 4A, 0.3 mL of pyridine, and 5 mL of acetonitrile was stirred with heating under reflux for 6 hours. After cooling, the reaction mixture was filtered and the filtrate was concentrated under reduced pressure. The residue thus obtained was subjected to silica gel column chromatography to obtain 0.075 g of 1-(2-{[1-(6-chloro-2-methoxypyridin-3-yl)-1H-pyrazol-3-yl]oxymethyl}-3-methylphenyl)-4-methyl-1,4-dihydrotetrazol-5-one (hereinafter referred to as the present compound 1).

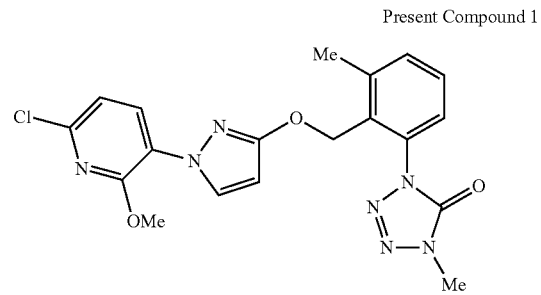 [SMILES: COc1nc(Cl)ccc1-n1ccc(OCc2c(C)cccc2-n2nnn(C)c2=O)n1]

Present Compound 1

¹H-NMR (CDCl₃) δ: 8.05-8.02 (2H, m), 7.40-7.37 (2H, m), 7.27-7.24 (1H, m), 7.01 (1H, d, J=8.2 Hz), 5.80 (1H, d, J=2.7 Hz), 5.30 (2H, s), 4.06 (3H, s), 3.64 (3H, s), 2.54 (3H, s).

Production Example 2

A mixture of 0.5 g of 1-(2-[{(1H-pyrazol-3-yl)}oxymethyl]-3-methylphenyl)-4-methyl-1,4-dihydrotetrazol-5-one mentioned in Reference Production Example 26, 0.38 g of 2,6-dimethoxypyridine-3-boronic acid, 0.48 g of copper(II) acetate, 0.75 g of Molecular Sieves 4A, 0.3 mL of pyridine, and 5 mL of acetonitrile was stirred with heating under reflux for 6 hours. After cooling, the reaction mixture was filtered and the filtrate was concentrated under reduced pressure. The residue thus obtained was subjected to silica gel column chromatography to obtain 0.09 g of 1-(2-{[1-(2,6-dimethoxypyridin-3-yl)-1H-pyrazol-3-yl]oxymethyl}-3-methylphenyl)-4-methyl-1,4-dihydrotetrazol-5-one (hereinafter referred to as the present compound 2).

¹H-NMR (CDCl₃) δ: 8.13 (1H, d, J=2.7 Hz), 8.08-8.07 (1H, m), 7.93-7.92 (1H, m), 7.41-7.38 (2H, m), 7.28-7.25 (1H, m), 5.80 (1H, d, J=2.7 Hz), 5.32 (2H, s), 4.04 (3H, s), 3.66 (3H, s), 2.55 (3H, s).

Production Example 4

A mixture of 0.5 g of 1-(2-[{(1H-pyrazol-3-yl)}oxymethyl]-3-methylphenyl)-4-methyl-1,4-dihydrotetrazol-5-one mentioned in Reference Production Example 26, 0.43 g of 2-methoxyquinoline-3-boronic acid, 0.48 g of copper(II) acetate, 0.75 g of Molecular Sieves 4A, 0.3 mL of pyridine, and 5 mL of acetonitrile was stirred with heating under reflux for 8 hours. After cooling, the reaction mixture was filtered and the filtrate was concentrated under reduced pressure. The residue thus obtained was subjected to silica gel column chromatography to obtain 0.1 g of 1-(2-{[1-(2-methoxyquinolin-3-yl)-1H-pyrazol-3-yl]oxymethyl}-3-methylphenyl)-4-methyl-1,4-dihydrotetrazol-5-one (hereinafter referred to as the present compound 4).

Present Compound 2

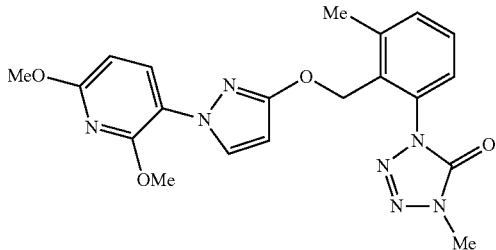

Present Compound 4

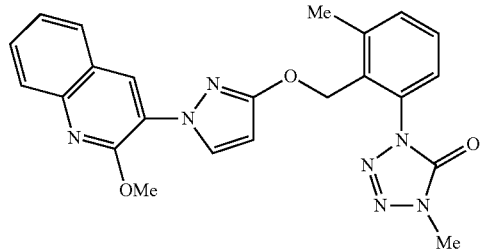

¹H-NMR (CDCl₃) δ: 7.89 (1H, d, J=5 HZ), 7.81 (1H, d, J=2.5 Hz), 7.39-7.36 (2H, m), 7.27-7.23 (1H, m), 6.40 (1H, d, J=8.5 Hz), 5.74 (1H, d, J=2.5 Hz), 5.28 (2H, s), 4.01 (3H, s), 3.93 (3H, s), 3.63 (3H, s), 2.54 (3H, s).

Production Example 3

A mixture of 0.5 g of 1-(2-[{(1H-pyrazol-3-yl)}oxymethyl]-3-methylphenyl)-4-methyl-1,4-dihydrotetrazol-5-one mentioned in Reference Production Example 26, 0.4 g of 5-chloro-2-methoxypyridine-3-boronic acid, 0.48 g of copper(II) acetate, 0.75 g of Molecular Sieves 4A, 0.3 mL of pyridine, and 5 mL of acetonitrile was stirred with heating under reflux for 8 hours. After cooling, the reaction mixture was filtered and the filtrate was concentrated under reduced pressure. The residue thus obtained was subjected to silica gel column chromatography to obtain 0.04 g of 1-(2-{[1-(5-chloro-2-methoxypyridin-3-yl)-1H-pyrazol-3-yl]oxymethyl}-3-methylphenyl)-4-methyl-1,4-dihydrotetrazol-5-one (hereinafter referred to as the present compound 3).

¹H-NMR (CDCl₃) δ: 8.40 (1H, s), 8.16 (1H, d, J=2.7 Hz), 7.85-7.82 (2H, m), 7.62-7.57 (1H, m), 7.44-7.38 (3H, m), 7.29-7.25 (1H, m), 5.84 (1H, d, J=2.7 Hz), 5.38 (2H, s), 4.18 (3H, s), 3.61 (3H, s), 2.58 (3H, s).

Production Example 5

A mixture of 0.5 g of 1-(2-[{(1H-pyrazol-3-yl)}oxymethyl]-3-methylphenyl)-4-methyl-1,4-dihydrotetrazol-5-one mentioned in Reference Production Example 26, 0.35 g of 6-methyl-2-methoxypyridine-3-boronic acid, 0.48 g of copper(II) acetate, 0.75 g of Molecular Sieves 4A, 0.3 mL of pyridine, and 5 mL of acetonitrile was stirred with heating under reflux for 6 hours. After cooling, the reaction mixture was filtered and the filtrate was concentrated under reduced pressure. The residue thus obtained was subjected to silica gel column chromatography to obtain 0.13 g of 1-(2-{[1-(6-methyl-2-methoxypyridin-3-yl)-1H-pyrazol-3-yl]oxymethyl}-3-methylphenyl)-4-methyl-1,4-dihydrotetrazol-5-one (hereinafter referred to as the present compound 5).

Present Compound 3

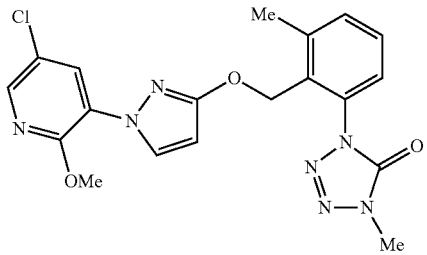

Present Compound 5

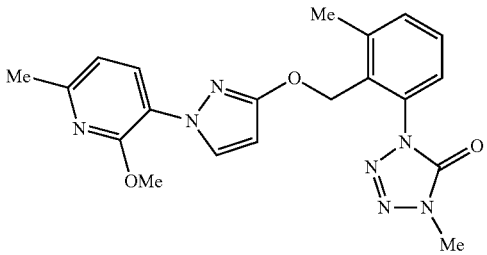

¹H-NMR (CDCl₃) δ: 8.01 (1H, d, J=2.7 Hz), 7.90 (1H, d, J=7.7 Hz), 7.39-7.36 (2H, m), 7.27-7.23 (1H, m), 6.82 (1H, d, J=7.7 Hz), 5.77 (1H, d, J=2.7 Hz), 5.30 (2H, s), 4.01 (3H, s), 3.62 (3H, s), 2.54 (3H, s), 2.46 (3H, s).

Production Example 6

A mixture of 0.5 g of 1-(2-[{(1H-pyrazol-3-yl)}oxymethyl]-3-methylphenyl)-4-methyl-1,4-dihydrotetrazol-5-one mentioned in Reference Production Example 26, 0.35 g of 3,4-(methylenedioxy)phenylboronic acid, 0.48 g of copper (II) acetate, 0.75 g of Molecular Sieves 4A, 0.3 mL of pyridine, and 5 mL of acetonitrile was stirred with heating under reflux for 4 hours. After cooling, the reaction mixture was filtered and the filtrate was concentrated under reduced pressure. The residue thus obtained was subjected to silica gel column chromatography to obtain 0.31 g of 1-(2-{[1-(3,4-methylenedioxyphenyl)-1H-pyrazol-3-yl]oxymethyl}-3-methylphenyl)-4-methyl-1,4-dihydrotetrazol-5-one (hereinafter referred to as the present compound 6).

Present Compound 6

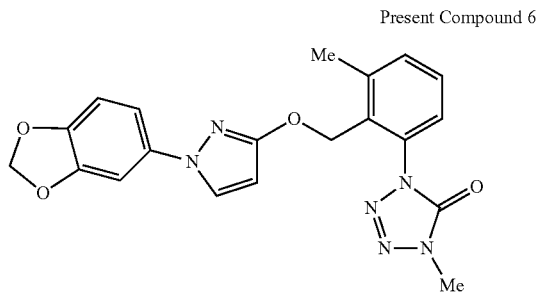 [SMILES: Cc1cccc(-n2nnn(C)c2=O)c1COc1ccn(-c2ccc3c(c2)OCO3)n1]

¹H-NMR (CDCl₃) δ: 7.53 (1H, d, J=2.5 Hz), 7.38-7.35 (2H, m), 7.26-7.23 (1H, m), 7.10-7.09 (1H, m), 6.97-6.94 (1H, m), 6.79 (1H, d, J=8.2 Hz), 5.98 (2H, s), 5.75 (1H, d, J=2.5 Hz), 5.31 (2H, s), 3.62 (3H, s), 2.55 (3H, s).

Production Example 7

A mixture of 0.5 g of 1-{2-[(1H-pyrazol-3-yl)oxymethyl]-3-chlorophenyl}-4-methyl-1,4-dihydrotetrazol-5-one mentioned in Reference Production Example 28, 0.36 g of 2,6-dimethoxypyridine-3-boronic acid, 0.44 g of copper(II) acetate, 0.75 g of Molecular Sieves 4A, 0.3 mL of pyridine, and 5 mL of acetonitrile was stirred with heating under reflux for 6 hours. After cooling, the reaction mixture was filtered and the filtrate was concentrated under reduced pressure. The residue thus obtained was subjected to silica gel column chromatography to obtain 0.07 g of 1-(2-{[1-(2,6-dimethoxypyridin-3-yl)-1H-pyrazol-3-yl]oxymethyl}-3-chlorophenyl)-4-methyl-1,4-dihydrotetrazol-5-one (hereinafter referred to as the present compound 7).

Present Compound 7

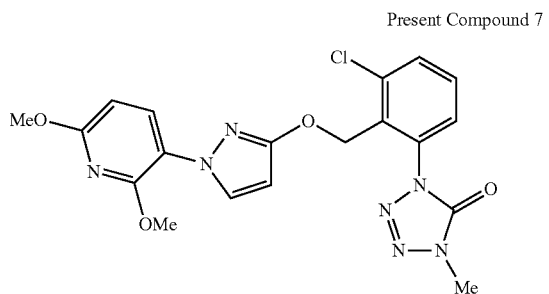

¹H-NMR (CDCl₃) δ: 7.91 (1H, d, J=8.2 Hz), 7.82 (1H, d, J=2.5 Hz), 7.60-7.58 (1H, m), 7.45-7.42 (1H, m), 7.38-7.35 (1H, m), 6.40 (1H, d, J=8.2 Hz), 5.73 (1H, d, J=2.5 Hz), 5.49 (2H, s), 4.01 (3H, s), 3.94 (3H, s), 3.60 (3H, s).

Production Example 8

A mixture of 0.5 g of 1-{2-[(1H-pyrazol-3-yl)oxymethyl]-3-ethylphenyl}-4-methyl-1,4-dihydrotetrazol-5-one mentioned in Reference Production Example 27, 0.37 g of 2,6-dimethoxypyridine-3-boronic acid, 0.46 g of copper(II) acetate, 0.75 g of Molecular Sieves 4A, 0.3 mL of pyridine, and 5 mL of acetonitrile was stirred with heating under reflux for 6 hours. After cooling, the reaction mixture was filtered and the filtrate was concentrated under reduced pressure. The residue thus obtained was subjected to silica gel column chromatography to obtain 0.1 g of 1-(2-{[1-(2,6-dimethoxypyridin-3-yl)-1H-pyrazol-3-yl]oxymethyl}-3-ethylphenyl)-4-methyl-1,4-dihydrotetrazol-5-one (hereinafter referred to as the present compound 8).

Present Compound 8

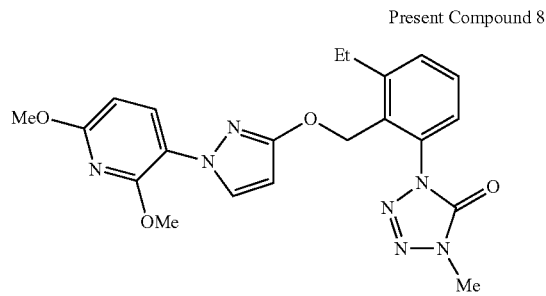 [SMILES: COc1ccc(-n2ccc(OCc3c(Cl)cccc3-n3nnn(C)c3=O)n2)c(OC)n1]

¹H-NMR (CDCl₃) δ: 7.91 (1H, d, J=6.5 Hz) 7.82 (1H, d, J=2.5 Hz), 7.44-7.41 (2H, m), 7.27-7.24 (1H, m), 6.40 (1H, d, J=8.5 Hz), 5.74 (1H, d, J=2.5 Hz), 5.30 (2H, s), 4.01 (3H, s), 3.93 (3H, s), 3.61 (3H, s), 2.89 (2H, q, J=7.6 Hz), 1.29 (3H, t, J=7.6 Hz).

Production Example 9

A mixture of 1.0 g of 1-{2-[(1H-pyrazol-3-yl)oxymethyl]-3-cyclopropylphenyl}-4-methyl-1,4-dihydrotetrazol-5-one mentioned in Reference Production Example 29, 0.7 g of 2,6-dimethoxypyridine-3-boronic acid, 0.87 g of copper(II) acetate, 1.5 g of Molecular Sieves 4A, 0.6 mL of pyridine, and 10 mL of acetonitrile was stirred with heating under reflux for 8 hours. After cooling, the reaction mixture was filtered and the filtrate was concentrated under reduced pressure. The residue thus obtained was subjected to silica gel column chromatography to obtain 0.17 g of 1-(2-{[1-(2,6-dimethoxypyridin-3-yl)-1H-pyrazol-3-yl]oxymethyl}-3-cyclopropylphenyl)-4-methyl-1,4-dihydrotetrazol-5-one (hereinafter referred to as the present compound 9).

Present Compound 9

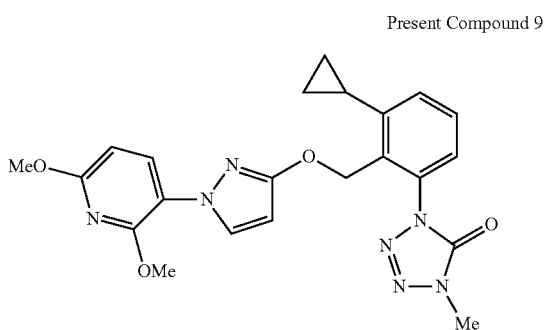 [SMILES: COc1ccc(-n2ccc(OCc3c(C4CC4)cccc3-n3nnn(C)c3=O)n2)c(OC)n1]

¹H-NMR (CDCl₃) δ: 7.91 (1H, d, J=8.4 Hz), 7.82 (1H, d, J=2.5 Hz), 7.42-7.38 (1H, m), 7.25-7.22 (2H, m), 6.40 (1H, d, J=8.4 Hz), 5.75 (1H, d, J=2.5 Hz), 5.49 (2H, s), 4.01 (3H, s), 3.94 (3H, s), 3.62 (3H, s), 2.27-2.20 (1H, m), 1.04-0.99 (2H, m), 0.79-0.74 (2H, m).

Production Example 10

A mixture of 0.68 g of 1-{2-[(1H-pyrazol-3-yl)oxymethyl]-3-methoxyphenyl}-4-methyl-1,4-dihydrotetrazol-5-one mentioned in Reference Production Example 30, 0.5 g of 2,6-dimethoxypyridine-3-boronic acid, 0.61 g of copper (II) acetate, 0.85 g of Molecular Sieves 4A, 0.4 mL of pyridine, and 8 mL of acetonitrile was stirred with heating under reflux for 8 hours. After cooling, the reaction mixture was filtered and the filtrate was concentrated under reduced pressure. The residue thus obtained was subjected to silica gel column chromatography to obtain 0.16 g of 1-(2-{[1-(2,6-dimethoxypyridin-3-yl)-1H-pyrazol-3-yl]oxymethyl}-3-methoxyphenyl)-4-methyl-1,4-dihydrotetrazol-5-one (hereinafter referred to as the present compound 10).

Present Compound 10

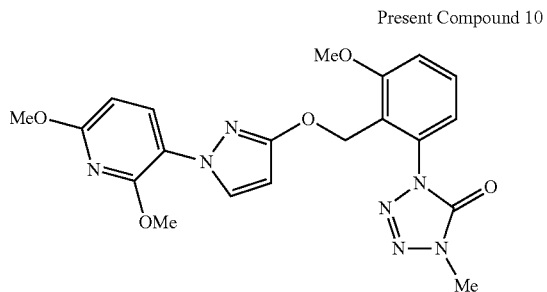 [SMILES: COc1ccc(-n2ccc(OCc3c(OC)cccc3-n3nnn(C)c3=O)n2)c(OC)n1]

¹H-NMR (CDCl₃) δ: 7.92 (1H, d, J=8.5 Hz), 7.81 (1H, d, J=2.5 Hz), 7.45-7.41 (1H, m), 7.06-7.02 (2H, m), 6.38 (1H, d, J=8.5 Hz), 5.72 (1H, d, J=2.5 Hz), 5.40 (2H, s), 4.00 (3H, s), 3.92 (3H, s), 3.88 (3H, s), 3.57 (3H, s).

Production Example 11

A mixture of 0.5 g of 1-{2-[(1H-pyrazol-3-yl)oxymethyl]-3-methylthiophenyl}-4-methyl-, 4-dihydrotetrazol-5-one mentioned in Reference Production Example 31, 0.35 g of 2,6-dimethoxypyridine-3-boronic acid, 0.48 g of copper(II) acetate, 0.75 g of Molecular Sieves 4A, 0.3 mL of pyridine, and 5 mL of acetonitrile was stirred with heating under reflux for 8 hours. After cooling, the reaction mixture was filtered and the filtrate was concentrated under reduced pressure. The residue thus obtained was subjected to silica gel column chromatography to obtain 0.12 g of 1-(2-{[1-(2,6-dimethoxypyridin-3-yl)-1H-pyrazol-3-yl]oxymethyl}-3-methylthiophenyl)-4-methyl-1,4-dihydrotetrazol-5-one (hereinafter referred to as the present compound 11).

Present Compound 11

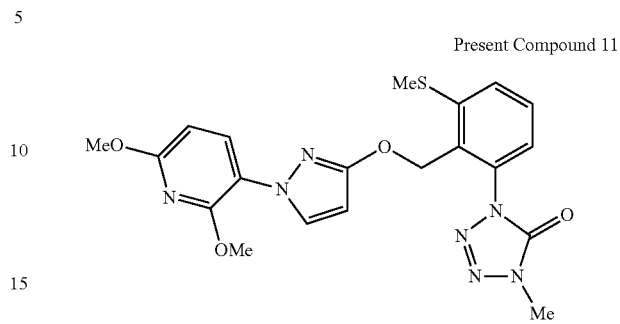

¹H-NMR (CDCl₃) δ: 7.94 (1H, d, J=8.2 Hz), 7.82 (1H, d, J=2.5 Hz), 7.47-7.42 (2H, m), 7.24-7.21 (1H, m), 6.39 (1H, d, J=8.2 Hz), 5.76 (1H, d, J=2.5 Hz), 5.42 (2H, s), 4.00 (3H, s), 3.93 (3H, s), 3.60 (3H, s), 2.51 (3H, s).

Production Example 12

A mixture of 1.0 g of 1-(2-{[1H-pyrazol-3-yl]oxymethyl}-3-methylphenyl)-4-methyl-1,4-dihydrotetrazol-5-one mentioned in Reference Production Example 26, 0.80 g of 2-methoxypyridine-3-boronic acid, 0.98 g of copper(II) acetate, 1.5 g of Molecular Sieves 4A, 0.59 mg of pyridine, and 15 mL of acetonitrile was stirred with heating under reflux for 15 hours. After cooling, the reaction mixture was concentrated under reduced pressure. The residue thus obtained was subjected to silica gel column chromatography to obtain 0.30 g of 1-(2-{[1-(2-methoxypyridin-3-yl)-1H-pyrazol-3-yl]oxymethyl}-3-methylphenyl)-4-methyl-1,4-dihydrotetrazol-5-one (hereinafter referred to as the present compound 12).

Present Compound 12

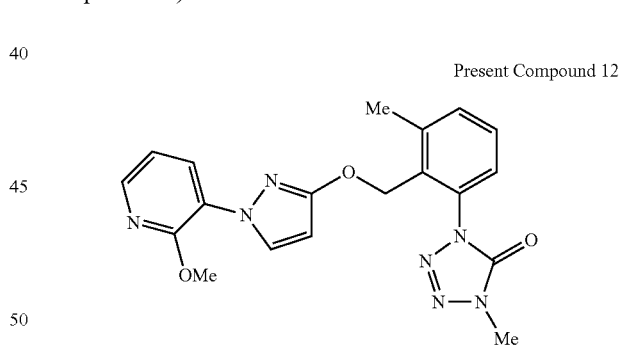

¹H-NMR (CDCl₃) δ: 8.09 (1H, d, J=2.5 Hz), 8.06 (1H, dd, J=7.8, 1.6 Hz), 8.02 (1H, dd, J=4.8, 1.6 Hz), 7.42-7.37 (2H, m), 7.26-7.25 (1H, m), 7.01 (1H, dd, J=7.8, 4.8 Hz), 5.79 (1H, d, J=2.7 Hz), 5.32 (2H, s), 4.06 (3H, s), 3.63 (3H, s), 2.55 (3H, s).

Production Example 13

A mixture of 0.30 g of 1-methyl-4-[3-methyl-2-(1H-pyrazol-3-yloxymethyl)-phenyl]-1,4-dihydrotetrazol-5-one mentioned in Reference Production Example 26, 0.18 g of 2-chloropyridine-5-boronic acid, 0.27 g of copper(II) acetate, 0.18 g of pyridine, 1.00 g of Molecular Sieves 4A, and 8 mL of acetonitrile was stirred with heating under reflux for 2 hours. Water was poured into the reaction mixture allowed to cool and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.03 g of 1-{2-[1-(6-chloropyridin-3-yl)-1H-pyrazol-3-yl]oxymethyl-3-methylphenyl}-4-methyl-1,4-dihydrotetrazol-5-one (hereinafter referred to as the present compound 13).

Present Compound 13

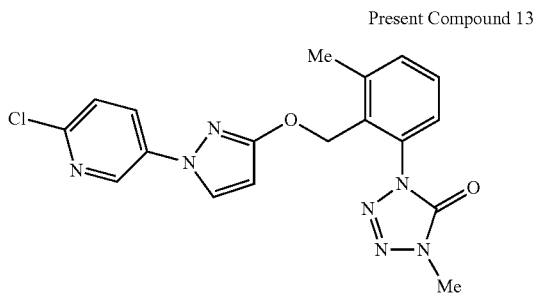 [SMILES: Cc1cccc(-n2nnn(C)c2=O)c1COc1ccn(-c2ccc(Cl)nc2)n1]

$^1$H-NMR (CDCl$_3$) δ (ppm): 8.60 (1H, d, J=2.9 Hz), 7.88 (1H, dd, J=8.7, 2.9 Hz), 7.68 (1H, d, J=2.7 Hz), 7.42-7.36 (3H, m), 7.28-7.24 (1H, m), 5.88 (1H, d, J=2.7 Hz), 5.33 (2H, s), 3.66 (3H, s), 2.56 (3H, s).

Production Example 14

A mixture of 0.65 g of 1-(2-bromomethyl-3-methylphenyl)-4-methyl-1,4-dihydrotetrazol-5-one mentioned in Reference Production Example 19, 0.56 g of 1-(6-bromo-2-methoxypyridin-3-yl)-1H-pyrazol-3-ol mentioned in Reference Production Example 33, 0.57 g of potassium carbonate, and 6 mL of N,N-dimethylformamide was stirred at room temperature for 3 hours. Water was poured into the reaction solution and the mixture was extracted with ethyl acetate. The organic layer was washed with water and a saline solution, dried over anhydrous sodium sulfate, and then concentrated under reduced pressure. The residue thus obtained was subjected to silica gel column chromatography to obtain 1 g of 1-(2-{[1-(6-bromo-2-methoxypyridin-3-yl)-1H-pyrazol-3-yl]oxymethyl}-3-methylphenyl)-4-methyl-1,4-dihydrotetrazol-5-one (hereinafter referred to as the present compound 14).

Present Compound 14

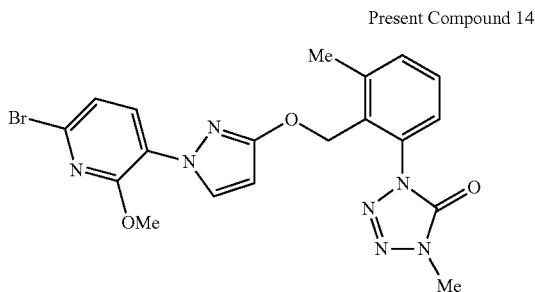 [SMILES: COc1nc(Br)ccc1-n1ccc(OCc2c(C)cccc2-n2nnn(C)c2=O)n1]

$^1$H-NMR (CDCl$_3$) δ: 8.05 (1H, d, J=2.7 Hz), 7.94 (1H, d, J=8.0 Hz), 7.40-7.37 (2H, m), 7.26-7.24 (1H, m), 7.16 (1H, d, J=8.0 Hz), 5.80 (1H, d, J=2.7 Hz), 5.30 (2H, s), 4.06 (3H, s), 3.64 (3H, s), 2.54 (3H, s).

Production Example 15

A mixture of 0.1 g of 1-(2-{[1-(6-bromo-2-methoxypyridin-3-yl)-1H-pyrazol-3-yl]oxymethyl}-3-methylphenyl)-4-methyl-1,4-dihydrotetrazol-5-one mentioned in Production Example 14, 0.01 g of tris(dibenzylideneacetone)dipalladium, 0.012 g of 1,1'-bisdiphenylphosphinoferrocene, 0.02 g of zinc cyanide, 0.01 g of a zinc powder, and 2 mL of N,N-dimethylformamide was stirred at 100° C. for 2 hours. Water was poured into the reaction solution and the mixture was extracted with ethyl acetate. The organic layer was washed with water and a saline solution, dried over anhydrous sodium sulfate, and then concentrated under reduced pressure. The residue thus obtained was subjected to silica gel column chromatography to obtain 0.08 g of 1-(2-{[1-(6-cyano-2-methoxypyridin-3-yl)-1H-pyrazol-3-yl]oxymethyl}-3-methylphenyl)-4-methyl-1,4-dihydrotetrazol-5-one (hereinafter referred to as the present compound 15).

Present Compound 15

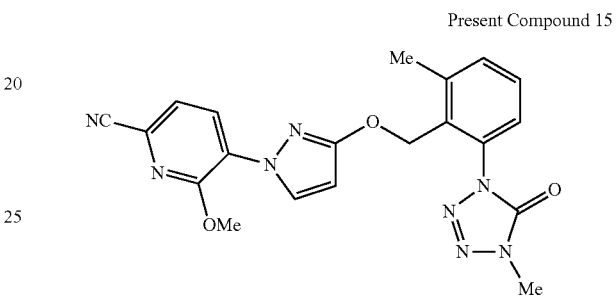

$^1$H-NMR (CDCl$_3$) δ: 8.25 (1H, d, J=2.7 Hz), 8.20 (1H, d, J=8.0 Hz), 7.45-7.38 (3H, m), 7.28-7.25 (1H, m), 5.86 (1H, d, J=2.7 Hz), 5.32 (2H, s), 4.10 (3H, s), 3.65 (3H, s), 2.54 (3H, s).

Production Example 16

A mixture of 0.3 g of 1-(2-bromomethyl-3-methylphenyl)-4-methyl-1,4-dihydro-tetrazol-5-one mentioned in Reference Production Example 19, 0.26 g of 1-(5-trifluoromethyl-pyridin-2-yl)-1H-pyrazol-3-ol mentioned in Reference Production Example 34, 0.19 g of potassium carbonate, and 20 ml of acetonitrile was stirred with heating under reflux for 7 hours. The reaction mixture was filtered and the filtrate was concentrated. The residue thus obtained was subjected to silica gel chromatography to obtain 0.2 g of 1-methyl-4-{3-methyl-2-[1-(5-trifluoromethyl-pyridin-2-yl)-1H-pyrazol-3-yl]oxymethyl-phenyl}1, 4-dihydro-tetrazol-5-one (hereinafter referred to as the present compound 16).

Present Compound 16

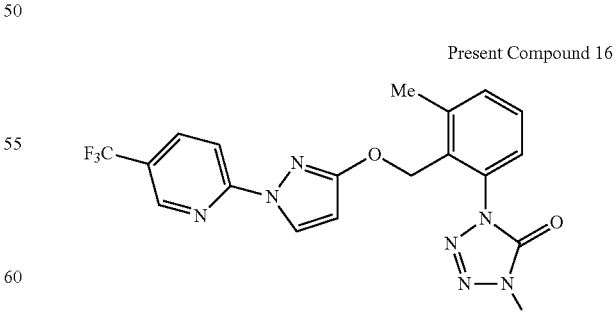

$^1$H-NMR (CDCl$_3$) δ: 8.58-8.58 (1H, m), 8.35 (1H, d, J=2.9 Hz), 7.97 (1H, dd, J=8.7, 2.2 Hz), 7.85 (1H, d, J=8.7 Hz), 7.43-7.38 (2H, m), 7.27 (1H, dd, J=6.6, 2.5 Hz), 5.90 (1H, d, J=2.7 Hz), 5.35 (2H, s), 3.66 (3H, s), 2.56 (3H, s).

Production Example 17

A mixture of 0.38 g of 2-{[1-(4,5-dihydro-4-methyl-5-oxo-1H-tetrazol-1-yl)-3-methylphenyl-2-yl]methyloxy}-4-bromothiazole mentioned in Reference Production Example 36, 0.17 g of 2-bromo-5-methylpyridine, 0.33 g of hexamethylditin, 0.07 g of tetrakis(triphenylphosphine)palladium (0), and 10 mL of dioxane was stirred with heating under reflux for 15 hours. Water and ethyl acetate were poured into the reaction mixture allowed to cool and the mixture was filtered through Cerite. The filtrate was extracted with ethyl acetate and the organic layer was washed with water and a saturated saline solution, dried over anhydrous sodium sulfate, and then concentrated under reduced pressure. The residue thus obtained was subjected to silica gel column chromatography to obtain 0.25 g of 2-{[1-(4,5-dihydro-4-methyl-5-oxo-1H-tetrazol-1-yl)-3-methylphenyl-2-yl]methyloxy}-4-(5-methylpyridin-2-yl)thiazole (hereinafter referred to as the present compound 17).

Present Compound 17

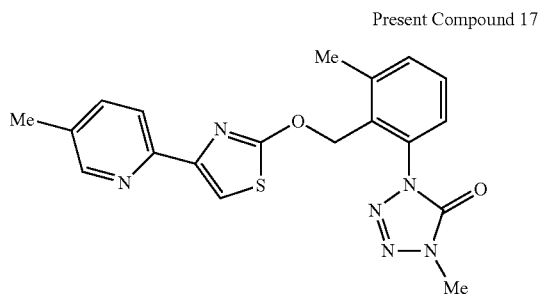 [SMILES: Cc1ccc(-c2csc(OCc3c(C)cccc3-n3nnn(C)c3=O)n2)nc1]

$^1$H-NMR (CDCl$_3$) δ: 2.34 (3H, s), 2.55 (3H, s), 3.61 (3H, s), 5.58 (2H, s), 7.25-7.29 (1H, m), 7.38-7.41 (3H, m), 7.54 (1H, d, J=8.1 Hz), 7.83 (1H, d, J=8.1 Hz), 8.39 (1H, s).

Production Example 18

A mixture of 0.38 g of 2-{[1-(4,5-dihydro-4-methyl-5-oxo-1H-tetrazol-1-yl)-3-methylphenyl-2-yl]methyloxy}-4-bromothiazole mentioned in Reference Production Example 36, 0.17 g of 2-bromo-6-methylpyridine, 0.33 g of hexamethylditin, 0.12 g of tetrakis(triphenylphosphine)palladium (0), and 10 mL of dioxane was stirred with heating under reflux for 3 hours. Water and ethyl acetate were poured into the reaction mixture allowed to cool and the mixture was filtered through Cerite. The filtrate was extracted with ethyl acetate. The organic layer was washed with water and a saturated saline solution, dried over anhydrous sodium sulfate, and then concentrated under reduced pressure. The residue thus obtained was subjected to silica gel column chromatography to obtain 0.08 g of 2-{[1-(4,5-dihydro-4-methyl-5-oxo-1H-tetrazol-1-yl)-3-methylphenyl-2-yl]methyloxy}-4-(6-methylpyridin-2-yl)thiazole (hereinafter referred to as the present compound 18).

Present Compound 18

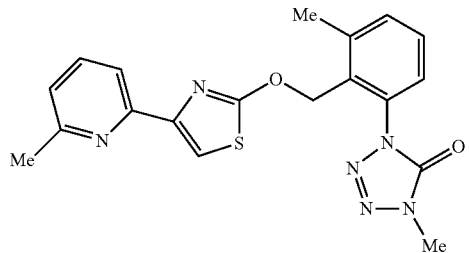

$^1$H-NMR (CDCl$_3$) δ: 2.56 (3H, s), 2.57 (3H, s), 3.60 (3H, s), 5.58 (2H, s), 7.05 (1H, d, J=7.8 Hz), 7.24-7.29 (1H, m), 7.38-7.44 (2H, m), 7.47 (1H, s), 7.62 (1H, t, J=7.7 Hz), 7.73 (1H, d, J=7.7 Hz).

Production Example 19

A mixture of 0.40 g of 1-(2-bromomethyl-3-methylphenyl)-4-methyl-1,4-dihydrotetrazol-5-one mentioned in Reference Production Example 19, 0.25 g of 4-(pyridin-2-yl)-2-oxo-thiazole, 0.55 g of cesium carbonate, and 10 mL of acetonitrile was stirred with heating under reflux for 4 hours. Water was poured into the reaction mixture allowed to cool and the mixture was extracted with ethyl acetate. The organic layer was washed with water and a saturated saline solution, dried over anhydrous sodium sulfate, and then concentrated under reduced pressure. The residue thus obtained was subjected to silica gel column chromatography to obtain 0.33 g of 2-{[1-(4,5-dihydro-4-methyl-5-oxo-1H-tetrazol-1-yl)-3-methylphenyl-2-yl]methyloxy}-4-(pyridin-2-yl)thiazole (hereinafter referred to as the present compound 19).

Present Compound 19

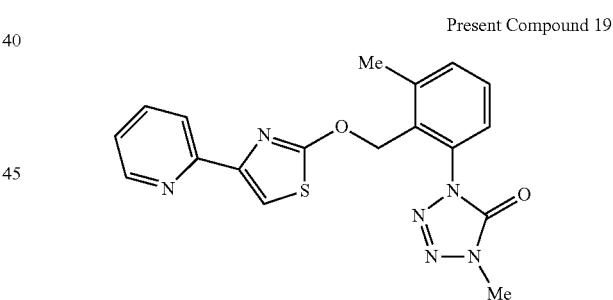

$^1$H-NMR (CDCl$_3$) δ: 2.56 (3H, s), 3.60 (3H, s), 5.60 (2H, s), 7.21-7.15 (1H, m), 7.28 (1H, d, J=6.8 Hz), 7.40-7.47 (3H, m), 7.74 (1H, t, J=7.5 Hz), 7.93 (1H, d, J=8.0 Hz), 8.57 (1H, d, J=4.1 Hz).

Production Example 20

A mixture of 0.45 g of 1-(2-bromomethyl-3-methylphenyl)-4-methyl-1,4-dihydrotetrazol-5-one mentioned in Reference Production Example 19, 0.30 g of 4-(pyridin-4-yl)-2-oxo-thiazole, 0.68 g of cesium carbonate, and 10 mL of acetonitrile was stirred with heating under reflux for 2 hours. The reaction mixture allowed to cool was filtered and then concentrated under reduced pressure. The residue thus obtained was subjected to silica gel column chromatography to obtain 0.13 g of 2-{[1-(4,5-dihydro-4-methyl-5-oxo-1H- tetrazol-1-yl)-3-methylphenyl-2-yl]methyloxy}-4-(pyridin-4-yl)thiazole (hereinafter referred to as the present compound 20).

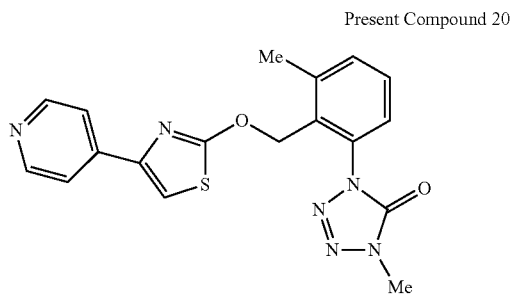 [SMILES: Cc1cccc(-n2nnn(C)c2=O)c1COc1nc(-c2ccncc2)cs1]

Present Compound 20

¹H-NMR (CDCl₃) δ: 8.64 (2H, dd, J=4.5, 1.6 Hz), 7.65 (2H, dd, J=4.6, 1.7 Hz), 7.46-7.41 (2H, m), 7.29-7.27 (1H, m), 7.10 (1H, s), 5.61 (2H, s), 3.61 (3H, s), 2.58 (3H, s).

Production Example 21

A mixture of 0.60 g of 1-(2-bromomethyl-3-methylphenyl)-4-methyl-1,4-dihydrotetrazol-5-one mentioned in Reference Production Example 19, 0.40 g of 4-(pyridin-3-yl)-2-oxo-thiazole, 0.90 g of cesium carbonate, and 10 mL of acetonitrile was stirred with heating under reflux for 2 hours. The reaction mixture allowed to cool was filtered and then concentrated under reduced pressure. The residue thus obtained was subjected to silica gel column chromatography to obtain 0.18 g of 2-{[1-(4,5-dihydro-4-methyl-5-oxo-1H-tetrazol-1-yl)-3-methylphenyl-2-yl]methyloxy}-4-(pyridin-3-yl)thiazole (hereinafter referred to as the present compound 21).

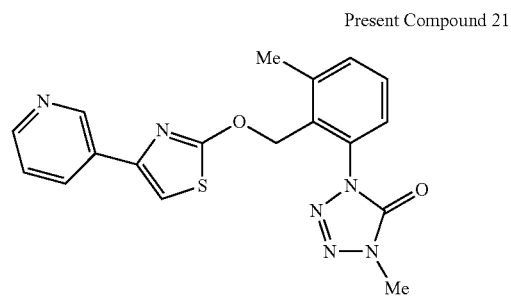 [SMILES: Cc1cccc(-n2nnn(C)c2=O)c1COc1nc(-c2cccnc2)cs1]

Present Compound 21

¹H-NMR (CDCl₃) δ: 9.00 (1H, dd, J=2.2, 1.0 Hz), 8.54 (1H, dd, J=4.9, 1.7 Hz), 8.07-8.04 (1H, m), 7.45-7.40 (2H, m), 7.33 (1H, ddd, J=7.9, 4.9, 0.9 Hz), 7.28-7.27 (1H, m), 6.93 (1H, s), 5.61 (2H, s), 3.63 (3H, s), 2.58 (3H, s).

Production Example 22

A mixture of 0.3 g of 1-(2-[{(1H-pyrazol-3-yl)}oxymethyl]-3-methylphenyl)-4-methyl-1,4-dihydrotetrazol-5-one mentioned in Reference Production Example 26, 0.18 g of indole, 0.53 g of iodine, 2 mL of an aqueous saturated ammonium formate solution, and 2 mL of acetonitrile was stirred at room temperature for 1 hour. Water was poured into the reaction mixture and the mixture was extracted with ethyl acetate. The organic layer was washed with water and a saturated saline solution, dried over anhydrous sodium sulfate, and then concentrated under reduced pressure. The residue thus obtained was subjected to silica gel column chromatography to obtain 0.11 g of 1-methyl-4-{3-methyl-2-[1-(1H-indol-2-yl)-1H-pyrazol-3-yl]oxymethyl-phenyl}1,4-dihydro-tetrazol-5-one (hereinafter referred to as the present compound 22).

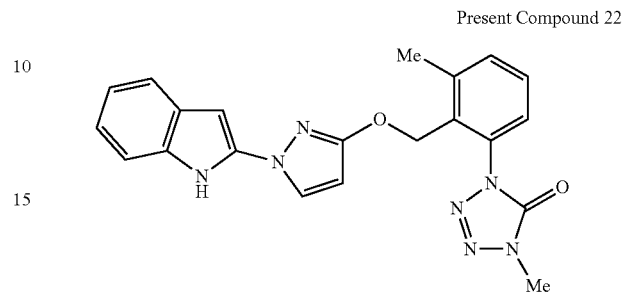

Present Compound 22

¹H-NMR (CDCl₃) δ: 9.52 (1H, s), 7.54-7.52 (1H, m), 7.49-7.45 (2H, m), 7.42-7.40 (1H, m), 7.34-7.30 (2H, m), 7.11-7.07 (2H, m), 6.41 (1H, dd, J=2.2, 0.8 Hz), 5.64 (1H, d, J=2.0 Hz), 5.23 (2H, s), 3.54 (3H, s), 2.50 (3H, s).

Production Example 23

A mixture of 0.3 g of 1-(2-[{(1H-pyrazol-3-yl)}oxymethyl]-3-methylphenyl)-4-methyl-1,4-dihydrotetrazol-5-one mentioned in Reference Production Example 26, 0.21 g of 1-methyl-indole, 0.53 g of iodine, 2 mL of an aqueous saturated ammonium formate solution, and 2 mL of acetonitrile was stirred at room temperature for 4 hours. Water was poured into the reaction mixture and the mixture was extracted with ethyl acetate. The organic layer was washed with water and a saturated saline solution, dried over anhydrous sodium sulfate, and then concentrated under reduced pressure. The residue thus obtained was subjected to silica gel column chromatography to obtain 0.12 g of 1-methyl-4-{3-methyl-2-[1-(1-methyl-indol-2-yl)-1H-pyrazol-3-yl]oxymethyl-phenyl}1,4-dihydro-tetrazol-5-one (hereinafter referred to as the present compound 23).

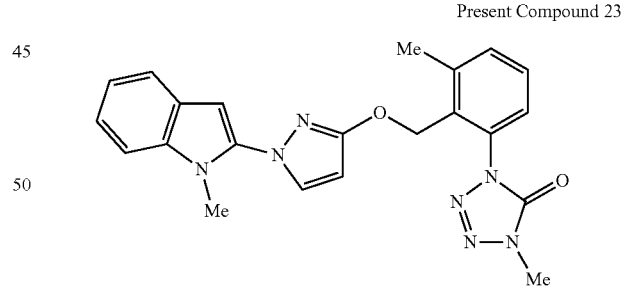

Present Compound 23

¹H-NMR (CDCl₃) δ: 7.62-7.60 (1H, m), 7.52 (1H, d, J=2.1 Hz), 7.38-7.21 (5H, m), 7.15-7.11 (1H, m), 6.49-6.48 (1H, m), 5.57 (1H, d, J=2.1 Hz), 5.18 (2H, s), 3.49 (3H, s), 3.43 (3H, s), 2.39 (3H, s).

Production Example 24

A mixture of 0.3 g of 1-(2-[{(1H-pyrazol-3-yl)}oxymethyl]-3-methylphenyl)-4-methyl-1,4-dihydrotetrazol-5-one mentioned in Reference Production Example 26, 0.21 g of 2-hydroxybenzoimidazole, and 2 mL of phosphoryl chloride was stirred at 110° C. for 8 hours. Water was poured into the reaction mixture allowed to cool and the mixture was extracted with ethyl acetate. The organic layer was washed with water and a saturated saline solution, dried over anhydrous sodium sulfate, and then concentrated under reduced pressure. The residue thus obtained was subjected to silica gel column chromatography to obtain 0.1 g of 1-methyl-4-{3-methyl-2-[1-(1H-benzoimidazol-2-yl)-1H-pyrazol-3-yl]oxymethyl-phenyl}1,4-dihydro-tetrazol-5-one (hereinafter referred to as the present compound 24).

Present Compound 24

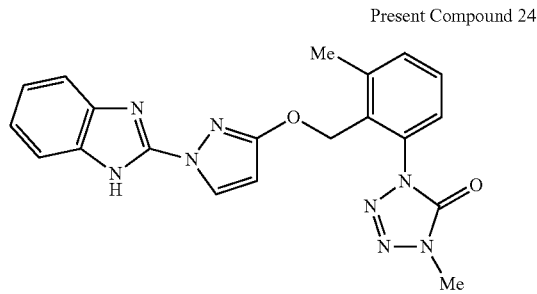 [SMILES: Cc1cccc(-n2nnn(C)c2=O)c1COc1ccn(-c2nc3ccccc3[nH]2)n1]

$^1$H-NMR (CDCl$_3$) δ: 11.07 (1H, s), 8.17 (1H, d, J=2.7 Hz), 7.61-7.59 (1H, m), 7.52-7.50 (1H, m), 7.38-7.31 (2H, m), 7.27-7.24 (1H, m), 7.22-7.19 (2H, m), 5.88 (1H, d, J=2.7 Hz), 5.25 (2H, s), 3.73 (3H, s), 2.53 (3H, s).

In the same manner as in Production Example 1, the present compounds 25 to 27 were synthesized.

The structural formulas of the present compounds and $^1$H-NMR data thereof are shown in Table 1.

Production Example 25

To 0.3 g of 1-(2-[{(1H-pyrazol-3-yl)}oxymethyl]-3-methylphenyl)-4-methyl-1,4-dihydrotetrazol-5-one mentioned in Reference Production Example 26 and 5 mL of N,N-dimethylformamide, 0.06 g of 55' sodium hydride was added, followed by stirring at room temperature for 30 minutes. To the reaction mixture was added 0.16 g of 2,5-dichloropyridine, followed by stirring at 100° C. for 2 hours. Water was poured into the reaction mixture allowed to cool and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 0.1 g of 1-{2-[1-(5-chloropyridin-2-yl)-1H-pyrazol-3-yl]oxymethyl-3-methylphenyl}-4-methyl-1,4-dihydrotetrazol-5-one (hereinafter referred to as the present compound 28).

Present Compound 28

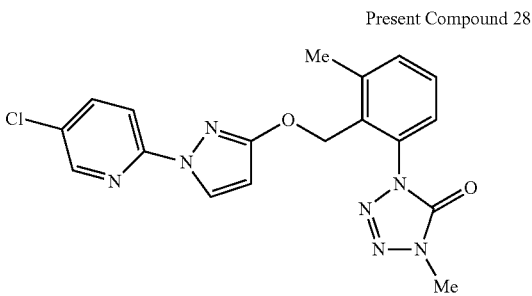 [SMILES: Cc1cccc(-n2nnn(C)c2=O)c1COc1ccn(-c2ccc(Cl)cn2)n1]

TABLE 1

| Present compound No. | Structural formula | $^1$H-NMR data |
|---|---|---|
| 25 | ![compound 25] | $^1$H-NMR (CDCl$_3$) δ: 7.52 (1H, d, J = 2.5 Hz), 7.39-7.36 (2H, m), 7.33-7.31 (1H, m), 7.26-7.23 (2H, m), 7.18-7.17 (1H, m), 5.74 (1H, d, J = 2.7 Hz), 5.31 (2H, s), 3.62 (3H, s), 2.55 (3H, s). |
| 26 | ![compound 26] | $^1$H-NMR (CDCl$_3$) δ: 8.09 (1H, d, J = 2.7 Hz), 7.66-7.64 (1H, m), 7.40-7.37 (2H, m), 7.25-7.23 (1H, m), 7.03-7.02 (1H, m), 6.94-6.90 (1H, m), 5.76 (1H, d, J = 2.7 Hz), 5.32 (2H, s), 4.67 (2H, t, J = 8.8 Hz), 3.63 (3H, s), 3.27 (2H, t, J = 8.8 Hz), 2.55 (3H, s). |
| 27 | ![compound 27] | $^1$H-NMR (CDCl$_3$) δ: 7.73-7.69 (1H, m), 7.40-7.38 (2H, m), 7.34 (1H, d, J = 2.5 Hz), 7.26-7.23 (1H, m), 6.86-6.83 (1H, m), 5.81 (1H, d, J = 2.5 Hz), 5.29 (2H, s), 3.59 (3H, s), 2.55 (3H, s), 2.42 (3H, s). |

¹H-NMR (CDCl₃) δ: 8.26-8.25 (2H, m), 7.71-7.70 (2H, m), 7.42-7.37 (2H, m), 7.30-7.24 (1H, m), 5.85 (1H, d, J=2.7 Hz), 5.33 (2H, s), 3.64 (3H, s), 2.54 (3H, s).

In the same manner as in Production Example 25, the present compounds 29 to 61 were synthesized.

The structural formulas of the present compounds and ¹H-NMR data thereof are shown in Table 2.

TABLE 2

| Present compound No. | Structural formula | ¹H-NMR data |
|---|---|---|
| 29 | 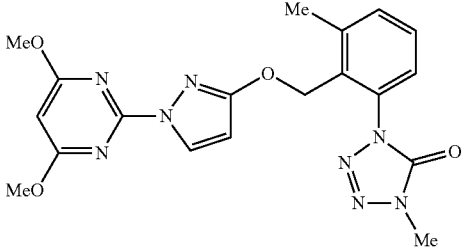 [SMILES: COc1cc(OC)nc(-n2ccc(OCc3c(C)cccc3-n3nnn(C)c3=O)n2)n1] | ¹H-NMR (CDCl₃) δ: 8.34 (1H, d, J = 2.7 Hz), 7.41-7.38 (2H, m), 7.26-7.23 (1H, m), 5.89 (1H, d, J = 2.9 Hz), 5.86 (1H, s), 5.39 (2H, s), 4.01 (6H, s), 3.67 (3H, s), 2.58 (3H, s). |
| 30 | 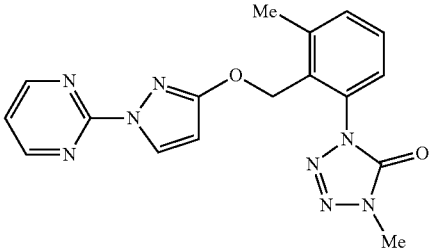 [SMILES: Cc1cccc(-n2nnn(C)c2=O)c1COc1ccn(-c2ncccn2)n1] | ¹H-NMR (CDCl₃) δ: 8.27-8.25 (2H, m), 7.71 (2H, d, J = 1.6 Hz), 7.41-7.37 (2H, m), 7.27-7.25 (1H, m), 5.85 (1H, d, J = 2.7 Hz), 5.33 (2H, s), 3.65 (3H, s), 2.55 (3H, s). |
| 31 | 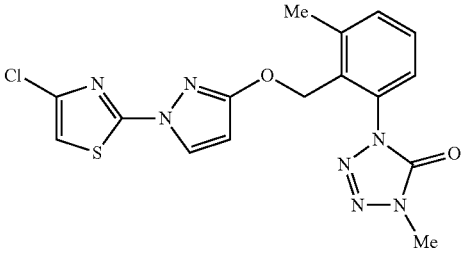 [SMILES: Cc1cccc(-n2nnn(C)c2=O)c1COc1ccn(-c2nc(Cl)cs2)n1] | ¹H-NMR (CDCl₃) δ: 8.05 (1H, d, J = 2.5 Hz), 7.43-7.37 (2H, m), 7.29-7.25 (1H, m), 6.75 (1H, s), 5.87 (1H, d, J = 2.7 Hz), 5.31 (2H, s), 3.67 (3H, s), 2.55 (3H, s). |
| 32 | 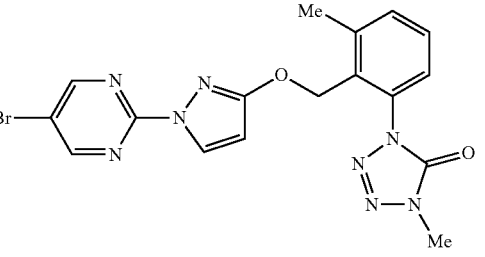 | ¹H-NMR (CDCl₃) δ: 8.71 (2H, s), 8.36 (1H, d, J = 2.7 Hz), 7.44-7.39 (2H, m), 7.28-7.26 (1H, m), 5.98 (1H, d, J = 2.7 Hz), 5.36 (2H, s), 3.66 (3H, s), 2.53 (3H, s). |
| 33 | 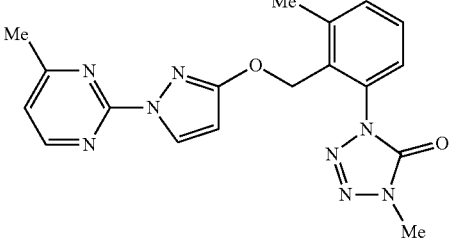 | ¹H-NMR (CDCl₃) δ: 8.54 (1H, d, J = 5.0 Hz), 8.44 (1H, d, J = 2.7 Hz), 7.42-7.38 (2H, m), 7.27-7.24 (1H, m), 6.97 (1H, d, J = 5.0 Hz), 5.94 (1H, d, J = 2.7 Hz), 5.38 (2H, s), 3.65 (3H, s), 2.55 (3H, s), 2.53 (3H, s). |

TABLE 2-continued
| Present compound No. | Structural formula | ¹H-NMR data |
|---|---|---|
| 34 | 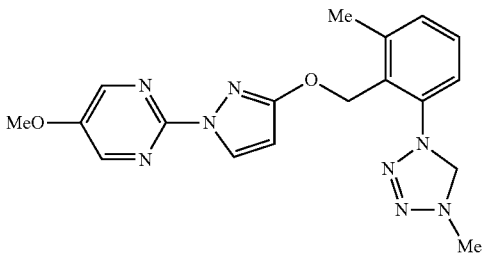 [SMILES: COc1cnc(-n2ccc(OCc3c(C)cccc3N3CN(C)N=N3)n2)nc1] | ¹H-NMR (CDCl₃) δ: 8.36 (2H, s), 8.32 (1H, d, J = 2.7 Hz), 7.40-7.36 (2H, m), 7.26-7.23 (1H, m), 5.91 (1H, d, J = 2.7 Hz), 5.36 (2H, s), 3.91 (3H, s), 3.64 (3H, s), 2.52 (3H, s). |
| 35 | 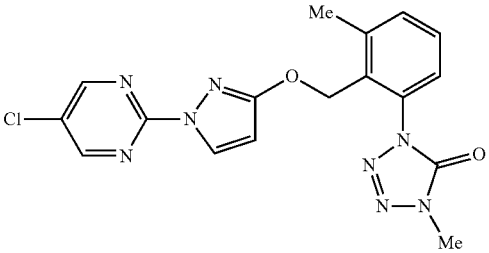 [SMILES: Cc1cccc(-n2nnn(C)c2=O)c1COc1ccn(-c2ncc(Cl)cn2)n1] | ¹H-NMR (CDCl₃) δ: 8.63 (2H, s), 8.36 (1H, d, J = 2.7 Hz), 7.45-7.39 (2H, m), 7.28-7.26 (1H, m), 5.98 (1H, d, J = 2.7 Hz), 5.36 (2H, s), 3.66 (3H, s), 2.53 (3H, s). |
| 36 | 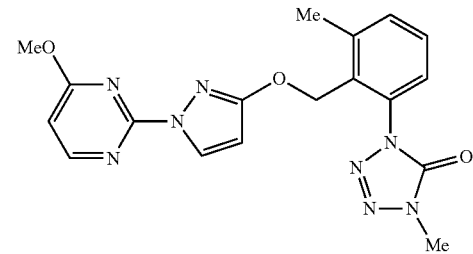 [SMILES: COc1ccnc(-n2ccc(OCc3c(C)cccc3-n3nnn(C)c3=O)n2)n1] | ¹H-NMR (CDCl₃) δ: 8.42 (1H, d, J = 5.9 Hz), 8.37 (1H, d, J = 2.7 Hz), 7.44-7.38 (2H, m), 7.28-7.25 (1H, m), 6.53 (1H, d, J = 5.9 Hz), 5.94 (1H, d, J = 2.7 Hz), 5.37 (2H, s), 4.04 (3H, s), 3.66 (3H, s), 2.54 (3H, s). |
| 37 | 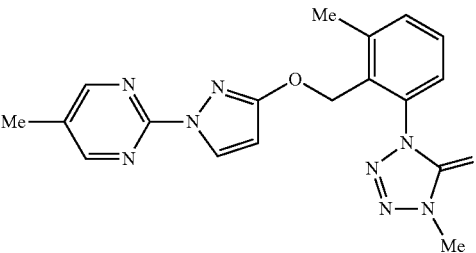 | ¹H-NMR (CDCl₃) δ: 8.52 (2H, s), 8.39 (1H, d, J = 2.7 Hz), 7.42-7.39 (2H, m), 7.28-7.25 (1H, m), 5.94 (1H, d, J = 2.7 Hz), 5.36 (2H, s), 3.66 (3H, s), 2.53 (3H, s), 2.32 (3H, s). |
| 38 | 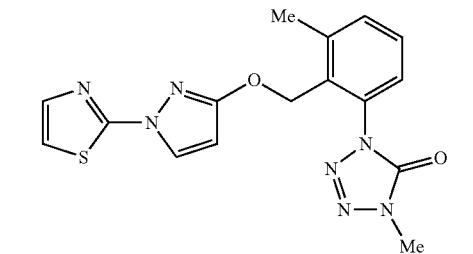 [SMILES: Cc1cccc(-n2nnn(C)c2=O)c1COc1ccn(-c2nccs2)n1] | ¹H-NMR (CDCl₃) δ: 8.07 (1H, d, J = 2.7 Hz), 7.44 (1H, d, J = 3.4 Hz), 7.41-7.38 (2H, m), 7.27-7.25 (1H, m), 7.00 (2H, d, J = 3.4 Hz), 5.85 (1H, d, J = 2.7 Hz), 5.33 (2H, s), 3.67 (3H, s), 2.57 (3H, s). |
| 39 | 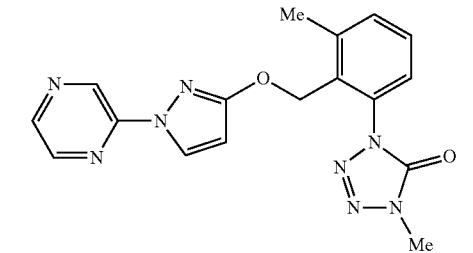 [SMILES: Cc1cccc(-n2nnn(C)c2=O)c1COc1ccn(-c2cnccn2)n1] | ¹H-NMR (CDCl₃) δ: 9.07 (1H, d, J = 1.4 Hz), 8.36 (1H, d, J = 2.7 Hz), 8.25-8.24 (2H, m), 7.40-7.37 (2H, m), 7.28-7.25 (1H, m), 5.89 (1H, d, J = 2.7 Hz), 5.38 (2H, s), 3.67 (3H, s), 2.57 (3H, s). |

TABLE 2-continued

| Present compound No. | Structural formula | ¹H-NMR data |
|---|---|---|
| 40 | (5-F-pyridin-2-yl)-pyrazole-O-CH₂-(Me,aryl)-tetrazolone structure | ¹H-NMR (CDCl₃) δ: 8.58 (1H, d, J = 3.6 Hz), 7.77 (1H, dd, J = 8.6, 2.9 Hz), 7.68 (1H, d, J = 2.7 Hz), 7.51-7.49 (1H, m), 7.40-7.37 (2H, m), 7.26-7.24 (1H, m), 5.87 (1H, d, J = 2.7 Hz), 5.33 (2H, s), 3.66 (3H, s), 2.55 (3H, s). |
| 41 | (5-Me-pyridin-2-yl)-pyrazole-O-CH₂-(Me,aryl)-tetrazolone structure | ¹H-NMR (CDCl₃) δ: 8.28 (1H, d, J = 2.7 Hz), 8.15-8.14 (1H, m), 7.66 (1H, d, J = 8.4 Hz), 7.58-7.56 (1H, m), 7.40-7.38 (2H, m), 7.27-7.25 (1H, m), 5.82 (1H, d, J = 2.7 Hz), 5.33 (2H, s), 3.64 (3H, s), 2.56 (3H, s), 2.33 (3H, s). |
| 42 | (5-Br-pyridin-2-yl)-pyrazole-O-CH₂-(Me,aryl)-tetrazolone structure | ¹H-NMR (CDCl₃) δ: 8.34-8.33 (1H, m), 8.25 (1H, d, J = 2.7 Hz), 7.83 (1H, dd, J = 8.8, 2.4 Hz), 7.66-7.64 (1H, m), 7.41-7.36 (2H, m), 7.28-7.24 (1H, m), 5.85 (1H, d, J = 2.7 Hz), 5.33 (2H, s), 3.64 (3H, s), 2.54 (3H, s). |
| 43 | (5-Me-thiazol-2-yl)-pyrazole-O-CH₂-(Me,aryl)-tetrazolone structure | ¹H-NMR (CDCl₃) δ: 8.01 (1H, d, J = 2.7 Hz), 7.41-7.36 (2H, m), 7.27-7.24 (1H, m), 7.08-7.07 (1H, m), 5.82 (1H, d, J = 2.7 Hz), 5.32 (2H, s), 3.66 (3H, s), 2.55 (3H, s), 2.40 (3H, s). |
| 44 | (6-MeO-pyridazin-3-yl)-pyrazole-O-CH₂-(Me,aryl)-tetrazolone structure | ¹H-NMR (CDCl₃) δ: 8.40 (1H, d, J = 2.7 Hz), 7.96 (1H, d, J = 9.3 Hz), 7.43-7.38 (2H, m), 7.28-7.25 (1H, m), 7.09 (1H, d, J = 9.3 Hz), 5.89 (1H, d, J = 2.7 Hz), 5.31 (2H, s), 4.13 (3H, s), 3.66 (3H, s), 2.55 (3H, s). |

TABLE 2-continued

| Present compound No. | Structural formula | ¹H-NMR data |
|---|---|---|
| 45 | | ¹H-NMR (CDCl$_3$) δ: 8.00 (1H, d, J = 2.7 Hz), 7.41-7.37 (2H, m), 7.34 (1H, s), 7.27-7.26 (1H, m), 5.85 (1H, d, J = 2.7 Hz), 5.31 (2H, s), 3.69 (3H, s), 2.56 (3H, s). |
| 46 | | ¹H-NMR (CDCl$_3$) δ: 8.84 (2H, s), 7.71 (1H, d, J = 2.7 Hz), 7.42-7.38 (2H, m), 7.27-7.24 (1H, m), 5.93 (1H, d, J = 2.7 Hz), 5.34 (2H, s), 3.69 (3H, s), 2.56 (3H, s). |
| 47 | | ¹H-NMR (CDCl$_3$) δ: 8.58-8.56 (1H, m), 8.32 (1H, d, J = 2.9 Hz), 7.97 (1H, d, J = 8.7 Hz), 7.82 (1H, d, J = 8.7 Hz), 7.42-7.36 (2H, m), 7.28-7.26 (1H, m), 5.93 (1H, d, J = 2.9 Hz), 5.35 (2H, s), 3.66 (3H, s), 2.54 (3H, s). |
| 48 | | ¹H-NMR (CDCl$_3$) δ: 8.21 (1H, d, J = 2.8 Hz), 7.81-7.76 (2H, m), 7.43-7.36 (3H, m), 7.30-7.25 (2H, m), 5.92 (1H, d, J = 2.8 Hz), 5.37 (2H, s), 3.65 (3H, s), 2.56 (3H, s). |
| 49 | | ¹H-NMR (CDCl$_3$) δ: 8.11 (1H, d, J = 2.9 Hz), 7.63 (1H, d, J = 7.7 Hz), 7.51 (1H, d, J = 7.7 Hz), 7.41-7.38 (2H, m), 7.34-7.24 (3H, m), 6.01 (1H, d, J = 2.9 Hz), 5.41 (2H, s), 3.64 (3H, s), 2.53 (3H, s). |
| 50 | | ¹H-NMR (CDCl$_3$) δ: 8.90 (1H, s), 8.38 (1H, d, J = 2.7 Hz), 8.31 (1H, d, J = 8.6 Hz), 7.82 (1H, d, J = 8.6 Hz), 7.44-7.39 (2H, m), 7.29-7.25 (1H, m), 5.91 (1H, d, J = 2.7 Hz), 5.35 (2H, s), 3.67 (3H, s), 2.63 (3H, s), 2.56 (3H, s). |

TABLE 2-continued
| Present compound No. | Structural formula | ¹H-NMR data |
|---|---|---|
| 51 | 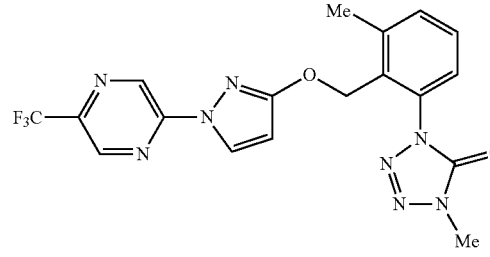 | ¹H-NMR (CDCl₃) δ: 9.11 (1H, s), 8.60 (1H, s), 8.29 (1H, d, J = 2.9 Hz), 7.41-7.38 (2H, m), 7.29-7.26 (1H, m), 5.96 (1H, d, J = 2.9 Hz), 5.39 (2H, s), 3.69 (3H, s), 2.58 (3H, s). |
| 52 | 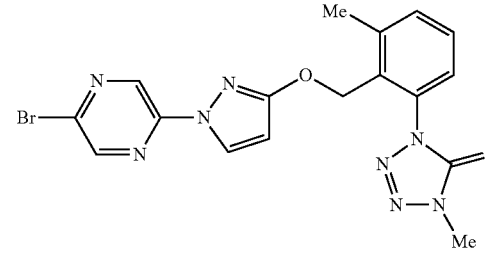 | ¹H-NMR (CDCl₃) δ: 8.81 (1H, d, J = 1.4 Hz), 8.34 (1H, d, J = 1.4 Hz), 8.19 (1H, d, J = 2.7 Hz), 7.41-7.38 (2H, m), 7.28-7.25 (1H, m), 5.91 (1H, d, J = 2.7 Hz), 5.36 (2H, s), 3.69 (3H, s), 2.56 (3H, s). |
| 53 | 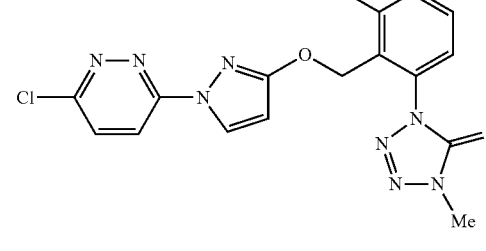 | ¹H-NMR (CDCl₃) δ: 8.48 (1H, d, J = 3.0 Hz), 7.99 (1H, d, J = 9.2 Hz), 7.57 (1H, d, J = 9.2 Hz), 7.42-7.39 (2H, m), 7.28-7.25 (1H, m), 5.95 (1H, d, J = 3.0 Hz), 5.31 (2H, s), 3.67 (3H, s), 2.54 (3H, s). |
| 54 | 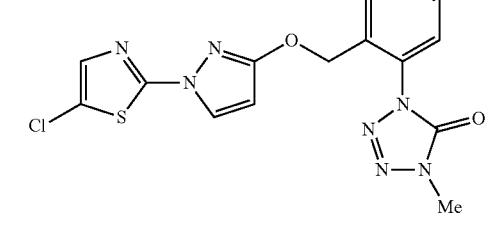 | ¹H-NMR (CDCl₃) δ: 7.99 (1H, d, J = 2.7 Hz), 7.42-7.39 (2H, m), 7.27-7.25 (2H, m), 5.85 (1H, d, J = 2.7 Hz), 5.31 (2H, s), 3.69 (3H, s), 2.56 (3H, s). |
| 55 | 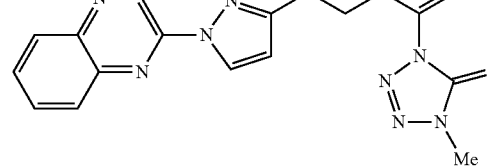 | ¹H-NMR (CDCl₃) δ: 9.45 (1H, s), 8.48 (1H, d, J = 2.7 Hz), 8.10 (1H, d, J = 7.2 Hz), 7.93 (1H, d, J = 7.2 Hz), 7.77-7.73 (1H, m), 7.69-7.65 (1H, m), 7.43-7.40 (2H, m), 7.29-7.26 (1H, m), 5.97 (1H, d, J = 2.7 Hz), 5.43 (2H, s), 3.70 (3H, s), 2.60 (3H, s). |

TABLE 2-continued

| Present compound No. | Structural formula | ¹H-NMR data |
|---|---|---|
| 56 | | ¹H-NMR (CDCl₃) δ: 8.20 (1H, d, J = 2.7 Hz), 7.78 (1H, d, J = 1.8 Hz), 7.73-7.71 (1H, m), 7.43-7.39 (3H, m), 7.29-7.27 (1H, m), 5.94 (1H, d, J = 2.7 Hz), 5.36 (2H, s), 3.69 (3H, s), 2.59 (3H, s). |
| 57 | | ¹H-NMR (CDCl₃) δ: 8.20 (1H, d, J = 2.9 Hz), 7.80 (1H, d, J = 2.0 Hz), 7.72-7.69 (1H, m), 7.42-7.40 (2H, m), 7.30-7.26 (2H, m), 5.94 (1H, d, J = 2.9 Hz), 5.36 (2H, s), 3.69 (3H, s), 2.59 (3H, s). |
| 58 | | ¹H-NMR (CDCl₃) δ: 8.56 (1H d, J = 2.7 Hz), 8.22 (1H, d, J = 8.8 Hz), 8.02 (1H, d, J = 8.8 Hz), 7.94 (1H, d, J = 7.9 Hz), 7.81-7.79 (1H, m), 7.71-7.67 (1H, m), 7.49-7.39 (3H, m), 7.29-7.26 (1H, m), 5.91 (1H, d, J = 2.7 Hz), 5.39 (2H, s), 3.64 (3H, s), 2.58 (3H, s). |
| 59 | | ¹H-NMR (CDCl₃) δ: 8.21 (1H, d, J = 2.9 Hz), 7.70 (1H, d, J = 8.4 Hz), 7.60 (1H, s), 7.43-7.40 (2H, m), 7.28-7.24 (2H, m), 5.92 (1H, d, J = 2.9 Hz), 5.36 (2H, s), 3.68 (3H, s), 2.59 (3H, s), 2.48 (3H, s). |
| 60 | | ¹H-NMR (CDCl₃) δ: 8.18 (1H, d, J = 2.7 Hz), 7.71 (1H, d, J = 9.1 Hz), 7.44-7.39 (2H, m), 7.29-7.26 (2H, m), 7.04 (1H, dd, J = 8.9, 2.6 Hz), 5.91 (1H, d, J = 2.7 Hz), 5.36 (2H, s), 3.88 (3H, s), 3.68 (3H, s), 2.59 (3H, s). |

TABLE 2-continued

| Present compound No. | Structural formula | ¹H-NMR data |
|---|---|---|
| 61 | | ¹H-NMR (CDCl₃) δ: 9.36 (1H, s), 8.59 (1H, d, J = 2.7 Hz), 8.02 (1H, d, J = 8.4 Hz), 7.91-7.87 (2H, m), 7.56-7.52 (1H, m), 7.43-7.39 (2H, m), 7.29-7.26 (1H, m), 6.00 (1H, d, J = 2.7 Hz), 5.45 (2H, s), 3.66 (3H, s), 2.56 (3H, s). |

Production Example 26

A mixture of 0.30 g of the present compound 1, 0.28 g of Lawesson's reagent (2,4-Bis(4-methoxyphenyl)-1,3,2,4-dithiadiphosphetane 2,4-disulfide), and 10 mL of toluene was stirred with heating under reflux for 5 hours, and then concentrated under reduced pressure. The residue thus obtained was subjected to silica gel column chromatography to obtain 0.18 g of 1-(2-{[1-(6-chloro-2-methoxypyridin-3-yl)-1H-pyrazol-3-yl]oxymethyl}-3-methylphenyl)-4-methyl-1,4-dihydrotetrazole-5-thione (hereinafter referred to as the present compound 62).

Present Compound 62

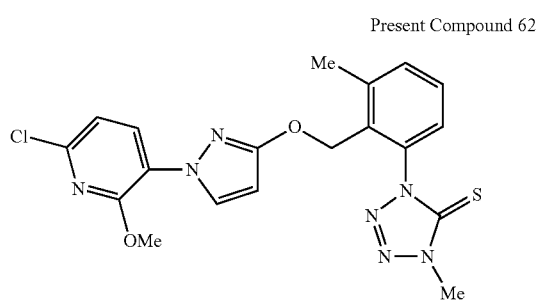 [SMILES: COc1nc(Cl)ccc1-n1ccc(OCc2c(C)cccc2-n2nnn(C)c2=S)n1]

¹H-NMR (CDCl₃) δ: 8.04-8.01 (2H, m), 7.45-7.43 (2H, m), 7.27-7.24 (1H, m), 7.01 (1H, d, J=8.2 Hz), 5.77 (1H, d, J=2.7 Hz), 5.23 (2H, s), 4.05 (3H, s), 3.89 (3H, s), 2.56 (3H, s).

With respect to the pyrazole compounds, Synthesis Examples will be shown below.

Synthesis Example 1

A mixture of 0.38 g of 2-(bromomethyl)-3-methyl-1-nitrobenzene (synthesized in accordance with the process mentioned in WO 2013/162072 A), 0.37 g of 1-(6-chloro-2-methoxypyridin-3-yl)-1H-pyrazol-3-ol mentioned in Reference Production Example 37, 0.45 g of potassium carbonate, and 10 mL of acetonitrile was stirred with heating under reflux for 2 hours. Water was poured into the reaction mixture allowed to cool and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.55 g of 3-[(2-nitro-6-methylphenyl)methyloxy]-1-(6-chloro-2-methoxypyridin-3-yl)pyrazole.

3-[(2-Nitro-6-methylphenyl)methyloxy]-1-(6-chloro-2-methoxypyridin-3-yl)pyrazole

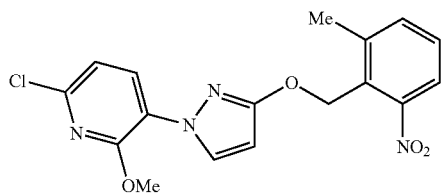 [SMILES: COc1nc(Cl)ccc1-n1ccc(OCc2c(C)cccc2[N+](=O)[O-])n1]

¹H-NMR (CDCl₃) δ: 8.06 (1H, d, J=2.7 Hz), 8.03 (1H, d, J=8.2 Hz), 7.62-7.60 (1H, m), 7.43-7.41 (1H, m), 7.35-7.31 (1H, m), 7.01 (1H, d, J=8.2 Hz), 5.84 (1H, d, J=2.7 Hz), 5.53 (2H, s), 4.04 (3H, s), 2.55 (3H, s).

Synthesis Example 2

A mixture of 0.55 g of 3-[(2-nitro-6-methylphenyl)methyloxy]-1-(6-chloro-2-methoxypyridin-3-yl)pyrazole mentioned in Synthesis Example 1, 0.05 g of 5% platinum-activated carbon, and 20 mL of ethyl acetate was stirred in a hydrogen atmosphere at room temperature for 6 hours. The reaction mixture was filtered and the filtrate was concentrated under reduced pressure to obtain 0.5 g of 3-[(2-amino-6-methylphenyl)methyloxy]-1-(6-chloro-2-methoxypyridin-3-yl)pyrazole.

3-[(2-Amino-6-methylphenyl)methyloxy]-1-(6-chloro-2-methoxypyridin-3-yl)pyrazole

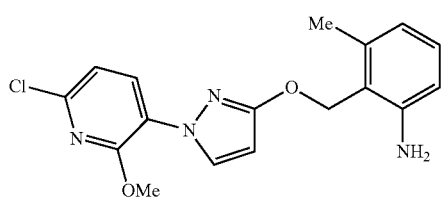 [SMILES: COc1nc(Cl)ccc1-n1ccc(OCc2c(C)cccc2N)n1]

¹H-NMR (CDCl₃) δ: 8.05-8.02 (2H, m), 7.03-6.99 (1H, m), 6.97 (1H, d, J=8.2 Hz), 6.61 (1H, d, J=7.2 Hz), 6.54 (1H, d, J=7.9 Hz), 5.87 (1H, d, J=2.7 Hz), 5.34 (2H, s), 4.18 (2H, br s), 4.03 (3H, s), 2.41 (3H, s).

Synthesis Example 3

A mixture of 0.5 g of 3-[(2-amino-6-methylphenyl)methyloxy]-1-(6-chloro-2-methoxypyridin-3-yl)pyrazole mentioned in Synthesis Example 2, 0.86 g of triphosgene, and 20 mL of toluene was stirred with heating under reflux for 4 hours. The reaction mixture allowed to cool was concentrated under reduced pressure to obtain 0.48 g of 3-[(2-isocyanato-6-methylphenyl)methyloxy]-1-(6-chloro-2-methoxypyridin-3-yl)pyrazole.

3-[(2-Isocyanato-6-methylphenyl)methyloxy]-1-(6-chloro-2-methoxypyridin-3-yl)pyrazole

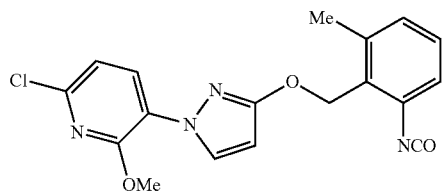

$^1$H-NMR (CDCl$_3$) δ: 8.15-8.06 (2H, m), 7.24-7.17 (1H, m), 7.07-6.98 (3H, m), 5.93-5.89 (1H, m), 5.36 (2H, s), 4.07 (3H, s), 2.45 (3H, s).

Synthesis Example 4

Under ice cooling, 0.26 g of anhydrous aluminum chloride was added to 10 mL of N,N-dimethylformamide, followed by stirring for 15 minutes. To this was added 0.21 g of sodium azide, followed by stirring for 15 minutes. After adding 0.48 g of 3-[(2-isocyanato-6-methylphenyl)methyloxy]-1-(6-chloro-2-methoxypyridin-3-yl)pyrazole mentioned in Synthesis Example 3, the mixture was heated at 80° C. for 4 hours. After cooling, the reaction solution was added in a mixture of 0.5 g of sodium nitrite and 10 mL of water while stirring. The mixture was acidified with 10% hydrochloric acid, and then the precipitated solid was collected by filtration. The residue thus obtained was washed with water, and then washed with tert-butyl methyl ether to obtain 0.31 g of 1-(2-{[1-(6-chloro-2-methoxypyridin-3-yl)-1H-pyrazol-3-yl]oxymethyl}-3-methylphenyl)-4H-1,4-dihydrotetrazol-5-one.

1-(2-{[1-(6-Chloro-2-methoxypyridin-3-yl)-1H-pyrazol-3-yl]oxymethyl}-3-methylphenyl)-4H-1,4-dihydrotetrazol-5-one

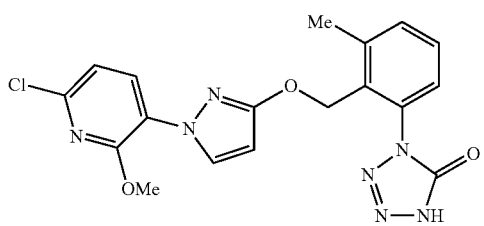 [SMILES: COc1nc(Cl)ccc1-n1ccc(OCc2c(C)cccc2-n2nn[nH]c2=O)n1]

$^1$H-NMR (DMSO-D$_6$) δ: 8.15 (1H, d, J=2.5 Hz), 7.99 (1H, d, J=8.2 Hz), 7.49-7.47 (2H, m), 7.36-7.33 (1H, m), 7.22 (1H, d, J=8.2 Hz), 5.92 (1H, d, J=2.5 Hz), 5.23 (2H, s), 3.99 (3H, s), 2.50 (3H, s).

With respect to the production of intermediates for the production of the above-mentioned present compounds, Reference Production Examples are shown below.

Reference Production Example 1

A mixture of 21.1 g of methyl 3-methoxyacrylate, 10.0 g of hydrazine hydrate, and 20 mL of methanol was stirred with heating under reflux for 2 hours. The reaction mixture was concentrated under reduced pressure to obtain 11.0 g of 1H-pyrazol-3-ol.

1H-pyrazol-3-ol

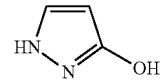

$^1$H-NMR (DMSO-d$_6$) δ (ppm): 10.22 (1H, s), 7.35 (1H, d, J=2.2 Hz), 5.43 (1H, d, J=2.2 Hz)

Reference Production Example 2

A mixture of 3.00 g of 1H-pyrazol-3-ol mentioned in Reference Production Example 1, 3.1 mL of acetic anhydride, and 90 mL of acetic acid was stirred at 25° C. for 2 hours. Water was poured into the reaction mixture and the mixture was extracted with ethyl acetate. The organic layer was washed with water, a saturated sodium bicarbonate solution, and a saturated saline solution, dried over anhydrous magnesium sulfate, and then concentrated under reduced pressure to obtain 1.50 g of 1-acetyl-1H-pyrazol-3-ol.

1-Acetyl-1H-pyrazol-3-ol

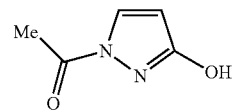

$^1$H-NMR (DMSO-d$_6$) δ (ppm): 11.04 (1H, s), 8.14 (1H, dd, J=2.9, 1.0 Hz), 6.02 (1H, dd, J=2.9, 1.0 Hz), 2.49 (3H, s).

Reference Production Example 3

A mixture of 25.0 g of 1-bromo-2-methyl-3-aminobenzene, 60.0 g of triphosgene, and 400 ml of toluene was stirred with heating under reflux for 3 hours. The reaction mixture allowed to cool was concentrated under reduced pressure to obtain 30.3 g of 1-bromo-3-isocyanato-2-methylbenzene.

1-Bromo-3-isocyanato-2-methylbenzene

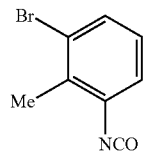

$^1$H-NMR (CDCl$_3$) δ (ppm): 7.39 (1H, dd, 1.5, 7.7 Hz), 7.05 (1H, dd, J=1.7, 8.0 Hz), 7.00 (1H, dt, J=0.5, 8.0 Hz), 2.42 (3H, s).

Reference Production Example 4

A mixture of 15.0 g of 3-amino-1-methoxy-2-methylbenzene, 48.7 g of triphosgene, and 350 ml of toluene was stirred with heating under reflux for 3 hours. The reaction mixture allowed to cool was concentrated under reduced pressure to obtain 17.0 g of 1-methoxy-3-isocyanato-2-methylbenzene.

1-Methoxy-3-isocyanato-2-methylbenzene

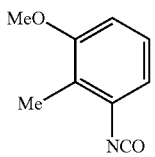

$^1$H-NMR (CDCl$_3$) δ (ppm): 7.09 (1H, t, J=8.2 Hz), 6.72 (1H, dd, J=0.5, 8.0 Hz), 6.69 (1H, d, J=8.2 Hz), 3.82 (3H, s), 2.19 (3H, s).

Reference Production Example 5

Under ice cooling, 21.9 g of anhydrous aluminum chloride was added to 250 mL of N,N-dimethylformamide, followed by stirring for 15 minutes. To this was added 10.7 g of sodium azide and, after stirring for 15 minutes, 25.0 g of 1-chloro-3-isocyanato-2-methylbenzene was added, followed by heating at 80° C. for 5 hours. After cooling, the reaction solution was added in a mixture of 35 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 17.0 g of 1-(2-methyl-3-chlorophenyl)-1,4-dihydrotetrazol-5-one.

1-(2-Methyl-3-chlorophenyl)-1,4-dihydrotetrazol-5-one

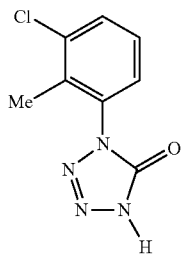

$^1$H-NMR (CDCl$_3$) δ (ppm): 13.08 (1H, s), 7.57 (1H, dd, J=6.8, 2.2 Hz), 7.28-7.36 (2H, m), 2.32 (3H, s).

Reference Production Example 6

Under ice cooling, 2.30 g of 60% sodium hydride was added to a mixture of 10.00 g of 1-(2-methyl-3-chlorophenyl)-1,4-dihydrotetrazol-5-one mentioned in Reference Production Example 5, and 100 mL of N,N-dimethylformamide. The temperature of the mixture was raised to room temperature, followed by stirring for 1 hour. To the reaction mixture, 3.2 mL of methyl iodide was added under ice cooling. The temperature of the mixture was raised to room temperature, followed by stirring for 14 hours. Water was poured into the reaction mixture and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 1.56 g of 1-(2-methyl-3-chlorophenyl)-4-methyl-1,4-dihydrotetrazol-5-one.

1-(2-Methyl-3-chlorophenyl)-4-methyl-1,4-dihydrotetrazol-5-one

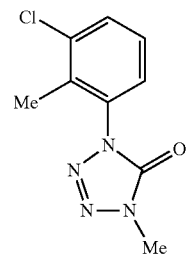

$^1$H-NMR (CDCl$_3$) δ (ppm): 7.52 (1H, dd, J=2.7, 6.8 Hz), 7.28 (1H, d, J=7.1 Hz), 7.27 (1H, d, J=2.7 Hz), 3.73 (3H, s), 2.30 (3H, s).

Reference Production Example 7

A mixture of 1.56 g of 1-(2-methyl-3-chlorophenyl)-4-methyl-1,4-dihydrotetrazol-5-one mentioned in Reference Production Example 6, 0.34 g of 1,1'-azobis(cyclohexane-1-carbonitrile), 1.42 g of N-bromosuccinimide, and 30 mL of chlorobenzene was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 1.94 g of 1-(2-bromomethyl-3-chlorophenyl)-4-methyl-1,4-dihydrotetrazol-5-one.

1-(2-Bromomethyl-3-chlorophenyl)-4-methyl-1,4-dihydrotetrazol-5-one

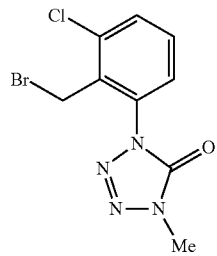 [SMILES: Cn1nnn(-c2cccc(Cl)c2CBr)c1=O]

$^1$H-NMR (CDCl$_3$) δ (ppm): 7.58 (1H, dd, J=1.2, 8.1 Hz), 7.43 (1H, t, J=8.1 Hz), 7.35 (1H, dd, J=1.2, 8.1 Hz), 4.69 (2H, s), 3.76 (3H, s).

Reference Production Example 8

Under ice cooling, 16.0 g of anhydrous aluminum chloride was added to 180 mL of N,N-dimethylformamide, followed by stirring for 15 minutes. To this was added 7.8 g of sodium azide and, after stirring for 15 minutes, 17.0 g of 1-methoxy-3-isocyanato-2-methylbenzene mentioned in Reference Production Example 4 was added, followed by heating at 80° C. for 4.5 hours. After cooling, the reaction solution was added in a mixture of 25 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 16.2 g of 1-(2-methyl-3-methoxyphenyl)-1,4-dihydrotetrazol-5-one.

1-(2-Methyl-3-methoxyphenyl)-1,4-dihydrotetrazol-5-one

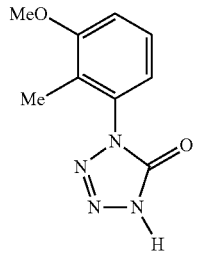

$^1$H-NMR (DMSO-d$_6$) δ (ppm): 14.63 (1H, s), 7.36 (1H, t, J=8.3 Hz), 7.17 (1H, d, J=8.1 Hz), 7.01 (1H, d, J=8.1 Hz), 3.87 (3H, s), 1.99 (3H, s).

Reference Production Example 9

To a mixture of 10.00 g of 1-(2-methyl-3-methoxyphenyl)-1,4-dihydrotetrazol-5-one mentioned in Reference Production Example 8 and 100 mL of N,N-dimethylformamide, 2.47 g of 60% sodium hydride was added under ice cooling. The temperature of the mixture was raised to room temperature, followed by stirring for 1 hour. To the reaction mixture, 3.5 mL of methyl iodide was added under ice cooling. The temperature of the mixture was raised to room temperature, followed by stirring for 14 hours. Water was poured into the reaction mixture and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 2.19 g of 1-(2-methyl-3-methoxyphenyl)-4-methyl-1,4-dihydrotetrazol-5-one.

1-(2-Methyl-3-methoxyphenyl)-4-methyl-1,4-dihydrotetrazol-5-one

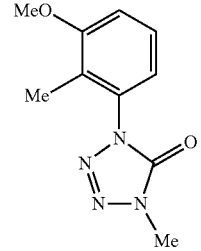

$^1$H-NMR (CDCl$_3$) δ (ppm): 7.29 (1H, t, J=8.2 Hz), 6.98 (1H, d, J=8.5 Hz), 6.95 (1H, d, J=8.2 Hz), 3.88 (3H, s), 3.72 (3H, s), 2.11 (3H, s).

Reference Production Example 10

A mixture of 2.19 g of 1-(2-methyl-3-methoxyphenyl)-4-methyl-1,4-dihydrotetrazol-5-one mentioned in Reference Production Example 9, 0.52 g of 1,1'-azobis(cyclohexane-1-carbonitrile), 2.16 g of N-bromosuccinimide, and 40 mL of chlorobenzene was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 2.36 g of 1-(2-bromomethyl-3-methoxyphenyl)-4-methyl-1,4-dihydrotetrazol-5-one.

1-(2-Bromomethyl-3-methoxyphenyl)-4-methyl-1,4-dihydrotetrazol-5-one

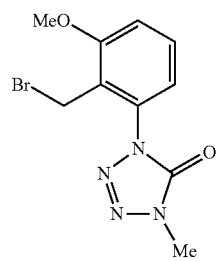 [SMILES: COc1cccc(-n2nnn(C)c2=O)c1CBr]

$^1$H-NMR (CDCl$_3$) δ (ppm): 7.43 (1H, t, J=8.1 Hz), 7.04 (1H, d, J=9.0 Hz), 7.02 (1H, dd, J=1.0, 8.5 Hz), 4.93 (2H, s), 3.96 (3H, s), 3.74 (3H, s).

Reference Production Example 11

Under ice cooling, 0.63 g of 60% sodium hydride was added to a mixture of 4.99 g of triisopropylsilanethiol and 30 mL of toluene, followed by stirring for 30 minutes. To the reaction mixture, 2.82 g of 1-(2-methyl-3-bromophenyl)-4-methyl-1,4-dihydrotetrazol-5-one mentioned in Synthesis Example 10 and 0.856 g of [1,1'-bis(diphenylphosphino)ferrocene]palladium(II) dichloride dichloromethane adduct were added. The temperature of the reaction mixture was raised to 90° C., followed by stirring for 4 hours. After cooling, water was poured into the reaction mixture and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 3.64 g of 1-(2-methyl-3-triisopropylsilanylthiophenyl)-4-methyl-1,4-dihydrotetrazol-5-one.

1-(2-Methyl-3-triisopropylsilanylthiophenyl)-4-methyl-1,4-dihydrotetrazol-5-one

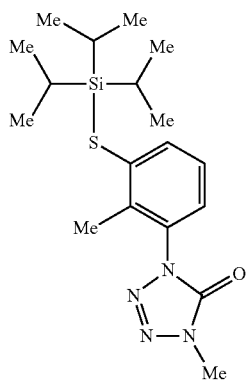 [SMILES: Cc1c(S[Si](C(C)C)(C(C)C)C(C)C)cccc1-n1nnn(C)c1=O]

$^1$H-NMR (CDCl$_3$) δ (ppm): 7.64 (1H, dd, J=6.6, 2.7 Hz), 7.16-7.21 (2H, m), 3.71 (3H, s), 2.45 (3H, s), 1.31 (3H, q, J=6.6 Hz), 1.09 (18H, d, J=6.6 Hz).

Reference Production Example 12

A mixture of 3.63 g of 1-(2-methyl-3-triisopropylsilanyl-thiophenyl)-4-methyl-1,4-dihydrotetrazol-5-one mentioned in Reference Production Example 11, 2.91 g of cesium fluoride, and 10 mL of N,N-dimethylformamide was stirred at room temperature for 30 minutes. To the mixture, 2.72 g of methyl iodide was added, followed by stirring at room temperature for 3 hours. Water was poured into the reaction mixture and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 1.65 g of 1-(2-methyl-3-methylthiophenyl)-4-methyl-1,4-dihydrotetrazol-5-one.

1-(2-Methyl-3-methylthiophenyl)-4-methyl-1,4-dihydrotetrazol-5-one

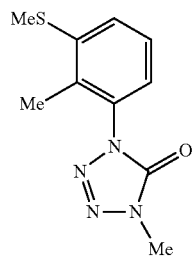 [SMILES: CSc1cccc(-n2nnn(C)c2=O)c1C]

$^1$H-NMR (CDCl$_3$) δ (ppm): 7.36-7.29 (2H, m), 7.10-7.16 (1H, m), 3.72 (3H, s), 2.51 (3H, s), 2.22 (3H, s).

Reference Production Example 13

A mixture of 1.50 g of 1-(2-methyl-3-methylthiophenyl)-4-methyl-1,4-dihydrotetrazol-5-one mentioned in Reference Production Example 12, 0.620 g of 1,1'-azobis(cyclohexane-1-carbonitrile), 1.30 g of N-bromosuccinimide, and 15 mL of chlorobenzene was stirred with heating under reflux for 4 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.400 g of 1-(2-bromomethyl-3-methyl-thiophenyl)-4-methyl-1,4-dihydrotetrazol-5-one.

1-(2-Bromomethyl-3-methylthiophenyl)-4-methyl-1,4-dihydrotetrazol-5-one

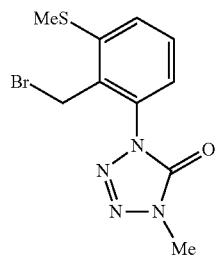 [SMILES: CSc1cccc(-n2nnn(C)c2=O)c1CBr]

$^1$H-NMR (CDCl$_3$) δ (ppm): 7.44 (2H, d, J=4.5 Hz), 7.20 (1H, t, J=4.5 Hz), 4.69 (2H, s), 3.75 (3H, s), 2.57 (3H, s).

Reference Production Example 14

Under ice cooling, 19.7 g of anhydrous aluminum chloride was added to 220 mL of N,N-dimethylformamide, followed by stirring for 15 minutes. To this was added 9.6 g of sodium azide, followed by stirring for 15 minutes, addition of 30.3 g of 1-bromo-3-isocyanato-2-methylbenzene mentioned in Reference Production Example 3 and further heating at 80° C. for hours. After cooling, the reaction solution was added in a mixture of 33 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 31.4 g of 1-(2-methyl-3-bromophenyl)-1,4-dihydrotetrazol-5-one.

1-(2-Methyl-3-bromophenyl)-1,4-dihydrotetrazol-5-one

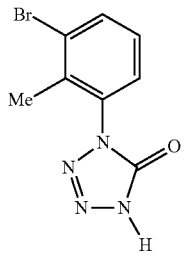

$^1$H-NMR (DMSO-d$_6$) δ (ppm): 14.72 (1H, s), 7.82 (1H, dd, J=8.0, 1.0 Hz), 7.49 (1H, dd, J=8.2, 1.1 Hz), 7.34 (1H, t, J=7.2 Hz), 2.22 (3H, s).

Reference Production Example 15

To a mixture of 31.40 g of 1-(2-methyl-3-bromophenyl)-1,4-dihydrotetrazol-5-one mentioned in Reference Production Example 14, and 250 mL of N,N-dimethylformamide, 5.90 g of 60% sodium hydride was added under ice cooling. The temperature of the mixture was raised to room temperature, followed by stirring for 1 hour. To the reaction mixture, 8.4 mL of methyl iodide was added under ice cooling. The temperature of the mixture was raised to room temperature, followed by stirring for 14 hours. Water was poured into the reaction mixture and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 8.47 g of 1-(2-methyl-3-bromophenyl)-4-methyl-1,4-dihydrotetrazol-5-one.

1-(2-Methyl-3-bromophenyl)-4-methyl-1,4-dihydrotetrazol-5-one

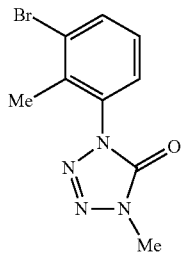

$^1$H-NMR (CDCl$_3$) δ (ppm): 7.71 (1H, dd, J=1.2, 8.3 Hz), 7.30 (1H, dd, J=1.0, 8.0 Hz), 7.21 (1H, dt, J=0.5, 7.8 Hz), 3.73 (3H, s), 2.33 (3H, s).

Reference Production Example 16

A mixture of 8.47 g of 1-(2-methyl-3-bromophenyl)-4-methyl-1,4-dihydrotetrazol-5-one mentioned in Reference Production Example 15, 1.54 g of 1,1'-azobis(cyclohexane-1-carbonitrile), 6.44 g of N-bromosuccinimide, and 125 mL of chlorobenzene was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 7.52 g of 1-(2-bromomethyl-3-bromophenyl)-4-methyl-1,4-dihydrotetrazol-5-one.

1-(2-Bromomethyl-3-bromophenyl)-4-methyl-1,4-dihydrotetrazol-5-one

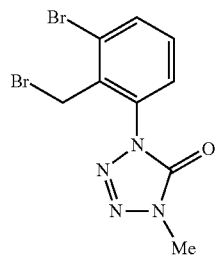

$^1$H-NMR (CDCl$_3$) δ (ppm): 7.77 (1H, dd, J=7.8, 1.7 Hz), 7.38 (1H, dd, J=8.0, 1.7 Hz), 7.34 (1H, t, J=7.8 Hz), 4.71 (2H, s), 3.76 (3H, s).

Reference Production Example 17

A mixture of 45.0 g of 1-(2-bromomethyl-3-bromophenyl)-4-methyl-1,4-dihydrotetrazol-5-one mentioned in Reference Production Example 16, 37.4 g of sodium methoxide, and 600 mL of tetrahydrofuran was stirred at room temperature for 3 hours. A saturated sodium bicarbonate solution was poured into the reaction mixture and the mixture was extracted with ethyl acetate. The organic layer was washed with a saturated sodium bicarbonate solution, dried over anhydrous sodium sulfate, and then concentrated under reduced pressure to obtain 36.2 g of 1-(2-methoxymethyl-3-bromophenyl)-4-methyl-1,4-dihydrotetrazol-5-one.

1-(2-Methoxymethyl-3-bromophenyl)-4-methyl-1,4-dihydrotetrazol-5-one

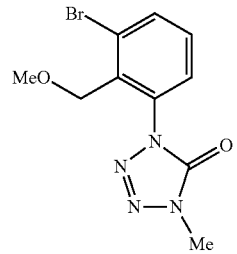 [SMILES: COCc1c(Br)cccc1-n1nnn(C)c1=O]

$^1$H-NMR (CDCl$_3$) δ (ppm): 7.76 (1H, dd, J=1.5, 7.8 Hz), 7.38 (1H, dd, J=1.2, 8.1 Hz), 7.33 (1H, t, J=7.8 Hz), 4.67 (2H, s), 3.72 (3H, s), 3.23 (3H, s).

Reference Production Example 18

A mixture of 36.2 g of 1-(2-methoxymethyl-3-bromophenyl)-4-methyl-1,4-dihydrotetrazol-5-one mentioned in Reference Production Example 17, 23.2 g of methylboronic acid, 66.7 g of cesium fluoride, 10.6 g of [1,1'-bis(diphenylphosphino)ferrocene]palladium(II) dichloride dichloromethane adduct, and 500 ml of dioxane was stirred at 90° C. for 5.5 hours. After cooling, the reaction mixture was filtered and the filtrate was concentrated under reduced pressure. The residue thus obtained was subjected to silica gel column chromatography to obtain 25.6 g of 1-(2-methoxymethyl-3-methylphenyl)-4-methyl-1,4-dihydrotetrazol-5-one.

1-(2-Methoxymethyl-3-methylphenyl)-4-methyl-1,4-dihydrotetrazol-5-one

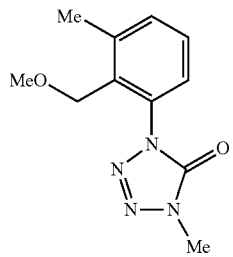 [SMILES: COCc1c(C)cccc1-n1nnn(C)c1=O]

$^1$H-NMR (CDCl$_3$) δ (ppm): 7.35 (2H, d, J=4.8 Hz), 7.21 (1H, t, J=5.1 Hz), 4.42 (2H, s), 3.72 (3H, s), 3.23 (3H, s), 2.48 (3H, s).

Reference Production Example 19

A mixture of 25.6 g of 1-(2-methoxymethyl-3-methylphenyl)-4-methyl-1,4-dihydrotetrazol-5-one mentioned in Reference Production Example 18, 50 mL of acetic acid, and 50 mL of a 25% hydrogen bromide-acetic acid solution was stirred at 65° C. for 1 hour. A saturated saline solution was poured into the reaction mixture and the mixture was extracted with ethyl acetate. The organic layer was washed with a saturated sodium bicarbonate solution, dried over anhydrous sodium sulfate, and then concentrated under reduced pressure to obtain 27.9 g of 1-(2-bromomethyl-3-methylphenyl)-4-methyl-1,4-dihydrotetrazol-5-one.

1-(2-Bromomethyl-3-methylphenyl)-4-methyl-1,4-dihydrotetrazol-5-one

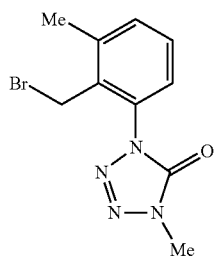 [SMILES: Cc1cccc(-n2nnn(C)c2=O)c1CBr]

$^1$H-NMR (CDCl$_3$) δ (ppm): 7.36-7.39 (2H, m), 7.22-7.24 (1H, m), 4.51 (2H, s), 3.75 (3H, s), 2.51 (3H, s).

Reference Production Example 20

A mixture of 30.1 g of 1-(2-methoxymethyl-3-bromophenyl)-4-methyl-1,4-dihydrotetrazol-5-one mentioned in Reference Production Example 17, 12.9 g of cyclopropylboronic acid, 46.2 g of cesium fluoride, 8.2 g of [1,1'-bis(diphenylphosphino)ferrocene]palladium(II) dichloride dichloromethane adduct, and 680 ml of dioxane was stirred at 90° C. for 4 hours. After cooling, the reaction mixture was filtered and the filtrate was concentrated under reduced pressure. The residue thus obtained was subjected to silica gel column chromatography to obtain 26.0 g of 1-(2-methoxymethyl-3-cyclopropylphenyl)-4-methyl-1,4-dihydrotetrazol-5-one.

1-(2-Methoxymethyl-3-cyclopropylphenyl)-4-methyl-, 4-dihydrotetrazol-5-one

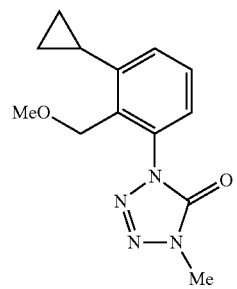 [SMILES: COCc1c(C2CC2)cccc1-n1nnn(C)c1=O]

$^1$H-NMR (CDCl$_3$) δ (ppm): 7.36 (1H, t, J=8.0 Hz), 7.20 (2H, d, J=8.0 Hz), 4.64 (2H, s), 3.72 (3H, s), 3.24 (3H, s), 2.20-2.13 (1H, m), 1.04-1.00 (2H, m), 0.76-0.72 (2H, m).

Reference Production Example 21

A mixture of 26.0 g of 1-(2-methoxymethyl-3-cyclopropylphenyl)-4-methyl-1,4-dihydrotetrazol-5-one mentioned in Reference Production Example 20, 40 mL of acetic acid, and 40 mL of a 25% hydrogen bromide-acetic acid solution was stirred at 65° C. for 2 hours. A saturated saline solution was poured into the reaction mixture and the mixture was extracted with ethyl acetate. The organic layer was washed with a saturated sodium bicarbonate solution, dried over anhydrous sodium sulfate, and then concentrated under reduced pressure to obtain 30.8 g of 1-(2-bromomethyl-3-cyclopropylphenyl)-4-methyl-1,4-dihydrotetrazol-5-one.

1-(2-Bromomethyl-3-cyclopropylphenyl)-4-methyl-1,4-dihydrotetrazol-5-one

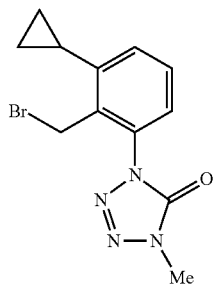 [SMILES: Cn1nnn(-c2cccc(C3CC3)c2CBr)c1=O]

$^1$H-NMR (CDCl$_3$) δ (ppm): 7.38 (1H, t, J=7.8 Hz), 7.26-7.22 (2H, m), 4.77 (2H, s), 3.75 (3H, s), 2.16-2.09 (1H, m), 1.10-1.06 (2H, m), 0.82-0.78 (2H, m).

Reference Production Example 22

A mixture of 29.8 g of 1-(2-methoxymethyl-3-bromophenyl)-4-methyl-1,4-dihydrotetrazol-5-one mentioned in Reference Production Example 17, 35.2 g of tributylvinyltin, 11.6 g of tetrakistriphenylphosphinepalladium, and 500 mL of toluene was stirred with heating under reflux for 14 hours. After cooling, an aqueous saturated ammonium chloride solution was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 19.7 g of 1-(2-methoxymethyl-3-ethenylphenyl)-4-methyl-1,4-dihydrotetrazol-5-one.

1-(2-Methoxymethyl-3-ethenylphenyl)-4-methyl-1,4-dihydrotetrazol-5-one

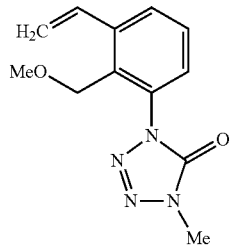 [SMILES: C=Cc1cccc(-n2nnn(C)c2=O)c1COC]

$^1$H-NMR (CDCl$_3$) δ (ppm): 7.67 (1H, dd, J=7.8, 1.3 Hz), 7.44 (1H, t, J=7.8 Hz), 7.29 (1H, dd, J=7.8, 1.3 Hz), 7.11 (1H, dd, J=17.4, 11.1 Hz), 5.72 (1H, dd, J=17.4, 1.3 Hz), 5.44 (1H, dd, J=11.1, 1.3 Hz), 4.45 (2H, s), 3.72 (3H, s), 3.23 (3H, s).

Reference Production Example 23

A mixture of 19.7 g of 1-(2-methoxymethyl-3-ethenylphenyl)-4-methyl-1,4-dihydrotetrazol-5-one mentioned in Reference Production Example 22, 3.02 g of a palladium-fibroin complex, and 1 L of methanol was stirred in a hydrogen atmosphere at room temperature for 11 hours. The reaction mixture was filtered and the filtrate was concentrated under reduced pressure. The residue thus obtained was subjected to silica gel column chromatography to obtain 19.3 g of 1-(2-methoxymethyl-3-ethylphenyl)-4-methyl-1,4-dihydrotetrazol-5-one.

1-(2-Methoxymethyl-3-ethylphenyl)-4-methyl-1,4-dihydrotetrazol-5-one

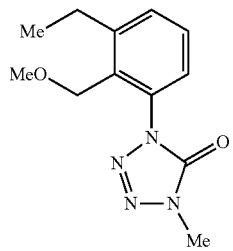 [SMILES: CCc1cccc(-n2nnn(C)c2=O)c1COC]

$^1$H-NMR (CDCl$_3$) δ (ppm): 7.42-7.38 (2H, m), 7.23-7.20 (1H, m), 4.44 (2H, s), 3.72 (3H, s), 3.22 (3H, s), 2.82 (2H, q, J=7.6 Hz), 1.27 (3H, t, J=7.6 Hz).

Reference Production Example 24

A mixture of 19.3 g of 1-(2-methoxymethyl-3-ethylphenyl)-4-methyl-1,4-dihydrotetrazol-5-one mentioned in Reference Production Example 23, 40 mL of acetic acid, and 40 mL of a 25% hydrogen bromide-acetic acid solution was stirred at 65° C. for 1.5 hours. A saturated saline solution was poured into the reaction mixture and the mixture was extracted with ethyl acetate. The organic layer was washed with a saturated sodium bicarbonate solution, dried over anhydrous sodium sulfate, and then concentrated under reduced pressure to obtain 23.3 g of 1-(2-bromomethyl-3-ethylphenyl)-4-methyl-1,4-dihydrotetrazol-5-one.

1-(2-Bromomethyl-3-ethylphenyl)-4-methyl-1,4-dihydrotetrazol-5-one

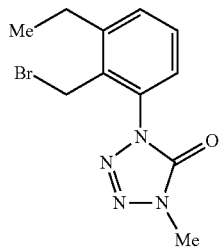 [SMILES: CCc1cccc(-n2nnn(C)c2=O)c1CBr]

$^1$H-NMR (CDCl$_3$) δ (ppm): 7.44-7.37 (2H, m), 7.23 (1H, dd, J=7.1, 2.0 Hz), 4.56 (2H, s), 3.75 (3H, s), 2.85 (2H, q, J=7.6 Hz), 1.33 (3H, t, J=7.6 Hz).

Reference Production Example 25

A mixture of 1.0 g of 1-(2-bromomethyl-3-methylphenyl)-4-methyl-1,4-dihydrotetrazol-5-one mentioned in Reference Production Example 19, 0.47 g of 1-acetyl-1H-pyrazol-3-ol mentioned in Reference Production Example 2, 0.63 g of potassium carbonate, and 20 mL of acetonitrile was stirred with heating under reflux for 2 hours. The reaction mixture allowed to cool was filtered and concentrated under reduced pressure. The residue thus obtained was subjected to silica gel column chromatography to obtain 0.58 g of 1-(2-{[1-acetyl-1H-pyrazol-3-yl]oxymethyl}-3-methylphenyl)-4-methyl-1,4-dihydrotetrazol-5-one.

1-(2-{[1-Acetyl-1H-pyrazol-3-yl]oxymethyl}-3-methylphenyl)-4-methyl-1,4-dihydrotetrazol-5-one

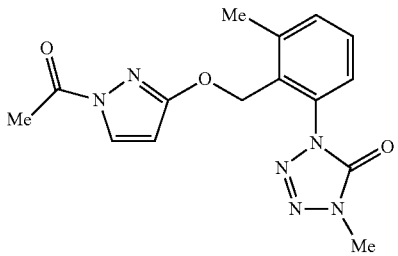 [SMILES: CC(=O)n1ccc(OCc2c(C)cccc2-n2nnn(C)c2=O)n1]

¹H-NMR (CDCl₃) δ (ppm): 8.01 (1H, d, J=2.9 Hz), 7.43-7.38 (2H, m), 7.26 (1H, dd, J=6.9, 2.1 Hz), 5.88 (1H, d, J=2.9 Hz), 5.31 (2H, s), 3.69 (3H, s), 2.55 (3H, s), 2.54 (3H, s).

Reference Production Example 26

A mixture of 3.4 g of 1-{2-[(1-acetyl-1H-pyrazol-3-yl)oxymethyl]-3-methylphenyl}-4-methyl-1,4-dihydrotetrazol-5-one mentioned in Reference Production Example 25, 0.59 g of sodium methoxide, and 30 mL of methanol was stirred at room temperature for 2 hours. The reaction mixture was poured into a saturated sodium bicarbonate solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 2.5 g of 1-(2-[{(H-pyrazol-3-yl)}oxymethyl]-3-methylphenyl)-4-methyl-1,4-dihydrotetrazol-5-one.

1-(2-[{(1H-pyrazol-3-yl)}oxymethyl]-3-methylphenyl)-4-methyl-1,4-dihydrotetrazol-5-one

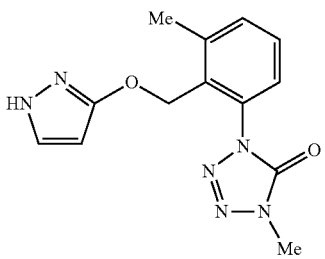 [SMILES: Cc1cccc(-n2nnn(C)c2=O)c1COc1cc[nH]n1]

¹H-NMR (CDCl₃) δ (ppm): 9.61 (1H, s), 7.40-7.35 (2H, m), 7.27 (1H, d, J=2.4 Hz), 7.24 (1H, dd, J=6.5, 2.8 Hz), 5.63 (1H, d, J=2.4 Hz), 5.23 (2H, d, J=11.2 Hz), 3.66 (3H, s), 2.52 (3H, s).

Reference Production Example 27

Using 1-(2-bromomethyl-3-ethylphenyl)-4-methyl-1,4-dihydrotetrazol-5-one mentioned in Reference Production Example 24 in place of 1-(2-bromomethyl-3-methylphenyl)-4-methyl-1,4-dihydrotetrazol-5-one in Reference Production Examples 25 and 26, the same reaction was performed to obtain 1-{2-[(1H-pyrazol-3-yl)oxymethyl]-3-ethylphenyl}-4-methyl-1,4-dihydrotetrazol-5-one.

1-{2-[(1H-pyrazol-3-yl)oxymethyl]-3-ethylphenyl}-4-methyl-1,4-dihydrotetrazol-5-one

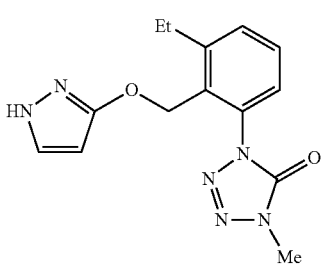

¹H-NMR (CDCl₃) δ: 9.96 (1H, s), 7.45-7.40 (2H, m), 7.27-7.24 (2H, m), 5.61 (1H, d, J=2.3 Hz), 5.23 (2H, s), 3.63 (3H, s), 2.86 (2H, q, J=7.6 Hz), 1.27 (3H, t, J=7.6 Hz).

Reference Production Example 28

Using 1-(2-bromomethyl-3-chlorophenyl)-4-methyl-1,4-dihydrotetrazol-5-one mentioned in Reference Production Example 7 in place of 1-(2-bromomethyl-3-methylphenyl)-4-methyl-1,4-dihydrotetrazol-5-one in Reference Production Examples 25 and 26, the same reaction was performed to obtain 1-{2-[(1H-pyrazol-3-yl)oxymethyl]-3-chlorophenyl}-4-methyl-1,4-dihydrotetrazol-5-one.

1-{2-[(1H-pyrazol-3-yl)oxymethyl]-3-chlorophenyl}-4-methyl-1,4-dihydrotetrazol-5-one

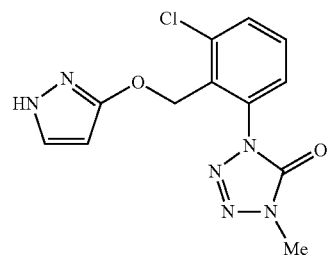 [SMILES: Cn1nnn(-c2cccc(Cl)c2COc2cc[nH]n2)c1=O]

¹H-NMR (CDCl₃) δ: 10.30 (1H, s), 7.58-7.56 (1H, m), 7.44-7.40 (1H, m), 7.37-7.34 (1H, m), 7.26 (1H, d, J=2.5 Hz), 5.60 (1H, d, J=2.5 Hz), 5.42 (2H, s), 3.61 (3H, s).

Reference Production Example 29

Using 1-(2-bromomethyl-3-cyclopropylphenyl)-4-methyl-1,4-dihydrotetrazol-5-one mentioned in Reference Production Example 21 in place of 1-(2-bromomethyl-3-methylphenyl)-4-methyl-1,4-dihydrotetrazol-5-one in Reference Production Examples 25 and 26, the same reaction was performed to obtain 1-{2-[(1H-pyrazol-3-yl)oxymethyl]-3-cyclopropylphenyl}-4-methyl-1,4-dihydrotetrazol-5-one.

1-{2-[(1H-pyrazol-3-yl)oxymethyl]-3-cyclopropylphenyl}-4-methyl-1,4-dihydrotetrazol-5-one

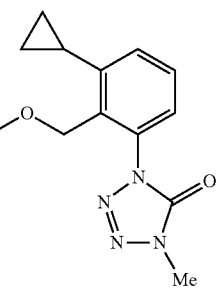

¹H-NMR (CDCl₃) δ: 10.45 (1H, s), 7.41-7.37 (1H, m), 7.24-7.21 (3H, m), 5.61 (1H, d, J=2.5 Hz), 5.42 (2H, s), 3.61 (3H, s), 2.25-2.15 (1H, m), 1.01-0.96 (2H, m), 0.76-0.72 (2H, m).

Reference Production Example 30

Using 1-(2-bromomethyl-3-methoxyphenyl)-4-methyl-1,4-dihydrotetrazol-5-one mentioned in Reference Production Example 10 in place of 1-(2-bromomethyl-3-methylphenyl)-4-methyl-1,4-dihydrotetrazol-5-one in Reference Production Examples 25 and 26, the same reaction was performed to obtain 1-{2-[(1H-pyrazol-3-yl)oxymethyl]-3-methoxyphenyl}-4-methyl-1,4-dihydrotetrazol-5-one.

1-{2-[(1H-pyrazol-3-yl)oxymethyl]-3-methoxyphenyl}-4-methyl-1,4-dihydrotetrazol-5-one

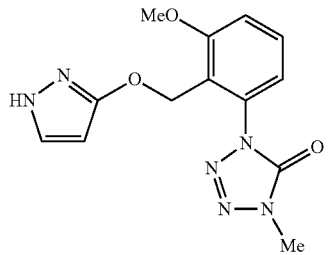

$^1$H-NMR (CDCl$_3$) δ: 10.40 (1H, s), 7.46-7.42 (1H, m), 7.26 (1H, d, J=2.5 Hz), 7.07-7.03 (2H, m), 5.59 (1H, d, J=2.5 Hz), 5.34 (2H, s), 3.89 (3H, s), 3.60 (3H, s).

Reference Production Example 31

Using 1-(2-bromomethyl-3-methylthiophenyl)-4-methyl-1,4-dihydrotetrazol-5-one mentioned in Reference Production Example 13 in place of 1-(2-bromomethyl-3-methylphenyl)-4-methyl-1,4-dihydrotetrazol-5-one in Reference Production Examples 25 and 26, the same reaction was performed to obtain 1-{2-[(1H-pyrazol-3-yl)oxymethyl]-3-methylthiophenyl}-4-methyl-1,4-dihydrotetrazol-5-one.

1-{2-[(1H-pyrazol-3-yl)oxymethyl]-3-methylthiophenyl}-4-methyl-1,4-dihydrotetrazol-5-one

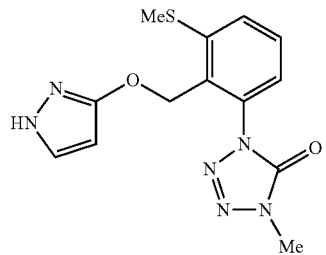 [SMILES: CSc1cccc(-n2nnn(C)c2=O)c1COc1cc[nH]n1]

$^1$H-NMR (CDCl$_3$) δ: 10.24 (1H, s), 7.46-7.44 (2H, m), 7.27 (1H, d, J=2.5 Hz), 7.24-7.20 (1H, m), 5.64 (1H, d, J=2.5 Hz), 5.36 (2H, s), 3.63 (3H, s), 2.51 (3H, s).

Reference Production Example 32

To 407 g of oxalyl chloride, 170 g of ethyl vinyl ether was added dropwise under ice cooling. After completion of the dropwise addition, the temperature was raised to room temperature, followed by stirring for 15 hours. The reaction mixture was concentrated under reduced pressure. The temperature of the residue thus obtained was raised to 120° C., followed by stirring for 30 minutes. After cooling, the mixture was distilled off under reduced pressure to obtain 137 g of 3-ethoxyacrylic acid chloride.

3-Ethoxyacrylic acidchloride

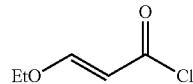

$^1$H-NMR (CDCl$_3$) δ (ppm): 7.79 (1H, d, J=12.0 Hz), 5.51 (1H, d, J=12.0 Hz), 4.06 (2H, q, J=7.1 Hz), 1.40 (3H, t, J=7.1 Hz).

Reference Production Example 33

To a mixture of 1.6 g of 3-amino-6-bromo-2-methoxypyridine (synthesized in accordance with the process mentioned in US 2011/237791 A), 3 mL of water, and 4 mL of concentrated hydrochloric acid, a solution of 0.6 g of sodium nitrite and 3 mL of water was added under ice cooling, followed by stirring at 0° C. for 30 minutes. To the reaction mixture thus obtained, a solution of 5 g of tin(II) chloride, 8 mL of water, and 8 mL of concentrated hydrochloric acid was added under ice cooling, followed by stirring at 0° C. for 3 hours. The mixture was made basic with an aqueous 35% sodium hydroxide solution and then extracted with ethyl acetate. The organic layer was washed with water and a saturated saline solution, dried over anhydrous sodium sulfate, and then concentrated under reduced pressure to obtain 0.9 g of 6-bromo-3-hydrazinyl-2-methoxypyridine.

To a mixture of 0.9 g of 6-bromo-3-hydrazinyl-2-methoxypyridine, 1.1 mL of pyridine, and 10 mL of tetrahydrofuran, 0.5 g of 3-ethoxyacrylic acid chloride mentioned in Reference Production Example 32 was added under ice cooling, followed by stirring at room temperature for 1 hour. Water was poured into the reaction solution and the mixture was extracted with ethyl acetate. The organic layer was washed with water and a saline solution, dried over anhydrous sodium sulfate, and then concentrated under reduced pressure. The residue thus obtained was subjected to silica gel column chromatography to obtain 0.7 g of 3-ethoxyacrylic acid N'-(6-bromo-2-methoxypyridin-3-yl)hydrazide. To 0.7 g of 3-ethoxyacrylic acid N'-(6-bromo-2-methoxypyridin-3-yl)hydrazide thus obtained, 6 mL of concentrated hydrochloric acid was added under ice cooling, followed by stirring at 0° C. for 30 minutes. Water was poured into the reaction solution and the mixture was extracted with ethyl acetate. The organic layer was washed with water and a saline solution, dried over anhydrous sodium sulfate, and then concentrated under reduced pressure. The residue thus obtained was subjected to silica gel column chromatography to obtain 0.56 g of 1-(6-bromo-2-methoxypyridin-3-yl)-1H-pyrazol-3-ol.

1-(6-Bromo-2-methoxypyridin-3-yl)-1H-pyrazol-3-ol

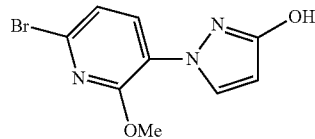

¹H-NMR (CDCl₃) δ: 7.96 (1H, d, J=2.7 Hz), 7.77 (1H, d, J=8.2 Hz), 7.20 (1H, d, J=8.2 Hz), 5.88 (1H, d, J=2.7 Hz), 4.07 (3H, s).

Reference Production Example 34

At room temperature, a mixture of 2 g of 2-hydrazinyl-5(trifluoromethylpyridine), 70 ml of tert-butanol, 1.2 g of 2-propionic acid-ethyl ester, and 2.5 g of potassium tert-butoxide was stirred for 20 hours. Water was poured into the mixture and pH was adjusted to 6 by adding 10% hydrochloric acid, followed by extraction with ethyl acetate. The organic layer was dried by adding magnesium sulfate, and then concentrated under reduced pressure. The residue thus obtained was washed with hexane to obtain 1 g of 1-(5-trifluoromethyl-pyridin-2-yl)-1H-pyrazol-3-ol.

1-(5-Trifluoromethyl-pyridin-2-yl)-1H-pyrazol-3-ol

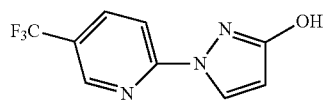 [SMILES: Oc1ccn(-c2ccc(C(F)(F)F)cn2)n1]

¹H-NMR (DMSO-D₆) δ: 10.78 (1H, s), 8.78 (1H, s), 8.42 (1H, d, J=2.9 Hz), 8.28 (1H, dd, J=8.8, 2.4 Hz), 7.78 (1H, d, J=8.8 Hz), 5.99 (1H, d, J=2.7 Hz).

Reference Production Example 35

A mixture of 28 g of 1-(2-bromomethyl-3-methylphenyl)-4-methyl-1,4-dihydrotetrazol-5-one mentioned in Reference Production Example 19, 40 g of calcium carbonate, 300 mL of dioxane, and 300 mL of water was stirred with heating under reflux for 5 hours. After allowing to cool, water was poured into the reaction solution and the mixture was extracted with ethyl acetate. The organic layer was washed with water and a saturated saline solution, dried over anhydrous sodium sulfate, and then concentrated under reduced pressure to obtain a solid. The solid thus obtained was washed with hexane to obtain 19 g of 1-(2-hydroxymethyl-3-methylphenyl)-4-methyl-1,4-dihydrotetrazol-5-one.

1-(2-Hydroxymethyl-3-methylphenyl)-4-methyl-1,4-dihydrotetrazol-5-one

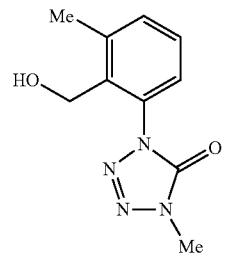 [SMILES: Cc1cccc(-n2nnn(C)c2=O)c1CO]

1H-NMR (CDCl₃) δ: 7.34-7.40 (2H, m), 7.19-7.23 (1H, m), 4.48 (2H, d, J=7.10 Hz), 3.76 (1H, t, J=7.10 Hz), 3.75 (3H, s), 2.56 (3H, s).

Reference Production Example 36

A mixture of 8.7 g of 1-(2-hydroxymethyl-3-methylphenyl)-4-methyl-1,4-dihydrotetrazol-5-one mentioned in Reference Production Example 35, 4.6 g of sodium tert-butoxide, and 250 mL of tetrahydrofuran was stirred at 25° C. for 15 minutes. After adding 9.6 g of 2,4-dibromo-thiazole, the mixture was stirred with heating under reflux for 30 minutes. Water was poured into the reaction mixture allowed to cool and the mixture was extracted with ethyl acetate. The organic layer was washed with a saturated sodium bicarbonate solution, and a saturated saline solution, dried over anhydrous sodium sulfate, and then concentrated under reduced pressure to obtain 12 g of 2-{[1-(4,5-dihydro-4-methyl-5-oxo-1H-tetrazol-1-yl)-3-methylphenyl-2-yl]methyloxy}-4-bromothiazole.

2-{[1-(4,5-Dihydro-4-methyl-5-oxo-1H-tetrazol-1-yl)-3-methylphenyl-2-yl]methyloxy}-4-bromothiazole

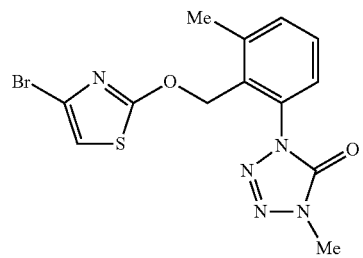 [SMILES: Cc1cccc(-n2nnn(C)c2=O)c1COc1nc(Br)cs1]

¹H-NMR (CDCl₃) δ: 7.44 (1H, t, J=7.8 Hz), 7.40 (1H, dd, J=7.8, 1.4 Hz), 7.28 (1H, dd, J=7.8, 1.4 Hz), 6.56 (1H, s), 5.49 (2H, s), 3.73 (3H, s), 2.53 (3H, s).

Reference Production Example 37

Using 3-amino-6-chloro-2-methoxypyridine (synthesized in accordance with the process mentioned in WO 2011/002067 A) in place of 3-amino-6-bromo-2-methoxypyridine in Reference Production Example 33, the same reaction was performed to obtain 1-(6-chloro-2-methoxypyridin-3-yl)-1H-pyrazol-3-ol.

1-(6-Chloro-2-methoxypyridin-3-yl)-1H-pyrazol-3-ol

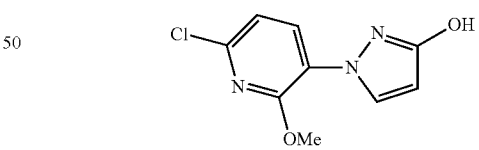

¹H-NMR (DMSO-D₆) δ: 10.38 (1H, br s), 8.11 (1H, d, J=2.7 Hz), 8.01 (1H, d, J=8.2 Hz), 7.21 (1H, d, J=8.2 Hz), 5.83 (1H, d, J=2.7 Hz), 3.99 (3H, s).

In accordance with the above-mentioned processes, it is possible to obtain compounds HA1001-0001 to HA1001-5991, HA1002-0001 to HA1002-5991, HA1003-0001 to HA1003-5991, HA1004-0001 to HA1004-5991, HA1005-0001 to HA1005-5991, HA1006-0001 to HA1006-5991, HA1007-0001 to HA1007-5991, HA1008-0001 to HA1008-5991, HA1009-0001 to HA1009-5991, HA1010-0001 to HA1010-5991, HA1011-0001 to HA1011-5991, HA1012-0001 to HA1012-5991, HA1013-0001 to HA1013-5991, HA1014-0001 to HA1014-5991, HA1015-0001 to HA1015-5991, HA1016-0001 to HA1016-5991, HA1017-0001 to HA1017-5991, HA1018-0001 to HA1018-5991, HA1019-0001 to HA1019-5991, HA1020-0001 to HA1020-5991, HA1021-0001 to HA1021-5991, HA1022-0001 to HA1022-5991, HA1023-0001 to HA1023-5991, HA1024-0001 to HA1024-5991, HA1025-0001 to HA1025-5991, HA1026-0001 to HA1026-5991, HA1027-0001 to HA1027-5991, HA1028-0001 to HA1028-5991, HA1029-0001 to HA1029-5991, HA1030-0001 to HA1030-5991, HA1031-0001 to HA1031-5991, HA1032-0001 to HA1032-5991, HA1033-0001 to HA1033-5991, HA1034-0001 to HA1034-5991, HA1035-0001 to HA1035-5991, HA1036-0001 to HA1036-5991, HA1037-0001 to HA1037-5991, HA1038-0001 to HA1038-5991, HA1039-0001 to HA1039-5991, HA1040-0001 to HA1040-5991, HA1041-0001 to HA1041-5991, HA1042-0001 to HA1042-5991, HA1043-0001 to HA1043-5991, HA1044-0001 to HA1044-5991, HA1045-0001 to HA1045-5991, HA1046-0001 to HA1046-5991, HA1047-0001 to HA1047-5991, HA1048-0001 to HA1048-5991, HA1049-0001 to HA1049-5991, HA1050-0001 to HA1050-5991, HA1051-0001 to HA1051-5991, HA1052-0001 to HA1052-5991, HA1053-0001 to HA1053-5991, HA1054-0001 to HA1054-5991, HA1055-0001 to HA1055-5991, HA1056-0001 to HA1056-5991, HA1057-0001 to HA1057-5991, HA1058-0001 to HA1058-5991, HA1059-0001 to HA1059-5991, HA1060-0001 to HA1060-5991, HA1061-0001 to HA1061-5991, HA1062-0001 to HA1062-5991, HA1063-0001 to HA1063-5991, HA1064-0001 to HA1064-5991, HA1065-0001 to HA1065-5991, HA1066-0001 to HA1066-5991, HA1067-0001 to HA1067-5991, HA1068-0001 to HA1068-5991, HA1069-0001 to HA1069-5991, HA2001-0001 to HA2001-5991, HA2002-0001 to HA2002-5991, HA2003-0001 to HA2003-5991, HA2004-0001 to HA2004-5991, HA2005-0001 to HA2005-5991, HA2006-0001 to HA2006-5991, HA2007-0001 to HA2007-5991, HA2008-0001 to HA2008-5991, HA2009-0001 to HA2009-5991, HA2010-0001 to HA2010-5991, HA2011-0001 to HA2011-5991, HA2012-0001 to HA2012-5991, HA2013-0001 to HA2013-5991, HA2014-0001 to HA2014-5991, HA2015-0001 to HA2015-5991, HA2016-0001 to HA2016-5991, HA2017-0001 to HA2017-5991, HA2018-0001 to HA2018-5991, HA2019-0001 to HA2019-5991, HA2020-0001 to HA2020-5991, HA2021-0001 to HA2021-5991, HA2022-0001 to HA2022-5991, HA2023-0001 to HA2023-5991, HA2024-0001 to HA2024-5991, HA2025-0001 to HA2025-5991, HA2026-0001 to HA2026-5991, HA2027-0001 to HA2027-5991, HA2028-0001 to HA2028-5991, HA2029-0001 to HA2029-5991, HA2030-0001 to HA2030-5991, HA2031-0001 to HA2031-5991, HA2032-0001 to HA2032-5991, HA2033-0001 to HA2033-5991, HA2034-0001 to HA2034-5991, HA2035-0001 to HA2035-5991, HA2036-0001 to HA2036-5991, HA2037-0001 to HA2037-5991, HA2038-0001 to HA2038-5991, HA2039-0001 to HA2039-5991, HA2040-0001 to HA2040-5991, HA2041-0001 to HA2041-5991, HA2042-0001 to HA2042-5991, HA2043-0001 to HA2043-5991, HA2044-0001 to HA2044-5991, HA2045-0001 to HA2045-5991, HA2046-0001 to HA2046-5991, HA2047-0001 to HA2047-5991, HA2048-0001 to HA2048-5991, HA2049-0001 to HA2049-5991, HA2050-0001 to HA2050-5991, HA2051-0001 to HA2051-5991, HA2052-0001 to HA2052-5991, HA2053-0001 to HA2053-5991, HA2054-0001 to HA2054-5991, HA2055-0001 to HA2055-5991, HA2056-0001 to HA2056-5991, HA2057-0001 to HA2057-5991, HA2058-0001 to HA2058-5991, HA2059-0001 to HA2059-5991, HA2060-0001 to HA2060-5991, HA2061-0001 to HA2061-5991, HA2062-0001 to HA2062-5991, HA2063-0001 to HA2063-5991, HA2064-0001 to HA2064-5991, HA2065-0001 to HA2065-5991, HA2066-0001 to HA2066-5991, HA2067-0001 to HA2067-5991, HA2068-0001 to HA2068-5991, and HA2069-0001 to HA2069-5991.

The above compounds HA1001-0001 to HA2069-5991 are tetrazolinone compounds represented by the following formulas:

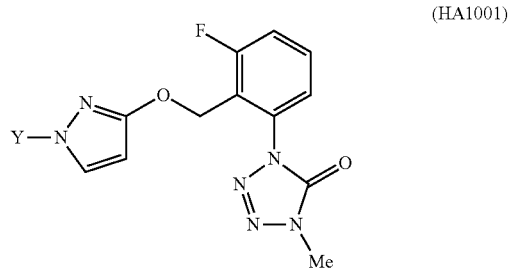
(HA1001)

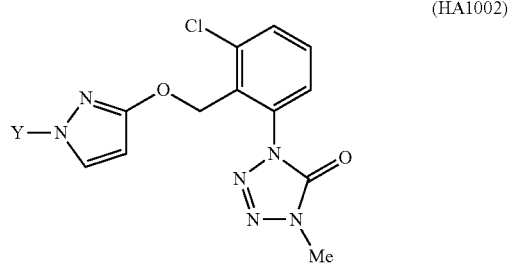
(HA1002)

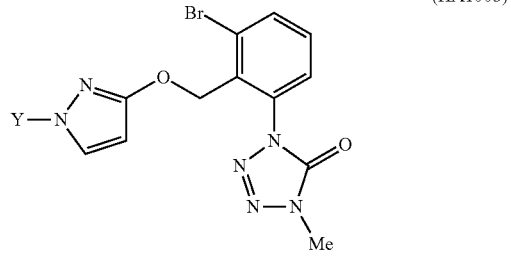
(HA1003)

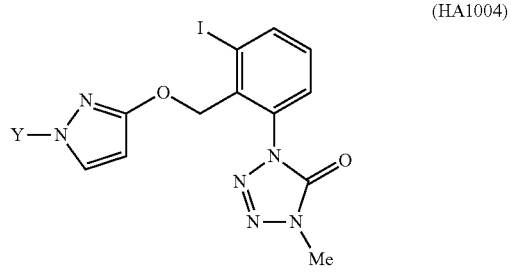
(HA1004)

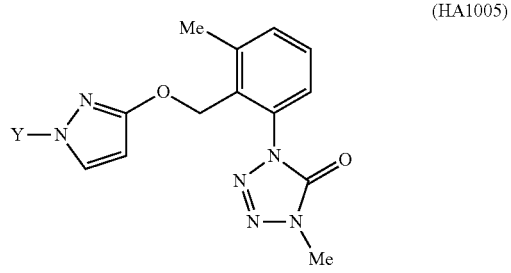
(HA1005)

-continued
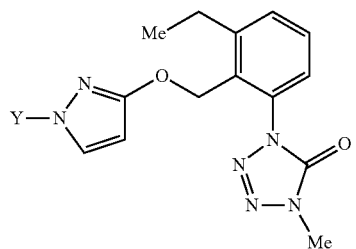 (HA1006)
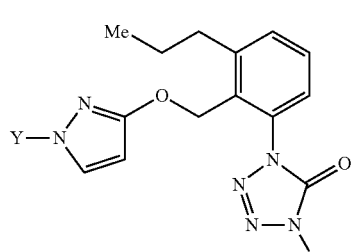 (HA1007)
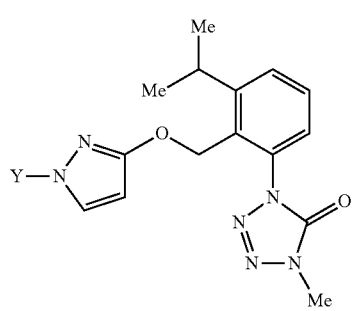 (HA1008)
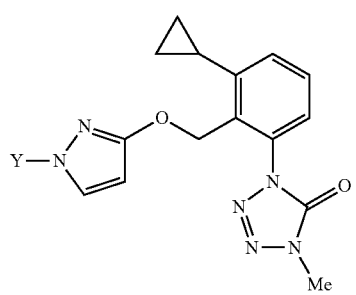 (HA1009)
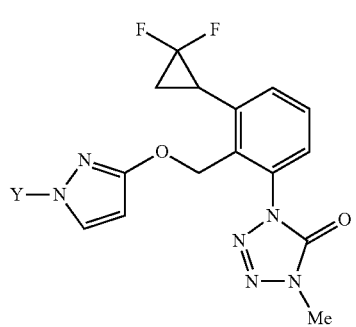 (HA1010)
-continued
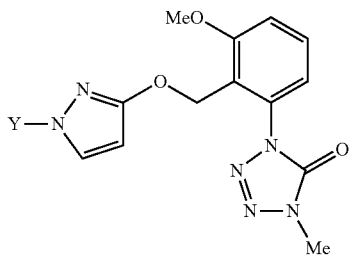 (HA1011)
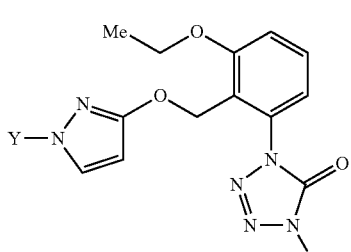 (HA1012)
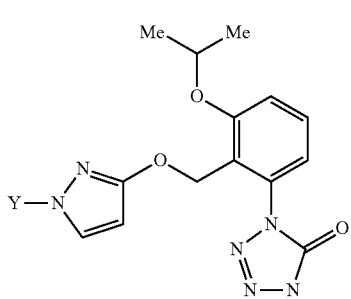 (HA1013)
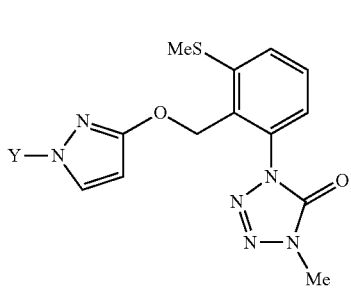 (HA1014)
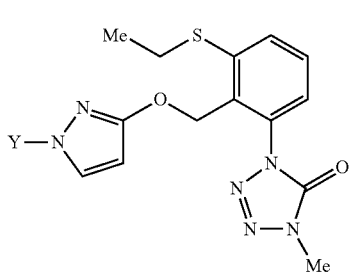 (HA1015)

(HA1016) 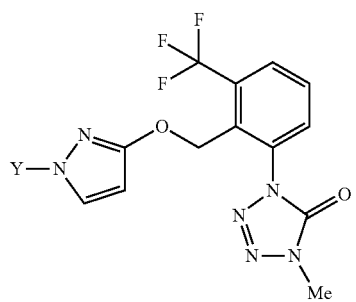
(HA1017) 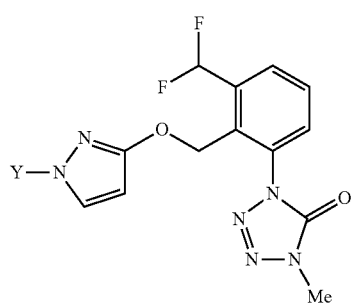
(HA1018) 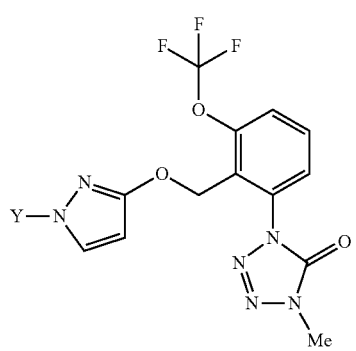
(HA1019) 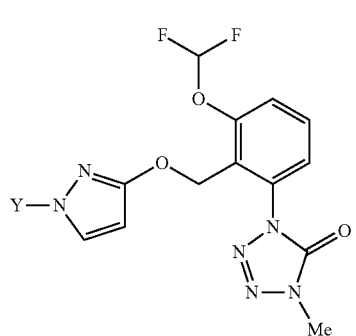
(HA1020) 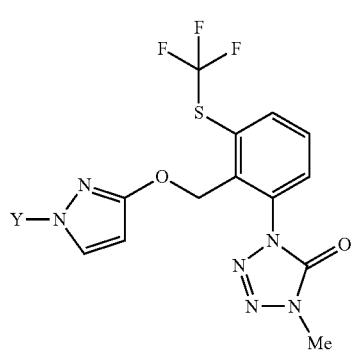
(HA1021) 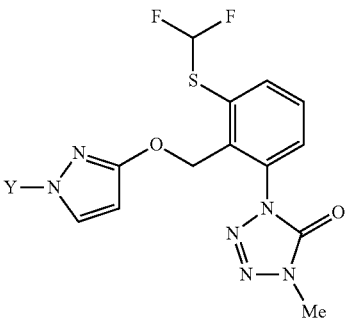
(HA1022) 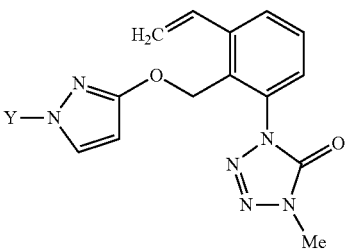
(HA1023) 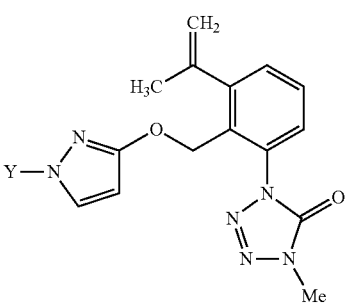
(HA1024) 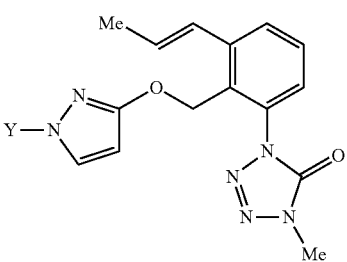
(HA1025) 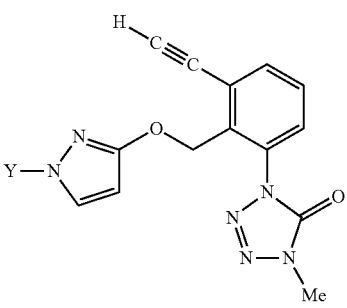

(HA1026)
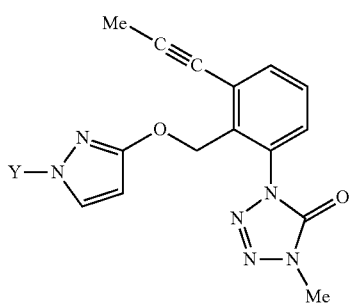
(HA1027)
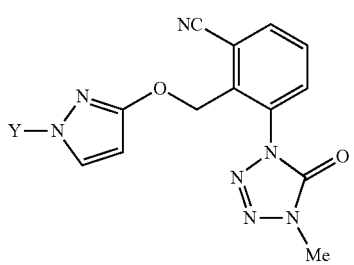
(HA1028)
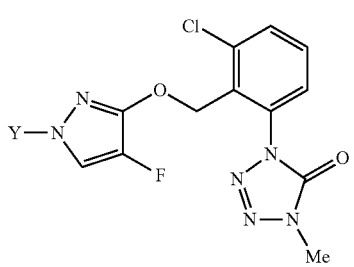
(HA1029)
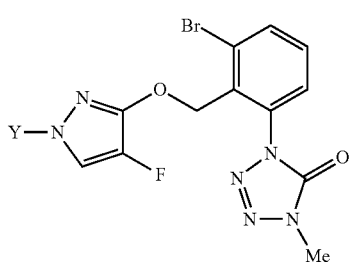
(HA1030)
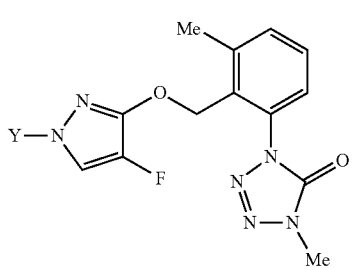
(HA1031)
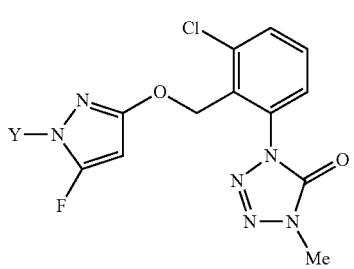
(HA1032)
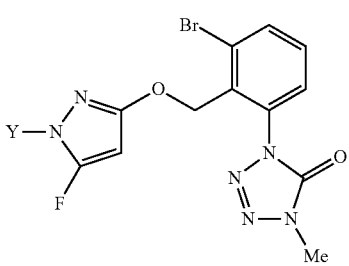
(HA1033)
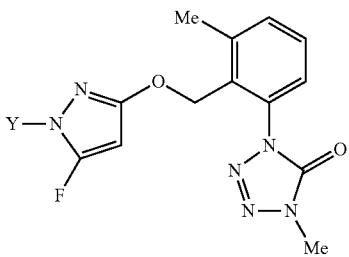
(HA1034)
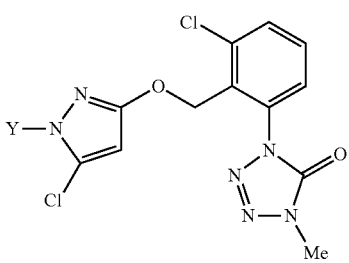
(HA1035)
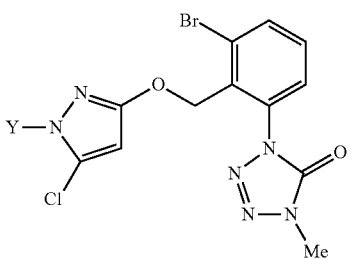
(HA1036)
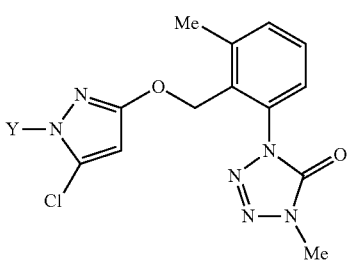
(HA1037)
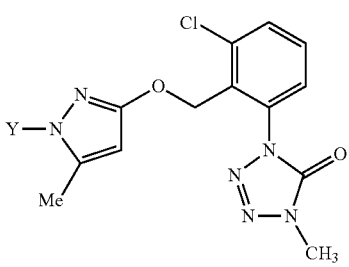

|  |  |
|---|---|
| (HA1038) 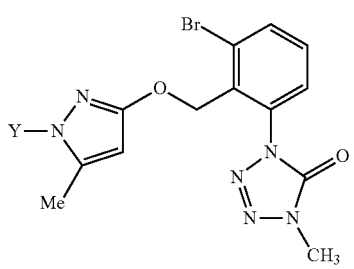 | (HA1044) 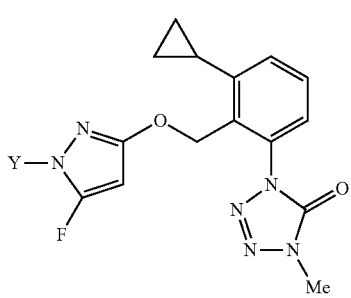 |
| (HA1039) 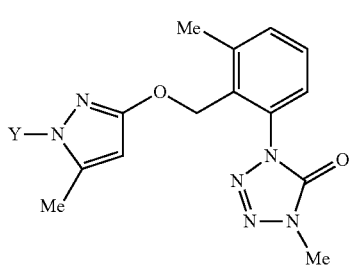 | (HA1045) 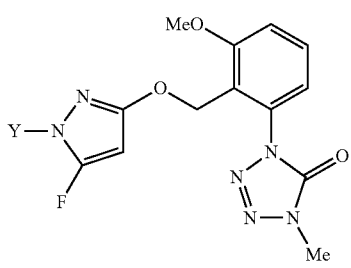 |
| (HA1040) 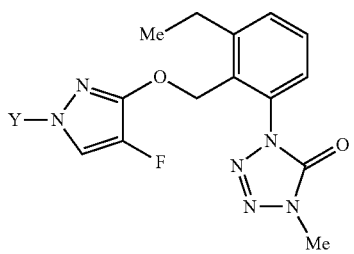 | (HA1046) 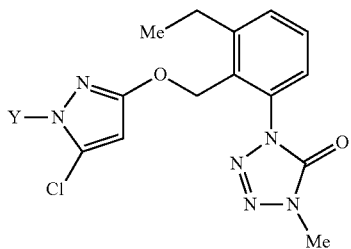 |
| (HA1041) 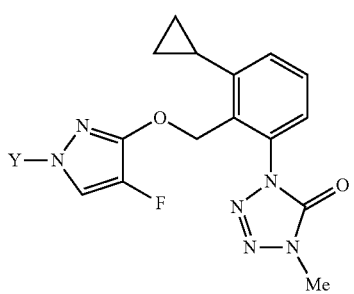 | (HA1047) 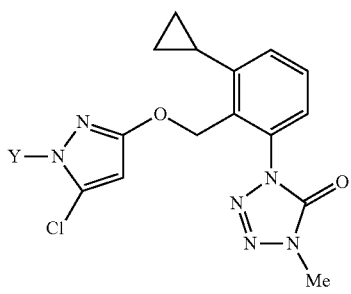 |
| (HA1042) 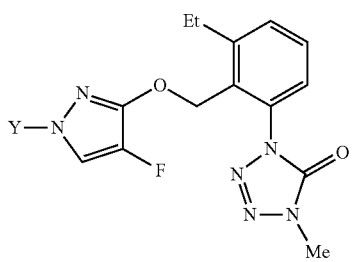 | (HA1048) 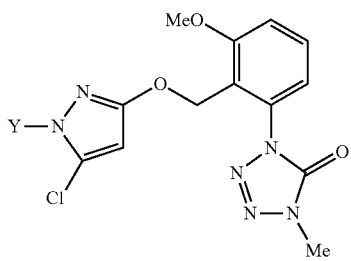 |
| (HA1043) 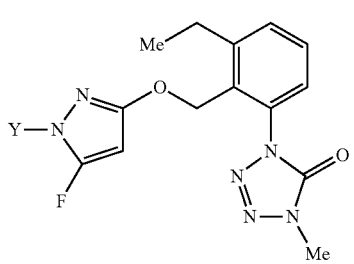 | (HA1049) 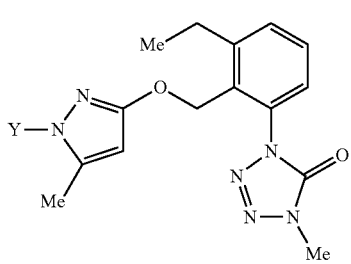 |

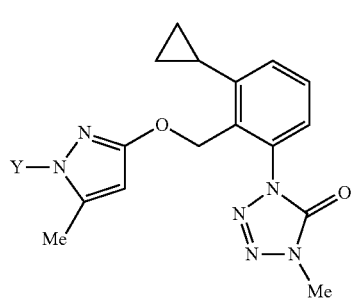
(HA1050)
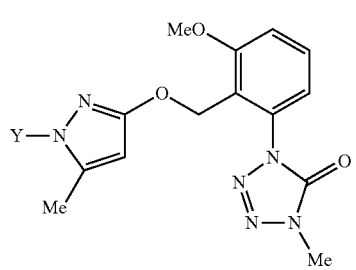
(HA1051)
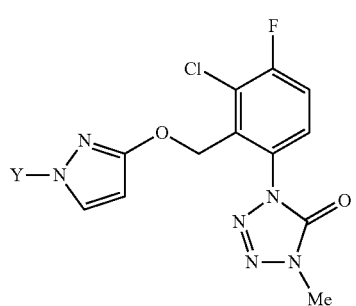
(HA1052)
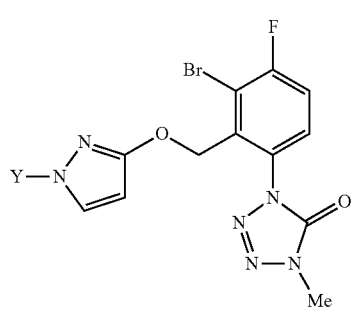
(HA1053)
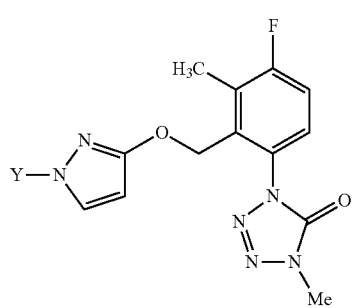
(HA1054)
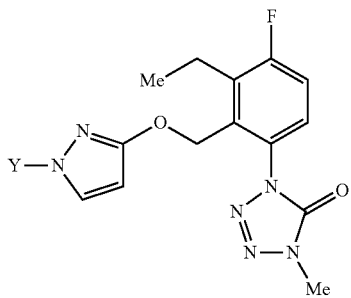
(HA1055)
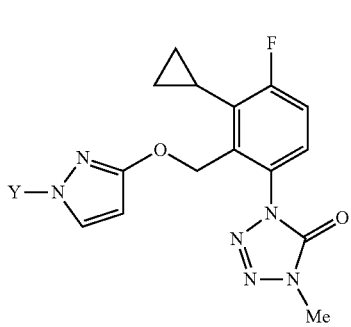
(HA1056)
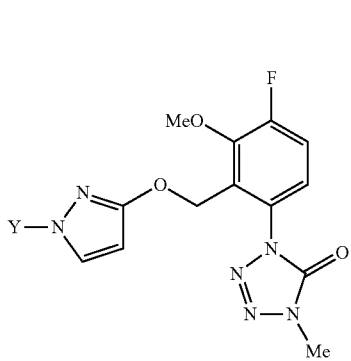
(HA1057)
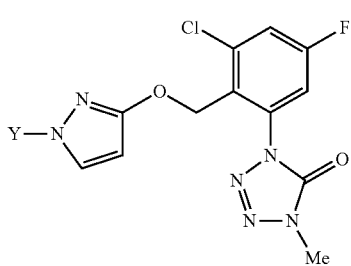
(HA1058)
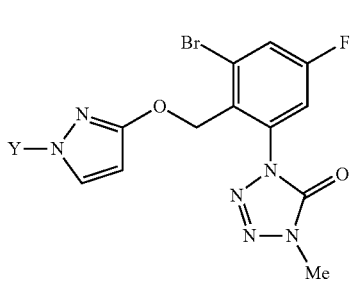
(HA1059)

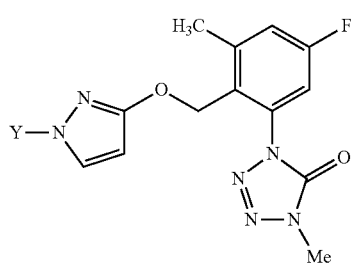
(HA1060)
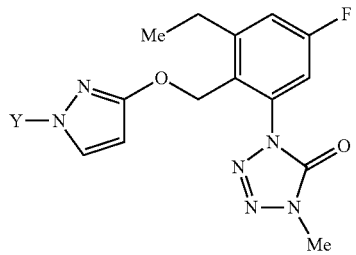
(HA1061)
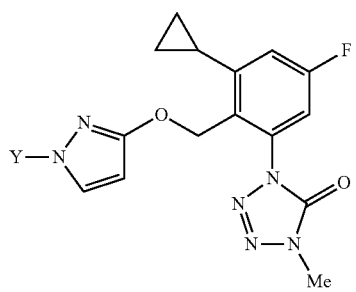
(HA1062)
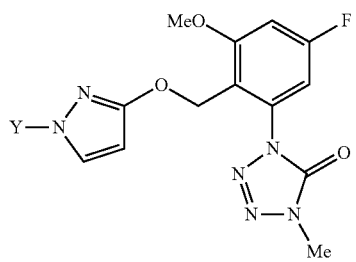
(HA1063)
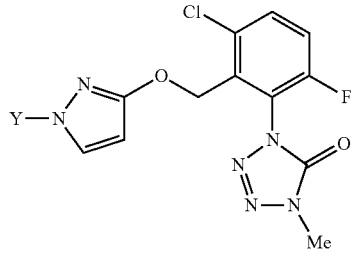
(HA1064)
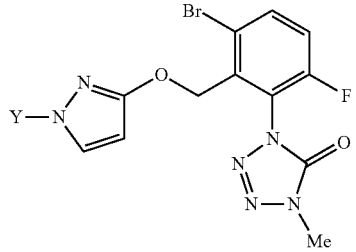
(HA1065)
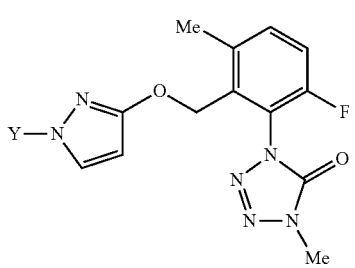
(HA1066)
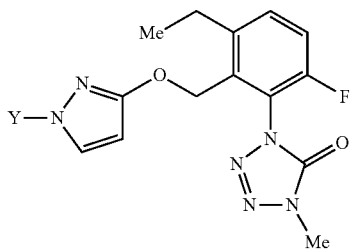
(HA1067)
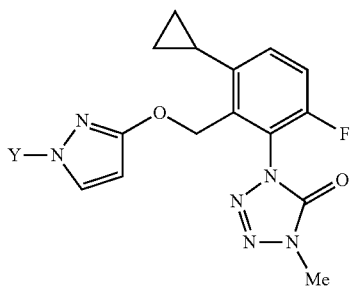
(HA1068)
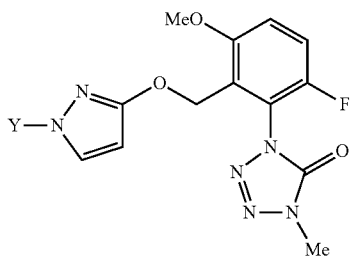
(HA1069)
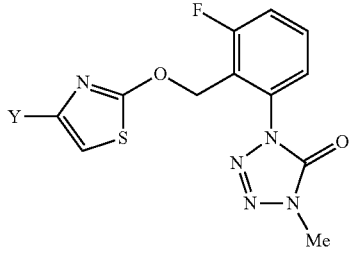
(HA2001)
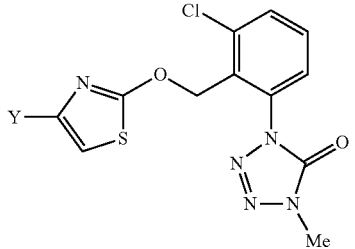
(HA2002)

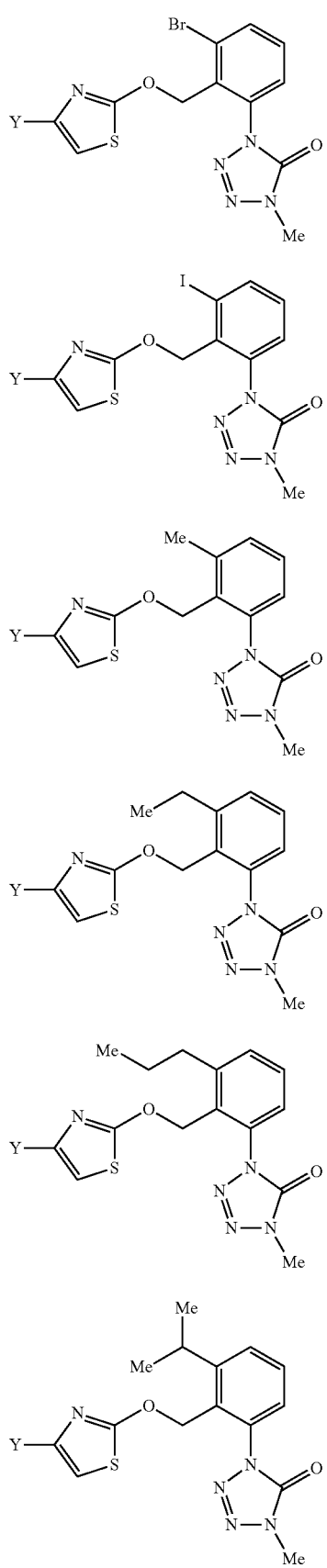
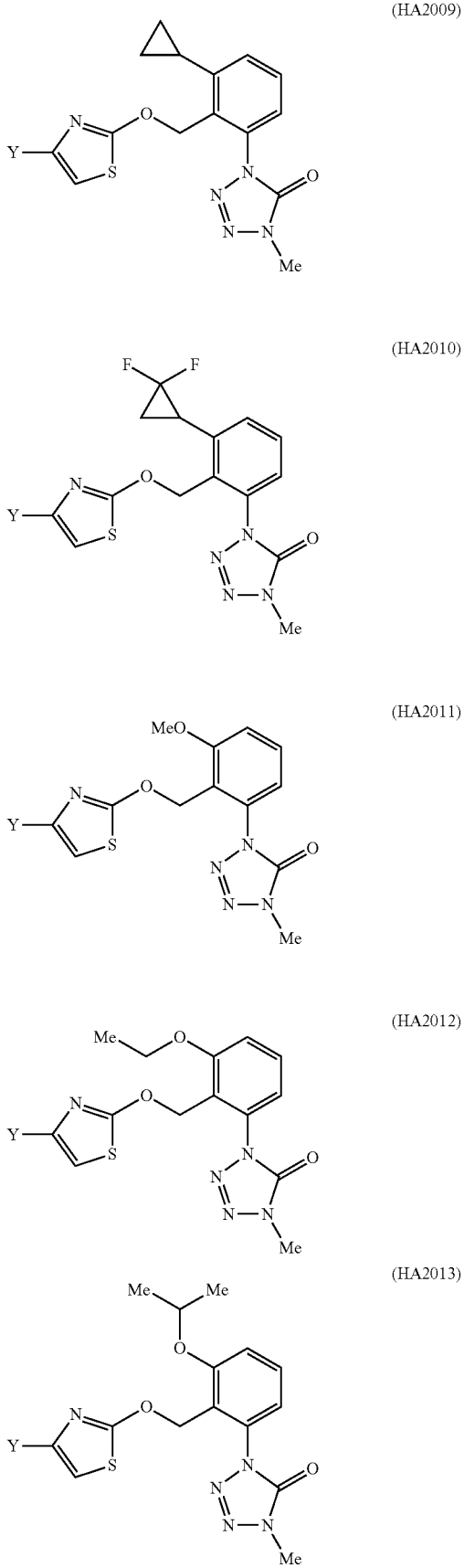

-continued
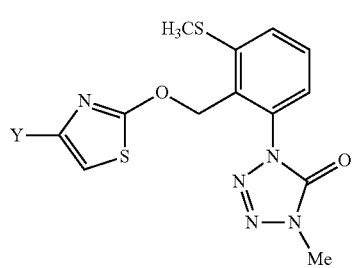
(HA2014)
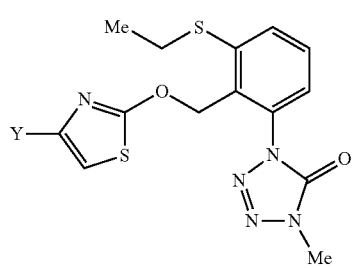
(HA2015)
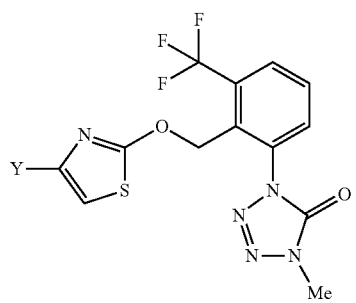
(HA2016)
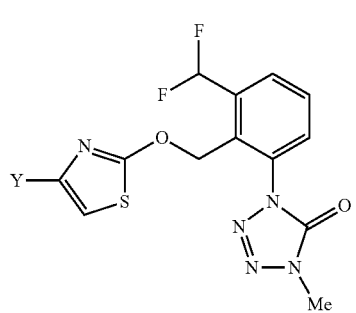
(HA2017)
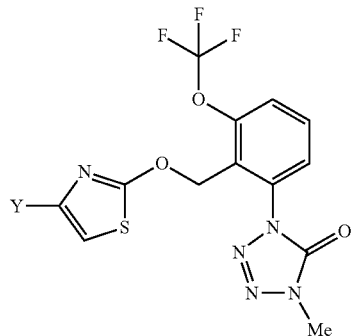
(HA2018)
-continued
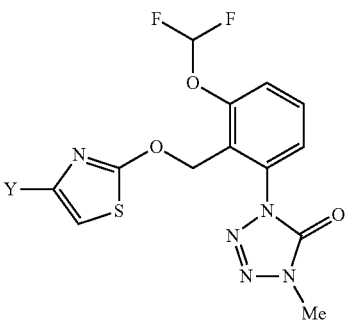
(HA2019)
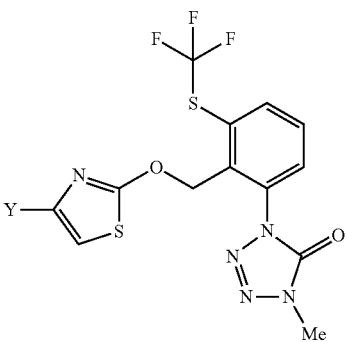
(HA2020)
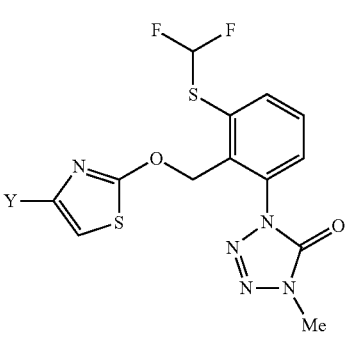
(HA2021)
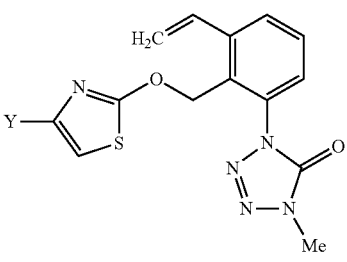
(HA2022)
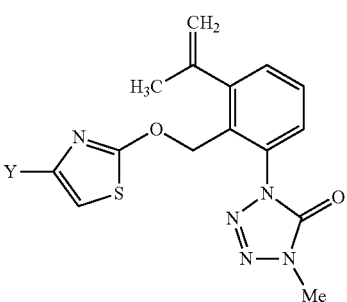
(HA2023)

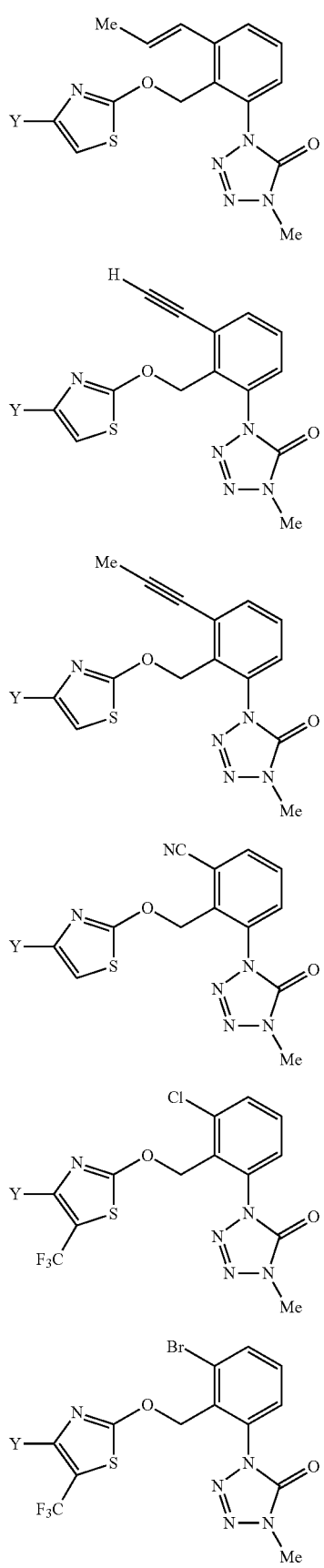
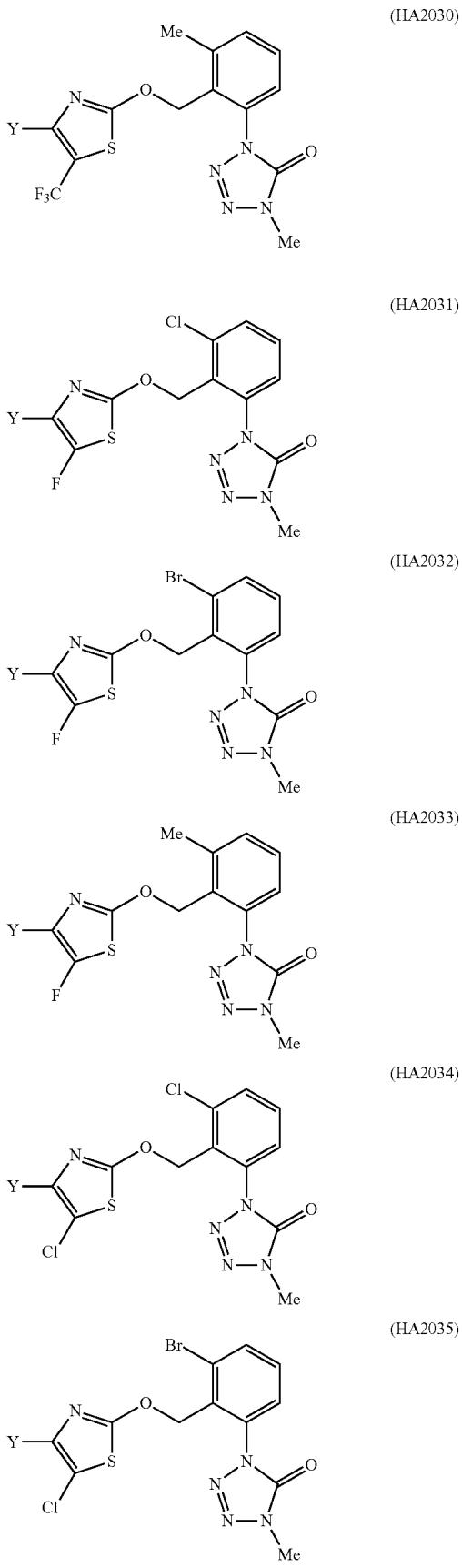

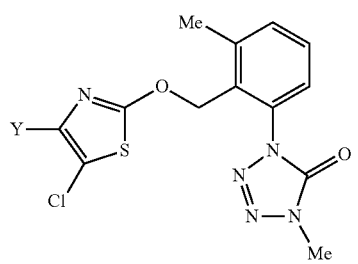
(HA2036)
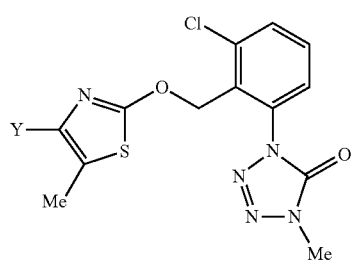
(HA2037)
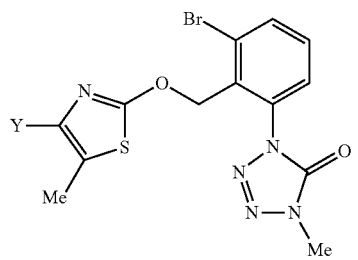
(HA2038)
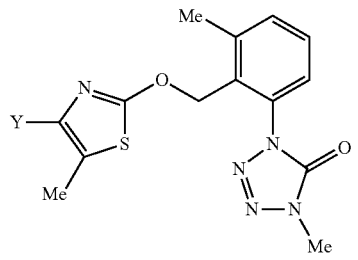
(HA2039)
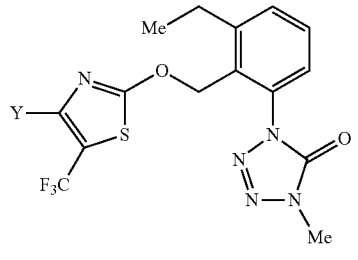
(HA2040)
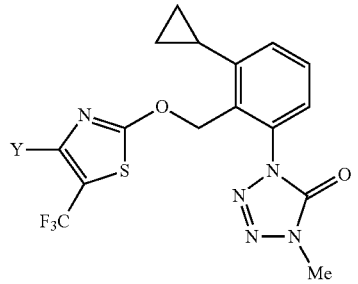
(HA2041)
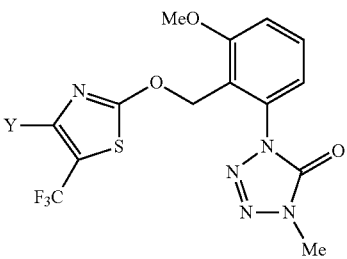
(HA2042)
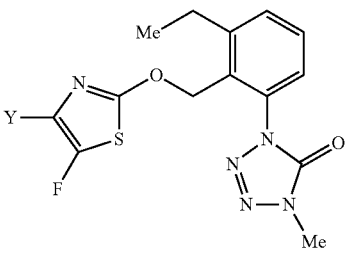
(HA2043)
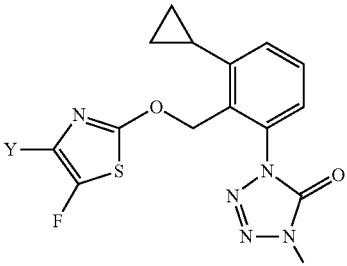
(HA2044)
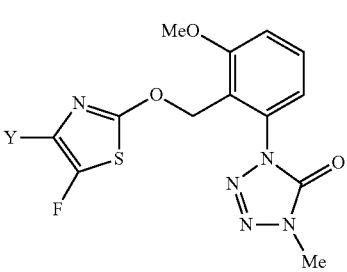
(HA2045)
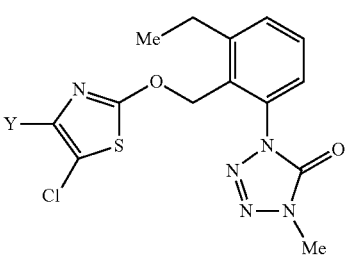
(HA2046)
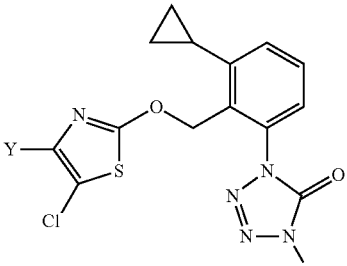
(HA2047)

(HA2048), (HA2049), (HA2050), (HA2051), (HA2052), (HA2053), (HA2054), (HA2055), (HA2056), (HA2057)

(HA2058) 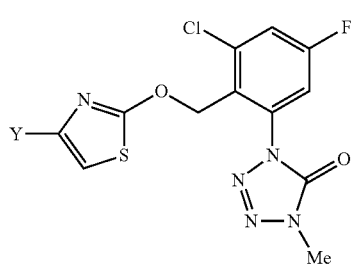
(HA2059) 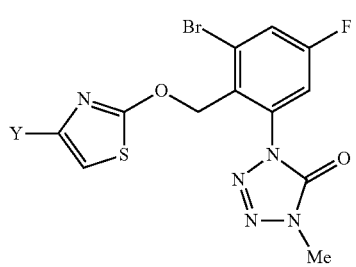
(HA2060) 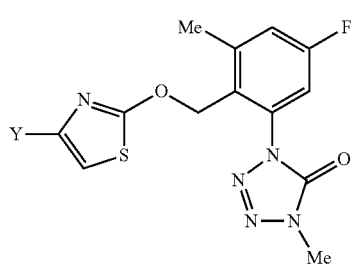
(HA2061) 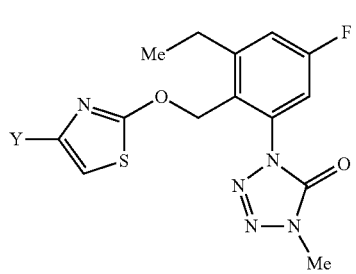
(HA2062) 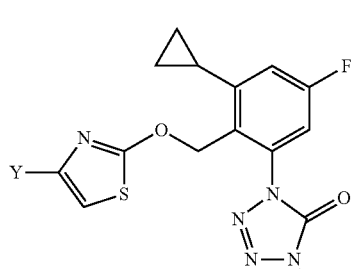
(HA2063) 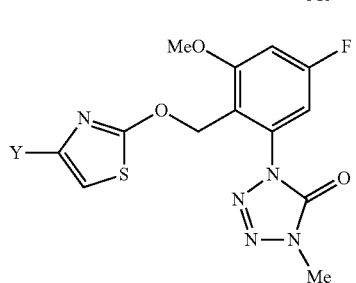
(HA2064) 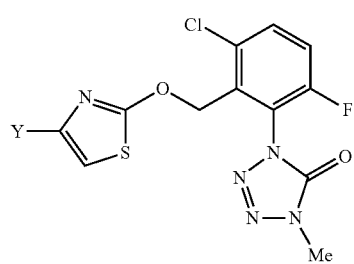
(HA2065) 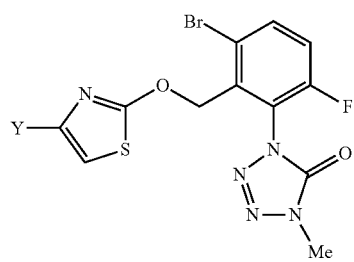
(HA2066) 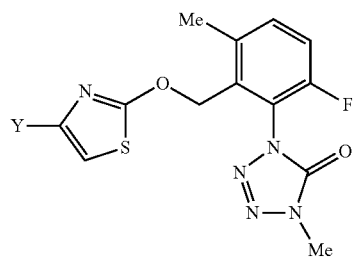
(HA2067) 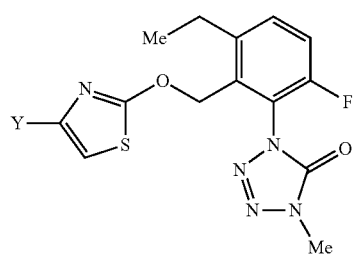
(HA2068) 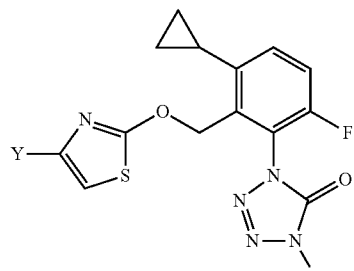
(HA2069) 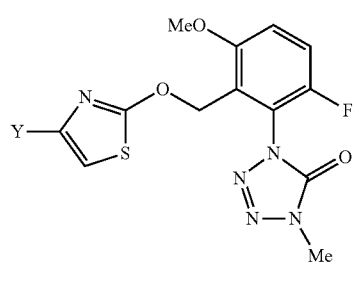

wherein Y is a substituent corresponding to each of substituent numbers 1 to 5971. 2-Py mentioned in the following [substituent number; Y] represents pyridin-2-yl, 3-Py represents pyridin-3-yl, 4-Py represents pyridin-4-yl, F represents fluoro, Cl represents chloro, Br represents bromo, I represents iodo, CN represents cyano, Me represents methyl, Et represents ethyl, Pr represents propyl, CF3 represents trifluoromethyl, CH2CF3 represents 2,2,2-trifluoroethyl, CHF2 represents difluoromethyl, OMe represents methoxy, OCH2CF3 represents 2,2,2-trifluoroethoxy, OEt represents ethoxy, OPr represents propoxy, OCF3 represents trifluoromethoxy, OCHF2 represents difluoromethoxy, SMe represents methylthio, S(O)Me represents methylsulfinyl, S(O)2Me represents methylsulfonyl, SCF3 represents trifluoromethylthio, S(O)CF3 represents trifluoromethylsulfinyl, S(O)2CF3 represents trifluoromethylsulfonyl, COOMe represents methoxycarbonyl, NO2 represents nitro, NH2 represents amino, NHMe represents methylamino, NMe2 represents dimethylamino, AC represents acetyl, ACNH represents acetylamino, and N-AC-N-Me-N represents N-acetyl-N-methylamino.

[1:2-Py], [2:3-F-2-Py], [3:4-Cl-3-F-2-Py], [4:5-Cl-3-F-2-Py], [5:6-Cl-3-F-2-Py], [6:4-Me-3-F-2-Py], [7:5-Me-3-F-2-Py], [8:6-Me-3-F-2-Py], [9:4-CF3-3-F-2-Py], [10:5-CF3-3-F-2-Py], [11:6-CF3-3-F-2-Py], [12:4-CN-3-F-2-Py], [13:5-CN-3-F-2-Py], [14:6-CN-3-F-2-Py], [15:4-OMe-3-F-2-Py], [16:5-OMe-3-F-2-Py], [17:6-OMe-3-F-2-Py], [18:4-F-2-Py], [19:3-Cl-4-F-2-Py], [20:5-Cl-4-F-2-Py], [21:6-Cl-4-F-2-Py], [22:3-Me-4-F-2-Py], [23:5-Me-4-F-2-Py], [24:6-Me-4-F-2-Py], [25:3-CF3-4-F-2-Py], [26:5-CF3-4-F-2-Py], [27:6-CF3-4-F-2-Py], [28:3-CN-4-F-2-Py], [29:5-CN-4-F-2-Py], [30:6-CN-4-F-2-Py], [31:3-OMe-4-F-2-Py], [32:5-OMe-4-F-2-Py], [33:6-OMe-4-F-2-Py], [34:5-F-2-Py], [35:3-Cl-5-F-2-Py], [36:4-Cl-5-F-2-Py], [37:6-Cl-5-F-2-Py], [38:3-Me-5-F-2-Py], [39:4-Me-5-F-2-Py], [40:6-Me-5-F-2-Py], [41:3-CF3-5-F-2-Py], [42:4-CF3-5-F-2-Py], [43:6-CF3-5-F-2-Py], [44:3-CN-5-F-2-Py], [45:4-CN-5-F-2-Py], [46:6-CN-5-F-2-Py], [47:3-OMe-5-F-2-Py], [48:4-OMe-5-F-2-Py], [49:6-OMe-5-F-2-Py], [50:6-F-2-Py], [51:3-Cl-6-F-2-Py], [52:4-Cl-6-F-2-Py], [53:5-Cl-6-F-2-Py], [54:3-Me-6-F-2-Py], [55:4-Me-6-F-2-Py], [56:5-Me-6-F-2-Py], [57:3-CF3-6-F-2-Py], [58:4-CF3-6-F-2-Py], [59:5-CF3-6-F-2-Py], [60:3-CN-6-F-2-Py], [61:4-CN-6-F-2-Py], [62:5-CN-6-F-2-Py], [63:3-OMe-6-F-2-Py], [64:4-OMe-6-F-2-Py], [65:5-OMe-6-F-2-Py], [66:3-Cl-2-Py], [67:4-Cl-3-Cl-2-Py], [68:5-Cl-3-Cl-2-Py], [69:6-Cl-3-Cl-2-Py], [70:4-Me-3-Cl-2-Py], [71:5-Me-3-Cl-2-Py], [72:6-Me-3-Cl-2-Py], [73:4-CF3-3-Cl-2-Py], [74:5-CF3-3-Cl-2-Py], [75:6-CF3-3-Cl-2-Py], [76:4-CN-3-Cl-2-Py], [77:5-CN-3-Cl-2-Py], [78:6-CN-3-Cl-2-Py], [79:4-OMe-3-Cl-2-Py], [80:5-OMe-3-Cl-2-Py], [81:6-OMe-3-Cl-2-Py], [82:4-Cl-2-Py], [83:3-Cl-4-Cl-2-Py], [84:5-Cl-4-Cl-2-Py], [85:6-Cl-4-Cl-2-Py], [86:3-Me-4-Cl-2-Py], [87:5-Me-4-Cl-2-Py], [88:6-Me-4-Cl-2-Py], [89:3-CF3-4-Cl-2-Py], [90:5-CF3-4-Cl-2-Py], [91:6-CF3-4-Cl-2-Py], [92:3-CN-4-Cl-2-Py], [93:5-CN-4-Cl-2-Py], [94:6-CN-4-Cl-2-Py], [95:3-OMe-4-Cl-2-Py], [96:5-OMe-4-Cl-2-Py], [97:6-OMe-4-Cl-2-Py], [98:5-Cl-2-Py], [99:4-Cl-5-Cl-2-Py], [100:5-Cl-5-Cl-2-Py],

[101:6-Cl-5-Cl-2-Py], [102:4-Me-5-Cl-2-Py], [103:5-Me-5-Cl-2-Py], [104:6-Me-5-Cl-2-Py], [105:4-CF3-5-Cl-2-Py], [106:5-CF3-5-Cl-2-Py], [107:6-CF3-5-Cl-2-Py], [108:4-CN-5-Cl-2-Py], [109:3-CN-5-Cl-2-Py], [110:6-CN-5-Cl-2-Py], [111:4-OMe-5-Cl-2-Py], [112:5-OMe-5-Cl-2-Py], [113:6-OMe-5-Cl-2-Py], [114:6-Cl-2-Py], [115:3-Cl-6-Cl-2-Py], [116:4-Cl-6-Cl-2-Py], [117:5-Cl-6-Cl-2-Py], [118:3-Me-6-Cl-2-Py], [119:4-Me-6-Cl-2-Py], [120:5-Me-6-Cl-2-Py], [121:3-CF3-6-Cl-2-Py], [122:4-CF3-6-Cl-2-Py], [123:5-CF3-6-Cl-2-Py], [124:3-CN-6-Cl-2-Py], [125:4-CN-6-Cl-2-Py], [126:5-CN-6-Cl-2-Py], [127:3-OMe-6-Cl-2-Py], [128:4-OMe-6-Cl-2-Py], [129:5-OMe-6-Cl-2-Py], [130:3-Br-2-Py], [131:4-Cl-3-Br-2-Py], [132:5-Cl-3-Br-2-Py], [133:6-Cl-3-Br-2-Py], [134:4-Me-3-Br-2-Py], [135:5-Me-3-Br-2-Py], [136:6-Me-3-Br-2-Py], [137:4-CF3-3-Br-2-Py], [138:5-CF3-3-Br-2-Py], [139:6-CF3-3-Br-2-Py], [140:4-CN-3-Br-2-Py], [141:5-CN-3-Br-2-Py], [142:6-CN-3-Br-2-Py], [143:4-OMe-3-Br-2-Py], [144:5-OMe-3-Br-2-Py], [145:6-OMe-3-Br-2-Py], [146:4-Br-2-Py], [147:3-Cl-4-Br-2-Py], [148:5-Cl-4-Br-2-Py], [149:6-Cl-4-Br-2-Py], [150:3-Me-4-Br-2-Py], [151:5-Me-4-Br-2-Py], [152:6-Me-4-Br-2-Py], [153:3-CF3-4-Br-2-Py], [154:5-CF3-4-Br-2-Py], [155:6-CF3-4-Br-2-Py], [156:3-CN-4-Br-2-Py], [157:5-CN-4-Br-2-Py], [158:6-CN-4-Br-2-Py], [159:3-OMe-4-Br-2-Py], [160:5-OMe-4-Br-2-Py], [161:6-OMe-4-Br-2-Py], [162:5-Br-2-Py], [163:3-Cl-5-Br-2-Py], [164:4-Cl-5-Br-2-Py], [165:6-Cl-5-Br-2-Py], [166:3-Me-5-Br-2-Py], [167:4-Me-5-Br-2-Py], [168:6-Me-5-Br-2-Py], [169:3-CF3-5-Br-2-Py], [170:4-CF3-5-Br-2-Py], [171:6-CF3-5-Br-2-Py], [172:3-CN-5-Br-2-Py], [173:4-CN-5-Br-2-Py], [174:6-CN-5-Br-2-Py], [175:3-OMe-5-Br-2-Py], [176:4-OMe-5-Br-2-Py], [177:6-OMe-5-Br-2-Py], [178:6-Br-2-Py], [179:3-Cl-6-Br-2-Py], [180:4-Cl-6-Br-2-Py], [181:5-Cl-6-Br-2-Py], [182:3-Me-6-Br-2-Py], [183:4-Me-6-Br-2-Py], [184:5-Me-6-Br-2-Py], [185:3-CF3-6-Br-2-Py], [186:4-CF3-6-Br-2-Py], [187:5-CF3-6-Br-2-Py], [188:3-CN-6-Br-2-Py], [189:4-CN-6-Br-2-Py], [190:5-CN-6-Br-2-Py], [191:3-OMe-6-Br-2-Py], [192:4-OMe-6-Br-2-Py], [193:5-OMe-6-Br-2-Py], [194:3-I-2-Py], [195:4-Cl-3-I-2-Py], [196:5-Cl-3-I-2-Py], [197:6-Cl-3-I-2-Py], [198:4-Me-3-I-2-Py], [199:5-Me-3-I-2-Py], [200:6-Me-3-I-2-Py],

[201:4-CF3-3-I-2-Py], [202:5-CF3-3-I-2-Py], [203:6-CF3-3-I-2-Py], [204:4-CN-3-I-2-Py], [205:5-CN-3-I-2-Py], [206:6-CN-3-I-2-Py], [207:4-OMe-3-I-2-Py], [208:5-OMe-3-I-2-Py], [209:6-OMe-3-I-2-Py], [210:4-I-2-Py], [211:3-Cl-4-I-2-Py], [212:5-Cl-4-I-2-Py], [213:6-Cl-4-I-2-Py], [214:3-Me-4-I-2-Py], [215:5-Me-4-I-2-Py], [216:6-Me-4-I-2-Py], [217:3-CF3-4-I-2-Py], [218:5-CF3-4-I-2-Py], [219:6-CF3-4-I-2-Py], [220:3-CN-4-I-2-Py], [221:5-CN-4-I-2-Py], [222:6-CN-4-I-2-Py], [223:3-OMe-4-I-2-Py], [224:5-OMe-4-I-2-Py], [225:6-OMe-4-I-2-Py], [226:5-I-2-Py], [227:3-Cl-5-I-2-Py], [228:4-Cl-5-I-2-Py], [229:6-Cl-5-I-2-Py], [230:3-Me-5-I-2-Py], [231:4-Me-5-I-2-Py], [232:6-Me-5-I-2-Py], [233:3-CF3-5-I-2-Py], [234:4-CF3-5-I-2-Py], [235:6-CF3-5-I-2-Py], [236:3-CN-5-I-2-Py], [237:4-CN-5-I-2-Py], [238:6-CN-5-I-2-Py], [239:3-OMe-5-I-2-Py], [240:4-OMe-5-I-2-Py], [241:6-OMe-5-I-2-Py], [242:6-I-2-Py], [243:3-Cl-6-I-2-Py], [244:4-Cl-6-I-2-Py], [245:5-Cl-6-I-2-Py], [246:3-Me-6-I-2-Py], [247:4-Me-6-I-2-Py], [248:5-Me-6-I-2-Py], [249:3-CF3-6-I-2-Py], [250:4-CF3-6-I-2-Py], [251:5-CF3-6-I-2-Py], [252:3-CN-6-I-2-Py], [253:4-CN-6-I-2-Py], [254:5-CN-6-I-2-Py], [255:3-OMe-6-I-2-Py], [256:4-OMe-6-I-2-Py], [257:5-OMe-6-I-2-Py], [258:3-Me-2-Py], [259:4-Cl-3-Me-2-Py], [260:5-Cl-3-Me-2-Py], [261:6-Cl-3-Me-2-Py], [262:4-Me-3-Me-2-Py], [263:5-Me-3-Me-2-Py], [264:6-Me-3-Me-2-Py], [265:4-CF3-3-Me-2-Py], [266:5-CF3-3-Me-2-Py], [267:6-CF3-3-Me-2-Py], [268:4-CN-3-Me-2-Py], [269:5-CN-3-Me-2-Py], [270:6-CN-3-Me-2-Py], [271:4-OMe-3-Me-2-Py], [272:5-OMe-3-Me-2-Py], [273:6-OMe-3-Me-2-Py], [274:4-Me-2-Py], [275:3-Cl-4-Me-2-Py], [276:5-Cl-4-Me-2-Py], [277:6-Cl-4-Me-2-Py], [278:3-Me-4-Me-2-Py], [279:5-Me-4-Me-2-Py], [280:6-Me-4-Me-2-Py], [281:3-CF3-4-Me-2-Py], [282:5-CF3-4-Me-2-Py], [283:6-CF3-4-Me-2-Py], [284:3-CN-4-Me-2-Py], [285:5-CN-4-Me-2-Py], [286:6-CN-4-Me-2-Py], [287:3-OMe-4-Me-2-Py], [288:5-OMe-4-Me-2-Py], [289:6-OMe-4-Me-2-

Py], [290:5-Me-2-Py], [291:3-Cl-5-Me-2-Py], [292:4-Cl-5-Me-2-Py], [293:6-Cl-5-Me-2-Py], [294:3-Me-5-Me-2-Py], [295:4-Me-5-Me-2-Py], [296:6-Me-5-Me-2-Py], [297:3-CF3-5-Me-2-Py], [298:4-CF3-5-Me-2-Py], [299:6-CF3-5-Me-2-Py], [300:3-CN-5-Me-2-Py],
[301:4-CN-5-Me-2-Py], [302:6-CN-5-Me-2-Py], [303:3-OMe-5-Me-2-Py], [304:4-OMe-5-Me-2-Py], [305:6-OMe-5-Me-2-Py], [306:6-Me-2-Py], [307:3-Cl-6-Me-2-Py], [308:4-Cl-6-Me-2-Py], [309:5-Cl-6-Me-2-Py], [310:3-Me-6-Me-2-Py], [311:4-Me-6-Me-2-Py], [312:5-Me-6-Me-2-Py], [313:3-CF3-6-Me-2-Py], [314:4-CF3-6-Me-2-Py], [315:5-CF3-6-Me-2-Py], [316:3-CN-6-Me-2-Py], [317:4-CN-6-Me-2-Py], [318:5-CN-6-Me-2-Py], [319:3-OMe-6-Me-2-Py], [320:4-OMe-6-Me-2-Py], [321:5-OMe-6-Me-2-Py], [322:3-OMe-2-Py], [323:4-Cl-3-OMe-2-Py], [324:5-Cl-3-OMe-2-Py], [325:6-Cl-3-OMe-2-Py], [326:4-Me-3-OMe-2-Py], [327:5-Me-3-OMe-2-Py], [328:6-Me-3-OMe-2-Py], [329:4-CF3-3-OMe-2-Py], [330:5-CF3-3-OMe-2-Py], [331:6-CF3-3-OMe-2-Py], [332:4-CN-3-OMe-2-Py], [333:5-CN-3-OMe-2-Py], [334:6-CN-3-OMe-2-Py], [335:4-OMe-3-OMe-2-Py], [336:5-OMe-3-OMe-2-Py], [337:6-OMe-3-OMe-2-Py], [338:4-OMe-2-Py], [339:3-Cl-4-OMe-2-Py], [340:5-Cl-4-OMe-2-Py], [341:6-Cl-4-OMe-2-Py], [342:3-Me-4-OMe-2-Py], [343:5-Me-4-OMe-2-Py], [344:6-Me-4-OMe-2-Py], [345:3-CF3-4-OMe-2-Py], [346:5-CF3-4-OMe-2-Py], [347:6-CF3-4-OMe-2-Py], [348:3-CN-4-OMe-2-Py], [349:5-CN-4-OMe-2-Py], [350:6-CN-4-OMe-2-Py], [351:3-OMe-4-OMe-2-Py], [352:5-OMe-4-OMe-2-Py], [353:6-OMe-4-OMe-2-Py], [354:5-OMe-2-Py], [355:3-Cl-5-OMe-2-Py], [356:4-Cl-5-OMe-2-Py], [357:6-Cl-5-OMe-2-Py], [358:3-Me-5-OMe-2-Py], [359:4-Me-5-OMe-2-Py], [360:6-Me-5-OMe-2-Py], [361:3-CF3-5-OMe-2-Py], [362:4-CF3-5-OMe-2-Py], [363:6-CF3-5-OMe-2-Py], [364:3-CN-5-OMe-2-Py], [365:4-CN-5-OMe-2-Py], [366:6-CN-5-OMe-2-Py], [367:3-OMe-5-OMe-2-Py], [368:4-OMe-5-OMe-2-Py], [369:6-OMe-5-OMe-2-Py], [370:6-OMe-2-Py], [371:3-Cl-6-OMe-2-Py], [372:4-Cl-6-OMe-2-Py], [373:5-Cl-6-OMe-2-Py], [374:3-Me-6-OMe-2-Py], [375:4-Me-6-OMe-2-Py], [376:5-Me-6-OMe-2-Py], [377:3-CF3-6-OMe-2-Py], [378:4-CF3-6-OMe-2-Py], [379:5-CF3-6-OMe-2-Py], [380:3-CN-6-OMe-2-Py], [381:4-CN-6-OMe-2-Py], [382:5-CN-6-OMe-2-Py], [383:3-OMe-6-OMe-2-Py], [384:4-OMe-6-OMe-2-Py], [385:5-OMe-6-OMe-2-Py], [386:3-CF3-2-Py], [387:4-Cl-3-CF3-2-Py], [388:5-Cl-3-CF3-2-Py], [389:6-Cl-3-CF3-2-Py], [390:4-Me-3-CF3-2-Py], [391:5-Me-3-CF3-2-Py], [392:6-Me-3-CF3-2-Py], [393:4-CF3-3-CF3-2-Py], [394:5-CF3-3-CF3-2-Py], [395:6-CF3-3-CF3-2-Py], [396:4-CN-3-CF3-2-Py], [397:5-CN-3-CF3-2-Py], [398:6-CN-3-CF3-2-Py], [399:4-OMe-3-CF3-2-Py], [400:5-OMe-3-CF3-2-Py],
[401:6-OMe-3-CF3-2-Py], [402:4-CF3-2-Py], [403:3-Cl-4-CF3-2-Py], [404:5-Cl-4-CF3-2-Py], [405:6-Cl-4-CF3-2-Py], [406:3-Me-4-CF3-2-Py], [407:5-Me-4-CF3-2-Py], [408:6-Me-4-CF3-2-Py], [409:3-CF3-4-CF3-2-Py], [410:5-CF3-4-CF3-2-Py], [411:6-CF3-4-CF3-2-Py], [412:3-CN-4-CF3-2-Py], [413:5-CN-4-CF3-2-Py], [414:6-CN-4-CF3-2-Py], [415:3-OMe-4-CF3-2-Py], [416:5-OMe-4-CF3-2-Py], [417:6-OMe-4-CF3-2-Py], [418:5-CF3-2-Py], [419:3-Cl-5-CF3-2-Py], [420:4-Cl-5-CF3-2-Py], [421:6-Cl-5-CF3-2-Py], [422:3-Me-5-CF3-2-Py], [423:4-Me-5-CF3-2-Py], [424:6-Me-5-CF3-2-Py], [425:3-CF3-5-CF3-2-Py], [426:4-CF3-5-CF3-2-Py], [427:6-CF3-5-CF3-2-Py], [428:3-CN-5-CF3-2-Py], [429:4-CN-5-CF3-2-Py], [430:6-CN-5-CF3-2-Py], [431:3-OMe-5-CF3-2-Py], [432:4-OMe-5-CF3-2-Py], [433:6-OMe-5-CF3-2-Py], [434:6-CF3-2-Py], [435:3-Cl-6-CF3-2-Py], [436:4-Cl-6-CF3-2-Py], [437:5-Cl-6-CF3-2-Py], [438:3-Me-6-CF3-2-Py], [439:4-Me-6-CF3-2-Py], [440:5-Me-6-CF3-2-Py], [441:3-CF3-6-CF3-2-Py], [442:4-CF3-6-CF3-2-Py], [443:5-CF3-6-CF3-2-Py], [444:3-CN-6-CF3-2-Py], [445:4-CN-6-CF3-2-Py], [446:5-CN-6-CF3-2-Py], [447:3-OMe-6-CF3-2-Py], [448:4-OMe-6-CF3-2-Py], [449:5-OMe-6-CF3-2-Py], [450:3-OCF3-2-Py], [451:4-Cl-3-OCF3-2-Py], [452:5-Cl-3-OCF3-2-Py], [453:6-Cl-3-OCF3-2-Py], [454:4-Me-3-OCF3-2-Py], [455:5-Me-3-OCF3-2-Py], [456:6-Me-3-OCF3-2-Py], [457:4-CF3-3-OCF3-2-Py], [458:5-CF3-3-OCF3-2-Py], [459:6-CF3-3-OCF3-2-Py], [460:4-CN-3-OCF3-2-Py], [461:5-CN-3-OCF3-2-Py], [462:6-CN-3-OCF3-2-Py], [463:4-OMe-3-OCF3-2-Py], [464:5-OMe-3-OCF3-2-Py], [465:6-OMe-3-OCF3-2-Py], [466:4-OCF3-2-Py], [467:3-Cl-4-OCF3-2-Py], [468:5-Cl-4-OCF3-2-Py], [469:6-Cl-4-OCF3-2-Py], [470:3-Me-4-OCF3-2-Py], [471:5-Me-4-OCF3-2-Py], [472:6-Me-4-OCF3-2-Py], [473:3-CF3-4-OCF3-2-Py], [474:5-CF3-4-OCF3-2-Py], [475:6-CF3-4-OCF3-2-Py], [476:3-CN-4-OCF3-2-Py], [477:5-CN-4-OCF3-2-Py], [478:6-CN-4-OCF3-2-Py], [479:3-OMe-4-OCF3-2-Py], [480:5-OMe-4-OCF3-2-Py], [481:6-OMe-4-OCF3-2-Py], [482:5-OCF3-2-Py], [483:3-Cl-5-OCF3-2-Py], [484:4-Cl-5-OCF3-2-Py], [485:6-Cl-5-OCF3-2-Py], [486:3-Me-5-OCF3-2-Py], [487:4-Me-5-OCF3-2-Py], [488:6-Me-5-OCF3-2-Py], [489:3-CF3-5-OCF3-2-Py], [490:4-CF3-5-OCF3-2-Py], [491:6-CF3-5-OCF3-2-Py], [492:3-CN-5-OCF3-2-Py], [493:4-CN-5-OCF3-2-Py], [494:6-CN-5-OCF3-2-Py], [495:3-OMe-5-OCF3-2-Py], [496:4-OMe-5-OCF3-2-Py], [497:6-OMe-5-OCF3-2-Py], [498:6-OCF3-2-Py], [499:3-Cl-6-OCF3-2-Py], [500:4-Cl-6-OCF3-2-Py],
[501:5-Cl-6-OCF3-2-Py], [502:3-Me-6-OCF3-2-Py], [503:4-Me-6-OCF3-2-Py], [504:5-Me-6-OCF3-2-Py], [505:3-CF3-6-OCF3-2-Py], [506:4-CF3-6-OCF3-2-Py], [507:5-CF3-6-OCF3-2-Py], [508:3-CN-6-OCF3-2-Py], [509:4-CN-6-OCF3-2-Py], [510:5-CN-6-OCF3-2-Py], [511:3-OMe-6-OCF3-2-Py], [512:4-OMe-6-OCF3-2-Py], [513:5-OMe-6-OCF3-2-Py], [514:3-CHF2-2-Py], [515:4-Cl-3-CHF2-2-Py], [516:5-Cl-3-CHF2-2-Py], [517:6-Cl-3-CHF2-2-Py], [518:4-Me-3-CHF2-2-Py], [519:5-Me-3-CHF2-2-Py], [520:6-Me-3-CHF2-2-Py], [521:4-CF3-3-CHF2-2-Py], [522:5-CF3-3-CHF2-2-Py], [523:6-CF3-3-CHF2-2-Py], [524:4-CN-3-CHF2-2-Py], [525:5-CN-3-CHF2-2-Py], [526:6-CN-3-CHF2-2-Py], [527:4-OMe-3-CHF2-2-Py], [528:5-OMe-3-CHF2-2-Py], [529:6-OMe-3-CHF2-2-Py], [530:4-CHF2-2-Py], [531:3-Cl-4-CHF2-2-Py], [532:5-Cl-4-CHF2-2-Py], [533:6-Cl-4-CHF2-2-Py], [534:3-Me-4-CHF2-2-Py], [535:5-Me-4-CHF2-2-Py], [536:6-Me-4-CHF2-2-Py], [537:3-CF3-4-CHF2-2-Py], [538:5-CF3-4-CHF2-2-Py], [539:6-CF3-4-CHF2-2-Py], [540:3-CN-4-CHF2-2-Py], [541:5-CN-4-CHF2-2-Py], [542:6-CN-4-CHF2-2-Py], [543:3-OMe-4-CHF2-2-Py], [544:5-OMe-4-CHF2-2-Py], [545:6-OMe-4-CHF2-2-Py], [546:5-CHF2-2-Py], [547:3-Cl-5-CHF2-2-Py], [548:4-Cl-5-CHF2-2-Py], [549:6-Cl-5-CHF2-2-Py], [550:3-Me-5-CHF2-2-Py], [551:4-Me-5-CHF2-2-Py], [552:6-Me-5-CHF2-2-Py], [553:3-CF3-5-CHF2-2-Py], [554:4-CF3-5-CHF2-2-Py], [555:6-CF3-5-CHF2-2-Py], [556:3-CN-5-CHF2-2-Py], [557:4-CN-5-CHF2-2-Py], [558:6-CN-5-CHF2-2-Py], [559:3-OMe-5-CHF2-2-Py], [560:4-OMe-5-CHF2-2-Py], [561:6-OMe-5-CHF2-2-Py], [562:6-CHF2-2-Py], [563:3-Cl-6-CHF2-2-Py], [564:4-Cl-6-CHF2-2-Py], [565:5-Cl-6-CHF2-2-Py], [566:3-Me-6-CHF2-2-Py], [567:4-Me-6-CHF2-2-Py], [568:5-Me-6-CHF2-2-Py], [569:3-CF3-6-CHF2-2-Py], [570:4-CF3-6-CHF2-2-Py], [571:5-CF3-6-CHF2-2-Py], [572:3-CN-6-CHF2-2-Py], [573:4-CN-6-CHF2-2-Py], [574:5-CN-6-CHF2-2-Py], [575:3-OMe-6-CHF2-2-Py], [576:4-OMe-6-CHF2-2-Py], [577:5-OMe-6-CHF2-2-Py], [578:3-OCHF2-2-Py], [579:4-Cl-3-OCHF2-2-Py], [580:5-Cl-3-OCHF2-2-Py], [581:6-Cl-3-OCHF2-2-

Py], [582:4-Me-3-OCHF2-2-Py], [583:5-Me-3-OCHF2-2-Py], [584:6-Me-3-OCHF2-2-Py], [585:4-Cl-3-OCHF2-2-Py], [586:5-Cl-3-OCHF2-2-Py], [587:6-Cl-3-OCHF2-2-Py], [588:4-CN-3-OCHF2-2-Py], [589:5-CN-3-OCHF2-2-Py], [590:6-CN-3-OCHF2-2-Py], [591:4-OMe-3-OCHF2-2-Py], [592:5-OMe-3-OCHF2-2-Py], [593:6-OMe-3-OCHF2-2-Py], [594:4-OCHF2-2-Py], [595:3-Cl-4-OCHF2-2-Py], [596:5-Cl-4-OCHF2-2-Py], [597:6-Cl-4-OCHF2-2-Py], [598:3-Me-4-OCHF2-2-Py], [599:5-Me-4-OCHF2-2-Py], [600:6-Me-4-OCHF2-2-Py], [601:3-CF3-4-OCHF2-2-Py], [602:5-CF3-4-OCHF2-2-Py], [603:6-CF3-4-OCHF2-2-Py], [604:3-CN-4-OCHF2-2-Py], [605:5-CN-4-OCHF2-2-Py], [606:6-CN-4-OCHF2-2-Py], [607:3-OMe-4-OCHF2-2-Py], [608:5-OMe-4-OCHF2-2-Py], [609:6-OMe-4-OCHF2-2-Py], [610:5-OCHF2-2-Py], [611:3-Cl-5-OCHF2-2-Py], [612:4-Cl-5-OCHF2-2-Py], [613:6-Cl-5-OCHF2-2-Py], [614:3-Me-5-OCHF2-2-Py], [615:4-Me-5-OCHF2-2-Py], [616:6-Me-5-OCHF2-2-Py], [617:3-CF3-5-OCHF2-2-Py], [618:4-CF3-5-OCHF2-2-Py], [619:6-CF3-5-OCHF2-2-Py], [620:3-CN-5-OCHF2-2-Py], [621:4-CN-5-OCHF2-2-Py], [622:6-CN-5-OCHF2-2-Py], [623:3-OMe-5-OCHF2-2-Py], [624:4-OMe-5-OCHF2-2-Py], [625:6-OMe-5-OCHF2-2-Py], [626:6-OCHF2-2-Py], [627:3-Cl-6-OCHF2-2-Py], [628:4-Cl-6-OCHF2-2-Py], [629:5-Cl-6-OCHF2-2-Py], [630:3-Me-6-OCHF2-2-Py], [631:4-Me-6-OCHF2-2-Py], [632:5-Me-6-OCHF2-2-Py], [633:3-CF3-6-OCHF2-2-Py], [634:4-CF3-6-OCHF2-2-Py], [635:5-CF3-6-OCHF2-2-Py], [636:3-CN-6-OCHF2-2-Py], [637:4-CN-6-OCHF2-2-Py], [638:5-CN-6-OCHF2-2-Py], [639:3-OMe-6-OCHF2-2-Py], [640:4-OMe-6-OCHF2-2-Py], [641:5-OMe-6-OCHF2-2-Py], [642:3-Et-2-Py], [643:4-Cl-3-Et-2-Py], [644:5-Cl-3-Et-2-Py], [645:6-Cl-3-Et-2-Py], [646:4-Me-3-Et-2-Py], [647:5-Me-3-Et-2-Py], [648:6-Me-3-Et-2-Py], [649:4-CF3-3-Et-2-Py], [650:5-CF3-3-Et-2-Py], [651:6-CF3-3-Et-2-Py], [652:4-CN-3-Et-2-Py], [653:5-CN-3-Et-2-Py], [654:6-CN-3-Et-2-Py], [655:4-OMe-3-Et-2-Py], [656:5-OMe-3-Et-2-Py], [657:6-OMe-3-Et-2-Py], [658:4-Et-2-Py], [659:3-Cl-4-Et-2-Py], [660:5-Cl-4-Et-2-Py], [661:6-Cl-4-Et-2-Py], [662:3-Me-4-Et-2-Py], [663:5-Me-4-Et-2-Py], [664:6-Me-4-Et-2-Py], [665:3-CF3-4-Et-2-Py], [666:5-CF3-4-Et-2-Py], [667:6-CF3-4-Et-2-Py], [668:3-CN-4-Et-2-Py], [669:5-CN-4-Et-2-Py], [670:6-CN-4-Et-2-Py], [671:3-OMe-4-Et-2-Py], [672:5-OMe-4-Et-2-Py], [673:6-OMe-4-Et-2-Py], [674:5-Et-2-Py], [675:3-Cl-5-Et-2-Py], [676:4-Cl-5-Et-2-Py], [677:6-Cl-5-Et-2-Py], [678:3-Me-5-Et-2-Py], [679:4-Me-5-Et-2-Py], [680:6-Me-5-Et-2-Py], [681:3-CF3-5-Et-2-Py], [682:4-CF3-5-Et-2-Py], [683:6-CF3-5-Et-2-Py], [684:3-CN-5-Et-2-Py], [685:4-CN-5-Et-2-Py], [686:6-CN-5-Et-2-Py], [687:3-OMe-5-Et-2-Py], [688:4-OMe-5-Et-2-Py], [689:6-OMe-5-Et-2-Py], [690:6-Et-2-Py], [691:3-Cl-6-Et-2-Py], [692:4-Cl-6-Et-2-Py], [693:5-Cl-6-Et-2-Py], [694:3-Me-6-Et-2-Py], [695:4-Me-6-Et-2-Py], [696:5-Me-6-Et-2-Py], [697:3-CF3-6-Et-2-Py], [698:4-CF3-6-Et-2-Py], [699:5-CF3-6-Et-2-Py], [700:3-CN-6-Et-2-Py], [701:4-CN-6-Et-2-Py], [702:5-CN-6-Et-2-Py], [703:3-OMe-6-Et-2-Py], [704:4-OMe-6-Et-2-Py], [705:5-OMe-6-Et-2-Py], [706:3-CH2CF3-2-Py], [707:4-Cl-3-CH2CF3-2-Py], [708:5-Cl-3-CH2CF3-2-Py], [709:6-Cl-3-CH2CF3-2-Py], [710:4-Me-3-CH2CF3-2-Py], [711:5-Me-3-CH2CF3-2-Py], [712:6-Me-3-CH2CF3-2-Py], [713:4-CF3-3-CH2CF3-2-Py], [714:5-CF3-3-CH2CF3-2-Py], [715:6-CF3-3-CH2CF3-2-Py], [716:4-CN-3-CH2CF3-2-Py], [717:5-CN-3-CH2CF3-2-Py], [718:6-CN-3-CH2CF3-2-Py], [719:4-OMe-3-CH2CF3-2-Py], [720:5-OMe-3-CH2CF3-2-Py], [721:6-OMe-3-CH2CF3-2-Py], [722:4-CH2CF3-2-Py], [723:3-Cl-4-CH2CF3-2-Py], [724:5-Cl-4-CH2CF3-2-Py], [725:6-Cl-4-CH2CF3-2-Py], [726:3-Me-4-CH2CF3-2-Py], [727:5-Me-4-CH2CF3-2-Py], [728:6-Me-4-CH2CF3-2-Py], [729:3-CF3-4-CH2CF3-2-Py], [730:5-CF3-4-CH2CF3-2-Py], [731:6-CF3-4-CH2CF3-2-Py], [732:3-CN-4-CH2CF3-2-Py], [733:5-CN-4-CH2CF3-2-Py], [734:6-CN-4-CH2CF3-2-Py], [735:3-OMe-4-CH2CF3-2-Py], [736:5-OMe-4-CH2CF3-2-Py], [737:6-OMe-4-CH2CF3-2-Py], [738:5-CH2CF3-2-Py], [739:3-Cl-5-CH2CF3-2-Py], [740:4-Cl-5-CH2CF3-2-Py], [741:6-Cl-5-CH2CF3-2-Py], [742:3-Me-5-CH2CF3-2-Py], [743:4-Me-5-CH2CF3-2-Py], [744:6-Me-5-CH2CF3-2-Py], [745:3-CF3-5-CH2CF3-2-Py], [746:4-CF3-5-CH2CF3-2-Py], [747:6-CF3-5-CH2CF3-2-Py], [748:3-CN-5-CH2CF3-2-Py], [749:4-CN-5-CH2CF3-2-Py], [750:6-CN-5-CH2CF3-2-Py], [751:3-OMe-5-CH2CF3-2-Py], [752:4-OMe-5-CH2CF3-2-Py], [753:6-OMe-5-CH2CF3-2-Py], [754:6-CH2CF3-2-Py], [755:3-Cl-6-CH2CF3-2-Py], [756:4-Cl-6-CH2CF3-2-Py], [757:5-Cl-6-CH2CF3-2-Py], [758:3-Me-6-CH2CF3-2-Py], [759:4-Me-6-CH2CF3-2-Py], [760:5-Me-6-CH2CF3-2-Py], [761:3-CF3-6-CH2CF3-2-Py], [762:4-CF3-6-CH2CF3-2-Py], [763:5-CF3-6-CH2CF3-2-Py], [764:3-CN-6-CH2CF3-2-Py], [765:4-CN-6-CH2CF3-2-Py], [766:5-CN-6-CH2CF3-2-Py], [767:3-OMe-6-CH2CF3-2-Py], [768:4-OMe-6-CH2CF3-2-Py], [769:5-OMe-6-CH2CF3-2-Py], [770:3-OEt-2-Py], [771:4-Cl-3-OEt-2-Py], [772:5-Cl-3-OEt-2-Py], [773:6-Cl-3-OEt-2-Py], [774:4-Me-3-OEt-2-Py], [775:5-Me-3-OEt-2-Py], [776:6-Me-3-OEt-2-Py], [777:4-CF3-3-OEt-2-Py], [778:5-CF3-3-OEt-2-Py], [779:6-CF3-3-OEt-2-Py], [780:4-CN-3-OEt-2-Py], [781:5-CN-3-OEt-2-Py], [782:6-CN-3-OEt-2-Py], [783:4-OMe-3-OEt-2-Py], [784:5-OMe-3-OEt-2-Py], [785:6-OMe-3-OEt-2-Py], [786:4-OEt-2-Py], [787:3-Cl-4-OEt-2-Py], [788:5-Cl-4-OEt-2-Py], [789:6-Cl-4-OEt-2-Py], [790:3-Me-4-OEt-2-Py], [791:5-Me-4-OEt-2-Py], [792:6-Me-4-OEt-2-Py], [793:3-CF3-4-OEt-2-Py], [794:5-CF3-4-OEt-2-Py], [795:6-CF3-4-OEt-2-Py], [796:3-CN-4-OEt-2-Py], [797:5-CN-4-OEt-2-Py], [798:6-CN-4-OEt-2-Py], [799:3-OMe-4-OEt-2-Py], [800:5-OMe-4-OEt-2-Py], [801:6-OMe-4-OEt-2-Py], [802:5-OEt-2-Py], [803:3-Cl-5-OEt-2-Py], [804:4-Cl-5-OEt-2-Py], [805:6-Cl-5-OEt-2-Py], [806:3-Me-5-OEt-2-Py], [807:4-Me-5-OEt-2-Py], [808:6-Me-5-OEt-2-Py], [809:3-CF3-5-OEt-2-Py], [810:4-CF3-5-OEt-2-Py], [811:6-CF3-5-OEt-2-Py], [812:3-CN-5-OEt-2-Py], [813:4-CN-5-OEt-2-Py], [814:6-CN-5-OEt-2-Py], [815:3-OMe-5-OEt-2-Py], [816:4-OMe-5-OEt-2-Py], [817:6-OMe-5-OEt-2-Py], [818:6-OEt-2-Py], [819:3-Cl-6-OEt-2-Py], [820:4-Cl-6-OEt-2-Py], [821:5-Cl-6-OEt-2-Py], [822:3-Me-6-OEt-2-Py], [823:4-Me-6-OEt-2-Py], [824:5-Me-6-OEt-2-Py], [825:3-CF3-6-OEt-2-Py], [826:4-CF3-6-OEt-2-Py], [827:5-CF3-6-OEt-2-Py], [828:3-CN-6-OEt-2-Py], [829:4-CN-6-OEt-2-Py], [830:5-CN-6-OEt-2-Py], [831:3-OMe-6-OEt-2-Py], [832:4-OMe-6-OEt-2-Py], [833:5-OMe-6-OEt-2-Py], [834:3-OCH2CF3-2-Py], [835:4-Cl-3-OCH2CF3-2-Py], [836:5-Cl-3-OCH2CF3-2-Py], [837:6-Cl-3-OCH2CF3-2-Py], [838:4-Me-3-OCH2CF3-2-Py], [839:5-Me-3-OCH2CF3-2-Py], [840:6-Me-3-OCH2CF3-2-Py], [841:4-CF3-3-OCH2CF3-2-Py], [842:5-CF3-3-OCH2CF3-2-Py], [843:6-CF3-3-OCH2CF3-2-Py], [844:4-CN-3-OCH2CF3-2-Py], [845:5-CN-3-OCH2CF3-2-Py], [846:6-CN-3-OCH2CF3-2-Py], [847:4-OMe-3-OCH2CF3-2-Py], [848:5-OMe-3-OCH2CF3-2-Py], [849:6-OMe-3-OCH2CF3-2-Py], [850:4-OCH2CF3-2-Py], [851:3-Cl-4-OCH2CF3-2-Py], [852:5-Cl-4-OCH2CF3-2-Py], [853:6-Cl-4-OCH2CF3-2-Py], [854:3-Me-4-OCH2CF3-2-Py], [855:5-Me-4-OCH2CF3-2-Py], [856:6-Me-4-OCH2CF3-2-Py], [857:3-CF3-4-OCH2CF3-2-Py], [858:5-CF3-4-OCH2CF3-2-Py], [859:6-CF3-4-OCH2CF3-2-Py], [860:3-CN-4-OCH2CF3-2-Py], [861:5-CN-4-OCH2CF3-2-Py], [862:6-

CN-4-OCH2CF3-2-Py], [863:3-OMe-4-OCH2CF3-2-Py], [864:5-OMe-4-OCH2CF3-2-Py], [865:6-OMe-4-OCH2CF3-2-Py], [866:5-OCH2CF3-2-Py], [867:3-Cl-5-OCH2CF3-2-Py], [868:4-Cl-5-OCH2CF3-2-Py], [869:6-Cl-5-OCH2CF3-2-Py], [870:3-Me-5-OCH2CF3-2-Py], [871:4-Me-5-OCH2CF3-2-Py], [872:6-Me-5-OCH2CF3-2-Py], [873:3-CF3-5-OCH2CF3-2-Py], [874:4-CF3-5-OCH2CF3-2-Py], [875:6-CF3-5-OCH2CF3-2-Py], [876:3-CN-5-OCH2CF3-2-Py], [877:4-CN-5-OCH2CF3-2-Py], [878:6-CN-5-OCH2CF3-2-Py], [879:3-OMe-5-OCH2CF3-2-Py], [880:4-OMe-5-OCH2CF3-2-Py], [881:6-OMe-5-OCH2CF3-2-Py], [882:6-OCH2CF3-2-Py], [883:3-Cl-6-OCH2CF3-2-Py], [884:4-Cl-6-OCH2CF3-2-Py], [885:5-Cl-6-OCH2CF3-2-Py], [886:3-Me-6-OCH2CF3-2-Py], [887:4-Me-6-OCH2CF3-2-Py], [888:5-Me-6-OCH2CF3-2-Py], [889:3-CF3-6-OCH2CF3-2-Py], [890:4-CF3-6-OCH2CF3-2-Py], [891:5-CF3-6-OCH2CF3-2-Py], [892:3-CN-6-OCH2CF3-2-Py], [893:4-CN-6-OCH2CF3-2-Py], [894:5-CN-6-OCH2CF3-2-Py], [895:3-OMe-6-OCH2CF3-2-Py], [896:4-OMe-6-OCH2CF3-2-Py], [897:5-OMe-6-OCH2CF3-2-Py], [898:3-Pr-2-Py], [899:4-Cl-3-Pr-2-Py], [900:5-Cl-3-Pr-2-Py],
[901:6-Cl-3-Pr-2-Py], [902:4-Me-3-Pr-2-Py], [903:5-Me-3-Pr-2-Py], [904:6-Me-3-Pr-2-Py], [905:4-CF3-3-Pr-2-Py], [906:5-CF3-3-Pr-2-Py], [907:6-CF3-3-Pr-2-Py], [908:4-CN-3-Pr-2-Py], [909:5-CN-3-Pr-2-Py], [910:6-CN-3-Pr-2-Py], [911:4-OMe-3-Pr-2-Py], [912:5-OMe-3-Pr-2-Py], [913:6-OMe-3-Pr-2-Py], [914:4-Pr-2-Py], [915:3-Cl-4-Pr-2-Py], [916:5-Cl-4-Pr-2-Py], [917:6-Cl-4-Pr-2-Py], [918:3-Me-4-Pr-2-Py], [919:5-Me-4-Pr-2-Py], [920:6-Me-4-Pr-2-Py], [921:3-CF3-4-Pr-2-Py], [922:5-CF3-4-Pr-2-Py], [923:6-CF3-4-Pr-2-Py], [924:3-CN-4-Pr-2-Py], [925:5-CN-4-Pr-2-Py], [926:6-CN-4-Pr-2-Py], [927:3-OMe-4-Pr-2-Py], [928:5-OMe-4-Pr-2-Py], [929:6-OMe-4-Pr-2-Py], [930:5-Pr-2-Py], [931:3-Cl-5-Pr-2-Py], [932:4-Cl-5-Pr-2-Py], [933:6-Cl-5-Pr-2-Py], [934:3-Me-5-Pr-2-Py], [935:4-Me-5-Pr-2-Py], [936:6-Me-5-Pr-2-Py], [937:3-CF3-5-Pr-2-Py], [938:4-CF3-5-Pr-2-Py], [939:6-CF3-5-Pr-2-Py], [940:3-CN-5-Pr-2-Py], [941:4-CN-5-Pr-2-Py], [942:6-CN-5-Pr-2-Py], [943:3-OMe-5-Pr-2-Py], [944:4-OMe-5-Pr-2-Py], [945:6-OMe-5-Pr-2-Py], [946:6-Pr-2-Py], [947:3-Cl-6-Pr-2-Py], [948:4-Cl-6-Pr-2-Py], [949:5-Cl-6-Pr-2-Py], [950:3-Me-6-Pr-2-Py], [951:4-Me-6-Pr-2-Py], [952:5-Me-6-Pr-2-Py], [953:3-CF3-6-Pr-2-Py], [954:4-CF3-6-Pr-2-Py], [955:5-CF3-6-Pr-2-Py], [956:3-CN-6-Pr-2-Py], [957:4-CN-6-Pr-2-Py], [958:5-CN-6-Pr-2-Py], [959:3-OMe-6-Pr-2-Py], [960:4-OMe-6-Pr-2-Py], [961:5-OMe-6-Pr-2-Py], [962:3-OPr-2-Py], [963:4-Cl-3-OPr-2-Py], [964:5-Cl-3-OPr-2-Py], [965:6-Cl-3-OPr-2-Py], [966:4-Me-3-OPr-2-Py], [967:5-Me-3-OPr-2-Py], [968:6-Me-3-OPr-2-Py], [969:4-CF3-3-OPr-2-Py], [970:5-CF3-3-OPr-2-Py], [971:6-CF3-3-OPr-2-Py], [972:4-CN-3-OPr-2-Py], [973:5-CN-3-OPr-2-Py], [974:6-CN-3-OPr-2-Py], [975:4-OMe-3-OPr-2-Py], [976:5-OMe-3-OPr-2-Py], [977:6-OMe-3-OPr-2-Py], [978:4-OPr-2-Py], [979:3-Cl-4-OPr-2-Py], [980:5-Cl-4-OPr-2-Py], [981:6-Cl-4-OPr-2-Py], [982:3-Me-4-OPr-2-Py], [983:5-Me-4-OPr-2-Py], [984:6-Me-4-OPr-2-Py], [985:3-CF3-4-OPr-2-Py], [986:5-CF3-4-OPr-2-Py], [987:6-CF3-4-OPr-2-Py], [988:3-CN-4-OPr-2-Py], [989:5-CN-4-OPr-2-Py], [990:6-CN-4-OPr-2-Py], [991:3-OMe-4-OPr-2-Py], [992:5-OMe-4-OPr-2-Py], [993:6-OMe-4-OPr-2-Py], [994:5-OPr-2-Py], [995:3-Cl-5-OPr-2-Py], [996:4-Cl-5-OPr-2-Py], [997:6-Cl-5-OPr-2-Py], [998:3-Me-5-OPr-2-Py], [999:4-Me-5-OPr-2-Py], [1000:6-Me-5-OPr-2-Py],
[1001:3-CF3-5-OPr-2-Py], [1002:4-CF3-5-OPr-2-Py], [1003:6-CF3-5-OPr-2-Py], [1004:3-CN-5-OPr-2-Py], [1005:4-CN-5-OPr-2-Py], [1006:6-CN-5-OPr-2-Py], [1007:3-OMe-5-OPr-2-Py], [1008:4-OMe-5-OPr-2-Py], [1009:6-OMe-5-OPr-2-Py], [1010:6-OPr-2-Py], [1011:3-Cl-6-OPr-2-Py], [1012:4-Cl-6-OPr-2-Py], [1013:5-Cl-6-OPr-2-Py], [1014:3-Me-6-OPr-2-Py], [1015:4-Me-6-OPr-2-Py], [1016:5-Me-6-OPr-2-Py], [1017:3-CF3-6-OPr-2-Py], [1018:4-CF3-6-OPr-2-Py], [1019:5-CF3-6-OPr-2-Py], [1020:3-CN-6-OPr-2-Py], [1021:4-CN-6-OPr-2-Py], [1022:5-CN-6-OPr-2-Py], [1023:3-OMe-6-OPr-2-Py], [1024:4-OMe-6-OPr-2-Py], [1025:5-OMe-6-OPr-2-Py], [1026:3-SMe-2-Py], [1027:4-Cl-3-SMe-2-Py], [1028:5-Cl-3-SMe-2 Py], [1029:6-Cl-3-SMe-2-Py], [1030:4-Me-3-SMe-2-Py], [1031:5-Me-3-SMe-2-Py], [1032:6-Me-3-SMe-2-Py], [1033:4-CF3-3-SMe-2-Py], [1034:5-CF3-3-SMe-2-Py], [1035:6-CF3-3-SMe-2-Py], [1036:4-CN-3-SMe-2-Py], [1037:5-CN-3-SMe-2-Py], [1038:6-CN-3-SMe-2-Py], [1039:4-OMe-3-SMe-2-Py], [1040:5-OMe-3-SMe-2-Py], [1041:6-OMe-3-SMe-2-Py], [1042:4-SMe-2-Py], [1043:3-Cl-4-SMe-2-Py], [1044:5-Cl-4-SMe-2-Py], [1045:6-Cl-4-SMe-2-Py], [1046:3-Me-4-SMe-2-Py], [1047:5-Me-4-SMe-2-Py], [1048:6-Me-4-SMe-2-Py], [1049:3-CF3-4-SMe-2-Py], [1050:5-CF3-4-SMe-2-Py], [1051:6-CF3-4-SMe-2-Py], [1052:3-CN-4-SMe-2-Py], [1053:5-CN-4-SMe-2-Py], [1054:6-CN-4-SMe-2-Py], [1055:3-OMe-4-SMe-2-Py], [1056:5-OMe-4-SMe-2-Py], [1057:6-OMe-4-SMe-2-Py], [1058:5-SMe-2-Py], [1059:3-Cl-5-SMe-2-Py], [1060:4-Cl-5-SMe-2-Py], [1061:6-Cl-5-SMe-2-Py], [1062:3-Me-5-SMe-2-Py], [1063:4-Me-5-SMe-2-Py], [1064:6-Me-5-SMe-2-Py], [1065:3-CF3-5-SMe-2-Py], [1066:4-CF3-5-SMe-2-Py], [1067:6-CF3-5-SMe-2-Py], [1068:3-CN-5-SMe-2-Py], [1069:4-CN-5-SMe-2-Py], [1070:6-CN-5-SMe-2-Py], [1071:3-OMe-5-SMe-2-Py], [1072:4-OMe-5-SMe-2-Py], [1073:6-OMe-5-SMe-2-Py], [1074:6-SMe-2-Py], [1075:3-Cl-6-SMe-2-Py], [1076:4-Cl-6-SMe-2-Py], [1077:5-Cl-6-SMe-2-Py], [1078:3-Me-6-SMe-2-Py], [1079:4-Me-6-SMe-2-Py], [1080:5-Me-6-SMe-2-Py], [1081:3-CF3-6-SMe-2-Py], [1082:4-CF3-6-SMe-2-Py], [1083:5-CF3-6-SMe-2-Py], [1084:3-CN-6-SMe-2-Py], [1085:4-CN-6-SMe-2-Py], [1086:5-CN-6-SMe-2-Py], [1087:3-OMe-6-SMe-2-Py], [1088:4-OMe-6-SMe-2-Py], [1089:5-OMe-6-SMe-2-Py], [1090:3-SCF3-2-Py], [1091:4-Cl-3-SCF3-2-Py], [1092:5-Cl-3-SCF3-2-Py], [1093:6-Cl-3-SCF3-2-Py], [1094:4-Me-3-SCF3-2-Py], [1095:5-Me-3-SCF3-2-Py], [1096:6-Me-3-SCF3-2-Py], [1097:4-CF3-3-SCF3-2-Py], [1098:5-CF3-3-SCF3-2-Py], [1099:6-CF3-3-SCF3-2-Py], [1100:4-CN-3-SCF3-2-Py], [1101:5-CN-3-SCF3-2-Py], [1102:6-CN-3-SCF3-2-Py], [1103:4-OMe-3-SCF3-2-Py], [1104:5-OMe-3-SCF3-2-Py], [1105:6-OMe-3-SCF3-2-Py], [1106:4-SCF3-2-Py], [1107:3-Cl-4-SCF3-2-Py], [1108:5-Cl-4-SCF3-2-Py], [1109:6-Cl-4-SCF3-2-Py], [1110:3-Me-4-SCF3-2-Py], [1111:5-Me-4-SCF3-2-Py], [1112:6-Me-4-SCF3-2-Py], [1113:3-CF3-4-SCF3-2-Py], [1114:5-CF3-4-SCF3-2-Py], [1115:6-CF3-4-SCF3-2-Py], [1116:3-CN-4-SCF3-2-Py], [1117:5-CN-4-SCF3-2-Py], [1118:6-CN-4-SCF3-2-Py], [1119:3-OMe-4-SCF3-2-Py], [1120:5-OMe-4-SCF3-2-Py], [1121:6-OMe-4-SCF3-2-Py], [1122:5-SCF3-2-Py], [1123:3-Cl-5-SCF3-2-Py], [1124:4-Cl-5-SCF3-2-Py], [1125:6-Cl-5-SCF3-2-Py], [1126:3-Me-5-SCF3-2-Py], [1127:4-Me-5-SCF3-2-Py], [1128:6-Me-5-SCF3-2-Py], [1129:3-CF3-5-SCF3-2-Py], [1130:4-CF3-5-SCF3-2-Py], [1131:6-CF3-5-SCF3-2-Py], [1132:3-CN-5-SCF3-2-Py], [1133:4-CN-5-SCF3-2-Py], [1134:6-CN-5-SCF3-2-Py], [1135:3-OMe-5-SCF3-2-Py], [1136:4-OMe-5-SCF3-2-Py], [1137:6-OMe-5-SCF3-2-Py], [1138:6-SCF3-2-Py], [1139:3-Cl-6-SCF3-2-Py], [1140:4-Cl-6-SCF3-2-Py], [1141:6-Cl-6-SCF3-2-Py], [1142:3-Me-6-SCF3-2-Py], [1143:4-Me-6-SCF3-2-Py], [1144:6-Me-6-SCF3-2-Py], [1145:3-CF3-6-SCF3-2-Py], [1146:4-CF3-6-SCF3-2-Py], [1147:6-CF3-6-SCF3-2-Py], [1148:3-CN-6-

SCF3-2-Py], [1149:4-CN-6-SCF3-2-Py], [1150:6-CN-6-SCF3-2-Py], [1151:3-OMe-6-SCF3-2-Py], [1152:4-OMe-6-SCF3-2-Py], [1153:6-OMe-6-SCF3-2-Py], [1154:3-S(O)Me-2-Py], [1155:4-Cl-3-S(O)Me-2-Py], [1156:5-Cl-3-S(O)Me-2-Py], [1157:6-Cl-3-S(O)Me-2-Py], [1158:4-Me-3-S(O)Me-2-Py], [1159:5-Me-3-S(O)Me-2-Py], [1160:6-Me-3-S(O)Me-2-Py], [1161:4-CF3-3-S(O)Me-2-Py], [1162:5-CF3-3-S(O)Me-2-Py], [1163:6-CF3-3-S(O)Me-2-Py], [1164:4-CN-3-S(O)Me-2-Py], [1165:5-CN-3-S(O)Me-2-Py], [1166:6-CN-3-S(O)Me-2-Py], [1167:4-OMe-3-S(O)Me-2-Py], [1168:5-OMe-3-S(O)Me-2-Py], [1169:6-OMe-3-S(O)Me-2-Py], [1170:4-S(O)Me-2-Py], [1171:3-Cl-4-S(O)Me-2-Py], [1172:5-Cl-4-S(O)Me-2-Py], [1173:6-Cl-4-S(O)Me-2-Py], [1174:3-Me-4-S(O)Me-2-Py], [1175:5-Me-4-S(O)Me-2-Py], [1176:6-Me-4-S(O)Me-2-Py], [1177:3-CF3-4-S(O)Me-2-Py], [1178:5-CF3-4-S(O)Me-2-Py], [1179:6-CF3-4-S(O)Me-2-Py], [1180:3-CN-4-S(O)Me-2-Py], [1181:5-CN-4-S(O)Me-2-Py], [1182:6-CN-4-S(O)Me-2-Py], [1183:3-OMe-4-S(O)Me-2-Py], [1184:5-OMe-4-S(O)Me-2-Py], [1185:6-OMe-4-S(O)Me-2-Py], [1186:5-S(O)Me-2-Py], [1187:3-Cl-5-S(O)Me-2-Py], [1188:4-Cl-5-S(O)Me-2-Py], [1189:6-Cl-5-S(O)Me-2-Py], [1190:3-Me-5-S(O)Me-2-Py], [1191:4-Me-5-S(O)Me-2-Py], [1192:6-Me-5-S(O)Me-2-Py], [1193:3-CF3-5-S(O)Me-2-Py], [1194:4-CF3-5-S(O)Me-2-Py], [1195:6-CF3-5-S(O)Me-2-Py], [1196:3-CN-5-S(O)Me-2-Py], [1197:4-CN-5-S(O)Me-2-Py], [1198:6-CN-5-S(O)Me-2-Py], [1199:3-OMe-5-S(O)Me-2-Py], [1200:4-OMe-5-S(O)Me-2-Py],

[1201:6-OMe-5-S(O)Me-2-Py], [1202:6-S(O)Me-2-Py], [1203:3-Cl-6-S(O)Me-2-Py], [1204:4-Cl-6-S(O)Me-2-Py], [1205:5-Cl-6-S(O)Me-2-Py], [1206:3-Me-6-S(O)Me-2-Py], [1207:4-Me-6-S(O)Me-2-Py], [1208:5-Me-6-S(O)Me-2-Py], [1209:3-CF3-6-S(O)Me-2-Py], [1210:4-CF3-6-S(O)Me-2-Py], [1211:5-CF3-6-S(O)Me-2-Py], [1212:3-CN-6-S(O)Me-2-Py], [1213:4-CN-6-S(O)Me-2-Py], [1214:5-CN-6-S(O)Me-2-Py], [1215:3-OMe-6-S(O)Me-2-Py], [1216:4-OMe-6-S(O)Me-2-Py], [1217:5-OMe-6-S(O)Me-2-Py], [1218:3-S(O)CF3-2-Py], [1219:4-Cl-3-S(O)CF3-2-Py], [1220:5-Cl-3-S(O)CF3-2-Py], [1221:6-Cl-3-S(O)CF3-2-Py], [1222:4-Me-3-S(O)CF3-2-Py], [1223:5-Me-3-S(O)CF3-2-Py], [1224:6-Me-3-S(O)CF3-2-Py], [1225:4-CF3-3-S(O)CF3-2-Py], [1226:5-CF3-3-S(O)CF3-2-Py], [1227:6-CF3-3-S(O)CF3-2-Py], [1228:4-CN-3-S(O)CF3-2-Py], [1229:5-CN-3-S(O)CF3-2-Py], [1230:6-CN-3-S(O)CF3-2-Py], [1231:4-OMe-3-S(O)CF3-2-Py], [1232:5-OMe-3-S(O)CF3-2-Py], [1233:6-OMe-3-S(O)CF3-2-Py], [1234:4-S(O)CF3-2-Py], [1235:3-Cl-4-S(O)CF3-2-Py], [1236:5-Cl-4-S(O)CF3-2-Py], [1237:6-Cl-4-S(O)CF3-2-Py], [1238:3-Me-4-S(O)CF3-2-Py], [1239:5-Me-4-S(O)CF3-2-Py], [1240:6-Me-4-S(O)CF3-2-Py], [1241:3-CF3-4-S(O)CF3-2-Py], [1242:5-CF3-4-S(O)CF3-2-Py], [1243:6-CF3-4-S(O)CF3-2-Py], [1244:3-CN-4-S(O)CF3-2-Py], [1245:5-CN-4-S(O)CF3-2-Py], [1246:6-CN-4-S(O)CF3-2-Py], [1247:3-OMe-4-S(O)CF3-2-Py], [1248:5-OMe-4-S(O)CF3-2-Py], [1249:6-OMe-4-S(O)CF3-2-Py], [1250:5-S(O)CF3-2-Py], [1251:3-Cl-5-S(O)CF3-2-Py], [1252:4-Cl-5-S(O)CF3-2-Py], [1253:6-Cl-5-S(O)CF3-2-Py], [1254:3-Me-5-S(O)CF3-2-Py], [1255:4-Me-5-S(O)CF3-2-Py], [1256:6-Me-5-S(O)CF3-2-Py], [1257:3-CF3-5-S(O)CF3-2-Py], [1258:4-CF3-5-S(O)CF3-2-Py], [1259:6-CF3-5-S(O)CF3-2-Py], [1260:3-CN-5-S(O)CF3-2-Py], [1261:4-CN-5-S(O)CF3-2-Py], [1262:6-CN-5-S(O)CF3-2-Py], [1263:3-OMe-5-S(O)CF3-2-Py], [1264:4-OMe-5-S(O)CF3-2-Py], [1265:6-OMe-5-S(O)CF3-2-Py], [1266:6-S(O)CF3-2-Py], [1267:3-Cl-6-S(O)CF3-2-Py], [1268:4-Cl-6-S(O)CF3-2-Py], [1269:5-Cl-6-S(O)CF3-2-Py], [1270:3-Me-6-S(O)CF3-2-Py], [1271:4-Me-6-S(O)CF3-2-Py], [1272:5-Me-6-S(O)CF3-2-Py], [1273:3-CF3-6-S(O)CF3-2-Py], [1274:4-CF3-6-S(O)CF3-2-Py], [1275:5-CF3-6-S(O)CF3-2-Py], [1276:3-CN-6-S(O)CF3-2-Py], [1277:4-CN-6-S(O)CF3-2-Py], [1278:5-CN-6-S(O)CF3-2-Py], [1279:3-OMe-6-S(O)CF3-2-Py], [1280:4-OMe-6-S(O)CF3-2-Py], [1281:5-OMe-6-S(O)CF3-2-Py], [1282:3-S(O)2Me-2-Py], [1283:4-Cl-3-S(O)2Me-2-Py], [1284:5-Cl-3-S(O)2Me-2-Py], [1285:6-Cl-3-S(O)2Me-2-Py], [1286:4-Me-3-S(O)2Me-2-Py], [1287:5-Me-3-S(O)2Me-2-Py], [1288:6-Me-3-S(O)2Me-2-Py], [1289:4-CF3-3-S(O)2Me-2-Py], [1290:5-CF3-3-S(O)2Me-2-Py], [1291:6-CF3-3-S(O)2Me-2-Py], [1292:4-CN-3-S(O)2Me-2-Py], [1293:5-CN-3-S(O)2Me-2-Py], [1294:6-CN-3-S(O)2Me-2-Py], [1295:4-OMe-3-S(O)2Me-2-Py], [1296:5-OMe-3-S(O)2Me-2-Py], [1297:6-OMe-3-S(O)2Me-2-Py], [1298:4-S(O)2Me-2-Py], [1299:3-Cl-4-S(O)2Me-2-Py], [1300:5-Cl-4-S(O)2Me-2-Py],

[1301:6-Cl-4-S(O)2Me-2-Py], [1302:3-Me-4-S(O)2Me-2-Py], [1303:5-Me-4-S(O)2Me-2-Py], [1304:6-Me-4-S(O)2Me-2-Py], [1305:3-CF3-4-S(O)2Me-2-Py], [1306:5-CF3-4-S(O)2Me-2-Py], [1307:6-CF3-4-S(O)2Me-2-Py], [1308:3-CN-4-S(O)2Me-2-Py], [1309:5-CN-4-S(O)2Me-2-Py], [1310:6-CN-4-S(O)2Me-2-Py], [1311:3-OMe-4-S(O)2Me-2-Py], [1312:5-OMe-4-S(O)2Me-2-Py], [1313:6-OMe-4-S(O)2Me-2-Py], [1314:5-S(O)2Me-2-Py], [1315:3-Cl-5-S(O)2Me-2-Py], [1316:4-Cl-5-S(O)2Me-2-Py], [1317:6-Cl-5-S(O)2Me-2-Py], [1318:3-Me-5-S(O)2Me-2-Py], [1319:4-Me-5-S(O)2Me-2-Py], [1320:6-Me-5-S(O)2Me-2-Py], [1321:3-CF3-5-S(O)2Me-2-Py], [1322:4-CF3-5-S(O)2Me-2-Py], [1323:6-CF3-5-S(O)2Me-2-Py], [1324:3-CN-5-S(O)2Me-2-Py], [1325:4-CN-5-S(O)2Me-2-Py], [1326:6-CN-5-S(O)2Me-2-Py], [1327:3-OMe-5-S(O)2Me-2-Py], [1328:4-OMe-5-S(O)2Me-2-Py], [1329:6-OMe-5-S(O)2Me-2-Py], [1330:6-S(O)2Me-2-Py], [1331:3-Cl-6-S(O)2Me-2-Py], [1332:4-Cl-6-S(O)2Me-2-Py], [1333:5-Cl-6-S(O)2Me-2-Py], [1334:3-Me-6-S(O)2Me-2-Py], [1335:4-Me-6-S(O)2Me-2-Py], [1336:5-Me-6-S(O)2Me-2-Py], [1337:3-CF3-6-S(O)2Me-2-Py], [1338:4-CF3-6-S(O)2Me-2-Py], [1339:5-CF3-6-S(O)2Me-2-Py], [1340:3-CN-6-S(O)2Me-2-Py], [1341:4-CN-6-S(O)2Me-2-Py], [1342:5-CN-6-S(O)2Me-2-Py], [1343:3-OMe-6-S(O)2Me-2-Py], [1344:4-OMe-6-S(O)2Me-2-Py], [1345:5-OMe-6-S(O)2Me-2-Py], [1346:3-S(O)2CF3-2-Py], [1347:4-Cl-3-S(O)2CF3-2-Py], [1348:5-Cl-3-S(O)2CF3-2-Py], [1349:6-Cl-3-S(O)2CF3-2-Py], [1350:4-Me-3-S(O)2CF3-2-Py], [1351:5-Me-3-S(O)2CF3-2-Py], [1352:6-Me-3-S(O)2CF3-2-Py], [1353:4-CF3-3-S(O)2CF3-2-Py], [1354:5-CF3-3-S(O)2CF3-2-Py], [1355:6-CF3-3-S(O)2CF3-2-Py], [1356:4-CN-3-S(O)2CF3-2-Py], [1357:5-CN-3-S(O)2CF3-2-Py], [1358:6-CN-3-S(O)2CF3-2-Py], [1359:4-OMe-3-S(O)2CF3-2-Py], [1360:5-OMe-3-S(O)2CF3-2-Py], [1361:6-OMe-3-S(O)2CF3-2-Py], [1362:4-S(O)2CF3-2-Py], [1363:3-Cl-4-S(O)2CF3-2-Py], [1364:5-Cl-4-S(O)2CF3-2-Py], [1365:6-Cl-4-S(O)2CF3-2-Py], [1366:3-Me-4-S(O)2CF3-2-Py], [1367:5-Me-4-S(O)2CF3-2-Py], [1368:6-Me-4-S(O)2CF3-2-Py], [1369:3-CF3-4-S(O)2CF3-2-Py], [1370:5-CF3-4-S(O)2CF3-2-Py], [1371:6-CF3-4-S(O)2CF3-2-Py], [1372:3-CN-4-S(O)2CF3-2-Py], [1373:5-CN-4-S(O)2CF3-2-Py], [1374:6-CN-4-S(O)2CF3-2-Py], [1375:3-OMe-4-S(O)2CF3-2-Py], [1376:5-OMe-4-S(O)2CF3-2-Py], [1377:6-OMe-4-S(O)2CF3-2-Py], [1378:5-S(O)2CF3-2-Py], [1379:3-Cl-5-S(O)2CF3-2-Py], [1380:4-Cl-5-S(O)2CF3-2-Py], [1381:6-Cl-5-S(O)2CF3-2-Py], [1382:3-Me-5-S(O)2CF3-2-Py], [1383:4-Me-5-S(O)2CF3-2-Py], [1384:6-Me-5-S(O)2CF3-2-Py], [1385:3-CF3-5-S(O)2CF3-2-Py], [1386:4-CF3-5-S(O)2CF3-2-Py], [1387:6-CF3-5-S(O)2CF3-2-Py], [1388:3-CN-5-S(O)2CF3-2-Py], [1389:4-CN-5-S(O)2CF3-2-Py], [1390:6-CN-5-S(O)2CF3-2-Py], [1391:3-OMe-5-S(O)2CF3-2-Py], [1392:4-OMe-5-S (O)2CF3-2-Py], [1393:6-OMe-5-S(O)2CF3-2-Py], [1394:6-S(O)2CF3-2-Py], [1395:3-Cl-6-S(O)2CF3-2-Py], [1396:4-Cl-6-S(O)2CF3-2-Py], [1397:5-Cl-6-S(O)2CF3-2-Py], [1398:3-Me-6-S(O)2CF3-2-Py], [1399:4-Me-6-S(O)2CF3-2-Py], [1400:5-Me-6-S(O)2CF3-2-Py], [1401:3-CF3-6-S(O)2CF3-2-Py], [1402:4-CF3-6-S(O)2CF3-2-Py], [1403:5-CF3-6-S(O)2CF3-2-Py], [1404:3-CN-6-S(O)2CF3-2-Py], [1405:4-CN-6-S(O)2CF3-2-Py], [1406:5-CN-6-S(O)2CF3-2-Py], [1407:3-OMe-6-S(O)2CF3-2-Py], [1408:4-OMe-6-S(O)2CF3-2-Py], [1409:5-OMe-6-S(O)2CF3-2-Py], [1410:3-CN-2-Py], [1411:4-Cl-3-CN-2-Py], [1412:5-Cl-3-CN-2-Py], [1413:6-Cl-3-CN-2-Py], [1414:4-Me-3-CN-2-Py], [1415:5-Me-3-CN-2-Py], [1416:6-Me-3-CN-2-Py], [1417:4-CF3-3-CN-2-Py], [1418:5-CF3-3-CN-2-Py], [1419:6-CF3-3-CN-2-Py], [1420:4-CN-3-CN-2-Py], [1421:5-CN-3-CN-2-Py], [1422:6-CN-3-CN-2-Py], [1423:4-OMe-3-CN-2-Py], [1424:5-OMe-3-CN-2-Py], [1425:6-OMe-3-CN-2-Py], [1426:4-CN-2-Py], [1427:3-Cl-4-CN-2-Py], [1428:5-Cl-4-CN-2-Py], [1429:6-Cl-4-CN-2-Py], [1430:3-Me-4-CN-2-Py], [1431:5-Me-4-CN-2-Py], [1432:6-Me-4-CN-2-Py], [1433:3-CF3-4-CN-2-Py], [1434:5-CF3-4-CN-2-Py], [1435:6-CF3-4-CN-2-Py], [1436:3-CN-4-CN-2-Py], [1437:5-CN-4-CN-2-Py], [1438:6-CN-4-CN-2-Py], [1439:3-OMe-4-CN-2-Py], [1440:5-OMe-4-CN-2-Py], [1441:6-OMe-4-CN-2-Py], [1442:5-CN-2-Py], [1443:3-Cl-5-CN-2-Py], [1444:4-Cl-5-CN-2-Py], [1445:6-Cl-5-CN-2-Py], [1446:3-Me-5-CN-2-Py], [1447:4-Me-5-CN-2-Py], [1448:6-Me-5-CN-2-Py], [1449:3-CF3-5-CN-2-Py], [1450:4-CF3-5-CN-2-Py], [1451:6-CF3-5-CN-2-Py], [1452:3-CN-5-CN-2-Py], [1453:4-CN-5-CN-2-Py], [1454:6-CN-5-CN-2-Py], [1455:3-OMe-5-CN-2-Py], [1456:4-OMe-5-CN-2-Py], [1457:6-OMe-5-CN-2-Py], [1458:6-CN-2-Py], [1459:3-Cl-6-CN-2-Py], [1460:4-Cl-6-CN-2-Py], [1461:5-Cl-6-CN-2-Py], [1462:3-Me-6-CN-2-Py], [1463:4-Me-6-CN-2-Py], [1464:5-Me-6-CN-2-Py], [1465:3-CF3-6-CN-2-Py], [1466:4-CF3-6-CN-2-Py], [1467:5-CF3-6-CN-2-Py], [1468:3-CN-6-CN-2-Py], [1469:4-CN-6-CN-2-Py], [1470:5-CN-6-CN-2-Py], [1471:3-OMe-6-CN-2-Py], [1472:4-OMe-6-CN-2-Py], [1473:5-OMe-6-CN-2-Py], [1474:3-COOMe-2-Py], [1475:4-Cl-3-COOMe-2-Py], [1476:5-Cl-3-COOMe-2-Py], [1477:6-Cl-3-COOMe-2-Py], [1478:4-Me-3-COOMe-2-Py], [1479:5-Me-3-COOMe-2-Py], [1480:6-Me-3-COOMe-2-Py], [1481:4-CF3-3-COOMe-2-Py], [1482:5-CF3-3-COOMe-2-Py], [1483:6-CF3-3-COOMe-2-Py], [1484:4-CN-3-COOMe-2-Py], [1485:5-CN-3-COOMe-2-Py], [1486:6-CN-3-COOMe-2-Py], [1487:4-OMe-3-COOMe-2-Py], [1488:5-OMe-3-COOMe-2-Py], [1489:6-OMe-3-COOMe-2-Py], [1490:4-COOMe-2-Py], [1491:3-Cl-4-COOMe-2-Py], [1492:5-Cl-4-COOMe-2-Py], [1493:6-Cl-4-COOMe-2-Py], [1494:3-Me-4-COOMe-2-Py], [1495:5-Me-4-COOMe-2-Py], [1496:6-Me-4-COOMe-2-Py], [1497:3-CF3-4-COOMe-2-Py], [1498:5-CF3-4-COOMe-2-Py], [1499:6-CF3-4-COOMe-2-Py], [1500:3-CN-4-COOMe-2-Py], [1501:5-CN-4-COOMe-2-Py], [1502:6-CN-4-COOMe-2-Py], [1503:3-OMe-4-COOMe-2-Py], [1504:5-OMe-4-COOMe-2-Py], [1505:6-OMe-4-COOMe-2-Py], [1506:5-COOMe-2-Py], [1507:3-Cl-5-COOMe-2-Py], [1508:4-Cl-5-COOMe-2-Py], [1509:6-Cl-5-COOMe-2-Py], [1510:3-Me-5-COOMe-2-Py], [1511:4-Me-5-COOMe-2-Py], [1512:6-Me-5-COOMe-2-Py], [1513:3-CF3-5-COOMe-2-Py], [1514:4-CF3-5-COOMe-2-Py], [1515:6-CF3-5-COOMe-2-Py], [1516:3-CN-5-COOMe-2-Py], [1517:4-CN-5-COOMe-2-Py], [1518:6-CN-5-COOMe-2-Py], [1519:3-OMe-5-COOMe-2-Py], [1520:4-OMe-5-COOMe-2-Py], [1521:6-OMe-5-COOMe-2-Py], [1522:6-COOMe-2-Py], [1523:3-Cl-6-COOMe-2-Py], [1524:4-Cl-6-COOMe-2-Py], [1525:5-Cl-6-COOMe-2-Py], [1526:3-Me-6-COOMe-2-Py], [1527:4-Me-6-COOMe-2-Py], [1528:5-Me-6-COOMe-2-Py], [1529:3-CF3-6-COOMe-2-Py], [1530:4-CF3-6-COOMe-2-Py], [1531:5-CF3-6-COOMe-2-Py], [1532:3-CN-6-COOMe-2-Py], [1533:4-CN-6-COOMe-2-Py], [1534:5-CN-6-COOMe-2-Py], [1535:3-OMe-6-COOMe-2-Py], [1536:4-OMe-6-COOMe-2-Py], [1537:5-OMe-6-COOMe-2-Py], [1538:3-NO2-2-Py], [1539:4-Cl-3-NO2-2-Py], [1540:5-Cl-3-NO2-2-Py], [1541:6-Cl-3-NO2-2-Py], [1542:4-Me-3-NO2-2-Py], [1543:5-Me-3-NO2-2-Py], [1544:6-Me-3-NO2-2-Py], [1545:4-CF3-3-NO2-2-Py], [1546:5-CF3-3-NO2-2-Py], [1547:6-CF3-3-NO2-2-Py], [1548:4-CN-3-NO2-2-Py], [1549:5-CN-3-NO2-2-Py], [1550:6-CN-3-NO2-2-Py], [1551:4-OMe-3-NO2-2-Py], [1552:5-OMe-3-NO2-2-Py], [1553:6-OMe-3-NO2-2-Py], [1554:4-NO2-2-Py], [1555:3-Cl-4-NO2-2-Py], [1556:5-Cl-4-NO2-2-Py], [1557:6-Cl-4-NO2-2-Py], [1558:3-Me-4-NO2-2-Py], [1559:5-Me-4-NO2-2-Py], [1560:6-Me-4-NO2-2-Py], [1561:3-CF3-4-NO2-2-Py], [1562:5-CF3-4-NO2-2-Py], [1563:6-CF3-4-NO2-2-Py], [1564:3-CN-4-NO2-2-Py], [1565:5-CN-4-NO2-2-Py], [1566:6-CN-4-NO2-2-Py], [1567:3-OMe-4-NO2-2-Py], [1568:5-OMe-4-NO2-2-Py], [1569:6-OMe-4-NO2-2-Py], [1570:5-NO2-2-Py], [1571:3-Cl-5-NO2-2-Py], [1572:4-Cl-5-NO2-2-Py], [1573:6-Cl-5-NO2-2-Py], [1574:3-Me-5-NO2-2-Py], [1575:4-Me-5-NO2-2-Py], [1576:6-Me-5-NO2-2-Py], [1577:3-CF3-5-NO2-2-Py], [1578:4-CF3-5-NO2-2-Py], [1579:6-CF3-5-NO2-2-Py], [1580:3-CN-5-NO2-2-Py], [1581:4-CN-5-NO2-2-Py], [1582:6-CN-5-NO2-2-Py], [1583:3-OMe-5-NO2-2-Py], [1584:4-OMe-5-NO2-2-Py], [1585:6-OMe-5-NO2-2-Py], [1586:6-NO2-2-Py], [1587:3-Cl-6-NO2-2-Py], [1588:4-Cl-6-NO2-2-Py], [1589:5-Cl-6-NO2-2-Py], [1590:3-Me-6-NO2-2-Py], [1591:4-Me-6-NO2-2-Py], [1592:5-Me-6-NO2-2-Py], [1593:3-CF3-6-NO2-2-Py], [1594:4-CF3-6-NO2-2-Py], [1595:5-CF3-6-NO2-2-Py], [1596:3-CN-6-NO2-2-Py], [1597:4-CN-6-NO2-2-Py], [1598:5-CN-6-NO2-2-Py], [1599:3-OMe-6-NO2-2-Py], [1600:4-OMe-6-NO2-2-Py], [1601:5-OMe-6-NO2-2-Py], [1602:3-NH2-2-Py], [1603:4-Cl-3-NH2-2-Py], [1604:5-Cl-3-NH2-2-Py], [1605:6-Cl-3-NH2-2-Py], [1606:4-Me-3-NH2-2-Py], [1607:5-Me-3-NH2-2-Py], [1608:6-Me-3-NH2-2-Py], [1609:4-CF3-3-NH2-2-Py], [1610:5-CF3-3-NH2-2-Py], [1611:6-CF3-3-NH2-2-Py], [1612:4-CN-3-NH2-2-Py], [1613:5-CN-3-NH2-2-Py], [1614:6-CN-3-NH2-2-Py], [1615:4-OMe-3-NH2-2-Py], [1616:5-OMe-3-NH2-2-Py], [1617:6-OMe-3-NH2-2-Py], [1618:4-NH2-2-Py], [1619:3-Cl-4-NH2-2-Py], [1620:5-Cl-4-NH2-2-Py], [1621:6-Cl-4-NH2-2-Py], [1622:3-Me-4-NH2-2-Py], [1623:5-Me-4-NH2-2-Py], [1624:6-Me-4-NH2-2-Py], [1625:3-CF3-4-NH2-2-Py], [1626:5-CF3-4-NH2-2-Py], [1627:6-CF3-4-NH2-2-Py], [1628:3-CN-4-NH2-2-Py], [1629:5-CN-4-NH2-2-Py], [1630:6-CN-4-NH2-2-Py], [1631:3-OMe-4-NH2-2-Py], [1632:5-OMe-4-NH2-2-Py], [1633:6-OMe-4-NH2-2-Py], [1634:5-NH2-2-Py], [1635:3-Cl-5-NH2-2-Py], [1636:4-Cl-5-NH2-2-Py], [1637:6-Cl-5-NH2-2-Py], [1638:3-Me-5-NH2-2-Py], [1639:4-Me-5-NH2-2-Py], [1640:6-Me-5-NH2-2-Py], [1641:3-CF3-5-NH2-2-Py], [1642:4-CF3-5-NH2-2-Py], [1643:6-CF3-5-NH2-2-Py], [1644:3-CN-5-NH2-2-Py], [1645:4-CN-5-NH2-2-Py], [1646:6-CN-5-NH2-2-Py], [1647:3-OMe-5-NH2-2-Py], [1648:4-OMe-5-NH2-2-Py], [1649:6-OMe-5-NH2-2-Py], [1650:6-NH2-2-Py], [1651:3-Cl-6-NH2-2-Py], [1652:4-Cl-6-NH2-2-Py], [1653:5-Cl-6-NH2-2-Py], [1654:3-Me-6-NH2-2-Py], [1655:4-Me-6-NH2-2-Py], [1656:5-Me-6-NH2-2-Py], [1657:3-CF3-6-NH2-2-Py], [1658:4-CF3-6-NH2-2-Py], [1659:5-CF3-6-NH2-2-Py], [1660:3-CN-6-NH2-2-Py], [1661:4-CN-6-NH2-2-Py], [1662:5-CN-

6-NH2-2-Py], [1663:3-OMe-6-NH2-2-Py], [1664:4-OMe-6-NH2-2-Py], [1665:5-OMe-6-NH2-2-Py], [1666:3-NHMe-2-Py], [1667:4-Cl-3-NHMe-2-Py], [1668:5-Cl-3-NHMe-2-Py], [1669:6-Cl-3-NHMe-2-Py], [1670:4-Me-3-NHMe-2-Py], [1671:5-Me-3-NHMe-2-Py], [1672:6-Me-3-NHMe-2-Py], [1673:4-CF3-3-NHMe-2-Py], [1674:5-CF3-3-NHMe-2-Py], [1675:6-CF3-3-NHMe-2-Py], [1676:4-CN-3-NHMe-2-Py], [1677:5-CN-3-NHMe-2-Py], [1678:6-CN-3-NHMe-2-Py], [1679:4-OMe-3-NHMe-2-Py], [1680:5-OMe-3-NHMe-2-Py], [1681:6-OMe-3-NHMe-2-Py], [1682:4-NHMe-2-Py], [1683:3-Cl-4-NHMe-2-Py], [1684:5-Cl-4-NHMe-2-Py], [1685:6-Cl-4-NHMe-2-Py], [1686:3-Me-4-NHMe-2-Py], [1687:5-Me-4-NHMe-2-Py], [1688:6-Me-4-NHMe-2-Py], [1689:3-CF3-4-NHMe-2-Py], [1690:5-CF3-4-NHMe-2-Py], [1691:6-CF3-4-NHMe-2-Py], [1692:3-CN-4-NHMe-2-Py], [1693:5-CN-4-NHMe-2-Py], [1694:6-CN-4-NHMe-2-Py], [1695:3-OMe-4-NHMe-2-Py], [1696:5-OMe-4-NHMe-2-Py], [1697:6-OMe-4-NHMe-2-Py], [1698:5-NHMe-2-Py], [1699:3-Cl-5-NHMe-2-Py], [1700:4-Cl-5-NHMe-2-Py],

[1701:6-Cl-5-NHMe-2-Py], [1702:3-Me-5-NHMe-2-Py], [1703:4-Me-5-NHMe-2-Py], [1704:6-Me-5-NHMe-2-Py], [1705:3-CF3-5-NHMe-2-Py], [1706:4-CF3-5-NHMe-2-Py], [1707:6-CF3-5-NHMe-2-Py], [1708:3-CN-5-NHMe-2-Py], [1709:4-CN-5-NHMe-2-Py], [1710:6-CN-5-NHMe-2-Py], [1711:3-OMe-5-NHMe-2-Py], [1712:4-OMe-5-NHMe-2-Py], [1713:6-OMe-5-NHMe-2-Py], [1714:6-NHMe-2-Py], [1715:3-Cl-6-NHMe-2-Py], [1716:4-Cl-6-NHMe-2-Py], [1717:5-Cl-6-NHMe-2-Py], [1718:3-Me-6-NHMe-2-Py], [1719:4-Me-6-NHMe-2-PIy], [1720:5-Me-6-NHMe-2-Py], [1721:3-CF3-6-NHMe-2-Py], [1722:4-CF3-6-NHMe-2-Py], [1723:5-CF3-6-NHMe-2-Py], [1724:3-CN-6-NHMe-2-Py], [1725:4-CN-6-NHMe-2-Py], [1726:5-CN-6-NHMe-2-Py], [1727:3-OMe-6-NHMe-2-Py], [1728:4-OMe-6-NHMe-2-Py], [1729:5-OMe-6-NHMe-2-Py], [1730:3-NMe2-2-Py], [1731:4-Cl-3-NMe2-2-Py], [1732:5-Cl-3-NMe2-2-Py], [1733:6-Cl-3-NMe2-2-Py], [1734:4-Me-3-NMe2-2-Py], [1735:5-Me-3-NMe2-2-Py], [1736:6-Me-3-NMe2-2-Py], [1737:4-CF3-3-NMe2-2-Py], [1738:5-CF3-3-NMe2-2-Py], [1739:6-CF3-3-NMe2-2-Py], [1740:4-CN-3-NMe2-2-Py], [1741:5-CN-3-NMe2-2-Py], [1742:6-CN-3-NMe2-2-Py], [1743:4-OMe-3-NMe2-2-Py], [1744:5-OMe-3-NMe2-2-Py], [1745:6-OMe-3-NMe2-2-Py], [1746:4-NMe2-2-Py], [1747:3-Cl-4-NMe2-2-Py], [1748:5-Cl-4-NMe2-2-Py], [1749:6-Cl-4-NMe2-2-Py], [1750:3-Me-4-NMe2-2-Py], [1751:5-Me-4-NMe2-2-Py], [1752:6-Me-4-NMe2-2-Py], [1753:3-CF3-4-NMe2-2-Py], [1754:5-CF3-4-NMe2-2-Py], [1755:6-CF3-4-NMe2-2-Py], [1756:3-CN-4-NMe2-2-Py], [1757:5-CN-4-NMe2-2-Py], [1758:6-CN-4-NMe2-2-Py], [1759:3-OMe-4-NMe2-2-Py], [1760:5-OMe-4-NMe2-2-Py], [1761:6-OMe-4-NMe2-2-Py], [1762:5-NMe2-2-Py], [1763:3-Cl-5-NMe2-2-Py], [1764:4-Cl-5-NMe2-2-Py], [1765:6-Cl-5-NMe2-2-Py], [1766:3-Me-5-NMe2-2-Py], [1767:4-Me-5-NMe2-2-Py], [1768:6-Me-5-NMe2-2-Py], [1769:3-CF3-5-NMe2-2-Py], [1770:4-CF3-5-NMe2-2-Py], [1771:6-CF3-5-NMe2-2-Py], [1772:3-CN-5-NMe2-2-Py], [1773:4-CN-5-NMe2-2-Py], [1774:6-CN-5-NMe2-2-Py], [1775:3-OMe-5-NMe2-2-Py], [1776:4-OMe-5-NMe2-2-Py], [1777:6-OMe-5-NMe2-2-Py], [1778:6-NMe2-2-Py], [1779:3-Cl-6-NMe2-2-Py], [1780:4-Cl-6-NMe2-2-Py], [1781:5-Cl-6-NMe2-2-Py], [1782:3-Me-6-NMe2-2-Py], [1783:4-Me-6-NMe2-2-Py], [1784:5-Me-6-NMe2-2-Py], [1785:3-CF3-6-NMe2-2-Py], [1786:4-CF3-6-NMe2-2-Py], [1787:5-CF3-6-NMe2-2-Py], [1788:3-CN-6-NMe2-2-Py], [1789:4-CN-6-NMe2-2-Py], [1790:5-CN-6-NMe2-2-Py], [1791:3-OMe-6-NMe2-2-Py], [1792:4-OMe-6-NMe2-2-Py], [1793:5-OMe-6-NMe2-2-Py], [1794:3-ACNH-2-Py], [1795:4-Cl-3-ACNH-2-Py], [1796:5-Cl-3-ACNH-2-Py], [1797:6-Cl-3-ACNH-2-Py], [1798:4-Me-3-ACNH-2-Py], [1799:5-Me-3-ACNH-2-Py], [1800:6-Me-3-ACNH-2-Py],
[1801:4-CF3-3-ACNH-2-Py], [1802:5-CF3-3-ACNH-2-Py], [1803:6-CF3-3-ACNH-2-Py], [1804:4-CN-3-ACNH-2-Py], [1805:5-CN-3-ACNH-2-Py], [1806:6-CN-3-ACNH-2-Py], [1807:4-OMe-3-ACNH-2-Py], [1808:5-OMe-3-ACNH-2-Py], [1809:6-OMe-3-ACNH-2-Py], [1810:4-ACNH-2-Py], [1811:3-Cl-4-ACNH-2-Py], [1812:5-Cl-4-ACNH-2-Py], [1813:6-Cl-4-ACNH-2-Py], [1814:3-Me-4-ACNH-2-Py], [1815:5-Me-4-ACNH-2-Py], [1816:6-Me-4-ACNH-2-Py], [1817:3-CF3-4-ACNH-2-Py], [1818:5-CF3-4-ACNH-2-Py], [1819:6-CF3-4-ACNH-2-Py], [1820:3-CN-4-ACNH-2-Py], [1821:5-CN-4-ACNH-2-Py], [1822:6-CN-4-ACNH-2-Py], [1823:3-OMe-4-ACNH-2-Py], [1824:5-OMe-4-ACNH-2-Py], [1825:6-OMe-4-ACNH-2-Py], [1826:5-ACNH-2-Py], [1827:3-Cl-5-ACNH-2-Py], [1828:4-Cl-5-ACNH-2-Py], [1829:6-Cl-5-ACNH-2-Py], [1830:3-Me-5-ACNH-2-Py], [1831:4-Me-5-ACNH-2-Py], [1832:6-Me-5-ACNH-2-Py], [1833:3-CF3-5-ACNH-2-Py], [1834:4-CF3-5-ACNH-2-Py], [1835:6-CF3-5-ACNH-2-Py], [1836:3-CN-5-ACNH-2-Py], [1837:4-CN-5-ACNH-2-Py], [1838:6-CN-5-ACNH-2-Py], [1839:3-OMe-5-ACNH-2-Py], [1840:4-OMe-5-ACNH-2-Py], [1841:6-OMe-5-ACNH-2-Py], [1842:6-ACNH-2-Py], [1843:3-Cl-6-ACNH-2-Py], [1844:4-Cl-6-ACNH-2-Py], [1845:5-Cl-6-ACNH-2-Py], [1846:3-Me-6-ACNH-2-Py], [1847:4-Me-6-ACNH-2-Py], [1848:5-Me-6-ACNH-2-Py], [1849:3-CF3-6-ACNH-2-Py], [1850:4-CF3-6-ACNH-2-Py], [1851:5-CF3-6-ACNH-2-Py], [1852:3-CN-6-ACNH-2-Py], [1853:4-CN-6-ACNH-2-Py], [1854:5-CN-6-ACNH-2-Py], [1855:3-OMe-6-ACNH-2-Py], [1856:4-OMe-6-ACNH-2-Py], [1857:5-OMe-6-ACNH-2-Py], [858:3-(N-AC-N-Me-N)-2-Py], [1859:4-Cl-3-(N-AC-N-Me-N)-2-Py], [1860:5-Cl-3-(N-AC-N-Me-N)-2-Py], [1861:6-Cl-3-(N-AC-N-Me-N)-2-Py], [1862:4-Me-3-(N-AC-N-Me-N)-2-Py], [1863:5-Me-3-(N-AC-N-Me-N)-2-Py], [1864:6-Me-3-(N-AC-N-Me-N)-2-Py], [1865:4-CF3-3-(N-AC-N-Me-N)-2-Py], [1866:5-CF3-3-(N-AC-N-Me-N)-2-Py], [1867:6-CF3-3-(N-AC-N-Me-N)-2-Py], [1868:4-CN-3-(N-AC-N-Me-N)-2-Py], [1869:5-CN-3-(N-AC-N-Me-N)-2-Py], [1870:6-CN-3-(N-AC-N-Me-N)-2-Py], [1871:4-OMe-3-(N-AC-N-Me-N)-2-Py], [1872:5-OMe-3-(N-AC-N-Me-N)-2-Py], [1873:6-OMe-3-(N-AC-N-Me-N)-2-Py], [1874:4-(N-AC-N-Me-N)-2-Py], [1875:3-Cl-4-(N-AC-N-Me-N)-2-Py], [1876:5-Cl-4-(N-AC-N-Me-N)-2-Py], [1877:6-Cl-4-(N-AC-N-Me-N)-2-Py], [1878:3-Me-4-(N-AC-N-Me-N)-2-Py], [1879:5-Me-4-(N-AC-N-Me-N)-2-Py], [1880:6-Me-4-(N-AC-N-Me-N)-2-Py], [1881:3-CF3-4-(N-AC-N-Me-N)-2-Py], [1882:5-CF3-4-(N-AC-N-Me-N)-2-Py], [1883:6-CF3-4-(N-AC-N-Me-N)-2-Py], [1884:3-CN-4-(N-AC-N-Me-N)-2-Py], [1885:5-CN-4-(N-AC-N-Me-N)-2-Py], [1886:6-CN-4-(N-AC-N-Me-N)-2-Py], [1887:3-OMe-4-(N-AC-N-Me-N)-2-Py], [1888:5-OMe-4-(N-AC-N-Me-N)-2-Py], [1889:6-OMe-4-(N-AC-N-Me-N)-2-Py], [1890:5-(N-AC-N-Me-N)-2-Py], [1891:3-Cl-5-(N-AC-N-Me-N)-2-Py], [1892:4-Cl-5-(N-AC-N-Me-N)-2-Py], [1893:6-Cl-5-(N-AC-N-Me-N)-2-Py], [1894:3-Me-5-(N-AC-N-Me-N)-2-Py], [1895:4-Me-5-(N-AC-N-Me-N)-2-Py], [1896:6-Me-5-(N-AC-N-Me-N)-2-Py], [1897:3-CF3-5-(N-AC-N-Me-N)-2-Py], [1898:4-CF3-5-(N-AC-N-Me-N)-2-Py], [1899:6-CF3-5-(N-AC-N-Me-N)-2-Py], [1900:3-CN-5-(N-AC-N-Me-N)-2-Py],
[1901:4-CN-5-(N-AC-N-Me-N)-2-Py], [1902:6-CN-5-(N-AC-N-Me-N)-2-Py], [1903:3-OMe-5-(N-AC-N-Me-N)-2-Py], [1904:4-OMe-5-(N-AC-N-Me-N)-2-Py], [1905:6-OMe-5-(N-AC-N-Me-N)-2-Py], [1906:6-(N-AC-N-Me-N)-

2-Py], [1907:3-Cl-6-(N-AC-N-Me-N)-2-Py], [1908:4-Cl-6-(N-AC-N-Me-N)-2-Py], [1909:5-Cl-6-(N-AC-N-Me-N)-2-Py], [1910:3-Me-6-(N-AC-N-Me-N)-2-Py], [1911:4-Me-6-(N-AC-N-Me-N)-2-Py], [1912:5-Me-6-(N-AC-N-Me-N)-2-Py], [1913:3-CF3-6-(N-AC-N-Me-N)-2-Py], [1914:4-CF3-6-(N-AC-N-Me-N)-2-Py], [1915:5-CF3-6-(N-AC-N-Me-N)-2-Py], [1916:3-CN-6-(N-AC-N-Me-N)-2-Py], [1917:4-CN-6-(N-AC-N-Me-N)-2-Py], [1918:5-CN-6-(N-AC-N-Me-N)-2-Py], [1919:3-OMe-6-(N-AC-N-Me-N)-2-Py], [1920:4-OMe-6-(N-AC-N-Me-N)-2-Py], [1921:5-OMe-6-(N-AC-N-Me-N)-2-Py], [1922:3-AC-2-Py], [1923:4-Cl-3-AC-2-Py], [1924:5-Cl-3-AC-2-Py], [1925:6-Cl-3-AC-2-Py], [1926:4-Me-3-AC-2-Py], [1927:5-Me-3-AC-2-Py], [1928:6-Me-3-AC-2-Py], [1929:4-CF3-3-AC-2-Py], [1930:5-CF3-3-AC-2-Py], [1931:6-CF3-3-AC-2-Py], [1932:4-CN-3-AC-2-Py], [1933:5-CN-3-AC-2-Py], [1934:6-CN-3-AC-2-Py], [1935:4-OMe-3-AC-2-Py], [1936:5-OMe-3-AC-2-Py], [1937:6-OMe-3-AC-2-Py], [1938:4-AC-2-Py], [1939:3-Cl-4-AC-2-Py], [1940:5-Cl-4-AC-2-Py], [1941:6-Cl-4-AC-2-Py], [1942:3-Me-4-AC-2-Py], [1943:5-Me-4-AC-2-Py], [1944:6-Me-4-AC-2-Py], [1945:3-CF3-4-AC-2-Py], [1946:5-CF3-4-AC-2-Py], [1947:6-CF3-4-AC-2-Py], [1948:3-CN-4-AC-2-Py], [1949:5-CN-4-AC-2-Py], [1950:6-CN-4-AC-2-Py], [1951:3-OMe-4-AC-2-Py], [1952:5-OMe-4-AC-2-Py], [1953:6-OMe-4-AC-2-Py], [1954:5-AC-2-Py], [1955:3-Cl-5-AC-2-Py], [1956:4-Cl-5-AC-2-Py], [1957:6-Cl-5-AC-2-Py], [1958:3-Me-5-AC-2-Py], [1959:4-Me-5-AC-2-Py], [1960:6-Me-5-AC-2-Py], [1961:3-CF3-5-AC-2-Py], [1962:4-CF3-5-AC-2-Py], [1963:6-CF3-5-AC-2-Py], [1964:3-CN-5-AC-2-Py], [1965:4-CN-5-AC-2-Py], [1966:6-CN-5-AC-2-Py], [1967:3-OMe-5-AC-2-Py], [1968:4-OMe-5-AC-2-Py], [1969:6-OMe-5-AC-2-Py], [1970:6-AC-2-Py], [1971:3-Cl-6-AC-2-Py], [1972:4-Cl-6-AC-2-Py], [1973:5-Cl-6-AC-2-Py], [1974:3-Me-6-AC-2-Py], [1975:4-Me-6-AC-2-Py], [1976:5-Me-6-AC-2-Py], [1977:3-CF3-6-AC-2-Py], [1978:4-CF3-6-AC-2-Py], [1979:5-CF3-6-AC-2-Py], [1980:3-CN-6-AC-2-Py], [1981:4-CN-6-AC-2-Py], [1982:5-CN-6-AC-2-Py], [1983:3-OMe-6-AC-2-Py], [1984:4-OMe-6-AC-2-Py], [1985:5-OMe-6-AC-2-Py], [1986:3-Py], [1987:2-F-3-Py], [1988:4-Cl-2-F-3-Py], [1989:5-Cl-2-F-3-Py], [1990:6-Cl-2-F-3-Py], [1991:4-Me-2-F-3-Py], [1992:5-Me-2-F-3-Py], [1993:6-Me-2-F-3-Py], [1994:4-CF3-2-F-3-Py], [1995:5-CF3-2-F-3-Py], [1996:6-CF3-2-F-3-Py], [1997:4-CN-2-F-3-Py], [1998:5-CN-2-F-3-Py], [1999:6-CN-2-F-3-Py], [2000:4-OMe-2-F-3-Py], [2001:5-OMe-2-F-3-Py], [2002:6-OMe-2-F-3-Py], [2003:4-F-3-Py], [2004:2-Cl-4-F-3-Py], [2005:5-Cl-4-F-3-Py], [2006:6-Cl-4-F-3-Py], [2007:2-Me-4-F-3-Py], [2008:5-Me-4-F-3-Py], [2009:6-Me-4-F-3-Py], [2010:2-CF3-4-F-3-Py], [2011:5-CF3-4-F-3-Py], [2012:6-CF3-4-F-3-Py], [2013:2-CN-4-F-3-Py], [2014:5-CN-4-F-3-Py], [2015:6-CN-4-F-3-Py], [2016:2-OMe-4-F-3-Py], [2017:5-OMe-4-F-3-Py], [2018:6-OMe-4-F-3-Py], [2019:5-F-3-Py], [2020:2-Cl-5-F-3-Py], [2021:4-Cl-5-F-3-Py], [2022:6-Cl-5-F-3-Py], [2023:2-Me-5-F-3-Py], [2024:4-Me-5-F-3-Py], [2025:6-Me-5-F-3-Py], [2026:2-CF3-5-F-3-Py], [2027:4-CF3-5-F-3-Py], [2028:6-CF3-5-F-3-Py], [2029:2-CN-5-F-3-Py], [2030:4-CN-5-F-3-Py], [2031:6-CN-5-F-3-Py], [2032:2-OMe-5-F-3-Py], [2033:4-OMe-5-F-3-Py], [2034:6-OMe-5-F-3-Py], [2035:6-F-3-Py], [2036:2-Cl-6-F-3-Py], [2037:4-Cl-6-F-3-Py], [2038:5-Cl-6-F-3-Py], [2039:2-Me-6-F-3-Py], [2040:4-Me-6-F-3-Py], [2041:5-Me-6-F-3-Py], [2042:2-CF3-6-F-3-Py], [2043:4-CF3-6-F-3-Py], [2044:5-CF3-6-F-3-Py], [2045:2-CN-6-F-3-Py], [2046:4-CN-6-F-3-Py], [2047:5-CN-6-F-3-Py], [2048:2-OMe-6-F-3-Py], [2049:4-OMe-6-F-3-Py], [2050:5-OMe-6-F-3-Py], [2051:2-Cl-3-Py], [2052:4-Cl-2-Cl-3-Py], [2053:5-Cl-2-Cl-3-Py], [2054:6-Cl-2-Cl-3-Py], [2055:4-Me-2-Cl-3-Py], [2056:5-Me-2-Cl-3-Py], [2057:6-Me-2-Cl-3-Py], [2058:4-CF3-2-Cl-3-Py], [2059:5-CF3-2-Cl-3-Py], [2060:6-CF3-2-Cl-3-Py], [2061:4-CN-2-Cl-3-Py], [2062:5-CN-2-Cl-3-Py], [2063:6-CN-2-Cl-3-Py], [2064:4-OMe-2-Cl-3-Py], [2065:5-OMe-2-Cl-3-Py], [2066:6-OMe-2-Cl-3-Py], [2067:4-Cl-3-Py], [2068:2-Cl-4-Cl-3-Py], [2069:5-Cl-4-Cl-3-Py], [2070:6-Cl-4-Cl-3-Py], [2071:2-Me-4-Cl-3-Py], [2072:5-Me-4-Cl-3-Py], [2073:6-Me-4-Cl-3-Py], [2074:2-CF3-4-Cl-3-Py], [2075:5-CF3-4-Cl-3-Py], [2076:6-CF3-4-Cl-3-Py], [2077:2-CN-4-Cl-3-Py], [2078:5-CN-4-Cl-3-Py], [2079:6-CN-4-Cl-3-Py], [2080:2-OMe-4-Cl-3-Py], [2081:5-OMe-4-Cl-3-Py], [2082:6-OMe-4-Cl-3-Py], [2083:5-Cl-3-Py], [2084:4-Cl-5-Cl-3-Py], [2085:5-Cl-5-Cl-3-Py], [2086:6-Cl-5-Cl-3-Py], [2087:4-Me-5-Cl-3-Py], [2088:5-Me-5-Cl-3-Py], [2089:6-Me-5-Cl-3-Py], [2090:4-CF3-5-Cl-3-Py], [2091:5-CF3-5-Cl-3-Py], [2092:6-CF3-5-Cl-3-Py], [2093:4-CN-5-Cl-3-Py], [2094:3-CN-5-Cl-3-Py], [2095:6-CN-5-Cl-3-Py], [2096:4-OMe-5-Cl-3-Py], [2097:5-OMe-5-Cl-3-Py], [2098:6-OMe-5-Cl-3-Py], [2099:6-Cl-3-Py], [2100:2-Cl-6-Cl-3-Py], [2101:4-Cl-6-Cl-3-Py], [2102:5-Cl-6-Cl-3-Py], [2103:2-Me-6-Cl-3-Py], [2104:4-Me-6-Cl-3-Py], [2105:5-Me-6-Cl-3-Py], [2106:2-CF3-6-Cl-3-Py], [2107:4-CF3-6-Cl-3-Py], [2108:5-CF3-6-Cl-3-Py], [2109:2-CN-6-Cl-3-Py], [2110:4-CN-6-Cl-3-Py], [2111:5-CN-6-Cl-3-Py], [2112:2-OMe-6-Cl-3-Py], [2113:4-OMe-6-Cl-3-Py], [2114:5-OMe-6-Cl-3-Py], [2115:2-Br-3-Py], [2116:4-Cl-2-Br-3-Py], [2117:5-Cl-2-Br-3-Py], [2118:6-Cl-2-Br-3-Py], [2119:4-Me-2-Br-3-Py], [2120:5-Me-2-Br-3-Py], [2121:6-Me-2-Br-3-Py], [2122:4-CF3-2-Br-3-Py], [2123:5-CF3-2-Br-3-Py], [2124:6-CF3-2-Br-3-Py], [2125:4-CN-2-Br-3-Py], [2126:5-CN-2-Br-3-Py], [2127:6-CN-2-Br-3-Py], [2128:4-OMe-2-Br-3-Py], [2129:5-OMe-2-Br-3-Py], [2130:6-OMe-2-Br-3-Py], [2131:4-Br-3-Py], [2132:2-Cl-4-Br-3-Py], [2133:5-Cl-4-Br-3-Py], [2134:6-Cl-4-Br-3-Py], [2135:2-Me-4-Br-3-Py], [2136:5-Me-4-Br-3-Py], [2137:6-Me-4-Br-3-Py], [2138:2-CF3-4-Br-3-Py], [2139:5-CF3-4-Br-3-Py], [2140:6-CF3-4-Br-3-Py], [2141:2-CN-4-Br-3-Py], [2142:5-CN-4-Br-3-Py], [2143:6-CN-4-Br-3-Py], [2144:2-OMe-4-Br-3-Py], [2145:5-OMe-4-Br-3-Py], [2146:6-OMe-4-Br-3-Py], [2147:5-Br-3-Py], [2148:2-Cl-5-Br-3-Py], [2149:4-Cl-5-Br-3-Py], [2150:6-Cl-5-Br-3-Py], [2151:2-Me-5-Br-3-Py], [2152:4-Me-5-Br-3-Py], [2153:6-Me-5-Br-3-Py], [2154:2-CF3-5-Br-3-Py], [2155:4-CF3-5-Br-3-Py], [2156:6-CF3-5-Br-3-Py], [2157:2-CN-5-Br-3-Py], [2158:4-CN-5-Br-3-Py], [2159:6-CN-5-Br-3-Py], [2160:2-OMe-5-Br-3-Py], [2161:4-OMe-5-Br-3-Py], [2162:6-OMe-5-Br-3-Py], [2163:6-Br-3-Py], [2164:2-Cl-6-Br-3-Py], [2165:4-Cl-6-Br-3-Py], [2166:5-Cl-6-Br-3-Py], [2167:2-Me-6-Br-3-Py], [2168:4-Me-6-Br-3-Py], [2169:5-Me-6-Br-3-Py], [2170:2-CF3-6-Br-3-Py], [2171:4-CF3-6-Br-3-Py], [2172:5-CF3-6-Br-3-Py], [2173:2-CN-6-Br-3-Py], [2174:4-CN-6-Br-3-Py], [2175:5-CN-6-Br-3-Py], [2176:2-OMe-6-Br-3-Py], [2177:4-OMe-6-Br-3-Py], [2178:5-OMe-6-Br-3-Py], [2179:2-I-3-Py], [2180:4-Cl-2-I-3-Py], [2181:5-Cl-2-I-3-Py], [2182:6-Cl-2-I-3-Py], [2183:4-Me-2-I-3-Py], [2184:5-Me-2-I-3-Py], [2185:6-Me-2-I-3-Py], [2186:4-CF3-2-I-3-Py], [2187:5-CF3-2-I-3-Py], [2188:6-CF3-2-I-3-Py], [2189:4-CN-2-I-3-Py], [2190:5-CN-2-I-3-Py], [2191:6-CN-2-I-3-Py], [2192:4-OMe-2-I-3-Py], [2193:5-OMe-2-I-3-Py], [2194:6-OMe-2-I-3-Py], [2195:4-I-3-Py], [2196:2-Cl-4-I-3-Py], [2197:5-Cl-4-I-3-Py], [2198:6-Cl-4-I-3-Py], [2199:2-Me-4-I-3-Py], [2200:5-Me-4-I-3-Py], [2201:6-Me-4-I-3-Py], [2202:2-CF3-4-I-3-Py], [2203:5-CF3-4-I-3-Py], [2204:6-CF3-4-I-3-Py], [2205:2-CN-4-I-3-Py], [2206:5-CN-4-I-3-Py], [2207:6-CN-4-I-3-Py], [2208:2-

OMe-4-I-3-Py], [2209:5-OMe-4-I-3-Py], [2210:6-OMe-4-I-3-Py], [2211:5-I-3-Py], [2212:2-Cl-5-I-3-Py], [2213:4-Cl-5-I-3-Py], [2214:6-Cl-5-I-3-Py], [2215:2-Me-5-I-3-Py], [2216:4-Me-5-I-3-Py], [2217:6-Me-5-I-3-Py], [2218:2-CF3-5-I-3-Py], [2219:4-CF3-5-I-3-Py], [2220:6-CF3-5-I-3-Py], [2221:2-CN-5-I-3-Py], [2222:4-CN-5-I-3-Py], [2223:6-CN-5-I-3-Py], [2224:2-OMe-5-I-3-Py], [2225:4-OMe-5-I-3-Py], [2226:6-OMe-5-I-3-Py], [2227:6-I-3-Py], [2228:2-Cl-6-I-3-Py], [2229:4-Cl-6-I-3-Py], [2230:5-Cl-6-I-3-Py], [2231:2-Me-6-I-3-Py], [2232:4-Me-6-I-3-Py], [2233:5-Me-6-I-3-Py], [2234:2-CF3-6-I-3-Py], [2235:4-CF3-6-I-3-Py], [2236:5-CF3-6-I-3-Py], [2237:2-CN-6-I-3-Py], [2238:4-CN-6-I-3-Py], [2239:5-CN-6-I-3-Py], [2240:2-OMe-6-I-3-Py], [2241:4-OMe-6-I-3-Py], [2242:5-OMe-6-I-3-Py], [2243:2-Me-3-Py], [2244:4-Cl-2-Me-3-Py], [2245:5-Cl-2-Me-3-Py], [2246:6-Cl-2-Me-3-Py], [2247:4-Me-2-Me-3-Py], [2248:5-Me-2-Me-3-Py], [2249:6-Me-2-Me-3-Py], [2250:4-CF3-2-Me-3-Py], [2251:5-CF3-2-Me-3-Py], [2252:6-CF3-2-Me-3-Py], [2253:4-CN-2-Me-3-Py], [2254:5-CN-2-Me-3-Py], [2255:6-CN-2-Me-3-Py], [2256:4-OMe-2-Me-3-Py], [2257:5-OMe-2-Me-3-Py], [2258:6-OMe-2-Me-3-Py], [2259:4-Me-3-Py], [2260:2-Cl-4-Me-3-Py], [2261:5-Cl-4-Me-3-Py], [2262:6-Cl-4-Me-3-Py], [2263:2-Me-4-Me-3-Py], [2264:5-Me-4-Me-3-Py], [2265:6-Me-4-Me-3-Py], [2266:2-CF3-4-Me-3-Py], [2267:5-CF3-4-Me-3-Py], [2268:6-CF3-4-Me-3-Py], [2269:2-CN-4-Me-3-Py], [2270:5-CN-4-Me-3-Py], [2271:6-CN-4-Me-3-Py], [2272:2-OMe-4-Me-3-Py], [2273:5-OMe-4-Me-3-Py], [2274:6-OMe-4-Me-3-Py], [2275:5-Me-3-Py], [2276:2-Cl-5-Me-3-Py], [2277:4-Cl-5-Me-3-Py], [2278:6-Cl-5-Me-3-Py], [2279:2-Me-5-Me-3-Py], [2280:4-Me-5-Me-3-Py], [2281:6-Me-5-Me-3-Py], [2282:2-CF3-5-Me-3-Py], [2283:4-CF3-5-Me-3-Py], [2284:6-CF3-5-Me-3-Py], [2285:2-CN-5-Me-3-Py], [2286:4-CN-5-Me-3-Py], [2287:6-CN-5-Me-3-Py], [2288:2-OMe-5-Me-3-Py], [2289:4-OMe-5-Me-3-Py], [2290:6-OMe-5-Me-3-Py], [2291:6-Me-3-Py], [2292:2-Cl-6-Me-3-Py], [2293:4-Cl-6-Me-3-Py], [2294:5-Cl-6-Me-3-Py], [2295:2-Me-6-Me-3-Py], [2296:4-Me-6-Me-3-Py], [2297:5-Me-6-Me-3-Py], [2298:2-CF3-6-Me-3-Py], [2299:4-CF3-6-Me-3-Py], [2300:5-CF3-6-Me-3-Py],
[2301:2-CN-6-Me-3-Py], [2302:4-CN-6-Me-3-Py], [2303:5-CN-6-Me-3-Py], [2304:2-OMe-6-Me-3-Py], [2305:4-OMe-6-Me-3-Py], [2306:5-OMe-6-Me-3-Py], [2307:2-OMe-3-Py], [2308:4-Cl-2-OMe-3-Py], [2309:5-Cl-2-OMe-3-Py], [2310:6-Cl-2-OMe-3-Py], [2311:4-Me-2-OMe-3-Py], [2312:5-Me-2-OMe-3-Py], [2313:6-Me-2-OMe-3-Py], [2314:4-CF3-2-OMe-3-Py], [2315:5-CF3-2-OMe-3-Py], [2316:6-CF3-2-OMe-3-Py], [2317:4-CN-2-OMe-3-Py], [2318:5-CN-2-OMe-3-Py], [2319:6-CN-2-OMe-3-Py], [2320:4-OMe-2-OMe-3-Py], [2321:5-OMe-2-OMe-3-Py], [2322:6-OMe-2-OMe-3-Py], [2323:4-OMe-3-Py], [2324:2-Cl-4-OMe-3-Py], [2325:5-Cl-4-OMe-3-Py], [2326:6-Cl-4-OMe-3-Py], [2327:2-Me-4-OMe-3-Py], [2328:5-Me-4-OMe-3-Py], [2329:6-Me-4-OMe-3-Py], [2330:2-CF3-4-OMe-3-Py], [2331:5-CF3-4-OMe-3-Py], [2332:6-CF3-4-OMe-3-Py], [2333:2-CN-4-OMe-3-Py], [2334:5-CN-4-OMe-3-Py], [2335:6-CN-4-OMe-3-Py], [2336:2-OMe-4-OMe-3-Py], [2337:5-OMe-4-OMe-3-Py], [2338:6-OMe-4-OMe-3-Py], [2339:5-OMe-3-Py], [2340:2-Cl-5-OMe-3-Py], [2341:4-Cl-5-OMe-3-Py], [2342:6-Cl-5-OMe-3-Py], [2343:2-Me-5-OMe-3-Py], [2344:4-Me-5-OMe-3-Py], [2345:6-Me-5-OMe-3-Py], [2346:2-CF3-5-OMe-3-Py], [2347:4-CF3-5-OMe-3-Py], [2348:6-CF3-5-OMe-3-Py], [2349:2-CN-5-OMe-3-Py], [2350:4-CN-5-OMe-3-Py], [2351:6-CN-5-OMe-3-Py], [2352:2-OMe-5-OMe-3-Py], [2353:4-OMe-5-OMe-3-Py], [2354:6-OMe-5-OMe-3-Py], [2355:6-OMe-3-Py], [2356:2-Cl-6-OMe-3-Py], [2357:4-Cl-6-OMe-3-Py], [2358:5-Cl-6-OMe-3-Py], [2359:2-Me-6-OMe-3-Py], [2360:4-Me-6-OMe-3-Py], [2361:5-Me-6-OMe-3-Py], [2362:2-CF3-6-OMe-3-Py], [2363:4-CF3-6-OMe-3-Py], [2364:5-CF3-6-OMe-3-Py], [2365:2-CN-6-OMe-3-Py], [2366:4-CN-6-OMe-3-Py], [2367:5-CN-6-OMe-3-Py], [2368:2-OMe-6-OMe-3-Py], [2369:4-OMe-6-OMe-3-Py], [2370:5-OMe-6-OMe-3-Py], [2371:2-CF3-3-Py], [2372:4-Cl-2-CF3-3-Py], [2373:5-Cl-2-CF3-3-Py], [2374:6-Cl-2-CF3-3-Py], [2375:4-Me-2-CF3-3-Py], [2376:5-Me-2-CF3-3-Py], [2377:6-Me-2-CF3-3-Py], [2378:4-CF3-2-CF3-3-Py], [2379:5-CF3-2-CF3-3-Py], [2380:6-CF3-2-CF3-3-Py], [2381:4-CN-2-CF3-3-Py], [2382:5-CN-2-CF3-3-Py], [2383:6-CN-2-CF3-3-Py], [2384:4-OMe-2-CF3-3-Py], [2385:5-OMe-2CF3-3-Py], [2386:6-OMe-2-CF3-3-Py], [2387:4-CF3-3-Py], [2388:2-Cl-4-CF3-3-Py], [2389:5-Cl-4-CF3-3-Py], [2390:6-Cl-4-CF3-3-Py], [2391:2-Me-4-CF3-3-Py], [2392:5-Me-4-CF3-3-Py], [2393:6-Me-4-CF3-3-Py], [2394:2-CF3-4-CF3-3-Py], [2395:5-CF3-4-CF3-3-Py], [2396:6-CF3-4-CF3-3-Py], [2397:2-CN-4-CF3-3-Py], [2398:5-CN-4-CF3-3-Py], [2399:6-CN-4-CF3-3-Py], [2400:2-OMe-4-CF3-3-Py],
[2401:5-OMe-4-CF3-3-Py], [2402:6-OMe-4-CF3-3-Py], [2403:5-CF3-3-Py], [2404:2-Cl-5-CF3-3-Py], [2405:4-Cl-5-CF3-3-Py], [2406:6-Cl-5-CF3-3-Py], [2407:2-Me-5-CF3-3-Py], [2408:4-Me-5-CF3-3-Py], [2409:6-Me-5-CF3-3-Py], [2410:2-CF3-5-CF3-3-Py], [2411:4-CF3-5-CF3-3-Py], [2412:6-CF3-5-CF3-3-Py], [2413:2-CN-5-CF3-3-Py], [2414:4-CN-5-CF3-3-Py], [2415:6-CN-5-CF3-3-Py], [2416:2-OMe-5-CF3-3-Py], [2417:4-OMe-5-CF3-3-Py], [2418:6-OMe-5-CF3-3-Py], [2419:6-CF3-3-Py], [2420:2-Cl-6-CF3-3-Py], [2421:4-Cl-6-CF3-3-Py], [2422:5-Cl-6-CF3-3-Py], [2423:2-Me-6-CF3-3-Py], [2424:4-Me-6-CF3-3-Py], [2425:5-Me-6-CF3-3-Py], [2426:2-CF3-6-CF3-3-Py], [2427:4-CF3-6-CF3-3-Py], [2428:5-CF3-6-CF3-3-Py], [2429:2-CN-6-CF3-3-Py], [2430:4-CN-6-CF3-3-Py], [2431:5-CN-6-CF3-3-Py], [2432:2-OMe-6-CF3-3-Py], [2433:4-OMe-6-CF3-3-Py], [2434:5-OMe-6-CF3-3-Py], [2435:2-OCF3-3-Py], [2436:4-Cl-2-OCF3-3-Py], [2437:5-Cl-2-OCF3-3-Py], [2438:6-Cl-2-OCF3-3-Py], [2439:4-Me-2-OCF3-3-Py], [2440:5-Me-2-OCF3-3-Py], [2441:6-Me-2-OCF3-3-Py], [2442:4-CF3-2-OCF3-3-Py], [2443:5-CF3-2-OCF3-3-Py], [2444:6-CF3-2-OCF3-3-Py], [2445:4-CN-2-OCF3-3-Py], [2446:5-CN-2-OCF3-3-Py], [2447:6-CN-2-OCF3-3-Py], [2448:4-OMe-2-OCF3-3-Py], [2449:5-OMe-2-OCF3-3-Py], [2450:6-OMe-2-OCF3-3-Py], [2451:4-OCF3-3-Py], [2452:2-Cl-4-OCF3-3-Py], [2453:5-Cl-4-OCF3-3-Py], [2454:6-Cl-4-OCF3-3-Py], [2455:2-Me-4-OCF3-3-Py], [2456:5-Me-4-OCF3-3-Py], [2457:6-Me-4-OCF3-3-Py], [2458:2-CF3-4-OCF3-3-Py], [2459:5-CF3-4-OCF3-3-Py], [2460:6-CF3-4-OCF3-3-Py], [2461:2-CN-4-OCF3-3-Py], [2462:5-CN-4-OCF3-3-Py], [2463:6-CN-4-OCF3-3-Py], [2464:2-OMe-4-OCF3-3-Py], [2465:5-OMe-4-OCF3-3-Py], [2466:6-OMe-4-OCF3-3-Py], [2467:5-OCF3-3-Py], [2468:2-Cl-5-OCF3-3-Py], [2469:4-Cl-5-OCF3-3-Py], [2470:6-Cl-5-OCF3-3-Py], [2471:2-Me-5-OCF3-3-Py], [2472:4-Me-5-OCF3-3-Py], [2473:6-Me-5-OCF3-3-Py], [2474:2-CF3-5-OCF3-3-Py], [2475:4-CF3-5-OCF3-3-Py], [2476:6-CF3-5-OCF3-3-Py], [2477:2-CN-5-OCF3-3-Py], [2478:4-CN-5-OCF3-3-Py], [2479:6-CN-5-OCF3-3-Py], [2480:2-OMe-5-OCF3-3-Py], [2481:4-OMe-5-OCF3-3-Py], [2482:6-OMe-5-OCF3-3-Py], [2483:6-OCF3-3-Py], [2484:2-Cl-6-OCF3-3-Py], [2485:4-Cl-6-OCF3-3-Py], [2486:5-Cl-6-OCF3-3-Py], [2487:2-Me-6-OCF3-3-Py], [2488:4-Me-6-OCF3-3-Py], [2489:5-Me-6-OCF3-3-Py], [2490:2-CF3-6-OCF3-3-Py], [2491:4-CF3-6-OCF3-3-Py], [2492:5-CF3-6-OCF3-3-Py], [2493:2-CN-6-OCF3-3-Py], [2494:4-CN-6-OCF3-3-Py], [2495:5-CN-6-

OCF3-3-Py], [2496:2-OMe-6-OCF3-3-Py], [2497:4-OMe-6-OCF3-3-Py], [2498:5-OMe-6-OCF3-3-Py], [2499:2-CHF2-3-Py], [2500:4-Cl-2-CHF2-3-Py], [2501:5-Cl-2-CHF2-3-Py], [2502:6-Cl-2-CHF2-3-Py], [2503:4-Me-2-CHF2-3-Py], [2504:5-Me-2-CHF2-3-Py], [2505:6-Me-2-CHF2-3-Py], [2506:4-CF3-2-CHF2-3-Py], [2507:5-CF3-2-CHF2-3-Py], [2508:6-CF3-2-CHF2-3-Py], [2509:4-CN-2-CHF2-3-Py], [2510:5-CN-2-CHF2-3-Py], [2511:6-CN-2-CHF2-3-Py], [2512:4-OMe-2-CHF2-3-Py], [2513:5-OMe-2-CHF2-3-Py], [2514:6-OMe-2-CHF2-3-Py], [2515:4-CHF2-3-Py], [2516:2-Cl-4-CHF2-3-Py], [2517:5-Cl-4-CHF2-3-Py], [2518:6-Cl-4-CHF2-3-Py], [2519:2-Me-4-CHF2-3-Py], [2520:5-Me-4-CHF2-3-Py], [2521:6-Me-4-CHF2-3-Py], [2522:2-CF3-4-CHF2-3-Py], [2523:5-CF3-4-CHF2-3-Py], [2524:6-CF3-4-CHF2-3-Py], [2525:2-CN-4-CHF2-3-Py], [2526:5-CN-4-CHF2-3-Py], [2527:6-CN-4-CHF2-3-Py], [2528:2-OMe-4-CHF2-3-Py], [2529:5-OMe-4-CHF2-3-Py], [2530:6-OMe-4-CHF2-3-Py], [2531:5-CHF2-3-Py], [2532:2-Cl-5-CHF2-3-Py], [2533:4-Cl-5-CHF2-3-Py], [2534:6-Cl-5-CHF2-3-Py], [2535:2-Me-5-CHF2-3-Py], [2536:4-Me-5-CHF2-3-Py], [2537:6-Me-5-CHF2-3-Py], [2538:2-CF3-5-CHF2-3-Py], [2539:4-CF3-5-CHF2-3-Py], [2540:6-CF3-5-CHF2-3-Py], [2541:2-CN-5-CHF2-3-Py], [2542:4-CN-5-CHF2-3-Py], [2543:6-CN-5-CHF2-3-Py], [2544:2-OMe-5-CHF2-3-Py], [2545:4-OMe-5-CHF2-3-Py], [2546:6-OMe-5-CHF2-3-Py], [2547:6-CHF2-3-Py], [2548:2-Cl-6-CHF2-3-Py], [2549:4-Cl-6-CHF2-3-Py], [2550:5-Cl-6-CHF2-3-Py], [2551:2-Me-6-CHF2-3-Py], [2552:4-Me-6-CHF2-3-Py], [2553:5-Me-6-CHF2-3-Py], [2554:2-CF3-6-CHF2-3-Py], [2555:4-CF3-6-CHF2-3-Py], [2556:5-CF3-6-CHF2-3-Py], [2557:2-CN-6-CHF2-3-Py], [2558:4-CN-6-CHF2-3-Py], [2559:5-CN-6-CHF2-3-Py], [2560:2-OMe-6-CHF2-3-Py], [2561:4-OMe-6-CHF2-3-Py], [2562:5-OMe-6-CHF2-3-Py], [2563:2-OCHF2-3-Py], [2564:4-Cl-2-OCHF2-3-Py], [2565:5-Cl-2-OCHF2-3-Py], [2566:6-Cl-2-OCHF2-3-Py], [2567:4-Me-2-OCHF2-3-Py], [2568:5-Me-2-OCHF2-3-Py], [2569:6-Me-2-OCHF2-3-Py], [2570:4-CF3-2-OCHF2-3-Py], [2571:5-CF3-2-OCHF2-3-Py], [2572:6-CF3-2-OCHF2-3-Py], [2573:4-CN-2-OCHF2-3-Py], [2574:5-CN-2-OCHF2-3-Py], [2575:6-CN-2-OCHF2-3-Py], [2576:4-OMe-2-OCHF2-3-Py], [2577:5-OMe-2-OCHF2-3-Py], [2578:6-OMe-2-OCHF2-3-Py], [2579:4-OCHF2-3-Py], [2580:2-Cl-4-OCHF2-3-Py], [2581:5-Cl-4-OCHF2-3-Py], [2582:6-Cl-4-OCHF2-3-Py], [2583:2-Me-4-OCHF2-3-Py], [2584:5-Me-4-OCHF2-3-Py], [2585:6-Me-4-OCHF2-3-Py], [2586:2-CF3-4-OCHF2-3-Py], [2587:5-CF3-4-OCHF2-3-Py], [2588:6-CF3-4-OCHF2-3-Py], [2589:2-CN-4-OCHF2-3-Py], [2590:5-CN-4-OCHF2-3-Py], [2591:6-CN-4-OCHF2-3-Py], [2592:2-OMe-4-OCHF2-3-Py], [2593:5-OMe-4-OCHF2-3-Py], [2594:6-OMe-4-OCHF2-3-Py], [2595:5-OCHF2-3-Py], [2596:2-Cl-5-OCHF2-3-Py], [2597:4-Cl-5-OCHF2-3-Py], [2598:6-Cl-5-OCHF2-3-Py], [2599:2-Me-5-OCHF2-3-Py], [2600:4-Me-5-OCHF2-3-Py],
[2601:6-Me-5-OCHF2-3-Py], [2602:2-CF3-5-OCHF2-3-Py], [2603:4-CF3-5-OCHF2-3-Py], [2604:6-CF3-5-OCHF2-3-Py], [2605:2-CN-5-OCHF2-3-Py], [2606:4-CN-5-OCHF2-3-Py], [2607:6-CN-5-OCHF2-3-Py], [2608:2-OMe-5-OCHF2-3-Py], [2609:4-OMe-5-OCHF2-3-Py], [2610:6-OMe-5-OCHF2-3-Py], [2611:6-OCHF2-3-Py], [2612:2-Cl-6-OCHF2-3-Py], [2613:4-Cl-6-OCHF2-3-Py], [2614:5-Cl-6-OCHF2-3-Py], [2615:2-Me-6-OCHF2-3-Py], [2616:4-Me-6-OCHF2-3-Py], [2617:5-Me-6-OCHF2-3-Py], [2618:2-CF3-6-OCHF2-3-Py], [2619:4-CF3-6-OCHF2-3-Py], [2620:5-CF3-6-OCHF2-3-Py], [2621:2-CN-6-OCHF2-3-Py], [2622:4-CN-6-OCHF2-3-Py], [2623:5-CN-6-OCHF2-3-Py], [2624:2-OMe-6-OCHF2-3-Py], [2625:4-OMe-6-OCHF2-3-Py], [2626:5-OMe-6-OCHF2-3-Py],
[2627:2Et-3-Py], [2628:4-Cl-2-Et-3-Py], [2629:5-Cl-2-Et-3-Py], [2630:6-Cl-2-Et-3-Py], [2631:4-Me-2-Et-3-Py], [2632:5-Me-2-Et-3-Py], [2633:6-Me-2-Et-3-Py], [2634:4-CF3-2-Et-3-Py], [2635:5-CF3-2-Et-3-Py], [2636:6-CF3-2-Et-3-Py], [2637:4-CN-2-Et-3-Py], [2638:5-CN-2-Et-3-Py], [2639:6-CN-2-Et-3-Py], [2640:4-OMe-2-Et-3-Py], [2641:5-OMe-2-Et-3-Py], [2642:6-OMe-2-Et-3-Py], [2643:4-Et-3-Py], [2644:2-Cl-4-Et-3-Py], [2645:5-Cl-4-Et-3-Py], [2646:6-Cl-4-Et-3-Py], [2647:2-Me-4-Et-3-Py], [2648:5-Me-4-Et-3-Py], [2649:6-Me-4-Et-3-Py], [2650:2-CF3-4-Et-3-Py], [2651:5-CF3-4-Et-3-Py], [2652:6-CF3-4-Et-3-Py], [2653:2-CN-4-Et-3-Py], [2654:5-CN-4-Et-3-Py], [2655:6-CN-4-Et-3-Py], [2656:2-OMe-4-Et-3-Py], [2657:5-OMe-4-Et-3-Py], [2658:6-OMe-4-Et-3-Py], [2659:5-Et-3-Py], [2660:2-Cl-5-Et-3-Py], [2661:4-Cl-5-Et-3-Py], [2662:6-Cl-5-Et-3-Py], [2663:2-Me-5-Et-3-Py], [2664:4-Me-5-Et-3-Py], [2665:6-Me-5-Et-3-Py], [2666:2-CF3-5-Et-3-Py], [2667:4-CF3-5-Et-3-Py], [2668:6-CF3-5-Et-3-Py], [2669:2-CN-5-Et-3-Py], [2670:4-CN-5-Et-3-Py], [2671:6-CN-5-Et-3-Py], [2672:2-OMe-5-Et-3-Py], [2673:4-OMe-5-Et-3-Py], [2674:6-OMe-5-Et-3-Py], [2675:6-Et-3-Py], [2676:2-Cl-6-Et-3-Py], [2677:4-Cl-6-Et-3-Py], [2678:5-Cl-6-Et-3-Py], [2679:2-Me-6-Et-3-Py], [2680:4-Me-6-Et-3-Py], [2681:5-Me-6-Et-3-Py], [2682:2-CF3-6-Et-3-Py], [2683:4-CF3-6-Et-3-Py], [2684:5-CF3-6-Et-3-Py], [2685:2-CN-6-Et-3-Py], [2686:4-CN-6-Et-3-Py], [2687:5-CN-6-Et-3-Py], [2688:2-OMe-6-Et-3-Py], [2689:4-OMe-6-Et-3-Py], [2690:5-OMe-6-Et-3-Py], [2691:2-CH2CF3-3-Py], [2692:4-Cl-2-CH2CF3-3-Py], [2693:5-Cl-2-CH2CF3-3-Py], [2694:6-Cl-2-CH2CF3-3-Py], [2695:4-Me-2-CH2CF3-3-Py], [2696:5-Me-2-CH2CF3-3-Py], [2697:6-Me-2-CH2CF3-3-Py], [2698:4-CF3-2-CH2CF3-3-Py], [2699:5-CF3-2-CH2CF3-3-Py], [2700:6-CF3-2-CH2CF3-3-Py],
[2701:4-CN-2-CH2CF3-3-Py], [2702:5-CN-2-CH2CF3-3-Py], [2703:6-CN-2-CH2CF3-3-Py], [2704:4-OMe-2-CH2CF3-3-Py], [2705:5-OMe-2-CH2CF3-3-Py], [2706:6-OMe-2-CH2CF3-3-Py], [2707:4-CH2CF3-3-Py], [2708:2-Cl-4-CH2CF3-3-Py], [2709:5-Cl-4-CH2CF3-3-Py], [2710:6-Cl-4-CH2CF3-3-Py], [2711:2-Me-4-CH2CF3-3-Py], [2712:5-Me-4-CH2CF3-3-Py], [2713:6-Me-4-CH2CF3-3-Py], [2714:2-CF3-4-CH2CF3-3-Py], [2715:5-CF3-4-CH2CF3-3-Py], [2716:6-CF3-4-CH2CF3-3-Py], [2717:2-CN-4-CH2CF3-3-Py], [2718:5-CN-4-CH2CF3-3-Py], [2719:6-CN-4-CH2CF3-3-Py], [2720:2-OMe-4-CH2CF3-3-Py], [2721:5-OMe-4-CH2CF3-3-Py], [2722:6-OMe-4-CH2CF3-3-Py], [2723:5-CH2CF3-3-Py], [2724:2-Cl-5-CH2CF3-3-Py], [2725:4-Cl-5-CH2CF3-3-Py], [2726:6-Cl-5-CH2CF3-3-Py], [2727:2-Me-5-CH2CF3-3-Py], [2728:4-Me-5-CH2CF3-3-Py], [2729:6-Me-5-CH2CF3-3-Py], [2730:2-CF3-5-CH2CF3-3-Py], [2731:4-CF3-5-CH2CF3-3-Py], [2732:6-CF3-5-CH2CF3-3-Py], [2733:2-CN-5-CH2CF3-3-Py], [2734:4-CN-5-CH2CF3-3-Py], [2735:6-CN-5-CH2CF3-3-Py], [2736:2-OMe-5-CH2CF3-3-Py], [2737:4-OMe-5-CH2CF3-3-Py], [2738:6-OMe-5-CH2CF3-3-Py], [2739:6-CH2CF3-3-Py], [2740:2-Cl-6-CH2CF3-3-Py], [2741:4-Cl-6-CH2CF3-3-Py], [2742:5-Cl-6-CH2CF3-3-Py], [2743:2-Me-6-CH2CF3-3-Py], [2744:4-Me-6-CH2CF3-3-Py], [2745:5-Me-6-CH2CF3-3-Py], [2746:2-CF3-6-CH2CF3-3-Py], [2747:4-CF3-6-CH2CF3-3-Py], [2748:5-CF3-6-CH2CF3-3-Py], [2749:2-CN-6-CH2CF3-3-Py], [2750:4-CN-6-CH2CF3-3-Py], [2751:5-CN-6-CH2CF3-3-Py], [2752:2-OMe-6-CH2CF3-3-Py], [2753:4-OMe-6-CH2CF3-3-Py], [2754:5-OMe-6-CH2CF3-3-Py], [2755:2-OEt-3-Py], [2756:4-Cl-2-OEt-3-Py], [2757:5-Cl-2-

OEt-3-Py], [2758:6-Cl-2-OEt-3-Py], [2759:4-Me-2-OEt-3-Py], [2760:5-Me-2-OEt-3-Py], [2761:6-Me-2-OEt-3-Py], [2762:4-CF3-2-OEt-3-Py], [2763:5-CF3-2-OEt-3-Py], [2764:6-CF3-2-OEt-3-Py], [2765:4-CN-2-OEt-3-Py], [2766:5-CN-2-OEt-3-Py], [2767:6-CN-2-OEt-3-Py], [2768:4-OMe-2-OEt-3-Py], [2769:5-OMe-2-OEt-3-Py], [2770:6-OMe-2-OEt-3-Py], [2771:4-OEt-3-Py], [2772:2-Cl-4-OEt-3-Py], [2773:5-Cl-4-OEt-3-Py], [2774:6-Cl-4-OEt-3-Py], [2775:2-Me-4-OEt-3-Py], [2776:5-Me-4-OEt-3-Py], [2777:6-Me-4-OEt-3-Py], [2778:2-CF3-4-OEt-3-Py], [2779:5-CF3-4-OEt-3-Py], [2780:6-CF3-4-OEt-3-Py], [2781:2-CN-4-OEt-3-Py], [2782:5-CN-4-OEt-3-Py], [2783:6-CN-4-OEt-3-Py], [2784:2-OMe-4-OEt-3-Py], [2785:5-OMe-4-OEt-3-Py], [2786:6-OMe-4-OEt-3-Py], [2787:5-OEt-3-Py], [2788:2-Cl-5-OEt-3-Py], [2789:4-Cl-5-OEt-3-Py], [2790:6-Cl-5-OEt-3-Py], [2791:2-Me-5-OEt-3-Py], [2792:4-Me-5-OEt-3-Py], [2793:6-Me-5-OEt-3-Py], [2794:2-CF3-5-OEt-3-Py], [2795:4-CF3-5-OEt-3-Py], [2796:6-CF3-5-OEt-3-Py], [2797:2-CN-5-OEt-3-Py], [2798:4-CN-5-OEt-3-Py], [2799:6-CN-5-OEt-3-Py], [2800:2-OMe-5-OEt-3-Py], [2801:4-OMe-5-OEt-3-Py], [2802:6-OMe-5-OEt-3-Py], [2803:6-OEt-3-Py], [2804:2-Cl-6-OEt-3-Py], [2805:4-Cl-6-OEt-3-Py], [2806:5-Cl-6-OEt-3-Py], [2807:2-Me-6-OEt-3-Py], [2808:4-Me-6-OEt-3-Py], [2809:5-Me-6-OEt-3-Py], [2810:2-CF3-6-OEt-3-Py], [2811:4-CF3-6-OEt-3-Py], [2812:5-CF3-6-OEt-3-Py], [2813:2-CN-6-OEt-3-Py], [2814:4-CN-6-OEt-3-Py], [2815:5-CN-6-OEt-3-Py], [2816:2-OMe-6-Oft-3-Py], [2817:4-OMe-6-OEt-3-Py], [2818:5-OMe-6-OEt-3-Py], [2819:2-OCH2CF3-3-Py], [2820:4-Cl-2-OCH2CF3-3-Py], [2821:5-Cl-2-OCH2CF3-3-Py], [2822:6-Cl-2-OCH2CF3-3-Py], [2823:4-Me-2-OCH2CF3-3-Py], [2824:5-Me-2-OCH2CF3-3-Py], [2825:6-Me-2-OCH2CF3-3-Py], [2826:4-CF3-2-OCH2CF3-3-Py], [2827:5-CF3-2-OCH2CF3-3-Py], [2828:6-CF3-2-OCH2CF3-3-Py], [2829:4-CN-2-OCH2CF3-3-Py], [2830:5-CN-2-OCH2CF3-3-Py], [2831:6-CN-2-OCH2CF3-3-Py], [2832:4-OMe-2-OCH2CF3-3-Py], [2833:5-OMe-2-OCH2CF3-3-Py], [2834:6-OMe-2-OCH2CF3-3-Py], [2835:4-OCH2CF3-3-Py], [2836:2-Cl-4-OCH2CF3-3-Py], [2837:5-Cl-4-OCH2CF3-3-Py], [2838:6-Cl-4-OCH2CF3-3-Py], [2839:2-Me-4-OCH2CF3-3-Py], [2840:5-Me-4-OCH2CF3-3-Py], [2841:6-Me-4-OCH2CF3-3-Py], [2842:2-CF3-4-OCH2CF3-3-Py], [2843:5-CF3-4-OCH2CF3-3-Py], [2844:6-CF3-4-OCH2CF3-3-Py], [2845:2-CN-4-OCH2CF3-3-Py], [2846:5-CN-4-OCH2CF3-3-Py], [2847:6-CN-4-OCH2CF3-3-Py], [2848:2-OMe-4-OCH2CF3-3-Py], [2849:5-OMe-4-OCH2CF3-3-Py], [2850:6-OMe-4-OCH2CF3-3-Py], [2851:5-OCH2CF3-3-Py], [2852:2-Cl-5-OCH2CF3-3-Py], [2853:4-Cl-5-OCH2CF3-3-Py], [2854:6-Cl-5-OCH2CF3-3-Py], [2855:2-Me-5-OCH2CF3-3-Py], [2856:4-Me-5-OCH2CF3-3-Py], [2857:6-Me-5-OCH2CF3-3-Py], [2858:2-CF3-5-OCH2CF3-3-Py], [2859:4-CF3-5-OCH2CF3-3-Py], [2860:6-CF3-5-OCH2CF3-3-Py], [2861:2-CN-5-OCH2CF3-3-Py], [2862:4-CN-5-OCH2CF3-3-Py], [2863:6-CN-5-OCH2CF3-3-Py], [2864:2-OMe-5-OCH2CF3-3-Py], [2865:4-OMe-5-OCH2CF3-3-Py], [2866:6-OMe-5-OCH2CF3-3-Py], [2867:6-OCH2CF3-3-Py], [2868:2-Cl-6-OCH2CF3-3-Py], [2869:4-Cl-6-OCH2CF3-3-Py], [2870:5-Cl-6-OCH2CF3-3-Py], [2871:2-Me-6-OCH2CF3-3-Py], [2872:4-Me-6-OCH2CF3-3-Py], [2873:5-Me-6-OCH2CF3-3-Py], [2874:2-CF3-6-OCH2CF3-3-Py], [2875:4-CF3-6-OCH2CF3-3-Py], [2876:5-CF3-6-OCH2CF3-3-Py], [2877:2-CN-6-OCH2CF3-3-Py], [2878:4-CN-6-OCH2CF3-3-Py], [2879:5-CN-6-OCH2CF3-3-Py], [2880:2-OMe-6-OCH2CF3-3-Py], [2881:4-OMe-6-OCH2CF3-3-Py], [2882:5-OMe-6-OCH2CF3-3-Py], [2883:2-Pr-3-Py], [2884:4-Cl-2-Pr-3-Py], [2885:5-Cl-2-Pr-3-Py], [2886:6-Cl-2-Pr-3-Py], [2887:4-Me-2-Pr-3-Py], [2888:5-Me-2-Pr-3-Py], [2889:6-Me-2-Pr-3-Py], [2890:4-CF3-2-Pr-3-Py], [2891:5-CF3-2-Pr-3-Py], [2892:6-CF3-2-Pr-3-Py], [2893:4-CN-2-Pr-3-Py], [2894:5-CN-2-Pr-3-Py], [2895:6-CN-2-Pr-3-Py], [2896:4-OMe-2-Pr-3-Py], [2897:5-OMe-2-Pr-3-Py], [2898:6-OMe-2-Pr-3-Py], [2899:4-Pr-3-Py], [2900:2-Cl-4-Pr-3-Py], [2901:5-Cl-4-Pr-3-Py], [2902:6-Cl-4-Pr-3-Py], [2903:2-Me-4-Pr-3-Py], [2904:5-Me-4-Pr-3-Py], [2905:6-Me-4-Pr-3-Py], [2906:2-CF3-4-Pr-3-Py], [2907:5-CF3-4-Pr-3-Py], [2908:6-CF3-4-Pr-3-Py], [2909:2-CN-4-Pr-3-Py], [2910:5-CN-4-Pr-3-Py], [2911:6-CN-4-Pr-3-Py], [2912:2-OMe-4-Pr-3-Py], [2913:5-OMe-4-Pr-3-Py], [2914:6-OMe-4-Pr-3-Py], [2915:5-Pr-3-Py], [2916:2-Cl-5-Pr-3-Py], [2917:4-Cl-5-Pr-3-Py], [2918:6-Cl-5-Pr-3-Py], [2919:2-Me-5-Pr-3-Py], [2920:4-Me-5-Pr-3-Py], [2921:6-Me-5-Pr-3-Py], [2922:2-CF3-5-Pr-3-Py], [2923:4-CF3-5-Pr-3-Py], [2924:6-CF3-5-Pr-3-Py], [2925:2-CN-5-Pr-3-Py], [2926:4-CN-5-Pr-3-Py], [2927:6-CN-5-Pr-3-Py], [2928:2-OMe-5-Pr-3-Py], [2929:4-OMe-5-Pr-3-Py], [2930:6-OMe-5-Pr-3-Py], [2931:6-Pr-3-Py], [2932:2-Cl-6-Pr-3-Py], [2933:4-Cl-6-Pr-3-Py], [2934:5-Cl-6-Pr-3-Py], [2935:2-Me-6-Pr-3-Py], [2936:4-Me-6-Pr-3-Py], [2937:5-Me-6-Pr-3-Py], [2938:2-CF3-6-Pr-3-Py], [2939:4-CF3-6-Pr-3-Py], [2940:5-CF3-6-Pr-3-Py], [2941:2-CN-6-Pr-3-Py], [2942:4-CN-6-Pr-3-Py], [2943:5-CN-6-Pr-3-Py], [2944:2-OMe-6-Pr-3-Py], [2945:4-OMe-6-Pr-3-Py], [2946:5-OMe-6-Pr-3-Py], [2947:2-OPr-3-Py], [2948:4-Cl-2-OPr-3-Py], [2949:5-Cl-2-OPr-3-Py], [2950:6-Cl-2-OPr-3-Py], [2951:4-Me-2-OPr-3-Py], [2952:5-Me-2-OPr-3-Py], [2953:6-Me-2-OPr-3-Py], [2954:4-CF3-2-OPr-3-Py], [2955:5-CF3-2-OPr-3-Py], [2956:6-CF3-2-OPr-3-Py], [2957:4-CN-2-OPr-3-Py], [2958:5-CN-2-OPr-3-Py], [2959:6-CN-2-OPr-3-Py], [2960:4-OMe-2-OPr-3-Py], [2961:5-OMe-2-OPr-3-Py], [2962:6-OMe-2-OPr-3-Py], [2963:4-OPr-3-Py], [2964:2-Cl-4-OPr-3-Py], [2965:5-Cl-4-OPr-3-Py], [2966:6-Cl-4-OPr-3-Py], [2967:2-Me-4-OPr-3-Py], [2968:5-Me-4-OPr-3-Py], [2969:6-Me-4-OPr-3-Py], [2970:2-CF3-4-OPr-3-Py], [2971:5-CF3-4-OPr-3-Py], [2972:6-CF3-4-OPr-3-Py], [2973:2-CN-4-OPr-3-Py], [2974:5-CN-4-OPr-3-Py], [2975:6-CN-4-OPr-3-Py], [2976:2-OMe-4-OPr-3-Py], [2977:5-OMe-4-OPr-3-Py], [2978:6-OMe-4-OPr-3-Py], [2979:5-OPr-3-Py], [2980:2-Cl-5-OPr-3-Py], [2981:4-Cl-5-OPr-3-Py], [2982:6-Cl-5-OPr-3-Py], [2983:2-Me-5-OPr-3-Py], [2984:4-Me-5-OPr-3-Py], [2985:6-Me-5-OPr-3-Py], [2986:2-CF3-5-OPr-3-Py], [2987:4-CF3-5-OPr-3-Py], [2988:6-CF3-5-OPr-3-Py], [2989:2-CN-5-OPr-3-Py], [2990:4-CN-5-OPr-3-Py], [2991:6-CN-5-OPr-3-Py], [2992:2-OMe-5-OPr-3-Py], [2993:4-OMe-5-OPr-3-Py], [2994:6-OMe-5-OPr-3-Py], [2995:6-OPr-3-Py], [2996:2-Cl-6-OPr-3-Py], [2997:4-Cl-6-OPr-3-Py], [2998:5-Cl-6-OPr-3-Py], [2999:2-Me-6-OPr-3-Py], [3000:4-Me-6-OPr-3-Py], [3001:5-Me-6-OPr-3-Py], [3002:2-CF3-6-OPr-3-Py], [3003:4-CF3-6-OPr-3-Py], [3004:5-CF3-6-OPr-3-Py], [3005:2-CN-6-OPr-3-Py], [3006:4-CN-6-OPr-3-Py], [3007:5-CN-6-OPr-3-Py], [3008:2-OMe-6-OPr-3-Py], [3009:4-OMe-6-OPr-3-Py], [3010:5-OMe-6-OPr-3-Py], [3011:2-SMe-3-Py], [3012:4-Cl-2-SMe-3-Py], [3013:5-Cl-2-SMe-3-Py], [3014:6-Cl-2-SMe-3-Py], [3015:4-Me-2-SMe-3-Py], [3016:5-Me-2-SMe-3-Py], [3017:6-Me-2-SMe-3-Py], [3018:4-CF3-2-SMe-3-Py], [3019:5-CF3-2-SMe-3-Py], [3020:6-CF3-2-SMe-3-Py], [3021:4-CN-2-SMe-3-Py], [3022:5-CN-2-SMe-3-Py], [3023:6-CN-2-SMe-3-Py], [3024:4-OMe-2-SMe-3-Py], [3025:5-OMe-2-SMe-3-Py], [3026:6-OMe-2-SMe-3-Py], [3027:4-SMe-3-Py], [3028:2-Cl-4-SMe-3-Py], [3029:5-Cl-4-SMe-3-Py], [3030:6-Cl-4-SMe-3-Py], [3031:2-Me-4-SMe-3-Py], [3032:5-Me-4-SMe-3-Py], [3033:6-Me-4-SMe-3-Py], [3034:2-CF3-4-SMe-3-Py], [3035:5-CF3-4-SMe-3-Py], [3036:6-CF3-4-SMe-3-

Py], [3037:2-CN-4-SMe-3-Py], [3038:5-CN-4-SMe-3-Py], [3039:6-CN-4-SMe-3-Py], [3040:2-OMe-4-SMe-3-Py], [3041:5-OMe-4-SMe-3-Py], [3042:6-OMe-4-SMe-3-Py], [3043:5-SMe-3-Py], [3044:2-Cl-5-SMe-3-Py], [3045:4-Cl-5-SMe-3-Py], [3046:6-Cl-5-SMe-3-Py], [3047:2-Me-5-SMe-3-Py], [3048:4-Me-5-SMe-3-Py], [3049:6-Me-5-SMe-3-Py], [3050:2-CF3-5-SMe-3-Py], [3051:4-CF3-5-SMe-3-Py], [3052:6-CF3-5-SMe-3-Py], [3053:2-CN-5-SMe-3-Py], [3054:4-CN-5-SMe-3-Py], [3055:6-CN-5-SMe-3-Py], [3056:2-OMe-5-SMe-3-Py], [3057:4-OMe-5-SMe-3-Py], [3058:6-OMe-5-SMe-3-Py], [3059:6-SMe-3-Py], [3060:2-Cl-6-SMe-3-Py], [3061:4-Cl-6-SMe-3-Py], [3062:5-Cl-6-SMe-3-Py], [3063:2-Me-6-SMe-3-Py], [3064:4-Me-6-SMe-3-Py], [3065:5-Me-6-SMe-3-Py], [3066:2-CF3-6-SMe-3-Py], [3067:4-CF3-6-SMe-3-Py], [3068:5-CF3-6-SMe-3-Py], [3069:2-CN-6-SMe-3-Py], [3070:4-CN-6-SMe-3-Py], [3071:5-CN-6-SMe-3-Py], [3072:2-OMe-6-SMe-3-Py], [3073:4-OMe-6-SMe-3-Py], [3074:5-OMe-6-SMe-3-Py], [3075:2-SCF3-3-Py], [3076:4-Cl-2-SCF3-3-Py], [3077:5-Cl-2-SCF3-3-Py], [3078:6-Cl-2-SCF3-3-Py], [3079:4-Me-2-SCF3-3-Py], [3080:5-Me-2-SCF3-3-Py], [3081:6-Me-2-SCF3-3-Py], [3082:4-CF3-2-SCF3-3-Py], [3083:5-CF3-2-SCF3-3-Py], [3084:6-CF3-2-SCF3-3-Py], [3085:4-CN-2-SCF3-3-Py], [3086:5-CN-2-SCF3-3-Py], [3087:6-CN-2-SCF3-3-Py], [3088:4-OMe-2-SCF3-3-Py], [3089:5-OMe-2-SCF3-3-Py], [3090:6-OMe-2-SCF3-3-Py], [3091:4-SCF3-3-Py], [3092:2-Cl-4-SCF3-3-Py], [3093:5-Cl-4-SCF3-3-Py], [3094:6-Cl-4-SCF3-3-Py], [3095:2-Me-4-SCF3-3-Py], [3096:5-Me-4-SCF3-3-Py], [3097:6-Me-4-SCF3-3-Py], [3098:2-CF3-4-SCF3-3-Py], [3099:5-CF3-4-SCF3-3-Py], [3100:6-CF3-4-SCF3-3-Py],
[3101:2-CN-4-SCF3-3-Py], [3102:5-CN-4-SCF3-3-Py], [3103:6-CN-4-SCF3-3-Py], [3104:2-OMe-4-SCF3-3-Py], [3105:5-OMe-4-SCF3-3-Py], [3106:6-OMe-4-SCF3-3-Py], [3107:5-SCF3-3-Py], [3108:2-Cl-5-SCF3-3-Py], [3109:4-Cl-5-SCF3-3-Py], [3110:6-Cl-5-SCF3-3-Py], [3111:2-Me-5-SCF3-3-Py], [3112:4-Me-5-SCF3-3-Py], [3113:6-Me-5-SCF3-3-Py], [3114:2-CF3-5-SCF3-3-Py], [3115:4-CF3-5-SCF3-3-Py], [3116:6-CF3-5-SCF3-3-Py], [3117:2-CN-5-SCF3-3-Py], [3118:4-CN-5-SCF3-3-Py], [3119:6-CN-5-SCF3-3-Py], [3120:2-OMe-5-SCF3-3-Py], [3121:4-OMe-5-SCF3-3-Py], [3122:6-OMe-5-SCF3-3-Py], [3123:6-SCF3-3-Py], [3124:2-Cl-6-SCF3-3-Py], [3125:4-Cl-6-SCF3-3-Py], [3126:6-Cl-6-SCF3-3-Py], [3127:2-Me-6-SCF3-3-Py], [3128:4-Me-6-SCF3-3-Py], [3129:6-Me-6-SCF3-3-Py], [3130:2-CF3-6-SCF3-3-Py], [3131:4-CF3-6-SCF3-3-Py], [3132:6-CF3-6-SCF3-3-Py], [3133:2-CN-6-SCF3-3-Py], [3134:4-CN-6-SCF3-3-Py], [3135:6-CN-6-SCF3-3-Py], [3136:2-OMe-6-SCF3-3-Py], [3137:4-OMe-6-SCF3-3-Py], [3138:6-OMe-6-SCF3-3-Py], [3139:2-S(O)Me-3-Py], [3140:4-Cl-2-S(O)Me-3-Py], [3141:5-Cl-2-S(O)Me-3-Py], [3142:6-Cl-2-S(O)Me-3-Py], [3143:4-Me-2-S(O)Me-3-Py], [3144:5-Me-2-S(O)Me-3-Py], [3145:6-Me-2-S(O)Me-3-Py], [3146:4-CF3-2-S(O)Me-3-Py], [3147:5-CF3-2-S(O)Me-3-Py], [3148:6-CF3-2-S(O)Me-3-Py], [3149:4-CN-2-S(O)Me-3-Py], [3150:5-CN-2-S(O)Me-3-Py], [3151:6-CN-2-S(O)Me-3-Py], [3152:4-OMe-2-S(O)Me-3-Py], [3153:5-OMe-2-S(O)Me-3-Py], [3154:6-OMe-2-S(O)Me-3-Py], [3155:4-S(O)Me-3-Py], [3156:2-Cl-4-S(O)Me-3-Py], [3157:5-Cl-4-S(O)Me-3-Py], [3158:6-Cl-4-S(O)Me-3-Py], [3159:2-Me-4-S(O)Me-3-Py], [3160:5-Me-4-S(O)Me-3-Py], [3161:6-Me-4-S(O)Me-3-Py], [3162:2-CF3-4-S(O)Me-3-Py], [3163:5-CF3-4-S(O)Me-3-Py], [3164:6-CF3-4-S(O)Me-3-Py], [3165:2-CN-4-S(O)Me-3-Py], [3166:5-CN-4-S(O)Me-3-Py], [3167:6-CN-4-S(O)Me-3-Py], [3168:2-OMe-4-S(O)Me-3-Py], [3169:5-OMe-4-S(O)Me-3-Py], [3170:6-OMe-4-S(O)Me-3-Py], [3171:5-S(O)Me-3-Py], [3172:2-Cl-5-S(O)Me-3-Py], [3173:4-Cl-5-S(O)Me-3-Py], [3174:6-Cl-5-S(O)Me-3-Py], [3175:2-Me-5-S(O)Me-3-Py], [3176:4-Me-5-S(O)Me-3-Py], [3177:6-Me-5-S(O)Me-3-Py], [3178:2-CF3-5-S(O)Me-3-Py], [3179:4-CF3-5-S(O)Me-3-Py], [3180:6-CF3-5-S(O)Me-3-Py], [3181:2-CN-5-S(O)Me-3-Py], [3182:4-CN-5-S(O)Me-3-Py], [3183:6-CN-5-S(O)Me-3-Py], [3184:2-OMe-5-S(O)Me-3-Py], [3185:4-OMe-5-S(O)Me-3-Py], [3186:6-OMe-5-S(O)Me-3-Py], [3187:6-S(O)Me-3-Py], [3188:2-Cl-6-S(O)Me-3-Py], [3189:4-Cl-6-S(O)Me-3-Py], [3190:5-Cl-6-S(O)Me-3-Py], [3191:2-Me-6-S(O)Me-3-Py], [3192:4-Me-6-S(O)Me-3-Py], [3193:5-Me-6-S(O)Me-3-Py], [3194:2-CF3-6-S(O)Me-3-Py], [3195:4-CF3-6-S(O)Me-3-Py], [3196:5-CF3-6-S(O)Me-3-Py], [3197:2-CN-6-S(O)Me-3-Py], [3198:4-CN-6-S(O)Me-3-Py], [3199:5-CN-6-S(O)Me-3-Py], [3200:2-OMe-6-S(O)Me-3-Py],
[3201:4-OMe-6-S(O)Me-3-Py], [3202:5-OMe-6-S(O)Me-3-Py], [3203:2-S(O)CF3-3-Py], [3204:4-Cl-2-S(O)CF3-3-Py], [3205:5-Cl-2-S(O)CF3-3-Py], [3206:6-Cl-2-S(O)CF3-3-Py], [3207:4-Me-2-S(O)CF3-3-Py], [3208:5-Me-2-S(O)CF3-3-Py], [3209:6-Me-2-S(O)CF3-3-Py], [3210:4-CF3-2-S(O)CF3-3-Py], [3211:5-CF3-2-S(O)CF3-3-Py], [3212:6-CF3-2-S(O)CF3-3-Py], [3213:4-CN-2-S(O)CF3-3-Py], [3214:5-CN-2-S(O)CF3-3-Py], [3215:6-CN-2-S(O)CF3-3-Py], [3216:4-OMe-2-S(O)CF3-3-Py], [3217:5-OMe-2-S(O)CF3-3-Py], [3218:6-OMe-2-S(O)CF3-3-Py], [3219:4-S(O)CF3-3-Py], [3220:2-Cl-4-S(O)CF3-3-Py], [3221:5-Cl-4-S(O)CF3-3-Py], [3222:6-Cl-4-S(O)CF3-3-Py], [3223:2-Me-4-S(O)CF3-3-Py], [3224:5-Me-4-S(O)CF3-3-Py], [3225:6-Me-4-S(O)CF3-3-Py], [3226:2-CF3-4-S(O)CF3-3-Py], [3227:5-CF3-4-S(O)CF3-3-Py], [3228:6-CF3-4-S(O)CF3-3-Py], [3229:2-CN-4-S(O)CF3-3-Py], [3230:5-CN-4-S(O)CF3-3-Py], [3231:6-CN-4-S(O)CF3-3-Py], [3232:2-OMe-4-S(O)CF3-3-Py], [3233:5-OMe-4-S(O)CF3-3-Py], [3234:6-OMe-4-S(O)CF3-3-Py], [3235:5-S(O)CF3-3-Py], [3236:2-Cl-5-S(O)CF3-3-Py], [3237:4-Cl-5-S(O)CF3-3-Py], [3238:6-Cl-5-S(O)CF3-3-Py], [3239:2-Me-5-S(O)CF3-3-Py], [3240:4-Me-5-S(O)CF3-3-Py], [3241:6-Me-5-S(O)CF3-3-Py], [3242:2-CF3-5-S(O)CF3-3-Py], [3243:4-CF3-5-S(O)CF3-3-Py], [3244:6-CF3-5-S(O)CF3-3-Py], [3245:2-CN-5-S(O)CF3-3-Py], [3246:4-CN-5-S(O)CF3-3-Py], [3247:6-CN-5-S(O)CF3-3-Py], [3248:2-OMe-5-S(O)CF3-3-Py], [3249:4-OMe-5-S(O)CF3-3-Py], [3250:6-OMe-5-S(O)CF3-3-Py], [3251:6-S(O)CF3-3-Py], [3252:2-Cl-6-S(O)CF3-3-Py], [3253:4-Cl-6-S(O)CF3-3-Py], [3254:5-Cl-6-S(O)CF3-3-Py], [3255:2-Me-6-S(O)CF3-3-Py], [3256:4-Me-6-S(O)CF3-3-Py], [3257:5-Me-6-S(O)CF3-3-Py], [3258:2-CF3-6-S(O)CF3-3-Py], [3259:4-CF3-6-S(O)CF3-3-Py], [3260:5-CF3-6-S(O)CF3-3-Py], [3261:2-CN-6-S(O)CF3-3-Py], [3262:4-CN-6-S(O)CF3-3-Py], [3263:5-CN-6-S(O)CF3-3-Py], [3264:2-OMe-6-S(O)CF3-3-Py], [3265:4-OMe-6-S(O)CF3-3-Py], [3266:5-OMe-6-S(O)CF3-3-Py], [3267:2-S(O)2Me-3-Py], [3268:4-Cl-2-S(O)2Me-3-Py], [3269:5-Cl-2-S(O)2Me-3-Py], [3270:6-Cl-2-S(O)2Me-3-Py], [3271:4-Me-2-S(O)2Me-3-Py], [3272:5-Me-2-S(O)2Me-3-Py], [3273:6-Me-2-S(O)2Me-3-Py], [3274:4-CF3-2-S(O)2Me-3-Py], [3275:5-CF3-2-S(O)2Me-3-Py], [3276:6-CF3-2-S(O)2Me-3-Py], [3277:4-CN-2-S(O)2Me-3-Py], [3278:5-CN-2-S(O)2Me-3-Py], [3279:6-CN-2-S(O)2Me-3-Py], [3280:4-OMe-2-S(O)2Me-3-Py], [3281:5-OMe-2-S(O)2Me-3-Py], [3282:6-OMe-2-S(O)2Me-3-Py], [3283:4-S(O)2Me-3-Py], [3284:2-Cl-4-S(O)2Me-3-Py], [3285:5-Cl-4-S(O)2Me-3-Py], [3286:6-Cl-4-S(O)2Me-3-Py], [3287:2-Me-4-S(O)2Me-3-Py], [3288:5-Me-4-S(O)2Me-3-Py], [3289:6-Me-4-S(O)2Me-3-Py], [3290:2-CF3-4-S(O)2Me-3-Py], [3291:5-CF3-4-S(O)2Me-3-Py], [3292:6-CF3-4-S(O)2Me-3-Py], [3293:2-CN-4-S(O)2Me-3-

Py], [3295:6-CN-4-S(O)2Me-3-Py], [3296:2-OMe-4-S(O)2Me-3-Py], [3297:5-OMe-4-S(O)2Me-3-Py], [3298:6-OMe-4-S(O)2Me-3-Py], [3299:5-S(O)2Me-3-Py], [3300:2-Cl-5-S(O)2Me-3-Py],
[3301:4-Cl-5-S(O)2Me-3-Py], [3302:6-Cl-5-S(O)2Me-3-Py], [3303:2-Me-5-S(O)2Me-3-Py], [3304:4-Me-5-S(O)2Me-3-Py], [3305:6-Me-5-S(O)2Me-3-Py], [3306:2-CF3-5-S(O)2Me-3-Py], [3307:4-CF3-5-S(O)2Me-3-Py], [3308:6-CF3-5-S(O)2Me-3-Py], [3309:2-CN-5-S(O)2Me-3-Py], [3310:4-CN-5-S(O)2Me-3-Py], [3311:6-CN-5-S(O)2Me-3-Py], [3312:2-OMe-5-S(O)2Me-3-Py], [3313:4-OMe-5-S(O)2Me-3-Py], [3314:6-OMe-5-S(O)2Me-3-Py], [3315:6-S(O)2Me-3-Py], [3316:2-Cl-6-S(O)2Me-3-Py], [3317:4-Cl-6-S(O)2Me-3-Py], [3318:5-Cl-6-S(O)2Me-3-Py], [3319:2-Me-6-S(O)2Me-3-Py], [3320:4-Me-6-S(O)2Me-3-Py], [3321:5-Me-6-S(O)2Me-3-Py], [3322:2-CF3-6-S(O)2Me-3-Py], [3323:4-CF3-6-S(O)2Me-3-Py], [3324:5-CF3-6-S(O)2Me-3-Py], [3325:2-CN-6-S(O)2Me-3-Py], [3326:4-CN-6-S(O)2Me-3-Py], [3327:5-CN-6-S(O)2Me-3-Py], [3328:2-OMe-6-S(O)2Me-3-Py], [3329:4-OMe-6-S(O)2Me-3-Py], [3330:5-OMe-6-S(O)2Me-3-Py], [3331:2-S(O)2CF3-3-Py], [3332:4-Cl-2-S(O)2CF3-3-Py], [3333:5-Cl-2-S(O)2CF3-3-Py], [3334:6-Cl-2-S(O)2CF3-3-Py], [3335:4-Me-2-S(O)2CF3-3-Py], [3336:5-Me-2-S(O)2CF3-3-Py], [3337:6-Me-2-S(O)2CF3-3-Py], [3338:4-CF3-2-S(O)2CF3-3-Py], [3339:5-CF3-2-S(O)2CF3-3-Py], [3340:6-CF3-2-S(O)2CF3-3-Py], [3341:4-CN-2-S(O)2CF3-3-Py], [3342:5-CN-2-S(O)2CF3-3-Py], [3343:6-CN-2-S(O)2CF3-3-Py], [3344:4-OMe-2-S(O)2CF3-3-Py], [3345:5-OMe-2-S(O)2CF3-3-Py], [3346:6-OMe-2-S(O)2CF3-3-Py], [3347:4-S(O)2CF3-3-Py], [3348:2-Cl-4-S(O)2CF3-3-Py], [3349:5-Cl-4-S(O)2CF3-3-Py], [3350:6-Cl-4-S(O)2CF3-3-Py], [3351:2-Me-4-S(O)2CF3-3-Py], [3352:5-Me-4-S(O)2CF3-3-Py], [3353:6-Me-4-S(O)2CF3-3-Py], [3354:2-CF3-4-S(O)2CF3-3-Py], [3355:5-CF3-4-S(O)2CF3-3-Py], [3356:6-CF3-4-S(O)2CF3-3-Py], [3357:2-CN-4-S(O)2CF3-3-Py], [3358:5-CN-4-S(O)2CF3-3-Py], [3359:6-CN-4-S(O)2CF3-3-Py], [3360:2-OMe-4-S(O)2CF3-3-Py], [3361:5-OMe-4-S(O)2CF3-3-Py], [3362:6-OMe-4-S(O)2CF3-3-Py], [3363:5-S(O)2CF3-3-Py], [3364:2-Cl-5-S(O)2CF3-3-Py], [3365:4-Cl-5-S(O)2CF3-3-Py], [3366:6-Cl-5-S(O)2CF3-3-Py], [3367:2-Me-5-S(O)2CF3-3-Py], [3368:4-Me-5-S(O)2CF3-3-Py], [3369:6-Me-5-S(O)2CF3-3-Py], [3370:2-CF3-5-S(O)2CF3-3-Py], [3371:4-CF3-5-S(O)2CF3-3-Py], [3372:6-CF3-5-S(O)2CF3-3-Py], [3373:2-CN-5-S(O)2CF3-3-Py], [3374:4-CN-5-S(O)2CF3-3-Py], [3375:6-CN-5-S(O)2CF3-3-Py], [3376:2-OMe-5-S(O)2CF3-3-Py], [3377:4-OMe-5-S(O)2CF3-3-Py], [3378:6-OMe-5-S(O)2CF3-3-Py], [3379:6-S(O)2CF3-3-Py], [3380:2-Cl-6-S(O)2CF3-3-Py], [3381:4-Cl-6-S(O)2CF3-3-Py], [3382:5-Cl-6-S(O)2CF3-3-Py], [3383:2-Me-6-S(O)2CF3-3-Py], [3384:4-Me-6-S(O)2CF3-3-Py], [3385:5-Me-6-S(O)2CF3-3-Py], [3386:2-CF3-6-S(O)2CF3-3-Py], [3387:4-CF3-6-S(O)2CF3-3-Py], [3388:5-CF3-6-S(O)2CF3-3-Py], [3389:2-CN-6-S(O)2CF3-3-Py], [3390:4-CN-6-S(O)2CF3-3-Py], [3391:5-CN-6-S(O)2CF3-3-Py], [3392:2-OMe-6-S(O)2CF3-3-Py], [3393:4-OMe-6-S(O)2CF3-3-Py], [3394:5-OMe-6-S(O)2CF3-3-Py], [3395:2-CN-3-Py], [3396:4-Cl-2-CN-3-Py], [3397:5-Cl-2-CN-3-Py], [3398:6-Cl-2-CN-3-Py], [3399:4-Me-2-CN-3-Py], [3400:5-Me-2-CN-3-Py],
[3401:6-Me-2-CN-3-Py], [3402:4-CF3-2-CN-3-Py], [3403:5-CF3-2-CN-3-Py], [3404:6-CF3-2-CN-3-Py], [3405:4-CN-2-CN-3-Py], [3406:5-CN-2-CN-3-Py], [3407:6-CN-2-CN-3-Py], [3408:4-OMe-2-CN-3-Py], [3409:5-OMe-2-CN-3-Py], [3410:6-OMe-2-CN-3-Py], [3411:4-CN-3-Py], [3412:2-Cl-4-CN-3-Py], [3413:5-Cl-4-CN-3-Py], [3414:6-Cl-4-CN-3-Py], [3415:2-Me-4-CN-3-Py], [3416:5-Me-4-CN-3-Py], [3417:6-Me-4-CN-3-Py], [3418:2-CF3-4-CN-3-Py], [3419:5-CF3-4-CN-3-Py], [3420:6-CF3-4-CN-3-Py], [3421:2-CN-4-CN-3-Py], [3422:5-CN-4-CN-3-Py], [3423:6-CN-4-CN-3-Py], [3424:2-OMe-4-CN-3-Py], [3425:5-OMe-4-CN-3-Py], [3426:6-OMe-4-CN-3-Py], [3427:5-CN-3-Py], [3428:2-Cl-5-CN-3-Py], [3429:4-Cl-5-CN-3-Py], [3430:6-Cl-5-CN-3-Py], [3431:2-Me-5-CN-3-Py], [3432:4-Me-5-CN-3-Py], [3433:6-Me-5-CN-3-Py], [3434:2-CF3-5-CN-3-Py], [3435:4-CF3-5-CN-3-Py], [3436:6-CF3-5-CN-3-Py], [3437:2-CN-5-CN-3-Py], [3438:4-CN-5-CN-3-Py], [3439:6-CN-5-CN-3-Py], [3440:2-OMe-5-CN-3-Py], [3441:4-OMe-5-CN-3-Py], [3442:6-OMe-5-CN-3-Py], [3443:6-CN-3-Py], [3444:2-Cl-6-CN-3-Py], [3445:4-Cl-6-CN-3-Py], [3446:5-Cl-6-CN-3-Py], [3447:2-Me-6-CN-3-Py], [3448:4-Me-6-CN-3-Py], [3449:5-Me-6-CN-3-Py], [3450:2-CF3-6-CN-3-Py], [3451:4-CF3-6-CN-3-Py], [3452:5-CF3-6-CN-3-Py], [3453:2-CN-6-CN-3-Py], [3454:4-CN-6-CN-3-Py], [3455:5-CN-6-CN-3-Py], [3456:2-OMe-6-CN-3-Py], [3457:4-OMe-6-CN-3-Py], [3458:5-OMe-6-CN-3-Py], [3459:2-COOMe-3-Py], [3460:4-Cl-2-COOMe-3-Py], [3461:5-Cl-2-COOMe-3-Py], [3462:6-Cl-2-COOMe-3-Py], [3463:4-Me-2-COOMe-3-Py], [3464:5-Me-2-COOMe-3-Py], [3465:6-Me-2-COOMe-3-Py], [3466:4-CF3-2-COOMe-3-Py], [3467:5-CF3-2-COOMe-3-Py], [3468:6-CF3-2-COOMe-3-Py], [3469:4-CN-2-COOMe-3-Py], [3470:5-CN-2-COOMe-3-Py], [3471:6-CN-2-COOMe-3-Py], [3472:4-OMe-2-COOMe-3-Py], [3473:5-OMe-2-COOMe-3-Py], [3474:6-OMe-2-COOMe-3-Py], [3475:4-COOMe-3-Py], [3476:2-Cl-4-COOMe-3-Py], [3477:5-Cl-4-COOMe-3-Py], [3478:6-Cl-4-COOMe-3-Py], [3479:2-Me-4-COOMe-3-Py], [3480:5-Me-4-COOMe-3-Py], [3481:6-Me-4-COOMe-3-Py], [3482:2-CF3-4-COOMe-3-Py], [3483:5-CF3-4-COOMe-3-Py], [3484:6-CF3-4-COOMe-3-Py], [3485:2-CN-4-COOMe-3-Py], [3486:5-CN-4-COOMe-3-Py], [3487:6-CN-4-COOMe-3-Py], [3488:2-OMe-4-COOMe-3-Py], [3489:5-OMe-4-COOMe-3-Py], [3490:6-OMe-4-COOMe-3-Py], [3491:5-COOMe-3-Py], [3492:2-Cl-5-COOMe-3-Py], [3493:4-Cl-5-COOMe-3-Py], [3494:6-Cl-5-COOMe-3-Py], [3495:2-Me-5-COOMe-3-Py], [3496:4-Me-5-COOMe-3-Py], [3497:6-Me-5-COOMe-3-Py], [3498:2-CF3-5-COOMe-3-Py], [3499:4-CF3-5-COOMe-3-Py], [3500:6-CF3-5-COOMe-3-Py],
[3501:2-CN-5-COOMe-3-Py], [3502:4-CN-5-COOMe-3-Py], [3503:6-CN-5-COOMe-3-Py], [3504:2-OMe-5-COOMe-3-Py], [3505:4-OMe-5-COOMe-3-Py], [3506:6-OMe-5-COOMe-3-Py], [3507:6-COOMe-3-Py], [3508:2-Cl-6-COOMe-3-Py], [3509:4-Cl-6-COOMe-3-Py], [3510:5-Cl-6-COOMe-3-Py], [3511:2-Me-6-COOMe-3-Py], [3512:4-Me-6-COOMe-3-Py], [3513:5-Me-6-COOMe-3-Py], [3514:2-CF3-6-COOMe-3-Py], [3515:4-CF3-6-COOMe-3-Py], [3516:5-CF3-6-COOMe-3-Py], [3517:2-CN-6-COOMe-3-Py], [3518:4-CN-6-COOMe-3-Py], [3519:5-CN-6-COOMe-3-Py], [3520:2-OMe-6-COOMe-3-Py], [3521:4-OMe-6-COOMe-3-Py], [3522:5-OMe-6-COOMe-3-Py], [3523:2-NO2-3-Py], [3524:4-Cl-2-NO2-3-Py], [3525:5-Cl-2-NO2-3-Py], [3526:6-Cl-2-NO2-3-Py], [3527:4-Me-2-NO2-3-Py], [3528:5-Me-2-NO2-3-Py], [3529:6-Me-2-NO2-3-Py], [3530:4-CF3-2-NO2-3-Py], [3531:5-CF3-2-NO2-3-Py], [3532:6-CF3-2-NO2-3-Py], [3533:4-CN-2-NO2-3-Py], [3534:5-CN-2-NO2-3-Py], [3535:6-CN-2-NO2-3-Py], [3536:4-OMe-2-NO2-3-Py], [3537:5-OMe-2-NO2-3-Py], [3538:6-OMe-2-NO2-3-Py], [3539:4-NO2-3-Py], [3540:2-Cl-4-NO2-3-Py], [3541:5-Cl-4-NO2-3-Py], [3542:6-Cl-4-NO2-3-Py], [3543:2-Me-4-NO2-3-Py], [3544:5-Me-4-NO2-3-Py], [3545:6-Me-4-NO2-3-Py], [3546:2-CF3-4-NO2-3-Py], [3547:5-CF3-4-

NO2-3-Py], [3548:6-CF3-4-NO2-3-Py], [3549:2-CN-4-NO2-3-Py], [3550:5-CN-4-NO2-3-Py], [3551:6-CN-4-NO2-3-Py], [3552:2-OMe-4-NO2-3-Py], [3553:5-OMe-4-NO2-3-Py], [3554:6-OMe-4-NO2-3-Py], [3555:5-NO2-3-Py], [3556:2-Cl-5-NO2-3-Py], [3557:4-Cl-5-NO2-3-Py], [3558:6-Cl-5-NO2-3-Py], [3559:2-Me-5-NO2-3-Py], [3560:4-Me-5-NO2-3-Py], [3561:6-Me-5-NO2-3-Py], [3562:2-CF3-5-NO2-3-Py], [3563:4-CF3-5-NO2-3-Py], [3564:6-CF3-5-NO2-3-Py], [3565:2-CN-5-NO2-3-Py], [3566:4-CN-5-NO2-3-Py], [3567:6-CN-5-NO2-3-Py], [3568:2-OMe-5-NO2-3-Py], [3569:4-OMe-5-NO2-3-Py], [3570:6-OMe-5-NO2-3-Py], [3571:6-NO2-3-Py], [3572:2-Cl-6-NO2-3-Py], [3573:4-Cl-6-NO2-3-Py], [3574:5-Cl-6-NO2-3-Py], [3575:2-Me-6-NO2-3-Py], [3576:4-Me-6-NO2-3-Py], [3577:5-Me-6-NO2-3-Py], [3578:2-CF3-6-NO2-3-Py], [3579:4-CF3-6-NO2-3-Py], [3580:5-CF3-6-NO2-3-Py], [3581:2-CN-6-NO2-3-Py], [3582:4-CN-6-NO2-3-Py], [3583:5-CN-6-NO2-3-Py], [3584:2-OMe-6-NO2-3-Py], [3585:4-OMe-6-NO2-3-Py], [3586:5-OMe-6-NO2-3-Py], [3587:2-NH2-3-Py], [3588:4-Cl-2-NH2-3-Py], [3589:5-Cl-2-NH2-3-Py], [3590:6-Cl-2-NH2-3-Py], [3591:4-Me-2-NH2-3-Py], [3592:5-Me-2-NH2-3-Py], [3593:6-Me-2-NH2-3-Py], [3594:4-CF3-2-NH2-3-Py], [3595:5-CF3-2-NH2-3-Py], [3596:6-CF3-2-NH2-3-Py], [3597:4-CN-2-NH2-3-Py], [3598:5-CN-2-NH2-3-Py], [3599:6-CN-2-NH2-3-Py], [3600:4-OMe-2-NH2-3-Py],
[3601:5-OMe-2-NH2-3-Py], [3602:6-OMe-2-NH2-3-Py], [3603:4-NH2-3-Py], [3604:2-Cl-4-NH2-3-Py], [3605:5-Cl-4-NH2-3-Py], [3606:6-Cl-4-NH2-3-Py], [3607:2-Me-4-NH2-3-Py], [3608:5-Me-4-NH2-3-Py], [3609:6-Me-4-NH2-3-Py], [3610:2-CF3-4-NH2-3-Py], [3611:5-CF3-4-NH2-3-Py], [3612:6-CF3-4-NH2-3-Py], [3613:2-CN-4-NH2-3-Py], [3614:5-CN-4-NH2-3-Py], [3615:6-CN-4-NH2-3-Py], [3616:2-OMe-4-NH2-3-Py], [3617:5-OMe-4-NH2-3-Py], [3618:6-OMe-4-NH2-3-Py], [3619:5-NH2-3-Py], [3620:2-Cl-5-NH2-3-Py], [3621:4-Cl-5-NH2-3-Py], [3622:6-Cl-5-NH2-3-Py], [3623:2-Me-5-NH2-3-Py], [3624:4-Me-5-NH2-3-Py], [3625:6-Me-5-NH2-3-Py], [3626:2-CF3-5-NH2-3-Py], [3627:4-CF3-5-NH2-3-Py], [3628:6-CF3-5-NH2-3-Py], [3629:2-CN-5-NH2-3-Py], [3630:4-CN-5-NH2-3-Py], [3631:6-CN-5-NH2-3-Py], [3632:2-OMe-5-NH2-3-Py], [3633:4-OMe-5-NH2-3-Py], [3634:6-OMe-5-NH2-3-Py], [3635:6-NH2-3-Py], [3636:2-Cl-6-NH2-3-Py], [3637:4-Cl-6-NH2-3-Py], [3638:5-Cl-6-NH2-3-Py], [3639:2-Me-6-NH2-3-Py], [3640:4-Me-6-NH2-3-Py], [3641:5-Me-6-NH2-3-Py], [3642:2-CF3-6-NH2-3-Py], [3643:4-CF3-6-NH2-3-Py], [3644:5-CF3-6-NH2-3-Py], [3645:2-CN-6-NH2-3-Py], [3646:4-CN-6-NH2-3-Py], [3647:5-CN-6-NH2-3-Py], [3648:2-OMe-6-NH2-3-Py], [3649:4-OMe-6-NH2-3-Py], [3650:5-OMe-6-NH2-3-Py], [3651:2-NHMe-3-Py], [3652:4-Cl-2-NHMe-3-Py], [3653:5-Cl-2-NHMe-3-Py], [3654:6-Cl-2-NHMe-3-Py], [3655:4-Me-2-NHMe-3-Py], [3656:5-Me-2-NHMe-3-Py], [3657:6-Me-2-NHMe-3-Py], [3658:4-CF3-2-NHMe-3-Py], [3659:5-CF3-2-NHMe-3-Py], [3660:6-CF3-2-NHMe-3-Py], [3661:4-CN-2-NHMe-3-Py], [3662:5-CN-2-NHMe-3-Py], [3663:6-CN-2-NHMe-3-Py], [3664:4-OMe-2-NHMe-3-Py], [3665:5-OMe-2-NHMe-3-Py], [3666:6-OMe-2-NHMe-3-Py], [3667:4-NHMe-3-Py], [3668:2-Cl-4-NHMe-3-Py], [3669:5-Cl-4-NHMe-3-Py], [3670:6-Cl-4-NHMe-3-Py], [3671:2-Me-4-NHMe-3-Py], [3672:5-Me-4-NHMe-3-Py], [3673:6-Me-4-NHMe-3-Py], [3674:2-CF3-4-NHMe-3-Py], [3675:5-CF3-4-NHMe-3-Py], [3676:6-CF3-4-NHMe-3-Py], [3677:2-CN-4-NHMe-3-Py], [3678:5-CN-4-NHMe-3-Py], [3679:6-CN-4-NHMe-3-Py], [3680:2-OMe-4-NHMe-3-Py], [3681:5-OMe-4-NHMe-3-Py], [3682:6-OMe-4-NHMe-3-Py], [3683:5-NHMe-3-Py], [3684:2-Cl-5-NHMe-3-Py], [3685:4-Cl-5-NHMe-3-Py], [3686:6-Cl-5-NHMe-3-Py], [3687:2-Me-5-NHMe-3-Py], [3688:4-Me-5-NHMe-3-Py], [3689:6-Me-5-NHMe-3-Py], [3690:2-CF3-5-NHMe-3-Py], [3691:4-CF3-5-NHMe-3-Py], [3692:6-CF3-5-NHMe-3-Py], [3693:2-CN-5-NHMe-3-Py], [3694:4-CN-5-NHMe-3-Py], [3695:6-CN-5-NHMe-3-Py], [3696:2-OMe-5-NHMe-3-Py], [3697:4-OMe-5-NHMe-3-Py], [3698:6-OMe-5-NHMe-3-Py], [3699:6-NHMe-3-Py], [3700:2-Cl-6-NHMe-3-Py], [3701:4-Cl-6-NHMe-3-Py], [3702:5-Cl-6-NHMe-3-Py], [3703:2-Me-6-NHMe-3-Py], [3704:4-Me-6-NHMe-3-Py], [3705:5-Me-6-NHMe-3-Py], [3706:2-CF3-6-NHMe-3-Py], [3707:4-CF3-6-NHMe-3-Py], [3708:5-CF3-6-NHMe-3-Py], [3709:2-CN-6-NHMe-3-Py], [3710:4-CN-6-NHMe-3-Py], [3711:5-CN-6-NHMe-3-Py], [3712:2-OMe-6-NHMe-3-Py], [3713:4-OMe-6-NHMe-3-Py], [3714:5-OMe-6-NHMe-3-Py], [3715:2-NMe2-3-Py], [3716:4-Cl-2-NMe2-3-Py], [3717:5-Cl-2-NMe2-3-Py], [3718:6-Cl-2-NMe2-3-Py], [3719:4-Me-2-NMe2-3-Py], [3720:5-Me-2-NMe2-3-Py], [3721:6-Me-2-NMe2-3-Py], [3722:4-CF3-2-NMe2-3-Py], [3723:5-CF3-2-NMe2-3-Py], [3724:6-CF3-2-NMe2-3-Py], [3725:4-CN-2-NMe2-3-Py], [3726:5-CN-2-NMe2-3-Py], [3727:6-CN-2-NMe2-3-Py], [3728:4-OMe-2-NMe2-3-Py], [3729:5-OMe-2-NMe2-3-Py], [3730:6-OMe-2NMe2-3-Py], [3731:4-NMe2-3-Py], [3732:2-Cl-4-NMe2-3-Py], [3733:5-Cl-4-NMe2-3-Py], [3734:6-Cl-4-NMe2-3-Py], [3735:2-Me-4-NMe2-3-Py], [3736:5-Me-4-NMe2-3-Py], [3737:6-Me-4-NMe2-3-Py], [3738:2-CF3-4-NMe2-3-Py], [3739:5-CF3-4-NMe2-3-Py], [3740:6-CF3-4-NMe2-3-Py], [3741:2-CN-4-NMe2-3-Py], [3742:5-CN-4-NMe2-3-Py], [3743:6-CN-4-NMe2-3-Py], [3744:2-OMe-4-NMe2-3-Py], [3745:5-OMe-4-NMe2-3-Py], [3746:6-OMe-4-NMe2-3-Py], [3747:5-NMe2-3-Py], [3748:2-Cl-5-NMe2-3-Py], [3749:4-Cl-5-NMe2-3-Py], [3750:6-Cl-5-NMe2-3-Py], [3751:2-Me-5-NMe2-3-Py], [3752:4-Me-5-NMe2-3-Py], [3753:6-Me-5-NMe2-3-Py], [3754:2-CF3-5-NMe2-3-Py], [3755:4-CF3-5-NMe2-3-Py], [3756:6-CF3-5-NMe2-3-Py], [3757:2-CN-5-NMe2-3-Py], [3758:4-CN-5-NMe2-3-Py], [3759:6-CN-5-NMe2-3-Py], [3760:2-OMe-5-NMe2-3-Py], [3761:4-OMe-5-NMe2-3-Py], [3762:6-OMe-5-NMe2-3-Py], [3763:6-NMe2-3-Py], [3764:2-Cl-6-NMe2-3-Py], [3765:4-Cl-6-NMe2-3-Py], [3766:5-Cl-6-NMe2-3-Py], [3767:2-Me-6-NMe2-3-Py], [3768:4-Me-6-NMe2-3-Py], [3769:5-Me-6-NMe2-3-Py], [3770:2-CF3-6-NMe2-3-Py], [3771:4-CF3-6-NMe2-3-Py], [3772:5-CF3-6-NMe2-3-Py], [3773:2-CN-6-NMe2-3-Py], [3774:4-CN-6-NMe2-3-Py], [3775:5-CN-6-NMe2-3-Py], [3776:2-OMe-6-NMe2-3-Py], [3777:4-OMe-6-NMe2-3-Py], [3778:5-OMe-6-NMe2-3-Py], [3779:2-ACNH-3-Py], [3780:4-Cl-2-ACNH-3-Py], [3781:5-Cl-2-ACNH-3-Py], [3782:6-Cl-2-ACNH-3-Py], [3783:4-Me-2-ACNH-3-Py], [3784:5-Me-2-ACNH-3-Py], [3785:6-Me-2-ACNH-3-Py], [3786:4-CF3-2-ACNH-3-Py], [3787:5-CF3-2-ACNH-3-Py], [3788:6-CF3-2-ACNH-3-Py], [3789:4-CN-2-ACNH-3-Py], [3790:5-CN-2-ACNH-3-Py], [3791:6-CN-2-ACNH-3-Py], [3792:4-OMe-2-ACNH-3-Py], [3793:5-OMe-2-ACNH-3-Py], [3794:6-OMe-2-ACNH-3-Py], [3795:4-ACNH-3-Py], [3796:2-Cl-4-ACNH-3-Py], [3797:5-Cl-4-ACNH-3-Py], [3798:6-Cl-4-ACNH-3-Py], [3799:2-Me-4-ACNH-3-Py], [3800:5-Me-4-ACNH-3-Py],
[3801:6-Me-4-ACNH-3-Py], [3802:2-CF3-4-ACNH-3-Py], [3803:5-CF3-4-ACNH-3-Py], [3804:6-CF3-4-ACNH-3-Py], [3805:2-CN-4-ACNH-3-Py], [3806:5-CN-4-ACNH-3-Py], [3807:6-CN-4-ACNH-3-Py], [3808:2-OMe-4-ACNH-3-Py], [3809:5-OMe-4-ACNH-3-Py], [3810:6-OMe-4-ACNH-3-Py], [3811:5-ACNH-3-Py], [3812:2-Cl-5-ACNH-3-Py], [3813:4-Cl-5-ACNH-3-Py], [3814:6-Cl-5-ACNH-3-Py], [3815:2-Me-5-ACNH-3-Py], [3816:4-Me-5-ACNH-3-

Py], [3817:6-Me-5-ACNH-3-Py], [3818:2-CF3-5-ACNH-3-Py], [3819:4-CF3-5-ACNH-3-Py], [3820:6-CF3-5-ACNH-3-Py], [3821:2-CN-5-ACNH-3-Py], [3822:4-CN-5-ACNH-3-Py], [3823:6-CN-5-ACNH-3-Py], [3824:2-OMe-5-ACNH-3-Py], [3825:4-OMe-5-ACNH-3-Py], [3826:6-OMe-5-ACNH-3-Py], [3827:6-ACNH-3-Py], [3828:2-Cl-6-ACNH-3-Py], [3829:4-Cl-6-ACNH-3-Py], [3830:5-Cl-6-ACNH-3-Py], [3831:2-Me-6-ACNH-3-Py], [3832:4-Me-6-ACNH-3-Py], [3833:5-Me-6-ACNH-3-Py], [3834:2-CF3-6-ACNH-3-Py], [3835:4-CF3-6-ACNH-3-Py], [3836:5-CF3-6-ACNH-3-Py], [3837:2-CN-6-ACNH-3-Py], [3838:4-CN-6-ACNH-3-Py], [3839:5-CN-6-ACNH-3-Py], [3840:2-OMe-6-ACNH-3-Py], [3841:4-OMe-6-ACNH-3-Py], [3842:5-OMe-6-ACNH-3-Py], [3843:2-(N-AC-N-Me-N)-3-Py], [3844:4-Cl-2-(N-AC-N-Me-N)-3-Py], [3845:5-Cl-2-(N-AC-N-Me-N)-3-Py], [3846:6-Cl-2-(N-AC-N-Me-N)-3-Py], [3847:4-Me-2-(N-AC-N-Me-N)-3-Py], [3848:5-Me-2-(N-AC-N-Me-N)-3-Py], [3849:6-Me-2-(N-AC-N-Me-N)-3-Py], [3850:4-CF3-2-(N-AC-N-Me-N)-3-Py], [3851:5-CF3-2-(N-AC-N-Me-N)-3-Py], [3852:6-CF3-2-(N-AC-N-Me-N)-3-Py], [3853:4-CN-2-(N-AC-N-Me-N)-3-Py], [3854:5-CN-2-(N-AC-N-Me-N)-3-Py], [3855:6-CN-2-(N-AC-N-Me-N)-3-Py], [3856:4-OMe-2-(N-AC-N-Me-N)-3-Py], [3857:5-OMe-2-(N-AC-N-Me-N)-3-Py], [3858:6-OMe-2-(N-AC-N-Me-N)-3-Py], [3859:4-(N-AC-N-Me-N)-3-Py], [3860:2-Cl-4-(N-AC-N-Me-N)-3-Py], [3861:5-Cl-4-(N-AC-N-Me-N)-3-Py], [3862:6-Cl-4-(N-AC-N-Me-N)-3-Py], [3863:2-Me-4-(N-AC-N-Me-N)-3-Py], [3864:5-Me-4-(N-AC-N-Me-N)-3-Py], [3865:6-Me-4-(N-AC-N-Me-N)-3-Py], [3866:2-CF3-4-(N-AC-N-Me-N)-3-Py], [3867:5-CF3-4-(N-AC-N-Me-N)-3-Py], [3868:6-CF3-4-(N-AC-N-Me-N)-3-Py], [3869:2-CN-4-(N-AC-N-Me-N)-3-Py], [3870:5-CN-4-(N-AC-N-Me-N)-3-Py], [3871:6-CN-4-(N-AC-N-Me-N)-3-Py], [3872:2-OMe-4-(N-AC-N-Me-N)-3-Py], [3873:5-OMe-4-(N-AC-N-Me-N)-3-Py], [3874:6-OMe-4-(N-AC-N-Me-N)-3-Py], [3875:5-(N-AC-N-Me-N)-3-Py], [3876:2-Cl-5-(N-AC-N-Me-N)-3-Py], [3877:4-Cl-5-(N-AC-N-Me-N)-3-Py], [3878:6-Cl-5-(N-AC-N-Me-N)-3-Py], [3879:2-Me-5-(N-AC-N-Me-N)-3-Py], [3880:4-Me-5-(N-AC-N-Me-N)-3-Py], [3881:6-Me-5-(N-AC-N-Me-N)-3-Py], [3882:2-CF3-5-(N-AC-N-Me-N)-3-Py], [3883:4-CF3-5-(N-AC-N-Me-N)-3-Py], [3884:6-CF3-5-(N-AC-N-Me-N)-3-Py], [3885:2-CN-5-(N-AC-N-Me-N)-3-Py], [3886:4-CN-5-(N-AC-N-Me-N)-3-Py], [3887:6-CN-5-(N-AC-N-Me-N)-3-Py], [3888:2-OMe-5-(N-AC-N-Me-N)-3-Py], [3889:4-OMe-5-(N-AC-N-Me-N)-3-Py], [3890:6-OMe-5-(N-AC-N-Me-N)-3-Py], [3891:6-(N-AC-N-Me-N)-3-Py], [3892:2-Cl-6-(N-AC-N-Me-N)-3-Py], [3893:4-Cl-6-(N-AC-N-Me-N)-3-Py], [3894:5-Cl-6-(N-AC-N-Me-N)-3-Py], [3895:2-Me-6-(N-AC-N-Me-N)-3-Py], [3896:4-Me-6-(N-AC-N-Me-N)-3-Py], [3897:5-Me-6-(N-AC-N-Me-N)-3-Py], [3898:2-CF3-6-(N-AC-N-Me-N)-3-Py], [3899:4-CF3-6-(N-AC-N-Me-N)-3-Py], [3900:5-CF3-6-(N-AC-N-Me-N)-3-Py],
[3901:2-CN-6-(N-AC-N-Me-N)-3-Py], [3902:4-CN-6-(N-AC-N-Me-N)-3-Py], [3903:5-CN-6-(N-AC-N-Me-N)-3-Py], [3904:2-OMe-6-(N-AC-N-Me-N)-3-Py], [3905:4-OMe-6-(N-AC-N-Me-N)-3-Py], [3906:5-OMe-6-(N-AC-N-Me-N)-3-Py], [3907:2-AC-3-Py], [3908:4-Cl-2-AC-3-Py], [3909:5-Cl-2-AC-3-Py], [3910:6-Cl-2-AC-3-Py], [3911:4-Me-2-AC-3-Py], [3912:5-Me-2-AC-3-Py], [3913:6-Me-2-AC-3-Py], [3914:4-CF3-2-AC-3-Py], [3915:5-CF3-2-AC-3-Py], [3916:6-CF3-2-AC-3-Py], [3917:4-CN-2-AC-3-Py], [3918:5-CN-2-AC-3-Py], [3919:6-CN-2-AC-3-Py], [3920:4-OMe-2-AC-3-Py], [3921:5-OMe-2-AC-3-Py], [3922:6-OMe-2-AC-3-Py], [3923:4-AC-3-Py], [3924:4-AC-3-Py], [3925:5-Cl-4-AC-3-Py], [3926:6-Cl-4-AC-3-Py], [3927:2-Me-4-AC-3-Py], [3928:5-Me-4-AC-3-Py], [3929:6-Me-4-AC-3-Py], [3930:2-CF3-4-AC-3-Py], [3931:5-CF3-4-AC-3-Py], [3932:6-CF3-4-AC-3-Py], [3933:2-CN-4-AC-3-Py], [3934:5-CN-4-AC-3-Py], [3935:6-CN-4-AC-3-Py], [3936:2-OMe-4-AC-3-Py], [3937:5-OMe-4-AC-3-Py], [3938:6-OMe-4-AC-3-Py], [3939:5-AC-3-Py], [3940:2-Cl-5-AC-3-Py], [3941:4-Cl-5-AC-3-Py], [3942:6-Cl-5-AC-3-Py], [3943:2-Me-5-AC-3-Py], [3944:4-Me-5-AC-3-Py], [3945:6-Me-5-AC-3-Py], [3946:2-CF3-5-AC-3-Py], [3947:4-CF3-5-AC-3-Py], [3948:6-CF3-5-AC-3-Py], [3949:2-CN-5-AC-3-Py], [3950:4-CN-5-AC-3-Py], [3951:6-CN-5-AC-3-Py], [3952:2-OMe-5-AC-3-Py], [3953:4-OMe-5-AC-3-Py], [3954:6-OMe-5-AC-3-Py], [3955:6-AC-3-Py], [3956:2-Cl-6-AC-3-Py], [3957:4-Cl-6-AC-3-Py], [3958:5-Cl-6-AC-3-Py], [3959:2-Me-6-AC-3-Py], [3960:4-Me-6-AC-3-Py], [3961:5-Me-6-AC-3-Py], [3962:2-CF3-6-AC-3-Py], [3963:4-CF3-6-AC-3-Py], [3964:5-CF3-6-AC-3-Py], [3965:2-CN-6-AC-3-Py], [3966:4-CN-6-AC-3-Py], [3967:5-CN-6-AC-3-Py], [3968:2-OMe-6-AC-3-Py], [3969:4-OMe-6-AC-3-Py], [3970:5-OMe-6-AC-3-Py], [3971:4-Py], [3972:3-F-4-Py], [3973:2-Cl-3-F-4-Py], [3974:5-Cl-3-F-4-Py], [3975:6-Cl-3-F-4-Py], [3976:2-Me-3-F-4-Py], [3977:5-Me-3-F-4-Py], [3978:6-Me-3-F-4-Py], [3979:2-CF3-3-F-4-Py], [3980:5-CF3-3-F-4-Py], [3981:6-CF3-3-F-4-Py], [3982:2-CN-3-F-4-Py], [3983:5-CN-3-F-4-Py], [3984:6-CN-3-F-4-Py], [3985:2-OMe-3-F-4-Py], [3986:5-OMe-3-F-4-Py], [3987:6-OMe-3-F-4-Py], [3988:2-F-4-Py], [3989:3-Cl-2-F-4-Py], [3990:5-Cl-2-F-4-Py], [3991:6-Cl-2-F-4-Py], [3992:3-Me-2-F-4-Py], [3993:5-Me-2-F-4-Py], [3994:6-Me-2-F-4-Py], [3995:3-CF3-2-F-4-Py], [3996:5-CF3-2-F-4-Py], [3997:6-CF3-2-F-4-Py], [3998:3-CN-2-F-4-Py], [3999:5-CN-2-F-4-Py], [4000:6-CN-2-F-4-Py],
[4001:3-OMe-2-F-4-Py], [4002:5-OMe-2-F-4-Py], [4003:6-OMe-2-F-4-Py], [4004:5-F-4-Py], [4005:3-Cl-5-F-4-Py], [4006:2-Cl-5-F-4-Py], [4007:6-Cl-5-F-4-Py], [4008:3-Me-5-F-4-Py], [4009:2-Me-5-F-4-Py], [4010:6-Me-5-F-4-Py], [4011:3-CF3-5-F-4-Py], [4012:2-CF3-5-F-4-Py], [4013:6-CF3-5-F-4-Py], [4014:3-CN-5-F-4-Py], [4015:2-CN-5-F-4-Py], [4016:6-CN-5-F-4-Py], [4017:3-OMe-5-F-4-Py], [4018:2-OMe-5-F-4-Py], [4019:6-OMe-5-F-4-Py], [4020:6-F-4-Py], [4021:3-Cl-6-F-4-Py], [4022:2-Cl-6-F-4-Py], [4023:5-Cl-6-F-4-Py], [4024:3-Me-6-F-4-Py], [4025:2-Me-6-F-4-Py], [4026:5-Me-6-F-4-Py], [4027:3-CF3-6-F-4-Py], [4028:2-CF3-6-F-4-Py], [4029:5-CF3-6-F-4-Py], [4030:3-CN-6-F-4-Py], [4031:2-CN-6-F-4-Py], [4032:5-CN-6-F-4-Py], [4033:3-OMe-6-F-4-Py], [4034:2-OMe-6-F-4-Py], [4035:5-OMe-6-F-4-Py], [4036:3-Cl-4-Py], [4037:2-Cl-3-Cl-4-Py], [4038:5-Cl-3-Cl-4-Py], [4039:6-Cl-3-Cl-4-Py], [4040:2-Me-3-Cl-4-Py], [4041:5-Me-3-Cl-4-Py], [4042:6-Me-3-Cl-4-Py], [4043:2-CF3-3-Cl-4-Py], [4044:5-CF3-3-Cl-4-Py], [4045:6-CF3-3-Cl-4-Py], [4046:2-CN-3-Cl-4-Py], [4047:5-CN-3-Cl-4-Py], [4048:6-CN-3-Cl-4-Py], [4049:2-OMe-3-Cl-4-Py], [4050:5-OMe-3-Cl-4-Py], [4051:6-OMe-3-Cl-4-Py], [4052:2-Cl-4-Py], [4053:3-Cl-2-Cl-4-Py], [4054:5-Cl-2-Cl-4-Py], [4055:6-Cl-2-Cl-4-Py], [4056:3-Me-2-Cl-4-Py], [4057:5-Me-2-Cl-4-Py], [4058:6-Me-2-Cl-4-Py], [4059:3-CF3-2-Cl-4-Py], [4060:5-CF3-2-Cl-4-Py], [4061:6-CF3-2-Cl-4-Py], [4062:3-CN-2-Cl-4-Py], [4063:5-CN-2-Cl-4-Py], [4064:6-CN-2-Cl-4-Py], [4065:3-OMe-2-Cl-4-Py], [4066:5-OMe-2-Cl-4-Py], [4067:6-OMe-2-Cl-4-Py], [4068:5-Cl-4-Py], [4069:2-Cl-5-Cl-4-Py], [4070:5-Cl-5-Cl-4-Py], [4071:6-Cl-5-Cl-4-Py], [4072:2-Me-5-Cl-4-Py], [4073:5-Me-5-Cl-4-Py], [4074:6-Me-5-Cl-4-Py], [4075:2-CF3-5-Cl-4-Py], [4076:5-CF3-5-Cl-4-Py], [4077:6-CF3-5-Cl-4-Py], [4078:2-CN-5-Cl-4-Py], [4079:3-CN-5-Cl-4-Py], [4080:6-CN-5-Cl-4-Py], [4081:2-OMe-5-Cl-4-Py], [4082:5-OMe-5-Cl-4-Py], [4083:6-OMe-5-Cl-4-Py], [4084:6-Cl-

4-Py], [4085:3-Cl-6-Cl-4-Py], [4086:2-Cl-6-Cl-4-Py], [4087:5-Cl-6-Cl-4-Py], [4088:3-Me-6-Cl-4-Py], [4089:2-Me-6-Cl-4-Py], [4090:5-Me-6-Cl-4-Py], [4091:3-CF3-6-Cl-4-Py], [4092:2-CF3-6-Cl-4-Py], [4093:5-CF3-6-Cl-4-Py], [4094:3-CN-6-Cl-4-Py], [4095:2-CN-6-Cl-4-Py], [4096:5-CN-6-Cl-4-Py], [4097:3-OMe-6-Cl-4-Py], [4098:2-OMe-6-Cl-4-Py], [4099:5-OMe-6-Cl-4-Py], [4100:3-Br-4-Py], [4101:2-Cl-3-Br-4-Py], [4102:5-Cl-3-Br-4-Py], [4103:6-Cl-3-Br-4-Py], [4104:2-Me-3-Br-4-Py], [4105:5-Me-3-Br-4-Py], [4106:6-Me-3-Br-4-Py], [4107:2-CF3-3-Br-4-Py], [4108:5-CF3-3-Br-4-Py], [4109:6-CF3-3-Br-4-Py], [4110:2-CN-3-Br-4-Py], [4111:5-CN-3-Br-4-Py], [4112:6-CN-3-Br-4-Py], [4113:2-OMe-3-Br-4-Py], [4114:5-OMe-3-Br-4-Py], [4115:6-OMe-3-Br-4-Py], [4116:2-Br-4-Py], [4117:3-Cl-2-Br-4-Py], [4118:5-Cl-2-Br-4-Py], [4119:6-Cl-2-Br-4-Py], [4120:3-Me-2-Br-4-Py], [4121:5-Me-2-Br-4-Py], [4122:6-Me-2-Br-4-Py], [4123:3-CF3-2-Br-4-Py], [4124:5-CF3-2-Br-4-Py], [4125:6-CF3-2-Br-4-Py], [4126:3-CN-2-Br-4-Py], [4127:5-CN-2-Br-4-Py], [4128:6-CN-2-Br-4-Py], [4129:3-OMe-2-Br-4-Py], [4130:5-OMe-2-Br-4-Py], [4131:6-OMe-2-Br-4-Py], [4132:5-Br-4-Py], [4133:3-Cl-5-Br-4-Py], [4134:2-Cl-5-Br-4-Py], [4135:6-Cl-5-Br-4-Py], [4136:3-Me-5-Br-4-Py], [4137:2-Me-5-Br-4-Py], [4138:6-Me-5-Br-4-Py], [4139:3-CF3-5-Br-4-Py], [4140:2-CF3-5-Br-4-Py], [4141:6-CF3-5-Br-4-Py], [4142:3-CN-5-Br-4-Py], [4143:2-CN-5-Br-4-Py], [4144:6-CN-5-Br-4-Py], [4145:3-OMe-5-Br-4-Py], [4146:2-OMe-5-Br-4-Py], [4147:6-OMe-5-Br-4-Py], [4148:6-Br-4-Py], [4149:3-Cl-6-Br-4-Py], [4150:2-Cl-6-Br-4-Py], [4151:5-Cl-6-Br-4-Py], [4152:3-Me-6-Br-4-Py], [4153:2-Me-6-Br-4-Py], [4154:5-Me-6-Br-4-Py], [4155:3-CF3-6-Br-4-Py], [4156:2-CF3-6-Br-4-Py], [4157:5-CF3-6-Br-4-Py], [4158:3-CN-6-Br-4-Py], [4159:2-CN-6-Br-4-Py], [4160:5-CN-6-Br-4-Py], [4161:3-OMe-6-Br-4-Py], [4162:2-OMe-6-Br-4-Py], [4163:5-OMe-6-Br-4-Py], [4164:3-I-4-Py], [4165:2-Cl-3-I-4-Py], [4166:5-Cl-3-I-4-Py], [4167:6-Cl-3-I-4-Py], [4168:2-Me-3-I-4-Py], [4169:5-Me-3-I-4-Py], [4170:6-Me-3-I-4-Py], [4171:2-CF3-3-I-4-Py], [4172:5-CF3-3-I-4-Py], [4173:6-CF3-3-I-4-Py], [4174:2-CN-3-I-4-Py], [4175:5-CN-3-I-4-Py], [4176:6-CN-3-I-4-Py], [4177:2-OMe-3-I-4-Py], [4178:5-OMe-3-I-4-Py], [4179:6-OMe-3-I-4-Py], [4180:2-I-4-Py], [4181:3-Cl-2-I-4-Py], [4182:5-Cl-2-I-4-Py], [4183:6-Cl-2-I-4-Py], [4184:3-Me-2-I-4-Py], [4185:5-Me-2-I-4-Py], [4186:6-Me-2-I-4-Py], [4187:3-CF3-2-I-4-Py], [4188:5-CF3-2-I-4-Py], [4189:6-CF3-2-I-4-Py], [4190:3-CN-2-I-4-Py], [4191:5-CN-2-I-4-Py], [4192:6-CN-2-I-4-Py], [4193:3-OMe-2-I-4-Py], [4194:5-OMe-2-I-4-Py], [4195:6-OMe-2-I-4-Py], [4196:5-I-4-Py], [4197:3-Cl-5-I-4-Py], [4198:2-Cl-5-I-4-Py], [4199:6-Cl-5-I-4-Py], [4200:3-Me-5-I-4-Py],
[4201:2-Me-5-I-4-Py], [4202:6-Me-5-I-4-Py], [4203:3-CF3-5-I-4-Py], [4204:2-CF3-5-I-4-Py], [4205:6-CF3-5-I-4-Py], [4206:3-CN-5-I-4-Py], [4207:2-CN-5-I-4-Py], [4208:6-CN-5-I-4-Py], [4209:3-OMe-5-I-4-Py], [4210:2-OMe-5-I-4-Py], [4211:6-OMe-5-I-4-Py], [4212:6-I-4-Py], [4213:3-Cl-6-I-4-Py], [4214:2-Cl-6-I-4-Py], [4215:5-Cl-6-I-4-Py], [4216:3-Me-6-I-4-Py], [4217:2-Me-6-I-4-Py], [4218:5-Me-6-I-4-Py], [4219:3-CF3-6-I-4-Py], [4220:2-CF3-6-I-4-Py], [4221:5-CF3-6-I-4-Py], [4222:3-CN-6-I-4-Py], [4223:2-CN-6-I-4-Py], [4224:5-CN-6-I-4-Py], [4225:3-OMe-6-I-4-Py], [4226:2-OMe-6-I-4-Py], [4227:5-OMe-6-I-4-Py], [4228:3-Me-4-Py], [4229:2-Cl-3-Me-4-Py], [4230:5-Cl-3-Me-4-Py], [4231:6-Cl-3-Me-4-Py], [4232:2-Me-3-Me-4-Py], [4233:5-Me-3-Me-4-Py], [4234:6-Me-3-Me-4-Py], [4235:2-CF3-3-Me-4-Py], [4236:5-CF3-3-Me-4-Py], [4237:6-CF3-3-Me-4-Py], [4238:2-CN-3-Me-4-Py], [4239:5-CN-3-Me-4-Py], [4240:6-CN-3-Me-4-Py], [4241:2-OMe-3-Me-4-Py], [4242:5-OMe-3-Me-4-Py], [4243:6-OMe-3-Me-4-Py], [4244:2-Me-4-Py], [4245:3-Cl-2-Me-4-Py], [4246:5-Cl-2-Me-4-Py], [4247:6-Cl-2-Me-4-Py], [4248:3-Me-2-Me-4-Py], [4249:5-Me-2-Me-4-Py], [4250:6-Me-2-Me-4-Py], [4251:3-CF3-2-Me-4-Py], [4252:5-CF3-2-Me-4-Py], [4253:6-CF3-2-Me-4-Py], [4254:3-CN-2-Me-4-Py], [4255:5-CN-2-Me-4-Py], [4256:6-CN-2-Me-4-Py], [4257:3-OMe-2-Me-4-Py], [4258:5-OMe-2-Me-4-Py], [4259:6-OMe-2-Me-4-Py], [4260:5-Me-4-Py], [4261:3-Cl-5-Me-4-Py], [4262:2-Cl-5-Me-4-Py], [4263:6-Cl-5-Me-4-Py], [4264:3-Me-5-Me-4-Py], [4265:2-Me-5-Me-4-Py], [4266:6-Me-5-Me-4-Py], [4267:3-CF3-5-Me-4-Py], [4268:2-CF3-5-Me-4-Py], [4269:6-CF3-5-Me-4-Py], [4270:3-CN-5-Me-4-Py], [4271:2-CN-5-Me-4-Py], [4272:6-CN-5-Me-4-Py], [4273:3-OMe-5-Me-4-Py], [4274:2-OMe-5-Me-4-Py], [4275:6-OMe-5-Me-4-Py], [4276:6-Me-4-Py], [4277:3-Cl-6-Me-4-Py], [4278:2-Cl-6-Me-4-Py], [4279:5-Cl-6-Me-4-Py], [4280:3-Me-6-Me-4-Py], [4281:2-Me-6-Me-4-Py], [4282:5-Me-6-Me-4-Py], [4283:3-CF3-6-Me-4-Py], [4284:2-CF3-6-Me-4-Py], [4285:5-CF3-6-Me-4-Py], [4286:3-CN-6-Me-4-Py], [4287:2-CN-6-Me-4-Py], [4288:5-CN-6-Me-4-Py], [4289:3-OMe-6-Me-4-Py], [4290:2-OMe-6-Me-4-Py], [4291:5-OMe-6-Me-4-Py], [4292:3-OMe-4-Py], [4293:2-Cl-3-OMe-4-Py], [4294:5-Cl-3-OMe-4-Py], [4295:6-Cl-3-OMe-4-Py], [4296:2-Me-3-OMe-4-Py], [4297:5-Me-3-OMe-4-Py], [4298:6-Me-3-OMe-4-Py], [4299:2-CF3-3-OMe-4-Py], [4300:5-CF3-3-OMe-4-Py],
[4301:6-CF3-3-OMe-4-Py], [4302:2-CN-3-OMe-4-Py], [4303:5-CN-3-OMe-4-Py], [4304:6-CN-3-OMe-4-Py], [4305:2-OMe-3-OMe-4-Py], [4306:5-OMe-3-OMe-4-Py], [4307:6-OMe-3-OMe-4-Py], [4308:2-OMe-4-Py], [4309:3-Cl-2-OMe-4-Py], [4310:5-Cl-2-OMe-4-Py], [4311:6-Cl-2-OMe-4-Py], [4312:3-Me-2-OMe-4-Py], [4313:5-Me-2-OMe-4-Py], [4314:6-Me-2-OMe-4-Py], [4315:3-CF3-2-OMe-4-Py], [4316:5-CF3-2-OMe-4-Py], [4317:6-CF3-2-OMe-4-Py], [4318:3-CN-2-OMe-4-Py], [4319:5-CN-2-OMe-4-Py], [4320:6-CN-2-OMe-4-Py], [4321:3-OMe-2-OMe-4-Py], [4322:5-OMe-2-OMe-4-Py], [4323:6-OMe-2-OMe-4-Py], [4324:5-OMe-4-Py], [4325:3-Cl-5-OMe-4-Py], [4326:2-Cl-5-OMe-4-Py], [4327:6-Cl-5-OMe-4-Py], [4328:3-Me-5-OMe-4-Py], [4329:2-Me-5-OMe-4-Py], [4330:6-Me-5-OMe-4-Py], [4331:3-CF3-5-OMe-4-Py], [4332:2-CF3-5-OMe-4-Py], [4333:6-CF3-5-OMe-4-Py], [4334:3-CN-5-OMe-4-Py], [4335:2-CN-5-OMe-4-Py], [4336:6-CN-5-OMe-4-Py], [4337:3-OMe-5-OMe-4-Py], [4338:2-OMe-5-OMe-4-Py], [4339:6-OMe-5-OMe-4-Py], [4340:6-OMe-4-Py], [4341:3-Cl-6-OMe-4-Py], [4342:2-Cl-6-OMe-4-Py], [4343:5-Cl-6-OMe-4-Py], [4344:3-Me-6-OMe-4-Py], [4345:2-Me-6-OMe-4-Py], [4346:5-Me-6-OMe-4-Py], [4347:3-CF3-6-OMe-4-Py], [4348:2-CF3-6-OMe-4-Py], [4349:5-CF3-6-OMe-4-Py], [4350:3-CN-6-OMe-4-Py], [4351:2-CN-6-OMe-4-Py], [4352:5-CN-6-OMe-4-Py], [4353:3-OMe-6-OMe-4-Py], [4354:2-OMe-6-OMe-4-Py], [4355:5-OMe-6-OMe-4-Py], [4356:3-CF3-4-Py], [4357:2-Cl-3-CF3-4-Py], [4358:5-Cl-3-CF3-4-Py], [4359:6-Cl-3-CF3-4-Py], [4360:2-Me-3-CF3-4-Py], [4361:5-Me-3-CF3-4-Py], [4362:6-Me-3-CF3-4-Py], [4363:2-CF3-3-CF3-4-Py], [4364:5-CF3-3-CF3-4-Py], [4365:6-CF3-3-CF3-4-Py], [4366:2-CN-3-CF3-4-Py], [4367:5-CN-3-CF3-4-Py], [4368:6-CN-3-CF3-4-Py], [4369:2-OMe-3-CF3-4-Py], [4370:5-OMe-3-CF3-4-Py], [4371:6-OMe-3-CF3-4-Py], [4372:2-CF3-4-Py], [4373:3-Cl-2-CF3-4-Py], [4374:5-Cl-2-CF3-4-Py], [4375:6-Cl-2-CF3-4-Py], [4376:3-Me-2-CF3-4-Py], [4377:5-Me-2-CF3-4-Py], [4378:6-Me-2-CF3-4-Py], [4379:3-CF3-2-CF3-4-Py], [4380:5-CF3-2-CF3-4-Py], [4381:6-CF3-2-CF3-4-Py], [4382:3-CN-2-CF3-4-Py], [4383:5-CN-2-CF3-4-Py], [4384:6-CN-2-CF3-4-Py], [4385:3-OMe-2-CF3-4-Py], [4386:5-OMe-2-CF3-4-Py],

[4387:6-OMe-2-CF3-4-Py], [4388:5-CF3-4-Py], [4389:3-Cl-5-CF3-4-Py], [4390:2-Cl-5-CF3-4-Py], [4391:6-Cl-5-CF3-4-Py], [4392:3-Me-5-CF3-4-Py], [4393:2-Me-5-CF3-4-Py], [4394:6-Me-5-CF3-4-Py], [4395:3-CF3-5-CF3-4-Py], [4396:2-CF3-5-CF3-4-Py], [4397:6-CF3-5-CF3-4-Py], [4398:3-CN-5-CF3-4-Py], [4399:2-CN-5-CF3-4-Py], [4400:6-CN-5-CF3-4-Py],
[4401:3-OMe-5-CF3-4-Py], [4402:2-OMe-5-CF3-4-Py], [4403:6-OMe-5-CF3-4-Py], [4404:6-CF3-4-Py], [4405:3-Cl-6-CF3-4-Py], [4406:2-Cl-6-CF3-4-Py], [4407:5-Cl-6-CF3-4-Py], [4408:3-Me-6-CF3-4-Py], [4409:2-Me-6-CF3-4-Py], [4410:5-Me-6-CF3-4-Py], [4411:3-CF3-6-CF3-4-Py], [4412:2-CF3-6-CF3-4-Py], [4413:5-CF3-6-CF3-4-Py], [4414:3-CN-6-CF3-4-Py], [4415:2-CN-6-CF3-4-Py], [4416:5-CN-6-CF3-4-Py], [4417:3-OMe-6-CF3-4-Py], [4418:2-OMe-6-CF3-4-Py], [4419:5-OMe-6-CF3-4-Py], [4420:3-OCF3-4-Py], [4421:2-Cl-3-OCF3-4-Py], [4422:5-Cl-3-OCF3-4-Py], [4423:6-Cl-3-OCF3-4-Py], [4424:2-Me-3-OCF3-4-Py], [4425:5-Me-3-OCF3-4-Py], [4426:6-Me-3-OCF3-4-Py], [4427:2-CF3-3-OCF3-4-Py], [4428:5-CF3-3-OCF3-4-Py], [4429:6-CF3-3-OCF3-4-Py], [4430:2-CN-3-OCF3-4-Py], [4431:5-CN-3-OCF3-4-Py], [4432:6-CN-3-OCF3-4-Py], [4433:2-OMe-3-OCF3-4-Py], [4434:5-OMe-3-OCF3-4-Py], [4435:6-OMe-3-OCF3-4-Py], [4436:2-OCF3-4-Py], [4437:3-Cl-2-OCF3-4-Py], [4438:5-Cl-2-OCF3-4-Py], [4439:6-Cl-2-OCF3-4-Py], [4440:3-Me-2-OCF3-4-Py], [4441:5-Me-2-OCF3-4-Py], [4442:6-Me-2-OCF3-4-Py], [4443:3-CF3-2-OCF3-4-Py], [4444:5-CF3-2-OCF3-4-Py], [4445:6-CF3-2-OCF3-4-Py], [4446:3-CN-2-OCF3-4-Py], [4447:5-CN-2-OCF3-4-Py], [4448:6-CN-2-OCF3-4-Py], [4449:3-OMe-2-OCF3-4-Py], [4450:5-OMe-2-OCF3-4-Py], [4451:6-OMe-2-OCF3-4-Py], [4452:5-OCF3-4-Py], [4453:3-Cl-5-OCF3-4-Py], [4454:2-Cl-5-OCF3-4-Py], [4455:6-Cl-5-OCF3-4-Py], [4456:3-Me-5-OCF3-4-Py], [4457:2-Me-5-OCF3-4-Py], [4458:6-Me-5-OCF3-4-Py], [4459:3-CF3-5-OCF3-4-Py], [4460:2-CF3-5-OCF3-4-Py], [4461:6-CF3-5-OCF3-4-Py], [4462:3-CN-5-OCF3-4-Py], [4463:2-CN-5-OCF3-4-Py], [4464:6-CN-5-OCF3-4-Py], [4465:3-OMe-5-OCF3-4-Py], [4466:2-OMe-5-OCF3-4-Py], [4467:6-OMe-5-OCF3-4-Py], [4468:6-OCF3-4-Py], [4469:3-Cl-6-OCF3-4-Py], [4470:2-Cl-6-OCF3-4-Py], [4471:5-Cl-6-OCF3-4-Py], [4472:3-Me-6-OCF3-4-Py], [4473:2-Me-6-OCF3-4-Py], [4474:5-Me-6-OCF3-4-Py], [4475:3-CF3-6-OCF3-4-Py], [4476:2-CF3-6-OCF3-4-Py], [4477:5-CF3-6-OCF3-4-Py], [4478:3-CN-6-OCF3-4-Py], [4479:2-CN-6-OCF3-4-Py], [4480:5-CN-6-OCF3-4-Py], [4481:3-OMe-6-OCF3-4-Py], [4482:2-OMe-6-OCF3-4-Py], [4483:5-OMe-6-OCF3-4-Py], [4484:3-CHF2-4-Py], [4485:2-Cl-3-CHF2-4-Py], [4486:5-Cl-3-CHF2-4-Py], [4487:6-Cl-3-CHF2-4-Py], [4488:2-Me-3-CHF2-4-Py], [4489:5-Me-3-CHF2-4-Py], [4490:6-Me-3-CHF2-4-Py], [4491:2-CF3-3-CHF2-4-Py], [4492:5-CF3-3-CHF2-4-Py], [4493:6-CF3-3-CHF2-4-Py], [4494:2-CN-3-CHF2-4-Py], [4495:5-CN-3-CHF2-4-Py], [4496:6-CN-3-CHF2-4-Py], [4497:2-OMe-3-CHF2-4-Py], [4498:5-OMe-3-CHF2-4-Py], [4499:6-OMe-3-CHF2-4-Py], [4500:4-CHF2-4-Py],
[4501:3-Cl-4-CHF2-4-Py], [4502:5-Cl-4-CHF2-4-Py], [4503:6-Cl-4-CHF2-4-Py], [4504:3-Me-4-CHF2-4-Py], [4505:5-Me-4-CHF2-4-Py], [4506:6-Me-4-CHF2-4-Py], [4507:3-CF3-4-CHF2-4-Py], [4508:5-CF3-4-CHF2-4-Py], [4509:6-CF3-4-CHF2-4-Py], [4510:3-CN-4-CHF2-4-Py], [4511:5-CN-4-CHF2-4-Py], [4512:6-CN-4-CHF2-4-Py], [4513:3-OMe-4-CHF2-4-Py], [4514:5-OMe-4-CHF2-4-Py], [4515:6-OMe-4-CHF2-4-Py], [4516:5-CHF2-4-Py], [4517:3-Cl-5-CHF2-4-Py], [4518:2-Cl-5-CHF2-4-Py], [4519:6-Cl-5-CHF2-4-Py], [4520:3-Me-5-CHF2-4-Py], [4521:2-Me-5-CHF2-4-Py], [4522:6-Me-5-CHF2-4-Py], [4523:3-CF3-5-CHF2-4-Py], [4524:2-CF3-5-CHF2-4-Py], [4525:6-CF3-5-CHF2-4-Py], [4526:3-CN-5-CHF2-4-Py], [4527:2-CN-5-CHF2-4-Py], [4528:6-CN-5-CHF2-4-Py], [4529:3-OMe-5-CHF2-4-Py], [4530:2-OMe-5-CHF2-4-Py], [4531:6-OMe-5-CHF2-4-Py], [4532:6-CHF2-4-Py], [4533:3-Cl-6-CHF2-4-Py], [4534:2-Cl-6-CHF2-4-Py], [4535:5-Cl-6-CHF2-4-Py], [4536:3-Me-6-CHF2-4-Py], [4537:2-Me-6-CHF2-4-Py], [4538:5-Me-6-CHF2-4-Py], [4539:3-CF3-6-CHF2-4-Py], [4540:2-CF3-6-CHF2-4-Py], [4541:5-CF3-6-CHF2-4-Py], [4542:3-CN-6-CHF2-4-Py], [4543:2-CN-6-CHF2-4-Py], [4544:5-CN-6-CHF2-4-Py], [4545:3-OMe-6-CHF2-4-Py], [4546:2-OMe-6-CHF2-4-Py], [4547:5-OMe-6-CHF2-4-Py], [4548:3-OCHF2-4-Py], [4549:2-Cl-3-OCHF2-4-Py], [4550:5-Cl-3-OCHF2-4-Py], [4551:6-Cl-3-OCHF2-4-Py], [4552:2-Me-3-OCHF2-4-Py], [4553:5-Me-3-OCHF2-4-Py], [4554:6-Me-3-OCHF2-4-Py], [4555:2-CF3-3-OCHF2-4-Py], [4556:5-CF3-3-OCHF2-4-Py], [4557:6-CF3-3-OCHF2-4-Py], [4558:2-CN-3-OCHF2-4-Py], [4559:5-CN-3-OCHF2-4-Py], [4560:6-CN-3-OCHF2-4-Py], [4561:2-OMe-3-OCHF2-4-Py], [4562:5-OMe-3-OCHF2-4-Py], [4563:6-OMe-3-OCHF2-4-Py], [4564:4-OCHF2-4-Py], [4565:3-Cl-4-OCHF2-4-Py], [4566:5-Cl-4-OCHF2-4-Py], [4567:6-Cl-4-OCHF2-4-Py], [4568:3-Me-4-OCHF2-4-Py], [4569:5-Me-4-OCHF2-4-Py], [4570:6-Me-4-OCHF2-4-Py], [4571:3-CF3-4-OCHF2-4-Py], [4572:5-CF3-4-OCHF2-4-Py], [4573:6-CF3-4-OCHF2-4-Py], [4574:3-CN-4-OCHF2-4-Py], [4575:5-CN-4-OCHF2-4-Py], [4576:6-CN-4-OCHF2-4-Py], [4577:3-OMe-4-OCHF2-4-Py], [4578:5-OMe-4-OCHF2-4-Py], [4579:6-OMe-4-OCHF2-4-Py], [4580:5-OCHF2-4-Py], [4581:3-Cl-5-OCHF2-4-Py], [4582:2-Cl-5-OCHF2-4-Py], [4583:6-Cl-5-OCHF2-4-Py], [4584:3-Me-5-OCHF2-4-Py], [4585:2-Me-5-OCHF2-4-Py], [4586:6-Me-5-OCHF2-4-Py], [4587:3-CF3-5-OCHF2-4-Py], [4588:2-CF3-5-OCHF2-4-Py], [4589:6-CF3-5-OCHF2-4-Py], [4590:3-CN-5-OCHF2-4-Py], [4591:2-CN-5-OCHF2-4-Py], [4592:6-CN-5-OCHF2-4-Py], [4593:3-OMe-5-OCHF2-4-Py], [4594:2-OMe-5-OCHF2-4-Py], [4595:6-OMe-5-OCHF2-4-Py], [4596:6-OCHF2-4-Py], [4597:3-Cl-6-OCHF2-4-Py], [4598:2-Cl-6-OCHF2-4-Py], [4599:5-Cl-6-OCHF2-4-Py], [4600:3-Me-6-OCHF2-4-Py],
[4601:2-Me-6-OCHF2-4-Py], [4602:5-Me-6-OCHF2-4-Py], [4603:3-CF3-6-OCHF2-4-Py], [4604:2-CF3-6-OCHF2-4-Py], [4605:5-CF3-6-OCHF2-4-Py], [4606:3-CN-6-OCHF2-4-Py], [4607:2-CN-6-OCHF2-4-Py], [4608:5-CN-6-OCHF2-4-Py], [4609:3-OMe-6-OCHF2-4-Py], [4610:2-OMe-6-OCHF2-4-Py], [4611:5-OMe-6-OCHF2-4-Py], [4612:3-Et-4-Py], [4613:2-Cl-3-Et-4-Py], [4614:5-Cl-3-Et-4-Py], [4615:6-Cl-3-Et-4-Py], [4616:2-Me-3-Et-4-Py], [4617:5-Me-3-Et-4-Py], [4618:6-Me-3-Et-4-Py], [4619:2-CF3-3-Et-4-Py], [4620:5-CF3-3-Et-4-Py], [4621:6-CF3-3-Et-4-Py], [4622:2-CN-3-Et-4-Py], [4623:5-CN-3-Et-4-Py], [4624:6-CN-3-Et-4-Py], [4625:2-OMe-3-Et-4-Py], [4626:5-OMe-3-Et-4-Py], [4627:6-OMe-3-Et-4-Py], [4628:2-Et-4-Py], [4629:3-Cl-2-Et-4-Py], [4630:5-Cl-2-Et-4-Py], [4631:6-Cl-2-Et-4-Py], [4632:3-Me-2-Et-4-Py], [4633:5-Me-2-Et-4-Py], [4634:6-Me-2-Et-4-Py], [4635:3-CF3-2-Et-4-Py], [4636:5-CF3-2-Et-4-Py], [4637:6-CF3-2-Et-4-Py], [4638:3-CN-2-Et-4-Py], [4639:5-CN-2-Et-4-Py], [4640:6-CN-2-Et-4-Py], [4641:3-OMe-2-Et-4-Py], [4642:5-OMe-2-Et-4-Py], [4643:6-OMe-2-Et-4-Py], [4644:5-Et-4-Py], [4645:3-Cl-5-Et-4-Py], [4646:2-Cl-5-Et-4-Py], [4647:6-Cl-5-Et-4-Py], [4648:3-Me-5-Et-4-Py], [4649:2-Me-5-Et-4-Py], [4650:6-Me-5-Et-4-Py], [4651:3-CF3-5-Et-4-Py], [4652:2-CF3-5-Et-4-Py], [4653:6-CF3-5-Et-4-Py], [4654:3-CN-5-Et-4-Py], [4655:2-CN-5-Et-4-Py], [4656:6-CN-5-Et-4-Py], [4657:3-

OMe-5-Et-4-Py], [4658:2-OMe-5-Et-4-Py], [4659:6-OMe-5-Et-4-Py], [4660:6-Et-4-Py], [4661:3-Cl-6-Et-4-Py], [4662:2-Cl-6-Et-4-Py],[4663:5-Cl-6-Et-4-Py], [4664:3-Me-6-Et-4-Py], [4665:2-Me-6-Et-4-Py], [4666:5-Me-6-Et-4-Py], [4667:3-CF3-6-Et-4-Py], [4668:2-CF3-6-Et-4-Py], [4669:5-CF3-6-Et-4-Py], [4670:3-CN-6-Et-4-Py], [4671:2-CN-6-Et-4-Py], [4672:5-CN-6-Et-4-Py], [4673:3-OMe-6-Et-4-Py], [4674:2-OMe-6-Et-4-Py], [4675:5-OMe-6-Et-4-Py], [4676:3-CH2CF3-4-Py], [4677:2-Cl-3-CH2CF3-4-Py], [4678:5-Cl-3-CH2CF3-4-Py], [4679:6-Cl-3-CH2CF3-4-Py], [4680:2-Me-3-CH2CF3-4-Py], [4681:5-Me-3-CH2CF3-4-Py], [4682:6-Me-3-CH2CF3-4-Py], [4683:2-CF3-3-CH2CF3-4-Py], [4684:5-CF3-3-CH2CF3-4-Py], [4685:6-CF3-3-CH2CF3-4-Py], [4686:2-CN-3-CH2CF3-4-Py], [4687:5-CN-3-CH2CF3-4-Py], [4688:6-CN-3-CH2CF3-4-Py], [4689:2-OMe-3-CH2CF3-4-Py], [4690:5-OMe-3-CH2CF3-4-Py], [4691:6-OMe-3-CH2CF3-4-Py], [4692:2-CH2CF3-4-Py], [4693:3-Cl-2-CH2CF3-4-Py], [4694:5-Cl-2-CH2CF3-4-Py], [4695:6-Cl-2-CH2CF3-4-Py], [4696:3-Me-2-CH2CF3-4-Py], [4697:5-Me-2-CH2CF3-4-Py], [4698:6-Me-2-CH2CF3-4-Py], [4699:3-CF3-2-CH2CF3-4-Py], [4700:5-CF3-2-CH2CF3-4-Py], [4701:6-CF3-2-CH2CF3-4-Py], [4702:3-CN-2-CH2CF3-4-Py], [4703:5-CN-2-CH2CF3-4-Py], [4704:6-CN-2-CH2CF3-4-Py], [4705:3-OMe-2-CH2CF3-4-Py], [4706:5-OMe-2-CH2CF3-4-Py], [4707:6-OMe-2-CH2CF3-4-Py], [4708:5-CH2CF3-4-Py], [4709:3-Cl-5-CH2CF3-4-Py], [4710:2-Cl-5-CH2CF3-4-Py], [4711:6-Cl-5-CH2CF3-4-Py], [4712:3-Me-5-CH2CF3-4-Py], [4713:2-Me-5-CH2CF3-4-Py], [4714:6-Me-5-CH2CF3-4-Py], [4715:3-CF3-5-CH2CF3-4-Py], [4716:2-CF3-5-CH2CF3-4-Py], [4717:6-CF3-5-CH2CF3-4-Py], [4718:3-CN-5-CH2CF3-4-Py], [4719:2-CN-5-CH2CF3-4-Py], [4720:6-CN-5-CH2CF3-4-Py], [4721:3-OMe-5-CH2CF3-4-Py], [4722:2-OMe-5-CH2CF3-4-Py], [4723:6-OMe-5-CH2CF3-4-Py], [4724:6-CH2CF3-4-Py], [4725:3-Cl-6-CH2CF3-4-Py], [4726:2-Cl-6-CH2CF3-4-Py], [4727:5-Cl-6-CH2CF3-4-Py], [4728:3-Me-6-CH2CF3-4-Py], [4729:2-Me-6-CH2CF3-4-Py], [4730:5-Me-6-CH2CF3-4-Py], [4731:3-CF3-6-CH2CF3-4-Py], [4732:2-CF3-6-CH2CF3-4-Py], [4733:5-CF3-6-CH2CF3-4-Py], [4734:3-CN-6-CH2CF3-4-Py], [4735:2-CN-6-CH2CF3-4-Py], [4736:5-CN-6-CH2CF3-4-Py], [4737:3-OMe-6-CH2CF3-4-Py], [4738:2-OMe-6-CH2CF3-4-Py], [4739:5-OMe-6-CH2CF3-4-Py], [4740:3-OEt-4-Py], [4741:2-Cl-3-OEt-4-Py], [4742:5-Cl-3-OEt-4-Py], [4743:6-Cl-3-OEt-4-Py], [4744:2-Me-3-OEt-4-Py], [4745:5-Me-3-OEt-4-Py], [4746:6-Me-3-OEt-4-Py], [4747:2-CF3-3-OEt-4-Py], [4748:5-CF3-3-OEt-4-Py], [4749:6-CF3-3-OEt-4-Py], [4750:2-CN-3-OEt-4-Py], [4751:5-CN-3-OEt-4-Py], [4752:6-CN-3-OEt-4-Py], [4753:2-OMe-3-OEt-4-Py], [4754:5-OMe-3-OEt-4-Py], [4755:6-OMe-3-OEt-4-Py], [4756:2-OEt-4-Py], [4757:3-Cl-2-OEt-4-Py], [4758:5-Cl-2-OEt-4-Py], [4759:6-Cl-2-OEt-4-Py], [4760:3-Me-2-OEt-4-Py], [4761:5-Me-2-Oft-4-Py], [4762:6-Me-2-OEt-4-Py], [4763:3-CF3-2-OEt-4-Py], [4764:5-CF3-2-OEt-4-Py], [4765:6-CF3-2-OEt-4-Py], [4766:3-CN-2-OEt-4-Py], [4767:5-CN-2-OEt-4-Py], [4768:6-CN-2-OEt-4-Py], [4769:3-OMe-2-OEt-4-Py], [4770:5-OMe-2-OEt-4-Py], [4771:6-OMe-2-Oft-4-Py], [4772:5-OEt-4-Py], [4773:3-Cl-5-OEt-4-Py], [4774:2-Cl-5-OEt-4-Py], [4775:6-Cl-5-OEt-4-Py], [4776:3-Me-5-OEt-4-Py], [4777:2-Me-5-OEt-4-Py], [4778:6-Me-5-OEt-4-Py], [4779:3-CF3-5-OEt-4-Py], [4780:2-CF3-5-OEt-4-Py], [4781:6-CF3-5-OEt-4-Py], [4782:3-CN-5-OEt-4-Py], [4783:2-CN-5-OEt-4-Py], [4784:6-CN-5-OEt-4-Py], [4785:3-OMe-5-OEt-4-Py], [4786:2-OMe-5-OEt-4-Py], [4787:6-OMe-5-OEt-4-Py], [4788:6-OEt-4-Py], [4789:3-Cl-6-OEt-4-Py], [4790:2-Cl-6-OEt-4-Py], [4791:5-Cl-6-OEt-4-Py], [4792:3-Me-6-OEt-4-Py], [4793:2-Me-6-OEt-4-Py], [4794:5-Me-6-OEt-4-Py], [4795:3-CF3-6-OEt-4-Py], [4796:2-CF3-6-OEt-4-Py], [4797:5-CF3-6-OEt-4-Py], [4798:3-CN-6-OEt-4-Py], [4799:2-CN-6-OEt-4-Py], [4800:5-CN-6-OEt-4-Py], [4801:3-OMe-6-OEt-4-Py], [4802:2-OMe-6-OEt-4-Py], [4803:5-OMe-6-OEt-4-Py], [4804:3-OCH2CF3-4-Py], [4805:2-Cl-3-OCH2CF3-4-Py], [4806:5-Cl-3-OCH2CF3-4-Py], [4807:6-Cl-3-OCH2CF3-4-Py], [4808:2-Me-3-OCH2CF3-4-Py], [4809:5-Me-3-OCH2CF3-4-Py], [4810:6-Me-3-OCH2CF3-4-Py], [4811:2-CF3-3-OCH2CF3-4-Py], [4812:5-CF3-3-OCH2CF3-4-Py], [4813:6-CF3-3-OCH2CF3-4-Py], [4814:2-CN-3-OCH2CF3-4-Py], [4815:5-CN-3-OCH2CF3-4-Py], [4816:6-CN-3-OCH2CF3-4-Py], [4817:2-OMe-3-OCH2CF3-4-Py], [4818:5-OMe-3-OCH2CF3-4-Py], [4819:6-OMe-3-OCH2CF3-4-Py], [4820:2-OCH2CF3-4-Py], [4821:3-Cl-2-OCH2CF3-4-Py], [4822:5-Cl-2-OCH2CF3-4-Py], [4823:6-Cl-2-OCH2CF3-4-Py], [4824:3-Me-2-OCH2CF3-4-Py], [4825:5-Me-2-OCH2CF3-4-Py], [4826:6-Me-2-OCH2CF3-4-Py], [4827:3-CF3-2-OCH2CF3-4-Py], [4828:5-CF3-2-OCH2CF3-4-Py], [4829:6-CF3-2-OCH2CF3-4-Py], [4830:3-CN-2-OCH2CF3-4-Py], [4831:5-CN-2-OCH2CF3-4-Py], [4832:6-CN-2-OCH2CF3-4-Py], [4833:3-OMe-2-OCH2CF3-4-Py], [4834:5-OMe-2-OCH2CF3-4-Py], [4835:6-OMe-2-OCH2CF3-4-Py], [4836:5-OCH2CF3-4-Py], [4837:3-Cl-5-OCH2CF3-4-Py], [4838:2-Cl-5-OCH2CF3-4-Py], [4839:6-Cl-5-OCH2CF3-4-Py], [4840:3-Me-5-OCH2CF3-4-Py], [4841:2-Me-5-OCH2CF3-4-Py], [4842:6-Me-5-OCH2CF3-4-Py], [4843:3-CF3-5-OCH2CF3-4-Py], [4844:2-CF3-5-OCH2CF3-4-Py], [4845:6-CF3-5-OCH2CF3-4-Py], [4846:3-CN-5-OCH2CF3-4-Py], [4847:2CN-5-OCH2CF3-4-Py], [4848:6-CN-5-OCH2CF3-4-Py], [4849:3-OMe-5-OCH2CF3-4-Py], [4850:2-OMe-5-OCH2CF3-4-Py], [4851:6-OMe-5-OCH2CF3-4-Py], [4852:6-OCH2CF3-4-Py], [4853:3-Cl-6-OCH2CF3-4-Py], [4854:2-Cl-6-OCH2CF3-4-Py], [4855:5-Cl-6-OCH2CF3-4-Py], [4856:3-Me-6-OCH2CF3-4-Py], [4857:2-Me-6-OCH2CF3-4-Py], [4858:5-Me-6-OCH2CF3-4-Py], [4859:3-CF3-6-OCH2CF3-4-Py], [4860:2-CF3-6-OCH2CF3-4-Py], [4861:5-CF3-6-OCH2CF3-4-Py], [4862:3-CN-6-OCH2CF3-4-Py], [4863:2-CN-6-OCH2CF3-4-Py], [4864:5-CN-6-OCH2CF3-4-Py], [4865:3-OMe-6-OCH2CF3-4-Py], [4866:2-OMe-6-OCH2CF3-4-Py], [4867:5-OMe-6-OCH2CF3-4-Py], [4868:3-Pr-4-Py], [4869:2-Cl-3-Pr-4-Py], [4870:5-Cl-3-Pr-4-Py], [4871:6-Cl-3-Pr-4-Py], [4872:2-Me-3-Pr-4-Py], [4873:5-Me-3-Pr-4-Py], [4874:6-Me-3-Pr-4-Py], [4875:2-CF3-3-Pr-4-Py], [4876:5-CF3-3-Pr-4-Py], [4877:6-CF3-3-Pr-4-Py], [4878:2-CN-3-Pr-4-Py], [4879:5-CN-3-Pr-4-Py], [4880:6-CN-3-Pr-4-Py], [4881:2-OMe-3-Pr-4-Py], [4882:5-OMe-3-Pr-4-Py], [4883:6-OMe-3-Pr-4-Py], [4884:2-Pr-4-Py], [4885:3-Cl-2-Pr-4-Py], [4886:5-Cl-2-Pr-4-Py], [4887:6-Cl-2-Pr-4-Py], [4888:3-Me-2-Pr-4-Py], [4889:5-Me-2-Pr-4-Py], [4890:6-Me-2-Pr-4-Py], [4891:3-CF3-2-Pr-4-Py], [4892:5-CF3-2-Pr-4-Py], [4893:6-CF3-2-Pr-4-Py], [4894:3-CN-2-Pr-4-Py], [4895:5-CN-2-Pr-4-Py], [4896:6-CN-2-Pr-4-Py], [4897:3-OMe-2-Pr-4-Py], [4898:5-OMe-2-Pr-4-Py], [4899:6-OMe-2-Pr-4-Py], [4900:5-Pr-4-Py], [4901:3-Cl-5-Pr-4-Py], [4902:2-Cl-5-Pr-4-Py], [4903:6-Cl-5-Pr-4-Py], [4904:3-Me-5-Pr-4-Py], [4905:2-Me-5-Pr-4-Py], [4906:6-Me-5-Pr-4-Py], [4907:3-CF3-5-Pr-4-Py], [4908:2-CF3-5-Pr-4-Py], [4909:6-CF3-5-Pr-4-Py], [4910:3-CN-5-Pr-4-Py], [4911:2-CN-5-Pr-4-Py], [4912:6-CN-5-Pr-4-Py], [4913:3-OMe-5-Pr-4-Py], [4914:2-OMe-5-Pr-4-Py], [4915:6-OMe-5-Pr-4-Py], [4916:6-Pr-4-Py], [4917:3-Cl-6-Pr-4-Py], [4918:2-Cl-6-Pr-4-Py], [4919:5-Cl-6-Pr-4-Py], [4920:3-Me-6-Pr-4-Py], [4921:2-Me-6-Pr-4-Py], [4922:5-

Me-6-Pr-4-Py], [4923:3-CF3-6-Pr-4-Py], [4924:2-CF3-6-Pr-4-Py], [4925:5-CF3-6-Pr-4-Py], [4926:3-CN-6-Pr-4-Py], [4927:2-CN-6-Pr-4-Py], [4928:5-CN-6-Pr-4-Py], [4929:3-OMe-6-Pr-4-Py], [4930:2-OMe-6-Pr-4-Py], [4931:5-OMe-6-Pr-4-Py], [4932:3-OPr-4-Py], [4933:2-Cl-3-OPr-4-Py], [4934:5-Cl-3-OPr-4-Py], [4935:6-Cl-3-OPr-4-Py], [4936:2-Me-3-OPr-4-Py], [4937:5-Me-3-OPr-4-Py], [4938:6-Me-3-OPr-4-Py], [4939:2-CF3-3-OPr-4-Py], [4940:5-CF3-3-OPr-4-Py], [4941:6-CF3-3-OPr-4-Py], [4942:2-CN-3-OPr-4-Py], [4943:5-CN-3-OPr-4-Py], [4944:6-CN-3-OPr-4-Py], [4945:2-OMe-3-OPr-4-Py], [4946:5-OMe-3-OPr-4-Py], [4947:6-OMe-3-OPr-4-Py], [4948:2-OPr-4-Py], [4949:3-Cl-2-OPr-4-Py], [4950:5-Cl-2-OPr-4-Py], [4951:6-Cl-2-OPr-4-Py], [4952:3-Me-2-OPr-4-Py], [4953:5-Me-2-OPr-4-Py], [4954:6-Me-2-OPr-4-Py], [4955:3-CF3-2-OPr-4-Py], [4956:5-CF3-2-OPr-4-Py], [4957:6-CF3-2-OPr-4-Py], [4958:3-CN-2-OPr-4-Py], [4959:5-CN-2-OPr-4-Py], [4960:6-CN-2-OPr-4-Py], [4961:3-OMe-2-OPr-4-Py], [4962:5-OMe-2-OPr-4-Py], [4963:6-OMe-2-OPr-4-Py], [4964:5-OPr-4-Py], [4965:3-Cl-5-OPr-4-Py], [4966:2-Cl-5-OPr-4-Py], [4967:6-Cl-5-OPr-4-Py], [4968:3-Me-5-OPr-4-Py], [4969:2-Me-5-OPr-4-Py], [4970:6-Me-5-OPr-4-Py], [4971:3-CF3-5-OPr-4-Py], [4972:2CF3-5-OPr-4-Py], [4973:6-CF3-5-OPr-4-Py], [4974:3-CN-5-OPr-4-Py], [4975:2-CN-5-OPr-4-Py], [4976:6-CN-5-OPr-4-Py], [4977:3-OMe-5-OPr-4-Py], [4978:2-OMe-5-OPr-4-Py], [4979:6-OMe-5-OPr-4-Py], [4980:6-OPr-4-Py], [4981:3-Cl-6-OPr-4-Py], [4982:2-Cl-6-OPr-4-Py], [4983:5-Cl-6-OPr-4-Py], [4984:3-Me-6-OPr-4-Py], [4985:2-Me-6-OPr-4-Py], [4986:5-Me-6-OPr-4-Py], [4987:3-CF3-6-OPr-4-Py], [4988:2-CF3-6-OPr-4-Py], [4989:5-CF3-6-OPr-4-Py], [4990:3-CN-6-OPr-4-Py], [4991:2-CN-6-OPr-4-Py], [4992:5-CN-6-OPr-4-Py], [4993:3-OMe-6-OPr-4-Py], [4994:2-OMe-6-OPr-4-Py], [4995:5-OMe-6-OPr-4-Py], [4996:3-SMe-4-Py], [4997:2-Cl-3-SMe-4-Py], [4998:5-Cl-3-SMe-4-Py], [4999:6-Cl-3-SMe-4-Py], [5000:2-Me-3-SMe-4-Py],
[5001:5-Me-3-SMe-4-Py], [5002:6-Me-3-SMe-4-Py], [5003:2-CF3-3-SMe-4-Py], [5004:5-CF3-3-SMe-4-Py], [5005:6-CF3-3-SMe-4-Py], [5006:2-CN-3-SMe-4-Py], [5007:5-CN-3-SMe-4-Py], [5008:6-CN-3-SMe-4-Py], [5009:2-OMe-3-SMe-4-Py], [5010:5-OMe-3-SMe-4-Py], [5011:6-OMe-3-SMe-4-Py], [5012:2-SMe-4-Py], [5013:3-Cl-2-SMe-4-Py], [5014:5-Cl-2-SMe-4-Py], [5015:6-Cl-2-SMe-4-Py], [5016:3-Me-2-SMe-4-Py], [5017:5-Me-2-SMe-4-Py], [5018:6-Me-2-SMe-4-Py], [5019:3-CF3-2-SMe-4-Py], [5020:5-CF3-2-SMe-4-Py], [5021:6-CF3-2-SMe-4-Py], [5022:3-CN-2-SMe-4-Py], [5023:5-CN-2-SMe-4-Py], [5024:6-CN-2-SMe-4-Py], [5025:3-OMe-2-SMe-4-Py], [5026:5-OMe-2-SMe-4-Py], [5027:6-OMe-2-SMe-4-Py], [5028:5-SMe-4-Py], [5029:3-Cl-5-SMe-4-Py], [5030:2-Cl-5-SMe-4-Py], [5031:6-Cl-5-SMe-4-Py], [5032:3-Me-5-SMe-4-Py], [5033:2-Me-5-SMe-4-Py], [5034:6-Me-5-SMe-4-Py], [5035:3-CF3-5-SMe-4-Py], [5036:2-CF3-5-SMe-4-Py], [5037:6-CF3-5-SMe-4-Py], [5038:3-CN-5-SMe-4-Py], [5039:2-CN-5-SMe-4-Py], [5040:6-CN-5-SMe-4-Py], [5041:3-OMe-5-SMe-4-Py], [5042:2-OMe-5-SMe-4-Py], [5043:6-OMe-5-SMe-4-Py], [5044:6-SMe-4-Py], [5045:3-Cl-6-SMe-4-Py], [5046:2-Cl-6-SMe-4-Py], [5047:5-Cl-6-SMe-4-Py], [5048:3-Me-6-SMe-4-Py], [5049:2-Me-6-SMe-4-Py], [5050:5-Me-6-SMe-4-Py], [5051:3-CF3-6-SMe-4-Py], [5052:2-CF3-6-SMe-4-Py], [5053:5-CF3-6-SMe-4-Py], [5054:3-CN-6-SMe-4-Py], [5055:2-CN-6-SMe-4-Py], [5056:5-CN-6-SMe-4-Py], [5057:3-OMe-6-SMe-4-Py], [5058:2-OMe-6-SMe-4-Py], [5059:5-OMe-6-SMe-4-Py], [5060:3-SCF3-4-Py], [5061:2-Cl-3-SCF3-4-Py], [5062:5-Cl-3-SCF3-4-Py], [5063:6-Cl-3-SCF3-4-Py], [5064:2-Me-3-SCF3-4-Py], [5065:5-Me-3-SCF3-4-Py], [5066:6-Me-3-SCF3-4-Py], [5067:2-CF3-3-SCF3-4-Py], [5068:5-CF3-3-SCF3-4-Py], [5069:6-CF3-3-SCF3-4-Py], [5070:2-CN-3-SCF3-4-Py], [5071:5-CN-3-SCF3-4-Py], [5072:6-CN-3-SCF3-4-Py], [5073:2-OMe-3-SCF3-4-Py], [5074:5-OMe-3-SCF3-4-Py], [5075:6-OMe-3-SCF3-4-Py], [5076:2-SCF3-4-Py], [5077:3-Cl-2-SCF3-4-Py], [5078:5-Cl-2-SCF3-4-Py], [5079:6-Cl-2-SCF3-4-Py], [5080:3-Me-2SCF3-4-Py], [5081:5-Me-2-SCF3-4-Py], [5082:6-Me-2-SCF3-4-Py], [5083:3-CF3-2-SCF3-4-Py], [5084:5-CF3-2-SCF3-4-Py], [5085:6-CF3-2-SCF3-4-Py], [5086:3-CN-2-SCF3-4-Py], [5087:5-CN-2-SCF3-4-Py], [5088:6-CN-2-SCF3-4-Py], [5089:3-OMe-2-SCF3-4-Py], [5090:5-OMe-2-SCF3-4-Py], [5091:6-OMe-2-SCF3-4-Py], [5092:5-SCF3-4-Py], [5093:3-Cl-5-SCF3-4-Py], [5094:2-Cl-5-SCF3-4-Py], [5095:6-Cl-5-SCF3-4-Py], [5096:3-Me-5-SCF3-4-Py], [5097:2-Me-5-SCF3-4-Py], [5098:6-Me-5-SCF3-4-Py], [5099:3-CF3-5-SCF3-4-Py], [5100:2-CF3-5-SCF3-4-Py],
[5101:6-CF3-5-SCF3-4-Py], [5102:3-CN-5-SCF3-4-Py], [5103:2-CN-5-SCF3-4-Py], [5104:6-CN-5-SCF3-4-Py], [5105:3-OMe-5-SCF3-4-Py], [5106:2-OMe-5-SCF3-4-Py], [5107:6-OMe-5-SCF3-4-Py], [5108:6-SCF3-4-Py], [5109:3-Cl-6-SCF3-4-Py], [5110:2-Cl-6-SCF3-4-Py], [5111:6-Cl-6-SCF3-4-Py], [5112:3-Me-6-SCF3-4-Py], [5113:2-Me-6-SCF3-4-Py], [5114:6-Me-6-SCF3-4-Py], [5115:3-CF3-6-SCF3-4-Py], [5116:2-CF3-6-SCF3-4-Py], [5117:6-CF3-6-SCF3-4-Py], [5118:3-CN-6-SCF3-4-Py], [5119:2-CN-6-SCF3-4-Py], [5120:6-CN-6-SCF3-4-Py], [5121:3-OMe-6-SCF3-4-Py], [5122:2-OMe-6-SCF3-4-Py], [5123:6-OMe-6-SCF3-4-Py], [5124:3-S(O)Me-4-Py], [5125:2-Cl-3-S(O)Me-4-Py], [5126:5-Cl-3-S(O)Me-4-Py], [5127:6-Cl-3-S(O)Me-4-Py], [5128:2-Me-3-S(O)Me-4-Py], [5129:5-Me-3-S(O)Me-4-Py], [5130:6-Me-3-S(O)Me-4-Py], [5131:2-CF3-3-S(O)Me-4-Py], [5132:5-CF3-3-S(O)Me-4-Py], [5133:6-CF3-3-S(O)Me-4-Py], [5134:2-CN-3-S(O)Me-4-Py], [5135:5-CN-3-S(O)Me-4-Py], [5136:6-CN-3-S(O)Me-4-Py], [5137:2-OMe-3-S(O)Me-4-Py], [5138:5-OMe-3-S(O)Me-4-Py], [5139:6-OMe-3-S(O)Me-4-Py], [5140:2-S(O)Me-4-Py], [5141:3-Cl-2-S(O)Me-4-Py], [5142:5-Cl-2-S(O)Me-4-Py], [5143:6-Cl-2-S(O)Me-4-Py], [5144:3-Me-2-S(O)Me-4-Py], [5145:5-Me-2-S(O)Me-4-Py], [5146:6-Me-2-S(O)Me-4-Py], [5147:3-CF3-2-S(O)Me-4-Py], [5148:5-CF3-2-S(O)Me-4-Py], [5149:6-CF3-2-S(O)Me-4-Py], [5150:3-CN-2-S(O)Me-4-Py], [5151:5-CN-2-S(O)Me-4-Py], [5152:6-CN-2-S(O)Me-4-Py], [5153:3-OMe-2-S(O)Me-4-Py], [5154:5-OMe-2-S(O)Me-4-Py], [5155:6-OMe-2-S(O)Me-4-Py], [5156:5-S(O)Me-4-Py], [5157:3-Cl-5-S(O)Me-4-Py], [5158:2-Cl-5-S(O)Me-4-Py], [5159:6-Cl-5-S(O)Me-4-Py], [5160:3-Me-5-S(O)Me-4-Py], [5161:2-Me-5-S(O)Me-4-Py], [5162:6-Me-5-S(O)Me-4-Py], [5163:3-CF3-5-S(O)Me-4-Py], [5164:2-CF3-5-S(O)Me-4-Py], [5165:6-CF3-5-S(O)Me-4-Py], [5166:3-CN-5-S(O)Me-4-Py], [5167:2-CN-5-S(O)Me-4-Py], [5168:6-CN-5-S(O)Me-4-Py], [5169:3-OMe-5-S(O)Me-4-Py], [5170:2-OMe-5-S(O)Me-4-Py], [5171:6-OMe-5-S(O)Me-4-Py], [5172:6-S(O)Me-4-Py], [5173:3-Cl-6-S(O)Me-4-Py], [5174:2-Cl-6-S(O)Me-4-Py], [5175:5-Cl-6-S(O)Me-4-Py], [5176:3-Me-6-S(O)Me-4-Py], [5177:2-Me-6-S(O)Me-4-Py], [5178:5-Me-6-S(O)Me-4-Py], [5179:3-CF3-6-S(O)Me-4-Py], [5180:2-CF3-6-S(O)Me-4-Py], [5181:5-CF3-6-S(O)Me-4-Py], [5182:3-CN-6-S(O)Me-4-Py], [5183:2-CN-6-S(O)Me-4-Py], [5184:5-CN-6-S(O)Me-4-Py], [5185:3-OMe-6-S(O)Me-4-Py], [5186:2-OMe-6-S(O)Me-4-Py], [5187:5-OMe-6-S(O)Me-4-Py], [5188:3-S(O)CF3-4-Py], [5189:2-Cl-3-S(O)CF3-4-Py], [5190:5-Cl-3-S(O)CF3-4-Py], [5191:6-Cl-3-S(O)CF3-4-Py], [5192:2-Me-3-S(O)CF3-4-Py], [5193:5-Me-3-S(O)CF3-4-Py], [5194:6-Me-3-S(O)CF3-4-Py], [5195:2-CF3-3-S(O)CF3-4-Py], [5196:5-CF3-3-S(O)CF3-4-Py],

[5197:6-CF3-3-S(O)CF3-4-Py], [5198:2-CN-3-S(O)CF3-4-Py], [5199:5-CN-3-S(O)CF3-4-Py], [5200:6-CN-3-S(O)CF3-4-Py],
[5201:2-OMe-3-S(O)CF3-4-Py], [5202:5-OMe-3-S(O)CF3-4-Py], [5203:6-OMe-3-S(O)CF3-4-Py], [5204:2-S(O)CF3-4-Py], [5205:3-Cl-2-S(O)CF3-4-Py], [5206:5-Cl-2-S(O)CF3-4-Py], [5207:6-Cl-2-S(O)CF3-4-Py], [5208:3-Me-2-S(O)CF3-4-Py], [5209:5-Me-2-S(O)CF3-4-Py], [5210:6-Me-2-S(O)CF3-4-Py], [5211:3-CF3-2-S(O)CF3-4-Py], [5212:5-CF3-2-S(O)CF3-4-Py], [5213:6-CF3-2-S(O)CF3-4-Py], [5214:3-CN-2-S(O)CF3-4-Py], [5215:5-CN-2-S(O)CF3-4-Py], [5216:6-CN-2-S(O)CF3-4-Py], [5217:3-OMe-2-S(O)CF3-4-Py], [5218:5-OMe-2-S(O)CF3-4-Py], [5219:6-OMe-2-S(O)CF3-4-Py], [5220:5-S(O)CF3-4-Py], [5221:3-Cl-5-S(O)CF3-4-Py], [5222:2-Cl-5-S(O)CF3-4-Py], [5223:6-Cl-5-S(O)CF3-4-Py], [5224:3-Me-5-S(O)CF3-4-Py], [5225:2-Me-5-S(O)CF3-4-Py], [5226:6-Me-5-S(O)CF3-4-Py], [5227:3-CF3-5-S(O)CF3-4-Py], [5228:2-CF3-5-S(O)CF3-4-Py], [5229:6-CF3-5-S(O)CF3-4-Py], [5230:3-CN-5-S(O)CF3-4-Py], [5231:2-CN-5-S(O)CF3-4-Py], [5232:6-CN-5-S(O)CF3-4-Py], [5233:3-OMe-5-S(O)CF3-4-Py], [5234:2-OMe-5-S(O)CF3-4-Py], [5235:6-OMe-5-S(O)CF3-4-Py], [5236:6-S(O)CF3-4-Py], [5237:3-Cl-6-S(O)CF3-4-Py], [5238:2-Cl-6-S(O)CF3-4-Py], [5239:5-Cl-6-S(O)CF3-4-Py], [5240:3-Me-6-S(O)CF3-4-Py], [5241:2-Me-6-S(O)CF3-4-Py], [5242:5-Me-6-S(O)CF3-4-Py], [5243:3-CF3-6-S(O)CF3-4-Py], [5244:2-CF3-6-S(O)CF3-4-Py], [5245:5-CF3-6-S(O)CF3-4-Py], [5246:3-CN-6-S(O)CF3-4-Py], [5247:2-CN-6-S(O)CF3-4-Py], [5248:5-CN-6-S(O)CF3-4-Py], [5249:3-OMe-6-S(O)CF3-4-Py], [5250:2-OMe-6-S(O)CF3-4-Py], [5251:5-OMe-6-S(O)CF3-4-Py], [5252:3-S(O)2Me-4-Py], [5253:2-Cl-3-S(O)2Me-4-Py], [5254:5-Cl-3-S(O)2Me-4-Py], [5255:6-Cl-3-S(O)2Me-4-Py], [5256:2-Me-3-S(O)2Me-4-Py], [5257:5-Me-3-S(O)2Me-4-Py], [5258:6-Me-3-S(O)2Me-4-Py], [5259:2-CF3-3-S(O)2Me-4-Py], [5260:5-CF3-3-S(O)2Me-4-Py], [5261:6-CF3-3-S(O)2Me-4-Py], [5262:2-CN-3-S(O)2Me-4-Py], [5263:5-CN-3-S(O)2Me-4-Py], [5264:6-CN-3-S(O)2Me-4-Py], [5265:2-OMe-3-S(O)2Me-4-Py], [5266:5-OMe-3-S(O)2Me-4-Py], [5267:6-OMe-3-S(O)2Me-4-Py], [5268:2-S(O)2Me-4-Py], [5269:3-Cl-2-S(O)2Me-4-Py], [5270:5-Cl-2-S(O)2Me-4-Py], [5271:6-Cl-2-S(O)2Me-4-Py], [5272:3-Me-2-S(O)2Me-4-Py], [5273:5-Me-2-S(O)2Me-4-Py], [5274:6-Me-2-S(O)2Me-4-Py], [5275:3-CF3-2-S(O)2Me-4-Py], [5276:5-CF3-2-S(O)2Me-4-Py], [5277:6-CF3-2-S(O)2Me-4-Py], [5278:3-CN-2-S(O)2Me-4-Py], [5279:5-CN-2-S(O)2Me-4-Py], [5280:6-CN-2-S(O)2Me-4-Py], [5281:3-OMe-2-S(O)2Me-4-Py], [5282:5-OMe-2-S(O)2Me-4-Py], [5283:6-OMe-2-S(O)2Me-4-Py], [5284:5-S(O)2Me-4-Py], [5285:3-Cl-5-S(O)2Me-4-Py], [5286:2-Cl-5-S(O)2Me-4-Py], [5287:6-Cl-5-S(O)2Me-4-Py], [5288:3-Me-5-S(O)2Me-4-Py], [5289:2-Me-5-S(O)2Me-4-Py], [5290:6-Me-5-S(O)2Me-4-Py], [5291:3-CF3-5-S(O)2Me-4-Py], [5292:2-CF3-5-S(O)2Me-4-Py], [5293:6-CF3-5-S(O)2Me-4-Py], [5294:3-CN-5-S(O)2Me-4-Py], [5295:2-CN-5-S(O)2Me-4-Py], [5296:6-CN-5-S(O)2Me-4-Py], [5297:3-OMe-5-S(O)2Me-4-Py], [5298:2-OMe-5-S(O)2Me-4-Py], [5299:6-OMe-5-S(O)2Me-4-Py], [5300:6-S(O)2Me-4-Py],
[5301:3-Cl-6-S(O)2Me-4-Py], [5302:2-Cl-6-S(O)2Me-4-Py], [5303:5-Cl-6-S(O)2Me-4-Py], [5304:3-Me-6-S(O)2Me-4-Py], [5305:2-Me-6-S(O)2Me-4-Py], [5306:5-Me-6-S(O)2Me-4-Py], [5307:3-CF3-6-S(O)2Me-4-Py], [5308:2-CF3-6-S(O)2Me-4-Py], [5309:5-CF3-6-S(O)2Me-4-Py], [5310:3-CN-6-S(O)2Me-4-Py], [5311:2-CN-6-S(O)2Me-4-Py], [5312:5-CN-6-S(O)2Me-4-Py], [5313:3-OMe-6-S(O)2Me-4-Py], [5314:2-OMe-6-S(O)2Me-4-Py], [5315:5-OMe-6-S(O)2Me-4-Py], [5316:3-S(O)2CF3-4-Py], [5317:2-Cl-3-S(O)2CF3-4-Py], [5318:5-Cl-3-S(O)2CF3-4-Py], [5319:6-Cl-3-S(O)2CF3-4-Py], [5320:2-Me-3-S(O)2CF3-4-Py], [5321:5-Me-3-S(O)2CF3-4-Py], [5322:6-Me-3-S(O)2CF3-4-Py], [5323:2-CF3-3-S(O)2CF3-4-Py], [5324:5-CF3-3-S(O)2CF3-4-Py], [5325:6-CF3-3-S(O)2CF3-4-Py], [5326:2-CN-3-S(O)2CF3-4-Py], [5327:5-CN-3-S(O)2CF3-4-Py], [5328:6-CN-3-S(O)2CF3-4-Py], [5329:2-OMe-3-S(O)2CF3-4-Py], [5330:5-OMe-3-S(O)2CF3-4-Py], [5331:6-OMe-3-S(O)2CF3-4-Py], [5332:2-S(O)2CF3-4-Py], [5333:3-Cl-2-S(O)2CF3-4-Py], [5334:5-Cl-2-S(O)2CF3-4-Py], [5335:6-Cl-2-S(O)2CF3-4-Py], [5336:3-Me-2-S(O)2CF3-4-Py], [5337:5-Me-2-S(O)2CF3-4-Py], [5338:6-Me-2-S(O)2CF3-4-Py], [5339:3-CF3-2-S(O)2CF3-4-Py], [5340:5-CF3-2-S(O)2CF3-4-Py], [5341:6-CF3-2-S(O)2CF3-4-Py], [5342:3-CN-2-S(O)2CF3-4-Py], [5343:5-CN-2-S(O)2CF3-4-Py], [5344:6-CN-2-S(O)2CF3-4-Py], [5345:3-OMe-2-S(O)2CF3-4-Py], [5346:5-OMe-2-S(O)2CF3-4-Py], [5347:6-OMe-2-S(O)2CF3-4-Py], [5348:5-S(O)2CF3-4-Py], [5349:3-Cl-5-S(O)2CF3-4-Py], [5350:2-Cl-5-S(O)2CF3-4-Py], [5351:6-Cl-5-S(O)2CF3-4-Py], [5352:3-Me-5-S(O)2CF3-4-Py], [5353:2-Me-5-S(O)2CF3-4-Py], [5354:6-Me-5-S(O)2CF3-4-Py], [5355:3-CF3-5-S(O)2CF3-4-Py], [5356:2-CF3-5-S(O)2CF3-4-Py], [5357:6-CF3-5-S(O)2CF3-4-Py], [5358:3-CN-5-S(O)2CF3-4-Py], [5359:2-CN-5-S(O)2CF3-4-Py], [5360:6-CN-5-S(O)2CF3-4-Py], [5361:3-OMe-5-S(O)2CF3-4-Py], [5362:2-OMe-5-S(O)2CF3-4-Py], [5363:6-OMe-5-S(O)2CF3-4-Py], [5364:6-S(O)2CF3-4-Py], [5365:3-Cl-6-S(O)2CF3-4-Py], [5366:2-Cl-6-S(O)2CF3-4-Py], [5367:5-Cl-6-S(O)2CF3-4-Py], [5368:3-Me-6-S(O)2CF3-4-Py], [5369:2-Me-6-S(O)2CF3-4-Py], [5370:5-Me-6-S(O)2CF3-4-Py], [5371:3-CF3-6-S(O)2CF3-4-Py], [5372:2-CF3-6-S(O)2CF3-4-Py], [5373:5-CF3-6-S(O)2CF3-4-Py], [5374:3-CN-6-S(O)2CF3-4-Py], [5375:2-CN-6-S(O)2CF3-4-Py], [5376:5-CN-6-S(O)2CF3-4-Py], [5377:3-OMe-6-S(O)2CF3-4-Py], [5378:2-OMe-6-S(O)2CF3-4-Py], [5379:5-OMe-6-S(O)2CF3-4-Py], [5380:3-CN-4-Py], [5381:2-Cl-3-CN-4-Py], [5382:5-Cl-3-CN-4-Py], [5383:6-Cl-3-CN-4-Py], [5384:2-Me-3-CN-4-Py], [5385:5-Me-3-CN-4-Py], [5386:6-Me-3-CN-4-Py], [5387:2-CF3-3-CN-4-Py], [5388:5-CF3-3-CN-4-Py], [5389:6-CF3-3-CN-4-Py], [5390:2-CN-3-CN-4-Py], [5391:5-CN-3-CN-4-Py], [5392:6-CN-3-CN-4-Py], [5393:2-OMe-3-CN-4-Py], [5394:5-OMe-3-CN-4-Py], [5395:6-OMe-3-CN-4-Py], [5396:2-CN-4-Py], [5397:3-Cl-2-CN-4-Py], [5398:5-Cl-2-CN-4-Py], [5399:6-Cl-2-CN-4-Py], [5400:3-Me-2-CN-4-Py],
[5401:5-Me-2-CN-4-Py], [5402:6-Me-2-CN-4-Py], [5403:3-CF3-2-CN-4-Py], [5404:5-CF3-2-CN-4-Py], [5405:6-CF3-2-CN-4-Py], [5406:3-CN-2-CN-4-Py], [5407:5-CN-2-CN-4-Py], [5408:6-CN-2-CN-4-Py], [5409:3-OMe-2-CN-4-Py], [5410:5-OMe-2-CN-4-Py], [5411:6-OMe-2-CN-4-Py], [5412:5-CN-4-Py], [5413:3-Cl-5-CN-4-Py], [5414:2-Cl-5-CN-4-Py], [5415:6-Cl-5-CN-4-Py], [5416:3-Me-5-CN-4-Py], [5417:2-Me-5-CN-4-Py], [5418:6-Me-5-CN-4-Py], [5419:3-CF3-5-CN-4-Py], [5420:2-CF3-5-CN-4-Py], [5421:6-CF3-5-CN-4-Py], [5422:3-CN-5-CN-4-Py], [5423:2-CN-5-CN-4-Py], [5424:6-CN-5-CN-4-Py], [5425:3-OMe-5-CN-4-Py], [5426:2-OMe-5-CN-4-Py], [5427:6-OMe-5-CN-4-Py], [5428:6-CN-4-Py], [5429:3-Cl-6-CN-4-Py], [5430:2-Cl-6-CN-4-Py], [5431:5-Cl-6-CN-4-Py], [5432:3-Me-6-CN-4-Py], [5433:2-Me-6-CN-4-Py], [5434:5-Me-6-CN-4-Py], [5435:3-CF3-6-CN-4-Py], [5436:2-CF3-6-CN-4-Py], [5437:5-CF3-6-CN-4-Py], [5438:3-CN-6-CN-4-Py], [5439:2-CN-6-CN-4-Py], [5440:5-CN-6-CN-4-Py], [5441:3-OMe-6-CN-4-Py], [5442:2-OMe-6-CN-4-Py], [5443:5-OMe-6-CN-4-Py], [5444:3-COOMe-4-Py], [5445:2-Cl-3-COOMe-4-Py], [5446:5-Cl-3-COOMe-4-Py], [5447:6-Cl-3-COOMe-4-Py], [5448:2-Me-3-COOMe-4-Py], [5449:5-

Me-3-COOMe-4-Py], [5450:6-Me-3-COOMe-4-Py], [5451:2-CF3-3-COOMe-4-Py], [5452:5-CF3-3-COOMe-4-Py], [5453:6-CF3-3-COOMe-4-Py], [5454:2-CN-3-COOMe-4-Py], [5455:5-CN-3-COOMe-4-Py], [5456:6-CN-3-COOMe-4-Py], [5457:2-OMe-3-COOMe-4-Py], [5458:5-OMe-3-COOMe-4-Py], [5459:6-OMe-3-COOMe-4-Py], [5460:2-COOMe-4-Py], [5461:3-Cl-2-COOMe-4-Py], [5462:5-Cl-2-COOMe-4-Py], [5463:6-Cl-2-COOMe-4-Py], [5464:3-Me-2-COOMe-4-Py], [5465:5-Me-2-COOMe-4-Py], [5466:6-Me-2-COOMe-4-Py], [5467:3-CF3-2-COOMe-4-Py], [5468:5-CF3-2-COOMe-4-Py], [5469:6-CF3-2-COOMe-4-Py], [5470:3-CN-2-COOMe-4-Py], [5471:5-CN-2-COOMe-4-Py], [5472:6-CN-2-COOMe-4-Py], [5473:3-OMe-2-COOMe-4-Py], [5474:5-OMe-2-COOMe-4-Py], [5475:6-OMe-2-COOMe-4-Py], [5476:5-COOMe-4-Py], [5477:3-Cl-5-COOMe-4-Py], [5478:2-Cl-5-COOMe-4-Py], [5479:6-Cl-5-COOMe-4-Py], [5480:3-Me-5-COOMe-4-Py], [5481:2-Me-5-COOMe-4-Py], [5482:6-Me-5-COOMe-4-Py], [5483:3-CF3-5-COOMe-4-Py], [5484:2-CF3-5-COOMe-4-Py], [5485:6-CF3-5-COOMe-4-Py], [5486:3-CN-5-COOMe-4-Py], [5487:2-CN-5-COOMe-4-Py], [5488:6-CN-5-COOMe-4-Py], [5489:3-OMe-5-COOMe-4-Py], [5490:2-OMe-5-COOMe-4-Py], [5491:6-OMe-5-COOMe-4-Py], [5492:6-COOMe-4-Py], [5493:3-Cl-6-COOMe-4-Py], [5494:2-Cl-6-COOMe-4-Py], [5495:5-Cl-6-COOMe-4-Py], [5496:3-Me-6-COOMe-4-Py], [5497:2-Me-6-COOMe-4-Py], [5498:5-Me-6-COOMe-4-Py], [5499:3-CF3-6-COOMe-4-Py], [5500:2-CF3-6-COOMe-4-Py],
[5501:5-CF3-6-COOMe-4-Py], [5502:3-CN-6-COOMe-4-Py], [5503:2-CN-6-COOMe-4-Py], [5504:5-CN-6-COOMe-4-Py], [5505:3-OMe-6-COOMe-4-Py], [5506:2-OMe-6-COOMe-4-Py], [5507:5-OMe-6-COOMe-4-Py], [5508:3-NO2-4-Py], [5509:2-Cl-3-NO2-4-Py], [5510:5-Cl-3-NO2-4-Py], [5511:6-Cl-3-NO2-4-Py], [5512:2-Me-3-NO2-4-Py], [5513:5-Me-3-NO2-4-Py], [5514:6-Me-3-NO2-4-Py], [5515:2-CF3-3-NO2-4-Py], [5516:5-CF3-3-NO2-4-Py], [5517:6-CF3-3-NO2-4-Py], [5518:2-CN-3-NO2-4-Py], [5519:5-CN-3-NO2-4-Py], [5520:6-CN-3-NO2-4-Py], [5521:2-OMe-3-NO2-4-Py], [5522:5-OMe-3-NO2-4-Py], [5523:6-OMe-3-NO2-4-Py], [5524:2-NO2-4-Py], [5525:3-Cl-2-NO2-4-Py], [5526:5-Cl-2-NO2-4-Py], [5527:6-Cl-2-NO2-4-Py], [5528:3-Me-2-NO2-4-Py], [5529:5-Me-2-NO2-4-Py], [5530:6-Me-2-NO2-4-Py], [5531:3-CF3-2-NO2-4-Py], [5532:5-CF3-2-NO2-4-Py], [5533:6-CF3-2-NO2-4-Py], [5534:3-CN-2-NO2-4-Py], [5535:5-CN-2-NO2-4-Py], [5536:6-CN-2-NO2-4-Py], [5537:3-OMe-2-NO2-4-Py], [5538:5-OMe-2-NO2-4-Py], [5539:6-OMe-2-NO2-4-Py], [5540:5-NO2-4-Py], [5541:3-Cl-5-NO2-4-Py], [5542:2-Cl-5-NO2-4-Py], [5543:6-Cl-5-NO2-4-Py], [5544:3-Me-5-NO2-4-Py], [5545:2-Me-5-NO2-4-Py], [5546:6-Me-5-NO2-4-Py], [5547:3-CF3-5-NO2-4-Py], [5548:2-CF3-5-NO2-4-Py], [5549:6-CF3-5-NO2-4-Py], [5550:3-CN-5-NO2-4-Py], [5551:2-CN-5-NO2-4-Py], [5552:6-CN-5-NO2-4-Py], [5553:3-OMe-5-NO2-4-Py], [5554:2-OMe-5-NO2-4-Py], [5555:6-OMe-5-NO2-4-Py], [5556:6-NO2-4-Py], [5557:3-Cl-6-NO2-4-Py], [5558:2-Cl-6-NO2-4-Py], [5559:5-Cl-6-NO2-4-Py], [5560:3-Me-6-NO2-4-Py], [5561:2-Me-6-NO2-4-Py], [5562:5-Me-6-NO2-4-Py], [5563:3-CF3-6-NO2-4-Py], [5564:2-CF3-6-NO2-4-Py], [5565:5-CF3-6-NO2-4-Py], [5566:3-CN-6-NO2-4-Py], [5567:2-CN-6-NO2-4-Py], [5568:5-CN-6-NO2-4-Py], [5569:3-OMe-6-NO2-4-Py], [5570:2-OMe-6-NO2-4-Py], [5571:5-OMe-6-NO2-4-Py], [5572:3-NH2-4-Py], [5573:2-Cl-3-NH2-4-Py], [5574:5-Cl-3-NH2-4-Py], [5575:6-Cl-3-NH2-4-Py], [5576:2-Me-3-NH2-4-Py], [5577:5-Me-3-NH2-4-Py], [5578:6-Me-3-NH2-4-Py], [5579:2-CF3-3-NH2-4-Py], [5580:5-CF3-3-NH2-4-Py], [5581:6-CF3-3-NH2-4-Py], [5582:2-CN-3-NH2-4-Py], [5583:5-CN-3-NH2-4-Py], [5584:6-CN-3-NH2-4-Py], [5585:2-OMe-3-NH2-4-Py], [5586:5-OMe-3-NH2-4-Py], [5587:6-OMe-3-NH2-4-Py], [5588:2-NH2-4-Py], [5589:3-Cl-2-NH2-4-Py], [5590:5-Cl-2-NH2-4-Py], [5591:6-Cl-2-NH2-4-Py], [5592:3-Me-2-NH2-4-Py], [5593:5-Me-2-NH2-4-Py], [5594:6-Me-2-NH2-4-Py], [5595:3-CF3-2-NH2-4-Py], [5596:5-CF3-2-NH2-4-Py], [5597:6-CF3-2-NH2-4-Py], [5598:3-CN-2-NH2-4-Py], [5599:5-CN-2-NH2-4-Py], [5600:6-CN-2-NH2-4-Py],
[5601:3-OMe-2-NH2-4-Py], [5602:5-OMe-2-NH2-4-Py], [5603:6-OMe-2-NH2-4-Py], [5604:5-NH2-4-Py], [5605:3-Cl-5-NH2-4-Py], [5606:2-Cl-5-NH2-4-Py], [5607:6-Cl-5-NH2-4-Py], [5608:3-Me-5-NH2-4-Py], [5609:2-Me-5-NH2-4-Py], [5610:6-Me-5-NH2-4-Py], [5611:3-CF3-5-NH2-4-Py], [5612:2-CF3-5-NH2-4-Py], [5613:6-CF3-5-NH2-4-Py], [5614:3-CN-5-NH2-4-Py], [5615:2-CN-5-NH2-4-Py], [5616:6-CN-5-NH2-4-Py], [5617:3-OMe-5-NH2-4-Py], [5618:2-OMe-5-NH2-4-Py], [5619:6-OMe-5-NH2-4-Py], [5620:6-NH2-4-Py], [5621:3-Cl-6-NH2-4-Py], [5622:2-Cl-6-NH2-4-Py], [5623:5-Cl-6-NH2-4-Py], [5624:3-Me-6-NH2-4-Py], [5625:2-Me-6-NH2-4-Py], [5626:5-Me-6-NH2-4-Py], [5627:3-CF3-6-NH2-4-Py], [5628:2-CF3-6-NH2-4-Py], [5629:5-CF3-6-NH2-4-Py], [5630:3-CN-6-NH2-4-Py], [5631:2-CN-6-NH2-4-Py], [5632:5-CN-6-NH2-4-Py], [5633:3-OMe-6-NH2-4-Py], [5634:2-OMe-6-NH2-4-Py], [5635:5-OMe-6-NH2-4-Py], [5636:3-NHMe-4-Py], [5637:2-Cl-3-NHMe-4-Py], [5638:5-Cl-3-NHMe-4-Py], [5639:6-Cl-3-NHMe-4-Py], [5640:2-Me-3-NHMe-4-Py], [5641:5-Me-3-NHMe-4-Py], [5642:6-Me-3-NHMe-4-Py], [5643:2-CF3-3-NHMe-4-Py], [5644:5-CF3-3-NHMe-4-Py], [5645:6-CF3-3-NHMe-4-Py], [5646:2-CN-3-NHMe-4-Py], [5647:5-CN-3-NHMe-4-Py], [5648:6-CN-3-NHMe-4-Py], [5649:2-OMe-3-NHMe-4-Py], [5650:5-OMe-3-NHMe-4-Py], [5651:6-OMe-3-NHMe-4-Py], [5652:2-NHMe-4-Py], [5653:3-Cl-2-NHMe-4-Py], [5654:5-Cl-2-NHMe-4-Py], [5655:6-Cl-2-NHMe-4-Py], [5656:3-Me-2-NHMe-4-Py], [5657:5-Me-2-NHMe-4-Py], [5658:6-Me-2-NHMe-4-Py], [5659:3-CF3-2-NHMe-4-Py], [5660:5-CF3-2-NHMe-4-Py], [5661:6-CF3-2-NHMe-4-Py], [5662:3-CN-2-NHMe-4-Py], [5663:5-CN-2-NHMe-4-Py], [5664:6-CN-2-NHMe-4-Py], [5665:3-OMe-2-NHMe-4-Py], [5666:5-OMe-2-NHMe-4-Py], [5667:6-OMe-2-NHMe-4-Py], [5668:5-NHMe-4-Py], [5669:3-Cl-5-NHMe-4-Py], [5670:2-Cl-5-NHMe-4-Py], [5671:6-Cl-5-NHMe-4-Py], [5672:3-Me-5-NHMe-4-Py], [5673:2-Me-5-NHMe-4-Py], [5674:6-Me-5-NHMe-4-Py], [5675:3-CF3-5-NHMe-4-Py], [5676:2-CF3-5-NHMe-4-Py], [5677:6-CF3-5-NHMe-4-Py], [5678:3-CN-5-NHMe-4-Py], [5679:2-CN-5-NHMe-4-Py], [5680:6-CN-5-NHMe-4-Py], [5681:3-OMe-5-NHMe-4-Py], [5682:2-OMe-5-NHMe-4-Py], [5683:6-OMe-5-NHMe-4-Py], [5684:6-NHMe-4-Py], [5685:3-Cl-6-NHMe-4-Py], [5686:2-Cl-6-NHMe-4-Py], [5687:5-Cl-6-NHMe-4-Py], [5688:3-Me-6-NHMe-4-Py], [5689:2-Me-6-NHMe-4-Py], [5690:5-Me-6-NHMe-4-Py], [5691:3-CF3-6-NHMe-4-Py], [5692:2-CF3-6-NHMe-4-Py], [5693:5-CF3-6-NHMe-4-Py], [5694:3-CN-6-NHMe-4-Py], [5695:2-CN-6-NHMe-4-Py], [5696:5-CN-6-NHMe-4-Py], [5697:3-OMe-6-NHMe-4-Py], [5698:2-OMe-6-NHMe-4-Py], [5699:5-OMe-6-NHMe-4-Py], [5700:3-NMe2-4-Py],
[5701:2-Cl-3-NMe2-4-Py], [5702:5-Cl-3-NMe2-4-Py], [5703:6-Cl-3-NMe2-4-Py], [5704:2-Me-3-NMe2-4-Py], [5705:5-Me-3-NMe2-4-Py], [5706:6-Me-3-NMe2-4-Py], [5707:2-CF3-3-NMe2-4-Py], [5708:5-CF3-3-NMe2-4-Py], [5709:6-CF3-3-NMe2-4-Py], [5710:2-CN-3-NMe2-4-Py], [5711:5-CN-3-NMe2-4-Py], [5712:6-CN-3-NMe2-4-Py], [5713:2-OMe-3-NMe2-4-Py], [5714:5-OMe-3-NMe2-4-

Py], [5715:6-OMe-3-NMe2-4-Py], [5716:4-NMe2-4-Py], [5717:3-Cl-4-NMe2-4-Py], [5718:5-Cl-4-NMe2-4-Py], [5719:6-Cl-4-NMe2-4-Py], [5720:3-Me-4-NMe2-4-Py], [5721:5-Me-4-NMe2-4-Py], [5722:6-Me-4-NMe2-4-Py], [5723:3-CF3-4-NMe2-4-Py], [5724:5-CF3-4-NMe2-4-Py], [5725:6-CF3-4-NMe2-4-Py], [5726:3-CN-4-NMe2-4-Py], [5727:5-CN-4-NMe2-4-Py], [5728:6-CN-4-NMe2-4-Py], [5729:3-OMe-4-NMe2-4-Py], [5730:5-OMe-4-NMe2-4-Py], [5731:6-OMe-4-NMe2-4-Py], [5732:5-NMe2-4-Py], [5733:3-Cl-5-NMe2-4-Py], [5734:2-Cl-5-NMe2-4-Py], [5735:6-Cl-5-NMe2-4-Py], [5736:3-Me-5-NMe2-4-Py], [5737:2-Me-5-NMe2-4-Py], [5738:6-Me-5-NMe2-4-Py], [5739:3-CF3-5-NMe2-4-Py], [5740:2-CF3-5-NMe2-4-Py], [5741:6-CF3-5-NMe2-4-Py], [5742:3-CN-5-NMe2-4-Py], [5743:2-CN-5-NMe2-4-Py], [5744:6-CN-5-NMe2-4-Py], [5745:3-OMe-5-NMe2-4-Py], [5746:2-OMe-5-NMe2-4-Py], [5747:6-OMe-5-NMe2-4-Py], [5748:6-NMe2-4-Py], [5749:3-Cl-6-NMe2-4-Py], [5750:2-Cl-6-NMe2-4-Py], [5751:5-Cl-6-NMe2-4-Py], [5752:3-Me-6-NMe2-4-Py], [5753:2-Me-6-NMe2-4-Py], [5754:5-Me-6-NMe2-4-Py], [5755:3-CF3-6-NMe2-4-Py], [5756:2-CF3-6-NMe2-4-Py], [5757:5-CF3-6-NMe2-4-Py], [5758:3-CN-6-NMe2-4-Py], [5759:2-CN-6-NMe2-4-Py], [5760:5-CN-6-NMe2-4-Py], [5761:3-OMe-6-NMe2-4-Py], [5762:2-OMe-6-NMe2-4-Py], [5763:5-OMe-6-NMe2-4-Py], [5764:3-ACNH-4-Py], [5765:2-Cl-3-ACNH-4-Py], [5766:5-Cl-3-ACNH-4-Py], [5767:6-Cl-3-ACNH-4-Py], [5768:2-Me-3-ACNH-4-Py], [5769:5-Me-3-ACNH-4-Py], [5770:6-Me-3-ACNH-4-Py], [5771:2-CF3-3-ACNH-4-Py], [5772:5-CF3-3-ACNH-4-Py], [5773:6-CF3-3-ACNH-4-Py], [5774:2-CN-3-ACNH-4-Py], [5775:5-CN-3-ACNH-4-Py], [5776:6-CN-3-ACNH-4-Py], [5777:2-OMe-3-ACNH-4-Py], [5778:5-OMe-3-ACNH-4-Py], [5779:6-OMe-3-ACNH-4-Py], [5780:2-ACNH-4-Py], [5781:3-Cl-2-ACNH-4-Py], [5782:5-Cl-2-ACNH-4-Py], [5783:6-Cl-2-ACNH-4-Py], [5784:3-Me-2-ACNH-4-Py], [5785:5-Me-2-ACNH-4-Py], [5786:6-Me-2-ACNH-4-Py], [5787:3-CF3-2-ACNH-4-Py], [5788:5-CF3-2-ACNH-4-Py], [5789:6-CF3-2-ACNH-4-Py], [5790:3-CN-2-ACNH-4-Py], [5791:5-CN-2-ACNH-4-Py], [5792:6-CN-2-ACNH-4-Py], [5793:3-OMe-2-ACNH-4-Py], [5794:5-OMe-2-ACNH-4-Py], [5795:6-OMe-2ACNH-4-Py], [5796:5-ACNH-4-Py], [5797:3-Cl-5-ACNH-4-Py], [5798:2-Cl-5-ACNH-4-Py], [5799:6-Cl-5-ACNH-4-Py], [5800:3-Me-5-ACNH-4-Py], [5801:2-Me-5-ACNH-4-Py], [5802:6-Me-5-ACNH-4-Py], [5803:3-CF3-5-ACNH-4-Py], [5804:2-CF3-5-ACNH-4-Py], [5805:6-CF3-5-ACNH-4-Py], [5806:3-CN-5-ACNH-4-Py], [5807:2-CN-5-ACNH-4-Py], [5808:6-CN-5-ACNH-4-Py], [5809:3-OMe-5-ACNH-4-Py], [5810:2-OMe-5-ACNH-4-Py], [5811:6-OMe-5-ACNH-4-Py], [5812:6-ACNH-4-Py], [5813:3-Cl-6-ACNH-4-Py], [5814:2-Cl-6-ACNH-4-Py], [5815:5-Cl-6-ACNH-4-Py], [5816:3-Me-6-ACNH-4-Py], [5817:2-Me-6-ACNH-4-Py], [5818:5-Me-6-ACNH-4-Py], [5819:3-CF3-6-ACNH-4-Py], [5820:2-CF3-6-ACNH-4-Py], [5821:5-CF3-6-ACNH-4-Py], [5822:3-CN-6-ACNH-4-Py], [5823:2-CN-6-ACNH-4-Py], [5824:5-CN-6-ACNH-4-Py], [5825:3-OMe-6-ACNH-4-Py], [5826:2-OMe-6-ACNH-4-Py], [5827:5-OMe-6-ACNH-4-Py], [5828:3-(N-AC-N-Me-N)-4-Py], [5829:2-Cl-3-(N-AC-N-Me-N)-4-Py], [5830:5-Cl-3-(N-AC-N-Me-N)-4-Py], [5831:6-Cl-3-(N-AC-N-Me-N)-4-Py], [5832:2-Me-3-(N-AC-N-Me-N)-4-Py], [5833:5-Me-3-(N-AC-N-Me-N)-4-Py], [5834:6-Me-3-(N-AC-N-Me-N)-4-Py], [5835:2-CF3-3-(N-AC-N-Me-N)-4-Py], [5836:5-CF3-3-(N-AC-N-Me-N)-4-Py], [5837:6-CF3-3-(N-AC-N-Me-N)-4-Py], [5838:2-CN-3-(N-AC-N-Me-N)-4-Py], [5839:5-CN-3-(N-AC-N-Me-N)-4-Py], [5840:6-CN-3-(N-AC-N-Me-N)-4-Py], [5841:2-OMe-3-(N-AC-N-Me-N)-4-Py], [5842:5-OMe-3-(N-AC-N-Me-N)-4-Py], [5843:6-OMe-3-(N-AC-N-Me-N)-4-Py], [5844:2-(N-AC-N-Me-N)-4-Py], [5845:3-Cl-2-(N-AC-N-Me-N)-4-Py], [5846:5-Cl-2-(N-AC-N-Me-N)-4-Py], [5847:6-Cl-2-(N-AC-N-Me-N)-4-Py], [5848:3-Me-2-(N-AC-N-Me-N)-4-Py], [5849:5-Me-2-(N-AC-N-Me-N)-4-Py], [5850:6-Me-2-(N-AC-N-Me-N)-4-Py], [5851:3-CF3-2-(N-AC-N-Me-N)-4-Py], [5852:5-CF3-2-(N-AC-N-Me-N)-4-Py], [5853:6-CF3-2-(N-AC-N-Me-N)-4-Py], [5854:3-CN-2-(N-AC-N-Me-N)-4-Py], [5855:5-CN-2-(N-AC-N-Me-N)-4-Py], [5856:6-CN-2-(N-AC-N-Me-N)-4-Py], [5857:3-OMe-2-(N-AC-N-Me-N)-4-Py], [5858:5-OMe-2-(N-AC-N-Me-N)-4-Py], [5859:6-OMe-2-(N-AC-N-Me-N)-4-Py], [5860:5-(N-AC-N-Me-N)-4-Py], [5861:3-Cl-5-(N-AC-N-Me-N)-4-Py], [5862:2-Cl-5-(N-AC-N-Me-N)-4-Py], [5863:6-Cl-5-(N-AC-N-Me-N)-4-Py], [5864:3-Me-5-(N-AC-N-Me-N)-4-Py], [5865:2-Me-5-(N-AC-N-Me-N)-4-Py], [5866:6-Me-5-(N-AC-N-Me-N)-4-Py], [5867:3-CF3-5-(N-AC-N-Me-N)-4-Py], [5868:2-CF3-5-(N-AC-N-Me-N)-4-Py], [5869:6-CF3-5-(N-AC-N-Me-N)-4-Py], [5870:3-CN-5-(N-AC-N-Me-N)-4-Py], [5871:2-CN-5-(N-AC-N-Me-N)-4-Py], [5872:6-CN-5-(N-AC-N-Me-N)-4-Py], [5873:3-OMe-5-(N-AC-N-Me-N)-4-Py], [5874:2-OMe-5-(N-AC-N-Me-N)-4-Py], [5875:6-OMe-5-(N-AC-N-Me-N)-4-Py], [5876:6-(N-AC-N-Me-N)-4-Py], [5877:3-Cl-6-(N-AC-N-Me-N)-4-Py], [5878:2-Cl-6-(N-AC-N-Me-N)-4-Py], [5879:5-Cl-6-(N-AC-N-Me-N)-4-Py], [5880:3-Me-6-(N-AC-N-Me-N)-4-Py], [5881:2-Me-6-(N-AC-N-Me-N)-4-Py], [5882:5-Me-6-(N-AC-N-Me-N)-4-Py], [5883:3-CF3-6-(N-AC-N-Me-N)-4-Py], [5884:2-CF3-6-(N-AC-N-Me-N)-4-Py], [5885:5-CF3-6-(N-AC-N-Me-N)-4-Py], [5886:3-CN-6-(N-AC-N-Me-N)-4-Py], [5887:2-CN-6-(N-AC-N-Me-N)-4-Py], [5888:5-CN-6-(N-AC-N-Me-N)-4-Py], [5889:3-OMe-6-(N-AC-N-Me-N)-4-Py], [5890:2-OMe-6-(N-AC-N-Me-N)-4-Py], [5891:5-OMe-6-(N-AC-N-Me-N)-4-Py], [5892:3-AC-4-Py], [5893:2-Cl-3-AC-4-Py], [5894:5-Cl-3-AC-4-Py], [5895:6-Cl-3-AC-4-Py], [5896:2-Me-3-AC-4-Py], [5897:5-Me-3-AC-4-Py], [5898:6-Me-3-AC-4-Py], [5899:2-CF3-3-AC-4-Py], [5900:5-CF3-3-AC-4-Py], [5901:6-CF3-3-AC-4-Py], [5902:2-CN-3-AC-4-Py], [5903:5-CN-3-AC-4-Py], [5904:6-CN-3-AC-4-Py], [5905:2-OMe-3-AC-4-Py], [5906:5-OMe-3-AC-4-Py], [5907:6-OMe-3-AC-4-Py], [5908:2-AC-4-Py], [5909:3-Cl-2-AC-4-Py], [5910:5-Cl-2-AC-4-Py], [5911:6-Cl-2-AC-4-Py], [5912:3-Me-2-AC-4-Py], [5913:5-Me-2-AC-4-Py], [5914:6-Me-2-AC-4-Py], [5915:3-CF3-2-AC-4-Py], [5916:5-CF3-2-AC-4-Py], [5917:6-CF3-2-AC-4-Py], [5918:3-CN-2-AC-4-Py], [5919:5-CN-2-AC-4-Py], [5920:6-CN-2-AC-4-Py], [5921:3-OMe-2-AC-4-Py], [5922:5-OMe-2-AC-4-Py], [5923:6-OMe-2-AC-4-Py], [5924:5-AC-4-Py], [5925:3-Cl-5-AC-4-Py], [5926:2-Cl-5-AC-4-Py], [5927:6-Cl-5-AC-4-Py], [5928:3-Me-5-AC-4-Py], [5929:2-Me-5-AC-4-Py], [5930:6-Me-5-AC-4-Py], [5931:3-CF3-5-AC-4-Py], [5932:2-CF3-5-AC-4-Py], [5933:6-CF3-5-AC-4-Py], [5934:3-CN-5-AC-4-Py], [5935:2-CN-5-AC-4-Py], [5936:6-CN-5-AC-4-Py], [5937:3-OMe-5-AC-4-Py], [5938:2-OMe-5-AC-4-Py], [5939:6-OMe-5-AC-4-Py], [5940:6-AC-4-Py], [5941:3-Cl-6-AC-4-Py], [5942:2-Cl-6-AC-4-Py], [5943:5-Cl-6-AC-4-Py], [5944:3-Me-6-AC-4-Py], [5945:2-Me-6-AC-4-Py], [5946:5-Me-6-AC-4-Py], [5947:3-CF3-6-AC-4-Py], [5948:2-CF3-6-AC-4-Py], [5949:5-CF3-6-AC-4-Py], [5950:3-CN-6-AC-4-Py], [5951:2-CN-6-AC-4-Py], [5952:5-CN-6-AC-4-Py], [5953:3-OMe-6-AC-4-Py], [5954:2-OMe-6-AC-4-Py], [5955:5-OMe-6-AC-4-Py], [5956:1,2-(methylenedioxy)phenyl-4-yl], [5957:2,3-dihydrobenzofuran-5-yl], [5958:2,3-dihydrobenzofuran-6-yl], [5959:1,3-dihydroisobenzofuran-5-yl], [5960:

benzofuran-5-yl], [5961:benzofuran-6-yl], [5962:2,3-dihydrobenzothiophen-5-yl], [5963:2,3-dihydrobenzothiophen-6-yl], [5964:1,3-dihydroisobenzothiophen-5-yl], [5965:benzothiophen-5-yl], [5966:benzothiophen-6-yl], [5967:benzodioxane-4-yl], [5968:chroman-6-yl], [5969:chroman-7-yl], [5970:isochroman-6-yl], [5971:isochroman-7-yl], [5972:2-quinolyl], [5973:3-quinolyl], [5974:3,4-methylenedioxyphenyl], [5975:2-indolyl], [5976:3-indolyl], [5977:2-benzoimidazolyl], [5978:2-thienyl], [5979:3-thienyl], [5980:2,3-dihydrobenzofuran-7-yl], [5981:2-pyrimidyl], [5982:5-pyrimidyl], [5983:2-thiazolyl], [5984:4-thiazolyl], [5985:5-thiazolyl], [5986:pyrazyl], [5987:3-pyridazyl], [5988:2-benzoxazolyl], [5989:2-benzothiazolyl], [5990:2-quinazolyl], [5991:2-quinoxalyl]

For example, HA1001-0002 is a compound in which substituent number is 2 in a compound represented by formula (HA1001) and is a compound of the following structure.

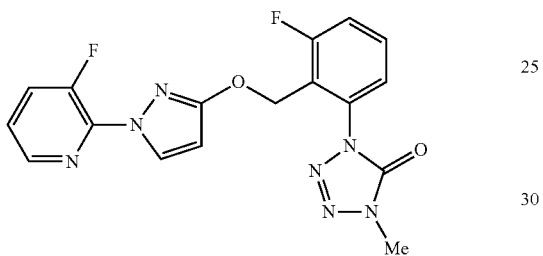
(HA1001-0002)

In accordance with the above processes, it is possible to obtain compounds RA1001-0001 to RA1001-1433, RA1002-0001 to RA1002-1433, RA1003-0001 to RA1003-1433, RA1004-0001 to RA1004-1433, RA1005-0001 to RA1005-1433, RA1006-0001 to RA1006-1433, RA1007-0001 to RA1007-1433, RA1008-0001 to RA1008-1433, RA1009-0001 to RA1009-1433, RA1010-0001 to RA1010-1433, RA1011-0001 to RA1011-1433, RA1012-0001 to RA1012-1433, RA1013-0001 to RA1013-1433, RA1014-0001 to RA1014-1433, RA1015-0001 to RA1015-1433, RA1016-0001 to RA1016-1433, RA1017-0001 to RA1017-1433, RA1018-0001 to RA1018-1433, RA1019-0001 to RA1019-1433, RA1020-0001 to RA1020-1433, RA1021-0001 to RA1021-1433, RA1022-0001 to RA1022-1433, RA1023-0001 to RA1023-1433, RA1024-0001 to RA1024-1433, RA1025-0001 to RA1025-1433, RA1026-0001 to RA1026-1433, RA1027-0001 to RA1027-1433, RA1028-0001 to RA1028-1433, RA1029-0001 to RA1029-1433, RA1030-0001 to RA1030-1433, RA1031-0001 to RA1031-1433, RA1032-0001 to RA1032-1433, RA1033-0001 to RA1033-1433, RA1034-0001 to RA1034-1433, RA1035-0001 to RA1035-1433, RA1036-0001 to RA1036-1433, RA1037-0001 to RA1037-1433, RA1038-0001 to RA1038-1433, RA1039-0001 to RA1039-1433, RA1040-0001 to RA1040-1433, RA1041-0001 to RA1041-1433, RA1042-0001 to RA1042-1433, RA1043-0001 to RA1043-1433, RA1044-0001 to RA1044-1433, RA1045-0001 to RA1045-1433, RA1046-0001 to RA1046-1433, RA1047-0001 to RA1047-1433, RA1048-0001 to RA1048-1433, RA1049-0001 to RA1049-1433, RA1050-0001 to RA1050-1433, RA1051-0001 to RA1051-1433, RA1052-0001 to RA1052-1433, RA1053-0001 to RA1053-1433, and RA1054-0001 to RA1054-1433.

The compounds RA1001-0001 to RA1054-1433 are pyrazole compounds represented by formulas:

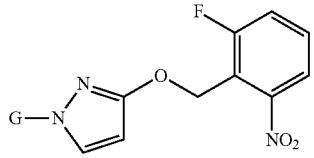
(RA1001)

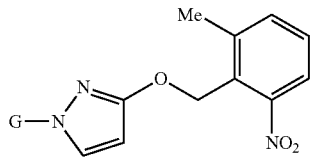
(RA1002)

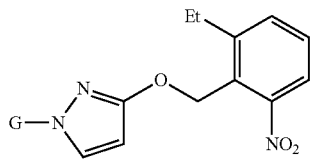
(RA1003)

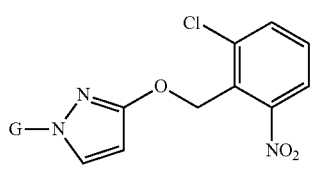
(RA1004)

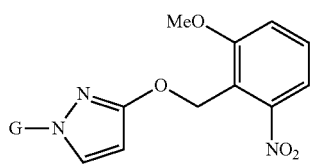
(RA1005)

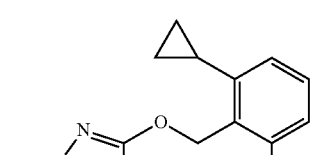
(RA1006)

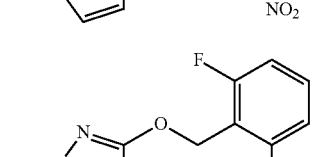
(RA1007)

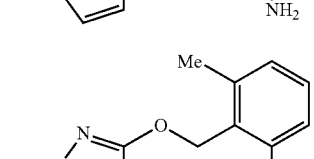
(RA1008)

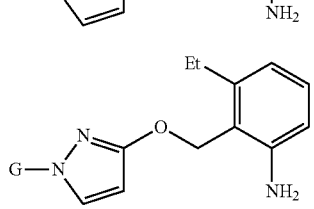
(RA1009)

-continued (RA1010)
(RA1011)
(RA1012)
(RA1013)
(RA1014)
(RA1015)
(RA1019)
(RA1020)
(RA1021)

-continued (RA1022)
(RA1023)
(RA1024)
(RA1025)
(RA1026)
(RA1027)
(RA1028)
(RA1029)
(RA1030)

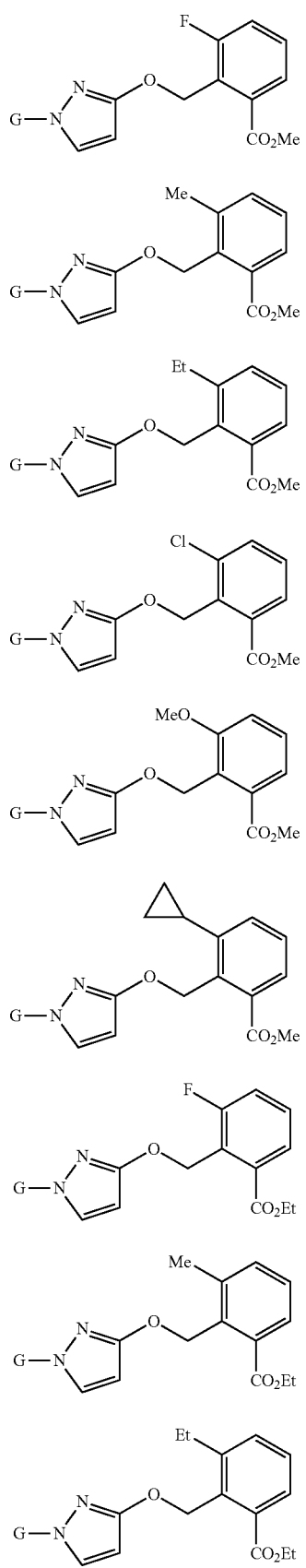
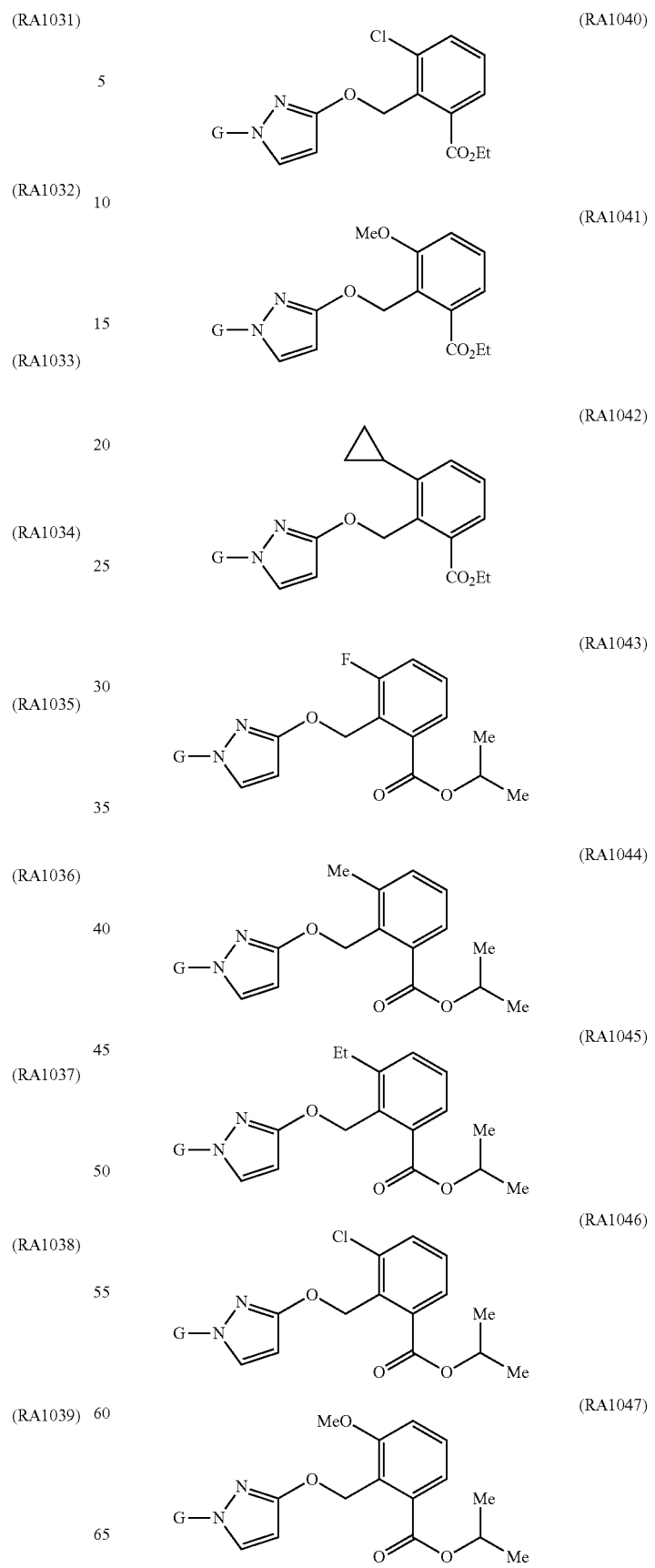

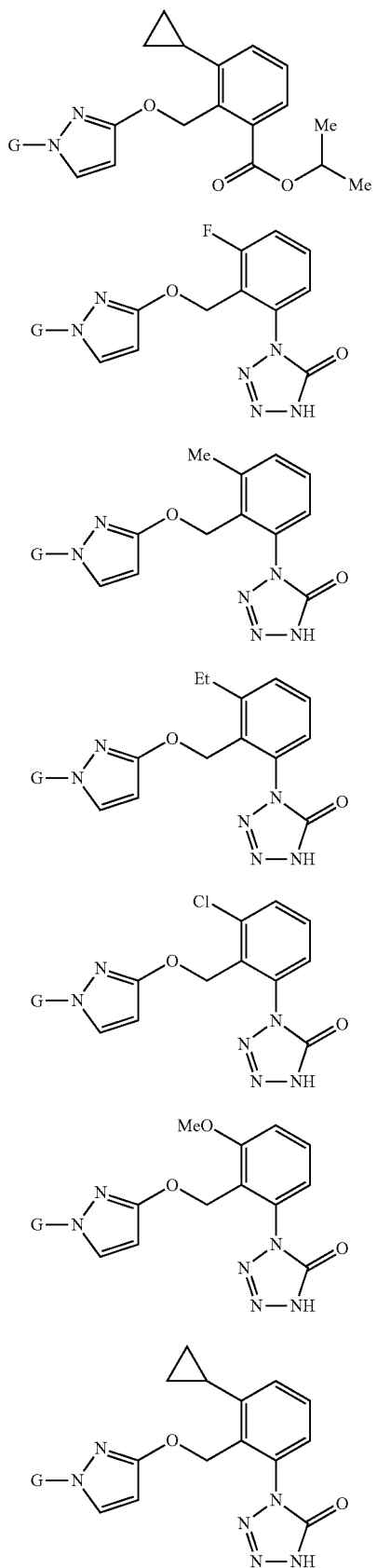

(RA1048)
(RA1049)
(RA1050)
(RA1051)
(RA1052)
(RA1053)
(RA1054)

wherein G is a substituent corresponding to each of substituent numbers 1 to 1433. 3-Py mentioned in the following [substituent number; G] represents pyridin-3-yl, F represents fluoro, Cl represents chloro, Br represents bromo, I represents iodo, CN represents cyano, Me represents methyl, Et represents ethyl, Pr represents propyl, CF3 represents trifluoromethyl, CH2CF3 represents 2,2,2-trifluoroethyl, CHF2 represents difluoromethyl, OMe represents methoxy, OCH2CF3 represents 2,2,2-trifluoroethoxy, OEt represents ethoxy, OPr represents propoxy, OCF3 represents trifluoromethoxy, OCHF2 represents difluoromethoxy, SMe represents methylthio, S(O)Me represents methylsulfinyl, S(O)2Me represents methylsulfonyl, SCF3 represents trifluoromethylthio, S(O)CF3 represents trifluoromethylsulfinyl, S(O)2CF3 represents trifluoromethylsulfonyl, COOMe represents methoxycarbonyl, and NO2 represents nitro.

[1:3-Py], [2:2-F-3-Py], [3:4-Cl-2-F-3-Py], [4:5-Cl-2-F-3-Py], [5:6-Cl-2-F-3-Py], [6:4-Me-2-F-3-Py], [7:5-Me-2-F-3-Py], [8:6-Me-2-F-3-Py], [9:4-CF3-2-F-3-Py], [10:5-CF3-2-F-3-Py], [11:6-CF3-2-F-3-Py], [12:4-CN-2-F-3-Py], [13:5-CN-2-F-3-Py], [14:6-CN-2-F-3-Py], [15:4-OMe-2-F-3-Py], [16:5-OMe-2-F-3-Py], [17:6-OMe-2-F-3-Py], [18:4-F-3-Py], [19:2-Cl-4-F-3-Py], [20:5-Cl-4-F-3-Py], [21:6-Cl-4-F-3-Py], [22:2-Me-4-F-3-Py], [23:5-Me-4-F-3-Py], [24:6-Me-4-F-3-Py], [25:2-CF3-4-F-3-Py], [26:5-CF3-4-F-3-Py], [27:6-CF3-4-F-3-Py], [28:2-CN-4-F-3-Py], [29:5-CN-4-F-3-Py], [30:6-CN-4-F-3-Py], [31:2-OMe-4-F-3-Py], [32:5-OMe-4-F-3-Py], [33:6-OMe-4-F-3-Py], [34:5-F-3-Py], [35:2-Cl-5-F-3-Py], [36:4-Cl-5-F-3-Py], [37:6-Cl-5-F-3-Py], [38:2-Me-5-F-3-Py], [39:4-Me-5-F-3-Py], [40:6-Me-5-F-3-Py], [41:2-CF3-5-F-3-Py], [42:4-CF3-5-F-3-Py], [43:6-CF3-5-F-3-Py], [44:2-CN-5-F-3-Py], [45:4-CN-5-F-3-Py], [46:6-CN-5-F-3-Py], [47:2-OMe-5-F-3-Py], [48:4-OMe-5-F-3-Py], [49:6-OMe-5-F-3-Py], [50:6-F-3-Py], [51:2-Cl-6-F-3-Py], [52:4-Cl-6-F-3-Py], [53:5-Cl-6-F-3-Py], [54:2-Me-6-F-3-Py], [55:4-Me-6-F-3-Py], [56:5-Me-6-F-3-Py], [57:2-CF3-6-F-3-Py], [58:4-CF3-6-F-3-Py], [59:5-CF3-6-F-3-Py], [60:2-CN-6-F-3-Py], [61:4-CN-6-F-3-Py], [62:5-CN-6-F-3-Py], [63:2-OMe-6-F-3-Py], [64:4-OMe-6-F-3-Py], [65:5-OMe-6-F-3-Py], [66:2-Cl-3-Py], [67:4-Cl-2-Cl-3-Py], [68:5-Cl-2-Cl-3-Py], [69:6-Cl-2-Cl-3-Py], [70:4-Me-2-Cl-3-Py], [71:5-Me-2-Cl-3-Py], [72:6-Me-2-Cl-3-Py], [73:4-CF3-2-Cl-3-Py], [74:5-CF3-2-Cl-3-Py], [75:6-CF3-2-Cl-3-Py], [76:4-CN-2-Cl-3-Py], [77:5-CN-2-Cl-3-Py], [78:6-CN-2-Cl-3-Py], [79:4-OMe-2-Cl-3-Py], [80:5-OMe-2-Cl-3-Py], [81:6-OMe-2-Cl-3-Py], [82:4-Cl-3-Py], [83:2-Cl-4-Cl-3-Py], [84:5-Cl-4-Cl-3-Py], [85:6-Cl-4-Cl-3-Py], [86:2-Me-4-Cl-3-Py], [87:5-Me-4-Cl-3-Py], [88:6-Me-4-Cl-3-Py], [89:2-CF3-4-Cl-3-Py], [90:5-CF3-4-Cl-3-Py], [91:6-CF3-4-Cl-3-Py], [92:2-CN-4-Cl-3-Py], [93:5-CN-4-Cl-3-Py], [94:6-CN-4-Cl-3-Py], [95:2-OMe-4-Cl-3-Py], [96:5-OMe-4-Cl-3-Py], [97:6-OMe-4-Cl-3-Py], [98:5-Cl-3-Py], [99:4-Cl-5-Cl-3-Py], [100:5-Cl-5-Cl-3-Py], [101:6-Cl-5-Cl-3-Py], [102:4-Me-5-Cl-3-Py], [103:5-Me-5-Cl-3-Py], [104:6-Me-5-Cl-3-Py], [105:4-CF3-5-Cl-3-Py], [106:5-CF3-5-Cl-3-Py], [107:6-CF3-5-Cl-3-Py], [108:4-CN-5-Cl-3-Py], [109:5-CN-5-Cl-3-Py], [110:6-CN-5-Cl-3-Py], [111:4-OMe-5-Cl-3-Py], [112:5-OMe-5-Cl-3-Py], [113:6-OMe-5-Cl-3-Py], [114:6-Cl-3-Py], [115:2-Cl-6-Cl-3-Py], [116:4-Cl-6-Cl-3-Py], [117:5-Cl-6-Cl-3-Py], [118:2-Me-6-Cl-3-Py], [119:4-Me-6-Cl-3-Py], [120:5-Me-6-Cl-3-Py], [121:2-CF3-6-Cl-3-Py], [122:4-CF3-6-Cl-3-Py], [123:5-CF3-6-Cl-3-Py], [124:2-CN-6-Cl-3-Py], [125:4-CN-6-Cl-3-Py], [126:5-CN-6-Cl-3-Py], [127:2-OMe-6-Cl-3-Py], [128:4-OMe-6-Cl-3-Py], [129:5-OMe-6-Cl-3-Py], [130:2-Br-3-Py], [131:4-Cl-2-Br-3-Py], [132:5-Cl-2-Br-3-Py],

[133:6-Cl-2-Br-3-Py], [134:4-Me-2-Br-3-Py], [135:5-Me-2-Br-3-Py], [136:6-Me-2-Br-3-Py], [137:4-CF3-2-Br-3-Py], [138:5-CF3-2-Br-3-Py], [139:6-CF3-2-Br-3-Py], [140:4-CN-2-Br-3-Py], [141:5-CN-2-Br-3-Py], [142:6-CN-2-Br-3-Py], [143:4-OMe-2-Br-3-Py], [144:5-OMe-2-Br-3-Py], [145:6-OMe-2-Br-3-Py], [146:4-Br-3-Py], [147:2-Cl-4-Br-3-Py], [148:5-Cl-4-Br-3-Py], [149:6-Cl-4-Br-3-Py], [150:2-Me-4-Br-3-Py], [151:5-Me-4-Br-3-Py], [152:6-Me-4-Br-3-Py], [153:2-CF3-4-Br-3-Py], [154:5-CF3-4-Br-3-Py], [155:6-CF3-4-Br-3-Py], [156:2-CN-4-Br-3-Py], [157:5-CN-4-Br-3-Py], [158:6-CN-4-Br-3-Py], [159:2-OMe-4-Br-3-Py], [160:5-OMe-4-Br-3-Py], [161:6-OMe-4-Br-3-Py], [162:5-Br-3-Py], [163:2-Cl-5-Br-3-Py], [164:4-Cl-5-Br-3-Py], [165:6-Cl-5-Br-3-Py], [166:2-Me-5-Br-3-Py], [167:4-Me-5-Br-3-Py], [168:6-Me-5-Br-3-Py], [169:2-CF3-5-Br-3-Py], [170:4-CF3-5-Br-3-Py], [171:6-CF3-5-Br-3-Py], [172:2-CN-5-Br-3-Py], [173:4-CN-5-Br-3-Py], [174:6-CN-5-Br-3-Py], [175:2-OMe-5-Br-3-Py], [176:4-OMe-5-Br-3-Py], [177:6-OMe-5-Br-3-Py], [178:6-Br-3-Py], [179:2-Cl-6-Br-3-Py], [180:4-Cl-6-Br-3-Py], [181:5-Cl-6-Br-3-Py], [182:2-Me-6-Br-3-Py], [183:4-Me-6-Br-3-Py], [184:5-Me-6-Br-3-Py], [185:2-CF3-6-Br-3-Py], [186:4-CF3-6-Br-3-Py], [187:5-CF3-6-Br-3-Py], [188:2-CN-6-Br-3-Py], [189:4-CN-6-Br-3-Py], [190:5-CN-6-Br-3-Py], [191:2-OMe-6-Br-3-Py], [192:4-OMe-6-Br-3-Py], [193:5-OMe-6-Br-3-Py], [194:2-I-3-Py], [195:4-Cl-2-I-3-Py], [196:5-Cl-2-I-3-Py], [197:6-Cl-2-I-3-Py], [198:4-Me-2-I-3-Py], [199:5-Me-2-I-3-Py], [200:6-Me-2-I-3-Py],

[201:4-CF3-2-I-3-Py], [202:5-CF3-2-I-3-Py], [203:6-CF3-2-I-3-Py], [204:4-CN-2-I-3-Py], [205:5-CN-2-I-3-Py], [206:6-CN-2-I-3-Py], [207:4-OMe-2-I-3-Py], [208:5-OMe-2-I-3-Py], [209:6-OMe-2-I-3-Py], [210:4-I-3-Py], [211:2-Cl-4-I-3-Py], [212:5-Cl-4-I-3-Py], [213:6-Cl-4-I-3-Py], [214:2-Me-4-I-3-Py], [215:5-Me-4-1-3-Py], [216:6-Me-4-I-3-Py], [217:2-CF3-4-I-3-Py], [218:5-CF3-4-I-3-Py], [219:6-CF3-4-I-3-Py], [220:2-CN-4-I-3-Py], [221:5-CN-4-I-3-Py], [222:6-CN-4-I-3-Py], [223:2-OMe-4-I-3-Py], [224:5-OMe-4-I-3-Py], [225:6-OMe-4-I-3-Py], [226:5-1-3-Py], [227:2-Cl-5-I-3-Py], [228:4-Cl-5-I-3-Py], [229:6-Cl-5-I-3-Py], [230:2-Me-5-I-3-Py], [231:4-Me-5-I-3-Py], [232:6-Me-5-I-3-Py], [233:2-CF3-5-I-3-Py], [234:4-CF3-5-I-3-Py], [235:6-CF3-5-I-3-Py], [236:2-CN-5-I-3-Py], [237:4-CN-5-I-3-Py], [238:6-CN-5-I-3-Py], [239:2-OMe-5-I-3-Py], [240:4-OMe-5-I-3-Py], [241:6-OMe-5-I-3-Py], [242:6-I-3-Py], [243:2-Cl-6-I-3-Py], [244:4-Cl-6-I-3-Py], [245:5-Cl-6-I-3-Py], [246:2-Me-6-I-3-Py], [247:4-Me-6-I-3-Py], [248:5-Me-6-I-3-Py], [249:2-CF3-6-I-3-Py], [250:4-CF3-6-I-3-Py], [251:5-CF3-6-I-3-Py], [252:2-CN-6-I-3-Py], [253:4-CN-6-I-3-Py], [254:5-CN-6-I-3-Py], [255:2-OMe-6-I-3-Py], [256:4-OMe-6-I-3-Py], [257:5-OMe-6-I-3-Py], [258:2-Me-3-Py], [259:4-Cl-2-Me-3-Py], [260:5-Cl-2-Me-3-Py], [261:6-Cl-2-Me-3-Py], [262:4-Me-2-Me-3-Py], [263:5-Me-2-Me-3-Py], [264:6-Me-2-Me-3-Py], [265:4-CF3-2-Me-3-Py], [266:5-CF3-2-Me-3-Py], [267:6-CF3-2-Me-3-Py], [268:4-CN-2-Me-3-Py], [269:5-CN-2-Me-3-Py], [270:6-CN-2-Me-3-Py], [271:4-OMe-2-Me-3-Py], [272:5-OMe-2-Me-3-Py], [273:6-OMe-2-Me-3-Py], [274:4-Me-3-Py], [275:2-Cl-4-Me-3-Py], [276:5-Cl-4-Me-3-Py], [277:6-Cl-4-Me-3-Py], [278:2-Me-4-Me-3-Py], [279:5-Me-4-Me-3-Py], [280:6-Me-4-Me-3-Py], [281:2-CF3-4-Me-3-Py], [282:5-CF3-4-Me-3-Py], [283:6-CF3-4-Me-3-Py], [284:2-CN-4-Me-3-Py], [285:5-CN-4-Me-3-Py], [286:6-CN-4-Me-3-Py], [287:2-OMe-4-Me-3-Py], [288:5-OMe-4-Me-3-Py], [289:6-OMe-4-Me-3-Py], [290:5-Me-3-Py], [291:2-Cl-5-Me-3-Py], [292:4-Cl-5-Me-3-Py], [293:6-Cl-5-Me-3-Py], [294:2-Me-5-Me-3-Py], [295:4-Me-5-Me-3-Py], [296:6-Me-5-Me-3-Py], [297:2-CF3-5-Me-3-Py], [298:4-CF3-5-Me-3-Py], [299:6-CF3-5-Me-3-Py], [300:2-CN-5-Me-3-Py],

[301:4-CN-5-Me-3-Py], [302:6-CN-5-Me-3-Py], [303:2-OMe-5-Me-3-Py], [304:4-OMe-5-Me-3-Py], [305:6-OMe-5-Me-3-Py], [306:6-Me-3-Py], [307:2-Cl-6-Me-3-Py], [308:4-Cl-6-Me-3-Py], [309:5-Cl-6-Me-3-Py], [310:2-Me-6-Me-3-Py], [311:4-Me-6-Me-3-Py], [312:5-Me-6-Me-3-Py], [313:2-CF3-6-Me-3-Py], [314:4-CF3-6-Me-3-Py], [315:5-CF3-6-Me-3-Py], [316:2-CN-6-Me-3-Py], [317:4-CN-6-Me-3-Py], [318:5-CN-6-Me-3-Py], [319:2-OMe-6-Me-3-Py], [320:4-OMe-6-Me-3-Py], [321:5-OMe-6-Me-3-Py], [322:2-OMe-3-Py], [323:4-Cl-2-OMe-3-Py], [324:5-Cl-2-OMe-3-Py], [325:6-Cl-2-OMe-3-Py], [326:4-Me-2-OMe-3-Py], [327:5-Me-2-OMe-3-Py], [328:6-Me-2-OMe-3-Py], [329:4-CF3-2-OMe-3-Py], [330:5-CF3-2-OMe-3-Py], [331:6-CF3-2-OMe-3-Py], [332:4-CN-2-OMe-3-Py], [333:5-CN-2-OMe-3-Py], [334:6-CN-2-OMe-3-Py], [335:4-OMe-2-OMe-3-Py], [336:5-OMe-2-OMe-3-Py], [337:6-OMe-2-OMe-3-Py], [338:4-OMe-3-Py], [339:2-Cl-4-OMe-3-Py], [340:5-Cl-4-OMe-3-Py], [341:6-Cl-4-OMe-3-Py], [342:2-Me-4-OMe-3-Py], [343:5-Me-4-OMe-3-Py], [344:6-Me-4-OMe-3-Py], [345:2-CF3-4-OMe-3-Py], [346:5-CF3-4-OMe-3-Py], [347:6-CF3-4-OMe-3-Py], [348:2-CN-4-OMe-3-Py], [349:5-CN-4-OMe-3-Py], [350:6-CN-4-OMe-3-Py], [351:2-OMe-4-OMe-3-Py], [352:5-OMe-4-OMe-3-Py], [353:6-OMe-4-OMe-3-Py], [354:5-OMe-3-Py], [355:2-Cl-5-OMe-3-Py], [356:4-Cl-5-OMe-3-Py], [357:6-Cl-5-OMe-3-Py], [358:2-Me-5-OMe-3-Py], [359:4-Me-5-OMe-3-Py], [360:6-Me-5-OMe-3-Py], [361:2-CF3-5-OMe-3-Py], [362:4-CF3-5-OMe-3-Py], [363:6-CF3-5-OMe-3-Py], [364:2-CN-5-OMe-3-Py], [365:4-CN-5-OMe-3-Py], [366:6-CN-5-OMe-3-Py], [367:2-OMe-5-OMe-3-Py], [368:4-OMe-5-OMe-3-Py], [369:6-OMe-5-OMe-3-Py], [370:6-OMe-3-Py], [371:2-Cl-6-OMe-3-Py], [372:4-Cl-6-OMe-3-Py], [373:5-Cl-6-OMe-3-Py], [374:2-Me-6-OMe-3-Py], [375:4-Me-6-OMe-3-Py], [376:5-Me-6-OMe-3-Py], [377:2-CF3-6-OMe-3-Py], [378:4-CF3-6-OMe-3-Py], [379:5-CF3-6-OMe-3-Py], [380:2-CN-6-OMe-3-Py], [381:4-CN-6-OMe-3-Py], [382:5-CN-6-OMe-3-Py], [383:2-OMe-6-OMe-3-Py], [384:4-OMe-6-OMe-3-Py], [385:5-OMe-6-OMe-3-Py], [386:2-CF3-3-Py], [387:4-Cl-2-CF3-3-Py], [388:5-Cl-2-CF3-3-Py], [389:6-Cl-2-CF3-3-Py], [390:4-Me-2-CF3-3-Py], [391:5-Me-2-CF3-3-Py], [392:6-Me-2-CF3-3-Py], [393:4-CF3-2-CF3-3-Py], [394:5-CF3-2-CF3-3-Py], [395:6-CF3-2-CF3-3-Py], [396:4-CN-2-CF3-3-Py], [397:5-CN-2-CF3-3-Py], [398:6-CN-2-CF3-3-Py], [399:4-OMe-2-CF3-3-Py], [400:5-OMe-2-CF3-3-Py],

[401:6-OMe-2-CF3-3-Py], [402:4-CF3-3-Py], [403:2-Cl-4-CF3-3-Py], [404:5-Cl-4-CF3-3-Py], [405:6-Cl-4-CF3-3-Py], [406:2-Me-4-CF3-3-Py], [407:5-Me-4-CF3-3-Py], [408:6-Me-4-CF3-3-Py], [409:2-CF3-4-CF3-3-Py], [410:5-CF3-4-CF3-3-Py], [411:6-CF3-4-CF3-3-Py], [412:2-CN-4-CF3-3-Py], [413:5-CN-4-CF3-3-Py], [414:6-CN-4-CF3-3-Py], [415:2-OMe-4-CF3-3-Py], [416:5-OMe-4-CF3-3-Py], [417:6-OMe-4-CF3-3-Py], [418:5-CF3-3-Py], [419:2-Cl-5-CF3-3-Py], [420:4-Cl-5-CF3-3-Py], [421:6-Cl-5-CF3-3-Py], [422:2-Me-5-CF3-3-Py], [423:4-Me-5-CF3-3-Py], [424:6-Me-5-CF3-3-Py], [425:2-CF3-5-CF3-3-Py], [426:4-CF3-5-CF3-3-Py], [427:6-CF3-5-CF3-3-Py], [428:2-CN-5-CF3-3-Py], [429:4-CN-5-CF3-3-Py], [430:6-CN-5-CF3-3-Py], [431:2-OMe-5-CF3-3-Py], [432:4-OMe-5-CF3-3-Py], [433:6-OMe-5-CF3-3-Py], [434:6-CF3-3-Py], [435:2-Cl-6-CF3-3-Py], [436:4-Cl-6-CF3-3-Py], [437:5-Cl-6-CF3-3-Py], [438:2-Me-6-CF3-3-Py], [439:4-Me-6-CF3-3-Py], [440:5-Me-6-CF3-3-Py], [441:2-CF3-6-CF3-3-Py], [442:4-CF3-6-CF3-3-Py], [443:5-CF3-6-CF3-3-Py], [444:2-CN-6-CF3-3-Py], [445:4-CN-6-CF3-3-Py], [446:5-CN-6-CF3-3-

Py], [447:2-OMe-6-CF3-3-Py], [448:4-OMe-6-CF3-3-Py], [449:5-OMe-6-CF3-3-Py], [450:2-OCF3-3-Py], [451:4-Cl-2-OCF3-3-Py], [452:5-Cl-2-OCF3-3-Py], [453:6-Cl-2-OCF3-3-Py], [454:4-Me-2-OCF3-3-Py], [455:5-Me-2-OCF3-3-Py], [456:6-Me-2-OCF3-3-Py], [457:4-CF3-2-OCF3-3-Py], [458:5-CF3-2-OCF3-3-Py], [459:6-CF3-2-OCF3-3-Py], [460:4-CN-2-OCF3-3-Py], [461:5-CN-2-OCF3-3-Py], [462:6-CN-2-OCF3-3-Py], [463:4-OMe-2-OCF3-3-Py], [464:5-OMe-2-OCF3-3-Py], [465:6-OMe-2-OCF3-3-Py], [466:4-OCF3-3-Py], [467:2-Cl-4-OCF3-3-Py], [468:5-Cl-4-OCF3-3-Py], [469:6-Cl-4-OCF3-3-Py], [470:2-Me-4-OCF3-3-Py], [471:5-Me-4-OCF3-3-Py], [472:6-Me-4-OCF3-3-Py], [473:2-CF3-4-OCF3-3-Py], [474:5-CF3-4-OCF3-3-Py], [475:6-CF3-4-OCF3-3-Py], [476:2-CN-4-OCF3-3-Py], [477:5-CN-4-OCF3-3-Py], [478:6-CN-4-OCF3-3-Py], [479:2-OMe-4-OCF3-3-Py], [480:5-OMe-4-OCF3-3-Py], [481:6-OMe-4-OCF3-3-Py], [482:5-OCF3-3-Py], [483:2-Cl-5-OCF3-3-Py], [484:4-Cl-5-OCF3-3-Py], [485:6-Cl-5-OCF3-3-Py], [486:2-Me-5-OCF3-3-Py], [487:4-Me-5-OCF3-3-Py], [488:6-Me-5-OCF3-3-Py], [489:2-CF3-5-OCF3-3-Py], [490:4-CF3-5-OCF3-3-Py], [491:6-CF3-5-OCF3-3-Py], [492:2-CN-5-OCF3-3-Py], [493:4-CN-5-OCF3-3-Py], [494:6-CN-5-OCF3-3-Py], [495:2-OMe-5-OCF3-3-Py], [496:4-OMe-5-OCF3-3-Py], [497:6-OMe-5-OCF3-3-Py], [498:6-OCF3-3-Py], [499:2-Cl-6-OCF3-3-Py], [500:4-Cl-6-OCF3-3-Py],

[501:5-Cl-6-OCF3-3-Py], [502:2-Me-6-OCF3-3-Py], [503:4-Me-6-OCF3-3-Py], [504:5-Me-6-OCF3-3-Py], [505:2-CF3-6-OCF3-3-Py], [506:4-CF3-6-OCF3-3-Py], [507:5-CF3-6-OCF3-3-Py], [508:2-CN-6-OCF3-3-Py], [509:4-CN-6-OCF3-3-Py], [510:5-CN-6-OCF3-3-Py], [511:2-OMe-6-OCF3-3-Py], [512:4-OMe-6-OCF3-3-Py], [513:5-OMe-6-OCF3-3-Py], [514:2-CHF2-3-Py], [515:4-Cl-2-CHF2-3-Py], [516:5-Cl-2-CHF2-3-Py], [517:6-Cl-2-CHF2-3-Py], [518:4-Me-2-CHF2-3-Py], [519:5-Me-2-CHF2-3-Py], [520:6-Me-2-CHF2-3-Py], [521:4-CF3-2-CHF2-3-Py], [522:5-CF3-2-CHF2-3-Py], [523:6-CF3-2-CHF2-3-Py], [524:4-CN-2-CHF2-3-Py], [525:5-CN-2-CHF2-3-Py], [526:6-CN-2-CHF2-3-Py], [527:4-OMe-2-CHF2-3-Py], [528:5-OMe-2-CHF2-3-Py], [529:6-OMe-2-CHF2-3-Py], [530:4-CHF2-3-Py], [531:2-Cl-4-CHF2-3-Py], [532:5-Cl-4-CHF2-3-Py], [533:6-Cl-4-CHF2-3-Py], [534:2-Me-4-CHF2-3-Py], [535:5-Me-4-CHF2-3-Py], [536:6-Me-4-CHF2-3-Py], [537:2-CF3-4-CHF2-3-Py], [538:5-CF3-4-CHF2-3-Py], [539:6-CF3-4-CHF2-3-Py], [540:2-CN-4-CHF2-3-Py], [541:5-CN-4-CHF2-3-Py], [542:6-CN-4-CHF2-3-Py], [543:2-OMe-4-CHF2-3-Py], [544:5-OMe-4-CHF2-3-Py], [545:6-OMe-4-CHF2-3-Py], [546:5-CHF2-3-Py], [547:2-Cl-5-CHF2-3-Py], [548:4-Cl-5-CHF2-3-Py], [549:6-Cl-5-CHF2-3-Py], [550:2-Me-5-CHF2-3-Py], [551:4-Me-5-CHF2-3-Py], [552:6-Me-5-CHF2-3-Py], [553:2-CF3-5-CHF2-3-Py], [554:4-CF3-5-CHF2-3-Py], [555:6-CF3-5-CHF2-3-Py], [556:2-CN-5-CHF2-3-Py], [557:4-CN-5-CHF2-3-Py], [558:6-CN-5-CHF2-3-Py], [559:2-OMe-5-CHF2-3-Py], [560:4-OMe-5-CHF2-3-Py], [561:6-OMe-5-CHF2-3-Py], [562:6-CHF2-3-Py], [563:2-Cl-6-CHF2-3-Py], [564:4-Cl-6-CHF2-3-Py], [565:5-Cl-6-CHF2-3-Py], [566:2-Me-6-CHF2-3-Py], [567:4-Me-6-CHF2-3-Py], [568:5-Me-6-CHF2-3-Py], [569:2-CF3-6-CHF2-3-Py], [570:4-CF3-6-CHF2-3-Py], [571:5-CF3-6-CHF2-3-Py], [572:2-CN-6-CHF2-3-Py], [573:4-CN-6-CHF2-3-Py], [574:5-CN-6-CHF2-3-Py], [575:2-OMe-6-CHF2-3-Py], [576:4-OMe-6-CHF2-3-Py], [577:5-OMe-6-CHF2-3-Py], [578:2-OCHF2-3-Py], [579:4-Cl-2-OCHF2-3-Py], [580:5-Cl-2-OCHF2-3-Py], [581:6-Cl-2-OCHF2-3-Py], [582:4-Me-2-OCHF2-3-Py], [583:5-Me-2-OCHF2-3-Py], [584:6-Me-2-OCHF2-3-Py], [585:4-CF3-2-OCHF2-3-Py], [586:5-CF3-2-OCHF2-3-Py], [587:6-CF3-2-OCHF2-3-Py], [588:4-CN-2-OCHF2-3-Py], [589:5-CN-2-OCHF2-3-Py], [590:6-CN-2-OCHF2-3-Py], [591:4-OMe-2-OCHF2-3-Py], [592:5-OMe-2-OCHF2-3-Py], [593:6-OMe-2-OCHF2-3-Py], [594:4-OCHF2-3-Py], [595:2-Cl-4-OCHF2-3-Py], [596:5-Cl-4-OCHF2-3-Py], [597:6-Cl-4-OCHF2-3-Py], [598:2-Me-4-OCHF2-3-Py], [599:5-Me-4-OCHF2-3-Py], [600:6-Me-4-OCHF2-3-Py],

[601:2-CF3-4-OCHF2-3-Py], [602:5-CF3-4-OCHF2-3-Py], [603:6-CF3-4-OCHF2-3-Py], [604:2-CN-4-OCHF2-3-Py], [605:5-CN-4-OCHF2-3-Py], [606:6-CN-4-OCHF2-3-Py], [607:2-OMe-4-OCHF2-3-Py], [608:5-OMe-4-OCHF2-3-Py], [609:6-OMe-4-OCHF2-3-Py], [610:5-OCHF2-3-Py], [611:2-Cl-5-OCHF2-3-Py], [612:4-Cl-5-OCHF2-3-Py], [613:6-Cl-5-OCHF2-3-Py], [614:2-Me-5-OCHF2-3-Py], [615:4-Me-5-OCHF2-3-Py], [616:6-Me-5-OCHF2-3-Py], [617:2-CF3-5-OCHF2-3-Py], [618:4-CF3-5-OCHF2-3-Py], [619:6-CF3-5-OCHF2-3-Py], [620:2-CN-5-OCHF2-3-Py], [621:4-CN-5-OCHF2-3-Py], [622:6-CN-5-OCHF2-3-Py], [623:2-OMe-5-OCHF2-3-Py], [624:4-OMe-5-OCHF2-3-Py], [625:6-OMe-5-OCHF2-3-Py], [626:6-OCHF2-3-Py], [627:2-Cl-6-OCHF2-3-Py], [628:4-Cl-6-OCHF2-3-Py], [629:5-Cl-6-OCHF2-3-Py], [630:2-Me-6-OCHF2-3-Py], [631:4-Me-6-OCHF2-3-Py], [632:5-Me-6-OCHF2-3-Py], [633:2-CF3-6-OCHF2-3-Py], [634:4-CF3-6-OCHF2-3-Py], [635:5-CF3-6-OCHF2-3-Py], [636:2-CN-6-OCHF2-3-Py], [637:4-CN-6-OCHF2-3-Py], [638:5-CN-6-OCHF2-3-Py], [639:2-OMe-6-OCHF2-3-Py], [640:4-OMe-6-OCHF2-3-Py], [641:5-OMe-6-OCHF2-3-Py], [642:2-Et-3-Py], [643:4-Cl-2-Et-3-Py], [644:5-Cl-2-Et-3-Py], [645:6-Cl-2-Et-3-Py], [646:4-Me-2-Et-3-Py], [647:5-Me-2-Et-3-Py], [648:6-Me-2-Et-3-Py], [649:4-CF3-2-Et-3-Py], [650:5-CF3-2-Et-3-Py], [651:6-CF3-2-Et-3-Py], [652:4-CN-2-Et-3-Py], [653:5-CN-2-Et-3-Py], [654:6-CN-2-Et-3-Py], [655:4-OMe-2-Et-3-Py], [656:5-OMe-2-Et-3-Py], [657:6-OMe-2-Et-3-Py], [658:4-Et-3-Py], [659:2-Cl-4-Et-3-Py], [660:5-Cl-4-Et-3-Py], [661:6-Cl-4-Et-3-Py], [662:2-Me-4-Et-3-Py], [663:5-Me-4-Et-3-Py], [664:6-Me-4-Et-3-Py], [665:2-CF3-4-Et-3-Py], [666:5-CF3-4-Et-3-Py], [667:6-CF3-4-Et-3-Py], [668:2-CN-4-Et-3-Py], [669:5-CN-4-Et-3-Py], [670:6-CN-4-Et-3-Py], [671:2-OMe-4-Et-3-Py], [672:5-OMe-4-Et-3-Py], [673:6-OMe-4-Et-3-Py], [674:5-Et-3-Py], [675:2-Cl-5-Et-3-Py], [676:4-Cl-5-Et-3-Py], [677:6-Cl-5-Et-3-Py], [678:2-Me-5-Et-3-Py], [679:4-Me-5-Et-3-Py], [680:6-Me-5-Et-3-Py], [681:2-CF3-5-Et-3-Py], [682:4-CF3-5-Et-3-Py], [683:6-CF3-5-Et-3-Py], [684:2-CN-5-Et-3-Py], [685:4-CN-5-Et-3-Py], [686:6-CN-5-Et-3-Py], [687:2-OMe-5-Et-3-Py], [688:4-OMe-5-Et-3-Py], [689:6-OMe-5-Et-3-Py], [690:6-Et-3-Py], [691:2-Cl-6-Et-3-Py], [692:4-Cl-6-Et-3-Py], [693:5-Cl-6-Et-3-Py], [694:2-Me-6-Et-3-Py], [695:4-Me-6-Et-3-Py], [696:5-Me-6-Et-3-Py], [697:2-CF3-6-Et-3-Py], [698:4-CF3-6-Et-3-Py], [699:5-CF3-6-Et-3-Py], [700:2-CN-6-Et-3-Py],

[701:4-CN-6-Et-3-Py], [702:5-CN-6-Et-3-Py], [703:2-OMe-6-Et-3-Py], [704:4-OMe-6-Et-3-Py], [705:5-OMe-6-Et-3-Py], [706:2-CH2CF3-3-Py], [707:4-Cl-2-CH2CF3-3-Py], [708:5-Cl-2-CH2CF3-3-Py], [709:6-Cl-2-CH2CF3-3-Py], [710:4-Me-2-CH2CF3-3-Py], [711:5-Me-2-CH2CF3-3-Py], [712:6-Me-2-CH2CF3-3-Py], [713:4-CF3-2-CH2CF3-3-Py], [714:5-CF3-2-CH2CF3-3-Py], [715:6-CF3-2-CH2CF3-3-Py], [716:4-CN-2-CH2CF3-3-Py], [717:5-CN-2-CH2CF3-3-Py], [718:6-CN-2-CH2CF3-3-Py], [719:4-OMe-2-CH2CF3-3-Py], [720:5-OMe-2-CH2CF3-3-Py], [721:6-OMe-2-CH2CF3-3-Py], [722:4-CH2CF3-3-Py], [723:2-Cl-4-CH2CF3-3-Py], [724:5-Cl-4-CH2CF3-3-Py], [725:6-Cl-4-CH2CF3-3-Py], [726:2-Me-4-CH2CF3-3-Py], [727:5-Me-4-CH2CF3-3-Py], [728:6-Me-4-CH2CF3-3-Py], [729:2-CF3-4-CH2CF3-3-Py], [730:5-CF3-4-CH2CF3-3-Py], [731:6-CF3-4-CH2CF3-3-Py], [732:2-CN-4-CH2CF3-

[733:5-CN-4-CH2CF3-3-Py], [734:6-CN-4-CH2CF3-3-Py], [735:2-OMe-4-CH2CF3-3-Py], [736:5-OMe-4-CH2CF3-3-Py], [737:6-OMe-4-CH2CF3-3-Py], [738:5-CH2CF3-3-Py], [739:2-Cl-5-CH2CF3-3-Py], [740:4-Cl-5-CH2CF3-3-Py], [741:6-Cl-5-CH2CF3-3-Py], [742:2-Me-5-CH2CF3-3-Py], [743:4-Me-5-CH2CF3-3-Py], [744:6-Me-5-CH2CF3-3-Py], [745:2-CF3-5-CH2CF3-3-Py], [746:4-CF3-5-CH2CF3-3-Py], [747:6-CF3-5-CH2CF3-3-Py], [748:2-CN-5-CH2CF3-3-Py], [749:4-CN-5-CH2CF3-3-Py], [750:6-CN-5-CH2CF3-3-Py], [751:2-OMe-5-CH2CF3-3-Py], [752:4-OMe-5-CH2CF3-3-Py], [753:6-OMe-5-CH2CF3-3-Py], [754:6-CH2CF3-3-Py], [755:2-Cl-6-CH2CF3-3-Py], [756:4-Cl-6-CH2CF3-3-Py], [757:5-Cl-6-CH2CF3-3-Py], [758:2-Me-6-CH2CF3-3-Py], [759:4-Me-6-CH2CF3-3-Py], [760:5-Me-6-CH2CF3-3-Py], [761:2-CF3-6-CH2CF3-3-Py], [762:4-CF3-6-CH2CF3-3-Py], [763:5-CF3-6-CH2CF3-3-Py], [764:2-CN-6-CH2CF3-3-Py], [765:4-CN-6-CH2CF3-3-Py], [766:5-CN-6-CH2CF3-3-Py], [767:2-OMe-6-CH2CF3-3-Py], [768:4-OMe-6-CH2CF3-3-Py], [769:5-OMe-6-CH2CF3-3-Py], [770:2-OEt-3-Py], [771:4-Cl-2-OEt-3-Py], [772:5-Cl-2-OEt-3-Py], [773:6-Cl-2-OEt-3-Py], [774:4-Me-2-OEt-3-Py], [775:5-Me-2-OEt-3-Py], [776:6-Me-2-OEt-3-Py], [777:4-CF3-2-OEt-3-Py], [778:5-CF3-2-OEt-3-Py], [779:6-CF3-2-OEt-3-Py], [780:4-CN-2-OEt-3-Py], [781:5-CN-2-OEt-3-Py], [782:6-CN-2-OEt-3-Py], [783:4-OMe-2-OEt-3-Py], [784:5-OMe-2-OEt-3-Py], [785:6-OMe-2-OEt-3-Py], [786:4-OEt-3-Py], [787:2-Cl-4-OEt-3-Py], [788:5-Cl-4-OEt-3-Py], [789:6-Cl-4-OEt-3-Py], [790:2-Me-4-OEt-3-Py], [791:5-Me-4-OEt-3-Py], [792:6-Me-4-OEt-3-Py], [793:2-CF3-4-OEt-3-Py], [794:5-CF3-4-OEt-3-Py], [795:6-CF3-4-OEt-3-Py], [796:2-CN-4-OEt-3-Py], [797:5-CN-4-OEt-3-Py], [798:6-CN-4-OEt-3-Py], [799:2-OMe-4-OEt-3-Py], [800:5-OMe-4-OEt-3-Py],

[801:6-OMe-4-Oft-3-Py], [802:5-OEt-3-Py], [803:2-Cl-5-OEt-3-Py], [804:4-Cl-5-OEt-3-Py], [805:6-Cl-5-OEt-3-Py], [806:2-Me-5-OEt-3-Py], [807:4-Me-5-OEt-3-Py], [808:6-Me-5-OEt-3-Py], [809:2-CF3-5-OEt-3-Py], [810:4-CF3-5-OEt-3-Py], [811:6-CF3-5-OEt-3-Py], [812:2-CN-5-OEt-3-Py], [813:4-CN-5-OEt-3-Py], [814:6-CN-5-OEt-3-Py], [815:2-OMe-5-OEt-3-Py], [816:4-OMe-5-OEt-3-Py], [817:6-OMe-5-OEt-3-Py], [818:6-OEt-3-Py], [819:2-Cl-6-OEt-3-Py], [820:4-Cl-6-OEt-3-Py], [821:5-Cl-6-OEt-3-Py], [822:2-Me-6-OEt-3-Py], [823:4-Me-6-OEt-3-Py], [824:5-Me-6-OEt-3-Py], [825:2-CF3-6-OEt-3-Py], [826:4-CF3-6-OEt-3-Py], [827:5-CF3-6-OEt-3-Py], [828:2-CN-6-OEt-3-Py], [829:4-CN-6-OEt-3-Py], [830:5-CN-6-OEt-3-Py], [831:2-OMe-6-OEt-3-Py], [832:4-OMe-6-OEt-3-Py], [833:5-OMe-6-OEt-3-Py], [834:2-CH2CF3-3-Py], [835:4-Cl-2-CH2CF3-3-Py], [836:5-Cl-2-CH2CF3-3-Py], [837:6-Cl-2-CH2CF3-3-Py], [838:4-Me-2-CH2CF3-3-Py], [839:5-Me-2-CH2CF3-3-Py], [840:6-Me-2-CH2CF3-3-Py], [841:4-CF3-2-CH2CF3-3-Py], [842:5-CF3-2-CH2CF3-3-Py], [843:6-CF3-2-CH2CF3-3-Py], [844:4-CN-2-CH2CF3-3-Py], [845:5-CN-2-CH2CF3-3-Py], [846:6-CN-2-CH2CF3-3-Py], [847:4-OMe-2-CH2CF3-3-Py], [848:5-OMe-2-CH2CF3-3-Py], [849:6-OMe-2-CH2CF3-3-Py], [850:4-CH2CF3-3-Py], [851:2-Cl-4-CH2CF3-3-Py], [852:5-Cl-4-CH2CF3-3-Py], [853:6-Cl-4-CH2CF3-3-Py], [854:2-Me-4-CH2CF3-3-Py], [855:5-Me-4-CH2CF3-3-Py], [856:6-Me-4-CH2CF3-3-Py], [857:2-CF3-4-CH2CF3-3-Py], [858:5-CF3-4-CH2CF3-3-Py], [859:6-CF3-4-CH2CF3-3-Py], [860:2-CN-4-CH2CF3-3-Py], [861:5-CN-4-CH2CF3-3-Py], [862:6-CN-4-CH2CF3-3-Py], [863:2-OMe-4-CH2CF3-3-Py], [864:5-OMe-4-CH2CF3-3-Py], [865:6-OMe-4-CH2CF3-3-Py], [866:5-CH2CF3-3-Py], [867:2-Cl-5-CH2CF3-3-Py], [868:4-Cl-5-CH2CF3-3-Py], [869:6-Cl-5-CH2CF3-3-Py], [870:2-Me-5-CH2CF3-3-Py], [871:4-Me-5-CH2CF3-3-Py], [872:6-Me-5-CH2CF3-3-Py], [873:2-CF3-5-CH2CF3-3-Py], [874:4-CF3-5-CH2CF3-3-Py], [875:6-CF3-5-CH2CF3-3-Py], [876:2-CN-5-CH2CF3-3-Py], [877:4-CN-5-CH2CF3-3-Py], [878:6-CN-5-CH2CF3-3-Py], [879:2-OMe-5-CH2CF3-3-Py], [880:4-OMe-5-CH2CF3-3-Py], [881:6-OMe-5-CH2CF3-3-Py], [882:6-CH2CF3-3-Py], [883:2-Cl-6-CH2CF3-3-Py], [884:4-Cl-6-CH2CF3-3-Py], [885:5-Cl-6-CH2CF3-3-Py], [886:2-Me-6-CH2CF3-3-Py], [887:4-Me-6-CH2CF3-3-Py], [888:5-Me-6-CH2CF3-3-Py], [889:2-CF3-6-CH2CF3-3-Py], [890:4-CF3-6-CH2CF3-3-Py], [891:5-CF3-6-CH2CF3-3-Py], [892:2-CN-6-CH2CF3-3-Py], [893:4-CN-6-CH2CF3-3-Py], [894:5-CN-6-CH2CF3-3-Py], [895:2-OMe-6-CH2CF3-3-Py], [896:4-OMe-6-CH2CF3-3-Py], [897:5-OMe-6-CH2CF3-3-Py], [898:2-Pr-3-Py], [899:4-Cl-2-Pr-3-Py], [900:5-Cl-2-Pr-3-Py],

[901:6-Cl-2-Pr-3-Py], [902:4-Me-2-Pr-3-Py], [903:5-Me-2-Pr-3-Py], [904:6-Me-2-Pr-3-Py], [905:4-CF3-2-Pr-3-Py], [906:5-CF3-2-Pr-3-Py], [907:6-CF3-2-Pr-3-Py], [908:4-CN-2-Pr-3-Py], [909:5-CN-2-Pr-3-Py], [910:6-CN-2-Pr-3-Py], [911:4-OMe-2-Pr-3-Py], [912:5-OMe-2-Pr-3-Py], [913:6-OMe-2-Pr-3-Py], [914:4-Pr-3-Py], [915:2-Cl-4-Pr-3-Py], [916:5-Cl-4-Pr-3-Py], [917:6-Cl-4-Pr-3-Py], [918:2-Me-4-Pr-3-Py], [919:5-Me-4-Pr-3-Py], [920:6-Me-4-Pr-3-Py], [921:2-CF3-4-Pr-3-Py], [922:5-CF3-4-Pr-3-Py], [923:6-CF3-4-Pr-3-Py], [924:2-CN-4-Pr-3-Py], [925:5-CN-4-Pr-3-Py], [926:6-CN-4-Pr-3-Py], [927:2-OMe-4-Pr-3-Py], [928:5-OMe-4-Pr-3-Py], [929:6-OMe-4-Pr-3-Py], [930:5-Pr-3-Py], [931:2-Cl-5-Pr-3-Py], [932:4-Cl-5-Pr-3-Py], [933:6-Cl-5-Pr-3-Py], [934:2-Me-5-Pr-3-Py], [935:4-Me-5-Pr-3-Py], [936:6-Me-5-Pr-3-Py], [937:2-CF3-5-Pr-3-Py], [938:4-CF3-5-Pr-3-Py], [939:6-CF3-5-Pr-3-Py], [940:2-CN-5-Pr-3-Py], [941:4-CN-5-Pr-3-Py], [942:6-CN-5-Pr-3-Py], [943:2-OMe-5-Pr-3-Py], [944:4-OMe-5-Pr-3-Py], [945:6-OMe-5-Pr-3-Py], [946:6-Pr-3-Py], [947:2-Cl-6-Pr-3-Py], [948:4-Cl-6-Pr-3-Py], [949:5-Cl-6-Pr-3-Py], [950:2-Me-6-Pr-3-Py], [951:4-Me-6-Pr-3-Py], [952:5-Me-6-Pr-3-Py], [953:2-CF3-6-Pr-3-Py], [954:4-CF3-6-Pr-3-Py], [955:5-CF3-6-Pr-3-Py], [956:2-CN-6-Pr-3-Py], [957:4-CN-6-Pr-3-Py], [958:5-CN-6-Pr-3-Py], [959:2-OMe-6-Pr-3-Py], [960:4-OMe-6-Pr-3-Py], [961:5-OMe-6-Pr-3-Py], [962:2-OPr-3-Py], [963:4-Cl-2-OPr-3-Py], [964:5-Cl-2-OPr-3-Py], [965:6-Cl-2-OPr-3-Py], [966:4-Me-2-OPr-3-Py], [967:5-Me-2-OPr-3-Py], [968:6-Me-2-OPr-3-Py], [969:4-CF3-2-OPr-3-Py], [970:5-CF3-2-OPr-3-Py], [971:6-CF3-2-OPr-3-Py], [972:4-CN-2-OPr-3-Py], [973:5-CN-2-OPr-3-Py], [974:6-CN-2-OPr-3-Py], [975:4-OMe-2-OPr-3-Py], [976:5-OMe-2-OPr-3-Py], [977:6-OMe-2-OPr-3-Py], [978:4-OPr-3-Py], [979:2-Cl-4-OPr-3-Py], [980:5-Cl-4-OPr-3-Py], [981:6-Cl-4-OPr-3-Py], [982:2-Me-4-OPr-3-Py], [983:5-Me-4-OPr-3-Py], [984:6-Me-4-OPr-3-Py], [985:2-CF3-4-OPr-3-Py], [986:5-CF3-4-OPr-3-Py], [987:6-CF3-4-OPr-3-Py], [988:2-CN-4-OPr-3-Py], [989:5-CN-4-OPr-3-Py], [990:6-CN-4-OPr-3-Py], [991:2-OMe-4-OPr-3-Py], [992:5-OMe-4-OPr-3-Py], [993:6-OMe-4-OPr-3-Py], [994:5-OPr-3-Py], [995:2-Cl-5-OPr-3-Py], [996:4-Cl-5-OPr-3-Py], [997:6-Cl-5-OPr-3-Py], [998:2-Me-5-OPr-3-Py], [999:4-Me-5-OPr-3-Py], [1000:6-Me-5-OPr-3-Py],

[1001:2-CF3-5-OPr-3-Py], [1002:4-CF3-5-OPr-3-Py], [1003:6-CF3-5-OPr-3-Py], [1004:2-CN-5-OPr-3-Py], [1005:4-CN-5-OPr-3-Py], [1006:6-CN-5-OPr-3-Py], [1007:2-OMe-5-OPr-3-Py], [1008:4-OMe-5-OPr-3-Py], [1009:6-OMe-5-OPr-3-Py], [1010:6-OPr-3-Py], [1011:2-Cl-6-OPr-3-Py], [1012:4-Cl-6-OPr-3-Py], [1013:5-Cl-6-OPr-3-Py], [1014:2-Me-6-OPr-3-Py], [1015:4-Me-6-OPr-3-Py], [1016:5-Me-6-OPr-3-Py], [1017:2-CF3-6-OPr-3-Py], [1018:4-

CF3-6-OPr-3-Py], [1019:5-CF3-6-OPr-3-Py], [1020:2-CN-6-OPr-3-Py], [1021:4-CN-6-OPr-3-Py], [1022:5-CN-6-OPr-3-Py], [1023:2-OMe-6-OPr-3-Py], [1024:4-OMe-6-OPr-3-Py], [1025:5-OMe-6-OPr-3-Py], [1026:2-SMe-3-Py], [1027:4-Cl-2-SMe-3-Py], [1028:5-Cl-2-SMe-3-Py], [1029:6-Cl-2-SMe-3-Py], [1030:4-Me-2-SMe-3-Py], [1031:5-Me-2-SMe-3-Py], [1032:6-Me-2-SMe-3-Py], [1033:4-CF3-2-SMe-3-Py], [1034:5-CF3-2-SMe-3-Py], [1035:6-CF3-2-SMe-3-Py], [1036:4-CN-2-SMe-3-Py], [1037:5-CN-2-SMe-3-Py], [1038:6-CN-2-SMe-3-Py], [1039:4-OMe-2-SMe-3-Py], [1040:5-OMe-2-SMe-3-Py], [1041:6-OMe-2-SMe-3-Py], [1042:4-SMe-3-Py], [1043:2-Cl-4-SMe-3-Py], [1044:5-Cl-4-SMe-3-Py], [1045:6-Cl-4-SMe-3-Py], [1046:2-Me-4-SMe-3-Py], [1047:5-Me-4-SMe-3-Py], [1048:6-Me-4-SMe-3-Py], [1049:2-CF3-4-SMe-3-Py], [1050:5-CF3-4-SMe-3-Py], [1051:6-CF3-4-SMe-3-Py], [1052:2-CN-4-SMe-3-Py], [1053:5-CN-4-SMe-3-Py], [1054:6-CN-4-SMe-3-Py], [1055:2-OMe-4-SMe-3-Py], [1056:5-OMe-4-SMe-3-Py], [1057:6-OMe-4-SMe-3-Py], [1058:5-SMe-3-Py], [1059:2-Cl-5-SMe-3-Py], [1060:4-Cl-5-SMe-3-Py], [1061:6-Cl-5-SMe-3-Py], [1062:2-Me-5-SMe-3-Py], [1063:4-Me-5-SMe-3-Py], [1064:6-Me-5-SMe-3-Py], [1065:2-CF3-5-SMe-3-Py], [1066:4-CF3-5-SMe-3-Py], [1067:6-CF3-5-SMe-3-Py], [1068:2-CN-5-SMe-3-Py], [1069:4-CN-5-SMe-3-Py], [1070:6-CN-5-SMe-3-Py], [1071:2-OMe-5-SMe-3-Py], [1072:4-OMe-5-SMe-3-Py], [1073:6-OMe-5-SMe-3-Py], [1074:6-SMe-3-Py], [1075:2-Cl-6-SMe-3-Py], [1076:4-Cl-6-SMe-3-Py], [1077:5-Cl-6-SMe-3-Py], [1078:2-Me-6-SMe-3-Py], [1079:4-Me-6-SMe-3-Py], [1080:5-Me-6-SMe-3-Py], [1081:2-CF3-6-SMe-3-Py], [1082:4-CF3-6-SMe-3-Py], [1083:5-CF3-6-SMe-3-Py], [1084:2-CN-6-SMe-3-Py], [1085:4-CN-6-SMe-3-Py], [1086:5-CN-6-SMe-3-Py], [1087:2-OMe-6-SMe-3-Py], [1088:4-OMe-6-SMe-3-Py], [1089:5-OMe-6-SMe-3-Py], [1090:2-SCF3-3-Py], [1091:4-Cl-2-SCF3-3-Py], [1092:5-Cl-2-SCF3-3-Py], [1093:6-Cl-2-SCF3-3-Py], [1094:4-Me-2-SCF3-3-Py], [1095:5-Me-2-SCF3-3-Py], [1096:6-Me-2-SCF3-3-Py], [1097:4-CF3-2-SCF3-3-Py], [1098:5-CF3-2-SCF3-3-Py], [1099:6-CF3-2-SCF3-3-Py], [1100:4-CN-2-SCF3-3-Py], [1101:5-CN-2-SCF3-3-Py], [1102:6-CN-2-SCF3-3-Py], [1103:4-OMe-2-SCF3-3-Py], [1104:5-OMe-2-SCF3-3-Py], [1105:6-OMe-2-SCF3-3-Py], [1106:4-SCF3-3-Py], [1107:2-Cl-4-SCF3-3-Py], [1108:5-Cl-4-SCF3-3-Py], [1109:6-Cl-4-SCF3-3-Py], [1110:2-Me-4-SCF3-3-Py], [1111:5-Me-4-SCF3-3-Py], [1112:6-Me-4-SCF3-3-Py], [1113:2-CF3-4-SCF3-3-Py], [1114:5-CF3-4-SCF3-3-Py], [1115:6-CF3-4-SCF3-3-Py], [1116:2-CN-4-SCF3-3-Py], [1117:5-CN-4-SCF3-3-Py], [1118:6-CN-4-SCF3-3-Py], [1119:2-OMe-4-SCF3-3-Py], [1120:5-OMe-4-SCF3-3-Py], [1121:6-OMe-4-SCF3-3-Py], [1122:5-SCF3-3-Py], [1123:2-Cl-5-SCF3-3-Py], [1124:4-Cl-5-SCF3-3-Py], [1125:6-Cl-5-SCF3-3-Py], [1126:2-Me-5-SCF3-3-Py], [1127:4-Me-5-SCF3-3-Py], [1128:6-Me-5-SCF3-3-Py], [1129:2-CF3-5-SCF3-3-Py], [1130:4-CF3-5-SCF3-3-Py], [1131:6-CF3-5-SCF3-3-Py], [1132:2-CN-5-SCF3-3-Py], [1133:4-CN-5-SCF3-3-Py], [1134:6-CN-5-SCF3-3-Py], [1135:2-OMe-5-SCF3-3-Py], [1136:4-OMe-5-SCF3-3-Py], [1137:6-OMe-5-SCF3-3-Py], [1138:6-SCF3-3-Py], [1139:2-Cl-6-SCF3-3-Py], [1140:4-Cl-6-SCF3-3-Py], [1141:6-Cl-6-SCF3-3-Py], [1142:2-Me-6-SCF3-3-Py], [1143:4-Me-6-SCF3-3-Py], [1144:6-Me-6-SCF3-3-Py], [1145:2-CF3-6-SCF3-3-Py], [1146:4-CF3-6-SCF3-3-Py], [1147:6-CF3-6-SCF3-3-Py], [1148:2-CN-6-SCF3-3-Py], [1149:4-CN-6-SCF3-3-Py], [1150:6-CN-6-SCF3-3-Py], [1151:2-OMe-6-SCF3-3-Py], [1152:4-OMe-6-SCF3-3-Py], [1153:6-OMe-6-SCF3-3-Py], [1154:2-S(O)Me-3-Py], [1155:4-Cl-2-S(O)Me-3-Py], [1156:5-Cl-2-S(O)Me-3-Py], [1157:6-Cl-2-S(O)Me-3-Py], [1158:4-Me-2-S(O)Me-3-Py], [1159:5-Me-2-S(O)Me-3-Py], [1160:6-Me-2-S(O)Me-3-Py], [1161:4-CF3-2-S(O)Me-3-Py], [1162:5-CF3-2-S(O)Me-3-Py], [1163:6-CF3-2-S(O)Me-3-Py], [1164:4-CN-2-S(O)Me-3-Py], [1165:5-CN-2-S(O)Me-3-Py], [1166:6-CN-2-S(O)Me-3-Py], [1167:4-OMe-2-S(O)Me-3-Py], [1168:5-OMe-2-S(O)Me-3-Py], [1169:6-OMe-2-S(O)Me-3-Py], [1170:4-S(O)Me-3-Py], [1171:2-Cl-4-S(O)Me-3-Py], [1172:5-Cl-4-S(O)Me-3-Py], [1173:6-Cl-4-S(O)Me-3-Py], [1174:2-Me-4-S(O)Me-3-Py], [1175:5-Me-4-S(O)Me-3-Py], [1176:6-Me-4-S(O)Me-3-Py], [1177:2-CF3-4-S(O)Me-3-Py], [1178:5-CF3-4-S(O)Me-3-Py], [1179:6-CF3-4-S(O)Me-3-Py], [1180:2-CN-4-S(O)Me-3-Py], [1181:5-CN-4-S(O)Me-3-Py], [1182:6-CN-4-S(O)Me-3-Py], [1183:2-OMe-4-S(O)Me-3-Py], [1184:5-OMe-4-S(O)Me-3-Py], [1185:6-OMe-4-S(O)Me-3-Py], [1186:5-S(O)Me-3-Py], [1187:2-Cl-5-S(O)Me-3-Py], [1188:4-Cl-5-S(O)Me-3-Py], [1189:6-Cl-5-S(O)Me-3-Py], [1190:2-Me-5-S(O)Me-3-Py], [1191:4-Me-5-S(O)Me-3-Py], [1192:6-Me-5-S(O)Me-3-Py], [1193:2-CF3-5-S(O)Me-3-Py], [1194:4-CF3-5-S(O)Me-3-Py], [1195:6-CF3-5-S(O)Me-3-Py], [1196:2-CN-5-S(O)Me-3-Py], [1197:4-CN-5-S(O)Me-3-Py], [1198:6-CN-5-S(O)Me-3-Py], [1199:2-OMe-5-S(O)Me-3-Py], [1200:4-OMe-5-S(O)Me-3-Py], [1201:6-OMe-5-S(O)Me-3-Py], [1202:6-S(O)Me-3-Py], [1203:2-Cl-6-S(O)Me-3-Py], [1204:4-Cl-6-S(O)Me-3-Py], [1205:5-Cl-6-S(O)Me-3-Py], [1206:2-Me-6-S(O)Me-3-Py], [1207:4-Me-6-S(O)Me-3-Py], [1208:5-Me-6-S(O)Me-3-Py], [1209:2-S(O)CF3-3-Py], [1210:4-Cl-2-S(O)CF3-3-Py], [1211:5-Cl-2-S(O)CF3-3-Py], [1212:6-Cl-2-S(O)CF3-3-Py], [1213:4-Me-2-S(O)CF3-3-Py], [1214:5-Me-2-S(O)CF3-3-Py], [1215:6-Me-2-S(O)CF3-3-Py], [1216:4-CF3-2-S(O)CF3-3-Py], [1217:5-CF3-2-S(O)CF3-3-Py], [1218:6-CF3-2-S(O)CF3-3-Py], [1219:4-CN-2-S(O)CF3-3-Py], [1220:5-CN-2-S(O)CF3-3-Py], [1221:6-CN-2-S(O)CF3-3-Py], [1222:4-OMe-2-S(O)CF3-3-Py], [1223:5-OMe-2-S(O)CF3-3-Py], [1224:6-OMe-2-S(O)CF3-3-Py], [1225:4-S(O)CF3-3-Py], [1226:2-Cl-4-S(O)CF3-3-Py], [1227:5-Cl-4-S(O)CF3-3-Py], [1228:6-Cl-4-S(O)CF3-3-Py], [1229:2-Me-4-S(O)CF3-3-Py], [1230:5-Me-4-S(O)CF3-3-Py], [1231:6-Me-4-S(O)CF3-3-Py], [1232:2-CF3-4-S(O)CF3-3-Py], [1233:5-CF3-4-S(O)CF3-3-Py], [1234:6-CF3-4-S(O)CF3-3-Py], [1235:2-CN-4-S(O)CF3-3-Py], [1236:5-CN-4-S(O)CF3-3-Py], [1237:6-CN-4-S(O)CF3-3-Py], [1238:2-OMe-4-S(O)CF3-3-Py], [1239:5-OMe-4-S(O)CF3-3-Py], [1240:6-OMe-4-S(O)CF3-3-Py], [1241:5-S(O)CF3-3-Py], [1242:2-Cl-5-S(O)CF3-3-Py], [1243:4-Cl-5-S(O)CF3-3-Py], [1244:6-Cl-5-S(O)CF3-3-Py], [1245:2-Me-5-S(O)CF3-3-Py], [1246:4-Me-5-S(O)CF3-3-Py], [1247:6-Me-5-S(O)CF3-3-Py], [1248:2-CF3-5-S(O)CF3-3-Py], [1249:4-CF3-5-S(O)CF3-3-Py], [1250:6-CF3-5-S(O)CF3-3-Py], [1251:2-CN-5-S(O)CF3-3-Py], [1252:4-CN-5-S(O)CF3-3-Py], [1253:6-CN-5-S(O)CF3-3-Py], [1254:2-OMe-5-S(O)CF3-3-Py], [1255:4-OMe-5-S(O)CF3-3-Py], [1256:6-OMe-5-S(O)CF3-3-Py], [1257:4-S(O)2Me-3-Py], [1258:5-S(O)2Me-3-Py], [1259:2-Cl-5-S(O)2Me-3-Py], [1260:4-Cl-5-S(O)2Me-3-Py], [1261:6-Cl-5-S(O)2Me-3-Py], [1262:2-Me-5-S(O)2Me-3-Py], [1263:4-Me-5-S(O)2Me-3-Py], [1264:6-Me-5-S(O)2Me-3-Py], [1265:2-CF3-5-S(O)2Me-3-Py], [1266:4-CF3-5-S(O)2Me-3-Py], [1267:6-CF3-5-S(O)2Me-3-Py], [1268:2-CN-5-S(O)2Me-3-Py], [1269:4-CN-5-S(O)2Me-3-Py], [1270:6-CN-5-S(O)2Me-3-Py], [1271:2-OMe-5-S(O)2Me-3-Py], [1272:4-OMe-5-S(O)2Me-3-Py], [1273:6-OMe-5-S(O)2Me-3-Py], [1274:2-S(O)2CF3-3-Py], [1275:4-Cl-2-S(O)2CF3-3-Py], [1276:5-Cl-2-S(O)2CF3-3-Py], [1277:6-Cl-2-S(O)2CF3-3-Py], [1278:4-Me-2-S(O)2CF3-3-Py], [1279:5-Me-2-S(O)2CF3-3-Py], [1280:6-Me-2-S(O)2CF3-3-Py], [1281:4-CF3-2-S(O)2CF3-3-Py],

[1282:5-CF3-2-S(O)2CF3-3-Py], [1283:6-CF3-2-S(O)2CF3-3-Py], [1284:4-CN-2-S(O)2CF3-3-Py], [1285:5-CN-2-S(O)2CF3-3-Py], [1286:6-CN-2-S(O)2CF3-3-Py], [1287:4-OMe-2-S(O)2CF3-3-Py], [1288:5-OMe-2-S(O)2CF3-3-Py], [1289:6-OMe-2-S(O)2CF3-3-Py], [1290:4-S(O)2CF3-3-Py], [1291:2-Cl-4-S(O)2CF3-3-Py], [1292:5-Cl-4-S(O)2CF3-3-Py], [1293:6-Cl-4-S(O)2CF3-3-Py], [1294:2-Me-4-S(O)2CF3-3-Py], [1295:5-Me-4-S(O)2CF3-3-Py], [1296:6-Me-4-S(O)2CF3-3-Py], [1297:2-CF3-4-S(O)2CF3-3-Py], [1298:5-CF3-4-S(O)2CF3-3-Py], [1299:6-CF3-4-S(O)2CF3-3-Py], [1300:2-CN-4-S(O)2CF3-3-Py],
[1301:5-CN-4-S(O)2CF3-3-Py], [1302:6-CN-4-S(O)2CF3-3-Py], [1303:2-OMe-4-S(O)2CF3-3-Py], [1304:5-OMe-4-S(O)2CF3-3-Py], [1305:6-OMe-4-S(O)2CF3-3-Py], [1306:5-S(O)2CF3-3-Py], [1307:2-Cl-5-S(O)2CF3-3-Py], [1308:4-Cl-5-S(O)2CF3-3-Py], [1309:6-Cl-5-S(O)2CF3-3-Py], [1310:2-Me-5-S(O)2CF3-3-Py], [1311:4-Me-5-S(O)2CF3-3-Py], [1312:6-Me-5-S(O)2CF3-3-Py], [1313:2-CF3-5-S(O)2CF3-3-Py], [1314:4-CF3-5-S(O)2CF3-3-Py], [1315:6-CF3-5-S(O)2CF3-3-Py], [1316:2-CN-5-S(O)2CF3-3-Py], [1317:4-CN-5-S(O)2CF3-3-Py], [1318:6-CN-5-S(O)2CF3-3-Py], [1319:2-OMe-5-S(O)2CF3-3-Py], [1320:4-OMe-5-S(O)2CF3-3-Py], [1321:6-OMe-5-S(O)2CF3-3-Py], [1322:6-S(O)2CF3-3-Py], [1323:2-Cl-6-S(O)2CF3-3-Py], [1324:4-Cl-6-S(O)2CF3-3-Py], [1325:5-Cl-6-S(O)2CF3-3-Py], [1326:2-Me-6-S(O)2CF3-3-Py], [1327:4-Me-6-S(O)2CF3-3-Py], [1328:5-Me-6-S(O)2CF3-3-Py], [1329:2-CF3-6-S(O)2CF3-3-Py], [1330:4-CF3-6-S(O)2CF3-3-Py], [1331:5-CF3-6-S(O)2CF3-3-Py], [1332:2-CN-6-S(O)2CF3-3-Py], [1333:4-CN-6-S(O)2CF3-3-Py], [1334:5-CN-6-S(O)2CF3-3-Py], [1335:2-OMe-6-S(O)2CF3-3-Py], [1336:4-OMe-6-S(O)2CF3-3-Py], [1337:5-OMe-6-S(O)2CF3-3-Py], [1338:2-CN-3-Py], [1339:4-Cl-2-CN-3-Py], [1340:5-Cl-2-CN-3-Py], [1341:6-Cl-2-CN-3-Py], [1342:4-Me-2-CN-3-Py], [1343:5-Me-2-CN-3-Py], [1344:6-Me-2-CN-3-Py], [1345:4-CF3-2-CN-3-Py], [1346:5-CF3-2-CN-3-Py], [1347:6-CF3-2-CN-3-Py], [1348:4-CN-2-CN-3-Py], [1349:5-CN-2-CN-3-Py], [1350:6-CN-2-CN-3-Py], [1351:4-OMe-2-CN-3-Py], [1352:5-OMe-2-CN-3-Py], [1353:6-OMe-2-CN-3-Py], [1354:4-CN-3-Py], [1355:2-Cl-4-CN-3-Py], [1356:5-Cl-4-CN-3-Py], [1357:6-Cl-4-CN-3-Py], [1358:2-Me-4-CN-3-Py], [1359:5-Me-4-CN-3-Py], [1360:6-Me-4-CN-3-Py], [1361:2-CF3-4-CN-3-Py], [1362:5-CF3-4-CN-3-Py], [1363:6-CF3-4-CN-3-Py], [1364:2-CN-4-CN-3-Py], [1365:5-CN-4-CN-3-Py], [1366:6-CN-4-CN-3-Py], [1367:2-OMe-4-CN-3-Py], [1368:5-OMe-4-CN-3-Py], [1369:6-OMe-4-CN-3-Py], [1370:5-CN-3-Py], [1371:2-Cl-5-CN-3-Py], [1372:4-Cl-5-CN-3-Py], [1373:6-Cl-5-CN-3-Py], [1374:2-Me-5-CN-3-Py], [1375:4-Me-5-CN-3-Py], [1376:6-Me-5-CN-3-Py], [1377:2-CF3-5-CN-3-Py], [1378:4-CF3-5-CN-3-Py], [1379:6-CF3-5-CN-3-Py], [1380:2-CN-5-CN-3-Py], [1381:4-CN-5-CN-3-Py], [1382:6-CN-5-CN-3-Py], [1383:2-OMe-5-CN-3-Py], [1384:4-OMe-5-CN-3-Py], [1385:6-OMe-5-CN-3-Py], [1386:6-CN-3-Py], [1387:2-Cl-6-CN-3-Py], [1388:4-Cl-6-CN-3-Py], [1389:5-Cl-6-CN-3-Py], [1390:2-Me-6-CN-3-Py], [1391:4-Me-6-CN-3-Py], [1392:5-Me-6-CN-3-Py], [1393:2-CF3-6-CN-3-Py], [1394:4-CF3-6-CN-3-Py], [1395:5-CF3-6-CN-3-Py], [1396:2-CN-6-CN-3-Py], [1397:4-CN-6-CN-3-Py], [1398:5-CN-6-CN-3-Py], [1399:2-OMe-6-CN-3-Py], [1400:4-OMe-6-CN-3-Py], [1401:5-OMe-6-CN-3-Py], [1402:5-COOMe-3-Py], [1403:2-Cl-5-COOMe-3-Py], [1404:4-Cl-5-COOMe-3-Py], [1405:6-Cl-5-COOMe-3-Py], [1406:2-Me-5-COOMe-3-Py], [1407:4-Me-5-COOMe-3-Py], [1408:6-Me-5-COOMe-3-Py], [1409:2-CF3-5-COOMe-3-Py], [1410:4-CF3-5-COOMe-3-Py], [1411:6-CF3-5-COOMe-3-Py], [1412:2-CN-5-COOMe-3-Py], [1413:4-CN-5-COOMe-3-Py], [1414:6-CN-5-COOMe-3-Py], [1415:2-OMe-5-COOMe-3-Py], [1416:4-OMe-5-COOMe-3-Py], [1417:6-OMe-5-COOMe-3-Py], [1418:6-COOMe-3-Py], [1419:2-Cl-6-COOMe-3-Py], [1420:4-Cl-6-COOMe-3-Py], [1421:5-Cl-6-COOMe-3-Py], [1422:2-Me-6-COOMe-3-Py], [1423:4-Me-6-COOMe-3-Py], [1424:5-Me-6-COOMe-3-Py], [1425:2-CF3-6-COOMe-3-Py], [1426:4-CF3-6-COOMe-3-Py], [1427:5-CF3-6-COOMe-3-Py], [1428:2-CN-6-COOMe-3-Py], [1429:4-CN-6-COOMe-3-Py], [1430:5-CN-6-COOMe-3-Py], [1431:2-OMe-6-COOMe-3-Py], [1432:4-OMe-6-COOMe-3-Py], [1433:5-OMe-6-COOMe-3-Py]

For example, RA1001-0003 is a compound in which substituent number is 3 in a compound represented by formula (RA1001) and is a compound of the following structure.

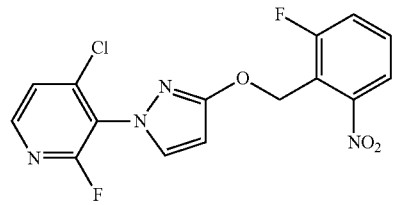

(RA1001-0003)

Examples of the present control agent include the followings:
a pest control composition comprising any one of the present compounds 1 to 62 and prothioconazole at a ratio of 0.1:1; a pest control composition comprising any one of the present compounds 1 to 62 and prothioconazole at a ratio of 1:1; a pest control composition comprising any one of the present compounds 1 to 62 and prothioconazole at a ratio of 10:1; a pest control composition comprising any one of the present compounds 1 to 62 and bromuconazole at a ratio of 0.1:1; a pest control composition comprising any one of the present compounds 1 to 62 and bromuconazole at a ratio of 1:1; a pest control composition comprising any one of the present compounds 1 to 62 and bromuconazole at a ratio of 10:1; a pest control composition comprising any one of the present compounds 1 to 62 and metconazole at a ratio of 0.1:1; a pest control composition comprising any one of the present compounds 1 to 62 and metconazole at a ratio of 1:1; a pest control composition comprising any one of the present compounds 1 to 62 and metconazole at a ratio of 10:1; a pest control composition comprising any one of the present compounds 1 to 62 and tebuconazole at a ratio of 0.1:1; a pest control composition comprising any one of the present compounds 1 to 62 and tebuconazole at a ratio of 1:1; a pest control composition comprising any one of the present compounds 1 to 62 and tebuconazole at a ratio of 10:1; a pest control composition comprising any one of the present compounds 1 to 62 and tetraconazole at a ratio of 0.1:1; a pest control composition comprising any one of the present compounds 1 to 62 and tetraconazole at a ratio of 1:1; a pest control composition comprising any one of the present compounds 1 to 62 and tetraconazole at a ratio of 10:1; a pest control composition comprising any one of the present compounds 1 to 62 and cyproconazole at a ratio of 0.1:1; a pest control composition comprising any one of the present compounds 1 to 62 and cyproconazole at a ratio of 1:1; a pest control composition comprising any one of the present compounds 1 to 62 and cyproconazole at a ratio of 10:1; a pest control composition comprising any one of the present compounds 1 to 62 and flusilazol at a ratio of 0.1:1; a pest control composition comprising any one of the present compounds 1 to 62 and flusilazol at a ratio of 1:1; a pest control composition comprising any one of the present compounds 1 to 62 and flusilazol at a ratio of 10:1;

a pest control composition comprising any one of the present compounds 1 to 62 and prochloraz at a ratio of 0.1:1; a pest control composition comprising any one of the present compounds 1 to 62 and prochloraz at a ratio of 1:1; a pest control composition comprising any one of the present compounds 1 to 62 and prochloraz at a ratio of 10:1; a pest control composition comprising any one of the present compounds 1 to 62 and imazalil at a ratio of 0.1:1; a pest control composition comprising any one of the present compounds 1 to 62 and imazalil at a ratio of 1:1; a pest control composition comprising any one of the present compounds 1 to 62 and imazalil at a ratio of 10:1; a pest control composition comprising any one of the present compounds 1 to 62 and epoxiconazol at a ratio of 0.1:1; a pest control composition comprising any one of the present compounds 1 to 62 and epoxiconazol at a ratio of 1:1; a pest control composition comprising any one of the present compounds 1 to 62 and epoxiconazol at a ratio of 10:1; a pest control composition comprising any one of the present compounds 1 to 62 and propiconazole at a ratio of 0.1:1; a pest control composition comprising any one of the present compounds 1 to 253 and propiconazole at a ratio of 1:1; a pest control composition comprising any one of the present compounds 1 to 62 and propiconazole at a ratio of 10:1; a pest control composition comprising any one of the present compounds 1 to 62 and difenoconazole at a ratio of 0.1:1; a pest control composition comprising any one of the present compounds 1 to 62 and difenoconazole at a ratio of 1:1; a pest control composition comprising any one of the present compounds 1 to 62 and difenoconazole at a ratio of 10:1; a pest control composition comprising any one of the present compounds 1 to 62 and myclobutanil at a ratio of 0.1:1; a pest control composition comprising any one of the present compounds 1 to 62 and myclobutanil at a ratio of 1:1; a pest control composition comprising any one of the present compounds 1 to 62 and myclobutanil at a ratio of 10:1; a pest control composition comprising any one of the present compounds 1 to 62 and triadimenol at a ratio of 0.1:1; a pest control composition comprising any one of the present compounds 1 to 62 and triadimenol at a ratio of 1:1; a pest control composition comprising any one of the present compounds 1 to 62 and triadimenol at a ratio of 10:1;

a pest control composition comprising any one of the present compounds 1 to 62 and triadimefon at a ratio of 0.1:1; a pest control composition comprising any one of the present compounds 1 to 62 and triadimefon at a ratio of 1:1; a pest control composition comprising any one of the present compounds 1 to 62 and triadimefon at a ratio of 10:1; a pest control composition comprising any one of the present compounds 1 to 62 and fluquinconazole at a ratio of 0.1:1; a pest control composition comprising any one of the present compounds 1 to 62 and fluquinconazole at a ratio of 1:1; a pest control composition comprising any one of the present compounds 1 to 62 and fluquinconazole at a ratio of 10:1; a pest control composition comprising any one of the present compounds 1 to 62 and triticonazole at a ratio of 0.1:1; a pest control composition comprising any one of the present compounds 1 to 62 and triticonazole at a ratio of 1:1; a pest control composition comprising any one of the present compounds 1 to 62 and triticonazole at a ratio of 10:1; a pest control composition comprising any one of the present compounds 1 to 62 and ipconazole at a ratio of 0.1:1; a pest control composition comprising any one of the present compounds 1 to 62 and ipconazole at a ratio of 1:1; a pest control composition comprising any one of the present compounds 1 to 62 and ipconazole at a ratio of 10:1; a pest control composition comprising any one of the present compounds 1 to 62 and triflumizol at a ratio of 0.1:1; a pest control composition comprising any one of the present compounds 1 to 62 and triflumizol at a ratio of 1:1; a pest control composition comprising any one of the present compounds 1 to 62 and triflumizol at a ratio of 10:1; a pest control composition comprising any one of the present compounds 1 to 62 and fenbuconazole at a ratio of 0.1:1; a pest control composition comprising any one of the present compounds 1 to 62 and fenbuconazole at a ratio of 1:1; a pest control composition comprising any one of the present compounds 1 to 62 and fenbuconazole at a ratio of 10:1; a pest control composition comprising any one of the present compounds 1 to 62 and hexaconazole at a ratio of 0.1:1;

a pest control composition comprising any one of the present compounds 1 to 62 and hexaconazole at a ratio of 1:1; a pest control composition comprising any one of the present compounds 1 to 62 and hexaconazole at a ratio of 10:1; a pest control composition comprising any one of the present compounds 1 to 62 and bitertanol at a ratio of 0.1:1; a pest control composition comprising any one of the present compounds 1 to 62 and bitertanol at a ratio of 1:1; a pest control composition comprising any one of the present compounds 1 to 62 and bitertanol at a ratio of 10:1; a pest control composition comprising any one of the present compounds 1 to 62 and flutriafol at a ratio of 0.1:1; a pest control composition comprising any one of the present compounds 1 to 62 and flutriafol at a ratio of 1:1; a pest control composition comprising any one of the present compounds 1 to 62 and flutriafol at a ratio of 10:1; a pest control composition comprising any one of the present compounds 1 to 62 and simeconazole at a ratio of 0.1:1; a pest control composition comprising any one of the present compounds 1 to 62 and simeconazole at a ratio of 1:1; a pest control composition comprising any one of the present compounds 1 to 62 and simeconazole at a ratio of 10:1; a pest control composition comprising any one of the present compounds 1 to 62 and imibenconazole at a ratio of 0.1:1; a pest control composition comprising any one of the present compounds 1 to 62 and imibenconazole at a ratio of 1:1; a pest control composition comprising any one of the present compounds 1 to 62 and imibenconazole at a ratio of 10:1; a pest control composition comprising any one of the present compounds 1 to 62 and oxpoconazole at a ratio of 0.1:1; a pest control composition comprising any one of the present compounds 1 to 62 and oxpoconazole at a ratio of 1:1; a pest control composition comprising any one of the present compounds 1 to 62 and oxpoconazole at a ratio of 10:1; a pest control composition comprising any one of the present compounds 1 to 62 and azoxystrobin at a ratio of 0.1:1; a pest control composition comprising any one of the present compounds 1 to 62 and azoxystrobin at a ratio of 1:1; a pest control composition comprising any one of the present compounds 1 to 62 and azoxystrobin at a ratio of 10:1;

a pest control composition comprising any one of the present compounds 1 to 62 and pyraclostrobin at a ratio of 0.1:1; a pest control composition comprising any one of the present compounds 1 to 62 and pyraclostrobin at a ratio of 1:1; a pest control composition comprising any one of the present compounds 1 to 62 and pyraclostrobin at a ratio of 10:1; a pest control composition comprising any one of the present compounds 1 to 62 and picoxystrobin at a ratio of 0.1:1; a pest control composition comprising any one of the present compounds 1 to 62 and picoxystrobin at a ratio of 1:1; a pest control composition comprising any one of the present compounds 1 to 62 and picoxystrobin at a ratio of 10:1; a pest control composition comprising any one of the present compounds 1 to 62 and fluoxastrobin at a ratio of 0.1:1; a pest control composition comprising any one of the present compounds 1 to 62 and fluoxastrobin at a ratio of 1:1; a pest control composition comprising any one of the present compounds 1 to 62 and fluoxastrobin at a ratio of 10:1; a pest control composition comprising any one of the present compounds 1 to 62 and trifloxystrobin at a ratio of 0.1:1; a pest control composition comprising any one of the present compounds 1 to 62 and trifloxystrobin at a ratio of 1:1; a pest control composition comprising any one of the present compounds 1 to 62 and trifloxystrobin at a ratio of 10:1; a pest control composition comprising any one of the present compounds 1 to 62 and mandestrobin at a ratio of 0.1:1; a pest control composition comprising any one of the present compounds 1 to 62 and mandestrobin at a ratio of 1:1; a pest control composition comprising any one of the present compounds 1 to 62 and mandestrobin at a ratio of 10:1; a pest control composition comprising any one of the present compounds 1 to 62 and kresoxim-methyl at a ratio of 0.1:1; a pest control composition comprising any one of the present compounds 1 to 62 and kresoxim-methyl at a ratio of 1:1; a pest control composition comprising any one of the present compounds 1 to 62 and kresoxim-methyl at a ratio of 10:1; a pest control composition comprising any one of the present compounds 1 to 62 and dimoxystrobin at a ratio of 0.1:1; a pest control composition comprising any one of the present compounds 1 to 62 and dimoxystrobin at a ratio of 1:1; a pest control composition comprising any one of the present compounds 1 to 62 and dimoxystrobin at a ratio of 10:1; a pest control composition comprising any one of the present compounds 1 to 62 and pyribencarb at a ratio of 0.1:1; a pest control composition comprising any one of the present compounds 1 to 62 and pyribencarb at a ratio of 1:1; a pest control composition comprising any one of the present compounds 1 to 62 and pyribencarb at a ratio of 10:1; a pest control composition comprising any one of the present compounds 1 to 62 and famoxadon at a ratio of 0.1:1; a pest control composition comprising any one of the present compounds 1 to 62 and famoxadon at a ratio of 1:1; a pest control composition comprising any one of the present compounds 1 to 62 and famoxadon at a ratio of 10:1; a pest control composition comprising any one of the present compounds 1 to 62 and fenamidone at a ratio of 0.1:1; a pest control composition comprising any one of the present compounds 1 to 62 and fenamidone at a ratio of 1:1; a pest control composition comprising any one of the present compounds 1 to 62 and fenamidone at a ratio of 10:1; a pest control composition comprising any one of the present compounds 1 to 62 and metominostrobin at a ratio of 0.1:1; a pest control composition comprising any one of the present compounds 1 to 62 and metominostrobin at a ratio of 1:1; a pest control composition comprising any one of the present compounds 1 to 62 and metominostrobin at a ratio of 10:1; a pest control composition comprising any one of the present compounds 1 to 62 and orysastrobin at a ratio of 0.1:1; a pest control composition comprising any one of the present compounds 1 to 62 and orysastrobin at a ratio of 1:1; a pest control composition comprising any one of the present compounds 1 to 62 and orysastrobin at a ratio of 10:1; a pest control composition comprising any one of the present compounds 1 to 62 and enestrobin at a ratio of 0.1:1; a pest control composition comprising any one of the present compounds 1 to 62 and enestrobin at a ratio of 1:1; a pest control composition comprising any one of the present compounds 1 to 62 and enestrobin at a ratio of 10:1; a pest control composition comprising any one of the present compounds 1 to 62 and pyraoxystrobin at a ratio of 0.1:1; a pest control composition comprising any one of the present compounds 1 to 62 and pyraoxystrobin at a ratio of 1:1; a pest control composition comprising any one of the present compounds 1 to 62 and pyraoxystrobin at a ratio of 10:1; a pest control composition comprising any one of the present compounds 1 to 62 and pyrametostrobin at a ratio of 0.1:1; a pest control composition comprising any one of the present compounds 1 to 62 and pyrametostrobin at a ratio of 1:1; a pest control composition comprising any one of the present compounds 1 to 62 and pyrametostrobin at a ratio of 10:1; a pest control composition comprising any one of the present compounds 1 to 62 and fenaminstrobin at a ratio of 0.1:1; a pest control composition comprising any one of the present compounds 1 to 62 and fenaminstrobin at a ratio of 1:1; a pest control composition comprising any one of the present compounds 1 to 62 and fenaminstrobin at a ratio of 10:1; a pest control composition comprising any one of the present compounds 1 to 62 and enoxastrobin at a ratio of 0.1:1; a pest control composition comprising any one of the present compounds 1 to 62 and enoxastrobin at a ratio of 1:1; a pest control composition comprising any one of the present compounds 1 to 62 and enoxastrobin at a ratio of 10:1; a pest control composition comprising any one of the present compounds 1 to 62 and coumoxystrobin at a ratio of 0.1:1; a pest control composition comprising any one of the present compounds 1 to 62 and coumoxystrobin at a ratio of 1:1; a pest control composition comprising any one of the present compounds 1 to 62 and coumoxystrobin at a ratio of 10:1; a pest control composition comprising any one of the present compounds 1 to 62 and triclopyricarb at a ratio of 0.1:1; a pest control composition comprising any one of the present compounds 1 to 62 and triclopyricarb at a ratio of 1:1; a pest control composition comprising any one of the present compounds 1 to 62 and triclopyricarb at a ratio of 10:1; a pest control composition comprising any one of the present compounds 1 to 62 and bixafen at a ratio of 0.1:1; a pest control composition comprising any one of the present compounds 1 to 62 and bixafen at a ratio of 1:1; a pest control composition comprising any one of the present compounds 1 to 62 and bixafen at a ratio of 10:1; a pest control composition comprising any one of the present compounds 1 to 62 and isopyrazam at a ratio of 0.1:1; a pest control composition comprising any one of the present compounds 1 to 62 and isopyrazam at a ratio of 1:1; a pest control composition comprising any one of the present compounds 1 to 62 and isopyrazam at a ratio of 10:1; a pest control composition comprising any one of the present compounds 1 to 62 and fluopyram at a ratio of 0.1:1; a pest control composition comprising any one of the present compounds 1 to 62 and fluopyram at a ratio of 1:1; a pest control composition comprising any one of the present compounds 1 to 62 and fluopyram at a ratio of 10:1; a pest control composition comprising any one of the present compounds 1 to 62 and penthiopyrad at a ratio of 0.1:1; a pest control composition comprising any one of the present compounds 1 to 62 and penthiopyrad at a ratio of 1:1; a pest control composition comprising any one of the present compounds 1 to 62 and penthiopyrad at a ratio of 10:1; a pest control composition comprising any one of the present compounds 1 to 62 and benzovindiflupyr at a ratio of 0.1:1; a pest control composition comprising any one of the present compounds 1 to 62 and benzovindiflupyr at a ratio of 1:1; a pest control composition comprising any one of the present compounds 1 to 62 and benzovindiflupyr at a ratio of 10:1; a pest control composition comprising any one of the present compounds 1 to 62 and fluxapyroxad at a ratio of 0.1:1; a pest control composition comprising any one of the present compounds 1 to 62 and fluxapyroxad at a ratio of 1:1; a pest control composition comprising any one of the present compounds 1 to 62 and fluxapyroxad at a ratio of 10:1; a pest control composition comprising any one of the present compounds 1 to 62 and boscalid at a ratio of 0.1:1;
a pest control composition comprising any one of the present compounds 1 to 62 and boscalid at a ratio of 1:1; a pest control composition comprising any one of the present compounds 1 to 62 and boscalid at a ratio of 10:1; a pest control composition comprising any one of the present compounds 1 to 62 and sedaxane at a ratio of 0.1:1; a pest control composition comprising any one of the present compounds 1 to 62 and sedaxane at a ratio of 1:1; a pest control composition comprising any one of the present compounds 1 to 62 and sedaxane at a ratio of 10:1; a pest control composition comprising any one of the present compounds 1 to 62 and penflufen at a ratio of 0.1:1; a pest control composition comprising any one of the present compounds 1 to 62 and penflufen at a ratio of 1:1; a pest control composition comprising any one of the present compounds 1 to 62 and penflufen at a ratio of 10:1; a pest control composition comprising any one of the present compounds 1 to 62 and carboxin at a ratio of 0.1:1; a pest control composition comprising any one of the present compounds 1 to 62 and carboxin at a ratio of 1:1; a pest control composition comprising any one of the present compounds 1 to 62 and carboxin at a ratio of 10:1; a pest control composition comprising any one of the present compounds 1 to 62 and mepronil at a ratio of 0.1:1; a pest control composition comprising any one of the present compounds 1 to 62 and mepronil at a ratio of 1:1; a pest control composition comprising any one of the present compounds 1 to 62 and mepronil at a ratio of 10:1; a pest control composition comprising any one of the present compounds 1 to 62 and flutolanil at a ratio of 0.1:1; a pest control composition comprising any one of the present compounds 1 to 62 and flutolanil at a ratio of 1:1; a pest control composition comprising any one of the present compounds 1 to 62 and flutolanil at a ratio of 10:1; a pest control composition comprising any one of the present compounds 1 to 62 and thifluzamide at a ratio of 0.1:1; a pest control composition comprising any one of the present compounds 1 to 62 and thifluzamide at a ratio of 1:1; a pest control composition comprising any one of the present compounds 1 to 62 and thifluzamide at a ratio of 10:1;
a pest control composition comprising any one of the present compounds 1 to 62 and furametpyr at a ratio of 0.1:1; a pest control composition comprising any one of the present compounds 1 to 62 and furametpyr at a ratio of 1:1; a pest control composition comprising any one of the present compounds 1 to 62 and furametpyr at a ratio of 10:1; a pest control composition comprising any one of the present compounds 1 to 62 and isofetamid at a ratio of 0.1:1; a pest control composition comprising any one of the present compounds 1 to 62 and isofetamid at a ratio of 1:1; a pest control composition comprising any one of the present compounds 1 to 62 and isofetamid at a ratio of 10:1; a pest control composition comprising any one of the present compounds 1 to 62 and N-[2-(3,4-difluorophenyl)phenyl]-3-trifluoromethylpyrazine-2-carboxylic acid amide at a ratio of 0.1:1; a pest control composition comprising any one of the present compounds 1 to 62 and N-[2-(3,4-difluorophenyl)phenyl]-3-trifluoromethylpyrazine-2-carboxylic acid amide at a ratio of 1:1; a pest control composition comprising any one of the present compounds 1 to 62 and N-[2-(3,4-difluorophenyl)phenyl]-3-trifluoromethylpyrazine-2-carboxylic acid amide at a ratio of 10:1; a pest control composition comprising any one of the present compounds 1 to 62 and (R)-(−)-N-(1,1,3-trimethylindan-4-yl)-1-methyl-3-difluoromethylpyrazole-4-carboxylic acid amide at a ratio of 0.1:1; a pest control composition comprising any one of the present compounds 1 to 62 and (R)-(−)-N-(1,1,3-trimethylindan-4-yl)-1-methyl-3-difluoromethylpyrazole-4-carboxylic acid amide at a ratio of 1:1; a pest control composition comprising any one of the present compounds 1 to 62 and (R)-(−)-N-(1,1,3-trimethylindan-4-yl)-1-methyl-3-difluoromethylpyrazole-4-carboxylic acid amide at a ratio of 10:1; a pest control composition comprising any one of the present compounds 1 to 62 and 3-chloro-4-(2,6-difluorophenyl)-6-methyl-5-phenylpyridazine at a ratio of 0.1:1;
a pest control composition comprising any one of the present compounds 1 to 62 and 3-chloro-4-(2,6-difluorophenyl)-6-methyl-5-phenylpyridazine at a ratio of 1:1; a pest control composition comprising any one of the present compounds 1 to 62 and 3-chloro-4-(2,6-difluorophenyl)-6-methyl-5-phenylpyridazine at a ratio of 10:1; a pest control composition comprising any one of the present compounds 1 to 62 and 3-cyano-4-(2,6-difluorophenyl)-6-methyl-5-phenylpyridazine at a ratio of 0.1:1; a pest control composition comprising any one of the present compounds 1 to 62 and 3-cyano-4-(2,6-difluorophenyl)-6-methyl-5-phenylpyridazine at a ratio of 1:1; a pest control composition comprising any one of the present compounds 1 to 62 and 3-cyano-4-(2,6-difluorophenyl)-6-methyl-5-phenylpyridazine at a ratio of 10:1; a pest control composition comprising any one of the present compounds 1 to 62 and fenpropimorph at a ratio of 0.1:1; a pest control composition comprising any one of the present compounds 1 to 62 and fenpropimorph at a ratio of 1:1; a pest control composition comprising any one of the present compounds 1 to 62 and fenpropimorph at a ratio of 10:1; a pest control composition comprising any one of the present compounds 1 to 62 and fenpropidin at a ratio of 0.1:1; a pest control composition comprising any one of the present compounds 1 to 62 and fenpropidin at a ratio of 1:1; a pest control composition comprising any one of the present compounds 1 to 62 and fenpropidin at a ratio of 10:1; a pest control composition comprising any one of the present compounds 1 to 62 and spiroxamine at a ratio of 0.1:1; a pest control composition comprising any one of the present compounds 1 to 62 and spiroxamine at a ratio of 1:1; a pest control composition comprising any one of the present compounds 1 to 62 and spiroxamine at a ratio of 10:1; a pest control composition comprising any one of the present compounds 1 to 62 and tridemorph at a ratio of 0.1:1; a pest control composition comprising any one of the present compounds 1 to 62 and tridemorph at a ratio of 1:1; a pest control composition comprising any one of the present compounds 1 to 62 and tridemorph at a ratio of 10:1;
a pest control composition comprising any one of the present compounds 1 to 62 and cyprodinil at a ratio of 0.1:1; a pest control composition comprising any one of the present compounds 1 to 62 and cyprodinil at a ratio of 1:1; a pest control composition comprising any one of the present compounds 1 to 62 and cyprodinil at a ratio of 10:1; a pest control composition comprising any one of the present compounds 1 to 62 and pyrimethanil at a ratio of 0.1:1; a pest control composition comprising any one of the present compounds 1 to 62 and pyrimethanil at a ratio of 1:1; a pest control composition comprising any one of the present compounds 1 to 62 and pyrimethanil at a ratio of 10:1; a pest control composition comprising any one of the present compounds 1 to 62 and mepanipyrim at a ratio of 0.1:1; a pest control composition comprising any one of the present compounds 1 to 62 and mepanipyrim at a ratio of 1:1; a pest control composition comprising any one of the present compounds 1 to 62 and mepanipyrim at a ratio of 10:1; a pest control composition comprising any one of the present compounds 1 to 62 and fenpiclonil at a ratio of 0.1:1; a pest control composition comprising any one of the present compounds 1 to 62 and fenpiclonil at a ratio of 1:1; a pest control composition comprising any one of the present compounds 1 to 62 and fenpiclonil at a ratio of 10:1; a pest control composition comprising any one of the present compounds 1 to 62 and fludioxonil at a ratio of 0.1:1; a pest control composition comprising any one of the present compounds 1 to 62 and fludioxonil at a ratio of 1:1; a pest control composition comprising any one of the present compounds 1 to 62 and fludioxonil at a ratio of 10:1; a pest control composition comprising any one of the present compounds 1 to 62 and procymidone at a ratio of 0.1:1; a pest control composition comprising any one of the present compounds 1 to 62 and procymidone at a ratio of 1:1; a pest control composition comprising any one of the present compounds 1 to 62 and procymidone at a ratio of 10:1; a pest control composition comprising any one of the present compounds 1 to 62 and iprodione at a ratio of 0.1:1;
a pest control composition comprising any one of the present compounds 1 to 62 and iprodione at a ratio of 1:1; a pest control composition comprising any one of the present compounds 1 to 62 and iprodione at a ratio of 10:1; a pest control composition comprising any one of the present compounds 1 to 62 and vinclozolin at a ratio of 0.1:1; a pest control composition comprising any one of the present compounds 1 to 62 and vinclozolin at a ratio of 1:1; a pest control composition comprising any one of the present compounds 1 to 62 and vinclozolin at a ratio of 10:1; a pest control composition comprising any one of the present compounds 1 to 62 and benomyl at a ratio of 0.1:1; a pest control composition comprising any one of the present compounds 1 to 62 and benomyl at a ratio of 1:1; a pest control composition comprising any one of the present compounds 1 to 62 and benomyl at a ratio of 10:1; a pest control composition comprising any one of the present compounds 1 to 62 and thiophanate-methyl at a ratio of 0.1:1; a pest control composition comprising any one of the present compounds 1 to 62 and thiophanate-methyl at a ratio of 1:1; a pest control composition comprising any one of the present compounds 1 to 62 and thiophanate-methyl at a ratio of 10:1; a pest control composition comprising any one of the present compounds 1 to 62 and carbendazim at a ratio of 0.1:1; a pest control composition comprising any one of the present compounds 1 to 62 and carbendazim at a ratio of 1:1; a pest control composition comprising any one of the present compounds 1 to 62 and carbendazim at a ratio of 10:1; a pest control composition comprising any one of the present compounds 1 to 62 and diethofencarb at a ratio of 0.1:1; a pest control composition comprising any one of the present compounds 1 to 62 and diethofencarb at a ratio of 1:1; a pest control composition comprising any one of the present compounds 1 to 62 and diethofencarb at a ratio of 10:1; a pest control composition comprising any one of the present compounds 1 to 62 and metalaxyl at a ratio of 0.1:1; a pest control composition comprising any one of the present compounds 1 to 62 and metalaxyl at a ratio of 1:1; a pest control composition comprising any one of the present compounds 1 to 62 and metalaxyl at a ratio of 10:1;

a pest control composition comprising any one of the present compounds 1 to 62 and metalaxyl-M (mefenoxam) at a ratio of 0.1:1; a pest control composition comprising any one of the present compounds 1 to 62 and metalaxyl-M (mefenoxam) at a ratio of 1:1; a pest control composition comprising any one of the present compounds 1 to 62 and metalaxyl-M (mefenoxam) at a ratio of 10:1; a pest control composition comprising any one of the present compounds 1 to 62 and benalaxyl at a ratio of 0.1:1; a pest control composition comprising any one of the present compounds 1 to 62 and benalaxyl at a ratio of 1:1; a pest control composition comprising any one of the present compounds 1 to 62 and benalaxyl at a ratio of 10:1; a pest control composition comprising any one of the present compounds 1 to 62 and benalaxyl-M (kiralaxyl) at a ratio of 0.1:1; a pest control composition comprising any one of the present compounds 1 to 62 and benalaxyl-M (kiralaxyl) at a ratio of 1:1; a pest control composition comprising any one of the present compounds 1 to 62 and benalaxyl-M (kiralaxyl) at a ratio of 10:1; a pest control composition comprising any one of the present compounds 1 to 62 and dimethomorph at a ratio of 0.1:1; a pest control composition comprising any one of the present compounds 1 to 62 and dimethomorph at a ratio of 1:1; a pest control composition comprising any one of the present compounds 1 to 62 and dimethomorph at a ratio of 10:1; a pest control composition comprising any one of the present compounds 1 to 62 and iprovalicarb at a ratio of 0.1:1; a pest control composition comprising any one of the present compounds 1 to 62 and iprovalicarb at a ratio of 1:1; a pest control composition comprising any one of the present compounds 1 to 62 and iprovalicarb at a ratio of 10:1; a pest control composition comprising any one of the present compounds 1 to 62 and benthivalicarb-isopropyl at a ratio of 0.1:1; a pest control composition comprising any one of the present compounds 1 to 62 and benthivalicarb-isopropyl at a ratio of 1:1; a pest control composition comprising any one of the present compounds 1 to 62 and benthivalicarb-isopropyl at a ratio of 10:1; a pest control composition comprising any one of the present compounds 1 to 62 and mandipropamid at a ratio of 0.1:1;
a pest control composition comprising any one of the present compounds 1 to 62 and mandipropamid at a ratio of 1:1; a pest control composition comprising any one of the present compounds 1 to 62 and mandipropamid at a ratio of 10:1; a pest control composition comprising any one of the present compounds 1 to 62 and valifenalate at a ratio of 0.1:1; a pest control composition comprising any one of the present compounds 1 to 62 and valifenalate at a ratio of 1:1; a pest control composition comprising any one of the present compounds 1 to 62 and valifenalate at a ratio of 10:1; a pest control composition comprising any one of the present compounds 1 to 62 and cymoxanil at a ratio of 0.1:1; a pest control composition comprising any one of the present compounds 1 to 62 and cymoxanil at a ratio of 1:1; a pest control composition comprising any one of the present compounds 1 to 62 and cymoxanil at a ratio of 10:1; a pest control composition comprising any one of the present compounds 1 to 62 and fluopicolide at a ratio of 0.1:1; a pest control composition comprising any one of the present compounds 1 to 62 and fluopicolide at a ratio of 1:1; a pest control composition comprising any one of the present compounds 1 to 62 and fluopicolide at a ratio of 10:1; a pest control composition comprising any one of the present compounds 1 to 62 and cyazofamid at a ratio of 0.1:1; a pest control composition comprising any one of the present compounds 1 to 62 and cyazofamid at a ratio of 1:1; a pest control composition comprising any one of the present compounds 1 to 62 and cyazofamid at a ratio of 10:1; a pest control composition comprising any one of the present compounds 1 to 62 and amisulbrom at a ratio of 0.1:1; a pest control composition comprising any one of the present compounds 1 to 62 and amisulbrom at a ratio of 1:1; a pest control composition comprising any one of the present compounds 1 to 62 and amisulbrom at a ratio of 10:1; a pest control composition comprising any one of the present compounds 1 to 62 and ametoctradin at a ratio of 0.1:1; a pest control composition comprising any one of the present compounds 1 to 62 and ametoctradin at a ratio of 1:1;
a pest control composition comprising any one of the present compounds 1 to 62 and ametoctradin at a ratio of 10:1; a pest control composition comprising any one of the present compounds 1 to 62 and ethaboxam at a ratio of 0.1:1; a pest control composition comprising any one of the present compounds 1 to 62 and ethaboxam at a ratio of 1:1; a pest control composition comprising any one of the present compounds 1 to 62 and ethaboxam at a ratio of 10:1; a pest control composition comprising any one of the present compounds 1 to 62 and zoxamide at a ratio of 0.1:1; a pest control composition comprising any one of the present compounds 1 to 62 and zoxamide at a ratio of 1:1; a pest control composition comprising any one of the present compounds 1 to 62 and zoxamide at a ratio of 10:1; a pest control composition comprising any one of the present compounds 1 to 62 and oxathiapiprolin at a ratio of 1:1; a pest control composition comprising any one of the present compounds 1 to 62 and oxathiapiprolin at a ratio of 10:1; a pest control composition comprising any one of the present compounds 1 to 62 and oxathiapiprolin at a ratio of 50:1; a pest control composition comprising any one of the present compounds 1 to 62 and picarbutrazox at a ratio of 0.1:1; a pest control composition comprising any one of the present compounds 1 to 62 and picarbutrazox at a ratio of 1:1; a pest control composition comprising any one of the present compounds 1 to 62 and picarbutrazox at a ratio of 10:1; a pest control composition comprising any one of the present compounds 1 to 62 and fosetyl-aluminum at a ratio of 0.01:1; a pest control composition comprising any one of the present compounds 1 to 62 and fosetyl-aluminum at a ratio of 0.1:1; a pest control composition comprising any one of the present compounds 1 to 62 and fosetyl-aluminum at a ratio of 1:1; a pest control composition comprising any one of the present compounds 1 to 62 and a potassium salt of phosphorous acid at a ratio of 0.01:1; a pest control composition comprising any one of the present compounds 1 to 62 and a potassium salt of phosphorous acid at a ratio of 0.1:1; a pest control composition comprising any one of the present compounds 1 to 62 and a potassium salt of phosphorous acid at a ratio of 1:1; a pest control composition comprising any one of the present compounds 1 to 62 and propamocarb hydrochloride at a ratio of 0.01:1;
a pest control composition comprising any one of the present compounds 1 to 62 and propamocarb hydrochloride at a ratio of 0.1:1; a pest control composition comprising any one of the present compounds 1 to 62 and propamocarb hydrochloride at a ratio of 1:1; a pest control composition comprising any one of the present compounds 1 to 62 and fenpyrazamine at a ratio of 0.1:1; a pest control composition comprising any one of the present compounds 1 to 62 and fenpyrazamine at a ratio of 1:1; a pest control composition comprising any one of the present compounds 1 to 62 and fenpyrazamine at a ratio of 10:1; a pest control composition comprising any one of the present compounds 1 to 62 and fenhexamid at a ratio of 0.1:1; a pest control composition comprising any one of the present compounds 1 to 62 and fenhexamid at a ratio of 1:1; a pest control composition comprising any one of the present compounds 1 to 62 and fenhexamid at a ratio of 10:1; a pest control composition comprising any one of the present compounds 1 to 62 and fluazinam at a ratio of 0.1:1; a pest control composition comprising any one of the present compounds 1 to 62 and fluazinam at a ratio of 1:1; a pest control composition comprising any one of the present compounds 1 to 62 and fluazinam at a ratio of 10:1; a pest control composition comprising any one of the present compounds 1 to 62 and flusulfamide at a ratio of 0.1:1; a pest control composition comprising any one of the present compounds 1 to 62 and flusulfamide at a ratio of 1:1; a pest control composition comprising any one of the present compounds 1 to 62 and flusulfamide at a ratio of 10:1; a pest control composition comprising any one of the present compounds 1 to 62 and ferimzone at a ratio of 0.1:1; a pest control composition comprising any one of the present compounds 1 to 62 and ferimzone at a ratio of 1:1; a pest control composition comprising any one of the present compounds 1 to 62 and ferimzone at a ratio of 10:1; a pest control composition comprising any one of the present compounds 1 to 62 and quinoxyfen at a ratio of 0.1:1; a pest control composition comprising any one of the present compounds 1 to 62 and quinoxyfen at a ratio of 1:1;
a pest control composition comprising any one of the present compounds 1 to 62 and quinoxyfen at a ratio of 10:1; a pest control composition comprising any one of the present compounds 1 to 62 and metrafenone at a ratio of 0.1:1; a pest control composition comprising any one of the present compounds 1 to 62 and metrafenone at a ratio of 1:1; a pest control composition comprising any one of the present compounds 1 to 62 and metrafenone at a ratio of 10:1; a pest control composition comprising any one of the present compounds 1 to 62 and pyriofenone at a ratio of 0.1:1; a pest control composition comprising any one of the present compounds 1 to 62 and pyriofenone at a ratio of 1:1; a pest control composition comprising any one of the present compounds 1 to 62 and pyriofenone at a ratio of 10:1; a pest control composition comprising any one of the present compounds 1 to 62 and proquinazid at a ratio of 0.1:1; a pest control composition comprising any one of the present compounds 1 to 62 and proquinazid at a ratio of 1:1; a pest control composition comprising any one of the present compounds 1 to 62 and proquinazid at a ratio of 10:1; a pest control composition comprising any one of the present compounds 1 to 62 and cyflufenamid at a ratio of 0.1:1; a pest control composition comprising any one of the present compounds 1 to 62 and cyflufenamid at a ratio of 1:1; a pest control composition comprising any one of the present compounds 1 to 62 and cyflufenamid at a ratio of 10:1; a pest control composition comprising any one of the present compounds 1 to 62 and tolclofos-methyl at a ratio of 0.01:1;
a pest control composition comprising any one of the present compounds 1 to 62 and tolclofos-methyl at a ratio of 0.1:1; a pest control composition comprising any one of the present compounds 1 to 62 and tolclofos-methyl at a ratio of 1:1; a pest control composition comprising any one of the present compounds 1 to 62 and laminaran at a ratio of 0.1:1; a pest control composition comprising any one of the present compounds 1 to 62 and laminaran at a ratio of 1:1; a pest control composition comprising any one of the present compounds 1 to 62 and laminaran at a ratio of 10:1; a pest control composition comprising any one of the present compounds 1 to 62 and pencycuron at a ratio of 0.1:1;
a pest control composition comprising any one of the present compounds 1 to 62 and pencycuron at a ratio of 1:1; a pest control composition comprising any one of the present compounds 1 to 62 and pencycuron at a ratio of 10:1; a pest control composition comprising any one of the present compounds 1 to 62 and carpropamid at a ratio of 0.1:1; a pest control composition comprising any one of the present compounds 1 to 62 and carpropamid at a ratio of 1:1; a pest control composition comprising any one of the present compounds 1 to 62 and carpropamid at a ratio of 10:1; a pest control composition comprising any one of the present compounds 1 to 62 and diclocymet at a ratio of 0.1:1; a pest control composition comprising any one of the present compounds 1 to 62 and diclocymet at a ratio of 1:1; a pest control composition comprising any one of the present compounds 1 to 62 and diclocymet at a ratio of 10:1; a pest control composition comprising any one of the present compounds 1 to 62 and tricyclazole at a ratio of 0.1:1; a pest control composition comprising any one of the present compounds 1 to 62 and tricyclazole at a ratio of 1:1; a pest control composition comprising any one of the present compounds 1 to 62 and tricyclazole at a ratio of 10:1; a pest control composition comprising any one of the present compounds 1 to 62 and pyroquilon at a ratio of 0.1:1; a pest control composition comprising any one of the present compounds 1 to 62 and pyroquilon at a ratio of 1:1; a pest control composition comprising any one of the present compounds 1 to 62 and pyroquilon at a ratio of 10:1; a pest control composition comprising any one of the present compounds 1 to 62 and fthalide at a ratio of 0.1:1; a pest control composition comprising any one of the present compounds 1 to 62 and fthalide at a ratio of 1:1; a pest control composition comprising any one of the present compounds 1 to 62 and fthalide at a ratio of 10:1; a pest control composition comprising any one of the present compounds 1 to 62 and probenazole at a ratio of 0.1:1; a pest control composition comprising any one of the present compounds 1 to 62 and probenazole at a ratio of 1:1; a pest control composition comprising any one of the present compounds 1 to 62 and probenazole at a ratio of 10:1; a pest control composition comprising any one of the present compounds 1 to 62 and isotianil at a ratio of 0.1:1;
a pest control composition comprising any one of the present compounds 1 to 62 and isotianil at a ratio of 1:1; a pest control composition comprising any one of the present compounds 1 to 62 and isotianil at a ratio of 10:1; a pest control composition comprising any one of the present compounds 1 to 62 and tiadinil at a ratio of 0.1:1; a pest control composition comprising any one of the present compounds 1 to 62 and tiadinil at a ratio of 1:1; a pest control composition comprising any one of the present compounds 1 to 62 and tiadinil at a ratio of 10:1; a pest control composition comprising any one of the present compounds 1 to 62 and tebufloquin at a ratio of 0.1:1; a pest control composition comprising any one of the present compounds 1 to 62 and tebufloquin at a ratio of 1:1; a pest control composition comprising any one of the present compounds 1 to 62 and tebufloquin at a ratio of 10:1; a pest control composition comprising any one of the present compounds 1 to 62 and tolprocarb at a ratio of 0.1:1; a pest control composition comprising any one of the present compounds 1 to 62 and tolprocarb at a ratio of 1:1; a pest control composition comprising any one of the present compounds 1 to 62 and tolprocarb at a ratio of 10:1; a pest control composition comprising any one of the present compounds 1 to 62 and diclomezine at a ratio of 0.1:1; a pest control composition comprising any one of the present compounds 1 to 62 and diclomezine at a ratio of 1:1; a pest control composition comprising any one of the present compounds 1 to 62 and diclomezine at a ratio of 10:1; a pest control composition comprising any one of the present compounds 1 to 62 and validamycin at a ratio of 0.1:1; a pest control composition comprising any one of the present compounds 1 to 62 and validamycin at a ratio of 1:1; a pest control composition comprising any one of the present compounds 1 to 62 and validamycin at a ratio of 10:1; a pest control composition comprising any one of the present compounds 1 to 62 and isoprothiolane at a ratio of 0.1:1; a pest control composition comprising any one of the present compounds 1 to 62 and isoprothiolane at a ratio of 1:1; a pest control composition comprising any one of the present compounds 1 to 62 and isoprothiolane at a ratio of 10:1;
a pest control composition comprising any one of the present compounds 1 to 62 and hydroxyisoxazole at a ratio of 0.1:1; a pest control composition comprising any one of the present compounds 1 to 62 and hydroxyisoxazole at a ratio of 1:1; a pest control composition comprising any one of the present compounds 1 to 62 and hydroxyisoxazole at a ratio of 10:1; a pest control composition comprising any one of the present compounds 1 to 62 and kasugamycin at a ratio of 0.1:1; a pest control composition comprising any one of the present compounds 1 to 62 and kasugamycin at a ratio of 1:1; a pest control composition comprising any one of the present compounds 1 to 62 and kasugamycin at a ratio of 10:1; a pest control composition comprising any one of the present compounds 1 to 62 and streptomycin at a ratio of 0.1:1; a pest control composition comprising any one of the present compounds 1 to 62 and streptomycin at a ratio of 1:1; a pest control composition comprising any one of the present compounds 1 to 62 and streptomycin at a ratio of 10:1; a pest control composition comprising any one of the present compounds 1 to 62 and oxolinic acid at a ratio of 0.1:1; a pest control composition comprising any one of the present compounds 1 to 62 and oxolinic acid at a ratio of 1:1; a pest control composition comprising any one of the present compounds 1 to 62 and oxolinic acid at a ratio of 10:1; a pest control composition comprising any one of the present compounds 1 to 62 and tetracycline at a ratio of 0.1:1; a pest control composition comprising any one of the present compounds 1 to 62 and tetracycline at a ratio of 1:1; a pest control composition comprising any one of the present compounds 1 to 62 and tetracycline at a ratio of 10:1; a pest control composition comprising any one of the present compounds 1 to 62 and oxytetracycline at a ratio of 0.1:1; a pest control composition comprising any one of the present compounds 1 to 62 and oxytetracycline at a ratio of 1:1; a pest control composition comprising any one of the present compounds 1 to 62 and oxytetracycline at a ratio of 10:1; a pest control composition comprising any one of the present compounds 1 to 62 and silthiofam at a ratio of 0.01:1;
a pest control composition comprising any one of the present compounds 1 to 62 and silthiofam at a ratio of 0.1:1; a pest control composition comprising any one of the present compounds 1 to 62 and silthiofam at a ratio of 1:1; a pest control composition comprising any one of the present compounds 1 to 62 and chlorothalonil at a ratio of 0.01:1; a pest control composition comprising any one of the present compounds 1 to 62 and chlorothalonil at a ratio of 0.1:1; a pest control composition comprising any one of the present compounds 1 to 62 and chlorothalonil at a ratio of 1:1; a pest control composition comprising any one of the present compounds 1 to 62 and mancozeb at a ratio of 0.01:1; a pest control composition comprising any one of the present compounds 1 to 62 and mancozeb at a ratio of 0.1:1; a pest control composition comprising any one of the present compounds 1 to 62 and mancozeb at a ratio of 1:1; a pest control composition comprising any one of the present compounds 1 to 62 and folpet at a ratio of 0.01:1; a pest control composition comprising any one of the present compounds 1 to 62 and folpet at a ratio of 0.1:1; a pest control composition comprising any one of the present compounds 1 to 62 and folpet at a ratio of 1:1; a pest control composition comprising any one of the present compounds 1 to 62 and captan at a ratio of 0.01:1; a pest control composition comprising any one of the present compounds 1 to 62 and captan at a ratio of 0.1:1; a pest control composition comprising any one of the present compounds 1 to 62 and captan at a ratio of 1:1; a pest control composition comprising any one of the present compounds 1 to 62 and thiuram at a ratio of 0.01:1; a pest control composition comprising any one of the present compounds 1 to 62 and thiuram at a ratio of 0.1:1; a pest control composition comprising any one of the present compounds 1 to 62 and thiuram at a ratio of 1:1; a pest control composition comprising any one of the present compounds 1 to 62 and metiram at a ratio of 0.01:1; a pest control composition comprising any one of the present compounds 1 to 62 and metiram at a ratio of 0.1:1; a pest control composition comprising any one of the present compounds 1 to 62 and metiram at a ratio of 1:1; a pest control composition comprising any one of the present compounds 1 to 62 and maneb at a ratio of 0.01:1;
a pest control composition comprising any one of the present compounds 1 to 62 and maneb at a ratio of 0.1:1; a pest control composition comprising any one of the present compounds 1 to 62 and maneb at a ratio of 1:1; a pest control composition comprising any one of the present compounds 1 to 62 and iminoctadine acetate at a ratio of 0.1:1; a pest control composition comprising any one of the present compounds 1 to 62 and iminoctadine acetate at a ratio of 1:1; a pest control composition comprising any one of the present compounds 1 to 62 and iminoctadine acetate at a ratio of 10:1; a pest control composition comprising any one of the present compounds 1 to 62 and sulfur at a ratio of 0.01:1; a pest control composition comprising any one of the present compounds 1 to 62 and sulfur at a ratio of 0.1:1; a pest control composition comprising any one of the present compounds 1 to 62 and sulfur at a ratio of 1:1; a pest control composition comprising any one of the present compounds 1 to 62 and copper oxychloride at a ratio of 0.01:1; a pest control composition comprising any one of the present compounds 1 to 62 and copper oxychloride at a ratio of 0.1:1; a pest control composition comprising any one of the present compounds 1 to 62 and copper oxychloride at a ratio of 1:1; a pest control composition comprising any one of the present compounds 1 to 62 and copper hydroxide at a ratio of 0.01:1; a pest control composition comprising any one of the present compounds 1 to 62 and copper hydroxide at a ratio of 0.1:1; a pest control composition comprising any one of the present compounds 1 to 62 and copper hydroxide at a ratio of 1:1; a pest control composition comprising any one of the present compounds 1 to 62 and copper hydroxide sulfate at a ratio of 0.01:1; a pest control composition comprising any one of the present compounds 1 to 62 and copper hydroxide sulfate at a ratio of 0.1:1; a pest control composition comprising any one of the present compounds 1 to 62 and copper hydroxide sulfate at a ratio of 1:1; a pest control composition comprising any one of the present compounds 1 to 62 and Bordeaux mixture at a ratio of 0.01:1; a pest control composition comprising any one of the present compounds 1 to 62 and Bordeaux mixture at a ratio of 0.1:1; a pest control composition comprising any one of the present compounds 1 to 62 and Bordeaux mixture at a ratio of 1:1;
a pest control composition comprising any one of the present compounds 1 to 62 and (3S,6S,7R,8R)-3-{[(3-hydroxy-4-methoxy-2-pyridinyl)carbonyl]amino}-6-methyl-4,9-dioxo-8-(phenylmethyl)-1,5-dioxonan-7-yl 2-methylpropanoate at a ratio of 0.1:1; a pest control composition comprising any one of the present compounds 1 to 62 and (3S,6S,7R,8R)-3-{[(3-hydroxy-4-methoxy-2-pyridinyl)carbonyl]amino}-6-methyl-4,9-dioxo-8-(phenylmethyl)-1,5-dioxonan-7-yl 2-methylpropanoate at a ratio of 1:1; a pest control composition comprising any one of the present compounds 1 to 62 and (3S,6S,7R,8R)-3-{[(3-hydroxy-4-methoxy-2-pyridinyl)carbonyl]amino}-6-methyl-4,9-dioxo-8-(phenylmethyl)-1,5-dioxonan-7-yl 2-methylpropanoate at a ratio of 10:1; a pest control composition comprising any one of the present compounds 1 to 62 and {[4-methoxy-2-({[(3S,7R,8R,9S)-9-methyl-8-(2-methyl-1-oxopropoxy)-2,6-dioxo-7-(phenylmethyl)-1,5-dioxonan-3-yl]amino}carbonyl)-3-pyridinyl]oxy}methyl 2-methylpropanoate at a ratio of 0.1:1; a pest control composition comprising any one of the present compounds 1 to 62 and carboxamide; {[4-methoxy-2-({[(3S,7R,8R,9S)-9-methyl-8-(2-methyl-1-oxopropoxy)-2,6-dioxo-7-(phenylmethyl)-1,5-dioxonan-3-yl]amino}carbonyl)-3-pyridinyl]oxy}methyl 2-methylpropanoate at a ratio of 1:1; a pest control composition comprising any one of the present compounds 1 to 62 and carboxamide; {[4-methoxy-2-({[(3S,7R,8R,9S)-9-methyl-8-(2-methyl-1-oxopropoxy)-2,6-dioxo-7-(phenylmethyl)-1,5-dioxonan-3-yl]amino}carbonyl)-3-pyridinyl]oxy}methyl 2-methylpropanoate at a ratio of 10:1;
a pest control composition comprising any one of the present compounds 1 to 62 and N'-[4-({3-[(4-chlorophenyl)methyl]-1,2,4-thiadiazol-5-yl}oxy)-2,5-dimethylphenyl]-N-ethyl-N-methylmethaneimidamide at a ratio of 0.1:1; a pest control composition comprising any one of the present compounds 1 to 62 and N'-[4-({3-[(4-chlorophenyl)methyl]-1,2,4-thiadiazol-5-yl}oxy)-2,5-dimethylphenyl]-N-ethyl-N-methylmethaneimidamide at a ratio of 1:1; a pest control composition comprising any one of the present compounds 1 to 62 and N'-[4-({3-[(4-chlorophenyl)methyl]-1,2,4-thiadiazol-5-yl}oxy)-2,5-dimethylphenyl]-N-ethyl-N-methylmethaneimidamide at a ratio of 10:1; a pest control composition comprising any one of the present compounds 1 to 62 and 2,6-dimethyl-1H,5H-[1,4]dithiino[2,3-c:5,6-c']dipyrrole-1,3,5,7(2H,6H)-tetrone at a ratio of 0.01:1; a pest control composition comprising any one of the present compounds 1 to 62 and 2,6-dimethyl-1H,5H-[1,4]dithiino[2,3-c:5,6-c']dipyrrole-1,3,5,7(2H,6H)-tetrone at a ratio of 0.1:1; a pest control composition comprising any one of the present compounds 1 to 62 and 2,6-dimethyl-1H,5H-[1,4]dithiino[2,3-c:5,6-c']dipyrrole-1,3,5,7(2H,6H)-tetrone at a ratio of 1:1; a pest control composition comprising any one of the present compounds 1 to 62 and 3-(4,4-difluoro-3,3-dimethyl-3,4-dihydroisoquinolin-1-yl)quinoline at a ratio of 0.1:1; a pest control composition comprising any one of the present compounds 1 to 62 and 3-(4,4-difluoro-3,3-dimethyl-3,4-dihydroisoquinolin-1-yl)quinoline at a ratio of 1:1; a pest control composition comprising any one of the present compounds 1 to 62 and 3-(4,4-difluoro-3,3-dimethyl-3,4-dihydroisoquinolin-1-yl)quinoline at a ratio of 10:1; a pest control composition comprising any one of the present compounds 1 to 62 and 3-(5-fluoro-3,3,4,4-tetramethyl-3,4-dihydroisoquinolin-1-yl)quinoline at a ratio of 0.1:1;
a pest control composition comprising any one of the present compounds 1 to 62 and 3-(5-fluoro-3,3,4,4-tetramethyl-3,4- dihydroisoquinolin-1-yl)quinoline at a ratio of 1:1; a pest control composition comprising any one of the present compounds 1 to 62 and 3-(5-fluoro-3,3,4,4-tetramethyl-3,4-dihydroisoquinolin-1-yl)quinoline at a ratio of 10:1; a pest control composition comprising any one of the present compounds 1 to 62 and 3-(4,4,5-trifluoro-3,3-dimethyl-3,4-dihydroisoquinolin-1-yl)quinoline at a ratio of 0.1:1; a pest control composition comprising any one of the present compounds 1 to 62 and 3-(4,4,5-trifluoro-3,3-dimethyl-3,4-dihydroisoquinolin-1-yl)quinoline at a ratio of 1:1; a pest control composition comprising any one of the present compounds 1 to 62 and 3-(4,4,5-trifluoro-3,3-dimethyl-3,4-dihydroisoquinolin-1-yl)quinoline at a ratio of 10:1; a pest control composition comprising any one of the present compounds 1 to 62 and [3-(4-chloro-2-fluorophenyl)-5-(2,4-difluorophenyl)-1,2-oxazol-4-yl](pyridin-3-yl)methanol at a ratio of 0.1:1; a pest control composition comprising any one of the present compounds 1 to 62 and [3-(4-chloro-2-fluorophenyl)-5-(2,4-difluorophenyl)-1,2-oxazol-4-yl](pyridin-3-yl)methanol at a ratio of 1:1; a pest control composition comprising any one of the present compounds 1 to 62 and [3-(4-chloro-2-fluorophenyl)-5-(2,4-difluorophenyl)-1,2-oxazol-4-yl](pyridin-3-yl)methanol at a ratio of 10:1; a pest control composition comprising any one of the present compounds 1 to 62 and (S)-[3-(4-chloro-2-fluorophenyl)-5-(2,4-difluorophenyl)-1,2-oxazol-4-yl](pyridin-3-yl)methanol at a ratio of 0.1:1;

a pest control composition comprising any one of the present compounds 1 to 62 and (S)-[3-(4-chloro-2-fluorophenyl)-5-(2,4-difluorophenyl)-1,2-oxazol-4-yl](pyridin-3-yl)methanol at a ratio of 1:1; a pest control composition comprising any one of the present compounds 1 to 62 and (S)-[3-(4-chloro-2-fluorophenyl)-5-(2,4-difluorophenyl)-1,2-oxazol-4-yl](pyridin-3-yl)methanol at a ratio of 10:1; a pest control composition comprising any one of the present compounds 1 to 62 and (R)-[3-(4-chloro-2-fluorophenyl)-5-(2,4-difluorophenyl)-1,2-oxazol-4-yl](pyridin-3-yl)methanol at a ratio of 0.1:1; a pest control composition comprising any one of the present compounds 1 to 62 and (R)-[3-(4-chloro-2-fluorophenyl)-5-(2,4-difluorophenyl)-1,2-oxazol-4-yl](pyridin-3-yl)methanol at a ratio of 1:1; a pest control composition comprising any one of the present compounds 1 to 62 and (R)-[3-(4-chloro-2-fluorophenyl)-5-(2,4-difluorophenyl)-1,2-oxazol-4-yl](pyridin-3-yl)methanol at a ratio of 10:1; a pest control composition comprising any one of the present compounds 1 to 62 and 2-{[3-(2-chlorophenyl)-2-(2,4-difluorophenyl)oxiran-2-yl]methyl}-2,4-dihydro-3H-1,2,4-triazole-3-thione at a ratio of 0.1:1; a pest control composition comprising any one of the present compounds 1 to 62 and 2-{[3-(2-chlorophenyl)-2-(2,4-difluorophenyl)oxiran-2-yl]methyl}-2,4-dihydro-3H-1,2,4-triazole-3-thione at a ratio of 1:1; a pest control composition comprising any one of the present compounds 1 to 62 and 2-{[3-(2-chlorophenyl)-2-(2,4-difluorophenyl)oxiran-2-yl]methyl}-2,4-dihydro-3H-1,2,4-triazole-3-thione at a ratio of 10:1; a pest control composition comprising any one of the present compounds 1 to 62 and 2-{[rel-(2R,3S)-3-(2-chlorophenyl)-2-(2,4-difluorophenyl)oxiran-2-yl]methyl}-2,4-dihydro-3H-1,2,4-triazole-3-thione at a ratio of 0.1:1;

a pest control composition comprising any one of the present compounds 1 to 62 and 2-{[rel-(2R,3S)-3-(2-chlorophenyl)-2-(2,4-difluorophenyl)oxiran-2-yl]methyl}-2,4-dihydro-3H-1,2,4-triazole-3-thione at a ratio of 1:1; a pest control composition comprising any one of the present compounds 1 to 62 and 2-{[rel-(2R,3S)-3-(2-chlorophenyl)-2-(2,4-difluorophenyl)oxiran-2-yl]methyl}-2,4-dihydro-3H-1,2,4-triazole-3-thione at a ratio of 10:1; a pest control composition comprising any one of the present compounds 1 to 62 and 2-{[rel-(2R,3R)-3-(2-chlorophenyl)-2-(2,4-difluorophenyl)oxiran-2-yl]methyl}-2,4-dihydro-3H-1,2,4-triazole-3-thione at a ratio of 0.1:1; a pest control composition comprising any one of the present compounds 1 to 62 and 2-{[rel-(2R,3R)-3-(2-chlorophenyl)-2-(2,4-difluorophenyl)oxiran-2-yl]methyl}-2,4-dihydro-3H-1,2,4-triazole-3-thione at a ratio of 1:1; a pest control composition comprising any one of the present compounds 1 to 62 and 2-{[rel-(2R,3R)-3-(2-chlorophenyl)-2-(2,4-difluorophenyl)oxiran-2-yl]methyl}-2,4-dihydro-3H-1,2,4-triazole-3-thione at a ratio of 10:1; a pest control composition comprising any one of the present compounds 1 to 62 and 2-{[(2R,3S)-3-(2-chlorophenyl)-2-(2,4-difluorophenyl)oxiran-2-yl]methyl}-2,4-dihydro-3H-1,2,4-triazole-3-thione at a ratio of 0.1:1; a pest control composition comprising any one of the present compounds 1 to 62 and 2-{[(2R,3S)-3-(2-chlorophenyl)-2-(2,4-difluorophenyl)oxiran-2-yl]methyl}-2,4-dihydro-3H-1,2,4-triazole-3-thione at a ratio of 1:1; a pest control composition comprising any one of the present compounds 1 to 62 and 2-{[(2R,3S)-3-(2-chlorophenyl)-2-(2,4-difluorophenyl)oxiran-2-yl]methyl}-2,4-dihydro-3H-1,2,4-triazole-3-thione at a ratio of 10:1;

a pest control composition comprising any one of the present compounds 1 to 62 and 2-{[(2S,3R)-3-(2-chlorophenyl)-2-(2,4-difluorophenyl)oxiran-2-yl]methyl}-2,4-dihydro-3H-1,2,4-triazole-3-thione at a ratio of 0.1:1; a pest control composition comprising any one of the present compounds 1 to 62 and 2-{[(2S,3R)-3-(2-chlorophenyl)-2-(2,4-difluorophenyl)oxiran-2-yl]methyl}-2,4-dihydro-3H-1,2,4-triazole-3-thione at a ratio of 1:1; a pest control composition comprising any one of the present compounds 1 to 62 and 2-{[(2S,3R)-3-(2-chlorophenyl)-2-(2,4-difluorophenyl)oxiran-2-yl]methyl}-2,4-dihydro-3H-1,2,4-triazole-3-thione at a ratio of 10:1; a pest control composition comprising any one of the present compounds 1 to 62 and 2-{[(2R,3R)-3-(2-chlorophenyl)-2-(2,4-difluorophenyl)oxiran-2-yl]methyl}-2,4-dihydro-3H-1,2,4-triazole-3-thione at a ratio of 0.1:1; a pest control composition comprising any one of the present compounds 1 to 62 and 2-{[(2R,3R)-3-(2-chlorophenyl)-2-(2,4-difluorophenyl)oxiran-2-yl]methyl}-2,4-dihydro-3H-1,2,4-triazole-3-thione at a ratio of 1:1; a pest control composition comprising any one of the present compounds 1 to 62 and 2-{[(2R,3R)-3-(2-chlorophenyl)-2-(2,4-difluorophenyl)oxiran-2-yl]methyl}-2,4-dihydro-3H-1,2,4-triazole-3-thione at a ratio of 10:1; a pest control composition comprising any one of the present compounds 1 to 62 and 2-{[(2S,3S)-3-(2-chlorophenyl)-2-(2,4-difluorophenyl)oxiran-2-yl]methyl}-2,4-dihydro-3H-1,2,4-triazole-3-thione at a ratio of 0.1:1;

a pest control composition comprising any one of the present compounds 1 to 62 and 2-{[(2S,3S)-3-(2-chlorophenyl)-2-(2,4-difluorophenyl)oxiran-2-yl]methyl}-2,4-dihydro-3H-1,2,4-triazole-3-thione at a ratio of 1:1; a pest control composition comprising any one of the present compounds 1 to 62 and 2-{[(2S,3S)-3-(2-chlorophenyl)-2-(2,4-difluorophenyl)oxiran-2-yl]methyl}-2,4-dihydro-3H-1,2,4-triazole-3-thione at a ratio of 10:1; a pest control composition comprising any one of the present compounds 1 to 62 and 1-{[3-(2-chlorophenyl)-2-(2,4-difluorophenyl)oxiran-2-yl]methyl}-1H-1,2,4-triazole-5-thiol at a ratio of 0.1:1; a pest control composition comprising any one of the present compounds 1 to 62 and 1-{[3-(2-chlorophenyl)-2-(2,4-difluorophenyl)oxiran-2-yl]methyl}-1H-1,2,4-triazole-5-thiol at a ratio of 1:1; a pest control composition comprising any one of the present compounds 1 to 62 and 1-{[3-(2-chlorophenyl)-2-(2,4-difluorophenyl)oxiran-2-yl]methyl}-1H-1,2, 4-triazole-5-thiol at a ratio of 10:1; a pest control composition comprising any one of the present compounds 1 to 62 and 1-{[rel-(2R,3S)-3-(2-chlorophenyl)-2-(2,4-difluorophenyl)oxiran-2-yl]methyl}-1H-1,2,4-triazole-5-thiol at a ratio of 0.1:1; a pest control composition comprising any one of the present compounds 1 to 62 and 1-{[rel-(2R,3S)-3-(2-chlorophenyl)-2-(2,4-difluorophenyl)oxiran-2-yl]methyl}-1H-1,2,4-triazole-5-thiol at a ratio of 1:1; a pest control composition comprising any one of the present compounds 1 to 62 and 1-{[rel-(2R,3S)-3-(2-chlorophenyl)-2-(2,4-difluorophenyl)oxiran-2-yl]methyl}-1H-1,2,4-triazole-5-thiol at a ratio of 10:1; a pest control composition comprising any one of the present compounds 1 to 62 and 1-{[rel-(2R,3R)-3-(2-chlorophenyl)-2-(2,4-difluorophenyl)oxiran-2-yl]methyl}-1H-1,2,4-triazole-5-thiol at a ratio of 0.1:1;
a pest control composition comprising any one of the present compounds 1 to 62 and 1-{[rel-(2R,3R)-3-(2-chlorophenyl)-2-(2,4-difluorophenyl)oxiran-2-yl]methyl}-1H-1,2,4-triazole-5-thiol at a ratio of 1:1; a pest control composition comprising any one of the present compounds 1 to 62 and 1-{[rel-(2R,3R)-3-(2-chlorophenyl)-2-(2,4-difluorophenyl)oxiran-2-yl]methyl}-1H-1,2,4-triazole-5-thiol at a ratio of 10:1; a pest control composition comprising any one of the present compounds 1 to 62 and 1-{[(2R,3S)-3-(2-chlorophenyl)-2-(2,4-difluorophenyl)oxiran-2-yl]methyl}-1H-1,2,4-triazole-5-thiol at a ratio of 0.1:1; a pest control composition comprising any one of the present compounds 1 to 62 and 1-{[(2R,3S)-3-(2-chlorophenyl)-2-(2,4-difluorophenyl)oxiran-2-yl]methyl}-1H-1,2,4-triazole-5-thiol at a ratio of 1:1; a pest control composition comprising any one of the present compounds 1 to 62 and 1-{[(2R,3S)-3-(2-chlorophenyl)-2-(2,4-difluorophenyl)oxiran-2-yl]methyl}-1H-1,2,4-triazole-5-thiol at a ratio of 10:1; a pest control composition comprising any one of the present compounds 1 to 62 and 1-{[(2S,3R)-3-(2-chlorophenyl)-2-(2,4-difluorophenyl)oxiran-2-yl]methyl}-1H-1,2,4-triazole-5-thiol at a ratio of 0.1:1; a pest control composition comprising any one of the present compounds 1 to 62 and 1-{[(2S,3R)-3-(2-chlorophenyl)-2-(2,4-difluorophenyl)oxiran-2-yl]methyl}-1H-1,2,4-triazole-5-thiol at a ratio of 1:1; a pest control composition comprising any one of the present compounds 1 to 62 and 1-{[(2S,3R)-3-(2-chlorophenyl)-2-(2,4-difluorophenyl)oxiran-2-yl]methyl}-1H-1,2,4-triazole-5-thiol at a ratio of 10:1; a pest control composition comprising any one of the present compounds 1 to 62 and 1-{[(2R,3R)-3-(2-chlorophenyl)-2-(2,4-difluorophenyl)oxiran-2-yl]methyl}-1H-1,2,4-triazole-5-thiol at a ratio of 0.1:1; a pest control composition comprising any one of the present compounds 1 to 62 and 1-{[(2R,3R)-3-(2-chlorophenyl)-2-(2,4-difluorophenyl)oxiran-2-yl]methyl}-1H-1,2,4-triazole-5-thiol at a ratio of 1:1; a pest control composition comprising any one of the present compounds 1 to 62 and 1-{[(2R,3R)-3-(2-chlorophenyl)-2-(2,4-difluorophenyl)oxiran-2-yl]methyl}-1H-1,2,4-triazole-5-thiol at a ratio of 10:1; a pest control composition comprising any one of the present compounds 1 to 62 and 1-{[(2S,3S)-3-(2-chlorophenyl)-2-(2,4-difluorophenyl)oxiran-2-yl]methyl}-1H-1,2,4-triazole-5-thiol at a ratio of 0.1:1; a pest control composition comprising any one of the present compounds 1 to 62 and 1-{[(2S,3S)-3-(2-chlorophenyl)-2-(2,4-difluorophenyl)oxiran-2-yl]methyl}-1H-1,2,4-triazole-5-thiol at a ratio of 1:1; a pest control composition comprising any one of the present compounds 1 to 62 and 1-{[(2S,3S)-3-(2-chlorophenyl)-2-(2,4-difluorophenyl)oxiran-2-yl]methyl}-1H-1,2,4-triazole-5-thiol at a ratio of 10:1; a pest control composition comprising any one of the present compounds 1 to 62 and 1-{[3-(2-chlorophenyl)-2-(2,4-difluorophenyl)oxiran-2-yl]methyl}-1H-1,2,4-triazol-5-yl thiocyanate at a ratio of 0.1:1; a pest control composition comprising any one of the present compounds 1 to 62 and 1-{[3-(2-chlorophenyl)-2-(2,4-difluorophenyl)oxiran-2-yl]methyl}-1H-1,2,4-triazol-5-yl thiocyanate at a ratio of 1:1; a pest control composition comprising any one of the present compounds 1 to 62 and 1-{[3-(2-chlorophenyl)-2-(2,4-difluorophenyl)oxiran-2-yl]methyl}-1H-1,2,4-triazol-5-yl thiocyanate at a ratio of 10:1;
a pest control composition comprising any one of the present compounds 1 to 62 and 1-{[rel-(2R,3S)-3-(2-chlorophenyl)-2-(2,4-difluorophenyl)oxiran-2-yl]methyl}-1H-1,2,4-triazol-5-yl thiocyanate at a ratio of 0.1:1; a pest control composition comprising any one of the present compounds 1 to 62 and 1-{[rel-(2R,3S)-3-(2-chlorophenyl)-2-(2,4-difluorophenyl)oxiran-2-yl]methyl}-1H-1,2,4-triazol-5-yl thiocyanate at a ratio of 1:1; a pest control composition comprising any one of the present compounds 1 to 62 and 1-{[rel-(2R,3S)-3-(2-chlorophenyl)-2-(2,4-difluorophenyl)oxiran-2-yl]methyl}-1H-1,2,4-triazol-5-yl thiocyanate at a ratio of 10:1; a pest control composition comprising any one of the present compounds 1 to 62 and 1-{[rel-(2R,3R)-3-(2-chlorophenyl)-2-(2,4-difluorophenyl)oxiran-2-yl]methyl}-1H-1,2,4-triazol-5-yl thiocyanate at a ratio of 0.1:1; a pest control composition comprising any one of the present compounds 1 to 62 and 1-{[rel-(2R,3R)-3-(2-chlorophenyl)-2-(2,4-difluorophenyl)oxiran-2-yl]methyl}-1H-1,2,4-triazol-5-yl thiocyanate at a ratio of 1:1; a pest control composition comprising any one of the present compounds 1 to 62 and 1-{[rel-(2R,3R)-3-(2-chlorophenyl)-2-(2,4-difluorophenyl)oxiran-2-yl]methyl}-1H-1,2,4-triazol-5-yl thiocyanate at a ratio of 10:1; a pest control composition comprising any one of the present compounds 1 to 62 and 1-{[(2R,3S)-3-(2-chlorophenyl)-2-(2,4-difluorophenyl)oxiran-2-yl]methyl}-1H-1,2,4-triazol-5-yl thiocyanate at a ratio of 0.1:1; a pest control composition comprising any one of the present compounds 1 to 62 and 1-{[(2R,3S)-3-(2-chlorophenyl)-2-(2,4-difluorophenyl)oxiran-2-yl]methyl}-1H-1,2,4-triazol-5-yl thiocyanate at a ratio of 1:1;
a pest control composition comprising any one of the present compounds 1 to 62 and 1-{[(2R,3S)-3-(2-chlorophenyl)-2-(2,4-difluorophenyl)oxiran-2-yl]methyl}-1H-1,2,4-triazol-5-yl thiocyanate at a ratio of 10:1; a pest control composition comprising any one of the present compounds 1 to 62 and 1-{[(2S,3R)-3-(2-chlorophenyl)-2-(2,4-difluorophenyl)oxiran-2-yl]methyl}-1H-1,2,4-triazol-5-yl thiocyanate at a ratio of 0.1:1; a pest control composition comprising any one of the present compounds 1 to 62 and 1-{[(2S,3R)-3-(2-chlorophenyl)-2-(2,4-difluorophenyl)oxiran-2-yl]methyl}-1H-1,2,4-triazol-5-yl thiocyanate at a ratio of 1:1; a pest control composition comprising any one of the present compounds 1 to 62 and 1-{[(2S,3R)-3-(2-chlorophenyl)-2-(2,4-difluorophenyl)oxiran-2-yl]methyl}-1H-1,2,4-triazol-5-yl thiocyanate at a ratio of 10:1; a pest control composition comprising any one of the present compounds 1 to 62 and 1-{[(2R,3R)-3-(2-chlorophenyl)-2-(2,4-difluorophenyl)oxiran-2-yl]methyl}-1H-1,2,4-triazol-5-yl thiocyanate at a ratio of 0.1:1; a pest control composition comprising any one of the present compounds 1 to 62 and 1-{[(2R,3R)-3-(2-chlorophenyl)-2-(2,4-difluorophenyl)oxiran-2-yl]methyl}-1H-1,2,4-triazol-5-yl thiocyanate at a ratio of 1:1; a pest control composition comprising any one of the present compounds 1 to 62 and 1-{[(2R,3R)-3-(2-chlorophenyl)-2-(2,4-difluorophenyl)oxiran-2-yl]methyl}-1H-1,2,4-triazol-5-yl thiocyanate at a ratio of 10:1; a pest control composition comprising any one of the present compounds 1 to 62 and 1-{[(2S,3S)-3-(2-chlorophenyl)-2-(2,4-difluorophenyl)oxiran-2-yl]methyl}-1H-1,2,4-triazol-5-yl thiocyanate at a ratio of 0.1:1;
any one of the present compounds 1 to 62 and 1-{[(2S,3S)-3-(2-chlorophenyl)-2-(2,4-difluorophenyl)oxiran-2-yl]methyl}-1H-1,2,4-triazol-5-yl thiocyanate at a ratio of 1:1; a pest control composition comprising any one of the present compounds 1 to 62 and 1-{[(2S,3S)-3-(2-chlorophenyl)-2-(2,4-difluorophenyl)oxiran-2-yl]methyl}-1H-1,2,4-triazol-5-yl thiocyanate at a ratio of 10:1; a pest control composition comprising any one of the present compounds 1 to 62 and 5-(4-chlorobenzyl)-2-chloromethyl-2-methyl-1-(1H-1,2,4-triazol-1-ylmethyl)cyclopentanol at a ratio of 0.1:1; a pest control composition comprising any one of the present compounds 1 to 62 and 5-(4-chlorobenzyl)-2-chloromethyl-2-methyl-1-(1H-1,2,4-triazol-1-ylmethyl)cyclopentanol at a ratio of 1:1; a pest control composition comprising any one of the present compounds 1 to 62 and 5-(4-chlorobenzyl)-2-chloromethyl-2-methyl-1-(1H-1,2,4-triazol-1-ylmethyl)cyclopentanol at a ratio of 10:1; a pest control composition comprising any one of the present compounds 1 to 62 and (1RS,2SR,5SR)-5-(4-chlorobenzyl)-2-chloromethyl-2-methyl-1-(1H-1,2,4-triazol-1-ylmethyl)cyclopentanol at a ratio of 0.1:1; a pest control composition comprising any one of the present compounds 1 to 62 and (1RS,2SR,5SR)-5-(4-chlorobenzyl)-2-chloromethyl-2-methyl-1-(1H-1,2,4-triazol-1-ylmethyl)cyclopentanol at a ratio of 1:1; a pest control composition comprising any one of the present compounds 1 to 62 and (1RS,2SR,5SR)-5-(4-chlorobenzyl)-2-chloromethyl-2-methyl-1-(1H-1,2,4-triazol-1-ylmethyl)cyclopentanol at a ratio of 10:1;
a pest control composition comprising any one of the present compounds 1 to 62 and (1RS,2RS,5RS)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and (1RS,2RS,5RS)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 62 and (1RS,2RS,5RS)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 62 and (1RS,2RS,5SR)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and (1RS,2RS,5SR)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 62 and (1RS,2RS,5SR)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 62 and (1RS,2SR,5RS)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and (1RS,2SR,5RS)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 62 and (1RS,2SR,5RS)-2-chloromethyl-5-(4-fluorobenzyl)-2-methyl-1-(1H-1,2,4-triazol-1-ylmethyl)cyclopentanol at a ratio of 10:1;
a pest control composition comprising any one of the present compounds 1 to 62 and (1R,2S,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and (1R,2S,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 62 and (1R,2S,5S)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 62 and (1S,2R,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and (1S,2R,5R)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 62 and (1S,2R,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 62 and (1R,2R,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and (1R,2R,5R)-2-chloromethyl-5-(4-fluorobenzyl)-2-methyl-1-(1H-1,2,4-triazol-1-ylmethyl)cyclopentanol at a ratio of 1:1;
a pest control composition comprising any one of the present compounds 1 to 62 and (1R,2R,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 62 and (1S,2S,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and (1S,2S,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 62 and (1S,2S,5S)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 62 and (1R,2R,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and (1R,2R,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 62 and (1R,2R,5S)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 62 and (1S,2S,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and (1S,2S,5R)-2-chloromethyl-5-(4-fluorobenzyl)-2-methyl-1-(1H-1,2,4-triazol-1-ylmethyl)cyclopentanol at a ratio of 1:1;
a pest control composition comprising any one of the present compounds 1 to 62 and (1S,2S,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 62 and (1R,2S,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and (1R,2S,5R)-2-chloromethyl- 5-(4-fluorobenzyl)-2-methyl-1-(1H-1,2,4-triazol-1-ylmethyl)cyclopentanol at a ratio of 1:1; a pest control composition comprising any one of the present compounds 1 to 62 and (1R,2S,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 62 and (1S,2R,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and (1S,2R,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 62 and (1S,2R,5S)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 62 and 2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and 2-chloromethyl-5-(4-fluorobenzyl)-2-methyl-1-(1H-1,2,4-triazol-1-ylmethyl)cyclopentanol at a ratio of 1:1;

a pest control composition comprising any one of the present compounds 1 to 62 and 2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 62 and (1RS,2SR,5SR)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and (1RS,2SR,5SR)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 62 and (1RS,2SR,5SR)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 62 and (1RS,2RS,5RS)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and (1RS,2RS,5RS)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 62 and (1RS,2RS,5RS)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 62 and (1RS,2RS,5SR)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and (1RS,2RS,5SR)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 62 and (1RS,2RS,5SR)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 62 and (1RS,2SR,5RS)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and (1RS,2SR,5RS)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 62 and (1RS,2SR,5RS)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 62 and (1R,2S,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and (1R,2S,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 62 and (1R,2S,5S)-2-chloromethyl-5-(4-fluorobenzyl)-2-methyl-1-(1H-1,2,4-triazol-1-ylmethyl)cyclopentanol at a ratio of 10:1;

a pest control composition comprising any one of the present compounds 1 to 62 and (1S,2R,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and (1S,2R,5R)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 62 and (1S,2R,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 62 and (1R,2R,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and (1R,2R,5R)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 62 and (1R,2R,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 62 and (1S,2S,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and (1S,2S,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 62 and (1S,2S,5S)-2-chloromethyl-5-(4-fluorobenzyl)-2-methyl-1-(1H-1,2,4-triazol-1-ylmethyl)cyclopentanol at a ratio of 10:1;

a pest control composition comprising any one of the present compounds 1 to 62 and (1R,2R,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and (1R,2R,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 62 and (1R,2R,5S)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 62 and (1S,2S,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and (1S,2S,5R)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 62 and (1S,2S,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 62 and (1R,2S,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and (1R,2S,5R)-2-chloromethyl-5-(4-fluorobenzyl)-2-methyl-1-(1H-1,2,4-triazol-1-ylmethyl)cyclopentanol at a ratio of 1:1;
a pest control composition comprising any one of the present compounds 1 to 62 and (1R,2S,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 62 and (1S,2R,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 62 and (1S,2R,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 62 and (1S,2R,5S)-2-chloromethyl-5-(4-fluorobenzyl)-2-methyl-1-(1H-1,2,4-triazol-1-ylmethyl)cyclopentanol at a ratio of 10:1;
a pest control composition comprising any one of the present compounds 1 to 62 and 5-amino-4-(2-chloro-4-fluorophenyl)-N-(2,6-difluorophenyl)-1,3-dimethyl-1H-pyrazole at a ratio of 0.1:1; a pest control composition comprising any one of the present compounds 1 to 62 and 5-amino-4-(2-chloro-4-fluorophenyl)-N-(2,6-difluorophenyl)-1,3-dimethyl-1H-pyrazole at a ratio of 1:1; a pest control composition comprising any one of the present compounds 1 to 62 and 5-amino-4-(2-chloro-4-fluorophenyl)-N-(2,6-difluorophenyl)-1,3-dimethyl-1H-pyrazole at a ratio of 10:1;
a pest control composition comprising any one of the present compounds 1 to 62 and 5-amino-4-(2-bromo-4-fluorophenyl)-N-(2,6-difluorophenyl)-1,3-dimethyl-1H-pyrazole at a ratio of 0.1:1; a pest control composition comprising any one of the present compounds 1 to 62 and 5-amino-4-(2-bromo-4-fluorophenyl)-N-(2,6-difluorophenyl)-1,3-dimethyl-1H-pyrazole at a ratio of 1:1; a pest control composition comprising any one of the present compounds 1 to 62 and 5-amino-4-(2-bromo-4-fluorophenyl)-N-(2,6-difluorophenyl)-1,3-dimethyl-1H-pyrazole at a ratio of 10:1;
a pest control composition comprising any one of the present compounds 1 to 62 and 5-amino-4-(2-chloro-4-fluorophenyl)-N-(2-chloro-6-fluorophenyl)-1,3-dimethyl-1H-pyrazole at a ratio of 0.1:1; a pest control composition comprising any one of the present compounds 1 to 62 and 5-amino-4-(2-chloro-4-fluorophenyl)-N-(2-chloro-6-fluorophenyl)-1,3-dimethyl-1H-pyrazole at a ratio of 1:1; a pest control composition comprising any one of the present compounds 1 to 62 and 5-amino-4-(2-chloro-4-fluorophenyl)-N-(2-chloro-6-fluorophenyl)-1,3-dimethyl-1H-pyrazole at a ratio of 10:1;
a pest control composition comprising any one of the present compounds 1 to 62 and 5-amino-4-(2-bromo-4-fluorophenyl)-N-(2-chloro-6-fluorophenyl)-1,3-dimethyl-1H-pyrazole at a ratio of 0.1:1; a pest control composition comprising any one of the present compounds 1 to 62 and 5-amino-4-(2-bromo-4-fluorophenyl)-N-(2-chloro-6-fluorophenyl)-1,3-dimethyl-1H-pyrazole at a ratio of 1:1; a pest control composition comprising any one of the present compounds 1 to 62 and 5-amino-4-(2-bromo-4-fluorophenyl)-N-(2-chloro-6-fluorophenyl)-1, 3-dimethyl-1H-pyrazole at a ratio of 10:1;
a pest control composition comprising any one of the present compounds 1 to 62 and 5-amino-4-(2-chloro-4-fluorophenyl)-N-(2,6-difluoro-4-methylphenyl)-1,3-dimethyl-1H-pyrazole at a ratio of 0.1:1; a pest control composition comprising any one of the present compounds 1 to 62 and 5-amino-4-(2-chloro-4-fluorophenyl)-N-(2,6-difluoro-4-methylphenyl)-1,3-dimethyl-1H-pyrazole at a ratio of 1:1; a pest control composition comprising any one of the present compounds 1 to 62 and 5-amino-4-(2-chloro-4-fluorophenyl)-N-(2,6-difluoro-4-methylphenyl)-1,3-dimethyl-1H-pyrazole at a ratio of 10:1;
a pest control composition comprising any one of the present compounds 1 to 62 and 5-amino-4-(2-bromo-4-fluorophenyl)-N-(2,6-difluoro-4-methylphenyl)-1,3-dimethyl-1H-pyrazole at a ratio of 0.1:1; a pest control composition comprising any one of the present compounds 1 to 62 and 5-amino-4-(2-bromo-4-fluorophenyl)-N-(2,6-difluoro-4-methylphenyl)-1,3-dimethyl-1H-pyrazole at a ratio of 1:1; a pest control composition comprising any one of the present compounds 1 to 62 and 5-amino-4-(2-bromo-4-fluorophenyl)-N-(2,6-difluoro-4-methylphenyl)-1,3-dimethyl-1H-pyrazole at a ratio of 10:1;
a pest control composition comprising any one of the present compounds 1 to 62 and 5-amino-N-(2-chloro-6-fluoro-4-methylphenyl)-4-(2-chloro-4-fluorophenyl)-1,3-dimethyl-1H-pyrazole at a ratio of 0.1:1; a pest control composition comprising any one of the present compounds 1 to 62 and 5-amino-N-(2-chloro-6-fluoro-4-methylphenyl)-4-(2-chloro-4-fluorophenyl)-1,3-dimethyl-1H-pyrazole at a ratio of 1:1; a pest control composition comprising any one of the present compounds 1 to 62 and 5-amino-N-(2-chloro-6-fluoro-4-methylphenyl)-4-(2-chloro-4-fluorophenyl)-1,3-dimethyl-1H-pyrazole at a ratio of 10:1;
a pest control composition comprising any one of the present compounds 1 to 62 and 5-amino-4-(2-bromo-4-fluorophenyl)-N-(2-chloro-6-fluoro-4-methylphenyl)-1,3-dimethyl-1H-pyrazole at a ratio of 0.1:1; a pest control composition comprising any one of the present compounds 1 to 62 and 5-amino-4-(2-bromo-4-fluorophenyl)-N-(2-chloro-6-fluoro-4-methylphenyl)-1,3-dimethyl-1H-pyrazole at a ratio of 1:1; a pest control composition comprising any one of the present compounds 1 to 62 and 5-amino-4-(2-bromo-4-fluorophenyl)-N-(2-chloro-6-fluoro-4-methylphenyl)-1,3-dimethyl-1H-pyrazole at a ratio of 10:1;
a pest control composition comprising any one of the present compounds 1 to 62 and 9-fluoro-2,3-dihydro-2,2-dimethyl-5-(quinolin-3-yl)-1,4-benzooxazepine at a ratio of 0.1:1; a pest control composition comprising any one of the present compounds 1 to 62 and 9-fluoro-2,3-dihydro-2,2-dimethyl-5-(quinolin-3-yl)-1,4-benzooxazepine at a ratio of 1:1; a pest control composition comprising any one of the present compounds 1 to 62 and 9-fluoro-2,3-dihydro-2,2-dimethyl-5-(quinolin-3-yl)-1,4-benzooxazepine at a ratio of 10:1; a pest control composition comprising any one of the present compounds 1 to 62 and N-cyclopropyl-3-(difluoromethyl)-5-fluoro-N-(2-isopropylbenzyl)-1-methyl-1H-pyrazole-4-carboxamide at a ratio of 0.1:1; a pest control composition comprising any one of the present compounds 1 to 62 and N-cyclopropyl-3-(difluoromethyl)-5-fluoro-N-(2-isopropylbenzyl)-1-methyl-1H-pyrazole-4-carboxamide at a ratio of 1:1; a pest control composition comprising any one of the present compounds 1 to 62 and N-cyclopropyl-3-(difluoromethyl)-5-fluoro-N-(2-isopropylbenzyl)-1-methyl-1H-pyrazole-4-carboxamide at a ratio of 10:1; a pest control composition comprising any one of the present compounds 1 to 62 and N-cyclopropyl-3-(difluoromethyl)-5-fluoro-N-(5-chloro-2-isopropylbenzyl)-1-methyl-1H-pyrazole-4-carboxamide at a ratio of 0.1:1; a pest control composition comprising any one of the present compounds 1 to 62 and N-cyclopropyl-3-(difluoromethyl)-5-fluoro-N-(5-chloro-2-isopropylbenzyl)-1-methyl-1H-pyrazole-4-carboxamide at a ratio of 1:1; a pest control composition comprising any one of the present compounds 1 to 62 and N-cyclopropyl-3-(difluoromethyl)-5-fluoro-N-(5-chloro-2-isopropylbenzyl)-1-methyl-1H-pyrazole-4-carboxamide at a ratio of 10:1; a pest control composition comprising any one of the present compounds 1 to 62 and N-[1-(2,4-dichlorophenyl)-1-methoxypropan-2-yl]-3-difluoromethyl-1-methyl-1H-pyrazole-4-carboxamide at a ratio of 0.1:1;
a pest control composition comprising any one of the present compounds 1 to 62 and N-[1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 62 and N-[1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 62 and N-[(1R,2R)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 62 and N-[(1R,2R)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 62 and N-[(1R,2R)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 62 and N-[(1R,2S)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 62 and N-[(1R,2S)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 62 and N-[(1R,2S)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 62 and N-[(1S,2R)1-(2,4-dichlorophenyl)-1-methoxypropan-2-yl]-3-difluoromethyl-1-methyl-1H-pyrazole-4-carboxamide at a ratio of 0.1:1;
a pest control composition comprising any one of the present compounds 1 to 62 and N-[(1S,2R)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 62 and N-[(1S,2R)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 62 and N-[(1S,2S)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 62 and N-[(1S,2S)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 62 and N-[(1S,2S)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 62 and rel-N-[(1R,2R)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 62 and rel-N-[(1R,2R)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 62 and rel-N-[(1R,2R)1-(2,4-dichlorophenyl)-1-methoxypropan-2-yl]-3-difluoromethyl-1-methyl-1H-pyrazole-4-carboxamide at a ratio of 10:1;
a pest control composition comprising any one of the present compounds 1 to 62 and rel-N-[(1R,2S)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 62 and rel-N-[(1R,2S)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 62 and rel-N-[(1R,2S)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 62 and N-[(1R,2RS)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 62 and N-[(1R,2RS)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 62 and N-[(1R,2RS)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 62 and N-[(1S,2RS)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 62 and N-[(1S,2RS)1-(2,4-dichlorophenyl)-1-methoxypropan-2-yl]-3-difluoromethyl-1-methyl-1H-pyrazole-4-carboxamide at a ratio of 1:1;
a pest control composition comprising any one of the present compounds 1 to 62 and N-[(1S,2RS)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 62 and N-[(1RS,2R)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 62 and N-[(1RS,2R)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 62 and N-[(1RS,2R)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 62 and N-[(1RS,2S)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 62 and N-[(1RS,2S)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 62 and N-[(1RS,2S)1-(2,4-dichlorophenyl)-1-methoxypropan-2-yl]-3-difluoromethyl-1-methyl-1H-pyrazole-4-carboxamide at a ratio of 10:1;

a pest control composition comprising any one of the present compounds 1 to 62 and 3-difluoromethyl-N-methoxy-1-methyl-N-[1-methyl-2-(2,4,6-trichlorophenyl)ethyl]pyrazole-4-carboxamide at a ratio of 0.1:1; a pest control composition comprising any one of the present compounds 1 to 62 and 3-difluoromethyl-N-methoxy-1-methyl-N-[1-methyl-2-(2,4,6-trichlorophenyl)ethyl]pyrazole-4-carboxamide at a ratio of 1:1; a pest control composition comprising any one of the present compounds 1 to 62 and 3-difluoromethyl-N-methoxy-1-methyl-N-[1-methyl-2-(2,4,6-trichlorophenyl)ethyl]pyrazole-4-carboxamide at a ratio of 10:1; a pest control composition comprising any one of the present compounds 1 to 62 and 3-difluoromethyl-N-methoxy-1-methyl-N-[(1R)-1-methyl-2-(2,4,6-trichlorophenyl)ethyl]pyrazole-4-carboxamide at a ratio of 0.1:1; a pest control composition comprising any one of the present compounds 1 to 62 and 3-difluoromethyl-N-methoxy-1-methyl-N-[(1R)-1-methyl-2-(2,4,6-trichlorophenyl)ethyl]pyrazole-4-carboxamide at a ratio of 1:1; a pest control composition comprising any one of the present compounds 1 to 62 and 3-difluoromethyl-N-methoxy-1-methyl-N-[(1R)-1-methyl-2-(2,4,6-trichlorophenyl)ethyl]pyrazole-4-carboxamide at a ratio of 10:1; a pest control composition comprising any one of the present compounds 1 to 62 and 3-difluoromethyl-N-methoxy-1-methyl-N-[(1S)-1-methyl-2-(2,4,6-trichlorophenyl)ethyl]pyrazole-4-carboxamide at a ratio of 0.1:1; a pest control composition comprising any one of the present compounds 1 to 62 and 3-difluoromethyl-N-methoxy-1-methyl-N-[(1S)-1-methyl-2-(2,4,6-trichlorophenyl)ethyl]pyrazole-4-carboxamide at a ratio of 1:1; a pest control composition comprising any one of the present compounds 1 to 62 and 3-difluoromethyl-N-methoxy-1-methyl-N-[(1S)-1-methyl-2-(2,4,6-trichlorophenyl)ethyl]pyrazole-4-carboxamide at a ratio of 10:1;

a pest control composition comprising any one of the present compounds 1 to 62 and 3-butyn-1-yl N-{6-[({(Z)-[(1-methyl-1H-tetrazol-5-yl)phenylmethylene]amino}oxy)methyl]-2-pyridinyl}carbamate at a ratio of 0.1:1; a pest control composition comprising any one of the present compounds 1 to 62 and 3-butyn-1-yl N-{6-[({(Z)-[(1-methyl-1H-tetrazol-5-yl)phenylmethylene]amino}oxy)methyl]-2-pyridinyl}carbamate at a ratio of 1:1; a pest control composition comprising any one of the present compounds 1 to 62 and 3-butyn-1-yl N-{6-[({(Z)-[(1-methyl-1H-tetrazol-5-yl)phenylmethylene]amino}oxy)methyl]-2-pyridinyl}carbamate at a ratio of 10:1; a pest control composition comprising any one of the present compounds 1 to 62 and 5-fluoro-2-[(4-methylphenyl)methoxy]-4-pyrimidineamine at a ratio of 0.1:1; a pest control composition comprising any one of the present compounds 1 to 62 and 5-fluoro-2-[(4-methylphenyl)methoxy]-4-pyrimidineamine at a ratio of 1:1; a pest control composition comprising any one of the present compounds 1 to 62 and 5-fluoro-2-[(4-methylphenyl)methoxy]-4-pyrimidineamine at a ratio of 10:1; a pest control composition comprising any one of the present compounds 1 to 62 and 2-[6-(3-fluoro-4-methoxyphenyl)-5-methylpyridin-2-yl]quinazoline at a ratio of 0.1:1; a pest control composition comprising any one of the present compounds 1 to 62 and 2-[6-(3-fluoro-4-methoxyphenyl)-5-methylpyridin-2-yl]quinazoline at a ratio of 1:1; a pest control composition comprising any one of the present compounds 1 to 62 and 2-[6-(3-fluoro-4-methoxyphenyl)-5-methylpyridin-2-yl]quinazoline at a ratio of 10:1; a pest control composition comprising any one of the present compounds 1 to 62 and azaconazole; a pest control composition comprising any one of the present compounds 1 to 62 and diniconazole-M; a pest control composition comprising any one of the present compounds 1 to 62 and etaconazole; a pest control composition comprising any one of the present compounds 1 to 62 and uniconazole; a pest control composition comprising any one of the present compounds 1 to 62 and (S)-(+)-N-(1,1,3-trimethylindan-4-yl)-1-methyl-3-difluoromethylpyrazole-4-carboxylic acid amide; a pest control composition comprising any one of the present compounds 1 to 62 and benodanil; a pest control composition comprising any one of the present compounds 1 to 62 and fenfuram; a pest control composition comprising any one of the present compounds 1 to 62 and oxycarboxin;

a pest control composition comprising any one of the present compounds 1 to 62 and dodemorph; a pest control composition comprising any one of the present compounds 1 to 62 and piperalin; a pest control composition comprising any one of the present compounds 1 to 62 and thiabendazole; a pest control composition comprising any one of the present compounds 1 to 62 and fuberidazole; a pest control composition comprising any one of the present compounds 1 to 62 and thiophanate; a pest control composition comprising any one of the present compounds 1 to 62 and furalaxyl; a pest control composition comprising any one of the present compounds 1 to 62 and ofurace; a pest control composition comprising any one of the present compounds 1 to 62 and oxadixyl; a pest control composition comprising any one of the present compounds 1 to 62 and flumorph; a pest control composition comprising any one of the present compounds 1 to 62 and dichlofluanid; a pest control composition comprising any one of the present compounds 1 to 62 and fenoxanil; a pest control composition comprising any one of the present compounds 1 to 62 and acibenzolar-S-methyl; a pest control composition comprising any one of the present compounds 1 to 62 and anilazine; a pest control composition comprising any one of the present compounds 1 to 62 and bethoxazine; a pest control composition comprising any one of the present compounds 1 to 62 and binapacryl; a pest control composition comprising any one of the present compounds 1 to 62 and biphenyl; a pest control composition comprising any one of the present compounds 1 to 62 and blastcidin S; a pest control composition comprising any one of the present compounds 1 to 62 and bupirimate; a pest control composition comprising any one of the present compounds 1 to 62 and captafol; a pest control composition comprising any one of the present compounds 1 to 62 and chloroneb; a pest control composition comprising any one of the present compounds 1 to 62 and dichloran; a pest control composition comprising any one of the present compounds 1 to 62 and diflumetorim; a pest control composition comprising any one of the present compounds 1 to 62 and dimethirimol; a pest control composition comprising any one of the present compounds 1 to 62 and dinocap; a pest control composition comprising any one of the present compounds 1 to 62 and dithianon;

a pest control composition comprising any one of the present compounds 1 to 62 and dodine; a pest control composition comprising any one of the present compounds 1 to 62 and edifenphos; a pest control composition comprising any one of the present compounds 1 to 62 and ethirimol; a pest control composition comprising any one of the present compounds 1 to 62 and etridiazol; a pest control composition comprising any one of the present compounds 1 to 62 and fenarimol; a pest control composition comprising any one of the present compounds 1 to 62 and fentin-acetate; a pest control composition comprising any one of the present compounds 1 to 62 and fentin-hydroxide; a pest control composition comprising any one of the present compounds 1 to 62 and ferbam; a pest control composition comprising any one of the present compounds 1 to 62 and fluoroimide; a pest control composition comprising any one of the present compounds 1 to 62 and flutianil; a pest control composition comprising any one of the present compounds 1 to 62 and furmecyclox; a pest control composition comprising any one of the present compounds 1 to 62 and iodocarb; a pest control composition comprising any one of the present compounds 1 to 62 and iprobenfos; a pest control composition comprising any one of the present compounds 1 to 62 and meptyldinocap; a pest control composition comprising any one of the present compounds 1 to 62 and methasulfocarb; a pest control composition comprising any one of the present compounds 1 to 62 and metiram; a pest control composition comprising any one of the present compounds 1 to 62 and naftifine; a pest control composition comprising any one of the present compounds 1 to 62 and nuarimol; a pest control composition comprising any one of the present compounds 1 to 62 and octhilinone; a pest control composition comprising any one of the present compounds 1 to 62 and pefurazoate; a pest control composition comprising any one of the present compounds 1 to 62 and phosphorous acid; a pest control composition comprising any one of the present compounds 1 to 62 and a sodium salt of phosphorous acid; a pest control composition comprising any one of the present compounds 1 to 62 and an ammonium salt of phosphorous acid; a pest control composition comprising any one of the present compounds 1 to 62 and polyoxin;

a pest control composition comprising any one of the present compounds 1 to 62 and propineb; a pest control composition comprising any one of the present compounds 1 to 62 and prothiocarb; a pest control composition comprising any one of the present compounds 1 to 62 and pyrazophos; a pest control composition comprising any one of the present compounds 1 to 62 and pyributicarb; a pest control composition comprising any one of the present compounds 1 to 62 and pyrifenox; a pest control composition comprising any one of the present compounds 1 to 62 and pyrrolnitrin; a pest control composition comprising any one of the present compounds 1 to 62 and PCNB; a pest control composition comprising any one of the present compounds 1 to 62 and TCNB; a pest control composition comprising any one of the present compounds 1 to 62 and tecloftalam; a pest control composition comprising any one of the present compounds 1 to 62 and terbinafine; a pest control composition comprising any one of the present compounds 1 to 62 and tolylfluanid; a pest control composition comprising any one of the present compounds 1 to 62 and triarimol; a pest control composition comprising any one of the present compounds 1 to 62 and triazoxide; a pest control composition comprising any one of the present compounds 1 to 62 and triforine; a pest control composition comprising any one of the present compounds 1 to 62 and trimorphamide; a pest control composition comprising any one of the present compounds 1 to 62 and zineb; a pest control composition comprising any one of the present compounds 1 to 62 and ziram; a pest control composition comprising any one of the present compounds 1 to 62 and acephate at a ratio of 1:1; a pest control composition comprising any one of the present compounds 1 to 62 and acephate at a ratio of 1:10; a pest control composition comprising any one of the present compounds 1 to 62 and acephate at a ratio of 1:50; a pest control composition comprising any one of the present compounds 1 to 62 and azamethiphos at a ratio of 1:1; a pest control composition comprising any one of the present compounds 1 to 62 and azamethiphos at a ratio of 1:10;

a pest control composition comprising any one of the present compounds 1 to 62 and azamethiphos at a ratio of 1:50; a pest control composition comprising any one of the present compounds 1 to 62 and azinphos-ethyl at a ratio of 1:1; a pest control composition comprising any one of the present compounds 1 to 62 and azinphos-ethyl at a ratio of 1:10; a pest control composition comprising any one of the present compounds 1 to 62 and azinphos-ethyl at a ratio of 1:50; a pest control composition comprising any one of the present compounds 1 to 62 and azinphos-methyl at a ratio of 1:1; a pest control composition comprising any one of the present compounds 1 to 62 and azinphos-methyl at a ratio of 1:10; a pest control composition comprising any one of the present compounds 1 to 62 and azinphos-methyl at a ratio of 1:50; a pest control composition comprising any one of the present compounds 1 to 62 and cadusafos at a ratio of 1:1; a pest control composition comprising any one of the present compounds 1 to 62 and cadusafos at a ratio of 1:10; a pest control composition comprising any one of the present compounds 1 to 62 and cadusafos at a ratio of 1:50; a pest control composition comprising any one of the present compounds 1 to 62 and chlorethoxyfos at a ratio of 1:1; a pest control composition comprising any one of the present compounds 1 to 62 and chlorethoxyfos at a ratio of 1:10; a pest control composition comprising any one of the present compounds 1 to 62 and chlorethoxyfos at a ratio of 1:50; a pest control composition comprising any one of the present compounds 1 to 62 and chlorfenvinphos at a ratio of 1:1; a pest control composition comprising any one of the present compounds 1 to 62 and chlorfenvinphos at a ratio of 1:10; a pest control composition comprising any one of the present compounds 1 to 62 and chlorfenvinphos at a ratio of 1:50; a pest control composition comprising any one of the present compounds 1 to 62 and chlormephos at a ratio of 1:1; a pest control composition comprising any one of the present compounds 1 to 62 and chlormephos at a ratio of 1:10; a pest control composition comprising any one of the present compounds 1 to 62 and chlormephos at a ratio of 1:50; a pest control composition comprising any one of the present compounds 1 to 62 and chlorpyrifos at a ratio of 1:1; a pest control composition comprising any one of the present compounds 1 to 62 and chlorpyrifos at a ratio of 1:10; a pest control composition comprising any one of the present compounds 1 to 62 and chlorpyrifos at a ratio of 1:50; a pest control composition comprising any one of the present compounds 1 to 62 and chlorpyrifos-methyl at a ratio of 1:1; a pest control composition comprising any one of the present compounds 1 to 62 and chlorpyrifos-methyl at a ratio of 1:10; a pest control composition comprising any one of the present compounds 1 to 62 and chlorpyrifos-methyl at a ratio of 1:50; a pest control composition comprising any one of the present compounds 1 to 62 and coumaphos at a ratio of 1:1; a pest control composition comprising any one of the present compounds 1 to 62 and coumaphos at a ratio of 1:10; a pest control composition comprising any one of the present compounds 1 to 62 and coumaphos at a ratio of 1:50; a pest control composition comprising any one of the present compounds 1 to 62 and cyanophos at a ratio of 1:1; a pest control composition comprising any one of the present compounds 1 to 62 and cyanophos at a ratio of 1:10; a pest control composition comprising any one of the present compounds 1 to 62 and cyanophos at a ratio of 1:50; a pest control composition comprising any one of the present compounds 1 to 62 and demeton-S-methyl at a ratio of 1:1; a pest control composition comprising any one of the present compounds 1 to 62 and demeton-S-methyl at a ratio of 1:10; a pest control composition comprising any one of the present compounds 1 to 62 and demeton-S-methyl at a ratio of 1:50; a pest control composition comprising any one of the present compounds 1 to 62 and diazinon at a ratio of 1:1; a pest control composition comprising any one of the present compounds 1 to 62 and diazinon at a ratio of 1:10; a pest control composition comprising any one of the present compounds 1 to 62 and diazinon at a ratio of 1:50; a pest control composition comprising any one of the present compounds 1 to 62 and dichlorvos at a ratio of 1:1; a pest control composition comprising any one of the present compounds 1 to 62 and dichlorvos at a ratio of 1:10; a pest control composition comprising any one of the present compounds 1 to 62 and dichlorvos at a ratio of 1:50; a pest control composition comprising any one of the present compounds 1 to 62 and dicrotophos at a ratio of 1:1; a pest control composition comprising any one of the present compounds 1 to 62 and dicrotophos at a ratio of 1:10; a pest control composition comprising any one of the present compounds 1 to 62 and dicrotophos at a ratio of 1:50; a pest control composition comprising any one of the present compounds 1 to 62 and dimethoate at a ratio of 1:1; a pest control composition comprising any one of the present compounds 1 to 62 and dimethoate at a ratio of 1:10; a pest control composition comprising any one of the present compounds 1 to 62 and dimethoate at a ratio of 1:50; a pest control composition comprising any one of the present compounds 1 to 62 and dimethylvinphos at a ratio of 1:1; a pest control composition comprising any one of the present compounds 1 to 62 and dimethylvinphos at a ratio of 1:10; a pest control composition comprising any one of the present compounds 1 to 62 and dimethylvinphos at a ratio of 1:50; a pest control composition comprising any one of the present compounds 1 to 62 and disulfoton at a ratio of 1:1; a pest control composition comprising any one of the present compounds 1 to 62 and disulfoton at a ratio of 1:10; a pest control composition comprising any one of the present compounds 1 to 62 and disulfoton at a ratio of 1:50; a pest control composition comprising any one of the present compounds 1 to 62 and EPN at a ratio of 1:1; a pest control composition comprising any one of the present compounds 1 to 62 and EPN at a ratio of 1:10; a pest control composition comprising any one of the present compounds 1 to 62 and EPN at a ratio of 1:50; a pest control composition comprising any one of the present compounds 1 to 62 and ethion at a ratio of 1:1; a pest control composition comprising any one of the present compounds 1 to 62 and ethion at a ratio of 1:10; a pest control composition comprising any one of the present compounds 1 to 62 and ethion at a ratio of 1:50; a pest control composition comprising any one of the present compounds 1 to 62 and ethoprophos at a ratio of 1:1; a pest control composition comprising any one of the present compounds 1 to 62 and ethoprophos at a ratio of 1:10; a pest control composition comprising any one of the present compounds 1 to 62 and ethoprophos at a ratio of 1:50; a pest control composition comprising any one of the present compounds 1 to 62 and famphur at a ratio of 1:1; a pest control composition comprising any one of the present compounds 1 to 62 and famphur at a ratio of 1:10; a pest control composition comprising any one of the present compounds 1 to 62 and famphur at a ratio of 1:50; a pest control composition comprising any one of the present compounds 1 to 62 and fenamiphos at a ratio of 1:1; a pest control composition comprising any one of the present compounds 1 to 62 and fenamiphos at a ratio of 1:10; a pest control composition comprising any one of the present compounds 1 to 62 and fenamiphos at a ratio of 1:50; a pest control composition comprising any one of the present compounds 1 to 62 and fenitrothion at a ratio of 1:1; a pest control composition comprising any one of the present compounds 1 to 62 and fenitrothion at a ratio of 1:10; a pest control composition comprising any one of the present compounds 1 to 62 and fenitrothion at a ratio of 1:50; a pest control composition comprising any one of the present compounds 1 to 62 and fenthion at a ratio of 1:1; a pest control composition comprising any one of the present compounds 1 to 62 and fenthion at a ratio of 1:10; a pest control composition comprising any one of the present compounds 1 to 62 and fenthion at a ratio of 1:50; a pest control composition comprising any one of the present compounds 1 to 62 and heptenophos at a ratio of 1:1; a pest control composition comprising any one of the present compounds 1 to 62 and heptenophos at a ratio of 1:10; a pest control composition comprising any one of the present compounds 1 to 62 and heptenophos at a ratio of 1:50; a pest control composition comprising any one of the present compounds 1 to 62 and Isofenphos at a ratio of 1:1; a pest control composition comprising any one of the present compounds 1 to 62 and isofenphos at a ratio of 1:10; a pest control composition comprising any one of the present compounds 1 to 62 and Isofenphos at a ratio of 1:50; a pest control composition comprising any one of the present compounds 1 to 62 and isocarbophos at a ratio of 1:1; a pest control composition comprising any one of the present compounds 1 to 62 and isocarbophos at a ratio of 1:10; a pest control composition comprising any one of the present compounds 1 to 62 and isocarbophos at a ratio of 1:50; a pest control composition comprising any one of the present compounds 1 to 62 and isoxathion at a ratio of 1:1; a pest control composition comprising any one of the present compounds 1 to 62 and isoxathion at a ratio of 1:10; a pest control composition comprising any one of the present compounds 1 to 62 and isoxathion at a ratio of 1:50; a pest control composition comprising any one of the present compounds 1 to 62 and malathion at a ratio of 1:1; a pest control composition comprising any one of the present compounds 1 to 62 and malathion at a ratio of 1:10; a pest control composition comprising any one of the present compounds 1 to 62 and malathion at a ratio of 1:50; a pest control composition comprising any one of the present compounds 1 to 62 and mecarbam at a ratio of 1:1; a pest control composition comprising any one of the present compounds 1 to 62 and mecarbam at a ratio of 1:10; a pest control composition comprising any one of the present compounds 1 to 62 and mecarbam at a ratio of 1:50; a pest control composition comprising any one of the present compounds 1 to 62 and methamidophos at a ratio of 1:1; a pest control composition comprising any one of the present compounds 1 to 62 and methamidophos at a ratio of 1:10; a pest control composition comprising any one of the present compounds 1 to 62 and methamidophos at a ratio of 1:50; a pest control composition comprising any one of the present compounds 1 to 62 and methidathion at a ratio of 1:1; a pest control composition comprising any one of the present compounds 1 to 62 and methidathion at a ratio of 1:10; a pest control composition comprising any one of the present compounds 1 to 62 and methidathion at a ratio of 1:50; a pest control composition comprising any one of the present compounds 1 to 62 and mevinphos at a ratio of 1:1; a pest control composition comprising any one of the present compounds 1 to 62 and mevinphos at a ratio of 1:10; a pest control composition comprising any one of the present compounds 1 to 62 and mevinphos at a ratio of 1:50; a pest control composition comprising any one of the present compounds 1 to 62 and monocrotophos at a ratio of 1:1;

a pest control composition comprising any one of the present compounds 1 to 62 and monocrotophos at a ratio of 1:10; a pest control composition comprising any one of the present compounds 1 to 62 and monocrotophos at a ratio of 1:50; a pest control composition comprising any one of the present compounds 1 to 62 and naled at a ratio of 1:1; a pest control composition comprising any one of the present compounds 1 to 62 and naled at a ratio of 1:10; a pest control composition comprising any one of the present compounds 1 to 62 and naled at a ratio of 1:50; a pest control composition comprising any one of the present compounds 1 to 62 and omethoate at a ratio of 1:1; a pest control composition comprising any one of the present compounds 1 to 62 and omethoate at a ratio of 1:10; a pest control composition comprising any one of the present compounds 1 to 62 and omethoate at a ratio of 1:50; a pest control composition comprising any one of the present compounds 1 to 62 and oxydemeton-methyl at a ratio of 1:1; a pest control composition comprising any one of the present compounds 1 to 62 and oxydemeton-methyl at a ratio of 1:10; a pest control composition comprising any one of the present compounds 1 to 62 and oxydemeton-methyl at a ratio of 1:50; a pest control composition comprising any one of the present compounds 1 to 62 and parathion at a ratio of 1:1; a pest control composition comprising any one of the present compounds 1 to 62 and parathion at a ratio of 1:10; a pest control composition comprising any one of the present compounds 1 to 62 and parathion at a ratio of 1:50; a pest control composition comprising any one of the present compounds 1 to 62 and methylparathion at a ratio of 1:1; a pest control composition comprising any one of the present compounds 1 to 62 and methylparathion at a ratio of 1:10; a pest control composition comprising any one of the present compounds 1 to 62 and methylparathion at a ratio of 1:50; a pest control composition comprising any one of the present compounds 1 to 62 and phenthoate at a ratio of 1:1; a pest control composition comprising any one of the present compounds 1 to 62 and phenthoate at a ratio of 1:10; a pest control composition comprising any one of the present compounds 1 to 62 and phenthoate at a ratio of 1:50; a pest control composition comprising any one of the present compounds 1 to 62 and phorate at a ratio of 1:1; a pest control composition comprising any one of the present compounds 1 to 62 and phorate at a ratio of 1:10; a pest control composition comprising any one of the present compounds 1 to 62 and phorate at a ratio of 1:50; a pest control composition comprising any one of the present compounds 1 to 62 and phosalone at a ratio of 1:1; a pest control composition comprising any one of the present compounds 1 to 62 and phosalone at a ratio of 1:10; a pest control composition comprising any one of the present compounds 1 to 62 and phosalone at a ratio of 1:50; a pest control composition comprising any one of the present compounds 1 to 62 and phosmet at a ratio of 1:1; a pest control composition comprising any one of the present compounds 1 to 62 and phosmet at a ratio of 1:10; a pest control composition comprising any one of the present compounds 1 to 62 and phosmet at a ratio of 1:50; a pest control composition comprising any one of the present compounds 1 to 62 and phosphamidon at a ratio of 1:1; a pest control composition comprising any one of the present compounds 1 to 62 and phosphamidon at a ratio of 1:10; a pest control composition comprising any one of the present compounds 1 to 62 and phosphamidon at a ratio of 1:50; a pest control composition comprising any one of the present compounds 1 to 62 and phoxim at a ratio of 1:1; a pest control composition comprising any one of the present compounds 1 to 62 and phoxim at a ratio of 1:10; a pest control composition comprising any one of the present compounds 1 to 62 and phoxim at a ratio of 1:50; a pest control composition comprising any one of the present compounds 1 to 62 and pirimiphos-methyl at a ratio of 1:1; a pest control composition comprising any one of the present compounds 1 to 62 and pirimiphos-methyl at a ratio of 1:10; a pest control composition comprising any one of the present compounds 1 to 62 and pirimiphos-methyl at a ratio of 1:50; a pest control composition comprising any one of the present compounds 1 to 62 and profenofos at a ratio of 1:1; a pest control composition comprising any one of the present compounds 1 to 62 and profenofos at a ratio of 1:10; a pest control composition comprising any one of the present compounds 1 to 62 and profenofos at a ratio of 1:50; a pest control composition comprising any one of the present compounds 1 to 62 and propetamphos at a ratio of 1:1; a pest control composition comprising any one of the present compounds 1 to 62 and propetamphos at a ratio of 1:10; a pest control composition comprising any one of the present compounds 1 to 62 and propetamphos at a ratio of 1:50; a pest control composition comprising any one of the present compounds 1 to 62 and prothiofos at a ratio of 1:1; a pest control composition comprising any one of the present compounds 1 to 62 and prothiofos at a ratio of 1:10; a pest control composition comprising any one of the present compounds 1 to 62 and prothiofos at a ratio of 1:50; a pest control composition comprising any one of the present compounds 1 to 62 and pyraclofos at a ratio of 1:1; a pest control composition comprising any one of the present compounds 1 to 62 and pyraclofos at a ratio of 1:10; a pest control composition comprising any one of the present compounds 1 to 62 and pyraclofos at a ratio of 1:50; a pest control composition comprising any one of the present compounds 1 to 62 and pyridaphenthion at a ratio of 1:1; a pest control composition comprising any one of the present compounds 1 to 62 and pyridaphenthion at a ratio of 1:10; a pest control composition comprising any one of the present compounds 1 to 62 and pyridaphenthion at a ratio of 1:50; a pest control composition comprising any one of the present compounds 1 to 62 and quinalphos at a ratio of 1:1; a pest control composition comprising any one of the present compounds 1 to 62 and quinalphos at a ratio of 1:10; a pest control composition comprising any one of the present compounds 1 to 62 and quinalphos at a ratio of 1:50; a pest control composition comprising any one of the present compounds 1 to 62 and sulfotep at a ratio of 1:1; a pest control composition comprising any one of the present compounds 1 to 62 and sulfotep at a ratio of 1:10; a pest control composition comprising any one of the present compounds 1 to 62 and sulfotep at a ratio of 1:50; a pest control composition comprising any one of the present compounds 1 to 62 and tebupirimfos at a ratio of 1:1; a pest control composition comprising any one of the present compounds 1 to 62 and tebupirimfos at a ratio of 1:10; a pest control composition comprising any one of the present compounds 1 to 62 and tebupirimfos at a ratio of 1:50; a pest control composition comprising any one of the present compounds 1 to 62 and temephos at a ratio of 1:1; a pest control composition comprising any one of the present compounds 1 to 62 and temephos at a ratio of 1:10; a pest control composition comprising any one of the present compounds 1 to 62 and temephos at a ratio of 1:50; a pest control composition comprising any one of the present compounds 1 to 62 and terbufos at a ratio of 1:1; a pest control composition comprising any one of the present compounds 1 to 62 and terbufos at a ratio of 1:10; a pest control composition comprising any one of the present compounds 1 to 62 and terbufos at a ratio of 1:50; a pest control composition comprising any one of the present compounds 1 to 62 and tetrachlorvinphos at a ratio of 1:1; a pest control composition comprising any one of the present compounds 1 to 62 and tetrachlorvinphos at a ratio of 1:10; a pest control composition comprising any one of the present compounds 1 to 62 and tetrachlorvinphos at a ratio of 1:50; a pest control composition comprising any one of the present compounds 1 to 62 and thiometon at a ratio of 1:1; a pest control composition comprising any one of the present compounds 1 to 62 and thiometon at a ratio of 1:10; a pest control composition comprising any one of the present compounds 1 to 62 and thiometon at a ratio of 1:50; a pest control composition comprising any one of the present compounds 1 to 62 and triazophos at a ratio of 1:1; a pest control composition comprising any one of the present compounds 1 to 62 and triazophos at a ratio of 1:10; a pest control composition comprising any one of the present compounds 1 to 62 and triazophos at a ratio of 1:50; a pest control composition comprising any one of the present compounds 1 to 62 and trichlorfon at a ratio of 1:1; a pest control composition comprising any one of the present compounds 1 to 62 and trichlorfon at a ratio of 1:10; a pest control composition comprising any one of the present compounds 1 to 62 and trichlorfon at a ratio of 1:50;
a pest control composition comprising any one of the present compounds 1 to 62 and vamidothion at a ratio of 1:1; a pest control composition comprising any one of the present compounds 1 to 62 and vamidothion at a ratio of 1:10; a pest control composition comprising any one of the present compounds 1 to 62 and vamidothion at a ratio of 1:50; a pest control composition comprising any one of the present compounds 1 to 62 and alanycarb at a ratio of 1:1; a pest control composition comprising any one of the present compounds 1 to 62 and alanycarb at a ratio of 1:10; a pest control composition comprising any one of the present compounds 1 to 62 and alanycarb at a ratio of 1:50; a pest control composition comprising any one of the present compounds 1 to 62 and aldicarb at a ratio of 1:1; a pest control composition comprising any one of the present compounds 1 to 62 and aldicarb at a ratio of 1:10; a pest control composition comprising any one of the present compounds 1 to 62 and aldicarb at a ratio of 1:50; a pest control composition comprising any one of the present compounds 1 to 62 and bendiocarb at a ratio of 1:1; a pest control composition comprising any one of the present compounds 1 to 62 and bendiocarb at a ratio of 1:10; a pest control composition comprising any one of the present compounds 1 to 62 and bendiocarb at a ratio of 1:50; a pest control composition comprising any one of the present compounds 1 to 62 and benfuracarb at a ratio of 1:1; a pest control composition comprising any one of the present compounds 1 to 62 and benfuracarb at a ratio of 1:10; a pest control composition comprising any one of the present compounds 1 to 62 and benfuracarb at a ratio of 1:50; a pest control composition comprising any one of the present compounds 1 to 62 and butocarboxim at a ratio of 1:1; a pest control composition comprising any one of the present compounds 1 to 62 and butocarboxim at a ratio of 1:10; a pest control composition comprising any one of the present compounds 1 to 62 and butocarboxim at a ratio of 1:50; a pest control composition comprising any one of the present compounds 1 to 62 and butoxycarboxim at a ratio of 1:1; a pest control composition comprising any one of the present compounds 1 to 62 and butoxycarboxim at a ratio of 1:10; a pest control composition comprising any one of the present compounds 1 to 62 and butoxycarboxim at a ratio of 1:50; a pest control composition comprising any one of the present compounds 1 to 62 and carbaryl at a ratio of 1:1; a pest control composition comprising any one of the present compounds 1 to 62 and carbaryl at a ratio of 1:10; a pest control composition comprising any one of the present compounds 1 to 62 and carbaryl at a ratio of 1:50; a pest control composition comprising any one of the present compounds 1 to 62 and carbofuran at a ratio of 1:1; a pest control composition comprising any one of the present compounds 1 to 62 and carbofuran at a ratio of 1:10; a pest control composition comprising any one of the present compounds 1 to 62 and carbofuran at a ratio of 1:50; a pest control composition comprising any one of the present compounds 1 to 62 and carbosolfan at a ratio of 1:1; a pest control composition comprising any one of the present compounds 1 to 62 and carbosulfan at a ratio of 1:10; a pest control composition comprising any one of the present compounds 1 to 62 and carbosolfan at a ratio of 1:50; a pest control composition comprising any one of the present compounds 1 to 62 and ethiofencarb at a ratio of 1:1; a pest control composition comprising any one of the present compounds 1 to 62 and ethiofencarb at a ratio of 1:10; a pest control composition comprising any one of the present compounds 1 to 62 and ethiofencarb at a ratio of 1:50; a pest control composition comprising any one of the present compounds 1 to 62 and fenobucarb at a ratio of 1:1; a pest control composition comprising any one of the present compounds 1 to 62 and fenobucarb at a ratio of 1:10; a pest control composition comprising any one of the present compounds 1 to 62 and fenobucarb at a ratio of 1:50; a pest control composition comprising any one of the present compounds 1 to 62 and formetanate at a ratio of 1:1; a pest control composition comprising any one of the present compounds 1 to 62 and formetanate at a ratio of 1:10; a pest control composition comprising any one of the present compounds 1 to 62 and formetanate at a ratio of 1:50; a pest control composition comprising any one of the present compounds 1 to 62 and furathiocarb at a ratio of 1:1;
a pest control composition comprising any one of the present compounds 1 to 62 and furathiocarb at a ratio of 1:10; a pest control composition comprising any one of the present compounds 1 to 62 and furathiocarb at a ratio of 1:50; a pest control composition comprising any one of the present compounds 1 to 62 and isoprocarb at a ratio of 1:1; a pest control composition comprising any one of the present compounds 1 to 62 and isoprocarb at a ratio of 1:10; a pest control composition comprising any one of the present compounds 1 to 62 and isoprocarb at a ratio of 1:50; a pest control composition comprising any one of the present compounds 1 to 62 and methiocarb at a ratio of 1:1; a pest control composition comprising any one of the present compounds 1 to 62 and methiocarb at a ratio of 1:10; a pest control composition comprising any one of the present compounds 1 to 62 and methiocarb at a ratio of 1:50; a pest control composition comprising any one of the present compounds 1 to 62 and methomyl at a ratio of 1:1; a pest control composition comprising any one of the present compounds 1 to 62 and methomyl at a ratio of 1:10; a pest control composition comprising any one of the present compounds 1 to 62 and methomyl at a ratio of 1:50; a pest control composition comprising any one of the present compounds 1 to 62 and metolcarb at a ratio of 1:1; a pest control composition comprising any one of the present compounds 1 to 62 and metolcarb at a ratio of 1:10; a pest control composition comprising any one of the present compounds 1 to 62 and metolcarb at a ratio of 1:50; a pest control composition comprising any one of the present compounds 1 to 62 and oxamyl at a ratio of 1:1; a pest control composition comprising any one of the present compounds 1 to 62 and oxamyl at a ratio of 1:10; a pest control composition comprising any one of the present compounds 1 to 62 and oxamyl at a ratio of 1:50; a pest control composition comprising any one of the present compounds 1 to 62 and pirimicarb at a ratio of 1:1;

a pest control composition comprising any one of the present compounds 1 to 62 and pirimicarb at a ratio of 1:10; a pest control composition comprising any one of the present compounds 1 to 62 and pirimicarb at a ratio of 1:50; a pest control composition comprising any one of the present compounds 1 to 62 and propoxur at a ratio of 1:1; a pest control composition comprising any one of the present compounds 1 to 62 and propoxur at a ratio of 1:10; a pest control composition comprising any one of the present compounds 1 to 62 and propoxur at a ratio of 1:50; a pest control composition comprising any one of the present compounds 1 to 62 and thiodicarb at a ratio of 1:1; a pest control composition comprising any one of the present compounds 1 to 62 and thiodicarb at a ratio of 1:10; a pest control composition comprising any one of the present compounds 1 to 62 and thiodicarb at a ratio of 1:50; a pest control composition comprising any one of the present compounds 1 to 62 and thiofanox at a ratio of 1:1; a pest control composition comprising any one of the present compounds 1 to 62 and thiofanox at a ratio of 1:10; a pest control composition comprising any one of the present compounds 1 to 62 and thiofanox at a ratio of 1:50; a pest control composition comprising any one of the present compounds 1 to 62 and triazamate at a ratio of 1:1; a pest control composition comprising any one of the present compounds 1 to 62 and triazamate at a ratio of 1:10; a pest control composition comprising any one of the present compounds 1 to 62 and triazamate at a ratio of 1:50; a pest control composition comprising any one of the present compounds 1 to 62 and trimethacarb at a ratio of 1:1; a pest control composition comprising any one of the present compounds 1 to 62 and trimethacarb at a ratio of 1:10; a pest control composition comprising any one of the present compounds 1 to 62 and trimethacarb at a ratio of 1:50; a pest control composition comprising any one of the present compounds 1 to 62 and XMC at a ratio of 1:1; a pest control composition comprising any one of the present compounds 1 to 62 and XMC at a ratio of 1:10; a pest control composition comprising any one of the present compounds 1 to 62 and XMC at a ratio of 1:50;

a pest control composition comprising any one of the present compounds 1 to 62 and xylylcarb at a ratio of 1:1; a pest control composition comprising any one of the present compounds 1 to 62 and xylylcarb at a ratio of 1:10; a pest control composition comprising any one of the present compounds 1 to 62 and xylylcarb at a ratio of 1:50; a pest control composition comprising any one of the present compounds 1 to 62 and acrinathrin at a ratio of 0.1:1; a pest control composition comprising any one of the present compounds 1 to 62 and acrinathrin at a ratio of 1:1; a pest control composition comprising any one of the present compounds 1 to 62 and acrinathrin at a ratio of 1:10; a pest control composition comprising any one of the present compounds 1 to 62 and allethrin at a ratio of 0.1:1; a pest control composition comprising any one of the present compounds 1 to 62 and allethrin at a ratio of 1:1; a pest control composition comprising any one of the present compounds 1 to 62 and allethrin at a ratio of 1:10; a pest control composition comprising any one of the present compounds 1 to 62 and bifenthrin at a ratio of 0.1:1; a pest control composition comprising any one of the present compounds 1 to 62 and bifenthrin at a ratio of 1:1; a pest control composition comprising any one of the present compounds 1 to 62 and bifenthrin at a ratio of 1:10; a pest control composition comprising any one of the present compounds 1 to 62 and bioallethrin at a ratio of 0.1:1; a pest control composition comprising any one of the present compounds 1 to 62 and bioallethrin at a ratio of 1:1; a pest control composition comprising any one of the present compounds 1 to 62 and bioallethrin at a ratio of 1:10; a pest control composition comprising any one of the present compounds 1 to 62 and bioresmethrin at a ratio of 0.1:1; a pest control composition comprising any one of the present compounds 1 to 62 and bioresmethrin at a ratio of 1:1; a pest control composition comprising any one of the present compounds 1 to 62 and bioresmethrin at a ratio of 1:10; a pest control composition comprising any one of the present compounds 1 to 62 and cycloprothrin at a ratio of 0.1:1; a pest control composition comprising any one of the present compounds 1 to 62 and cycloprothrin at a ratio of 1:1; a pest control composition comprising any one of the present compounds 1 to 62 and cycloprothrin at a ratio of 1:10;

a pest control composition comprising any one of the present compounds 1 to 62 and cyfluthrin at a ratio of 0.1:1; a pest control composition comprising any one of the present compounds 1 to 62 and cyfluthrin at a ratio of 1:1; a pest control composition comprising any one of the present compounds 1 to 62 and cyfluthrin at a ratio of 1:10; a pest control composition comprising any one of the present compounds 1 to 62 and beta-cyfluthrin at a ratio of 0.1:1; a pest control composition comprising any one of the present compounds 1 to 62 and beta-cyfluthrin at a ratio of 1:1; a pest control composition comprising any one of the present compounds 1 to 62 and beta-cyfluthrin at a ratio of 1:10; a pest control composition comprising any one of the present compounds 1 to 62 and cyhalothrin at a ratio of 0.1:1; a pest control composition comprising any one of the present compounds 1 to 62 and cyhalothrin at a ratio of 1:1; a pest control composition comprising any one of the present compounds 1 to 62 and cyhalothrin at a ratio of 1:10; a pest control composition comprising any one of the present compounds 1 to 62 and gamma-cyhalothrin at a ratio of 0.1:1; a pest control composition comprising any one of the present compounds 1 to 62 and gamma-cyhalothrin at a ratio of 1:1; a pest control composition comprising any one of the present compounds 1 to 62 and gamma-cyhalothrin at a ratio of 1:10; a pest control composition comprising any one of the present compounds 1 to 62 and lambda-cyhalothrin at a ratio of 0.1:1; a pest control composition comprising any one of the present compounds 1 to 62 and lambda-cyhalothrin at a ratio of 1:1; a pest control composition comprising any one of the present compounds 1 to 62 and lambda-cyhalothrin at a ratio of 1:10; a pest control composition comprising any one of the present compounds 1 to 62 and cypermethrin at a ratio of 0.1:1; a pest control composition comprising any one of the present compounds 1 to 62 and cypermethrin at a ratio of 1:1; a pest control composition comprising any one of the present compounds 1 to 62 and cypermethrin at a ratio of 1:10; a pest control composition comprising any one of the present compounds 1 to 62 and alpha-cypermethrin at a ratio of 0.1:1;

a pest control composition comprising any one of the present compounds 1 to 62 and alpha-cypermethrin at a ratio of 1:1; a pest control composition comprising any one of the present compounds 1 to 62 and alpha-cypermethrin at a ratio of 1:10; a pest control composition comprising any one of the present compounds 1 to 62 and beta-cypermethrin at a ratio of 0.1:1; a pest control composition comprising any one of the present compounds 1 to 62 and beta-cypermethrin at a ratio of 1:1; a pest control composition comprising any one of the present compounds 1 to 62 and beta-cypermethrin at a ratio of 1:10; a pest control composition comprising any one of the present compounds 1 to 62 and theta-cypermethrin at a ratio of 0.1:1; a pest control composition comprising any one of the present compounds 1 to 62 and theta-cypermethrin at a ratio of 1:1; a pest control composition comprising any one of the present compounds 1 to 62 and theta-cypermethrin at a ratio of 1:10; a pest control composition comprising any one of the present compounds 1 to 62 and zeta-cypermethrin at a ratio of 0.1:1; a pest control composition comprising any one of the present compounds 1 to 62 and theta-cypermethrin at a ratio of 1:1; a pest control composition comprising any one of the present compounds 1 to 62 and zeta-cypermethrin at a ratio of 1:10; a pest control composition comprising any one of the present compounds 1 to 62 and cyphenothrin at a ratio of 0.1:1; a pest control composition comprising any one of the present compounds 1 to 62 and cyphenothrin at a ratio of 1:1; a pest control composition comprising any one of the present compounds 1 to 62 and cyphenothrin at a ratio of 1:10; a pest control composition comprising any one of the present compounds 1 to 62 and deltamethrin at a ratio of 0.1:1; a pest control composition comprising any one of the present compounds 1 to 62 and deltamethrin at a ratio of 1:1; a pest control composition comprising any one of the present compounds 1 to 62 and deltamethrin at a ratio of 1:10; a pest control composition comprising any one of the present compounds 1 to 62 and empenthrin at a ratio of 0.1:1; a pest control composition comprising any one of the present compounds 1 to 62 and empenthrin at a ratio of 1:1; a pest control composition comprising any one of the present compounds 1 to 62 and empenthrin at a ratio of 1:10;

a pest control composition comprising any one of the present compounds 1 to 62 and esfenvalerate at a ratio of 0.1:1; a pest control composition comprising any one of the present compounds 1 to 62 and esfenvalerate at a ratio of 1:1; a pest control composition comprising any one of the present compounds 1 to 62 and esfenvalerate at a ratio of 1:10; a pest control composition comprising any one of the present compounds 1 to 62 and etofenprox at a ratio of 0.1:1; a pest control composition comprising any one of the present compounds 1 to 62 and etofenprox at a ratio of 1:1; a pest control composition comprising any one of the present compounds 1 to 62 and etofenprox at a ratio of 1:10; a pest control composition comprising any one of the present compounds 1 to 62 and fenpropathrin at a ratio of 0.1:1; a pest control composition comprising any one of the present compounds 1 to 62 and fenpropathrin at a ratio of 1:1; a pest control composition comprising any one of the present compounds 1 to 62 and fenpropathrin at a ratio of 1:10; a pest control composition comprising any one of the present compounds 1 to 62 and fenvalerate at a ratio of 0.1:1; a pest control composition comprising any one of the present compounds 1 to 62 and fenvalerate at a ratio of 1:1; a pest control composition comprising any one of the present compounds 1 to 62 and fenvalerate at a ratio of 1:10; a pest control composition comprising any one of the present compounds 1 to 62 and flucythrinate at a ratio of 0.1:1; a pest control composition comprising any one of the present compounds 1 to 62 and flucythrinate at a ratio of 1:1; a pest control composition comprising any one of the present compounds 1 to 62 and flucythrinate at a ratio of 1:10; a pest control composition comprising any one of the present compounds 1 to 62 and flumethrin at a ratio of 0.1:1; a pest control composition comprising any one of the present compounds 1 to 62 and flumethrin at a ratio of 1:1; a pest control composition comprising any one of the present compounds 1 to 62 and flumethrin at a ratio of 1:10; a pest control composition comprising any one of the present compounds 1 to 62 and fluvaldnate at a ratio of 0.1:1; a pest control composition comprising any one of the present compounds 1 to 62 and fluvalinate at a ratio of 1:1; a pest control composition comprising any one of the present compounds 1 to 62 and fluvaldnate at a ratio of 1:10; a pest control composition comprising any one of the present compounds 1 to 62 and tau-fluvalinate at a ratio of 0.1:1; a pest control composition comprising any one of the present compounds 1 to 62 and tau-fluvalinate at a ratio of 1:1; a pest control composition comprising any one of the present compounds 1 to 62 and tau-fluvalinate at a ratio of 1:10; a pest control composition comprising any one of the present compounds 1 to 62 and halfenprox at a ratio of 0.1:1; a pest control composition comprising any one of the present compounds 1 to 62 and halfenprox at a ratio of 1:1; a pest control composition comprising any one of the present compounds 1 to 62 and halfenprox at a ratio of 1:10; a pest control composition comprising any one of the present compounds 1 to 62 and heptafluthrin at a ratio of 0.1:1; a pest control composition comprising any one of the present compounds 1 to 62 and heptafluthrin at a ratio of 1:1; a pest control composition comprising any one of the present compounds 1 to 62 and heptafluthrin at a ratio of 1:10; a pest control composition comprising any one of the present compounds 1 to 62 and imiprothrin at a ratio of 0.1:1; a pest control composition comprising any one of the present compounds 1 to 62 and imiprothrin at a ratio of 1:1; a pest control composition comprising any one of the present compounds 1 to 62 and imiprothrin at a ratio of 1:10; a pest control composition comprising any one of the present compounds 1 to 62 and kadethrin at a ratio of 0.1:1; a pest control composition comprising any one of the present compounds 1 to 62 and kadethrin at a ratio of 1:1; a pest control composition comprising any one of the present compounds 1 to 62 and kadethrin at a ratio of 1:10; a pest control composition comprising any one of the present compounds 1 to 62 and meperfluthrin at a ratio of 0.1:1; a pest control composition comprising any one of the present compounds 1 to 62 and meperfluthrin at a ratio of 1:1;

a pest control composition comprising any one of the present compounds 1 to 62 and meperfluthrin at a ratio of 1:10; a pest control composition comprising any one of the present compounds 1 to 62 and momfluorothrin at a ratio of 0.1:1; a pest control composition comprising any one of the present compounds 1 to 62 and momfluorothrin at a ratio of 1:1; a pest control composition comprising any one of the present compounds 1 to 62 and momfluorothrin at a ratio of 1:10; a pest control composition comprising any one of the present compounds 1 to 62 and permethrin at a ratio of 0.1:1; a pest control composition comprising any one of the present compounds 1 to 62 and permethrin at a ratio of 1:1; a pest control composition comprising any one of the present compounds 1 to 62 and permethrin at a ratio of 1:10; a pest control composition comprising any one of the present compounds 1 to 62 and phenothrin at a ratio of 0.1:1; a pest control composition comprising any one of the present compounds 1 to 62 and phenothrin at a ratio of 1:1; a pest control composition comprising any one of the present compounds 1 to 62 and phenothrin at a ratio of 1:10; a pest control composition comprising any one of the present compounds 1 to 62 and prallethrin at a ratio of 0.1:1; a pest control composition comprising any one of the present compounds 1 to 62 and prallethrin at a ratio of 1:1; a pest control composition comprising any one of the present compounds 1 to 62 and prallethrin at a ratio of 1:10; a pest control composition comprising any one of the present compounds 1 to 62 and pyrethrins at a ratio of 0.1:1; a pest control composition comprising any one of the present compounds 1 to 62 and pyrethrins at a ratio of 1:1; a pest control composition comprising any one of the present compounds 1 to 62 and pyrethrins at a ratio of 1:10; a pest control composition comprising any one of the present compounds 1 to 62 and resmethrin at a ratio of 0.1:1; a pest control composition comprising any one of the present compounds 1 to 62 and resmethrin at a ratio of 1:1; a pest control composition comprising any one of the present compounds 1 to 62 and resmethrin at a ratio of 1:10; a pest control composition comprising any one of the present compounds 1 to 62 and silafluofen at a ratio of 0.1:1;
a pest control composition comprising any one of the present compounds 1 to 62 and silafluofen at a ratio of 1:1; a pest control composition comprising any one of the present compounds 1 to 62 and silafluofen at a ratio of 1:10; a pest control composition comprising any one of the present compounds 1 to 62 and tefluthrin at a ratio of 0.1:1; a pest control composition comprising any one of the present compounds 1 to 62 and tefluthrin at a ratio of 1:1; a pest control composition comprising any one of the present compounds 1 to 62 and tefluthrin at a ratio of 1:10; a pest control composition comprising any one of the present compounds 1 to 62 and tetramethrin at a ratio of 0.1:1; a pest control composition comprising any one of the present compounds 1 to 62 and tetramethrin at a ratio of 1:1; a pest control composition comprising any one of the present compounds 1 to 62 and tetramethrin at a ratio of 1:10; a pest control composition comprising any one of the present compounds 1 to 62 and tetramethylfluthrin at a ratio of 0.1:1;
a pest control composition comprising any one of the present compounds 1 to 62 and tetramethylfluthrin at a ratio of 1:1;
a pest control composition comprising any one of the present compounds 1 to 62 and tetramethylfluthrin at a ratio of 1:10;
a pest control composition comprising any one of the present compounds 1 to 62 and tralomethrin at a ratio of 0.1:1; a pest control composition comprising any one of the present compounds 1 to 62 and tralomethrin at a ratio of 1:1; a pest control composition comprising any one of the present compounds 1 to 62 and tralomethrin at a ratio of 1:10; a pest control composition comprising any one of the present compounds 1 to 62 and transfluthrin at a ratio of 0.1:1; a pest control composition comprising any one of the present compounds 1 to 62 and transfluthrin at a ratio of 1:1; a pest control composition comprising any one of the present compounds 1 to 62 and transfluthrin at a ratio of 1:10; a pest control composition comprising any one of the present compounds 1 to 62 and bensultap at a ratio of 1:1; a pest control composition comprising any one of the present compounds 1 to 62 and bensultap at a ratio of 1:10; a pest control composition comprising any one of the present compounds 1 to 62 and bensultap at a ratio of 1:50; a pest control composition comprising any one of the present compounds 1 to 62 and cartap at a ratio of 1:1;
a pest control composition comprising any one of the present compounds 1 to 62 and cartap at a ratio of 1:10; a pest control composition comprising any one of the present compounds 1 to 62 and cartap at a ratio of 1:50; a pest control composition comprising any one of the present compounds 1 to 62 and cartap hydrochloride at a ratio of 1:1;

a pest control composition comprising any one of the present compounds 1 to 62 and cartap hydrochloride at a ratio of 1:10; a pest control composition comprising any one of the present compounds 1 to 62 and cartap hydrochloride at a ratio of 1:50; a pest control composition comprising any one of the present compounds 1 to 62 and thiocyclam at a ratio of 1:1; a pest control composition comprising any one of the present compounds 1 to 62 and thiocyclam at a ratio of 1:10; a pest control composition comprising any one of the present compounds 1 to 62 and thiocyclam at a ratio of 1:50; a pest control composition comprising any one of the present compounds 1 to 62 and bisultap at a ratio of 1:1; a pest control composition comprising any one of the present compounds 1 to 62 and bisultap at a ratio of 1:10; a pest control composition comprising any one of the present compounds 1 to 62 and bisultap at a ratio of 1:50; a pest control composition comprising any one of the present compounds 1 to 62 and monosultap at a ratio of 1:1; a pest control composition comprising any one of the present compounds 1 to 62 and monosultap at a ratio of 1:10; a pest control composition comprising any one of the present compounds 1 to 62 and monosultap at a ratio of 1:50; a pest control composition comprising any one of the present compounds 1 to 62 and acetamiprid at a ratio of 1:1; a pest control composition comprising any one of the present compounds 1 to 62 and acetamiprid at a ratio of 1:10; a pest control composition comprising any one of the present compounds 1 to 62 and acetamiprid at a ratio of 1:50; a pest control composition comprising any one of the present compounds 1 to 62 and clothianidin at a ratio of 1:1; a pest control composition comprising any one of the present compounds 1 to 62 and clothianidin at a ratio of 1:10; a pest control composition comprising any one of the present compounds 1 to 62 and clothianidin at a ratio of 1:50;
a pest control composition comprising any one of the present compounds 1 to 62 and imidacloprid at a ratio of 1:1; a pest control composition comprising any one of the present compounds 1 to 62 and imidacloprid at a ratio of 1:10; a pest control composition comprising any one of the present compounds 1 to 62 and imidacloprid at a ratio of 1:50; a pest control composition comprising any one of the present compounds 1 to 62 and thiamethoxam at a ratio of 1:1; a pest control composition comprising any one of the present compounds 1 to 62 and thiamethoxam at a ratio of 1:10; a pest control composition comprising any one of the present compounds 1 to 62 and thiamethoxam at a ratio of 1:50; a pest control composition comprising any one of the present compounds 1 to 62 and dinotefuran at a ratio of 1:1; a pest control composition comprising any one of the present compounds 1 to 62 and dinotefuran at a ratio of 1:10; a pest control composition comprising any one of the present compounds 1 to 62 and dinotefuran at a ratio of 1:50; a pest control composition comprising any one of the present compounds 1 to 62 and sulfoxaflor at a ratio of 1:1; a pest control composition comprising any one of the present compounds 1 to 62 and sulfoxaflor at a ratio of 1:10; a pest control composition comprising any one of the present compounds 1 to 62 and sulfoxaflor at a ratio of 1:50; a pest control composition comprising any one of the present compounds 1 to 62 and flupyradifurone at a ratio of 1:1; a pest control composition comprising any one of the present compounds 1 to 62 and flupyradifurone at a ratio of 1:10; a pest control composition comprising any one of the present compounds 1 to 62 and flupyradifurone at a ratio of 1:50; a pest control composition comprising any one of the present compounds 1 to 62 and nitenpyram at a ratio of 1:1; a pest control composition comprising any one of the present compounds 1 to 62 and nitenpyram at a ratio of 1:10; a pest control composition comprising any one of the present compounds 1 to 62 and nitenpyram at a ratio of 1:50; a pest control composition comprising any one of the present compounds 1 to 62 and thiacloprid at a ratio of 1:1; a pest control composition comprising any one of the present compounds 1 to 62 and thiacloprid at a ratio of 1:10; a pest control composition comprising any one of the present compounds 1 to 62 and thiacloprid at a ratio of 1:50; a pest control composition comprising any one of the present compounds 1 to 62 and bistrifluron at a ratio of 0.1:1; a pest control composition comprising any one of the present compounds 1 to 62 and bistrifluron at a ratio of 1:1; a pest control composition comprising any one of the present compounds 1 to 62 and bistrifluron at a ratio of 1:10; a pest control composition comprising any one of the present compounds 1 to 62 and chlorfluazuron at a ratio of 0.1:1; a pest control composition comprising any one of the present compounds 1 to 62 and chlorfluazuron at a ratio of 1:1; a pest control composition comprising any one of the present compounds 1 to 62 and chlorfluazuron at a ratio of 1:10; a pest control composition comprising any one of the present compounds 1 to 62 and diflubenzuron at a ratio of 0.1:1; a pest control composition comprising any one of the present compounds 1 to 62 and diflubenzuron at a ratio of 1:1; a pest control composition comprising any one of the present compounds 1 to 62 and diflubenzuron at a ratio of 1:10; a pest control composition comprising any one of the present compounds 1 to 62 and flucycloxuron at a ratio of 0.1:1; a pest control composition comprising any one of the present compounds 1 to 62 and flucycloxuron at a ratio of 1:1; a pest control composition comprising any one of the present compounds 1 to 62 and flucycloxuron at a ratio of 1:10; a pest control composition comprising any one of the present compounds 1 to 62 and flufenoxuron at a ratio of 0.1:1; a pest control composition comprising any one of the present compounds 1 to 62 and flufenoxuron at a ratio of 1:1; a pest control composition comprising any one of the present compounds 1 to 62 and flufenoxuron at a ratio of 1:10; a pest control composition comprising any one of the present compounds 1 to 62 and hexaflumuron at a ratio of 0.1:1; a pest control composition comprising any one of the present compounds 1 to 62 and hexaflumuron at a ratio of 1:1; a pest control composition comprising any one of the present compounds 1 to 62 and hexaflumuron at a ratio of 1:10; a pest control composition comprising any one of the present compounds 1 to 62 and lufenuron at a ratio of 0.1:1; a pest control composition comprising any one of the present compounds 1 to 62 and lufenuron at a ratio of 1:1; a pest control composition comprising any one of the present compounds 1 to 62 and lufenuron at a ratio of 1:10; a pest control composition comprising any one of the present compounds 1 to 62 and novaluron at a ratio of 0.1:1; a pest control composition comprising any one of the present compounds 1 to 62 and novaluron at a ratio of 1:1; a pest control composition comprising any one of the present compounds 1 to 62 and novaluron at a ratio of 1:10; a pest control composition comprising any one of the present compounds 1 to 62 and noviflumuron at a ratio of 0.1:1; a pest control composition comprising any one of the present compounds 1 to 62 and noviflumuron at a ratio of 1:1; a pest control composition comprising any one of the present compounds 1 to 62 and noviflumuron at a ratio of 1:10; a pest control composition comprising any one of the present compounds 1 to 62 and teflubenzuron at a ratio of 0.1:1; a pest control composition comprising any one of the present compounds 1 to 62 and teflubenzuron at a ratio of 1:1; a pest control composition comprising any one of the present compounds 1 to 62 and teflubenzuron at a ratio of 1:10; a pest control composition comprising any one of the present compounds 1 to 62 and triflumuron at a ratio of 0.1:1; a pest control composition comprising any one of the present compounds 1 to 62 and triflumuron at a ratio of 1:1; a pest control composition comprising any one of the present compounds 1 to 62 and triflumuron at a ratio of 1:10; a pest control composition comprising any one of the present compounds 1 to 62 and ethiprole at a ratio of 1:1; a pest control composition comprising any one of the present compounds 1 to 62 and ethiprole at a ratio of 1:10; a pest control composition comprising any one of the present compounds 1 to 62 and ethiprole at a ratio of 1:50; a pest control composition comprising any one of the present compounds 1 to 62 and fipronil at a ratio of 1:1; a pest control composition comprising any one of the present compounds 1 to 62 and fipronil at a ratio of 1:10; a pest control composition comprising any one of the present compounds 1 to 62 and fipronil at a ratio of 1:50; a pest control composition comprising any one of the present compounds 1 to 62 and flufiprole at a ratio of 1:1; a pest control composition comprising any one of the present compounds 1 to 62 and flufiprole at a ratio of 1:10; a pest control composition comprising any one of the present compounds 1 to 62 and flufiprole at a ratio of 1:50; a pest control composition comprising any one of the present compounds 1 to 62 and chromafenozide at a ratio of 0.1:1; a pest control composition comprising any one of the present compounds 1 to 62 and chromafenozide at a ratio of 1:1; a pest control composition comprising any one of the present compounds 1 to 62 and chromafenozide at a ratio of 1:10; a pest control composition comprising any one of the present compounds 1 to 62 and halofenozide at a ratio of 0.1:1; a pest control composition comprising any one of the present compounds 1 to 62 and halofenozide at a ratio of 1:1; a pest control composition comprising any one of the present compounds 1 to 62 and halofenozide at a ratio of 1:10; a pest control composition comprising any one of the present compounds 1 to 62 and methoxyfenozide at a ratio of 0.1:1; a pest control composition comprising any one of the present compounds 1 to 62 and methoxyfenozide at a ratio of 1:1; a pest control composition comprising any one of the present compounds 1 to 62 and methoxyfenozide at a ratio of 1:10; a pest control composition comprising any one of the present compounds 1 to 62 and tebufenozide at a ratio of 0.1:1; a pest control composition comprising any one of the present compounds 1 to 62 and tebufenozide at a ratio of 1:1; a pest control composition comprising any one of the present compounds 1 to 62 and tebufenozide at a ratio of 1:10; a pest control composition comprising any one of the present compounds 1 to 62 and chlordane at a ratio of 1:1; a pest control composition comprising any one of the present compounds 1 to 62 and chlordane at a ratio of 1:10; a pest control composition comprising any one of the present compounds 1 to 62 and chlordane at a ratio of 1:50; a pest control composition comprising any one of the present compounds 1 to 62 and endosulfan at a ratio of 1:1; a pest control composition comprising any one of the present compounds 1 to 62 and endosulfan at a ratio of 1:10; a pest control composition comprising any one of the present compounds 1 to 62 and endosulfan at a ratio of 1:50; a pest control composition comprising any one of the present compounds 1 to 62 and alpha-endosulfan at a ratio of 1:1; a pest control composition comprising any one of the present compounds 1 to 62 and alpha-endosulfan at a ratio of 1:10; a pest control composition comprising any one of the present compounds 1 to 62 and alpha-endosulfan at a ratio of 1:50; a pest control composition comprising any one of the present compounds 1 to 62 and chlorantraniliprole at a ratio of 1:0.1; a pest control composition comprising any one of the present compounds 1 to 62 and chlorantraniliprole at a ratio of 1:1; a pest control composition comprising any one of the present compounds 1 to 62 and chlorantraniliprole at a ratio of 1:10; a pest control composition comprising any one of the present compounds 1 to 62 and chlorantraniliprole at a ratio of 1:50; a pest control composition comprising any one of the present compounds 1 to 62 and cyantraniliprole at a ratio of 1:0.1; a pest control composition comprising any one of the present compounds 1 to 62 and cyantraniliprole at a ratio of 1:1; a pest control composition comprising any one of the present compounds 1 to 62 and cyantraniliprole at a ratio of 1:10; a pest control composition comprising any one of the present compounds 1 to 62 and cyantraniliprole at a ratio of 1:50; a pest control composition comprising any one of the present compounds 1 to 62 and cycloniliprole at a ratio of 1:0.1; a pest control composition comprising any one of the present compounds 1 to 62 and cycloniliprole at a ratio of 1:1; a pest control composition comprising any one of the present compounds 1 to 62 and cycloniliprole at a ratio of 1:10; a pest control composition comprising any one of the present compounds 1 to 62 and cycloniliprole at a ratio of 1:50; a pest control composition comprising any one of the present compounds 1 to 62 and flubendiamide at a ratio of 1:0.1; a pest control composition comprising any one of the present compounds 1 to 62 and flubendiamide at a ratio of 1:1; a pest control composition comprising any one of the present compounds 1 to 62 and flubendiamide at a ratio of 1:10; a pest control composition comprising any one of the present compounds 1 to 62 and flubendiamide at a ratio of 1:50; a pest control composition comprising any one of the present compounds 1 to 62 and tetraniliprole at a ratio of 1:0.1; a pest control composition comprising any one of the present compounds 1 to 62 and tetraniliprole at a ratio of 1:1; a pest control composition comprising any one of the present compounds 1 to 62 and tetraniliprole at a ratio of 1:10; a pest control composition comprising any one of the present compounds 1 to 62 and tetraniliprole at a ratio of 1:50; a pest control composition comprising any one of the present compounds 1 to 62 and *Bacillus thuringiensis* var. *aizawai* at a ratio of 1:1; a pest control composition comprising any one of the present compounds 1 to 62 and *Bacillus thuringiensis* var. *aizawai* at a ratio of 1:10; a pest control composition comprising any one of the present compounds 1 to 62 and *Bacillus thuringiensis* var. *aizawai* at a ratio of 1:50; a pest control composition comprising any one of the present compounds 1 to 62 and *Bacillus thuringiensis* var. *kurstaki* at a ratio of 1:1; a pest control composition comprising any one of the present compounds 1 to 62 and *Bacillus thuringiensis* var, *kurstaki* at a ratio of 1:10; a pest control composition comprising any one of the present compounds 1 to 62 and *Bacillus thuringiensis* var. *kurstaki* at a ratio of 1:50; a pest control composition comprising any one of the present compounds 1 to 62 and *Bacillus thuringiensis* var. *israelensis* at a ratio of 1:1; a pest control composition comprising any one of the present compounds 1 to 62 and *Bacillus thuringiensis* var. *israelensis* at a ratio of 1:10; a pest control composition comprising any one of the present compounds 1 to 62 and *Bacillus thuringiensis* var. *israelensis* at a ratio of 1:50; a pest control composition comprising any one of the present compounds 1 to 62 and *Bacillus thuringiensis* var. *tenebriosis* at a ratio of 1:1; a pest control composition comprising any one of the present compounds 1 to 62 and *Bacillus thuringiensis* var. *tenebriosis* at a ratio of 1:10; a pest control composition comprising any one of the present compounds 1 to 62 and *Bacillus thuringiensis* var. *tenebriosis* at a ratio of 1:50; a pest control composition comprising any one of the present compounds 1 to 62 and *Bacillus firmus* at a ratio of 1:1; a pest control composition comprising any one of the present compounds 1 to 62 and *Bacillus firmus* at a ratio of 1:10; a pest control composition comprising any one of the present compounds 1 to 62 and *Bacillus firmus* at a ratio of 1:50; a pest control composition comprising any one of the present compounds 1 to 62 and *Bacillus sphaericus* at a ratio of 1:1; a pest control composition comprising any one of the present compounds 1 to 62 and *Bacillus sphaericus* at a ratio of 1:10; a pest control composition comprising any one of the present compounds 1 to 62 and *Bacillus sphaericus* at a ratio of 1:50; a pest control composition comprising any one of the present compounds 1 to 62 and *Beauveria bassiana* at a ratio of 1:1; a pest control composition comprising any one of the present compounds 1 to 62 and *Beauveria bassiana* at a ratio of 1:10; a pest control composition comprising any' one of the present compounds 1 to 62 and *Beauveria bassiana* at a ratio of 1:50; a pest control composition comprising any one of the present compounds 1 to 62 and *Beauveria brongniartii* at a ratio of 1:1; a pest control composition comprising any one of the present compounds 1 to 62 and *Beauveria brongniartii* at a ratio of 1:10; a pest control composition comprising any one of the present compounds 1 to 62 and *Beauveria brongniartii* at a ratio of 1:50; a pest control composition comprising any one of the present compounds 1 to 62 and *Paecilomyces fumosoroseus* at a ratio of 1:1; a pest control composition comprising any one of the present compounds 1 to 62 and *Paecilomyces fumosoroseus* at a ratio of 1:10; a pest control composition comprising any one of the present compounds 1 to 62 and *Paecilomyces fumosoroseus* at a ratio of 1:50;

a pest control composition comprising any one of the present compounds 1 to 62 and *Paecilomyces lilacinus* at a ratio of 1:1; a pest control composition comprising any one of the present compounds 1 to 62 and *Paecilomyces lilacinus* at a ratio of 1:10; a pest control composition comprising any one of the present compounds 1 to 62 and *Paecilomyces lilacinus* at a ratio of 1:50; a pest control composition comprising any one of the present compounds 1 to 62 and *Paecilomyces tenuipes* at a ratio of 1:1; a pest control composition comprising any one of the present compounds 1 to 62 and *Paecilomyces tenuipes* at a ratio of 1:10; a pest control composition comprising any one of the present compounds 1 to 62 and *Paecilomyces tenuipes* at a ratio of 1:50; a pest control composition comprising any one of the present compounds 1 to 62 and *Trichoderma harzianum* at a ratio of 1:1; a pest control composition comprising any one of the present compounds 1 to 62 and *Trichoderma harzianum* at a ratio of 1:10; a pest control composition comprising any one of the present compounds 1 to 62 and *Trichoderma harzianum* at a ratio of 1:50; a pest control composition comprising any one of the present compounds 1 to 62 and *Verticillium lecanii* at a ratio of 1:1; a pest control composition comprising any one of the present compounds 1 to 62 and *Verticillium lecanii* at a ratio of 1:10; a pest control composition comprising any one of the present compounds 1 to 62 and *Verticillium lecanii* at a ratio of 1:50; a pest control composition comprising any one of the present compounds 1 to 62 and *Pasteuria penetrans* at a ratio of 1:1; a pest control composition comprising any one of the present compounds 1 to 62 and *Pasteuria penetrans* at a ratio of 1:10; a pest control composition comprising any one of the present compounds 1 to 62 and *Pasteuria penetrans* at a ratio of 1:50; a pest control composition comprising any one of the present compounds 1 to 62 and dazomet at a ratio of 1:1; a pest control composition comprising any one of the present compounds 1 to 62 and dazomet at a ratio of 1:10; a pest control composition comprising any one of the present compounds 1 to 62 and dazomet at a ratio of 1:50; a pest control composition comprising any one of the present compounds 1 to 62 and fluensulfone at a ratio of 1:1;
a pest control composition comprising any one of the present compounds 1 to 62 and fluensulfone at a ratio of 1:10; a pest control composition comprising any one of the present compounds 1 to 62 and fluensulfone at a ratio of 1:50; a pest control composition comprising any one of the present compounds 1 to 62 and fosthiazate at a ratio of 1:1; a pest control composition comprising any one of the present compounds 1 to 62 and fosthiazate at a ratio of 1:10; a pest control composition comprising any one of the present compounds 1 to 62 and fosthiazate at a ratio of 1:50; a pest control composition comprising any one of the present compounds 1 to 62 and imicyafos at a ratio of 1:1; a pest control composition comprising any one of the present compounds 1 to 62 and imicyafos at a ratio of 1:10; a pest control composition comprising any one of the present compounds 1 to 62 and imicyafos at a ratio of 1:50; a pest control composition comprising any one of the present compounds 1 to 62 and metam at a ratio of 1:1; a pest control composition comprising any one of the present compounds 1 to 62 and metam at a ratio of 1:10; a pest control composition comprising any one of the present compounds 1 to 62 and metam at a ratio of 1:50; a pest control composition comprising any one of the present compounds 1 to 62 and tartar emetic at a ratio of 1:1; a pest control composition comprising any one of the present compounds 1 to 62 and tartar emetic at a ratio of 1:10; a pest control composition comprising any one of the present compounds 1 to 62 and tartar emetic at a ratio of 1:50; a pest control composition comprising any one of the present compounds 1 to 62 and tioxazafen at a ratio of 1:1; a pest control composition comprising any one of the present compounds 1 to 62 and tioxazafen at a ratio of 1:10; a pest control composition comprising any one of the present compounds 1 to 62 and tioxazafen at a ratio of 1:50; a pest control composition comprising any one of the present compounds 1 to 62 and *Arthrobotrys dactyloydes* at a ratio of 1:1; a pest control composition comprising any one of the present compounds 1 to 62 and *Arthrobotrys dactyloydes* at a ratio of 1:10; a pest control composition comprising any one of the present compounds 1 to 62 and *Arthrobotrys dactyloydes* at a ratio of 1:50;
a pest control composition comprising any one of the present compounds 1 to 62 and *Bacillus megaterium* at a ratio of 1:1; a pest control composition comprising any one of the present compounds 1 to 62 and *Bacillus megaterium* at a ratio of 1:10; a pest control composition comprising any one of the present compounds 1 to 62 and *Bacillus megaterium* at a ratio of 1:50; a pest control composition comprising any one of the present compounds 1 to 62 and *Hirsutella rhossiliensis* at a ratio of 1:1; a pest control composition comprising any one of the present compounds 1 to 62 and *Hirsutella rhossiliensis* at a ratio of 1:10; a pest control composition comprising any one of the present compounds 1 to 62 and *Hirsutella rhossiliensis* at a ratio of 1:50; a pest control composition comprising any one of the present compounds 1 to 62 and *Hirsutella minnesotensis* at a ratio of 1:1; a pest control composition comprising any one of the present compounds 1 to 62 and *Hirsutella minnesotensis* at a ratio of 1:10; a pest control composition comprising any one of the present compounds 1 to 62 and *Hirsutella minnesotensis* at a ratio of 1:50; a pest control composition comprising any one of the present compounds 1 to 62 and *Monacrosporium phymatopagum* at a ratio of 1:1; a pest control composition comprising any one of the present compounds 1 to 62 and *Monacrosporium phymatopagum* at a ratio of 1:10; a pest control composition comprising any one of the present compounds 1 to 62 and *Monacrosporium phymatopagum* at a ratio of 1:50; a pest control composition comprising any one of the present compounds 1 to 62 and *Pasteuria nishizawae* at a ratio of 1:1; a pest control composition comprising any one of the present compounds 1 to 62 and *Pasteuria nishizawae* at a ratio of 1:10; a pest control composition comprising any one of the present compounds 1 to 62 and *Pasteuria nishizawae* at a ratio of 1:50; a pest control composition comprising any one of the present compounds 1 to 62 and *Pasteuria usgae* at a ratio of 1:1; a pest control composition comprising any one of the present compounds 1 to 62 and *Pasteuria usgae* at a ratio of 1:10; a pest control composition comprising any one of the present compounds 1 to 62 and *Pasteuria usgae* at a ratio of 1:50; a pest control composition comprising any one of the present compounds 1 to 62 and *Verticillium chlamydosporium* at a ratio of 1:1; a pest control composition comprising any one of the present compounds 1 to 62 and *Verticillium chlamydosporium* at a ratio of 1:10; a pest control composition comprising any one of the present compounds 1 to 62 and *Verticillium chlamydosporium* at a ratio of 1:50; a pest control composition comprising any one of the present compounds 1 to 62 and Harpin protein at a ratio of 1:1; a pest control composition comprising any one of the present compounds 1 to 62 and Harpin protein at a ratio of 1:10; a pest control composition comprising any one of the present compounds 1 to 62 and Harpin protein at a ratio of 1:50; a pest control composition comprising any one of the present compounds 1 to 62 and 6-bromo-N-{[2-chloro-5-(trifluoromethyl)phenyl]sulfonyl}-imidazo[1,2-a]pyrimidine-2-carboxamide at a ratio of 1:1; a pest control composition comprising any one of the present compounds 1 to 62 and 6-bromo-N-{[2-chloro-5-(trifluoromethyl)phenyl]sulfonyl}-imidazo[1,2-a]pyrimidine-2-carboxamide at a ratio of 1:10; a pest control composition comprising any one of the present compounds 1 to 62 and 6-bromo-N-{[2-chloro-5-(trifluoromethyl)phenyl]sulfonyl}-imidazo[1,2-a]pyrimidine-2-carboxamide at a ratio of 1:50; a pest control composition comprising any one of the present compounds 1 to 62 and 8-chloro-N-[(2-chloro-5-methoxyphenyl)sulfonyl]-6-(trifluoromethyl)-imidazo[1,2-a]pyridine-2-carboxamide at a ratio of 1:1; a pest control composition comprising any one of the present compounds 1 to 62 and 8-chloro-N-[(2-chloro-5-methoxyphenyl)sulfonyl]-6-(trifluoromethyl)-imidazo[1,2-a]pyridine-2-carboxamide at a ratio of 1:10; a pest control composition comprising any one of the present compounds 1 to 62 and 8-chloro-N-[(2-chloro-5-methoxyphenyl)sulfonyl]-6-(trifluoromethyl)-imidazo[1,2-a]pyridine-2-carboxamide at a ratio of 1:50;
a pest control composition comprising any one of the present compounds 1 to 62 and acequinocyl at a ratio of 0.1:1; a pest control composition comprising any one of the present compounds 1 to 62 and acequinocyl at a ratio of 1:1; a pest control composition comprising any one of the present compounds 1 to 62 and acequinocyl at a ratio of 1:10; a pest control composition comprising any one of the present compounds 1 to 62 and amitraz at a ratio of 0.1:1; a pest control composition comprising any one of the present compounds 1 to 62 and amitraz at a ratio of 1:1; a pest control composition comprising any one of the present compounds 1 to 62 and amitraz at a ratio of 1:10; a pest control composition comprising any one of the present compounds 1 to 62 and Benzoximate at a ratio of 0.1:1; a pest control composition comprising any one of the present compounds 1 to 62 and Benzoximate at a ratio of 1:1; a pest control composition comprising any one of the present compounds 1 to 62 and Benzoximate at a ratio of 1:10; a pest control composition comprising any one of the present compounds 1 to 62 and bifenazate at a ratio of 0.1:1; a pest control composition comprising any one of the present compounds 1 to 62 and bifenazate at a ratio of 1:1; a pest control composition comprising any one of the present compounds 1 to 62 and bifenazate at a ratio of 1:10; a pest control composition comprising any one of the present compounds 1 to 62 and bromopropylate at a ratio of 0.1:1; a pest control composition comprising any one of the present compounds 1 to 62 and bromopropylate at a ratio of 1:1; a pest control composition comprising any one of the present compounds 1 to 62 and bromopropylate at a ratio of 1:10; a pest control composition comprising any one of the present compounds 1 to 62 and chinomethionat at a ratio of 0.1:1; a pest control composition comprising any one of the present compounds 1 to 62 and chinomethionat at a ratio of 1:1; a pest control composition comprising any one of the present compounds 1 to 62 and chinomethionat at a ratio of 1:10; a pest control composition comprising any one of the present compounds 1 to 62 and clofentezine at a ratio of 0.1:1; a pest control composition comprising any one of the present compounds 1 to 62 and clofentezine at a ratio of 1:1; a pest control composition comprising any one of the present compounds 1 to 62 and clofentezine at a ratio of 1:10; a pest control composition comprising any one of the present compounds 1 to 62 and cyenopyrafen at a ratio of 0.1:1; a pest control composition comprising any one of the present compounds 1 to 62 and cyenopyrafen at a ratio of 1:1; a pest control composition comprising any one of the present compounds 1 to 62 and cyenopyrafen at a ratio of 1:10; a pest control composition comprising any one of the present compounds 1 to 62 and cyflumetofen at a ratio of 0.1:1; a pest compounds 1 to 62 and cyflumetofen at a ratio of 1:1; a pest control composition comprising any one of the present compounds 1 to 62 and cyflumetofen at a ratio of 1:10; a pest control composition comprising any one of the present compounds 1 to 62 and cyhexatin at a ratio of 0.1:1; a pest control composition comprising any one of the present compounds 1 to 62 and cyhexatin at a ratio of 1:1; a pest control composition comprising any one of the present compounds 1 to 62 and cyhexatin at a ratio of 1:10; a pest control composition comprising any one of the present compounds 1 to 62 and dicofol at a ratio of 0.1:1; a pest control composition comprising any one of the present compounds 1 to 62 and dicofol at a ratio of 1:1; a pest control composition comprising any one of the present compounds 1 to 62 and dicofol at a ratio of 1:10; a pest control composition comprising any one of the present compounds 1 to 62 and etoxazole at a ratio of 0.1:1; a pest control composition comprising any one of the present compounds 1 to 62 and etoxazole at a ratio of 1:1; a pest control composition comprising any one of the present compounds 1 to 62 and etoxazole at a ratio of 1:10; a pest control composition comprising any one of the present compounds 1 to 62 and fenazaquin at a ratio of 0.1:1; a pest control composition comprising any one of the present compounds 1 to 62 and fenazaquin at a ratio of 1:1; a pest control composition comprising any one of the present compounds 1 to 62 and fenazaquin at a ratio of 1:10; a pest control composition comprising any one of the present compounds 1 to 62 and fenbutatin oxide at a ratio of 0.1:1; a pest control composition comprising any one of the present compounds 1 to 62 and fenbutatin oxide at a ratio of 1:1; a pest control composition comprising any one of the present compounds 1 to 62 and fenbutatin oxide at a ratio of 1:10; a pest control composition comprising any one of the present compounds 1 to 62 and fenpyroximate at a ratio of 0.1:1; a pest control composition comprising any one of the present compounds 1 to 62 and fenpyroximate at a ratio of 1:1; a pest control composition comprising any one of the present compounds 1 to 62 and fenpyroximate at a ratio of 1:10; a pest control composition comprising any one of the present compounds 1 to 62 and fluacrypyrim at a ratio of 0.1:1; a pest control composition comprising any one of the present compounds 1 to 62 and fluacrypyrim at a ratio of 1:1; a pest control composition comprising any one of the present compounds 1 to 62 and fluacrypyrim at a ratio of 1:10; a pest control composition comprising any one of the present compounds 1 to 62 and fluazuron at a ratio of 0.1:1; a pest control composition comprising any one of the present compounds 1 to 62 and fluazuron at a ratio of 1:1; a pest control composition comprising any one of the present compounds 1 to 62 and fluazuron at a ratio of 1:10; a pest control composition comprising any one of the present compounds 1 to 62 and flufenoxystrobin at a ratio of 0.1:1; a pest control composition comprising any one of the present compounds 1 to 62 and flufenoxystrobin at a ratio of 1:1; a pest control composition comprising any one of the present compounds 1 to 62 and flufenoxystrobin at a ratio of 1:10; a pest control composition comprising any one of the present compounds 1 to 62 and hexythiazox at a ratio of 0.1:1; a pest control composition comprising any one of the present compounds 1 to 62 and hexythiazox at a ratio of 1:1; a pest control composition comprising any one of the present compounds 1 to 62 and hexythiazox at a ratio of 1:10; a pest control composition comprising any one of the present compounds 1 to 62 and propargite at a ratio of 0.1:1; a pest control composition comprising any one of the present compounds 1 to 62 and propargite at a ratio of 1:1; a pest control composition comprising any one of the present compounds 1 to 62 and propargite at a ratio of 1:10; a pest control composition comprising any one of the present compounds 1 to 62 and pyflubumide at a ratio of 0.1:1; a pest control composition comprising any one of the present compounds 1 to 62 and pyflubumide at a ratio of 1:1; a pest control composition comprising any one of the present compounds 1 to 62 and pyflubumide at a ratio of 1:10; a pest control composition comprising any one of the present compounds 1 to 62 and pyridaben at a ratio of 0.1:1; a pest control composition comprising any one of the present compounds 1 to 62 and pyridaben at a ratio of 1:1; a pest control composition comprising any one of the present compounds 1 to 62 and pyridaben at a ratio of 1:10; a pest control composition comprising any one of the present compounds 1 to 62 and pyrimidifen at a ratio of 0.1:1; a pest control composition comprising any one of the present compounds 1 to 62 and pyrimidifen at a ratio of 1:1; a pest control composition comprising any one of the present compounds 1 to 62 and pyrimidifen at a ratio of 1:10; a pest control composition comprising any one of the present compounds 1 to 62 and pyriminostrobin at a ratio of 0.1:1; a pest control composition comprising any one of the present compounds 1 to 62 and pyriminostrobin at a ratio of 1:1; a pest control composition comprising any one of the present compounds 1 to 62 and pyriminostrobin at a ratio of 1:10; a pest control composition comprising any one of the present compounds 1 to 62 and spirodiclofen at a ratio of 0.1:1; a pest control composition comprising any one of the present compounds 1 to 62 and spirodiclofen at a ratio of 1:1; a pest control composition comprising any one of the present compounds 1 to 62 and spirodiclofen at a ratio of 1:10; a pest control composition comprising any one of the present compounds 1 to 62 and spiromesifen at a ratio of 0.1:1; a pest control composition comprising any one of the present compounds 1 to 62 and spiromesifen at a ratio of 1:1; a pest control composition comprising any one of the present compounds 1 to 62 and spiromesifen at a ratio of 1:10;

a pest control composition comprising any one of the present compounds 1 to 62 and tebufenpyrad at a ratio of 0.1:1; a pest control composition comprising any one of the present compounds 1 to 62 and tebufenpyrad at a ratio of 1:1; a pest control composition comprising any one of the present compounds 1 to 62 and tebufenpyrad at a ratio of 1:10; a pest control composition comprising any one of the present compounds 1 to 62 and tetradifon at a ratio of 0.1:1; a pest control composition comprising any one of the present compounds 1 to 62 and tetradifon at a ratio of 1:1; a pest control composition comprising any one of the present compounds 1 to 62 and tetradifon at a ratio of 1:10; a pest control composition comprising any one of the present compounds 1 to 62 and abamectin at a ratio of 1:1; a pest control composition comprising any one of the present compounds 1 to 62 and abamectin at a ratio of 1:10; a pest control composition comprising any one of the present compounds 1 to 62 and abamectin at a ratio of 1:50; a pest control composition comprising any one of the present compounds 1 to 62 and emamectin-benzoate at a ratio of 1:1; a pest control composition comprising any one of the present compounds 1 to 62 and emamectin-benzoate at a ratio of 1:10; a pest control composition comprising any one of the present compounds 1 to 62 and emamectin-benzoate at a ratio of 1:50; a pest control composition comprising any one of the present compounds 1 to 62 and lepimectin at a ratio of 1:1; a pest control composition comprising any one of the present compounds 1 to 62 and lepimectin at a ratio of 1:10; a pest control composition comprising any one of the present compounds 1 to 62 and lepimectin at a ratio of 1:50; a pest control composition comprising any one of the present compounds 1 to 62 and milbemectin at a ratio of 1:1; a pest control composition comprising any one of the present compounds 1 to 62 and milbemectin at a ratio of 1:10; a pest control composition comprising any one of the present compounds 1 to 62 and milbemectin at a ratio of 1:50; a pest control composition comprising any one of the present compounds 1 to 62 and spinetoram at a ratio of 1:1;

a pest control composition comprising any one of the present compounds 1 to 62 and spinetoram at a ratio of 1:10; a pest control composition comprising any one of the present compounds 1 to 62 and spinetoram at a ratio of 1:50; a pest control composition comprising any one of the present compounds 1 to 62 and spinosad at a ratio of 1:1; a pest control composition comprising any one of the present compounds 1 to 62 and spinosad at a ratio of 1:10; a pest control composition comprising any one of the present compounds 1 to 62 and spinosad at a ratio of 1:50; a pest control composition comprising any one of the present compounds 1 to 62 and afidopyropen at a ratio of 1:1; a pest control composition comprising any one of the present compounds 1 to 62 and afidopyropen at a ratio of 1:10; a pest control composition comprising any one of the present compounds 1 to 62 and afidopyropen at a ratio of 1:50; a pest control composition comprising any one of the present compounds 1 to 62 and aluminium phosphide at a ratio of 1:1; a pest control composition comprising any one of the present compounds 1 to 62 and aluminium phosphide at a ratio of 1:10; a pest control composition comprising any one of the present compounds 1 to 62 and aluminium phosphide at a ratio of 1:50; a pest control composition comprising any one of the present compounds 1 to 62 and calcium phosphide at a ratio of 1:1; a pest control composition comprising any one of the present compounds 1 to 62 and calcium phosphide at a ratio of 1:10; a pest control composition comprising any one of the present compounds 1 to 62 and calcium phosphide at a ratio of 1:50; a pest control composition comprising any one of the present compounds 1 to 62 and hydrogen phosphide at a ratio of 1:1; a pest control composition comprising any one of the present compounds 1 to 62 and hydrogen phosphide at a ratio of 1:10; a pest control composition comprising any one of the present compounds 1 to 62 and hydrogen phosphide at a ratio of 1:50; a pest control composition comprising any one of the present compounds 1 to 62 and zinc phosphide at a ratio of 1:1; a pest control composition comprising any one of the present compounds 1 to 62 and zinc phosphide at a ratio of 1:10; a pest control composition comprising any one of the present compounds 1 to 62 and zinc phosphide at a ratio of 1:50;

a pest control composition comprising any one of the present compounds 1 to 62 and azadirachtin at a ratio of 1:1; a pest control composition comprising any one of the present compounds 1 to 62 and azadirachtin at a ratio of 1:10; a pest control composition comprising any one of the present compounds 1 to 62 and azadirachtin at a ratio of 1:50; a pest control composition comprising any one of the present compounds 1 to 62 and buprofezin at a ratio of 1:1; a pest control composition comprising any one of the present compounds 1 to 62 and buprofezin at a ratio of 1:10; a pest control composition comprising any one of the present compounds 1 to 62 and buprofezin at a ratio of 1:50; a pest control composition comprising any one of the present compounds 1 to 62 and chlorfenapyr at a ratio of 1:1; a pest control composition comprising any one of the present compounds 1 to 62 and chlorfenapyr at a ratio of 1:10; a pest control composition comprising any one of the present compounds 1 to 62 and chlorfenapyr at a ratio of 1:50; a pest control composition comprising any one of the present compounds 1 to 62 and chloropicrin at a ratio of 1:1; a pest control composition comprising any one of the present compounds 1 to 62 and chloropicrin at a ratio of 1:10; a pest control composition comprising any one of the present compounds 1 to 62 and chloropicrin at a ratio of 1:50; a pest control composition comprising any one of the present compounds 1 to 62 and cyromazine at a ratio of 1:1; a pest control composition comprising any one of the present compounds 1 to 62 and cyromazine at a ratio of 1:10; a pest control composition comprising any one of the present compounds 1 to 62 and cyromazine at a ratio of 1:50; a pest control composition comprising any one of the present compounds 1 to 62 and diafenthiuron at a ratio of 1:1; a pest control composition comprising any one of the present compounds 1 to 62 and diafenthiuron at a ratio of 1:10; a pest control composition comprising any one of the present compounds 1 to 62 and diafenthiuron at a ratio of 1:50; a pest control composition comprising any one of the present compounds 1 to 62 and DNOC at a ratio of 1:1; a pest control composition comprising any one of the present compounds 1 to 62 and DNOC at a ratio of 1:10;

a pest control composition comprising any one of the present compounds 1 to 62 and DNOC at a ratio of 1:50; a pest control composition comprising any one of the present compounds 1 to 62 and fenoxycarb at a ratio of 1:1; a pest control composition comprising any one of the present compounds 1 to 62 and fenoxycarb at a ratio of 1:10; a pest control composition comprising any one of the present compounds 1 to 62 and fenoxycarb at a ratio of 1:50; a pest control composition comprising any one of the present compounds 1 to 62 and flometoquin at a ratio of 1:1; a pest control composition comprising any one of the present compounds 1 to 62 and flometoquin at a ratio of 1:10; a pest control composition comprising any one of the present compounds 1 to 62 and flometoquin at a ratio or 1:50; a pest control composition comprising any one of the present compounds 1 to 62 and flonicamid at a ratio or 1:1; a pest control composition comprising any one of the present compounds 1 to 62 and flonicamid at a ratio of 1:10; a pest control composition comprising any one of the present compounds 1 to 62 and flonicamid at a ratio of 1:50; a pest control composition comprising any one of the present compounds 1 to 62 and hydramethylnon at a ratio of 1:1; a pest control composition comprising any one of the present compounds 1 to 62 and hydramethylnon at a ratio of 1:10; a pest control composition comprising any one of the present compounds 1 to 62 and hydramethylnon at a ratio of 1:50; a pest control composition comprising any one of the present compounds 1 to 62 and hydroprene at a ratio of 1:1; a pest control composition comprising any one of the present compounds 1 to 62 and hydroprene at a ratio of 1:10; a pest control composition comprising any one of the present compounds 1 to 62 and hydroprene at a ratio of 1:50; a pest control composition comprising any one of the present compounds 1 to 62 and indoxacarb at a ratio of 1:1; a pest control composition comprising any one of the present compounds 1 to 62 and indoxacarb at a ratio of 1:10; a pest control composition comprising any one of the present compounds 1 to 62 and indoxacarb at a ratio of 1:50; a pest control composition comprising any one of the present compounds 1 to 62 and kinoprene at a ratio of 1:1;
a pest control composition comprising any one of the present compounds 1 to 62 and kinoprene at a ratio of 1:10; a pest control composition comprising any one of the present compounds 1 to 62 and kinoprene at a ratio of 1:50; a pest control composition comprising any one of the present compounds 1 to 62 and metaflumizone at a ratio of 1:1; a pest control composition comprising any one of the present compounds 1 to 62 and metaflumizone at a ratio of 1:10; a pest control composition comprising any one of the present compounds 1 to 62 and metaflumizone at a ratio of 1:50; a pest control composition comprising any one of the present compounds 1 to 62 and methoprene at a ratio of 1:1; a pest control composition comprising any one of the present compounds 1 to 62 and methoprene at a ratio of 1:10; a pest control composition comprising any one of the present compounds 1 to 62 and methoprene at a ratio of 1:50; a pest control composition comprising any one of the present compounds 1 to 62 and methoxychlor at a ratio of 1:1; a pest control composition comprising any one of the present compounds 1 to 62 and methoxychlor at a ratio of 1:10; a pest control composition comprising any one of the present compounds 1 to 62 and methoxychlor at a ratio of 1:50; a pest control composition comprising any one of the present compounds 1 to 62 and methyl bromide at a ratio of 1:1; a pest control composition comprising any one of the present compounds 1 to 62 and methyl bromide at a ratio of 1:10; a pest control composition comprising any one of the present compounds 1 to 62 and methyl bromide at a ratio of 1:50; a pest control composition comprising any one of the present compounds 1 to 62 and metoxadiazone at a ratio of 1:1; a pest control composition comprising any one of the present compounds 1 to 62 and metoxadiazone at a ratio of 1:10; a pest control composition comprising any one of the present compounds 1 to 62 and metoxadiazone at a ratio of 1:50; a pest control composition comprising any one of the present compounds 1 to 62 and pymetrozine at a ratio of 1:1; a pest control composition comprising any one of the present compounds 1 to 62 and pymetrozine at a ratio of 1:10; a pest control composition comprising any one of the present compounds 1 to 62 and pymetrozine at a ratio of 1:50; a pest control composition comprising any one of the present compounds 1 to 62 and pyrazophos at a ratio of 1:1;
a pest control composition comprising any one of the present compounds 1 to 62 and pyrazophos at a ratio of 1:10; a pest control composition comprising any one of the present compounds 1 to 62 and pyrazophos at a ratio of 1:50; a pest control composition comprising any one of the present compounds 1 to 62 and pyridalyl at a ratio of 1:1; a pest control composition comprising any one of the present compounds 1 to 62 and pyridalyl at a ratio of 1:10; a pest control composition comprising any one of the present compounds 1 to 62 and pyridalyl at a ratio of 1:50; a pest control composition comprising any one of the present compounds 1 to 62 and pyrifluquinazone at a ratio of 1:1; a pest control composition comprising any one of the present compounds 1 to 62 and pyrifluquinazone at a ratio of 1:10; a pest control composition comprising any one of the present compounds 1 to 62 and pyrifluquinazone at a ratio of 1:50; a pest control composition comprising any one of the present compounds 1 to 62 and pyriproxyfen at a ratio of 1:1; a pest control composition comprising any one of the present compounds 1 to 62 and pyriproxyfen at a ratio of 1:10; a pest control composition comprising any one of the present compounds 1 to 62 and pyriproxyfen at a ratio of 1:50; a pest control composition comprising any one of the present compounds 1 to 62 and sodium aluminum fluoride at a ratio of 1:1; a pest control composition comprising any one of the present compounds 1 to 62 and sodium aluminum fluoride at a ratio of 1:10; a pest control composition comprising any one of the present compounds 1 to 62 and sodium aluminum fluoride at a ratio of 1:50; a pest control composition comprising any one of the present compounds 1 to 62 and spirotetramat at a ratio of 1:1; a pest control composition comprising any one of the present compounds 1 to 62 and spirotetramat at a ratio of 1:10; a pest control composition comprising any one of the present compounds 1 to 62 and spirotetramat at a ratio of 1:50; a pest control composition comprising any one of the present compounds 1 to 62 and sulfluramid at a ratio of 1:1; a pest control composition comprising any one of the present compounds 1 to 62 and sulfluramid at a ratio of 1:10;
a pest control composition comprising any one of the present compounds 1 to 62 and suilfiluramid at a ratio of 1:50; a pest control composition comprising any one of the present compounds 1 to 62 and sulfuryl fluoride at a ratio of 1:1; a pest control composition comprising any one of the present compounds 1 to 62 and sulfuryl fluoride at a ratio of 1:10; a pest control composition comprising any one of the present compounds 1 to 62 and sulfuryl fluoride at a ratio of 1:50; a pest control composition comprising any one of the present compounds 1 to 62 and tolfenpyrad at a ratio of 1:1; a pest control composition comprising any one of the present compounds 1 to 62 and tolfenpyrad at a ratio of 1:10; a pest control composition comprising any one of the present compounds 1 to 62 and tolfenpyrad at a ratio of 1:50; a pest control composition comprising any one of the present compounds 1 to 62 and triflumezopyrim at a ratio of 1:1; a pest control composition comprising any one of the present compounds 1 to 62 and triflumezopyrim at a ratio of 1:10;

a pest control composition comprising any one of the present compounds 1 to 62 and triflumezopyrim at a ratio of 1:50; a pest control composition comprising any one of the present compounds 1 to 62 and 4-oxo-4-(2-phenylethyl)aminobutyric acid. At a ratio of 5:1; a pest control composition comprising any one of the present compounds 1 to 62 and 4-oxo-4-(2-phenylethyl)aminobutyric acid at a ratio of 1:10; a pest control composition comprising any one of the present compounds 1 to 62 and 4-oxo-4-(2-phenylethyl)aminobutyric acid at a ratio of 1:50; a pest control composition comprising any one of the present compounds 1 to 62 and methyl 5-(trifluoromethyl)benzo[h]thiophene-2-carboxylate at a ratio of 5:1; a pest control composition comprising any one of the present compounds 1 to 62 and methyl 5-(trifluoromethyl)benzo[b]thiophene-2-carboxylate at a ratio of 1:10; a pest control composition comprising any one of the present compounds 1 to 62 and methyl 5-(trifluoromethyl)benzo[b]thiophene-2-carboxylate at a ratio of 1:50;

a pest control composition comprising any one of the present compounds 1 to 62 and 5-(trifluoromethyl)benzo[b]thiophene-2-carboxylic acid at a ratio of 5:1; a pest control composition comprising any one of the present compounds 1 to 62 and 5-(trifluoromethyl)benzo[b]thiophene-2-carboxylic acid at a ratio of 1:10; a pest control composition comprising any one of the present compounds 1 to 62 and 5-(trifluoromethyl)benzo[b]thiophene-2-carboxylic acid at a ratio of 1:50; a pest control composition any one of the present compounds 1 to 62 and 2,4-D at a ratio of 0.1:1; a pest control composition comprising any one of the present compounds 1 to 62 and 2,4-D at a ratio of 1:1; a pest control composition comprising any one of the present compounds 1 to 62 and 2,4-D at a ratio of 1:20; a pest control composition comprising any one of the present compounds 1 to 62 and 2, 4-DB at a ratio of 0.1:1; a pest control composition comprising any one of the present compounds 1 to 62 and 2,4-DB at a ratio of 1:1; a pest control composition comprising any one of the present compounds 1 to 62 and 2,4-DB at a ratio of 1:20; a pest control composition comprising any one of the present compounds 1 to 62 and acetochlor at a ratio of 0.1:1; a pest control composition comprising any one of the present compounds 1 to 62 and acetochlor at a ratio of 1:1; a pest control composition comprising any one of the present compounds 1 to 62 and acetochlor at a ratio of 1:20; a pest control composition comprising any one of the present compounds 1 to 62 and acifluorfen at a ratio of 0.1:1; a pest control composition comprising any one of the present compounds 1 to 62 and acifluorfen at a ratio of 1:1; a pest control composition comprising any one of the present compounds 1 to 62 and acifluorfen at a ratio of 1:20; a pest control composition comprising any one of the present compounds 1 to 62 and alachlor at a ratio of 0.1:1; a pest control composition comprising any one of the present compounds 1 to 62 and alachlor at a ratio of 1:1; a pest control composition comprising any one of the present compounds 1 to 62 and alachlor at a ratio of 1:20; a pest control composition comprising any one of the present compounds 1 to 62 and ametryn at a ratio of 0.1:1; a pest control composition comprising any one of the present compounds 1 to 62 and ametryn at a ratio of 1:1; a pest control composition comprising any one of the present compounds 1 to 62 and ametryn at a ratio of 1:20;

a pest control composition comprising any one of the present compounds 1 to 62 and amicarbazone at a ratio of 0.1:1; a pest control composition comprising any one of the present compounds 1 to 62 and amicarbazone at a ratio of 1:1; a pest control composition comprising any one of the present compounds 1 to 62 and amicarbazone at a ratio of 1:20; a pest control composition comprising any one of the present compounds 1 to 62 and aminopyralid at a ratio of 0.1:1; a pest control composition comprising any one of the present compounds 1 to 62 and aminopyralid at a ratio of 1:1; a pest Control composition comprising any one of the present compounds 1 to 62 and aminopyralid at a ratio of 1:20; a pest control composition comprising any one of the present compounds 1 to 62 and atrazine at a ratio of 0.1:1; a pest control composition comprising any one of the present compounds 1 to 62 and atrazine at a ratio of 1:1; a pest control composition comprising any one of the present compounds 1 to 62 and atrazine at a ratio of 1:20; a pest control composition comprising any one of the present compounds 1 to 62 and benefin at a ratio of 0.1:1; a pest control composition comprising any one of the present compounds 1 to 62 and benefin at a ratio of 1:1; a pest Control composition comprising any one of the present compounds 1 to 62 and benefin at a ratio of 1:20; a pest control composition comprising any one of the present compounds 1 to 62 and bentazon at a ratio of 0.1:1; a pest control composition comprising any one of the present compounds 1 to 62 and bentazon at a ratio of 1:1; a pest control composition comprising any one of the present compounds 1 to 62 and bentazon at a ratio of 1:20; a pest control composition comprising any one of the present compounds 1 to 62 and bromoxynil at a ratio of 0.1:1; a pest control composition comprising any one of the present compounds 1 to 62 and bromoxynil at a ratio of 1:1; a pest control composition comprising any one of the present compounds 1 to 62 and bromoxynil at a ratio of 1:20; a pest control composition comprising any one of the present compounds 1 to 62 and carfentrazone at a ratio of 0.1:1; a pest control composition comprising any one of the present compounds 1 to 62 and carfentrazone at a ratio of 1:1;

a pest control composition comprising any one of the present compounds 1 to 62 and carfentrazone at a ratio of 1:20; a pest control composition comprising any one of the present compounds 1 to 62 and carfentrazone-ethyl at a ratio of 0.1:1; a pest control composition comprising any one of the present compounds 1 to 62 and carfentrazone-ethyl at a ratio of 1:1; a pest control composition comprising any one of the present compounds 1 to 62 and carfentrazone-ethyl at a ratio of 1:20; a pest control composition comprising any one of the present compounds 1 to 62 and chloransulam at a ratio of 0.1:1; a pest control composition comprising any one of the present compounds 1 to 62 and chloransulam at a ratio of 1:1; a pest control composition comprising any one of the present compounds 1 to 62 and chloransulam at a ratio of 1:20; a pest control composition comprising any one of the present compounds 1 to 62 and chlorimuron at a ratio of 0.1:1; a pest control composition comprising any one of the present compounds 1 to 62 and chlorimuron at a ratio of 1:1; a pest control composition comprising any one of the present compounds 1 to 62 and chlorimuron at a ratio of 1:20; a pest control composition comprising any one of the present compounds 1 to 62 and chlorimuronethyl at a ratio of 0.1:1; a pest control composition comprising any one of the present compounds 1 to 62 and chlorimuronethyl at a ratio of 1:1; a pest control composition comprising any one of the present compounds 1 to 62 and chlorimuronethyl at a ratio of 1:20; a pest control composition comprising any one of the present compounds 1 to 62 and chloridazon at a ratio of 0.1:1; a pest control composition comprising any one of the present compounds 1 to 62 and chloridazon at a ratio of 1:1; a pest control composition comprising any one of the present compounds 1 to 62 and chloridazon at a ratio of 1:20; a pest control composition comprising any one of the present compounds 1 to 62 and clethodim at a ratio of 0.1:1; a pest control composition comprising any one of the present compounds 1 to 62 and clethodim at a ratio of 1:1; a pest control composition comprising any one of the present compounds 1 to 62 and clethodim at a ratio of 1:20; a pest control composition comprising any one of the present compounds 1 to 62 and clodinafop at a ratio of 0.1:1; a pest control composition comprising any one of the present compounds 1 to 62 and clodinafop at a ratio of 1:1;
a pest control composition comprising any one of the present compounds 1 to 62 and clodinafop at a ratio of 1:20; a pest control composition comprising any one of the present compounds 1 to 62 and clomazone at a ratio of 0.1:1; a pest control composition comprising any one of the present compounds 1 to 62 and clomazone at a ratio of 1:1; a pest control composition comprising any one of the present compounds 1 to 62 and clomazone at a ratio of 1:20; a pest control composition comprising any one of the present compounds 1 to 62 and clopyralid at a ratio of 0.1:1; a pest control composition comprising any one of the present compounds 1 to 62 and clopyralid at a ratio of 1:1; a pest control composition comprising any one of the present compounds 1 to 62 and clopyralid at a ratio of 1:20; a pest control composition comprising any one of the present compounds 1 to 62 and cloransulam-methyl at a ratio of 0.1:1; a pest control composition comprising any one of the present compounds 1 to 62 and cloransulam-methyl at a ratio of 1:1; a pest control composition comprising any one of the present compounds 1 to 62 and cloransulam-methyl at a ratio of 1:20; a pest control composition comprising any one of the present compounds 1 to 62 and desmedipham at a ratio of 0.1:1; a pest control composition comprising any one of the present compounds 1 to 62 and desmedipham at a ratio of 1:1; a pest control composition comprising any one of the present compounds 1 to 62 and desmedipham at a ratio of 1:20; a pest control composition comprising any one of the present compounds 1 to 62 and dicamba at a ratio of 0.1:1; a pest control composition comprising any one of the present compounds 1 to 62 and dicamba at a ratio of 1:1; a pest control composition comprising any one of the present compounds 1 to 62 and dicamba at a ratio of 1:20; a pest control composition comprising any one of the present compounds 1 to 62 and diclofop at a ratio of 0.1:1; a pest control composition comprising any one of the present compounds 1 to 62 and diclofop at a ratio of 1:1; a pest control composition comprising any one of the present compounds 1 to 62 and diclofop at a ratio of 1:20;
a pest control composition comprising any one of the present compounds 1 to 62 and diclosulam at a ratio of 0.1:1; a pest control composition comprising any one of the present compounds 1 to 62 and diclosulam at a ratio of 1:1; a pest control composition comprising any one of the present compounds 1 to 62 and diclosulam at a ratio of 1:20; a pest control composition comprising any one of the present compounds 1 to 62 and diflufenzopyr at a ratio of 0.1:1; a pest control composition comprising any one of the present compounds 1 to 62 and diflufenzopyr at a ratio of 1:1; a pest control composition comprising any one of the present compounds 1 to 62 and diflufenzopyr at a ratio of 1:20; a pest control composition comprising any one of the present compounds 1 to 62 and dimethenamid at a ratio of 0.1:1; a pest control composition comprising any one of the present compounds 1 to 62 and dimethenamid at a ratio of 1:1; a pest control composition comprising any one of the present compounds 1 to 62 and dimethenamid at a ratio of 1:20; a pest control composition comprising any one of the present compounds 1 to 62 and diquat at a ratio of 0.1:1; a pest control composition comprising any one of the present compounds 1 to 62 and diquat at a ratio of 1:1; a pest control composition comprising any one of the present compounds 1 to 62 and diquat at a ratio of 1:20; a pest control composition comprising any one of the present compounds 1 to 62 and diuron at a ratio of 0.1:1; a pest control composition comprising any one of the present compounds 1 to 62 and diuron at a ratio of 1:1; a pest control composition comprising any one of the present. Compounds 1 to 62 and diuron at a ratio of 1:20; a pest control composition comprising any one of the present compounds 1 to 62 and EPTC at a ratio of 0.1:1; a pest control composition comprising any one of the present compounds 1 to 62 and EPTC at a ratio of 1:1; a pest control composition comprising any one of the present compounds 1 to 62 and EPIC at a ratio of 1:20;
a pest control composition comprising any one of the present compounds 1 to 62 and ethalfluralin at a ratio of 0.1:1; a pest control composition comprising any one of the present compounds 1 to 62 and ethalfluralin at a ratio of 1:1; a pest control composition comprising any one of the present compounds 1 to 62 and ethalfluralin at a ratio of 1:20; a pest control composition comprising any one of the present compounds 1 to 62 and ethofumesate at a ratio of 0.1:1; a pest control composition comprising any one of the present compounds 1 to 62 and ethofumesate at a ratio of 1:1; a pest control composition comprising any one of the present compounds 1 to 62 and ethofumesate at a ratio of 1:20; a pest control composition comprising any one of the present compounds 1 to 62 and fenoxaprop at a ratio of 0.1:1; a pest control composition comprising any one of the present compounds 1 to 62 and fenoxaprop at a ratio of 1:1; a pest control composition comprising any one of the present compounds 1 to 62 and fenoxaprop at a ratio of 1:20; a pest control composition comprising any one of the present compounds 1 to 62 and fenoxaprop-P-ethyl at a ratio of 0.1:1; a pest control composition comprising any one of the present compounds 1 to 62 and fenoxaprop-P-ethyl at a ratio of 1:1; a pest control composition comprising any one of the present compounds 1 to 62 and fenoxaprop-P-ethyl at a ratio of 1:20; a pest control composition comprising any one of the present compounds 1 to 62 and florasulam at a ratio of 0.1:1; a pest control composition comprising any one of the present compounds 1 to 62 and florasulam at a ratio of 1:1; a pest control composition comprising any one of the present compounds 1 to 62 and florasulam at a ratio of 1:20; a pest control composition comprising any one of the present compounds 1 to 62 and fluazifop-P-butyl at a ratio of 0.1:1; a pest control composition comprising any one of the present compounds 1 to 62 and fluazifop-P-butyl at a ratio of 1:1; a pest control composition comprising any one of the present compounds 1 to 62 and fluazifop-P-butyl at a ratio of 1:20; a pest control composition comprising any one of the present compounds 1 to 62 and flufenacet at a ratio of 0.1:1; a pest control composition comprising any one of the present compounds 1 to 62 and flufenacet at a ratio of 1:1;
a pest control composition comprising any one of the present compounds 1 to 62 and flufenacet at a ratio of 1:20; a pest control composition comprising any one of the present compounds 1 to 62 and flumetsulam at a ratio of 0.1:1; a pest control composition comprising any one of the present compounds 1 to 62 and flumetsulam at a ratio of 1:1; a pest control composition comprising any one of the present compounds 1 to 62 and flumetsulam at a ratio of 1:20; a pest control composition comprising any one of the present compounds 1 to 62 and flumiclorac at a ratio of 0.1:1; a pest control composition comprising any one of the present compounds 1 to 62 and flumiclorac at a ratio of 1:1; a pest control composition comprising any one of the present compounds 1 to 62 and flumiclorac at a ratio of 1:20; a pest control composition comprising any one of the present compounds 1 to 62 and flumioxazin at a ratio of 0.1:1; a pest control composition comprising any one of the present compounds 1 to 62 and flumioxazin at a ratio of 1:1; a pest control composition comprising any one of the present compounds 1 to 62 and flumioxazin at a ratio of 1:20; a pest Control composition comprising any one of the present compounds 1 to 62 and fluthiacet at a ratio of 0.1:1; a pest control composition comprising any one of the present compounds 1 to 62 and fluthiacet at a ratio of 1:1; a pest control composition comprising any one of the present compounds 1 to 62 and fluthiacet at a ratio of 1:20; a pest control composition comprising any one of the present compounds 1 to 62 and fomesafen at a ratio of 0.1:1; a pest control composition comprising any one of the present compounds 1 to 62 and fomesafen at a ratio of 1:1; a pest control composition comprising any one of the present compounds 1 to 62 and fomesafen at a ratio of 1:20; a pest control composition comprising any one of the present compounds 1 to 62 and foramsulfuron at a ratio of 0.1:1; a pest control composition comprising any one of the present compounds 1 to 62 and foramsulfuron at a ratio of 1:1; a pest control composition comprising any one of the present compounds 1 to 62 and foramsulfuron at a ratio of 1:20;

a pest control composition comprising any one of the present compounds 1 to 62 and glufosinate at a ratio of 0.1:1; a pest control composition comprising any one of the present compounds 1 to 62 and glufosinate at a ratio of 1:1; a pest control composition comprising any one of the present compounds 1 to 62 and glufosinate at a ratio of 1:20; a pest control composition comprising any one of the present compounds 1 to 62 and glufosinate-ammonium at a ratio of 0.1:1; a pest control composition comprising any one of the present compounds 1 to 62 and glufosinate-ammonium at a ratio of 1:1; a pest control composition comprising any one of the present compounds 1 to 62 and glufosinate-ammonium at a ratio of 1:20; a pest control composition comprising any one of the present compounds 1 to 62 and glyphosate at a ratio of 0.1:1; a pest control composition comprising any one of the present compounds 1 to 62 and glyphosate at a ratio of 1:1; a pest control composition comprising any one of the present compounds 1 to 62 and glyphosate at a ratio of 1:20; a pest control composition comprising any one of the present compounds 1 to 62 and glyphosate-trimesium at a ratio of 0.1:1; a pest control composition comprising any one of the present compounds 1 to 62 and glyphosate-trimesium at a ratio of 1:1; a pest control composition comprising any one of the present compounds 1 to 62 and glyphosate-trimesium at a ratio of 1:20; a pest control composition comprising any one of the present compounds 1 to 62 and glyphosate-isopropylamine at a ratio of 0.1:1; a pest control composition comprising any one of the present compounds 1 to 62 and glyphosate-isopropylamine at a ratio of 1:1; a pest control composition comprising any one of the present compounds 1 to 62 and glyphosate-isopropylamine at a ratio of 1:20; a pest control composition comprising any one of the present compounds 1 to 62 and glyphosate-potassium at a ratio of 0.1:1; a pest control composition comprising any one of the present compounds 1 to 62 and glyphosate-potassium at a ratio of 1:1; a pest control composition comprising any one of the present compounds 1 to 62 and glyphosate-potassium at a ratio of 1:20; a pest control composition comprising any one of the present compounds 1 to 62 and halosulfuron at a ratio of 0.1:1;

a pest control composition comprising any one of the present compounds 1 to 62 and halosulfuron at a ratio of 1:1; a pest control composition comprising any one of the present compounds 1 to 62 and halosulfuron at a ratio of 1:20; a pest control composition comprising any one of the present compounds 1 to 62 and halosulfuron-methyl at a ratio of 0.1:1; a pest control composition comprising any one of the present compounds 1 to 62 and halosulfuron-methyl at a ratio of 1:1; a pest control composition comprising any one of the present compounds 1 to 62 and halosulfuron-methyl at a ratio of 1:20; a pest control composition comprising any one of the present compounds 1 to 62 and haloxyfop-R-methyl at a ratio of 0.1:1; a pest control composition comprising any one of the present compounds 1 to 62 and haloxyfop-R-methyl at a ratio of 1:1; a pest control composition comprising any one of the present compounds 1 to 62 and haloxyfop-R-methyl at a ratio of 1:20; a pest control composition comprising any one of the present compounds 1 to 62 and hexazinone at a ratio of 0.1:1; a pest control composition comprising any one of the present compounds 1 to 62 and hexazinone at a ratio of 1:1; a pest control composition comprising any one of the present compounds 1 to 62 and hexazinone at a ratio of 1:20; a pest control composition comprising any one of the present compounds 1 to 62 and imazamox at a ratio of 0.1:1; a pest control composition comprising any one of the present compounds 1 to 62 and imazamox at a ratio of 1:1; a pest control composition comprising any one of the present compounds 1 to 62 and imazamox at a ratio of 1:20; a pest control composition comprising any one of the present compounds 1 to 62 and imazapic at a ratio of 0.1:1; a pest control composition comprising any one of the present compounds 1 to 62 and imazapic at a ratio of 1:1; a pest Control composition comprising any one of the present compounds 1 to 62 and imazapic at a ratio of 1:20; a pest control composition comprising any one of the present compounds 1 to 62 and imazaquine at a ratio of 0.1:1; a pest control composition comprising any one of the present compounds 1 to 62 and imazaquine at a ratio of 1:1; a pest control composition comprising any one of the present compounds 1 to 62 and imazaquine at a ratio of 1:20;

a pest control composition comprising any one of the present compounds 1 to 62 and imazethapyr at a ratio of 0.1:1; a pest control composition comprising any one of the present compounds 1 to 62 and imazethapyr at a ratio of 1:1; a pest control composition comprising any one of the present compounds 1 to 62 and imazethapyr at a ratio of 1:20; a pest control composition comprising any one of the present compounds 1 to 62 and iodosulfuron at a ratio of 0.1:1; a pest control composition comprising any one of the present compounds 1 to 62 and iodosulfuron at a ratio of 1:1; a pest control composition comprising any one of the present compounds 1 to 62 and iodosulfuron at a ratio of 1:20; a pest control composition comprising any one of the present compounds 1 to 62 and isoxaflutole at a ratio of 0.1:1; a pest control composition comprising any one of the present compounds 1 to 62 and isoxaflutole at a ratio of 1:1; a pest control composition comprising any one of the present compounds 1 to 62 and isoxaflutole at a ratio of 1:20; a pest control composition comprising any one of the present compounds 1 to 62 and lactofen at a ratio of 0.1:1; a pest control composition comprising any one of the present compounds 1 to 62 and lactofen at a ratio of 1:1; a pest control composition comprising any one of the present compounds 1 to 62 and lactofen at a ratio of 1:20; a pest control composition comprising any one of the present compounds 1 to 62 and lenacil at a ratio of 0.1:1; a pest control composition comprising any one of the present compounds 1 to 62 and lenacil at a ratio of 1:1; a pest Control composition comprising any one of the present compounds 1 to 62 and lenacil at a ratio of 1:20; a pest control composition comprising any one of the present compounds 1 to 62 and linuron at a ratio of 0.1:1; a pest control composition comprising any one of the present compounds 1 to 62 and linuron at a ratio of 1:1; a pest control composition comprising any one of the present compounds 1 to 62 and linuron at a ratio of 1:20; a pest control composition comprising any one of the present compounds 1 to 62 and mesosulfuron at a ratio of 0.1:1; a pest control composition comprising any one of the present compounds 1 to 62 and mesosulfuron at a ratio of 1:1; a pest control composition comprising any one of the present compounds 1 to 62 and mesosulfuron at a ratio of 1:20; a pest control composition comprising any one of the present compounds 1 to 62 and mesotrione at a ratio of 0.1:1; a pest control composition comprising any one of the present compounds 1 to 62 and mesotrione at a ratio of 1:1; a pest control composition comprising any one of the present compounds 1 to 62 and mesotrione at a ratio of 1:20; a pest control composition comprising any one of the present compounds 1 to 62 and metam at a ratio of 0.1:1; a pest control composition comprising any one of the present compounds 1 to 62 and metam at a ratio of 1:1; a pest control composition comprising any one of the present compounds 1 to 62 and metam at a ratio of 1:20; a pest control composition comprising any one of the present compounds 1 to 62 and metamitron at a ratio of 0.1:1; a pest control composition comprising any one of the present compounds 1 to 62 and metamitron at a ratio of 1:1; a pest control composition comprising any one of the present compounds 1 to 62 and metamitron at a ratio of 1:20; a pest control composition comprising any one of the present compounds 1 to 62 and metolachior at a ratio of 0.1:1; a pest control composition comprising any one of the present compounds 1 to 62 and metolachlor at a ratio of 1:1; a pest control composition comprising any one of the present compounds 1 to 62 and metolachlor at a ratio of 1:20; a pest control composition comprising any one of the present compounds 1 to 62 and metribuzin at a ratio of 0.1:1; a pest control composition comprising any one of the present compounds 1 to 62 and metribuzin at a ratio of 1:1; a pest control composition comprising any one of the present compounds 1 to 62 and metribuzin at a ratio of 1:20; a pest control composition comprising any one of the present compounds 1 to 62 and metsulfuron at a ratio of 0.1:1; a pest control composition comprising any one of the present compounds 1 to 62 and metsulfuron at a ratio of 1:1; a pest control composition comprising any one of the present compounds 1 to 62 and metsulfuron at a ratio of 1:20; a pest control composition comprising any one of the present compounds 1 to 62 and MPCA at a ratio of 0.1:1; a pest control composition comprising any one of the present compounds 1 to 62 and MPCA at a ratio of 1:1; a pest control composition comprising any one of the present compounds 1 to 62 and MPCA at a ratio of 1:20; a pest control composition comprising any one of the present compounds 1 to 62 and MSMA at a ratio of 0.1:1; a pest control composition comprising any one of the present compounds 1 to 62 and MSMA at a ratio of 1:1; a pest control composition comprising any one of the present compounds 1 to 62 and MSMA at a ratio of 1:20; a pest control composition comprising any one of the present compounds 1 to 62 and nicosulfuron at a ratio of 0.1:1; a pest control composition comprising any one of the present compounds 1 to 62 and nicosulfuron at a ratio of 1:1; a pest control composition comprising any one of the present compounds 1 to 62 and nicosulfuron at a ratio of 1:20; a pest control composition comprising any one of the present compounds 1 to 62 and oryzalin at a ratio of 0.1:1; a pest control composition comprising any one of the present compounds 1 to 62 and oryzalin at a ratio of 1:1; a pest control composition comprising any one of the present compounds 1 to 62 and oryzalin at a ratio of 1:20; a pest control composition comprising any one of the present compounds 1 to 62 and oxyfluorfen at a ratio of 0.1:1; a pest control composition comprising any one of the present compounds 1 to 62 and oxyfluorfen at a ratio of 1:1; a pest control composition comprising any one of the present compounds 1 to 62 and oxyfluorfen at a ratio of 1:20; a pest control composition comprising any one of the present compounds 1 to 62 and paraquat at a ratio of 0.1:1; a pest control composition comprising any one of the present compounds 1 to 62 and paraguat at a ratio of 1:1; a pest control composition comprising any one of the present compounds 1 to 62 and paraquat at a ratio of 1:20; a pest control composition comprising any one of the present compounds 1 to 62 and pendimethalin at a ratio of 0.1:1; a pest control composition comprising any one of the present compounds 1 to 62 and pendimethalin at a ratio of 1:1;
a pest control composition comprising any one of the present compounds 1 to 62 and pendimethalin at a ratio of 1:20; a pest control composition comprising any one of the present compounds 1 to 62 and phenmedipham at a ratio of 0.1:1; a pest control composition comprising any one of the present compounds 1 to 62 and phenmedipham at a ratio of 1:1; a pest control composition comprising any one of the present compounds 1 to 62 and phenmedipham at a ratio of 1:20; a pest control composition comprising any one of the present compounds 1 to 62 and picloram at a ratio of 0.1:1; a pest control composition comprising any one of the present compounds 1 to 62 and picloram at a ratio of 1:1; a pest control composition comprising any one of the present compounds 1 to 62 and picloram at a ratio of 1:20; a pest control composition comprising any one of the present compounds 1 to 62 and pyrimisulfuron at a ratio of 0.1:1; a pest control composition comprising any one of the present compounds 1 to 62 and pyrimisulfuron at a ratio of 1:1; a pest control composition comprising any one of the present compounds 1 to 62 and pyrimisulfuron at a ratio of 1:20; a pest control composition comprising any one of the present compounds 1 to 62 and pinoxaden at a ratio of 0.1:1; a pest control composition comprising any one of the present compounds 1 to 62 and pinoxaden at a ratio of 1:1; a pest control composition comprising any one of the present compounds 1 to 62 and pinoxaden at a ratio of 1:20; a pest control composition comprising any one of the present compounds 1 to 62 and prometryn at a ratio of 0.1:1; a pest control composition comprising any one of the present compounds 1 to 62 and prometryn at a ratio of 1:1; a pest control composition comprising any one of the present compounds 1 to 62 and prometryn at a ratio of 1:20; a pest control composition comprising any one of the present compounds 1 to 62 and pyraflufen-ethyl at a ratio of 0.1:1; a pest control composition comprising any one of the present compounds 1 to 62 and pyraflufen-ethyl at a ratio of 1:1; a pest control composition comprising any one of the present compounds 1 to 62 and pyraflufen-ethyl at a ratio of 1:20; a pest control composition comprising any one of the present compounds 1 to 62 and pyrithiobac at a ratio of 0.1:1;
a pest control composition comprising any one of the present compounds 1 to 62 and pyrithiobac at a ratio of 1:1; a pest control composition comprising any one of the present compounds 1 to 62 and pyrithiobac at a ratio of 1:20; a pest control composition comprising any one of the present compounds 1 to 62 and pyroxsulam at a ratio of 0.1:1; a pest control composition comprising any one of the present compounds 1 to 62 and pyroxsulam at a ratio of 1:1; a pest control composition comprising any one of the present compounds 1 to 62 and pyroxsulam at a ratio of 1:20; a pest control composition comprising any one of the present compounds 1 to 62 and pyroxasulfone at a ratio of 0.1:1; a pest control composition comprising any one of the present compounds 1 to 62 and pyroxasulfone at a ratio of 1:1; a pest control composition comprising any one of the present compounds 1 to 62 and pyroxasulfone at a ratio of 1:20; a pest control composition comprising any one of the present compounds 1 to 62 and quizalofop-P-ethyl at a ratio of 0.1:1; a pest control composition comprising any one of the present compounds 1 to 62 and quizalofop-P-ethyl at a ratio of 1:1; a pest control composition comprising any one of the present compounds 1 to 62 and quizalofop-P-ethyl at a ratio of 1:20; a pest control composition comprising any one of the present compounds 1 to 62 and salflufenacil at a ratio of 0.1:1; a pest control composition comprising any one of the present compounds 1 to 62 and salflufenacil at a ratio of 1:1; a pest control composition comprising any one of the present compounds 1 to 62 and salflufenacil at a ratio of 1:20; a pest control composition comprising any one of the present compounds 1 to 62 and sethoxydim at a ratio of 0.1:1; a pest control composition comprising any one of the present compounds 1 to 62 and sethoxydim at a ratio of 1:1; a pest control composition comprising any one of the present compounds 1 to 62 and sethoxydim at a ratio of 1:20; a pest control composition comprising any one of the present compounds 1 to 62 and simazine at a ratio of 0.1:1; a pest control composition comprising any one of the present compounds 1 to 62 and simazine at a ratio of 1:1; a pest control composition comprising any one of the present compounds 1 to 62 and simazine at a ratio of 1:20; a pest control composition comprising any one of the present compounds 1 to 62 and sulfentrazone at a ratio of 0.1:1; a pest control composition comprising any one of the present compounds 1 to 62 and sulfentrazone at a ratio of 1:1; a pest control composition comprising any one of the present compounds 1 to 62 and sulfentrazone at a ratio of 1:20; a pest control composition comprising any one of the present compounds 1 to 62 and tebuthiuron at a ratio of 0.1:1; a pest control composition comprising any one of the present compounds 1 to 62 and tebuthiuron at a ratio of 1:1; a pest control composition comprising any one of the present compounds 1 to 62 and tebuthiuron at a ratio of 1:20; a pest control composition comprising any one of the present compounds 1 to 62 and tembotrione at a ratio of 0.1:1; a pest control composition comprising any one of the present compounds 1 to 62 and tembotrione at a ratio of 1:1; a pest control composition comprising any one of the present compounds 1 to 62 and tembotrione at a ratio of 1:20; a pest control composition comprising any one of the present compounds 1 to 62 and tepraloxydim at a ratio of 0.1:1; a pest control composition comprising any one of the present compounds 1 to 62 and tepraloxydim at a ratio of 1:1; a pest control composition comprising any one of the present compounds 1 to 62 and tepraloxydim at a ratio of 1:20; a pest control composition comprising any one of the present compounds 1 to 62 and thifensulfuron at a ratio of 0.1:1; a pest control composition comprising any one of the present compounds 1 to 62 and thifensulfuron at a ratio of 1:1; a Control composition comprising any one of the present compounds 1 to 62 and thifensulfuron at a ratio of 1:20; a pest control composition comprising any one of the present compounds 1 to 62 and tribenuron-methyl at a ratio of 0.1:1; a pest control composition comprising any one of the present compounds 1 to 62 and tribenuron-methyl at a ratio of 1:1; a pest control composition comprising any one of the present compounds 1 to 62 and tribenuron-methyl at a ratio of 1:20; a pest control composition comprising any one of the present compounds 1 to 62 and triclopyr at a ratio of 0.1:1; a pest control composition comprising any one of the present compounds 1 to 62 and triclopyr at a ratio of 1:1; a pest control composition comprising any one of the present compounds 1 to 62 and triclopyr at a ratio of 1:20; a pest control composition comprising any one of the present compounds 1 to 62 and trifloxysulfuron at a ratio of 0.1:1; a pest control composition comprising any one of the present compounds 1 to 62 and trifloxysulfuron at a ratio of 1:1; a pest control composition comprising any one of the present compounds 1 to 62 and trifloxysulfuron at a ratio of 1:20; a pest control composition comprising any one of the present compounds 1 to 62 and trifluralin at a ratio of 0.1:1; a pest control composition comprising any one of the present compounds 1 to 62 and trifluralin at a ratio of 1:1; a pest control composition comprising any one of the present compounds 1 to 62 and trifluralin at a ratio of 1:20; a pest control composition comprising any one of the present compounds 1 to 62 and triflusulfuron-methyl at a ratio of 0.1:1; a pest control composition comprising any one of the present compounds 1 to 62 and triflusulfuron-methyl at a ratio of 1:1; a pest control composition comprising any one of the present compounds 1 to 62 and triflusulfuron-methyl at a ratio of 1:20.

Formulation Examples will be shown below.

Formulation Example 1

Fifty parts (50 parts) of any one of the present compounds 1 to 62, 3 parts of calcium ligninsulfoate, 2 parts of laurylmagnesium sulfate, and 45 parts of synthetic hydrated silicon oxide are thoroughly ground and mixed to obtain each formulation.

Formulation Example 2

Twenty parts (20 parts) of any one of the present compounds 1 to 62 and 1.5 parts of sorbitan trioleate are mixed with 28.5 parts of an aqueous solution containing 2 parts of polyvinyl alcohol, and the mixture was finely ground by a wet grinding method. Then, 40 parts of an aqueous solution containing 0.05 part of xanthan gum and 0.1 part of aluminum magnesium silicate is added thereto and 10 parts of propylene glycol is further added, followed by stirring and mixing to obtain each formulation.

Formulation Example 3

Two parts (2 parts) of any one of the present compounds 1 to 62, 88 parts of kaolin clay, and 10 parts of talc are thoroughly ground and mixed to obtain each formulation.

Formulation Example 4

Five parts (5 parts) of any one of the present compounds 1 to 62, 14 parts of polyoxyethylene styryl phenyl ether, 6 parts of calcium dodecylbenzenesulfonate, and 75 parts of xylene are thoroughly ground and mixed to obtain each formulation.

Formulation Example 5

Two parts (2 parts) of any one of the present compounds 1 to 62, 1 part of synthetic hydrated silicon oxide, 2 parts of calcium ligninsulfoate, 30 parts of bentonite, and 65 parts of kaolin clay are thoroughly ground and mixed. After the addition of water, the mixture is thoroughly kneaded and further granulated and dried to obtain each formulation.

Formulation Example 6

Ten parts (10 parts) of any one of the present compounds 1 to 62, 35 parts of white carbon containing 50 parts of a polyoxyethylene alkyl ether sulfate ammonium salt, and 55 parts of water were finely ground by a wet grinding method to obtain each formulation.

The following Test Examples will show that the present compounds are useful for controlling plant diseases.

The control effect was evaluated by visually observing the area of lesion. On each of test plants at the time of investigation, and comparing the area of lesion on a plant treated with the present compound with that on an untreated plant. The untreated plant is a plant tested under the same conditions as in Test Examples, except that foliar or foliage application of a solution of a formulation containing the present compound with water is not performed.

Test Example 1

Each of plastic pots was filled with soil and rice (cultivar: NIHONBARE) was sowed and grown in a greenhouse for 20 days. Then, each water dilution containing a surfactant prepared by adjusting so as to contain. A predetermined concentration (500 ppm) of any one compound of the present compounds 4, 5, 10 to 12, 25 to 28, 30, 42, 47, 48, 51, 54, 55, and 58 was sprayed over stems and leaves so that it sufficiently adhered to the surface of the leaves of the rice. After spraying, the plant was air-dried and placed for 6 days at 24° C. in the daytime and 20° C. at night under high humidity condition, while being in contact with the rice seedling (cultivar: NIHONBARE) infected by the rice blast fungus (*Magnaporthe grisea*), and then the area of lesion was investigated. As a result, the lesion areas on the plant treated with the present compound 4, 5, 10 to 12, 25 to 28, 30, 42, 47, 48, 51, 54, 55, or 58 were 30% or less with respect to the lesion area on the non-treated plant.

Test Example 2

Each of plastic pots was filled with soil and wheat (cultivar: SHIROGANE) was sowed and grown in a greenhouse for 9 days. Then, each water dilution containing a surfactant prepared by adjusting so as to contain a predetermined concentration. (500 ppm) of any one compound of the present compounds 5, 10 to 12, 17, 19 to 21, 26, 28, 30, 40, 42, 47, 48, or 58 was sprayed over stems and leaves of the wheat so that it sufficiently adhered to the surface of the leaves of the wheat. After spraying, the plant was air-dried. And cultivated at 20° C. for 5 days under illumination, and then inoculated. By sprinkling with spores of wheat rust fungus (*Puccinia recondita*). After the inoculation, the plant was placed at 23° C. for one day under dark and high humidity condition, and cultivated under illumination at 20° C. for 8 days, and then the area of lesion was investigated. As a result, it has been found that the area of lesion on the plant treated with the present compound 5, 10 to 12, 17, 19 to 21, 26, 28, 30, 40, 42, 47, 48, or 58 was 30% or less of that on an untreated plant.

Test Example 3

Each of plastic pots was filled with soil and barley (cultivar: NISHTNOHOSHI) was sowed and grown in a greenhouse for 7 days. Then, each water dilution containing a surfactant prepared by adjusting so as to contain a predetermined concentration (500 ppm) of any one compound of the present compounds 4 to 6, 10 to 12, 17, 19 to 21, 25 to 30, 32, 34, 36, 38 to 40, 42 to 48, 51, 52, 54, and 58 was sprayed over stems and leaves of the barley so that it sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was placed for 3 days in a greenhouse at 23° C. in the daytime and 20° C. at night under high humidity condition and cultivated in a greenhouse for 7 days, and then the area of lesion was investigated. As a result, the area of lesion on the plant treated with the present compound 4 to 6, 10 to 12, 17, 19 to 21, 25 to 30, 32, 34, 36, 38 to 40, 42 to 48, 51, 52, 54, or 58 was 30% or less of that on an untreated plant.

Test Example 4

Each of plastic pots was filled with soil and kidney bean (cultivar: NAGAUZURASAITOU) was sowed and grown in a greenhouse for 8 days. Then, each water dilution containing a surfactant prepared by adjusting so as to contain a predetermined concentration (500 ppm) of any one compound of the present compounds 5, 6, 10 to 12, 16, 30, 41, and 58 was sprayed over stems and leaves of the kidney bean so that it sufficiently adhered to the surface of the leaves of the kidney bean. After spraying, the plant was air-dried and a PDA medium containing hyphae of the kidney bean stem rot fungus (*Sclerotinia sclerotiorum*) was placed on the leaves of the kidney bean. After the inoculation, all kidney beans were placed under high humidity condition only at night. Four days after the inoculation, the area of lesion was investigated. As a result, the area of lesion on the plant treated with the present compound 5, 6, 10 to 12, 16, 30, 44, or 58 was 30% or less of that on an untreated plant.

Test Example 5

Each of plastic pots was filled with soil and wheat (cultivar: APOGEE) was sowed and grown in a greenhouse for 10 days. Then, each water dilution containing a surfactant prepared by adjusting so as to contain a predetermined concentration (500 ppm) of any one compound of the present compounds 4 to 6, 10 to 12, 19, 23, 25 to 28, 30, 32, 39, 40, 42, 44, 47, 50 to 53, 58, 60, and 61 was sprayed over stems and leaves of the wheat so that it sufficiently adhered to the surface of the leaves of the wheat. After spraying, the plant was air-dried. After 4 days, an aqueous suspension containing' spores of wheat leaf blotch fungus (*Septoria tritici*) was sprayed to inoculate the spores. After completion of the inoculation, the plant was placed at 18° C. under high humidity condition for 3 days and placed under illumination for 14 to 18 days, and then the area of lesion was investigated. As a result, the area of lesion on the plant treated with the present compound 4 to 6, 10 to 12, 19, 23, 25 to 28, 30, 32, 39, 40, 42, 44, 47, 50 to 53, 58, 60, or 61 was 30% or less of that on an untreated plant.

Test Example 6

Each of plastic pots was filled with soil and cucumber (cultivar: SAGAMI HANJIRO) was sowed and grown in a greenhouse for 12 days. Then, each water dilution containing a surfactant prepared by adjusting so as to contain a predetermined concentration (500 ppm) of any one compound of the present compounds 4 to 6, 10 to 12, 16, 17, 19 to 21, 25, 28 to 31, 40, 42, 44, 45, 54, and 58 was sprayed over stems and leaves of the cucumber so that it sufficiently adhered to the surface of the leaves of the cucumber. After spraying, the plant was air-dried and then inoculated by sprinkling with spores of cucumber powdery mildew fungus (*Sphaerotheca fuliginea*, a QoI-resistant strain in which, among the genes encoding cytochrome b, the amino acid residue at position 143 of cytochrome b is mutated from glycine to alanine). After the inoculation, the plant was cultivated in a greenhouse at 24° C. in the daytime and 20° C. at night for 8 days, and then the area of lesion was investigated. As a result, the area of lesion on the plant treated with the present compound 4 to 6, 10 to 12, 16, 17, 19 to 21, 25, 28 to 31, 40, 42, 44, 45, 54, or 58 was 30% or less of that on an untreated plant.

Test Example 7

Each of plastic pots was filled with soil and soybean (cultivar: KUROSENGOKU) was sowed and grown in a greenhouse for 13 days. Then, each water dilution containing a surfactant prepared by adjusting so as to contain a predetermined concentration (200 ppm) of any one compound of the present compounds 1, 2, 4, 5, 7 to 9, 12, and 26 was sprayed over stems and leaves of the soybean so that it sufficiently adhered to the surface of the leaves of the soybean. After spraying, the plant was air-dried. After 2 days, an aqueous suspension containing spores of soybean rust fungus (*Phakopsora pachyrhizi*) was sprayed to inoculate the spores. After completion of the inoculation, the plant was placed for 3 days in a greenhouse at 23° C. in the daytime and 20° C. at night under high humidity condition and cultivated in a greenhouse for 14 days, and then the area of lesion was investigated. As a result, it has been found that the area of lesion on the plant treated with the present compound 1, 2, 4, 5, 7 to 9, 12, or 26 was 30% or less of that on an untreated plant.

Test Example 8

Each of plastic pots was filled with soil and barley (cultivar: NISHINOHOSHI) was sowed and grown in a greenhouse for 7 days. Then, each water dilution containing a surfactant prepared by adjusting so as to contain a predetermined concentration (200 ppm) of any one compound of the present compounds 1 to 9, 12, 13, 20, 21, 25, 26, 28 to 30, 42 to 44, 48, 51, and 58 was sprayed over stems and leaves of the barley so that it sufficiently adhered to the surface of the leaves of the barley. After spraying, the plant was air-dried. After 2 days, an aqueous suspension containing spores of barley scald fungus (*Rhynchosporium secaljs*) was sprayed to inoculate the spores. After completion of the inoculation, the plant was placed for 3 days in a greenhouse at 23° C. in the daytime and 20° C. at night under high humidity condition and cultivated in a greenhouse for 7 days, and then the area of lesion was investigated. As a result, it has been found that the area of lesion on the plant treated with of the present compound 1 to 9, 12, 13, 20, 21, 25, 26, 28 to 30, 42 to 44, 48, 51, or 58 was 30% or less of that on an untreated plant.

Test Example 9

Each of plastic pots was filled with soil and cucumber (cultivar: SAGAMI HANJIRO) was sowed and grown in a greenhouse for 19 days. Then, each water dilution containing a surfactant prepared by adjusting so as to contain a predetermined concentration (200 ppm) of any one compound of the present compounds 12, 17, 19, 28, 30, 38, 40, 42, 44, 47, 48, 51, and 58 was sprayed over stems and leaves of the cucumber so that it sufficiently adhered to the surface of the leaves of the cucumber. After spraying, the plant was air-dried. After one day, an aqueous suspension containing spores of target spot fungus (*Corynespora cassiicola*) was sprayed to inoculate the spores. After the inoculation, the plant was cultivated at 24° C. in the daytime and 20° C. at night under high humidity condition for 7 days. Thereafter, the area of lesion was investigated. As a result, the area of lesion on the plant treated with the present compound 12, 17, 19, 28, 30, 38, 40, 42, 44, 47, 48, 51, or 58 was 30% or less of that on an untreated plant.

Test Example 10

Each of plastic pots was filled with soil and cucumber (cultivar: SAGAMI HANJIRO) was sowed and grown in a greenhouse for 19 days. Then, each water dilution containing a surfactant prepared by adjusting so as to contain a predetermined concentration (200 ppm) of any one compound of the present compounds 7 to 11, 14, 18, 26, 28, 30, 42, 48, 51, 53, and 58 was sprayed over stems and leaves of the cucumber so that it sufficiently adhered to the surface of the leaves of the cucumber. After spraying, the plant was air-dried. After one day, an aqueous suspension containing spores of anthracnose fungus (*Colletotrichum lagenarium*) was sprayed to inoculate the spores. After the inoculation, the plant was at first placed at 2:3° C. under high humidity condition for one day and then cultivated in a greenhouse at 24° C. in the daytime and 20° C. at night for 6 days. Thereafter, the area of lesion was investigated. As a result, the area of lesion on the plant treated with the present compound 7 to 11, 14, 18, 26, 28, 30, 42, 48, 51, 53, or 58 was 30% or less of that on an untreated plant.

Test Example 11

In the present Test Example, a water dilution containing a surfactant prepared by adjusting so as to contain a predetermined concentration (500 ppm) of the present compound was used as a test chemical solution.

Thirty (30) heads of cotton aphid. (*Aphis gossypii*) (including adults and larvae) were released on the leaves of cucumber grown in a polyethylene cup until the first true leaf was developed. Next day, 20 ml of the above test chemical solution was sprayed. After 6 days, the number of the surviving insects was counted and the control value was calculated by the following equation.

$$\text{Control value } (\%) = \{1 - (Cb \times Tai)/(Cai \times Tb)\} \times 100$$

wherein symbols in the equation represent the followings:
Cb: Number of insects before spraying chemical solution in untreated area;

Cai: Number of surviving insects in untreated area;
Tb: Number of insects before spraying chemical solution in treated area; and
Tai: Number of surviving insects in treated area.

As a result, the present compound 17 showed 90% or more of the control value.

Comparative Test Example

Each of plastic pots was filled with soil and wheat (cultivar: SHIROGANE) was sowed and grown in a greenhouse for 9 days. Then, each water dilution containing a surfactant prepared by adjusting so as to contain a predetermined concentration (50 ppm) of any one compound of 1-(2-{[1-(4-fluorophenyl)-1H-pyrazol-3-yl]oxymethyl}-phenyl)-4-methyl-1,4-dihydrotetrazol-5-one (control compound) and 1-{2-[1-(5-fluoropyridin-2-yl)-1H-pyrazol-3-yl]oxymethyl-3-methylphenyl}-4-methyl-1,4-dihydrotetrazol-5-one (Present Compound 40) was sprayed over stems and leaves of the wheat so that it sufficiently adhered to the surface of the leaves of the wheat. After spraying, the plant was air-dried so as to dry the dilution on the surface of the leaves. After spraying, the plant was air-dried and cultivated at 20° C. for 5 days under illumination, and then inoculated by sprinkling with spores of wheat rust fungus (*Puccinia recondita*). After the inoculation, the plant was placed at 23° C. for one day under dark and high humidity condition, and cultivated, under illumination at 20° C. for 8 days, and then the area of lesion was investigated. As a result, the area of lesion on the plant treated with 1-(2-{[1-(4-fluorophenyl)-1H-pyrazol-3-yl]oxymethyl}-phenyl)-4-methyl-1,4-dihydrotetrazol-5-one was 70% or more of that on an untreated plant, whereas, the area of Lesion on the plant treated with 1-{2-[1-(5-fluoropyridin-2-yl)-1H-pyrazol-3-yl]oxymethyl-3-methylphenyl}-4-methyl-1,4-dihydrotetrazol-5-one was 30% or less of that on an untreated plant.

The present compound has control activity against pests and is useful as an active ingredient of a pest control agent.

The invention claimed is:
1. A tetrazolinone compound represented by formula (1) or a salt thereof:

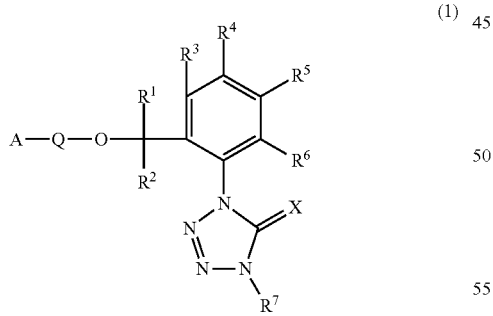

(1)

wherein
$R^1$ and $R^2$ each independently represents a hydrogen atom, a halogen atom, or a C1-C3 alkyl group;
$R^3$ represents a C1-C6 alkyl group, a C3-C6 cycloalkyl group, a halogen atom, a C1-C6 haloalkyl group, a C2-C6 alkenyl group, a C1-C6 alkoxy group, a C1-C6 alkylthio group, a C2-C6 alkynyl group, a nitro group, a cyano group, an aminocarbonyl group optionally substituted with a C1-C6 alkyl group, a C2-C6 haloalkenyl group, a C2-C6 haloalkynyl group, a C3-C6 halocycloalkyl group, a C1-C6 haloalkoxy group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a C2-C6 alkoxycarbonyl group, a hydroxy group, a sulfanyl group, an amino group optionally substituted with a C1-C6 alkyl group, a pentafluorosulfanyl group, a C3-C9 trialkylsilyl group, a C5-C14 trialkylsilylethynyl group, a C1-C6 alkylsulfonyl group, a C1-C6 haloalkylsulfonyl group, a C1-C6 alkylsulfinyl group, a C1-C6 haloalkylsulfinyl group, a C2-C5 alkoxyalkyl group, or a C2-C5 alkylthioalkyl group;
$R^4$, $R^5$, and $R^6$ each independently represents a hydrogen atom, a halogen atom, a C1-C3 alkyl group, a C1-C3 haloalkyl group, a C2-C3 alkenyl group, a C2-C3 haloalkenyl group, or a C1-C3 alkoxy group;
$R^7$ represents a C1-C3 alkyl group optionally substituted with one or more halogen atoms;
Q represents a divalent 5-membered aromatic heterocyclic group optionally substituted with one or more atoms or groups selected from Group $P^2$, provided that the heterocyclic group has one or more heteroatoms selected from a nitrogen atom, an oxygen atom, and a sulfur atom, the number of nitrogen atom is 0, 1, 2, 3, or 4, and the number of oxygen atom and sulfur atom is 0 or 1;
X represents an oxygen atom or a sulfur atom;
A represents a 5- to 10-membered monocyclic or fused ring heterocyclic group optionally substituted with one or more atoms or groups selected from Group $P^1$, provided that the heterocyclic group has one or more heteroatoms selected from the group consisting of a nitrogen atom, an oxygen atom, and a sulfur atom, the number of nitrogen atom is 0, 1, 2, 3, or 4, and the number of oxygen atom and sulfur atom is 0, 1, 2, or 3:
Group $P^1$ is selected from the group consisting of a halogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a hydroxycarbonyl group, a formyl group, a C2-C6 alkoxycarbonyl group, a nitro group, a cyano group, a hydroxy group, a C1-C6 alkylsulfonyl group, a C1-C6 haloalkylsulfonyl group, a C6-C16 arylsulfonyl group, a C6-C16 haloarylsulfonyl group, a C1-C6 alkylsulfinyl group, a C1-C6 haloalkylsulfinyl group, an amino group optionally substituted with a C1-C6 alkyl group, an aminosulfonyl group optionally substituted with a C1-C6 alkyl group, and an aminocarbonyl group optionally substituted with a C1-C6 alkyl group; and Group P² is selected from the group consisting of a halogen atom, a C1-C4 alkyl group, a C1-C4 haloalkyl group, a cyano group, a C3-C6 cycloalkyl group, a C3-C6 halocycloalkyl group, a C1-C4 alkoxy group, a C1-C4 haloalkoxy group, a C1-C4 alkylthio group, and a C1-C4 haloalkylthio group.

2. The tetrazolinone compound according to claim 1, wherein Q is a pyrazolyl group optionally substituted with one or more atoms or groups selected from Group P²;

A is a pyridyl group optionally substituted with one or more atoms or groups selected from Group P¹;

R¹, R², R⁴, R⁵, and R⁶ are hydrogen atoms;

R³ is a C1-C3 alkyl group optionally substituted with one or more halogen atoms, a C3-C4 cycloalkyl group optionally substituted with one or more halogen atoms, a halogen atom, a C1-C3 alkoxy group optionally substituted with one or more halogen atoms, or a C1-C3 alkylthio group optionally substituted with one or more halogen atoms;

R⁷ is a methyl group; and

X is an oxygen atom.

3. The tetrazolinone compound according to claim 1, wherein Q is a thiazolyl group optionally substituted with one or more atoms or groups selected from Group P²;

A is a pyridyl group optionally substituted with one or more atoms or groups selected from Group P¹;

R¹, R², R⁴, R⁵, and R⁶ are hydrogen atoms;

R³ is a C1-C3 alkyl group optionally substituted with one or more halogen atoms, a C3-C4 cycloalkyl group optionally substituted with one or more halogen atoms, a halogen atom, a C1-C3 alkoxy group optionally substituted with one or more halogen atoms, or a C1-C3 alkylthio group optionally substituted with one or more halogen atoms;

R⁷ is a methyl group; and

X is an oxygen atom.

4. The tetrazolinone compound according to claim 1, wherein Q is Q0;

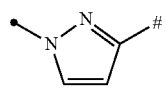

in which the symbol ● represents a binding site for A, and the symbol # represents a binding site for an oxygen atom;

A is a 2-pyridyl group, a 3-pyridyl group, a 2-quinolyl group, a 3-quinolyl group, a 3,4-methylenedioxyphenyl group, a 2-indolyl group, a 2-benzoimidazolyl group, a 3-thienyl group, a 2,3-dihydrobenzofuran-7-yl group, a 2-pyrimidinyl group, a 2-thiazolyl group, a pyrazinyl group, a 3-pyridazinyl group, a 2-benzoxazolyl group, a 2-benzothiazolyl group, a 2-quinazolyl group, or a 2-quinoxalinyl group;

R¹, R², R⁴, R⁵, and R⁶ are hydrogen atoms;

R³ is a C1-C3 alkyl group optionally substituted with one or more halogen atoms, a C3-C4 cycloalkyl group optionally substituted with one or more halogen atoms, a halogen atom, a C1-C3 alkoxy group optionally substituted with one or more halogen atoms, or a C1-C3 alkylthio group optionally substituted with one or more halogen atoms;

R⁷ is a methyl group; and

X is an oxygen atom.

5. The tetrazolinone compound according to claim 1, wherein Q is Q0:

in which the symbol ● represents a binding site for A, and the symbol # represents a binding site for an oxygen atom; and A is a 3-pyridyl group optionally substituted with a C1-C3 alkyl group optionally substituted with one or more halogen atoms, a halogen atom, a C1-C3 alkoxy group optionally substituted with one or more halogen atoms, or a cyano group.

6. A pest control agent comprising the tetrazolinone compound according to claim 1.

7. A method for controlling pests, which comprises treating plants or soil with an effective amount of the tetrazolinone compound according to claim 1.

8. A pyrazole compound represented by formula (II):

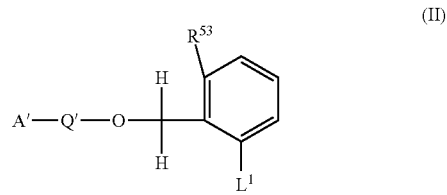

wherein Q' is a pyrazolyl group optionally substituted with one or more atoms or groups selected from Group P²;

A' is a pyridyl group optionally substituted with one or more atoms or groups selected from Group P¹;

R⁵³ is a C1-C3 alkyl group optionally substituted with one or more halogen atoms, a C3-C4 cycloalkyl group optionally ha-ng substituted with one or more halogen atoms, a halogen atom, a C1-C3 alkoxy group optionally substituted with one or more halogen atoms, or a C1-C3 alkylthio group optionally substituted with one or more halogen atoms;

Group P¹ is selected from the group consisting of a halogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a hydroxycarbonyl group, a formyl group, a C2-C6 alkoxycarbonyl group, a nitro group, a cyano group, a hydroxy group, a C1-C6 alkylsulfonyl group, a C1-C6 haloalkylsulfonyl group, a C6-C16 arylsulfonyl group, a C6-C16 haloarylsulfonyl group, a C1-C6 alkylsulfinyl group, a C1-C6 haloalkylsulfinyl group, an amino group optionally substituted with a C1-C6 alkyl group, an aminosulfonyl group optionally substituted with a C1-C6 alkyl group, and an aminocarbonyl group optionally substituted with a C1-C6 alkyl group;

Group $P^2$ is selected from the group consisting of a halogen atom, a C1-C4 alkyl group, a C1-C4 haloalkyl group, a cyano group, a C3-C6 cycloalkyl group, a C3-C6 halocycloalkyl group, a C1-C4 alkoxy group, a C1-C4 haloalkoxy group, a C1-C4 alkylthio group, and a C1-C4 haloalkylthio group;

$L^1$ is a nitro group, an amino group, an isocyanate group, a carboxyl group, a C2-C6 alkoxycarbonyl group, a halogen atom, a halogenated acyl group, NSO, $CON_3$, $CONH_2$, CONHCl, CONHBr, CONHOH, or $S^1$; and $S^1$ = 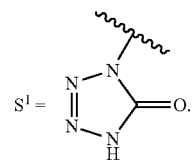 [SMILES: *n1nn[nH]c1=O]

9. The pyrazole compound according to claim 8, wherein Q' is Q0:

Q0 in which the symbol ● represents a binding site for A', and the symbol # represents a binding site for an oxygen atom;

A' is a 3-pyridyl group optionally substituted with a C1-C3 alkyl group optionally substituted with one or more halogen atoms, a halogen atom, a C1-C3 alkoxy group optionally substituted with one or more halogen atoms, or a cyano group; and $L^1$ is a nitro group, an amino group, an isocyanate group, or $S^1$.

* * * * *